US009206483B2

(12) United States Patent
Reddington et al.

(10) Patent No.: US 9,206,483 B2
(45) Date of Patent: Dec. 8, 2015

(54) DIAGNOSTIC METHOD

(75) Inventors: Kate Mary Reddington, Westport (IE); Thomas Gerard Barry, Kinvara (IE); Justin Joseph O'Grady, Galway (IE); Terence James Smith, Galway (IE)

(73) Assignee: National University of Ireland, Galway, Galway (IE)

( * ) Notice: Subject to any disclaimer, the term of this patent is extended or adjusted under 35 U.S.C. 154(b) by 0 days.

(21) Appl. No.: 13/700,025

(22) PCT Filed: May 25, 2011

(86) PCT No.: PCT/IB2011/001719

§ 371 (c)(1),
(2), (4) Date: Jun. 28, 2013

(87) PCT Pub. No.: WO2011/148269

PCT Pub. Date: Dec. 1, 2011

(65) Prior Publication Data

US 2013/0274121 A1 Oct. 17, 2013

(30) Foreign Application Priority Data

May 25, 2010 (GB) .................................. 1008719.5

(51) Int. Cl.
*C12Q 1/68* (2006.01)

(52) U.S. Cl.
CPC .............. *C12Q 1/689* (2013.01); *C12Q 1/6883* (2013.01); *C12Q 1/686* (2013.01); *C12Q 2600/16* (2013.01)

(58) Field of Classification Search
None
See application file for complete search history.

(56) References Cited

PUBLICATIONS

Warren et al. The International Journal of Tuberculosis and Lung Disease 10.7 (2006): 818-822.*

Brosch et al. Proceedings of the national academy of Sciences 99.6 (2002): 3684-3689.*

Lowe et al. Nucleic Acids Research, vol. 18, No. 7, p. 1757-1761, 1990.*

Vasconcellos et al. BMC infectious diseases 10.1 (2010): 80; 16 pages.*

Database EMBL, "*Mycobacterium tuberculosis* strain H2255 (W) insertion sequence I S6110, partial sequence; and flanking insertion site 21-9," Aug. 29, 2000, XP002663004, [Online] retrieved from EBI accession No. EM PRO:AF228674 Database accession No. AF228674.

Database Geneseq "IGFBP2 oligonucleotide #89.", Mar. 30, 2001, XP002663005, [Online] retrieved from EBI accession No. GSN:AAF45250 Database accession No. AAF45250.

Warren, R.M., et al., "Differentiation of *Mycobacterium tuberculosis* complex by PCR amplification of genomic regions of difference," The International Journal of Tuberculosis and Lung Disease : The Official Journal of the International Union Against Tuberculosis and Lung Disease Jul. 2006 Lnkd—Pubmed:16850559, Jul. 2006, pp. 818-822, vol. 10, No. 7.

Herrera-Leon Laura et al., "Aplicacion de metodos moleculares para la identificacion de las especies del complejo *Mycobacterium tuberculosis* [Differentiation of species within the *Mycobacterium tuberculosis* complex by molecular techniques]", Enfermedades Infecciosas y Microbiologiaclinica, Doyma, Barcelona, ES, Nov. 1, 2009, pp. 496-502, vol. 27, No. 9 (With English Summary).

Pinsky, B.A., et al., "Multiplex Real-Time PCR Assay for Rapid Identification of *Mycobacterium tuberculosis* Complex Members to the Species Level", Journal of Clinical Microbiology, Jul. 1, 2008, pp. 2241-2246, vol. 46, No. 7.

Pounder, J.I., et al., "*Mycobacterium tuberculosis* complex differentiation by genomic deletion patterns with multiplex polymerase chain reaction and melting analysis", Diagnostic Microbiology and Infectious Diseases, Mar. 12, 2010, pp. 101-105, vol. 67, No. I, Elsevier Science Publishing Co., Amsterdam, NL.

Reddington, K., et al., "Novel Multiplex Real-Time PCR Diagnostic Assay for Identification and Differentiation of *Mycobacterium tuberculosis, Mycobacterium canettii*, and *Mycobacterium tuberculosis* Complex Strains", Journal of Clinical Microbiology, Feb. 1, 2011, pp. 651-657, vol. 49, No. 2.

PCT International Search Report, PCT/IB2011/001719, Mar. 28, 2012, 8 Pages.

* cited by examiner

*Primary Examiner* — Stephanie K Mummert
*Assistant Examiner* — Aaron Priest
(74) *Attorney, Agent, or Firm* — Kilpatrick Townsend & Stockton LLP

(57) ABSTRACT

The present invention relates to a multiplex in vitro nucleic acid amplification method for identifying a species of the *Mycobacterium tuberculosis* complex present in a sample. The method includes detecting the presence or absence of a plurality of nucleic acid molecule targets in the sample in one reaction, wherein at least one of the nucleic acid molecule targets is present in the genome of one or more, but not all, of the species of the *Mycobacterium tuberculosis* complex. The invention also includes kits containing primers or probes for conducting this method, nucleic acids useful for performing this method and diagnostic techniques using these nucleic acids.

26 Claims, 50 Drawing Sheets

Figure 1A

```
SEQIDNO_1-M.tuberculosis_H37Rv        TCAGTGCCGCCCTTCTACCAGCTTCAGTTTCCGTCTGCGGGACCTGCGCA 50
SEQIDNO_2-M.tuberculosis_H37Ra        TCAGTGCCGCCCTTCTACCAGCTTCAGTTTCCGTCTGCGGGACCTGCGCA 50
SEQIDNO_3-M.tuberculosis_F11          TCAGTGCCGCCCTTCTACCAGCTTCAGTTTCCGTCTGCGGGACCTGCGCA 50
SEQIDNO_4-M.tuberculosis_KZN14        TCAGTGCCGCCCTTCTACCAGCTTCAGTTTCCGTCTGCGGGACCTGCGCA 50
SEQIDNO_5-M.tuberculosis_CDC15        TCAGTGCCGCCCTTCTACCAGCTTCAGTTTCCGTCTGCGGGACCTGCGCA 50
SEQIDNO_6-M.bovisBCG_Tokyo172         TCAGTGCCGCCCTTCTACCAGCTTCAGTTTCCGTCTGCGGGACCTGCGCA 50
SEQIDNO_7-M.bovisBCG_Pasteur11        TCAGTGCCGCCCTTCTACCAGCTTCAGTTTCCGTCTGCGGGACCTGCGCA 50
SEQIDNO_8-M.bovis_AF2122/97           TCAGTGCCGCCCTTCTACCAGCTTCAGTTTCCGTCTGCGGGACCTGCGCA 50
SEQIDNO_9-M.africanum_GM041182        TCAGTGCCGCCCTTCTACCAGCTTCAGTTTCCGTCTGCGGGACCTGCGCA 50
SEQIDNO_10-M.microti_OV254            TCAGTGCCGCCCTTCTACCAGCTTCAGTTTCCGTCTGCGGGACCTGCGCA 50
SEQIDNO_11-M.avium                    TCAGTGCCGCCCTTCTACCCGCCGC------------CCGGACTCGCGCA 38
SEQIDNO_12-M.avium_Paratubercu        TCAGTGCCGCCCTTCTACCCGCCGC------------CCGGACTCGCGCA 38
SEQIDNO_13-M.marinum_M                TCAGTGCCGCCCTTCTACCAGCTTTCG---------GCGCGAACTGCGCA 41
SEQIDNO_14-M.ulcerans_Agy99           TCAGTGCCGCCCTTCTACCAGCTTTCG---------GCGCGAACTGCGCA 41
                                      ******************** **             *  **   *****

SEQIDNO_1-M.tuberculosis_H37Rv        [redacted]CCATGAGGTGGGAACGCAGCGCCAGTGATCCCCGCAGG 100
SEQIDNO_2-M.tuberculosis_H37Ra        [redacted]CCATGAGGTGGGAACGCAGCGCCAGTGATCCCCGCAGG 100
SEQIDNO_3-M.tuberculosis_F11          [redacted]CCATGAGGTGGGAACGCAGCGCCAGTGATCCCCGCAGG 100
SEQIDNO_4-M.tuberculosis_KZN14        [redacted]CCATGAGGTGGGAACGCAGCGCCAGTGATCCCCGCAGG 100
SEQIDNO_5-M.tuberculosis_CDC15        [redacted]CCATGAGGTGGGAACGCAGCGCCAGTGATCCCCGCAGG 100
SEQIDNO_6-M.bovisBCG_Tokyo172         ------------CCATGAGGTGGGAACGCAGCGCCAGTGATCCCCGCAGG 88
SEQIDNO_7-M.bovisBCG_Pasteur11        ------------CCATGAGGTGGGAACGCAGCGCCAGTGATCCCCGCAGG 88
SEQIDNO_8-M.bovis_AF2122/97           ------------CCATGAGGTGGGAACGCAGCGCCAGTGATCCCCGCAGG 88
SEQIDNO_9-M.africanum_GM041182        ------------CCATGAGGTGGGAACGCAGCGCCAGTGATCCCCGCAGG 88
SEQIDNO_10-M.microti_OV254            ------------CCATGAGGTGGGAACGCAGCGCCAGTGATCCCCGCAGG 88
SEQIDNO_11-M.avium                    GCGCGCTGCGCACCATCAGCCGGGCGCGCACCGCCAGCGACGCGCGCAGC 88
SEQIDNO_12-M.avium_Paratubercu        GCGCGCTGCGCACCATCAGCCGGGCGCGCACCGCCAGCGACGCGCGCAGC 88
SEQIDNO_13-M.marinum_M                ------------CCATCAGACGGGAGCGTACCGCCAGCGATCCCCGCAAA 79
SEQIDNO_14-M.ulcerans_Agy99           ------------CCATCAGACGGGAGCGTACCGCCAGCGATCCCCGCAAA 79
                                                  **** **  ***  ** * ****** **  * ****

SEQIDNO_1-M.tuberculosis_H37Rv        GTCCAGCGCAGCGGAGCCCGCCACCAACCAGAATGTCGGTCGGCTAAGAA 150
SEQIDNO_2-M.tuberculosis_H37Ra        GTCCAGCGCAGCGGAGCCCGCCACCAACCAGAATGTCGGTCGGCTAAGAA 150
SEQIDNO_3-M.tuberculosis_F11          GTCCAGCGCAGCGGAGCCCGCCACCAACCAGAATGTCGGTCGGCTAAGAA 150
SEQIDNO_4-M.tuberculosis_KZN14        GTCCAGCGCAGCGGAGCCCGCCACCAACCAGAATGTCGGTCGGCTAAGAA 150
SEQIDNO_5-M.tuberculosis_CDC15        GTCCAGCGCAGCGGAGCCCGCCACCAACCAGAATGTCGGTCGGCTAAGAA 150
SEQIDNO_6-M.bovisBCG_Tokyo172         GTCCAGCGCAGCGGAGCCCGCCACCAACCAGAATGTCGGTCGGCTAAGAA 138
SEQIDNO_7-M.bovisBCG_Pasteur11        GTCCAGCGCAGCGGAGCCCGCCACCAACCAGAATGTCGGTCGGCTAAGAA 138
SEQIDNO_8-M.bovis_AF2122/97           GTCCAGCGCAGCGGAGCCCGCCACCAACCAGAATGTCGGTCGGCTAAGAA 138
SEQIDNO_9-M.africanum_GM041182        GTCCAGCGCAGCGGAGCCCGCCACCAACCAGAATGTCGGTCGGCTAAGAA 138
SEQIDNO_10-M.microti_OV254            GTCCAGCGCAGCGGAGCCCGCCACCAACCAGAATGTCGGTCGGCTAAGAA 138
SEQIDNO_11-M.avium                    GCCCAGCGCAGCGGCGCGCGCATCCAACCGGAATACCGGTCGGCCAGAAA 138
SEQIDNO_12-M.avium_Paratubercu        GCCCAGCGCAGCGGCGCGCGCATCCAACCGGAATACCGGTCGGCCAGAAA 138
SEQIDNO_13-M.marinum_M                GTCCAGCGCAATGGGGCCCGCCACCAGCCGGCATGGCGATCCGCCAGGAA 129
SEQIDNO_14-M.ulcerans_Agy99           GTCCAGCGCAATGGGGCCCGCCACCAGCCGGCATGGCGATCCGCCAGGAA 129
                                      * ********  ** ** ***  *** ** * **   ** ** ** *  **

SEQIDNO_1-M.tuberculosis_H37Rv        GATATAGGTGCTTTTGTGATGGGCGGCCAGATGGCTTGCCGGGTCGCGAC 200
SEQIDNO_2-M.tuberculosis_H37Ra        GATATAGGTGCTTTTGTGATGGGCGGCCAGATGGCTTGCCGGGTCGCGAC 200
SEQIDNO_3-M.tuberculosis_F11          GATATAGGTGCTTTTGTGATGGGCGGCCAGATGGCTTGCCGGGTCGCGAC 200
SEQIDNO_4-M.tuberculosis_KZN14        GATATAGGTGCTTTTGTGATGGGCGGCCAGATGGCTTGCCGGGTCGCGAC 200
SEQIDNO_5-M.tuberculosis_CDC15        GATATAGGTGCTTTTGTGATGGGCGGCCAGATGGCTTGCCGGGTCGCGAC 200
SEQIDNO_6-M.bovisBCG_Tokyo172         GATATAGGTGCTTTTGTGATGGGCGGCCAGATGGCTTGCCGGGTCGCGAC 188
SEQIDNO_7-M.bovisBCG_Pasteur11        GATATAGGTGCTTTTGTGATGGGCGGCCAGATGGCTTGCCGGGTCGCGAC 188
SEQIDNO_8-M.bovis_AF2122/97           GATATAGGTGCTTTTGTGATGGGCGGCCAGATGGCTTGCCGGGTCGCGAC 188
SEQIDNO_9-M.africanum_GM041182        GATATAGGTGCTTTTGTGATGGGCGGCCAGATGGCTTGCCGGGTCGCGAC 188
SEQIDNO_10-M.microti_OV254            GATATAGGTGCTTTTGTGATGGGCGGCCAGATGGCTTGCCGGGTCGCGAC 188
SEQIDNO_11-M.avium                    CATATAGGTGCTGCGGTGGTGGGCGGCCAGGTGGCTGGCCGGGTCGGCCC 188
SEQIDNO_12-M.avium_Paratubercu        CATATAGGTGCTGCGGTGGTGGGCGGCCAGGTGGCTGGCCGGGTCGGCCC 188
SEQIDNO_13-M.marinum_M                AATGTAGGTGCTTCGGTGGTGTGCCGCCAGGTGATTGGCCGGATCGCGTC 179
SEQIDNO_14-M.ulcerans_Agy99           AATGTAGGTGCTTCGGTGGTGTACCGCCAGGTGAGTGGCCGGATCGCGTC 179
                                       ** ********    *** **   * *****  **   * ***** ***    *

SEQIDNO_1-M.tuberculosis_H37Rv        CCGTCGAATGCGCCTTGTGGTGCAGAACCTCGGCTGACGGCACATACACC 250
SEQIDNO_2-M.tuberculosis_H37Ra        CCGTCGAATGCGCCTTGTGGTGCAGAACCTCGGCTGACGGCACATACACC 250
SEQIDNO_3-M.tuberculosis_F11          CCGTCGAATGCGCCTTGTGGTGCAGAACCTCGGCTGACGGCACATACACC 250
SEQIDNO_4-M.tuberculosis_KZN14        CCGTCGAATGCGCCTTGTGGTGCAGAACCTCGGCTGACGGCACATACACC 250
SEQIDNO_5-M.tuberculosis_CDC15        CCGTCGAATGCGCCTTGTGGTGCAGAACCTCGGCTGACGGCACATACACC 250
SEQIDNO_6-M.bovisBCG_Tokyo172         CCGTCGAATGCGCCTTGTGGTGCAGAACCTCGGCTGACGGCACATACACC 238
SEQIDNO_7-M.bovisBCG_Pasteur11        CCGTCGAATGCGCCTTGTGGTGCAGAACCTCGGCTGACGGCACATACACC 238
SEQIDNO_8-M.bovis_AF2122/97           CCGTCGAATGCGCCTTGTGGTGCAGAACCTCGGCTGACGGCACATACACC 238
SEQIDNO_9-M.africanum_GM041182        CCGTCGAATGCGCCTTGTGGTGCAGAACCTCGGCTGACGGCACATACACC 238
SEQIDNO_10-M.microti_OV254            CCGTCGAATGCGCCTTGTGGTGCAGAACCTCGGCTGACGGCACATACACC 238
SEQIDNO_11-M.avium                    CGGTGGAGTGGCCCTTGTGGTGCAGCACCTCGGCCGACGGCACGTAGACC 238
SEQIDNO_12-M.avium_Paratubercu        CGGTGGAGTGGCCCTTGTGGTGCAGCACCTCGGCCGACGGCACGTAGACC 238
SEQIDNO_13-M.marinum_M                CGGTGGAGTGGCCTTTGTGGTGCAGCACTTCCGCCGACGGCACATAGACG 229
SEQIDNO_14-M.ulcerans_Agy99           CGGTGGAGTGGCCTTTGTGGTGCAGCACTTCCGCCGACGGCACATAGACG 229
                                      * ** ** **  *  ********** **  ** **  ******** ** **

SEQIDNO_1-M.tuberculosis_H37Rv        GACAGCCAACCGGCTTTGCCAAGCCGGTCGCCAAGGTCGACGTCCTCCAT 300
SEQIDNO_2-M.tuberculosis_H37Ra        GACAGCCAACCGGCTTTGCCAAGCCGGTCGCCAAGGTCGACGTCCTCCAT 300
SEQIDNO_3-M.tuberculosis_F11          GACAGCCAACCGGCTTTGCCAAGCCGGTCGCCAAGGTCGACGTCCTCCAT 300
```

Figure 1A (cont)

```
SEQIDNO_4-M.tuberculosis_KZN14      GACAGCCAACCGGCTTTGCCAAGCCGGTCGCCAAGGTCGACGTCCTCCAT 300
SEQIDNO_5-M.tuberculosis_CDC15      GACAGCCAACCGGCTTTGCCAAGCCGGTCGCCAAGGTCGACGTCCTCCAT 300
SEQIDNO_6-M.bovisBCG_Tokyo172       GACAGCCAACCGGCTTTGCCAAGCCGGTCGCCAAGGTCGACGTCCTCCAT 288
SEQIDNO_7-M.bovisBCG_Pasteur11      GACAGCCAACCGGCTTTGCCAAGCCGGTCGCCAAGGTCGACGTCCTCCAT 288
SEQIDNO_8-M.bovis_AF2122/97         GACAGCCAACCGGCTTTGCCAAGCCGGTCGCCAAGGTCGACGTCCTCCAT 288
SEQIDNO_9-M.africanum_GM041182      GACAGCCAACCGGCTTTGCCAAGCCGGTCGCCAAGGTCGACGTCCTCCAT 288
SEQIDNO_10-M.microti_OV254          GACAGCCAACCGGCTTTGCCAAGCCGGTCGCCAAGGTCGACGTCCTCCAT 288
SEQIDNO_11-M.avium                  GACAGCCAGCCGGCCTTGCCCAGCCGGTCGCCGAGGTCGACGTCCTCCAT 288
SEQIDNO_12-M.avium_Paratubercu      GACAGCCAGCCGGCCTTGCCCAGCCGGTCGCCGAGGTCGACGTCCTCCAT 288
SEQIDNO_13-M.marinum_M              CTGACCCAGCCGGCCTGGCCCAGCCGGTCGCCGAGGTCCACGTCTTCCAT 279
SEQIDNO_14-M.ulcerans_Agy99         CTGAGCCAGCCGGCCTGGCCCAGCCGGTCGCCGAGGTCCACGTCTTCCAT 279
                                       ***** ***** * *** *********** ***** ***** *****

SEQIDNO_1-M.tuberculosis_H37Rv      GTACATGAAGTAACGTTCGTCGAATCCGCCGACCTGGCCAAACGCCGACC 350
SEQIDNO_2-M.tuberculosis_H37Ra      GTACATGAAGTAACGTTCGTCGAATCCGCCGACCTGGCCAAACGCCGACC 350
SEQIDNO_3-M.tuberculosis_F11        GTACATGAAGTAACGTTCGTCGAATCCGCCGACCTGGCCAAACGCCGACC 350
SEQIDNO_4-M.tuberculosis_KZN14      GTACATGAAGTAACGTTCGTCGAATCCGCCGACCTGGCCAAACGCCGACC 350
SEQIDNO_5-M.tuberculosis_CDC15      GTACATGAAGTAACGTTCGTCGAATCCGCCGACCTGGCCAAACGCCGACC 350
SEQIDNO_6-M.bovisBCG_Tokyo172       GTACATGAAGTAACGTTCGTCGAATCCGCCGACCTGGCCAAACGCCGACC 338
SEQIDNO_7-M.bovisBCG_Pasteur11      GTACATGAAGTAACGTTCGTCGAATCCGCCGACCTGGCCAAACGCCGACC 338
SEQIDNO_8-M.bovis_AF2122/97         GTACATGAAGTAACGTTCGTCGAATCCGCCGACCTGGCCAAACGCCGACC 338
SEQIDNO_9-M.africanum_GM041182      GTACATGAAGTAACGTTCGTCGAATCCGCCGACCTGGCCAAACGCCGACC 338
SEQIDNO_10-M.microti_OV254          GTACATGAAGTAACGTTCGTCGAATCCGCCGACCTGGCCAAACGCCGACC 338
SEQIDNO_11-M.avium                  GTACATGAAGTAGCGCTCGTCGAACCCGCCGACCCGCTCGAATGCCGAGC 338
SEQIDNO_12-M.avium_Paratubercu      GTACATGAAGTAGCGCTCGTCGAACCCGCCGACCCGCTCGAATGCCGAGC 338
SEQIDNO_13-M.marinum_M              ATACATGAAGTAGCGCTCGTCGAAACCGCCGATCTGGCGGAACGCGGAGC 329
SEQIDNO_14-M.ulcerans_Agy99         ATACATGAAGTAGCGCTCGTCGAAACCGCCGATCTGGCGGAACGCGGAGC 329
                                     *********** ** ******** ******* * *     ** ** ** *

SEQIDNO_1-M.tuberculosis_H37Rv      GGCGCACCAGTAGGCAAGACCCCGACAACCAACCCACCGGCCGTTCACTG 400
SEQIDNO_2-M.tuberculosis_H37Ra      GGCGCACCAGTAGGCAAGACCCCGACAACCAACCCACCGGCCGTTCACTG 400
SEQIDNO_3-M.tuberculosis_F11        GGCGCACCAGTAGGCAAGACCCCGACAACCAACCCACCGGCCGTTCACTG 400
SEQIDNO_4-M.tuberculosis_KZN14      GGCGCACCAGTAGGCAAGACCCCGACAACCAACCCACCGGCCGTTCACTG 400
SEQIDNO_5-M.tuberculosis_CDC15      GGCGCACCAGTAGGCAAGACCCCGACAACCAACCCACCGGCCGTTCACTG 400
SEQIDNO_6-M.bovisBCG_Tokyo172       GGCGCACCAGTAGGCAAGACCCCGACAACCAACCCACCGGCCGTTCACTG 388
SEQIDNO_7-M.bovisBCG_Pasteur11      GGCGCACCAGTAGGCAAGACCCCGACAACCAACCCACCGGCCGTTCACTG 388
SEQIDNO_8-M.bovis_AF2122/97         GGCGCACCAGTAGGCAAGACCCCGACAACCAACCCACCGGCCGTTCACTG 388
SEQIDNO_9-M.africanum_GM041182      GGCGCACCAGTAGGCAAGACCCCGACAACCAACCCACCGGCCGTTCACTG 388
SEQIDNO_10-M.microti_OV254          GGCGCACCAGTAGGCAAGACCCCGACAACCAACCCACCGGCCGTTCACTG 388
SEQIDNO_11-M.avium                  GGCGCACCAGCAGGCACGAACCCGACAGCCAGCCCACCGGCCGCTCGCTG 388
SEQIDNO_12-M.avium_Paratubercu      GGCGCACCAGCAGGCACGAACCCGACAGCCAGCCCACCGGCCGCTCGCTG 388
SEQIDNO_13-M.marinum_M              GGCGCACCAACAGGCACGAACCCGATAGCCAGCCCACCGGCCGTTCGCTG 379
SEQIDNO_14-M.ulcerans_Agy99         GGCGCACCAACAGGCACGAACCCGATAGCCAGCCCACCGGCCGTTCGCTG 379
                                    *********  ***** ** ***** * *** *********** ** ***

SEQIDNO_1-M.tuberculosis_H37Rv      GGCTCCAGCCGCTCCTGCCGGTAGGCCGTCGTCCACGGATTGCGCGGCCA 450
SEQIDNO_2-M.tuberculosis_H37Ra      GGCTCCAGCCGCTCCTGCCGGTAGGCCGTCGTCCACGGATTGCGCGGCCA 450
SEQIDNO_3-M.tuberculosis_F11        GGCTCCAGCCGCTCCTGCCGGTAGGCCGTCGTCCACGGATTGCGCGGCCA 450
SEQIDNO_4-M.tuberculosis_KZN14      GGCTCCAGCCGCTCCTGCCGGTAGGCCGTCGTCCACGGATTGCGCGGCCA 450
SEQIDNO_5-M.tuberculosis_CDC15      GGCTCCAGCCGCTCCTGCCGGTAGGCCGTCGTCCACGGATTGCGCGGCCA 450
SEQIDNO_6-M.bovisBCG_Tokyo172       GGCTCCAGCCGCTCCTGCCGGTAGGCCGTCGTCCACGGATTGCGCGGCCA 438
SEQIDNO_7-M.bovisBCG_Pasteur11      GGCTCCAGCCGCTCCTGCCGGTAGGCCGTCGTCCACGGATTGCGCGGCCA 438
SEQIDNO_8-M.bovis_AF2122/97         GGCTCCAGCCGCTCCTGCCGGTAGGCCGTCGTCCACGGATTGCGCGGCCA 438
SEQIDNO_9-M.africanum_GM041182      GGCTCCAGCCGCTCCTGCCGGTAGGCCGTCGTCCACGGATTGCGCGGCCA 438
SEQIDNO_10-M.microti_OV254          GGCTCCAGCCGCTCCTGCCGGTAGGCCGTCGTCCACGGATTGCGCGGCCA 438
SEQIDNO_11-M.avium                  GGCTCCAGCCGCTCCTGGCGATAGGCCGTCGACCACGGGTTGTTCTTCCA 438
SEQIDNO_12-M.avium_Paratubercu      GGCTCCAGCCGCTCCTGGCGGTAGGCCGTCGACCACGGGTTGTTCTTCCA 438
SEQIDNO_13-M.marinum_M              GGCTCGAGGTGTTCCTGGCGATAGGCCTTGGTCCAGGGATTGCGGGGCCA 429
SEQIDNO_14-M.ulcerans_Agy99         GGCTCGAGGTGTTCCTGGCGATAGGCCTTGGTCCAGGGATTGCGGGGCCA 429
                                    ***** **   * ***** ** ****** * * *** ** ***    ***

SEQIDNO_1-M.tuberculosis_H37Rv      GAACGGCCCGAGCACTGCGTGCATGCCGCCGCGGATCAGGCTGGGCATCT 500
SEQIDNO_2-M.tuberculosis_H37Ra      GAACGGCCCGAGCACTGCGTGCATGCCGCCGCGGATCAGGCTGGGCATCT 500
SEQIDNO_3-M.tuberculosis_F11        GAACGGCCCGAGCACTGCGTGCATGCCGCCGCGGATCAGGCTGGGCATCT 500
SEQIDNO_4-M.tuberculosis_KZN14      GAACGGCCCGAGCACTGCGTGCATGCCGCCGCGGATCAGGCTGGGCATCT 500
SEQIDNO_5-M.tuberculosis_CDC15      GAACGGCCCGAGCACTGCGTGCATGCCGCCGCGGATCAGGCTGGGCATCT 500
SEQIDNO_6-M.bovisBCG_Tokyo172       GAACGGCCCGAGCACTGCGTGCATGCCGCCGCGGATCAGGCTGGGCATCT 488
SEQIDNO_7-M.bovisBCG_Pasteur11      GAACGGCCCGAGCACTGCGTGCATGCCGCCGCGGATCAGGCTGGGCATCT 488
SEQIDNO_8-M.bovis_AF2122/97         GAACGGCCCGAGCACTGCGTGCATGCCGCCGCGGATCAGGCTGGGCATCT 488
SEQIDNO_9-M.africanum_GM041182      GAACGGCCCGAGCACTGCGTGCATGCCGCCGCGGATCAGGCTGGGCATCT 488
SEQIDNO_10-M.microti_OV254          GAACGGCCCGAGCACTGCGTGCATGCCGCCGCGGATCAGGCTGGGCATCT 488
SEQIDNO_11-M.avium                  GAACGGCCCGACGACCGCGTGCATGCCGCCGCGCACCAGGCTGGGCAGGT 488
SEQIDNO_12-M.avium_Paratubercu      GAACGGCCCGACGACCGCGTGCATGCCGCCGCGCACCAGGCTGGGCAGGT 488
SEQIDNO_13-M.marinum_M              TACCGGCCCGAGCACCGCGTGCATACCGCCGCGGACCAGGCTGGGCAGAT 479
SEQIDNO_14-M.ulcerans_Agy99         TACCGGCCCGAGCACCGCGTGCATACCGCCGCGGACCAGGCTGGGCAGAT 479
                                     * ******** ** ******** ******** * *********** *

SEQIDNO_1-M.tuberculosis_H37Rv      GCCGCGCCGACGGGTACACCGACCCGTCGGGGTCCCGAATCAGCGGGCCC 550
SEQIDNO_2-M.tuberculosis_H37Ra      GCCGCGCCGACGGGTACACCGACCCGTCGGGGTCCCGAATCAGCGGGCCC 550
SEQIDNO_3-M.tuberculosis_F11        GCCGCGCCGACGGGTACACCGACCCGTCGGGGTCCCGAATCAGCGGGCCC 550
SEQIDNO_4-M.tuberculosis_KZN14      GCCGCGCCGACGGGTACACCGACCCGTCGGGGTCCCGAATCAGCGGGCCC 550
SEQIDNO_5-M.tuberculosis_CDC15      GCCGCGCCGACGGGTACACCGACCCGTCGGGGTCCCGAATCAGCGGGCCC 550
SEQIDNO_6-M.bovisBCG_Tokyo172       GCCGCGCCGACGGGTACACCGACCCGTCGGGGTCCCGAATCAGCGGGCCC 538
SEQIDNO_7-M.bovisBCG_Pasteur11      GCCGCGCCGACGGGTACACCGACCCGTCGGGGTCCCGAATCAGCGGGCCC 538
SEQIDNO_8-M.bovis_AF2122/97         GCCGCGCCGACGGGTACACCGACCCGTCGGGGTCCCGAATCAGCGGGCCC 538
SEQIDNO_9-M.africanum_GM041182      GCCGCGCCGACGGGTACACCGACCCGTCGGGGTCCCGAATCAGCGGGCCC 538
SEQIDNO_10-M.microti_OV254          GCCGCGCCGACGGGTACACCGACCCGTCGGGGTCCCGAATCAGCGGGCCC 538
SEQIDNO_11-M.avium                  GCCGCGCCGACGGGTACACCGACCCGTCGGGGTCGGCACCAGCGGGCCC 538
```

Figure 1A (cont)

```
SEQIDNO_12-M.avium_Paratubercu     GCCGCGCCGACGGGTACACCGACCCGTCGGGGTCGCGCACCAGCGGGCCC 538
SEQIDNO_13-M.marinum_M             GGCGCGCCGAGGGGTACACCGATCCATCGGGATCGCGGATCAGCGGGCCC 529
SEQIDNO_14-M.ulcerans_Agy99        GGCGCGCCGAGGGGTACACCGATCCATCGGGATCGCGGATCAGCGGGCCC 529
                                   *  ******** *********** ** ***** ** ** * **********

SEQIDNO_1-M.tuberculosis_H37Rv     AGCGCGCCCGCGCGGGGCCAGCGGGAGGCGGCGTCCAGTAGTGCATCGAT 600
SEQIDNO_2-M.tuberculosis_H37Ra     AGCGCGCCCGCGCGGGGCCAGCGGGAGGCGGCGTCCAGTAGTGCATCGAT 600
SEQIDNO_3-M.tuberculosis_F11       AGCGCGCCCGCGCGGGGCCAGCGGGAGGCGGCGTCCAGTAGTGCATCGAT 600
SEQIDNO_4-M.tuberculosis_KZN14     AGCGCGCCCGCGCGGGGCCAGCGGGAGGCGGCGTCCAGTAGTGCATCGAT 600
SEQIDNO_5-M.tuberculosis_CDC15     AGCGCGCCCGCGCGGGGCCAGCGGGAGGCGGCGTCCAGTAGTGCATCGAT 600
SEQIDNO_6-M.bovisBCG_Tokyo172      AGCGCGCCCGCGCGGGGCCAGCGGGAGGCGGCGTCCAGTAGTGCATCGAT 588
SEQIDNO_7-M.bovisBCG_Pasteur11     AGCGCGCCCGCGCGGGGCCAGCGGGAGGCGGCGTCCAGTAGTGCATCGAT 588
SEQIDNO_8-M.bovis_AF2122/97        AGCGCGCCCGCGCGGGGCCAGCGGGAGGCGGCGTCCAGTAGTGCATCGAT 588
SEQIDNO_9-M.africanum_GM041182     AGCGCGCCCGCGCGGGGCCAGCGGGAGGCGGCGTCCAGTAGTGCATCGAT 588
SEQIDNO_10-M.microti_OV254         AGCGCGCCCGCGCGGGGCCAGCGGGAGGCGGCGTCCAGTAGTGCATCGAT 588
SEQIDNO_11-M.avium                 AGCGCGCCGGCCCGCGGCCAGCGCGCCGCGGCGTCCAGCAGCGCGTCGAT 588
SEQIDNO_12-M.avium_Paratubercu     AGCGCGCCGGCCCGCGGCCAGCGCGCCGCGGCGTCCAGCAGCGCGTCGAT 588
SEQIDNO_13-M.marinum_M             AACGCCCCGGCCTGGGGCCAGCGCTCGACGGCCTCGAGCAGCGCGTCGAT 579
SEQIDNO_14-M.ulcerans_Agy99        AACGCCCCGGCCTGGGGCCAGCGCTCGACGGCCTCGAGCAGCGCGTCGAT 579
                                   * *** ** **  * ********      **** ** ** ** ** *****

SEQIDNO_1-M.tuberculosis_H37Rv     ACTGCCCGGGCCCCATTGCACGTCCGGGTTGGCCACGATCACCCAGTCAT 650
SEQIDNO_2-M.tuberculosis_H37Ra     ACTGCCCGGGCCCCATTGCACGTCCGGGTTGGCCACGATCACCCAGTCAT 650
SEQIDNO_3-M.tuberculosis_F11       ACTGCCCGGGCCCCATTGCACGTCCGGGTTGGCCACGATCACCCAGTCAT 650
SEQIDNO_4-M.tuberculosis_KZN14     ACTGCCCGGGCCCCATTGCACGTCCGGGTTGGCCACGATCACCCAGTCAT 650
SEQIDNO_5-M.tuberculosis_CDC15     ACTGCCCGGGCCCCATTGCACGTCCGGGTTGGCCACGATCACCCAGTCAT 650
SEQIDNO_6-M.bovisBCG_Tokyo172      ACTGCCCGGGCCCCATTGCACGTCCGGGTTGGCCACGATCACCCAGTCAT 638
SEQIDNO_7-M.bovisBCG_Pasteur11     ACTGCCCGGGCCCCATTGCACGTCCGGGTTGGCCACGATCACCCAGTCAT 638
SEQIDNO_8-M.bovis_AF2122/97        ACTGCCCGGGCCCCATTGCACGTCCGGGTTGGCCACGATCACCCAGTCAT 638
SEQIDNO_9-M.africanum_GM041182     ACTGCCCGGGCCCCATTGCACGTCCGGGTTGGCCACGATCACCCAGTCAT 638
SEQIDNO_10-M.microti_OV254         ACTGCCCGGGCCCCATTGCACGTCCGGGTTGGCCACGATCACCCAGTCAT 638
SEQIDNO_11-M.avium                 GCTGCCGGGCCCCCACTGCACGTCCGGGTTGGCGACGATCACCCACTCGC 638
SEQIDNO_12-M.avium_Paratubercu     GCTGCCGGGCCCCCACTGCACGTCCGGGTTGGCGACGATCACCCACTCGC 638
SEQIDNO_13-M.marinum_M             GCTGCCCGGACCCCACTGCACGTCCGGGTTGGCCACGATCAGCCAGTCGT 629
SEQIDNO_14-M.ulcerans_Agy99        GCTGCCCGGACCCCACTGCACGTCCGGGTTGGCCACGATCAGCCAGTCGT 629
                                    ***** ** ***** **************** ******* *** **

SEQIDNO_1-M.tuberculosis_H37Rv     CGACCCAGGGTTCGCCGGCATCGCCCGCCATTTCACCGAGCTGGGCGATC 700
SEQIDNO_2-M.tuberculosis_H37Ra     CGACCCAGGGTTCGCCGGCATCGCCCGCCATTTCACCGAGCTGGGCGATC 700
SEQIDNO_3-M.tuberculosis_F11       CGACCCAGGGTTCGCCGGCATCGCCCGCCATTTCACCGAGCTGGGCGATC 700
SEQIDNO_4-M.tuberculosis_KZN14     CGACCCAGGGTTCGCCGGCATCGCCCGCCATTTCACCGAGCTGGGCGATC 700
SEQIDNO_5-M.tuberculosis_CDC15     CGACCCAGGGTTCGCCGGCATCGCCCGCCATTTCACCGAGCTGGGCGATC 700
SEQIDNO_6-M.bovisBCG_Tokyo172      CGACCCAGGGTTCGCCGGCATCGCCCGCCATTTCACCGAGCTGGGCGATC 688
SEQIDNO_7-M.bovisBCG_Pasteur11     CGACCCAGGGTTCGCCGGCATCGCCCGCCATTTCACCGAGCTGGGCGATC 688
SEQIDNO_8-M.bovis_AF2122/97        CGACCCAGGGTTCGCCGGCATCGCCCGCCATTTCACCGAGCTGGGCGATC 688
SEQIDNO_9-M.africanum_GM041182     CGACCCAGGGTTCGCCGGCATCGCCCGCCATTTCACCGAGCTGGGCGATC 688
SEQIDNO_10-M.microti_OV254         CGACCCAGGGTTCGCCGGCATCGCCCGCCATTTCACCGAGCTGGGCGATC 688
SEQIDNO_11-M.avium                 CG----------------------CCGCGAT-----CCAGCTGTGCCACA 661
SEQIDNO_12-M.avium_Paratubercu     CG----------------------CCGCGAT-----CCAGCTGTGCCACA 661
SEQIDNO_13-M.marinum_M             CTGGCT------------------CCGGTTGTTCGGTGAGCTGGGCGACG 661
SEQIDNO_14-M.ulcerans_Agy99        CTGGCT------------------CCGGTTGTTCGGTGAGTTGGGCGACG 661
                                   *                       ***             ** ** ** *

SEQIDNO_1-M.tuberculosis_H37Rv     GTCCGATTCACCGCGGTTCCGTACCCGAGGTTGGCCCCTGTGGGCAGCAG 750
SEQIDNO_2-M.tuberculosis_H37Ra     GTCCGATTCACCGCGGTTCCGTACCCGAGGTTGGCCCCTGTGGGCAGCAG 750
SEQIDNO_3-M.tuberculosis_F11       GTCCGATTCACCGCGGTTCCGTACCCGAGGTTGGCCCCTGTGGGCAGCAG 750
SEQIDNO_4-M.tuberculosis_KZN14     GTCCGATTCACCGCGGTTCCGTACCCGAGGTTGGCCCCTGTGGGCAGCAG 750
SEQIDNO_5-M.tuberculosis_CDC15     GTCCGATTCACCGCGGTTCCGTACCCGAGGTTGGCCCCTGTGGGCAGCAG 750
SEQIDNO_6-M.bovisBCG_Tokyo172      GTCCGATTCACCGCGGTTCCGTACCCGAGGTTGGCCCCTGTGGGCAGCAG 738
SEQIDNO_7-M.bovisBCG_Pasteur11     GTCCGATTCACCGCGGTTCCGTACCCGAGGTTGGCCCCTGTGGGCAGCAG 738
SEQIDNO_8-M.bovis_AF2122/97        GTCCGATTCACCGCGGTTCCGTACCCGAGGTTGGCCCCTGTGGGCAGCAG 738
SEQIDNO_9-M.africanum_GM041182     GTCCGATTCACCGCGGTTCCGTACCCGAGGTTGGCCCCTGTGGGCAGCAG 738
SEQIDNO_10-M.microti_OV254         GTCCGATTCACCGCGGTTCCGTACCCGAGGTTGGCCCCTGTGGGCAGCAG 738
SEQIDNO_11-M.avium                 GCACGATTCACCGCGGTGCCGTAGCCGAGGTTGGCGCCGGTGTGAAACAG 711
SEQIDNO_12-M.avium_Paratubercu     GCACGATTCACCGCGGTGCCGTAGCCGAGGTTGGCGCCGGTGTGAAACAG 711
SEQIDNO_13-M.marinum_M             GCCCGGTTCACCGCGGTGCCATACCCGAGGTTGGCCCCGGTGTGGAAGAT 711
SEQIDNO_14-M.ulcerans_Agy99        GCCCGGTTCACCGCGGTGCCGTACCCGAGGTTGGCCCCGGTGTGGAAGAT 711
                                   *   ** *********** ** ** *********** ** *** * *   *

SEQIDNO_1-M.tuberculosis_H37Rv     CCGCACGTTGGGGTAGCGCTGCACCGCGGCCTGCGGGGTGCCGTCGGTGG 800
SEQIDNO_2-M.tuberculosis_H37Ra     CCGCACGTTGGGGTAGCGCTGCACCGCGGCCTGCGGGGTGCCGTCGGTGG 800
SEQIDNO_3-M.tuberculosis_F11       CCGCACGTTGGGGTAGCGCTGCACCGCGGCCTGCGGGGTGCCGTCGGTGG 800
SEQIDNO_4-M.tuberculosis_KZN14     CCGCACGTTGGGGTAGCGCTGCACCGCGGCCTGCGGGGTGCCGTCGGTGG 800
SEQIDNO_5-M.tuberculosis_CDC15     CCGCACGTTGGGGTAGCGCTGCACCGCGGCCTGCGGGGTGCCGTCGGTGG 800
SEQIDNO_6-M.bovisBCG_Tokyo172      CCGCACGTTGGGGTAGCGCTGCACCGCGGCCTGCGGGGTGCCGTCGGTGG 788
SEQIDNO_7-M.bovisBCG_Pasteur11     CCGCACGTTGGGGTAGCGCTGCACCGCGGCCTGCGGGGTGCCGTCGGTGG 788
SEQIDNO_8-M.bovis_AF2122/97        CCGCACGTTGGGGTAGCGCTGCACCGCGGCCTGCGGGGTGCCGTCGGTGG 788
SEQIDNO_9-M.africanum_GM041182     CCGCACGTTGGGGTAGCGCTGCACCGCGGCCTGCGGGGTGCCGTCGGTGG 788
SEQIDNO_10-M.microti_OV254         CCGCACGTTGGGGTAGCGCTGCACCGCGGCCTGCGGGGTGCCGTCGGTGG 788
SEQIDNO_11-M.avium                 CCGCACGTTGGGGTAGCGCTCGACGGCGGCCTGCGGCGTCCCGTCGGTGG 761
SEQIDNO_12-M.avium_Paratubercu     CCGCACGTTGGGGTAGCGCTCGACGGCGGCCTGCGGCGTCCCGTCGGTGG 761
SEQIDNO_13-M.marinum_M             CCGCACGTTGGGGTAGCGCTCGACAGCCGCCTGAGGTGTTCCGTCGGTGG 761
SEQIDNO_14-M.ulcerans_Agy99        CCGCACGTTGGGGTAGCGCTCGACGGCCGCCTGAGGTGTTCCGTCGGTGG 761
                                   ********************   ** **  ***** ** ** *********

SEQIDNO_1-M.tuberculosis_H37Rv     AGCCGTTGTCTGCCAACAGCACGCTGACCGGCCGCTCGGTGGCCAGCGAC 850
SEQIDNO_2-M.tuberculosis_H37Ra     AGCCGTTGTCTGCCAACAGCACGCTGACCGGCCGCTCGGTGGCCAGCGAC 850
SEQIDNO_3-M.tuberculosis_F11       AGCCGTTGTCTGCCAACAGCACGCTGACCGGCCGCTCGGTGGCCAGCGAC 850
```

Figure 1A (cont)

```
SEQIDNO_4-M.tuberculosis_KZN14       AGCCGTTGTCTGCCAACAGCACGCTGACCGGCCGCTCGGTGGCCAGCGAC 850
SEQIDNO_5-M.tuberculosis_CDC15       AGCCGTTGTCTGCCAACAGCACGCTGACCGGCCGCTCGGTGGCCAGCGAC 850
SEQIDNO_6-M.bovisBCG_Tokyo172        AGCCGTTGTCTGCCAACAGCACGCTGACCGGCCGCTCGGTGGCCAGCGAC 838
SEQIDNO_7-M.bovisBCG_Pasteur11       AGCCGTTGTCTGCCAACAGCACGCTGACCGGCCGCTCGGTGGCCAGCGAC 838
SEQIDNO_8-M.bovis_AF2122/97          AGCCGTTGTCTGCCAACAGCACGCTGACCGGCCGCTCGGTGGCCAGCGAC 838
SEQIDNO_9-M.africanum_GM041182       AGCCGTTGTCTGCCAACAGCACGCTGACCGGCCGCTCGGTGGCCAGCGAC 838
SEQIDNO_10-M.microti_OV254           AGCCGTTGTCTGCCAACAGCACGCTGACCGGCCGCTCGGTGGCCAGCGAC 838
SEQIDNO_11-M.avium                   AGCCGTTGTCGGCCAGCAGCACGCACACCTCGCGTTCGGTGGCCAGCGAC 811
SEQIDNO_12-M.avium_Paratubercu       AGCCGTTGTCGGCCAGCAGCACGCACACCTCGCGTTCGGTGGCCAGCGAC 811
SEQIDNO_13-M.marinum_M               AGCCGTTGTCGGCCAGCAGCACACTCACCGGACGGTCGGTGGCCAGCGAC 811
SEQIDNO_14-M.ulcerans_Agy99          AGCCGTTGTCGGCCAGCAGCACACTCACCGGACGGTCGGTGGCCAGCGAC 811
                                     ********** **** ****** *   ***     ** **************

SEQIDNO_1-M.tuberculosis_H37Rv       AACGACGCCAGGAACCGCTCTAGATGGGGCCCCGGCGAGTAGGTCACCGC 900
SEQIDNO_2-M.tuberculosis_H37Ra       AACGACGCCAGGAACCGCTCTAGATGGGGCCCCGGCGAGTAGGTCACCGC 900
SEQIDNO_3-M.tuberculosis_F11         AACGACGCCAGGAACCGCTCTAGATGGGGCCCCGGCGAGTAGGTCACCGC 900
SEQIDNO_4-M.tuberculosis_KZN14       AACGACGCCAGGAACCGCTCTAGATGGGGCCCCGGCGAGTAGGTCACCGC 900
SEQIDNO_5-M.tuberculosis_CDC15       AACGACGCCAGGAACCGCTCTAGATGGGGCCCCGGCGAGTAGGTCACCGC 900
SEQIDNO_6-M.bovisBCG_Tokyo172        AACGACGCCAGGAACCGCTCTAGATGGGGCCCCGGCGAGTAGGTCACCGC 888
SEQIDNO_7-M.bovisBCG_Pasteur11       AACGACGCCAGGAACCGCTCTAGATGGGGCCCCGGCGAGTAGGTCACCGC 888
SEQIDNO_8-M.bovis_AF2122/97          AACGACGCCAGGAACCGCTCTAGATGGGGCCCCGGCGAGTAGGTCACCGC 888
SEQIDNO_9-M.africanum_GM041182       AACGACGCCAGGAACCGCTCTAGATGGGGCCCCGGCGAGTAGG------- 881
SEQIDNO_10-M.microti_OV254           AACGACGCCAGGAACCGCTCTAGATGGGGCCCCGGCGAGTAGGTCACCGC 888
SEQIDNO_11-M.avium                   AGCGACGCCAGGAAGCGCTCCAGGTGCGGGCCCGGTGAATAGGTCACCGT 861
SEQIDNO_12-M.avium_Paratubercu       AGCGACGCCAGGAAGCGCTCCAGGTGCGGGCCCGGTGAATAGGTCACCGT 861
SEQIDNO_13-M.marinum_M               AAAGACGCCAAGAAGCGCTCCAGGTGGGGGCCCGGCGAGTAGGTCACCGC 861
SEQIDNO_14-M.ulcerans_Agy99          AAAGACGCCAAGAAGCGCTCCAAGTGGGGGCCCGGCGAGTAGGTCACCGC 861
                                     *  ******** *** ***** *  ** ** ***** ** ****

SEQIDNO_1-M.tuberculosis_H37Rv       TACCAC------------------ 906
SEQIDNO_2-M.tuberculosis_H37Ra       TACCAC------------------ 906
SEQIDNO_3-M.tuberculosis_F11         TACCAC------------------ 906
SEQIDNO_4-M.tuberculosis_KZN14       TACCACCGGCAGGACGTCAGTCAC 924
SEQIDNO_5-M.tuberculosis_CDC15       TACCAC------------------ 906
SEQIDNO_6-M.bovisBCG_Tokyo172        TACCAC------------------ 894
SEQIDNO_7-M.bovisBCG_Pasteur11       TACCAC------------------ 894
SEQIDNO_8-M.bovis_AF2122/97          TACCAC------------------ 894
SEQIDNO_9-M.africanum_GM041182       ------------------------
SEQIDNO_10-M.microti_OV254           TACCACACCGCTACCAC------- 905
SEQIDNO_11-M.avium                   CACCACCGGCAGCAC--------- 876
SEQIDNO_12-M.avium_Paratubercu       CACCAC------------------ 867
SEQIDNO_13-M.marinum_M               CACGACCGGCAGGACGTCAGTCAC 885
SEQIDNO_14-M.ulcerans_Agy99          CACGACCGGCAGGACGTCAGTCAC 885
```

Figure 1B

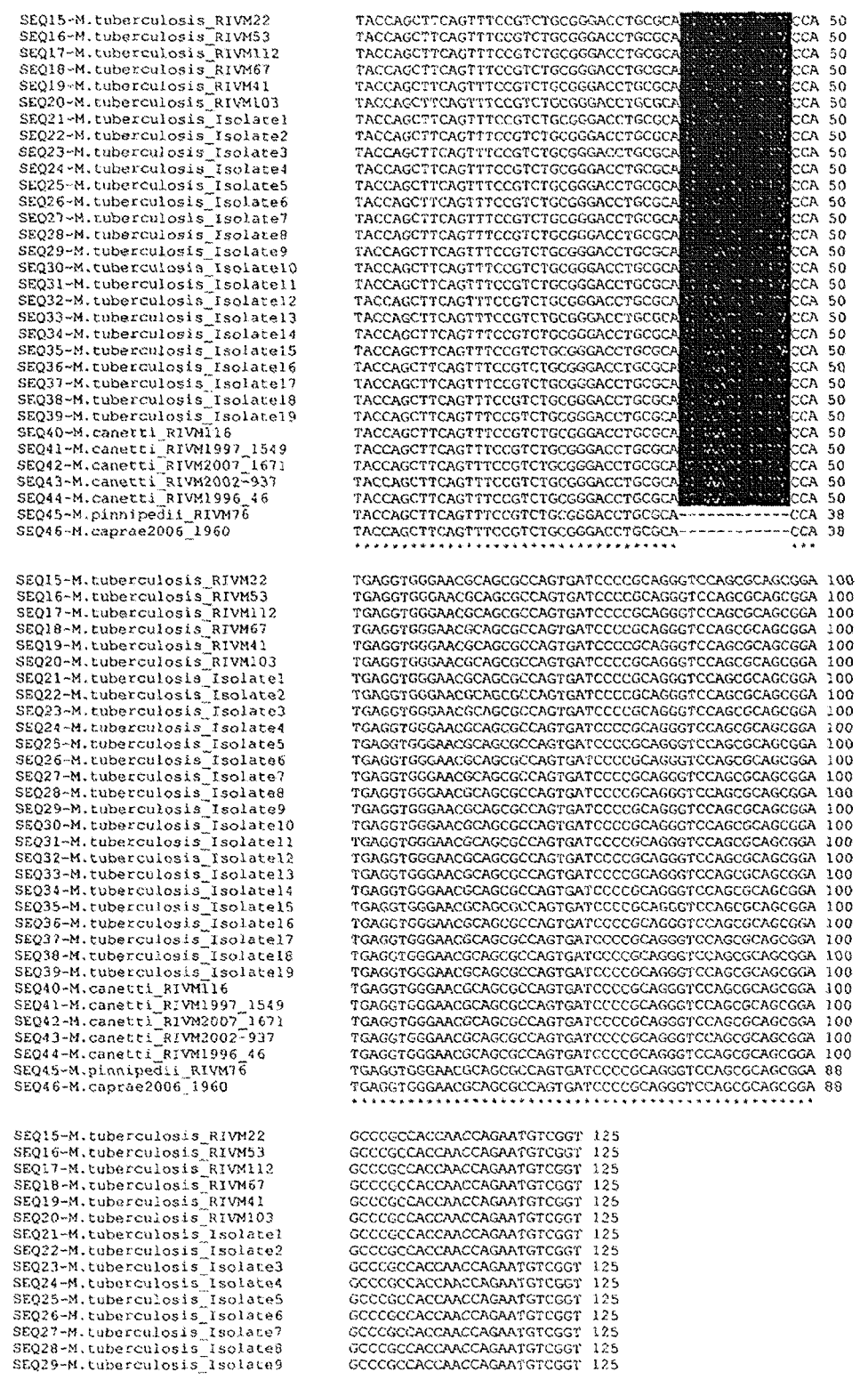

```
SEQ15-M.tuberculosis_RIVM22          TACCAGCTTCAGTTTCCGTCTGCGGGACCTGCGCA[redacted]CCA 50
SEQ16-M.tuberculosis_RIVM53          TACCAGCTTCAGTTTCCGTCTGCGGGACCTGCGCA[redacted]CCA 50
SEQ17-M.tuberculosis_RIVM112         TACCAGCTTCAGTTTCCGTCTGCGGGACCTGCGCA[redacted]CCA 50
SEQ18-M.tuberculosis_RIVM67          TACCAGCTTCAGTTTCCGTCTGCGGGACCTGCGCA[redacted]CCA 50
SEQ19-M.tuberculosis_RIVM41          TACCAGCTTCAGTTTCCGTCTGCGGGACCTGCGCA[redacted]CCA 50
SEQ20-M.tuberculosis_RIVM103         TACCAGCTTCAGTTTCCGTCTGCGGGACCTGCGCA[redacted]CCA 50
SEQ21-M.tuberculosis_Isolate1        TACCAGCTTCAGTTTCCGTCTGCGGGACCTGCGCA[redacted]CCA 50
SEQ22-M.tuberculosis_Isolate2        TACCAGCTTCAGTTTCCGTCTGCGGGACCTGCGCA[redacted]CCA 50
SEQ23-M.tuberculosis_Isolate3        TACCAGCTTCAGTTTCCGTCTGCGGGACCTGCGCA[redacted]CCA 50
SEQ24-M.tuberculosis_Isolate4        TACCAGCTTCAGTTTCCGTCTGCGGGACCTGCGCA[redacted]CCA 50
SEQ25-M.tuberculosis_Isolate5        TACCAGCTTCAGTTTCCGTCTGCGGGACCTGCGCA[redacted]CCA 50
SEQ26-M.tuberculosis_Isolate6        TACCAGCTTCAGTTTCCGTCTGCGGGACCTGCGCA[redacted]CCA 50
SEQ27-M.tuberculosis_Isolate7        TACCAGCTTCAGTTTCCGTCTGCGGGACCTGCGCA[redacted]CCA 50
SEQ28-M.tuberculosis_Isolate8        TACCAGCTTCAGTTTCCGTCTGCGGGACCTGCGCA[redacted]CCA 50
SEQ29-M.tuberculosis_Isolate9        TACCAGCTTCAGTTTCCGTCTGCGGGACCTGCGCA[redacted]CCA 50
SEQ30-M.tuberculosis_Isolate10       TACCAGCTTCAGTTTCCGTCTGCGGGACCTGCGCA[redacted]CCA 50
SEQ31-M.tuberculosis_Isolate11       TACCAGCTTCAGTTTCCGTCTGCGGGACCTGCGCA[redacted]CCA 50
SEQ32-M.tuberculosis_Isolate12       TACCAGCTTCAGTTTCCGTCTGCGGGACCTGCGCA[redacted]CCA 50
SEQ33-M.tuberculosis_Isolate13       TACCAGCTTCAGTTTCCGTCTGCGGGACCTGCGCA[redacted]CCA 50
SEQ34-M.tuberculosis_Isolate14       TACCAGCTTCAGTTTCCGTCTGCGGGACCTGCGCA[redacted]CCA 50
SEQ35-M.tuberculosis_Isolate15       TACCAGCTTCAGTTTCCGTCTGCGGGACCTGCGCA[redacted]CCA 50
SEQ36-M.tuberculosis_Isolate16       TACCAGCTTCAGTTTCCGTCTGCGGGACCTGCGCA[redacted]CCA 50
SEQ37-M.tuberculosis_Isolate17       TACCAGCTTCAGTTTCCGTCTGCGGGACCTGCGCA[redacted]CCA 50
SEQ38-M.tuberculosis_Isolate18       TACCAGCTTCAGTTTCCGTCTGCGGGACCTGCGCA[redacted]CCA 50
SEQ39-M.tuberculosis_Isolate19       TACCAGCTTCAGTTTCCGTCTGCGGGACCTGCGCA[redacted]CCA 50
SEQ40-M.canetti_RIVM116              TACCAGCTTCAGTTTCCGTCTGCGGGACCTGCGCA[redacted]CCA 50
SEQ41-M.canetti_RIVM1997_1549        TACCAGCTTCAGTTTCCGTCTGCGGGACCTGCGCA[redacted]CCA 50
SEQ42-M.canetti_RIVM2007_1671        TACCAGCTTCAGTTTCCGTCTGCGGGACCTGCGCA[redacted]CCA 50
SEQ43-M.canetti_RIVM2002-937         TACCAGCTTCAGTTTCCGTCTGCGGGACCTGCGCA[redacted]CCA 50
SEQ44-M.canetti_RIVM1996_46          TACCAGCTTCAGTTTCCGTCTGCGGGACCTGCGCA[redacted]CCA 50
SEQ45-M.pinnipedii_RIVM76            TACCAGCTTCAGTTTCCGTCTGCGGGACCTGCGCA------------CCA 38
SEQ46-M.caprae2006_1960              TACCAGCTTCAGTTTCCGTCTGCGGGACCTGCGCA------------CCA 38
                                     ***********************************            ***

SEQ15-M.tuberculosis_RIVM22          TGAGGTGGGAACGCAGCGCCAGTGATCCCCGCAGGGTCCAGCGCAGCGGA 100
SEQ16-M.tuberculosis_RIVM53          TGAGGTGGGAACGCAGCGCCAGTGATCCCCGCAGGGTCCAGCGCAGCGGA 100
SEQ17-M.tuberculosis_RIVM112         TGAGGTGGGAACGCAGCGCCAGTGATCCCCGCAGGGTCCAGCGCAGCGGA 100
SEQ18-M.tuberculosis_RIVM67          TGAGGTGGGAACGCAGCGCCAGTGATCCCCGCAGGGTCCAGCGCAGCGGA 100
SEQ19-M.tuberculosis_RIVM41          TGAGGTGGGAACGCAGCGCCAGTGATCCCCGCAGGGTCCAGCGCAGCGGA 100
SEQ20-M.tuberculosis_RIVM103         TGAGGTGGGAACGCAGCGCCAGTGATCCCCGCAGGGTCCAGCGCAGCGGA 100
SEQ21-M.tuberculosis_Isolate1        TGAGGTGGGAACGCAGCGCCAGTGATCCCCGCAGGGTCCAGCGCAGCGGA 100
SEQ22-M.tuberculosis_Isolate2        TGAGGTGGGAACGCAGCGCCAGTGATCCCCGCAGGGTCCAGCGCAGCGGA 100
SEQ23-M.tuberculosis_Isolate3        TGAGGTGGGAACGCAGCGCCAGTGATCCCCGCAGGGTCCAGCGCAGCGGA 100
SEQ24-M.tuberculosis_Isolate4        TGAGGTGGGAACGCAGCGCCAGTGATCCCCGCAGGGTCCAGCGCAGCGGA 100
SEQ25-M.tuberculosis_Isolate5        TGAGGTGGGAACGCAGCGCCAGTGATCCCCGCAGGGTCCAGCGCAGCGGA 100
SEQ26-M.tuberculosis_Isolate6        TGAGGTGGGAACGCAGCGCCAGTGATCCCCGCAGGGTCCAGCGCAGCGGA 100
SEQ27-M.tuberculosis_Isolate7        TGAGGTGGGAACGCAGCGCCAGTGATCCCCGCAGGGTCCAGCGCAGCGGA 100
SEQ28-M.tuberculosis_Isolate8        TGAGGTGGGAACGCAGCGCCAGTGATCCCCGCAGGGTCCAGCGCAGCGGA 100
SEQ29-M.tuberculosis_Isolate9        TGAGGTGGGAACGCAGCGCCAGTGATCCCCGCAGGGTCCAGCGCAGCGGA 100
SEQ30-M.tuberculosis_Isolate10       TGAGGTGGGAACGCAGCGCCAGTGATCCCCGCAGGGTCCAGCGCAGCGGA 100
SEQ31-M.tuberculosis_Isolate11       TGAGGTGGGAACGCAGCGCCAGTGATCCCCGCAGGGTCCAGCGCAGCGGA 100
SEQ32-M.tuberculosis_Isolate12       TGAGGTGGGAACGCAGCGCCAGTGATCCCCGCAGGGTCCAGCGCAGCGGA 100
SEQ33-M.tuberculosis_Isolate13       TGAGGTGGGAACGCAGCGCCAGTGATCCCCGCAGGGTCCAGCGCAGCGGA 100
SEQ34-M.tuberculosis_Isolate14       TGAGGTGGGAACGCAGCGCCAGTGATCCCCGCAGGGTCCAGCGCAGCGGA 100
SEQ35-M.tuberculosis_Isolate15       TGAGGTGGGAACGCAGCGCCAGTGATCCCCGCAGGGTCCAGCGCAGCGGA 100
SEQ36-M.tuberculosis_Isolate16       TGAGGTGGGAACGCAGCGCCAGTGATCCCCGCAGGGTCCAGCGCAGCGGA 100
SEQ37-M.tuberculosis_Isolate17       TGAGGTGGGAACGCAGCGCCAGTGATCCCCGCAGGGTCCAGCGCAGCGGA 100
SEQ38-M.tuberculosis_Isolate18       TGAGGTGGGAACGCAGCGCCAGTGATCCCCGCAGGGTCCAGCGCAGCGGA 100
SEQ39-M.tuberculosis_Isolate19       TGAGGTGGGAACGCAGCGCCAGTGATCCCCGCAGGGTCCAGCGCAGCGGA 100
SEQ40-M.canetti_RIVM116              TGAGGTGGGAACGCAGCGCCAGTGATCCCCGCAGGGTCCAGCGCAGCGGA 100
SEQ41-M.canetti_RIVM1997_1549        TGAGGTGGGAACGCAGCGCCAGTGATCCCCGCAGGGTCCAGCGCAGCGGA 100
SEQ42-M.canetti_RIVM2007_1671        TGAGGTGGGAACGCAGCGCCAGTGATCCCCGCAGGGTCCAGCGCAGCGGA 100
SEQ43-M.canetti_RIVM2002-937         TGAGGTGGGAACGCAGCGCCAGTGATCCCCGCAGGGTCCAGCGCAGCGGA 100
SEQ44-M.canetti_RIVM1996_46          TGAGGTGGGAACGCAGCGCCAGTGATCCCCGCAGGGTCCAGCGCAGCGGA 100
SEQ45-M.pinnipedii_RIVM76            TGAGGTGGGAACGCAGCGCCAGTGATCCCCGCAGGGTCCAGCGCAGCGGA 88
SEQ46-M.caprae2006_1960              TGAGGTGGGAACGCAGCGCCAGTGATCCCCGCAGGGTCCAGCGCAGCGGA 88
                                     **************************************************

SEQ15-M.tuberculosis_RIVM22          GCCCGCCACCAACCAGAATGTCGGT 125
SEQ16-M.tuberculosis_RIVM53          GCCCGCCACCAACCAGAATGTCGGT 125
SEQ17-M.tuberculosis_RIVM112         GCCCGCCACCAACCAGAATGTCGGT 125
SEQ18-M.tuberculosis_RIVM67          GCCCGCCACCAACCAGAATGTCGGT 125
SEQ19-M.tuberculosis_RIVM41          GCCCGCCACCAACCAGAATGTCGGT 125
SEQ20-M.tuberculosis_RIVM103         GCCCGCCACCAACCAGAATGTCGGT 125
SEQ21-M.tuberculosis_Isolate1        GCCCGCCACCAACCAGAATGTCGGT 125
SEQ22-M.tuberculosis_Isolate2        GCCCGCCACCAACCAGAATGTCGGT 125
SEQ23-M.tuberculosis_Isolate3        GCCCGCCACCAACCAGAATGTCGGT 125
SEQ24-M.tuberculosis_Isolate4        GCCCGCCACCAACCAGAATGTCGGT 125
SEQ25-M.tuberculosis_Isolate5        GCCCGCCACCAACCAGAATGTCGGT 125
SEQ26-M.tuberculosis_Isolate6        GCCCGCCACCAACCAGAATGTCGGT 125
SEQ27-M.tuberculosis_Isolate7        GCCCGCCACCAACCAGAATGTCGGT 125
SEQ28-M.tuberculosis_Isolate8        GCCCGCCACCAACCAGAATGTCGGT 125
SEQ29-M.tuberculosis_Isolate9        GCCCGCCACCAACCAGAATGTCGGT 125
```

Figure 1B (cont)

```
SEQ30-M.tuberculosis_Isolate10        GCCCGCCACCAACCAGAATGTCGGT 125
SEQ31-M.tuberculosis_Isolate11        GCCCGCCACCAACCAGAATGTCGGT 125
SEQ32-M.tuberculosis_Isolate12        GCCCGCCACCAACCAGAATGTCGGT 125
SEQ33-M.tuberculosis_Isolate13        GCCCGCCACCAACCAGAATGTCGGT 125
SEQ34-M.tuberculosis_Isolate14        GCCCGCCACCAACCAGAATGTCGGT 125
SEQ35-M.tuberculosis_Isolate15        GCCCGCCACCAACCAGAATGTCGGT 125
SEQ36-M.tuberculosis_Isolate16        GCCCGCCACCAACCAGAATGTCGGT 125
SEQ37-M.tuberculosis_Isolate17        GCCCGCCACCAACCAGAATGTCGGT 125
SEQ38-M.tuberculosis_Isolate18        GCCCGCCACCAACCAGAATGTCGGT 125
SEQ39-M.tuberculosis_Isolate19        GCCCGCCACCAACCAGAATGTCGGT 125
SEQ40-M.canetti_RIVM116               GCCCGCCACCAACCAGAATGTCGGT 125
SEQ41-M.canetti_RIVM1997_1549         GCCCGCCACCAACCAGAATGTCGGT 125
SEQ42-M.canetti_RIVM2007_1671         GCCCGCCACCAACCAGAATGTCGGT 125
SEQ43-M.canetti_RIVM2002-937          GCCCGCCACCAACCAGAATGTCGGT 125
SEQ44-M.canetti_RIVM1996_46           GCCCGCCACCAACCAGAATGTCGGT 125
SEQ45-M.pinnipedii_RIVM76             GCCCGCCACCAACCAGAATGTCGGT 113
SEQ46-M.caprae2006_1960               GCCCGCCACCAACCAGAATGTCGGT 113
                                      *************************
```

Figure 2

```
SEQIDNO_47-M.tuberculosis_H37R      TCACTTCTTGCCTTTGTCCCCGGCGGCATCGGTGGACAATGCCGCGACGA 50
SEQIDNO_48-M.tuberculosis_H37R      TCACTTCTTGCCTTTGTCCCCGGCGGCATCGGTGGACAATGCCGCGACGA 50
SEQIDNO_49-M.tuberculosis_F11       TCACTTCTTGCCTTTGTCCCCGGCGGCATCGGTGGACAATGCCGCGACGA 50
SEQIDNO_50-M.tuberculosis_KZN1      TCACTTCTTGCCTTTGTCCCCGGCGGCATCGGTGGACAATGCCGCGACGA 50
SEQIDNO_51-M.tuberculosis_CDC1      TCACTTCTTGCCTTTGTCCCCGGCGGCATCGGTGGACAATGCCGCGACGA 50
SEQIDNO_52-M.tuberculosis_Haar      TCACTTCTTGCCTTTGTCCCCGGCGGCATCGGTGGACAATGCCGCGACGA 50
SEQIDNO_53-M.tuberculosis_C         TCACTTCTTGCCTTTGTCCCCGGCGGCATCGGTGGACAATGCCGCGACGA 50
SEQIDNO_54-M.bovisAF2122/97         TCACTTCTTGCCTTTGTCCCCGGCGGCATCGGTGGACAATGCCGCGACGA 50
SEQIDNO_55-M.bovisBCG_Pasteur1      TCACTTCTTGCCTTTGTCCCCGGCGGCATCGGTGGACAATGCCGCGACGA 50
SEQIDNO_56-M.bovisBCG_Tokyo172      TCACTTCTTGCCTTTGTCCCCGGCGGCATCGGTGGACAATGCCGCGACGA 50
SEQIDNO_57-M.microtti               TCACTTCTTGCCTTTGTCCCCGGCGGCATCGGTGGACAATGCCGCGACGA 50
SEQIDNO_58-M.canetti_CIPT14001      TCACTTCTTGCCTTTGTCCCCGGCGGCATCGGTGGACAATGCCGCGACGA 50
SEQIDNO_59-M.africanum_GM04118      --------------------------------------------------
SEQIDNO_76-M.capraeRIVM2006_19      --------------------------------------------------
SEQIDNO_60-M.avium_subsp_Parat      TTACTTCTTGGATTTGTCGCCCGCGGCGTCGGCGGACAGCGCGGCGACGA 50
SEQIDNO_61-M.leprae_cosmid_B19      TTATTTCTTGTCCTTGTCTCCTGCGGCATCGGCGGACAACGCGGCGACAA 50
SEQIDNO_62-M.ulcerans_Agy99         CTACTTCTTGCCCTTATCCCCCGCGGCGTCGGTGGACAGTGCCGCGACAA 50
SEQIDNO_63-M.avium_104              TTACTTCTTGGATTTGTCGCCCGCGGCGTCGGCGGACAGCGCCGCGACGA 50
SEQIDNO_64-M.vanbaalenii_PYR-1      TCATTTCTTCGGCTTGTCCGCGGTGGATTCGGTGGACAGCGCGGCGACGA 50
SEQIDNO_65-M.gilvum_PYR-GCK         CTACTTCTTCGGCTTGTCCGCGGCGGACTCGGTCGACAGTGCCGCGACGA 50
SEQIDNO_66-M.abscessus              CTACTTCTTCGGTTTGTCCGCCGTCGACTCGGTGGACAGTGCCGCCACAA 50
SEQIDNO_67-M.marinum_M              CTACTTCTTGCCCTTATCCCCCGCGGCGTCGGTGGACAGTGCCGCGACAA 50
SEQIDNO_68-M.smegmatis              CTACTTCTTGGGCTTGTCGCCCGCCGCGTCGGTGGACAGCGCCGCGACGA 50

SEQIDNO_47-M.tuberculosis_H37R      AAGCCTCCTGTGGCACCTCGACGCGCCCGATGGTCTTCATCCGCTTCTTG 100
SEQIDNO_48-M.tuberculosis_H37R      AAGCCTCCTGTGGCACCTCGACGCGCCCGATGGTCTTCATCCGCTTCTTG 100
SEQIDNO_49-M.tuberculosis_F11       AAGCCTCCTGTGGCACCTCGACGCGCCCGATGGTCTTCATCCGCTTCTTG 100
SEQIDNO_50-M.tuberculosis_KZN1      AAGCCTCCTGTGGCACCTCGACGCGCCCGATGGTCTTCATCCGCTTCTTG 100
SEQIDNO_51-M.tuberculosis_CDC1      AAGCCTCCTGTGGCACCTCGACGCGCCCGATGGTCTTCATCCGCTTCTTG 100
SEQIDNO_52-M.tuberculosis_Haar      AAGCCTCCTGTGGCACCTCGACGCGCCCGATGGTCTTCATCCGCTTCTTG 100
SEQIDNO_53-M.tuberculosis_C         AAGCCTCCTGTGGCACCTCGACGCGCCCGATGGTCTTCATCCGCTTCTTG 100
SEQIDNO_54-M.bovisAF2122/97         AAGCCTCCTGTGGCACCTCGACGCGCCCGATGGTCTTCATCCGCTTCTTG 100
SEQIDNO_55-M.bovisBCG_Pasteur1      AAGCCTCCTGTGGCACCTCGACGCGCCCGATGGTCTTCATCCGCTTCTTG 100
SEQIDNO_56-M.bovisBCG_Tokyo172      AAGCCTCCTGTGGCACCTCGACGCGCCCGATGGTCTTCATCCGCTTCTTG 100
SEQIDNO_57-M.microtti               AAGCCTCCTGTGGCACCTCGACGCGCCCGATGGTCTTCATCCGCTTCTTG 100
SEQIDNO_58-M.canetti_CIPT14001      AAGCCTCCTGTGGCACCTCGACGCGCCCGATGGTCTTCATCCGCTTCTTG 100
SEQIDNO_59-M.africanum_GM04118      --------------------------------------------------
SEQIDNO_76-M.capraeRIVM2006_19      --------------------------------------------------
SEQIDNO_60-M.avium_subsp_Parat      ACGCCTCCTGCGGCACGTCGACCCGGCCGATGGTCTTCATCCGCTTCTTG 100
SEQIDNO_61-M.leprae_cosmid_B19      ACGCTTCCTGCGGCACCTCGACCCGCCCAATGGTCTTCATCCGTTTCTTG 100
SEQIDNO_62-M.ulcerans_Agy99         ACGCCTCCTGCGGCACCTCGACCCGGCCGATGGACTTCATCCGCTTCTTG 100
SEQIDNO_63-M.avium_104              ACGCCTCCTGCGGCACGTCGACCCGGCCGATGGTCTTCATCCGCTTCTTG 100
SEQIDNO_64-M.vanbaalenii_PYR-1      AGGCCTCCTGCGGGACGTCGACCCGGCCGATGGTCTTCATCCGCTTCTTG 100
SEQIDNO_65-M.gilvum_PYR-GCK         AGGCCTCCTGCGGCACCTCGACCCGGCCGATCGTCTTCATCCGCTTCTTG 100
SEQIDNO_66-M.abscessus              ACGCCTCCTGCGGCACCTCGACGCGACCGATGGTCTTCATGCGCTTCTTG 100
SEQIDNO_67-M.marinum_M              ACGCCTCCTGCGGCACCTCGACCCGGCCGATGGTCTTCATCCGCTTCTTG 100
SEQIDNO_68-M.smegmatis              ATGCCTCCTGCGGCACGTCGACCCGGCCGATCGTCTTCATGCGCTTCTTG 100

SEQIDNO_47-M.tuberculosis_H37R      CCTTCCTTCTGCTTCTCCAGCAGCTTGCGTTTGCGCGTGATGTCGCCGCC 150
SEQIDNO_48-M.tuberculosis_H37R      CCTTCCTTCTGCTTCTCCAGCAGCTTGCGTTTGCGCGTGATGTCGCCGCC 150
SEQIDNO_49-M.tuberculosis_F11       CCTTCCTTCTGCTTCTCCAGCAGCTTGCGTTTGCGCGTGATGTCGCCGCC 150
SEQIDNO_50-M.tuberculosis_KZN1      CCTTCCTTCTGCTTCTCCAGCAGCTTGCGTTTGCGCGTGATGTCGCCGCC 150
SEQIDNO_51-M.tuberculosis_CDC1      CCTTCCTTCTGCTTCTCCAGCAGCTTGCGTTTGCGCGTGATGTCGCCGCC 150
SEQIDNO_52-M.tuberculosis_Haar      CCTTCCTTCTGCTTCTCCAGCAGCTTGCGTTTGCGCGTGATGTCGCCGCC 150
SEQIDNO_53-M.tuberculosis_C         CCTTCCTTCTGCTTCTCCAGCAGCTTGCGTTTGCGCGTGATGTCGCCGCC 150
SEQIDNO_54-M.bovisAF2122/97         CCTTCCTTCTGCTTCTCCAGCAGCTTGCGTTTGCGCGTGATGTCGCCGCC 150
SEQIDNO_55-M.bovisBCG_Pasteur1      CCTTCCTTCTGCTTCTCCAGCAGCTTGCGTTTGCGCGTGATGTCGCCGCC 150
SEQIDNO_56-M.bovisBCG_Tokyo172      CCTTCCTTCTGCTTCTCCAGCAGCTTGCGTTTGCGCGTGATGTCGCCGCC 150
SEQIDNO_57-M.microtti               CCTTCCTTCTGCTTCTCCAGCAGCTTGCGTTTGCGCGTGATGTCGCCGCC 150
SEQIDNO_58-M.canetti_CIPT14001      CCTTCCTTCTGCTTCTCCAGCAGCTTGCGTTTGCGCGTGATGTCGCCGCC 150
SEQIDNO_59-M.africanum_GM04118      --------------------------------------------------
SEQIDNO_76-M.capraeRIVM2006_19      --------------------------------------------------
SEQIDNO_60-M.avium_subsp_Parat      CCCTCCTTCTGCTTTTCCAGAAGTTTGCGCTTGCGGGTGATGTCACCGCC 150
SEQIDNO_61-M.leprae_cosmid_B19      CCTTCCTTCTGCTTTTCCAGAAGCTTACGTTTGCGGGTGATATCGCCGCC 150
SEQIDNO_62-M.ulcerans_Agy99         CCCTCTTTCTGCTTTTCCAGCAGCTTGCGTTTGCGGGTGATGTCACCGCC 150
SEQIDNO_63-M.avium_104              CCCTCCTTCTGCTTTTCCAGAAGTTTGCGCTTACGGGTGATGTCACCGCC 150
SEQIDNO_64-M.vanbaalenii_PYR-1      CCTTCCTTCTGCTTTTCCAGCAGCTTGCGCTTACGGGTGATGTCACCGCC 150
SEQIDNO_65-M.gilvum_PYR-GCK         CCTTCCTTCTGCTTCTCCAGCAGCTTGCGCTTACGAGTGATGTCACCGCC 150
SEQIDNO_66-M.abscessus              CCCTCCTTCTGCTTCTCGAGCAGCTTGCGCTTACGGGTGATATCACCGCC 150
SEQIDNO_67-M.marinum_M              CCCTCTTTCTGCTTTTCCAGCAGCTTGCGTTTGCGGGTGATGTCACCGCC 150
SEQIDNO_68-M.smegmatis              CCCTCTTTCTGCTTCTCGAGCAGCTTGCGCTTACGGGTGATGTCACCGCC 150

SEQIDNO_47-M.tuberculosis_H37R      GTAGCACTTGGACAACACGTCCTTGCGGATCGCGCGGATGTTTTCGCGGG 200
SEQIDNO_48-M.tuberculosis_H37R      GTAGCACTTGGACAACACGTCCTTGCGGATCGCGCGGATGTTTTCGCGGG 200
SEQIDNO_49-M.tuberculosis_F11       GTAGCACTTGGACAACACGTCCTTGCGGATCGCGCGGATGTTTTCGCGGG 200
SEQIDNO_50-M.tuberculosis_KZN1      GTAGCACTTGGACAACACGTCCTTGCGGATCGCGCGGATGTTTTCGCGGG 200
SEQIDNO_51-M.tuberculosis_CDC1      GTAGCACTTGGACAACACGTCCTTGCGGATCGCGCGGATGTTTTCGCGGG 200
SEQIDNO_52-M.tuberculosis_Haar      GTAGCACTTGGACAACACGTCCTTGCGGATCGCGCGGATGTTTTCGCGGG 200
SEQIDNO_53-M.tuberculosis_C         GTAGCACTTGGACAACACGTCCTTGCGGATCGCGCGGATGTTTTCGCGGG 200
SEQIDNO_54-M.bovisAF2122/97         GTAGCACTTGGACAACACGTCCTTGCGGATCGCGCGGATGTTTTCGCGGG 200
SEQIDNO_55-M.bovisBCG_Pasteur1      GTAGCACTTGGACAACACGTCCTTGCGGATCGCGCGGATGTTTTCGCGGG 200
```

Figure 2 (cont)

```
SEQIDNO_56-M.bovisBCG_Tokyo172      GTAGCACTTGGACAACACGTCCTTGCGGATCGCGCGGATGTTTTCGCGGG 200
SEQIDNO_57-M.microtti               GTAGCACTTGGACAACACGTCCTTGCGGATCGCGCGGATGTTTTCGCGGG 200
SEQIDNO_58-M.canetti_CIPT14001      GTAGCACTTGGACAACACGTCCTTGCGGATCGCGCGGATGTTTTCGCGGG 200
SEQIDNO_59-M.africanum_GM04118      --------------------------------------------------
SEQIDNO_76-M.capraeRIVM2006_19      --------------------------------------------------
SEQIDNO_60-M.avium_subsp_Parat      GTAACACTTGGACAGCACGTCCTTGCGGATGGCCCGAATGTTCTCGCGGG 200
SEQIDNO_61-M.leprae_cosmid_B19      ATAACATTTCGACAGCACATCCTTGCGTATCGCCCTAATATTTTCGCGCG 200
SEQIDNO_62-M.ulcerans_Agy99         GTAGCACTTCGACAACACATCCTTGAGGATCGCGCGGATGTTCTCGCGCG 200
SEQIDNO_63-M.avium_104              GTAACACTTGGACAGCACGTCCTTGCGGATGGCCCGAATGTTCTCGCGGG 200
SEQIDNO_64-M.vanbaalenii_PYR-1      GTAGCACTTGGACAGCACATCCTTGCGGATCGCCCGAATGTTCTCGCGGG 200
SEQIDNO_65-M.gilvum_PYR-GCK         GTAGCACTTCGACAGCACGTCCTTGCGGATCGCCCGGATGTTCTCTCGCG 200
SEQIDNO_66-M.abscessus              GTAGCACTTGGAGAGCACATCCTTACGGATGGCCCGAATATTCTCGCGCG 200
SEQIDNO_67-M.marinum_M              GTAGCACTTCGACAACACATCCTTGCGGATCGCGCGGATGTTCTCGCGCG 200
SEQIDNO_68-M.smegmatis              GTAGCACTTCGAGAGCACGTCCTTGCGGATGGCCCGGATGTTTTCGCGCG 200

SEQIDNO_47-M.tuberculosis_H37R      CAATGATTTTCGATCCGATGGCGGCCTGCACCGGCACCTCGAACTGCTGG 250
SEQIDNO_48-M.tuberculosis_H37R      CAATGATTTTCGATCCGATGGCGGCCTGCACCGGCACCTCGAACTGCTGG 250
SEQIDNO_49-M.tuberculosis_F11       CAATGATTTTCGATCCGATGGCGGCCTGCACCGGCACCTCGAACTGCTGG 250
SEQIDNO_50-M.tuberculosis_KZN1      CAATGATTTTCGATCCGATGGCGGCCTGCACCGGCACCTCGAACTGCTGG 250
SEQIDNO_51-M.tuberculosis_CDC1      CAATGATTTTCGATCCGATGGCGGCCTGCACCGGCACCTCGAACTGCTGG 250
SEQIDNO_52-M.tuberculosis_Haar      CAATGATTTTCGATCCGATGGCGGCCTGCACCGGCACCTCGAACTGCTGG 250
SEQIDNO_53-M.tuberculosis_C         CAATGATTTTCGATCCGATGGCGGCCTGCACCGGCACCTCGAACTGCTGG 250
SEQIDNO_54-M.bovisAF2122/97         CAATGATTTTCGATCCGATGGCGGCCTGCACCGGCACCTCGAACTGCTGG 250
SEQIDNO_55-M.bovisBCG_Pasteur1      CAATGATTTTCGATCCGATGGCGGCCTGCACCGGCACCTCGAACTGCTGG 250
SEQIDNO_56-M.bovisBCG_Tokyo172      CAATGATTTTCGATCCGATGGCGGCCTGCACCGGCACCTCGAACTGCTGG 250
SEQIDNO_57-M.microtti               CAATGATTTTCGATCCGATGGCGGCCTGCACCGGCACCTCGAACTGCTGG 250
SEQIDNO_58-M.canetti_CIPT14001      CAATGATTTTCGATCCGATGGCGGCCTGCACCGGCACCTCGAACTGCTGG 250
SEQIDNO_59-M.africanum_GM04118      --------------------------------------------------
SEQIDNO_76-M.capraeRIVM2006_19      --------------------------------------------------
SEQIDNO_60-M.avium_subsp_Parat      CAATGATTTTCGAGCCGATCGCGGCCTGGACGGGCACCTCGAACTGCTGG 250
SEQIDNO_61-M.leprae_cosmid_B19      CAATGACTTTCGATCCAATAGCCGCCTGTACTGGCACCTCAAACTGCTGA 250
SEQIDNO_62-M.ulcerans_Agy99         CGATGATCTTGGAACCGATGGCCGCCTGCACCGGCACCTCGAACTGCTGA 250
SEQIDNO_63-M.avium_104              CAATGATTTTCGAGCCGATCGCGGCCTGGACGGGCACCTCGAACTGCTGA 250
SEQIDNO_64-M.vanbaalenii_PYR-1      CAATGATTCTCGAGCCGACGGCGGCCTGCACGGGCACCTCGAACTGCTGG 250
SEQIDNO_65-M.gilvum_PYR-GCK         CAATGATTCTCGAGCCGATCGCGGCCTGCACGGGCACCTCGAACTGCTGG 250
SEQIDNO_66-M.abscessus              CAATGATTCTCGATCCGACAGCGGCCTGCACCGGCACCTCGAACTGCTGG 250
SEQIDNO_67-M.marinum_M              CGATGATCTTGGAACCGATGGCCGCCTGCACCGGCACCTCGAACTGCTGA 250
SEQIDNO_68-M.smegmatis              CAATGATTCTCGAGCCGATCGCGGCCTGCACCGGGACCTCGAACTGCTGT 250

SEQIDNO_47-M.tuberculosis_H37R      CGCGGGATCAGCTCCTTGAGTTTGGTGGTCATCTTGTTGCCGTAGGCATA 300
SEQIDNO_48-M.tuberculosis_H37R      CGCGGGATCAGCTCCTTGAGTTTGGTGGTCATCTTGTTGCCGTAGGCATA 300
SEQIDNO_49-M.tuberculosis_F11       CGCGGGATCAGCTCCTTGAGTTTGGTGGTCATCTTGTTGCCGTAGGCATA 300
SEQIDNO_50-M.tuberculosis_KZN1      CGCGGGATCAGCTCCTTGAGTTTGGTGGTCATCTTGTTGCCGTAGGCATA 300
SEQIDNO_51-M.tuberculosis_CDC1      CGCGGGATCAGCTCCTTGAGTTTGGTGGTCATCTTGTTGCCGTAGGCATA 300
SEQIDNO_52-M.tuberculosis_Haar      CGCGGGATCAGCTCCTTGAGTTTGGTGGTCATCTTGTTGCCGTAGGCATA 300
SEQIDNO_53-M.tuberculosis_C         CGCGGGATCAGCTCCTTGAGTTTGGTGGTCATCTTGTTGCCGTAGGCATA 300
SEQIDNO_54-M.bovisAF2122/97         CGCGGGATCAGCTCCTTGAGTTTGGTGGTCATCTTGTTGCCGTAGGCATA 300
SEQIDNO_55-M.bovisBCG_Pasteur1      CGCGGGATCAGCTCCTTGAGTTTGGTGGTCATCTTGTTGCCGTAGGCATA 300
SEQIDNO_56-M.bovisBCG_Tokyo172      CGCGGGATCAGCTCCTTGAGTTTGGTGGTCATCTTGTTGCCGTAGGCATA 300
SEQIDNO_57-M.microtti               CGCGGGATCAGCTCCTTGAGTTTGGTGGTCATCTTGTTGCCGTAGGCATA 300
SEQIDNO_58-M.canetti_CIPT14001      CGCGGGATCAGCTCCTTGAGTTTGGTGGTCATCTTGTTGCCGTAGGCATA 300
SEQIDNO_59-M.africanum_GM04118      --------------------------------------------------
SEQIDNO_76-M.capraeRIVM2006_19      --------------------------------------------------
SEQIDNO_60-M.avium_subsp_Parat      CGCGGGATCAGCTCCTTGAGCTTGGTGGTCATCTTGTTGCCGTACGCGAA 300
SEQIDNO_61-M.leprae_cosmid_B19      CGTGGGATCAGTTCTTTGAGCTTGTTGGTCATCTTGTTGCCATAGGCAGA 300
SEQIDNO_62-M.ulcerans_Agy99         CGCGGAATCAGCTCCTTGAGCTTGGTGGTCATCTTGTTGCCGTAGGCGAA 300
SEQIDNO_63-M.avium_104              CGGGGGATCAGCTCCTTGAGCTTGGTGGTCATCTTGTTGCCGTAGGCGAA 300
SEQIDNO_64-M.vanbaalenii_PYR-1      CGCGGGATGAGCTCCTTGAGCTTGGTGGTCATCTTGTTGCCGTAGGCCGA 300
SEQIDNO_65-M.gilvum_PYR-GCK         CGTGGGATCAGTTCCTTCAGCTTGGTCGTCATCTTGTTGCCGTACGCCGC 300
SEQIDNO_66-M.abscessus              CGCGGGATGAGTTCCTTGAGCTTGACGGTCATCTTGTTGCCATAGGCCGA 300
SEQIDNO_67-M.marinum_M              CGCGGAATCAGCTCCTTGAGCTTGGTGGTCATCTTGTTGCCGTAGGCGAA 300
SEQIDNO_68-M.smegmatis              CGCGGGATCAGTTCTTTGAGCTTGGAGGTCATCTTGTTGCCGTAGGCCGA 300

SEQIDNO_47-M.tuberculosis_H37R      CGCCGTGTCCTTGTGCACGATCGCGCTGAACGCATCCACCGCCTCGCCCT 350
SEQIDNO_48-M.tuberculosis_H37R      CGCCGTGTCCTTGTGCACGATCGCGCTGAACGCATCCACCGCCTCGCCCT 350
SEQIDNO_49-M.tuberculosis_F11       CGCCGTGTCCTTGTGCACGATCGCGCTGAACGCATCCACCGCCTCGCCCT 350
SEQIDNO_50-M.tuberculosis_KZN1      CGCCGTGTCCTTGTGCACGATCGCGCTGAACGCATCCACCGCCTCGCCCT 350
SEQIDNO_51-M.tuberculosis_CDC1      CGCCGTGTCCTTGTGCACGATCGCGCTGAACGCATCCACCGCCTCGCCCT 350
SEQIDNO_52-M.tuberculosis_Haar      CGCCGTGTCCTTGTGCACGATCGCGCTGAACGCATCCACCGCCTCGCCCT 350
SEQIDNO_53-M.tuberculosis_C         CGCCGTGTCCTTGTGCACGATCGCGCTGAACGCATCCACCGCCTCGCCCT 350
SEQIDNO_54-M.bovisAF2122/97         CGCCGTGTCCTTGTGCACGATCGCGCTGAACGCATCCACCGCCTCGCCCT 350
SEQIDNO_55-M.bovisBCG_Pasteur1      CGCCGTGTCCTTGTGCACGATCGCGCTGAACGCATCCACCGCCTCGCCCT 350
SEQIDNO_56-M.bovisBCG_Tokyo172      CGCCGTGTCCTTGTGCACGATCGCGCTGAACGCATCCACCGCCTCGCCCT 350
SEQIDNO_57-M.microtti               CGCCGTGTCCTTGTGCACGATCGCGCTGAACGCATCCACCGCCTCGCCCT 350
SEQIDNO_58-M.canetti_CIPT14001      CGCCGTATCCTTGTGCACGATCGCGCTGAACGCATCCACCGCCTCGCCCT 350
SEQIDNO_59-M.africanum_GM04118      --------------------------------CATCCACCGCCTCGCCCT 18
SEQIDNO_76-M.capraeRIVM2006_19      --------------------------------------------------
SEQIDNO_60-M.avium_subsp_Parat      CGCCGCATCCTTGTGCACGATCGCGCTGAACGCGTCGACGGCCTCCCCCT 350
SEQIDNO_61-M.leprae_cosmid_B19      GGCTGAATCCTTGTGCACAATCGCGCTGAATGCGTCGACGGCCTCGCCTT 350
SEQIDNO_62-M.ulcerans_Agy99         CGCCGAATCCTTGTGGACGATAGCGCTGAACGCATCGACGGCCTCGCCTT 350
SEQIDNO_63-M.avium_104              CGCCGCATCCTTGTGCACGATCGCGCTGAACGCGTCGACGGCCTCCCCCT 350
SEQIDNO_64-M.vanbaalenii_PYR-1      GGCCCCGTCCTTGTGCACGATCGCCGAGAACGCGTCGACGGCCTCGCCCT 350
SEQIDNO_65-M.gilvum_PYR-GCK         GGCACCGTCCTTGTGGACGATGGCGCTGAACGCGTCGACGGCTTCGCCCT 350
SEQIDNO_66-M.abscessus              GGCCCCGTCCTTGTGGACGATGGCGCTGAACGCGTCGACCGCCTCGCCCT 350
SEQIDNO_67-M.marinum_M              CGCCGAATCCTTGTGGACGATAGCGCTGAACGCATCGACGGCCTCGCCTT 350
```

Figure 2 (cont)

```
SEQIDNO_68-M.smegmatis            CGCACCGTCCTTGTGGACGATAGCCGAGAACGCGTCGACGGCCTCGCCCT 350


SEQIDNO_47-M.tuberculosis_H37R    GCAGCAGGATGTCGACCTTGACCAGCGCGGCCTCCTGTTCGCCGGCCTCC 400
SEQIDNO_48-M.tuberculosis_H37R    GCAGCAGGATGTCGACCTTGACCAGCGCGGCCTCCTGTTCGCCGGCCTCC 400
SEQIDNO_49-M.tuberculosis_F11     GCAGCAGGATGTCGACCTTGACCAGCGCGGCCTCCTGTTCGCCGGCCTCC 400
SEQIDNO_50-M.tuberculosis_KZN1    GCAGCAGGATGTCGACCTTGACCAGCGCGGCCTCCTGTTCGCCGGCCTCC 400
SEQIDNO_51-M.tuberculosis_CDC1    GCAGCAGGATGTCGACCTTGACCAGCGCGGCCTCCTGTTCGCCGGCCTCC 400
SEQIDNO_52-M.tuberculosis_Haar    GCAGCAGGATGTCGACCTTGACCAGCGCGGCCTCCTGTTCGCCGGCCTCC 400
SEQIDNO_53-M.tuberculosis_C       GCAGCAGGATGTCGACCTTGACCAGCGCGGCCTCCTGTTCGCCGGCCTCC 400
SEQIDNO_54-M.bovisAF2122/97       GCAGCAGGATGTCGACCTTGACCAGCGCGGCCTCCTGTTCGCCGGCCTCC 400
SEQIDNO_55-M.bovisBCG_Pasteur1    GCAGCAGGATGTCGACCTTGACCAGCGCGGCCTCCTGTTCGCCGGCCTCC 400
SEQIDNO_56-M.bovisBCG_Tokyo172    GCAGCAGGATGTCGACCTTGACCAGCGCGGCCTCCTGTTCGCCGGCCTCC 400
SEQIDNO_57-M.microtti             GCAGCAGGATGTCGACCTTGACCAGCGCGGCCTCCTGTTCGCCGGCCTCC 400
SEQIDNO_58-M.canetti_CIPT14001    GCAGCAGGATGTCGACCTTGACCAGCGCGGCCTCCTGTTCGCCGGCCTCC 400
SEQIDNO_59-M.africanum_GM04118    GCAGCAGGATGTCGACCTTGACCAGCGCGGCATCCTGTTCGCCGGCCTCC 68
SEQIDNO_76-M.capraeRIVM2006_19    --------------------------------------------------
SEQIDNO_60-M.avium_subsp_Parat    GCAACAGGATGTCCACCTTGACCAGCTGGGCCTCCTGCTCGCCGGCCTCC 400
SEQIDNO_61-M.leprae_cosmid_B19    GCAGCAGGATGTCAACCTTGACCAGTTGGGCCTCCTGCTCGCCAGCCTCC 400
SEQIDNO_62-M.ulcerans_Agy99       GCAGCAGGATGTCGACCTTGACCAGTTGGGCTTCCTGCTCGCCGGACTCC 400
SEQIDNO_63-M.avium_104            GCAACAGGATGTCCACCTTGACCAGCTGGGCCTCCTGCTCGCCGGCCTCC 400
SEQIDNO_64-M.vanbaalenii_PYR-1    GCAGCAGGATGTCGACCTTGACCAGGTCGGCCTCCTGCTCGCCTGCCTCC 400
SEQIDNO_65-M.gilvum_PYR-GCK       GCAGCAGGATGTCGACCTTGACCAGGTCGGCCTCCTGCTCGCCCGCCTCC 400
SEQIDNO_66-M.abscessus            GCAGCAGGATGTCGACCTTGACCAGATCGGCCTCCTGCTCGCCGGCCTCC 400
SEQIDNO_67-M.marinum_M            GCAGCAGGATGTCGACCTTGACCAGTTGGGCTTCCTGCTCGCCGGACTCC 400
SEQIDNO_68-M.smegmatis            GCAGCAGGATGTCGACCTTGACCAGATCGGCCTCCTGCTCACCGGCCTCC 400


SEQIDNO_47-M.tuberculosis_H37R    TCGTAGTCGAGGCTGGCATAGCCGCGGGTGCGCGATTTCAGTGCGTCGAA 450
SEQIDNO_48-M.tuberculosis_H37R    TCGTAGTCGAGGCTGGCATAGCCGCGGGTGCGCGATTTCAGTGCGTCGAA 450
SEQIDNO_49-M.tuberculosis_F11     TCGTAGTCGAGGCTGGCATAGCCGCGGGTGCGCGATTTCAGTGCGTCGAA 450
SEQIDNO_50-M.tuberculosis_KZN1    TCGTAGTCGAGGCTGGCATAGCCGCGGGTGCGCGATTTCAGTGCGTCGAA 450
SEQIDNO_51-M.tuberculosis_CDC1    TCGTAGTCGAGGCTGGCATAGCCGCGGGTGCGCGATTTCAGTGCGTCGAA 450
SEQIDNO_52-M.tuberculosis_Haar    TCGTAGTCGAGGCTGGCATAGCCGCGGGTGCGCGATTTCAGTGCGTCGAA 450
SEQIDNO_53-M.tuberculosis_C       TCGTAGTCGAGGCTGGCATAGCCGCGGGTGCGCGATTTCAGTGCGTCGAA 450
SEQIDNO_54-M.bovisAF2122/97       TCGTAGTCGAGGCTGGCATAGCCGCGGGTGCGCGATTTCAGTGCGTCGAA 450
SEQIDNO_55-M.bovisBCG_Pasteur1    TCGTAGTCGAGGCTGGCATAGCCGCGGGTGCGCGATTTCAGTGCGTCGAA 450
SEQIDNO_56-M.bovisBCG_Tokyo172    TCGTAGTCGAGGCTGGCATAGCCGCGGGTGCGCGATTTCAGTGCGTCGAA 450
SEQIDNO_57-M.microtti             TCGTAGTCGAGGCTGGCATAGCCGCGGGTGCGCGATTTCAGTGCGTCGAA 450
SEQIDNO_58-M.canetti_CIPT14001    TCGTAGTCGAGGCTGGCATAGCCGCGGGTGCGCGATTTCAGTGCGTCGAA 450
SEQIDNO_59-M.africanum_GM04118    TAGTAGTCGAGGCTGGCATAGCCGCGGGTGCGCGATTTCAGTGCATCGAA 118
SEQIDNO_76-M.capraeRIVM2006_19    --------------------------------------------------
SEQIDNO_60-M.avium_subsp_Parat    TCGTAGTCCAGGCTGGCGTAGCCGCGGGTCCGCGACTTCAGCGAGTCGAA 450
SEQIDNO_61-M.leprae_cosmid_B19    TCATAGTCGAGGCTAGCGTAGCCCCGGGTGCGTGACTTCAGCGAATCGAA 450
SEQIDNO_62-M.ulcerans_Agy99       TCGTAATCGAGACTGGCGTAGCCACGGGTCCGCGATATGAGCGAGTCGAA 450
SEQIDNO_63-M.avium_104            TCGTAGTCCAGGCTGGCGTAGCCGCGGGTCCGCGACTTCAGCGAGTCGAA 450
SEQIDNO_64-M.vanbaalenii_PYR-1    TCGTAGTCCAGGCTGGCGTAGCCGCGGGTGCGCGATTTCAGCGAGTCGAA 450
SEQIDNO_65-M.gilvum_PYR-GCK       TCGTAGTCGAGGCTCGCGTAGCCGCGGGTGCGGGACTTCAGCGAGTCGAA 450
SEQIDNO_66-M.abscessus            TCGTAATCCAGGCTGGCGTAGCCGCGCGTACGCGACTTCAACGAGTCGAA 450
SEQIDNO_67-M.marinum_M            TCGTAATCGAGACTGGCGTAGCCACGGGTCCGCGACTTGAGCGAGTCGAA 450
SEQIDNO_68-M.smegmatis            TCGTAGTCGAGGCTCGCGTAGCCGCGGGTGCGGGACTTCAGCGAGTCGAA 450


SEQIDNO_47-M.tuberculosis_H37R    GAAGTCGAAGATGATCTCGCCGAGCGGCATGGTGTAGCGCAGTTCCACCC 500
SEQIDNO_48-M.tuberculosis_H37R    GAAGTCGAAGATGATCTCGCCGAGCGGCATGGTGTAGCGCAGTTCCACCC 500
SEQIDNO_49-M.tuberculosis_F11     GAAGTCGAAGATGATCTCGCCGAGCGGCATGGTGTAGCGCAGTTCCACCC 500
SEQIDNO_50-M.tuberculosis_KZN1    GAAGTCGAAGATGATCTCGCCGAGCGGCATGGTGTAGCGCAGTTCCACCC 500
SEQIDNO_51-M.tuberculosis_CDC1    GAAGTCGAAGATGATCTCGCCGAGCGGCATGGTGTAGCGCAGTTCCACCC 500
SEQIDNO_52-M.tuberculosis_Haar    GAAGTCGAAGATGATCTCGCCGAGCGGCATGGTGTAGCGCAGTTCCACCC 500
SEQIDNO_53-M.tuberculosis_C       GAAGTCGAAGATGATCTCGCCGAGCGGCATGGTGTAGCGCAGTTCCACCC 500
SEQIDNO_54-M.bovisAF2122/97       GAAGTCGAAGATGATCTCGCCGAGCGGCATGGTGTAGCGCAGTTCCACCC 500
SEQIDNO_55-M.bovisBCG_Pasteur1    GAAGTCGAAGATGATCTCGCCGAGCGGCATGGTGTAGCGCAGTTCCACCC 500
SEQIDNO_56-M.bovisBCG_Tokyo172    GAAGTCGAAGATGATCTCGCCGAGCGGCATGGTGTAGCGCAGTTCCACCC 500
SEQIDNO_57-M.microtti             GAAGTCGAAGATGATCTCGCCGAGCGGCATGGTGTAGCGCAGTTCCACCC 500
SEQIDNO_58-M.canetti_CIPT14001    GAAGTCGAAGATGATCTCGCCGAGCGGCATGGTGTAGCGCAGTTCCACCC 500
SEQIDNO_59-M.africanum_GM04118    GAAGTCGAAGATGATCTCGCCGAGCGGCATGGTGTAGCGCAGTTCCACCC 168
SEQIDNO_76-M.capraeRIVM2006_19    ------------------------CGGCATGGTGTAGCGCAGTTCCACCC 26
SEQIDNO_60-M.avium_subsp_Parat    GAAGTCGAAGATGATCTCGCCCAACGGCATGGTGTAGCGCAGCTCAACCC 500
SEQIDNO_61-M.leprae_cosmid_B19    GAAATCGAAGATGATTTCCCCGAGCGGCATAATGTAGCGTAACTCGACTC 500
SEQIDNO_62-M.ulcerans_Agy99       GAAGTCAAAGATGATCTCCCCCAACGGCATTGTGTATCGCAGTTCCACCC 500
SEQIDNO_63-M.avium_104            GAAGTCGAAGATGATCTCGCCCAACGGCATGGTGTAGCGCAGCTCGACCC 500
SEQIDNO_64-M.vanbaalenii_PYR-1    GAAGTCGAAGATGATCTCGCCCAGCGGCATGGTGTAGCGCAGCTCGACGC 500
SEQIDNO_65-M.gilvum_PYR-GCK       GAAGTCGAAGATGATCTCGCCCAGCGGCATCGTGTAGCGCAGCTCGACCC 500
SEQIDNO_66-M.abscessus            GAAGTCGAAGATGATCTCGCCCAACGGCATCGTGTAGCGCAGCTCGACGC 500
SEQIDNO_67-M.marinum_M            GAAGTCAAAGATGATCTCCCCCAACGGCATTGTGTATCGCAGTTCCACCC 500
SEQIDNO_68-M.smegmatis            GAAGTCGAAGATGATCTCGCCCAACGGCATGATGTAGCGCAGTTCGACAC 500
                                                          ****** **** ** *  ** ** *

SEQIDNO_47-M.tuberculosis_H37R    GCTCGGGGGAGAGATAGTCCATGCCGCCCAACTCGCCGCGGCGCGACTGG 550
SEQIDNO_48-M.tuberculosis_H37R    GCTCGGGGGAGAGATAGTCCATGCCGCCCAACTCGCCGCGGCGCGACTGG 550
SEQIDNO_49-M.tuberculosis_F11     GCTCGGGGGAGAGATAGTCCATGCCGCCCAACTCGCCGCGGCGCGACTGG 550
SEQIDNO_50-M.tuberculosis_KZN1    GCTCGGGGGAGAGATAGTCCATGCCGCCCAACTCGCCGCGGCGCGACTGG 550
SEQIDNO_51-M.tuberculosis_CDC1    GCTCGGGGGAGAGATAGTCCATGCCGCCCAACTCGCCGCGGCGCGACTGG 550
SEQIDNO_52-M.tuberculosis_Haar    GCTCGGGGGAGAGATAGTCCATGCCGCCCAACTCGCCGCGGCGCGACTGG 550
SEQIDNO_53-M.tuberculosis_C       GCTCGGGGGAGAGATAGTCCATGCCGCCCAACTCGCCGCGGCGCGACTGG 550
SEQIDNO_54-M.bovisAF2122/97       GCTCGGGGGAGAGATAGTCCATGCCGCCCAACTCGCCGCGGCGCGACTGG 550
SEQIDNO_55-M.bovisBCG_Pasteur1    GCTCGGGGGAGAGATAGTCCATGCCGCCCAACTCGCCGCGGCGCGACTGG 550
SEQIDNO_56-M.bovisBCG_Tokyo172    GCTCGGGGGAGAGATAGTCCATGCCGCCCAACTCGCCGCGGCGCGACTGG 550
```

Figure 2 (cont)

```
SEQIDNO_57-M.microtti              GCTCGGGGGAGAGATAGTCCATGCCGCCCAACTCGCCGCGGCGCGACTGG 550
SEQIDNO_58-M.canetti_CIPT14001     GCTCGGGGGAGAGATAGTCCATGCCGCCCAACTCGCCGCGGCGCGACTGG 550
SEQIDNO_59-M.africanum_GM04118     GCTCGGCGGAGAGATAGTCCATGCCGCCCAACTCGCCGCGGCGCGACTGG 218
SEQIDNO_76-M.capraeRIVM2006_19     GCTCGGGGGAGAGATAGTCCATGCCGCCCAACTCGCCGCGGCGCGACTGG 76
SEQIDNO_60-M.avium_subsp_Parat     GTTCCGGCGACAGGTAATCCATGCCGCCCAGCTCGCCGCGGCGGGACTGG 550
SEQIDNO_61-M.leprae_cosmid_B19     GCTCAGGTGAAAGATAGTCCATGCCACCTAATTCGCCACGGCGCGACTGG 550
SEQIDNO_62-M.ulcerans_Agy99        GTTCGGGCGACAAATAGTCCATGCCCCCCAGCTCGCCGCGCCGCGACTGG 550
SEQIDNO_63-M.avium_104             GTTCCGGCGACAGGTAATCCATGCCGCCCAGCTCGCCGCGGCGGGACTGG 550
SEQIDNO_64-M.vanbaalenii_PYR-1     GCTCGGGCGACAGGTAGTCCATTCCGCCGAGTTCACCGCGCCGCGACTGG 550
SEQIDNO_65-M.gilvum_PYR-GCK        GCTCGGGTGACAGGTAGTCCATGCCGCCGAGCTCGCCACGGCGCGACTGG 550
SEQIDNO_66-M.abscessus             GTTCGGGTGACAGGTAGTCCATGCCGCCGAGCTCGCCGCGCCGCGATTGG 550
SEQIDNO_67-M.marinum_M             GTTCGGGCGACAAATAGTCCATGCCCCCCAGCTCGCCGCGCCGCGACTGG 550
SEQIDNO_68-M.smegmatis             GCTCGGGCGACAGGTAGTCCATGCCCTGCAGTTCGCCGCGACGGGACTGG 550
                                   * ** *   ** *  ** ***** **     *  ** ** ** ** ** ***

SEQIDNO_47-M.tuberculosis_H37R     CACAGCTCCATGATGGTGCCGATGAACTCGCTGGGCGCGATGATGGTGGT 600
SEQIDNO_48-M.tuberculosis_H37R     CACAGCTCCATGATGGTGCCGATGAACTCGCTGGGCGCGATGATGGTGGT 600
SEQIDNO_49-M.tuberculosis_F11      CACAGCTCCATGATGGTGCCGATGAACTCGCTGGGCGCGATGATGGTGGT 600
SEQIDNO_50-M.tuberculosis_KZN1     CACAGCTCCATGATGGTGCCGATGAACTCGCTGGGCGCGATGATGGTGGT 600
SEQIDNO_51-M.tuberculosis_CDC1     CACAGCTCCATGATGGTGCCGATGAACTCGCTGGGCGCGATGATGGTGGT 600
SEQIDNO_52-M.tuberculosis_Haar     CACAGCTCCATGATGGTGCCGATGAACTCGCTGGGCGCGATGATGGTGGT 600
SEQIDNO_53-M.tuberculosis_C        CACAGCTCCATGATGGTGCCGATGAACTCGCTGGGCGCGATGATGGTGGT 600
SEQIDNO_54-M.bovisAF2122/97        CACAGCTCCATGATGGTGCCGATGAACTCGCTGGGCGCGATGATGGTGGT 600
SEQIDNO_55-M.bovisBCG_Pasteur1     CACAGCTCCATGATGGTGCCGATGAACTCGCTGGGCGCGATGATGGTGGT 600
SEQIDNO_56-M.bovisBCG_Tokyo172     CACAGCTCCATGATGGTGCCGATGAACTCGCTGGGCGCGATGATGGTGGT 600
SEQIDNO_57-M.microtti              CACAGCTCCATGATGGTGCCGATGAACTCGCTGGGCGCGATGATGGTGGT 600
SEQIDNO_58-M.canetti_CIPT14001     CACAGCTCCATGATGGTGCCGATGAACTCGCTGGGCGCGATGATGGTGGT 600
SEQIDNO_59-M.africanum_GM04118     CACAGCTCCATGATGGTGCCGATGAACTCGCTGGGCGCGATGATGGTGGT 268
SEQIDNO_76-M.capraeRIVM2006_19     CACAGCTCCATGATGGTGCCGATGAACTCGCTGGGCGCGATGATGGTGGT 126
SEQIDNO_60-M.avium_subsp_Parat     CACAGCTCCATGATGGTGCCGATGAATTCGCTGGGCGCGATGATGGTGGT 600
SEQIDNO_61-M.leprae_cosmid_B19     CACAGCTCCATGATCGTTCCGATGAACTCGCTGGGCGCAATGATGGTGAT 600
SEQIDNO_62-M.ulcerans_Agy99        CACAGCTCCATGATGGTGCCGATGAATTCGCTGGGCGCGATGATGGTGGT 600
SEQIDNO_63-M.avium_104             CACAGCTCCATGATGGTGCCGATGAATTCGCTGGGCGCGATGATGGTGGT 600
SEQIDNO_64-M.vanbaalenii_PYR-1     CACAGCTCCATGATCGTGCCGATGAACTCGCTGGGCGCGATCACCGTCGT 600
SEQIDNO_65-M.gilvum_PYR-GCK        CACAGCTCCATGATCGTTCCGATGAACTCACTCGGCGCGATCACCGTCGT 600
SEQIDNO_66-M.abscessus             CACAGCTCCATGATCGAACCGATGAATTCACTCGGCGCGATCACCGTCGT 600
SEQIDNO_67-M.marinum_M             CACAGCTCCATGATGGTGCCGATGAATTCGCTGGGCGCGATGATGGTGGT 600
SEQIDNO_68-M.smegmatis             CACAGCTCCATGATGGTGCCGATGAACTCGCTGGGCGCGATGATCGTGGT 600
                                   ************** *  ******** ** ** ***** ** *  **  *
```

SEQ ID NO : 173 - MTC_FW (Position 618-634 bp)
AGACCGTGCGGATCTTG

SEQ ID NO : 174 - MTC_RV (Position 755-772 bp)
CATGGAGATCACCCGTGA

SEQ ID NO : 175 - MTC_Probe(Position 655-675 bp)
ATTGGTCACCCGGATTTCGGT

```
FORWARD PRIMER                                       AGACCGTGCGGATCTTG
SEQIDNO_47-M.tuberculosis_H37R     CTTGACGACGGGCTCGT[redacted]CCCTCCGG-CCAGTCC 649
SEQIDNO_48-M.tuberculosis_H37R     CTTGACGACGGGCTCGTAGACCGTGCGGATCTTGCCCTCCGG-CCAGTCC 649
SEQIDNO_49-M.tuberculosis_F11      CTTGACGACGGGCTCGTAGACCGTGCGGATCTTGCCCTCCGG-CCAGTCC 649
SEQIDNO_50-M.tuberculosis_KZN1     CTTGACGACGGGCTCGTAGACCGTGCGGATCTTGCCCTCCGG-CCAGTCC 649
SEQIDNO_51-M.tuberculosis_CDC1     CTTGACGACGGGCTCGTAGACCGTGCGGATCTTGCCCTCCGG-CCAGTCC 649
SEQIDNO_52-M.tuberculosis_Haar     CTTGACGACGGGCTCGTAGACCGTGCGGATCTTGCCCTCCGG-CCAGTCC 649
SEQIDNO_53-M.tuberculosis_C        CTTGACGACGGGCTCGTAGACCGTGCGGATCTTGCCCTCCGG-CCAGTCC 649
SEQIDNO_54-M.bovisAF2122/97        CTTGACGACGGGCTCGTAGACCGTGCGGATCTTGCCCTCCGG-CCAGTCC 649
SEQIDNO_55-M.bovisBCG_Pasteur1     CTTGACGACGGGCTCGTAGACCGTGCGGATCTTGCCCTCCGG-CCAGTCC 649
SEQIDNO_56-M.bovisBCG_Tokyo172     CTTGACGACGGGCTCGTAGACCGTGCGGATCTTGCCCTCCGG-CCAGTCC 649
SEQIDNO_57-M.microtti              CTTGACGACGGGCTCGTAGACCGTGCGGATCTTGCCCTCCGG-CCAGTCC 649
SEQIDNO_58-M.canetti_CIPT14001     CTTGACGACGGGCTCGTAGACCGTGCGGATCTTGCCCTCCGG-CCAGTCC 649
SEQIDNO_59-M.africanum_GM04118     CTCAACGACGGGCTCGTAGACCTTGCGGATCTTGCCCTCCGGACCAGTCC 318
SEQIDNO_76-M.capraeRIVM2006_19     CTTGACGACGGGCTCGTAGACCGTGCGGATCTTGCCCTCCGG-CCAGTCC 175
SEQIDNO_60-M.avium_subsp_Parat     CTTGACCACCGGCTCGTA[redacted]ACCGTGCG[redacted]A[redacted]CTTGCCCTCGGG-CCAGTCC 649
SEQIDNO_61-M.leprae_cosmid_B19     CTTCACCACTGGCTCGTA[redacted]ACCGT[redacted]CGGATCTTGCCCTCCGG-CCAGTCT 649
SEQIDNO_62-M.ulcerans_Agy99        CTTCACCACCGGCTCGTAGACGGTGCGGATCTTGCCCTCGGG-CCAGTCC 649
SEQIDNO_63-M.avium_104             CTTGACCACCGGCTCGTA[redacted]ACCGTGCG[redacted]A[redacted]CTTGCCCTCGGG-CCAGTCC 649
SEQIDNO_64-M.vanbaalenii_PYR-1     CTTGACCACCGGCTCGAA[redacted]ACCG[redacted]CG[redacted]ACCTTGCCCTCGGG-CCAGTCC 649
SEQIDNO_65-M.gilvum_PYR-GCK        CTTGACGACCGGCTCGAA[redacted]ACCG[redacted]CG[redacted]A[redacted]CTTGCCCTCGGG-CCAGTCC 649
SEQIDNO_66-M.abscessus             CTTGACCACCGGCTCGAA[redacted]ACCG[redacted]CGGATCTTGCCCTCGGG-CCAGATG 649
SEQIDNO_67-M.marinum_M             CTTCACCACCGGCTCGTAGAC[redacted]GTGCGGATCTTGCCCTCGGG-CCAGTCC 649
SEQIDNO_68-M.smegmatis             CTTCACGACGGGCTCGAA[redacted]ACCGTGCGGATCTTGCCTTCCGG-CCAGTCC 649
                                   **   ** ** ****** * **     ** * ****** ** ** ****
```

Figure 2 (cont)

```
MTC PROBE                                   ATTGGTCACCCGGATTTCGGT
SEQIDNO_47-M.tuberculosis_H37R        GACGGATTGGTCACCCGGATTTCGGTCCGTCG--------TC-TT----  686
SEQIDNO_48-M.tuberculosis_H37R        GACGGATTGGTCACCCGGATTTCGGTCCGTCG--------TC-TT----  686
SEQIDNO_49-M.tuberculosis_F11         GACGGATTGGTCACCCGGATTTCGGTCCGTCG--------TC-TT----  686
SEQIDNO_50-M.tuberculosis_KZN1        GACGGATTGGTCACCCGGATTTCGGTCCGTCG--------TC-TT----  686
SEQIDNO_51-M.tuberculosis_CDC1        GACGGATTGGTCACCCGGATTTCGGTCCGTCG--------TC-TT----  686
SEQIDNO_52-M.tuberculosis_Haar        GACGGATTGGTCACCCGGATTTCGGTCCGTCG--------TC-TT----  686
SEQIDNO_53-M.tuberculosis_C           GACGGATTGGTCACCCGGATTTCGGTCCGTCG--------TC-TT----  686
SEQIDNO_54-M.bovisAF2122/97           GACGGATTGGTCACCCGGATTTCGGTCCGTCG--------TC-TT----  686
SEQIDNO_55-M.bovisBCG_Pasteur1        GACGGATTGGTCACCCGGATTTCGGTCCGTCG--------TC-TT----  686
SEQIDNO_56-M.bovisBCG_Tokyo172        GACGGATTGGTCACCCGGATTTCGGTCCGTCG--------TC-TT----  686
SEQIDNO_57-M.microtti                 GACGGATTGGTCACCCGGATTTCGGTCCGTCG--------TC-TT----  686
SEQIDNO_58-M.canetti_CIPT14001        GACGGATTGGTCACCCGGATTTCGGTCCGTCG--------TC-TT----  686
SEQIDNO_59-M.africanum_GM04118        GACGGATTGGTCACCCGGATTTCGGTCCGTCG--------TC-TT----  355
SEQIDNO_76-M.capraeRIVM2006_19        GACGGATTGGTCACCCGGATTTCGGTCCGTCG--------TC-TT----  212
SEQIDNO_60-M.avium_subsp_Parat        GACGGTTTGGTCACCCGGATTTCGGTCCGTCG--------TCGTT----  687
SEQIDNO_61-M.leprae_cosmid_B19        GACGGTTTGGTCACCCGGATTTCGGTTGGTCG--------TCGTTG---  688
SEQIDNO_62-M.ulcerans_Agy99           GACGGTTTGGTCACCCGGATTTCGGTCCGTCG--------TCGTT----  687
SEQIDNO_63-M.avium_104                GACGGTTTGGTCACCCGGATTTCGGTCCGTCC--------TCGTT----  687
SEQIDNO_64-M.vanbaalenii_PYR-1        GAGGGTTTGGTCACGCGGATTTCGGTCCGTCG--------TCGTT----  687
SEQIDNO_65-M.gilvum_PYR-GCK           GACGGTTTGGTCACCCGGATCCCGGCCGGTCG--------TCGTT----  687
SEQIDNO_66-M.abscessus                GACGGATTGGTCACCCGGATTCCGGATCGTCGCCGGCCGGTCGTTCGGG  699
SEQIDNO_67-M.marinum_M                GACGGTTTGGTCACCCGGATTTCGGTCCGTCG--------TCGTT----  687
SEQIDNO_68-M.smegmatis                GACGGTTTGGTCACGCGGATTTCGGACCGTCG--------      ---  688
                                      ** ** ** ** **         *        **       **
IAC Probe                                     ACGACCTTCTCGGAACCGT
M. caprae probe (Reverse compliment of SEQ ID NO: 166)    TCG       TC TT

SEQIDNO_47-M.tuberculosis_H37R        TGTGCACCCGATACACCACATTGGGTGAGGTCGAGATCAGGTCCAGGCCG 736
SEQIDNO_48-M.tuberculosis_H37R        TGTGCACCCGATACACCACATTGGGTGAGGTCGAGATCAGGTCCAGGCCG 736
SEQIDNO_49-M.tuberculosis_F11         TGTGCACCCGATACACCACATTGGGTGAGGTCGAGATCAGGTCCAGGCCG 736
SEQIDNO_50-M.tuberculosis_KZN1        TGTGCACCCGATACACCACATTGGGTGAGGTCGAGATCAGGTCCAGGCCG 736
SEQIDNO_51-M.tuberculosis_CDC1        TGTGCACCCGATACACCACATTGGGTGAGGTCGAGATCAGGTCCAGGCCG 736
SEQIDNO_52-M.tuberculosis_Haar        TGTGCACCCGATACACCACATTGGGTGAGGTCGAGATCAGGTCCAGGCCG 736
SEQIDNO_53-M.tuberculosis_C           TGTGCACCCGATACACCACATTGGGTGAGGTCGAGATCAGGTCCAGGCCG 736
SEQIDNO_54-M.bovisAF2122/97           TGTGCACCCGATACACCACATTGGGTGAGGTCGAGATCAGGTCCAGGCCG 736
SEQIDNO_55-M.bovisBCG_Pasteur1        TGTGCACCCGATACACCACATTGGGTGAGGTCGAGATCAGGTCCAGGCCG 736
SEQIDNO_56-M.bovisBCG_Tokyo172        TGTGCACCCGATACACCACATTGGGTGAGGTCGAGATCAGGTCCAGGCCG 736
SEQIDNO_57-M.microtti                 TGTGCACCCGATACACCACATTGGGTGAGGTCGAGATCAGGTCCAGGCCG 736
SEQIDNO_58-M.canetti_CIPT14001        TGTGCACCCGGTACACCACATTGGGTGAAGTCGAGATCAGGTCCAGGCCG 736
SEQIDNO_59-M.africanum_GM04118        CGTGCACCCGATACACCACATTGGGTGAGGTCGAGATCAGGTCCAGGCCG 405
SEQIDNO_76-M.capraeRIVM2006_19        TGTGTACCCGATACACCACATTGGGTGAGGTCGAGATCAGGTCCAGGCCG 262
SEQIDNO_60-M.avium_subsp_Parat        GCTCCACCCGCTACACCACGTTGGGCGACGTCGAGATCAGGTCGAGGTCG 736
SEQIDNO_61-M.leprae_cosmid_B19        GCCCCACGCGCTATACGACGTTGGGCGACGTGGAGATCAGGTCCAGGTCG 736
SEQIDNO_62-M.ulcerans_Agy99           GCTGCACGCGCTACACGACGTTGGGCGAGGTCGAGATCAGGTCGAGGTCG 736
SEQIDNO_63-M.avium_104                GCTCCACCCGCTACACCACGTTGGGCGACGTCGAGATCAGGTCGAGGTCG 736
SEQIDNO_64-M.vanbaalenii_PYR-1        GCCGCACGCGCTAGACCACGTTGGGCGCGGTCGAGATCAGGTCCAGGTTG 736
SEQIDNO_65-M.gilvum_PYR-GCK           GCTGCACGCGCTAGACGACGTTGGGCGCGGTCGAGATCAGGTCGAGGTTG 736
SEQIDNO_66-M.abscessus                GCTCCACCCGCTACACCACGTTGGGAGCCGTCGAGATGAGGTCGAGGTTG 748
SEQIDNO_67-M.marinum_M                GCTGCACGCGCTACACGACGTTGGGCGAGGTCGAGATCAGGTCGAGGTCG 736
SEQIDNO_68-M.smegmatis                GCCCCACGCGCTACACCACGTTGGGTGAGGTGGAGATCAGCTCCAGGCCG 736
                                          ** **  ** ** ** ***** *   ** ***** ***** ***  *
M. caprae probe                       TGTGTACCCGATA

REVERSE PRIMER (Reverse somplIment of SEQ ID NO 165)  TCACGGGTGATCTCCATG
SEQIDNO_47-M.tuberculosis_H37R        AACTCGCGCTCAAGGCGCTCACGGGTGATCTCCATGTGCA-GCAGGCCCA 785
SEQIDNO_48-M.tuberculosis_H37R        AACTCGCGCTCAAGGCGCTCACGGGTGATCTCCATGTGCA-GCAGGCCCA 785
SEQIDNO_49-M.tuberculosis_F11         AACTCGCGCTCAAGGCGCTCACGGGTGATCTCCATGTGCA-GCAGGCCCA 785
SEQIDNO_50-M.tuberculosis_KZN1        AACTCGCGCTCAAGGCGCTCACGGGTGATCTCCATGTGCA-GCAGGCCCA 785
SEQIDNO_51-M.tuberculosis_CDC1        AACTCGCGCTCAAGGCGCTCACGGGTGATCTCCATGTGCA-GCAGGCCCA 785
SEQIDNO_52-M.tuberculosis_Haar        AACTCGCGCTCAAGGCGCTCACGGGTGATCTCCATGTGCA-GCAGGCCCA 785
SEQIDNO_53-M.tuberculosis_C           AACTCGCGCTCAAGGCGCTCACGGGTGATCTCCATGTGCA-GCAGGCCCA 785
SEQIDNO_54-M.bovisAF2122/97           AACTCGCGCTCAAGGCGCTCACGGGTGATCTCCATGTGCA-GCAGGCCCA 785
SEQIDNO_55-M.bovisBCG_Pasteur1        AACTCGCGCTCAAGGCGCTCACGGGTGATCTCCATGTGCA-GCAGGCCCA 785
SEQIDNO_56-M.bovisBCG_Tokyo172        AACTCGCGCTCAAGGCGCTCACGGGTGATCTCCATGTGCA-GCAGGCCCA 785
SEQIDNO_57-M.microtti                 AACTCGCGCTCAAGGCGCTCACGGGTGATCTCCATGTGCA-GCAGGCCCA 785
SEQIDNO_58-M.canetti_CIPT14001        AACTCGCGCTCAAGGCGCTCACGGGTGATCTCCATGTGCA-GCAGGCCCA 785
SEQIDNO_59-M.africanum_GM04118        AACTCGCGCTCAAGGCGCTCACGGGTGATCTCCATGTGCATGCAGGCCCA 455
SEQIDNO_76-M.capraeRIVM2006_19        AACTCGCGCTCAAGGCGCTCACGGGTGATCTCCATGTGCA-GCAGGCCCA 311
SEQIDNO_60-M.avium_subsp_Parat        AACTCGCGCTCCAGGCGCTCGCGGGTGATCTCCATGTGCA-GCAAACCCA 785
SEQIDNO_61-M.leprae_cosmid_B19        AACTCGCGCTCTAAGCGTTCGCGGGTCATCTCGATGTGCA-GCAAACCGA 785
SEQIDNO_62-M.ulcerans_Agy99           AACTCGCGCTCCAGACGTTCGCGCCTGATCTCCATGTGCA-GCAGGCCCA 785
SEQIDNO_63-M.avium_104                AACTCGCGCTCCAGGCGCTCGCGGGTGATCTCCATGTGCA-GCAAACCCA 785
SEQIDNO_64-M.vanbaalenii_PYR-1        AACTCGCGCTCCAGGCGTTCGCGGGTGATCTCCATGTGCA-GCAGCCCGA 785
SEQIDNO_65-M.gilvum_PYR-GCK           AACTCGCGTTCGAGCCGCTCGCGCGTGATCTCCATGTGCA-GCAAGCCCA 785
SEQIDNO_66-M.abscessus                AACTCGCGTTCGAGGCGCTCACGGGTGATCTCCATGTGCA-GCAATCCCA 797
SEQIDNO_67-M.marinum_M                AACTCGCGCTCCAGACGTTCGCGCCTGATCTCCATGTGCA-GCAGGCCCA 785
SEQIDNO_68-M.smegmatis                AACTCGCGCTCCAGGCGTTCACGGGTGATCTGCATGTGCA-GCAGTCCGA 785
                                      ******** ** *  ** ** **  * ** ** ******* ***  ** *

SEQIDNO_47-M.tuberculosis_H37R        AGAAACCGCACCGGAACCCAAAACCCAGCGCCACCGAGGTTTCCGGCTCA 835
SEQIDNO_48-M.tuberculosis_H37R        AGAAACCGCACCGGAACCCAAAACCCAGCGCCACCGAGGTTTCCGGCTCA 835
SEQIDNO_49-M.tuberculosis_F11         AGAAACCGCACCGGAACCCAAAACCCAGCGCCACCGAGGTTTCCGGCTCA 835
SEQIDNO_50-M.tuberculosis_KZN1        AGAAACCGCACCGGAACCCAAAACCCAGCGCCACCGAGGTTTCCGGCTCA 835
SEQIDNO_51-M.tuberculosis_CDC1        AGAAACCGCACCGGAACCCAAAACCCAGCGCCACCGAGGTTTCCGGCTCA 835
SEQIDNO_52-M.tuberculosis_Haar        AGAAACCGCACCGGAACCCAAAACCCAGCGCCACCGAGGTTTCCGGCTCA 835
```

Figure 2 (cont)

```
SEQIDNO_53-M.tuberculosis_C        AGAAACCGCACCGGAACCCAAAACCCAGCGCCACCGAGGTTTCCGGCTCA 835
SEQIDNO_54-M.bovisAF2122/97        AGAAACCGCACCGGAACCCAAAACCCAGCGCCACCGAGGTTTCCGGCTCA 835
SEQIDNO_55-M.bovisBCG_Pasteur1     AGAAACCGCACCGGAACCCAAAACCCAGCGCCACCGAGGTTTCCGGCTCA 835
SEQIDNO_56-M.bovisBCG_Tokyo172     AGAAACCGCACCGGAACCCAAAACCCAGCGCCACCGAGGTTTCCGGCTCA 835
SEQIDNO_57-M.microtti              AGAAACCGCACCGGAACCCAAAACCCAGCGCCACCGAGGTTTCCGGCTCA 835
SEQIDNO_58-M.canetti_CIPT14001     AGAAACCGCACCGGAACCCAAAACCCAGCGCCACCGAGGTTTCCGGCTCA 835
SEQIDNO_59-M.africanum_GM04118     AGAAACCGCACCGGAACCCAAAACCCAGCGCCACCGAGGTTTCCGGCTCA 505
SEQIDNO_76-M.capraeRIVM2006_19     AGAAACCGCACCGGAACCCAAAACCCAGCGCCACCGAGGTTTCCGGCTCA 361
SEQIDNO_60-M.avium_subsp_Parat     AAAAGCCACAACGGAATCCGCAGCCCAGCGCCACCGATGTCTCCGGTTCG 835
SEQIDNO_61-M.leprae_cosmid_B19     GGAAGCCGCACCGGTACCCAACGCCCAGCGCCACCGATGTTTCCGGCTCG 835
SEQIDNO_62-M.ulcerans_Agy99        GGAAGCCGCACCGGAATCCGAAACCCAGCGCCACCGACGTTTCGGGCTCA 835
SEQIDNO_63-M.avium_104             AAAAGCCGCAACGGAATCCGAAGCCCAGCGCCACCGACGTCTCCGGTTCG 835
SEQIDNO_64-M.vanbaalenii_PYR-1     GGAACCCGCAGCGGAACCCGAACCCGAGCGCCACCGACGTCTCGGGTTCG 835
SEQIDNO_65-M.gilvum_PYR-GCK        GGAAGCCGCAGCGGAAGCCGAACCCGAGCGCGACCGACGTCTCCGGCTCG 835
SEQIDNO_66-M.abscessus             GGAAGCCACAACGGAATCCGAAGCCCAGCGCCACCGAGGTCTCCGGCTCG 847
SEQIDNO_67-M.marinum_M             GGAAGCCGCACCGGAATCCGAAACCCAGCGCCACCGACGTTTCGGGCTCA 835
SEQIDNO_68-M.smegmatis             GGAAGCCGCAGCGGAACCCGAAGCCCAGGGCCACCGAGGTCTCCGGCTCA 835
                                     ** ** ** *** * **     ** ** ** ***** ** ** ** **

SEQIDNO_47-M.tuberculosis_H37R     TAGGTCAAGGCCGCGTCGTTGAGCTGCAGCTTGTCCAGGGCGTCGCGCAG 885
SEQIDNO_48-M.tuberculosis_H37R     TAGGTCAAGGCCGCGTCGTTGAGCTGCAGCTTGTCCAGGGCGTCGCGCAG 885
SEQIDNO_49-M.tuberculosis_F11      TAGGTCAAGGCCGCGTCGTTGAGCTGCAGCTTGTCCAGGGCGTCGCGCAG 885
SEQIDNO_50-M.tuberculosis_KZN1     TAGGTCAAGGCCGCGTCGTTGAGCTGCAGCTTGTCCAGGGCGTCGCGCAG 885
SEQIDNO_51-M.tuberculosis_CDC1     TAGGTCAAGGCCGCGTCGTTGAGCTGCAGCTTGTCCAGGGCGTCGCGCAG 885
SEQIDNO_52-M.tuberculosis_Haar     TAGGTCAAGGCCGCGTCGTTGAGCTGCAGCTTGTCCAGGGCGTCGCGCAG 885
SEQIDNO_53-M.tuberculosis_C        TAGGTCAAGGCCGCGTCGTTGAGCTGCAGCTTGTCCAGGGCGTCGCGCAG 885
SEQIDNO_54-M.bovisAF2122/97        TAGGTCAAGGCCGCGTCGTTGAGCTGCAGCTTGTCCAGGGCGTCGCGCAG 885
SEQIDNO_55-M.bovisBCG_Pasteur1     TAGGTCAAGGCCGCGTCGTTGAGCTGCAGCTTGTCCAGGGCGTCGCGCAG 885
SEQIDNO_56-M.bovisBCG_Tokyo172     TAGGTCAAGGCCGCGTCGTTGAGCTGCAGCTTGTCCAGGGCGTCGCGCAG 885
SEQIDNO_57-M.microtti              TAGGTCAAGGCCGCGTCGTTGAGCTGCAGCTTGTCCAGGGCGTCGCGCAG 885
SEQIDNO_58-M.canetti_CIPT14001     TAGGTCAAGGCCGCGTCGTTGAGCTGCAGCTTGTCCAGGGCGTCGCGCAG 885
SEQIDNO_59-M.africanum_GM04118     TAGGTCAAGGCCGCGTCGTTGAGCTGCAGCTTGTCCAGGGCGTCGCGCAG 555
SEQIDNO_76-M.capraeRIVM2006_19     TAGGTCAAGGCCGCGTCGTTGAGCTGCAGCTTGTCCAGGGCGTCGCGCAG 411
SEQIDNO_60-M.avium_subsp_Parat     TAGGTGAGCGCGGCGTCGTTGAGCCGCAGCCGGTCCAGCGCGTCGCGCAG 885
SEQIDNO_61-M.leprae_cosmid_B19     TAGGTCAGCGCCGCGTCGTTGAGCTGTAACTTACCTAGAGCGTCACGCAA 885
SEQIDNO_62-M.ulcerans_Agy99        TAGGTCAGGGCCGCGTCGTTGAGCTGCAGCTTGTCCAGGGCGTCCCGCAG 885
SEQIDNO_63-M.avium_104             TAGGTGAGCGCGGCGTCGTTGAGCCGCAGCCGGTCCAGCGCGTCGCGCAG 885
SEQIDNO_64-M.vanbaalenii_PYR-1     TACGTCAGCGCCGCGTCGTTGAGTTGCAGCTTGTCCAGCGCCTCGCGCAG 885
SEQIDNO_65-M.gilvum_PYR-GCK        TAAGTCAGTGCCGCGTCGTTCAGCTGCAGTTTGTCGAGCGCCTCGCGCAA 885
SEQIDNO_66-M.abscessus             TAGGTGAGCGCGGCGTCGTTGAGCTGGAGTTTGTCCAGCGCCTCGCGCAG 897
SEQIDNO_67-M.marinum_M             TAGGTCAGGGCCGCGTCGTTGAGCTGCAGCTTGTCCAGGGCGTCCCGCAG 885
SEQIDNO_68-M.smegmatis             TACGTCAGTGCGGCGTCGTTGAGTTGCAGCTTGTCCAGCGCGTCACGCAG 885
                                   ** ** *  ** ******** **  * *       * ** ** ** ****

SEQIDNO_47-M.tuberculosis_H37R     GTTCGGGTAGTCCGAACCGTCGACCGGATACAACCCCGAGTAGACCATCG 935
SEQIDNO_48-M.tuberculosis_H37R     GTTCGGGTAGTCCGAACCGTCGACCGGATACAACCCCGAGTAGACCATCG 935
SEQIDNO_49-M.tuberculosis_F11      GTTCGGGTAGTCCGAACCGTCGACCGGATACAACCCCGAGTAGACCATCG 935
SEQIDNO_50-M.tuberculosis_KZN1     GTTCGGGTAGTCCGAACCGTCGACCGGATACAACCCCGAGTAGACCATCG 935
SEQIDNO_51-M.tuberculosis_CDC1     GTTCGGGTAGTCCGAACCGTCGACCGGATACAACCCCGAGTAGACCATCG 935
SEQIDNO_52-M.tuberculosis_Haar     GTTCGGGTAGTCCGAACCGTCGACCGGATACAACCCCGAGTAGACCATCG 935
SEQIDNO_53-M.tuberculosis_C        GTTCGGGTAGTCCGAACCGTCGACCGGATACAACCCCGAGTAGACCATCG 935
SEQIDNO_54-M.bovisAF2122/97        GTTCGGGTAGTCCGAACCGTCGACCGGATACAACCCCGAGTAGACCATCG 935
SEQIDNO_55-M.bovisBCG_Pasteur1     GTTCGGGTAGTCCGAACCGTCGACCGGATACAACCCCGAGTAGACCATCG 935
SEQIDNO_56-M.bovisBCG_Tokyo172     GTTCGGGTAGTCCGAACCGTCGACCGGATACAACCCCGAGTAGACCATCG 935
SEQIDNO_57-M.microtti              GTTCGGGTAGTCCGAACCGTCGACCGGATACAACCCCGAGTAGACCATCG 935
SEQIDNO_58-M.canetti_CIPT14001     GTTCGGGTAGTCCGAACCGTCGACCGGATACAACCCCGAGTAGACCATCG 935
SEQIDNO_59-M.africanum_GM04118     GTTCGGGTAGTCCGAACCGTCGACCGGATACAACCCCGAGTAGACCATCG 605
SEQIDNO_76-M.capraeRIVM2006_19     GTTCGGGTAGTCCGAACCGTCGACCGGATACAACCCCGAGTAGACCATCG 461
SEQIDNO_60-M.avium_subsp_Parat     ATCCGGATAGTCCGAGCCGTCCACCGGATACAGACCCGAATAGACCATCG 935
SEQIDNO_61-M.leprae_cosmid_B19     ACTCGGGTAGTCCGAACTGTCGACGGGATACAGCCCGGAGTACACCATGG 935
SEQIDNO_62-M.ulcerans_Agy99        GTTCGGATAGTCCGATCCGTCAACGGGATACAGTCCCGAATACACCATCG 935
SEQIDNO_63-M.avium_104             ATCCGGATAGTCCGAGCCGTCCACCGGATACAGACCCGAATAGACCATCG 935
SEQIDNO_64-M.vanbaalenii_PYR-1     CACCGGGTAGTCCGAGCCGTCGACCGGATACAGGCCCGAGTAGACCATCG 935
SEQIDNO_65-M.gilvum_PYR-GCK        CACCGGGTAGTCGGAACCGTCCACGGGATACAGGCCCGAGTAGACCATCG 935
SEQIDNO_66-M.abscessus             GTTCGGGTAGTCGGATCCGTCCACCGGGTACAGCCCGGAATAGACCATCG 947
SEQIDNO_67-M.marinum_M             GTTCGGATAGTCCGATCCGTCAACGGGATACAGTCCCGAATACACCATCG 935
SEQIDNO_68-M.smegmatis             ATCCGGGTAGTCCGAACCGTCGACGGGATACAGGCCCGAGTACACCATCG 935
                                      *** ***** ** * *** ** ** ****  ** ** ** ***** *

SEQIDNO_47-M.tuberculosis_H37R     GTTTGGGCTCACGGTAGCCGGTCAACGCTTCGGCGGCAGCCCCGCGGGCC 985
SEQIDNO_48-M.tuberculosis_H37R     GTTTGGGCTCACGGTAGCCGGTCAACGCTTCGGCGGCAGCCCCGCGGGCC 985
SEQIDNO_49-M.tuberculosis_F11      GTTTGGGCTCACGGTAGCCGGTCAACGCTTCGGCGGCAGCCCCGCGGGCC 985
SEQIDNO_50-M.tuberculosis_KZN1     GTTTGGGCTCACGGTAGCCGGTCAACGCTTCGGCGGCAGCCCCGCGGGCC 985
SEQIDNO_51-M.tuberculosis_CDC1     GTTTGGGCTCACGGTAGCCGGTCAACGCTTCGGCGGCAGCCCCGCGGGCC 985
SEQIDNO_52-M.tuberculosis_Haar     GTTTGGGCTCACGGTAGCCGGTCAACGCTTCGGCGGCAGCCCCGCGGGCC 985
SEQIDNO_53-M.tuberculosis_C        GTTTGGGCTCACGGTAGCCGGTCAACGCTTCGGCGGCAGCCCCGCGGGCC 985
SEQIDNO_54-M.bovisAF2122/97        GTTTGGGCTCACGGTAGCCGGTCAACGCTTCGGCGGCAGCCCCGCGGGCC 985
SEQIDNO_55-M.bovisBCG_Pasteur1     GTTTGGGCTCACGGTAGCCGGTCAACGCTTCGGCGGCAGCCCCGCGGGCC 985
SEQIDNO_56-M.bovisBCG_Tokyo172     GTTTGGGCTCACGGTAGCCGGTCAACGCTTCGGCGGCAGCCCCGCGGGCC 985
SEQIDNO_57-M.microtti              GTTTGGGCTCACGGTAGCCGGTCAACGCTTCGGCGGCAGCCCCGCGGGCC 985
SEQIDNO_58-M.canetti_CIPT14001     GTTTGGGCTCACGGTAGCCGGTCAACGCTTCGGCTGCAGCCCCGCGGGCC 985
SEQIDNO_59-M.africanum_GM04118     GTTTGGGCTCACGGTAGCCGGG---------------------------- 627
SEQIDNO_76-M.capraeRIVM2006_19     GTTTGGGCTCACGG------------------------------------ 475
SEQIDNO_60-M.avium_subsp_Parat     GCTTGGGTTCGCGGTATCCGGTCAGCGCCTCTTGCGCGCCGTGGCGCGC- 984
SEQIDNO_61-M.leprae_cosmid_B19     GCTTGGGTTCTCGGTAGCCAGTTAACGGTTCAGTGGCACCATAACGAAC- 984
SEQIDNO_62-M.ulcerans_Agy99        GCTTGGGTTCGCGGTAGCCGGTCAGTGCCTCGGTGGCACCTTTTCGGGC- 984
SEQIDNO_63-M.avium_104             GCTTGGGTTCGCGATATCCGGTCAGCGCCTCTTGCGCGCCGTGGCGCGC- 984
SEQIDNO_64-M.vanbaalenii_PYR-1     GCCTGGGCTCCCGGTAGCCGGTCAACGCTTCCTTGGCACCGTTACGCGC- 984
```

Figure 2 (cont)

```
SEQIDNO_65-M.gilvum_PYR-GCK        GCTTGGGCTCGCGGTAGCCGGTCAGCGCTTCGGTGGCACCCTTGCGTGC- 984
SEQIDNO_66-M.abscessus             GCTTGGGTTCGCGGTAGCCGGTCAGCGGCTCCTTGGCGCCGTTGCGCGC- 996
SEQIDNO_67-M.marinum_M             GCTTGGGTTCGCGGTAGCCGGTCAGTGCCTCGGTGGCACCTTTTCGGGC- 984
SEQIDNO_68-M.smegmatis             GCTTGGGCTCGCGATAACCCGTGAGCGCCTCGGTCGCGCCCTTGCGCGC- 984
                                   *   **** ** **

SEQIDNO_47-M.tuberculosis_H37R     CGGGAGAGGCTGGTCACGGTGTCGCCCACCTTGGACTGGCGGACGTCCTT 1035
SEQIDNO_48-M.tuberculosis_H37R     CGGGAGAGGCTGGTCACGGTGTCGCCCACCTTGGACTGGCGGACCTCCTT 1035
SEQIDNO_49-M.tuberculosis_F11      CGGGAGAGGCTGGTCACGGTGTCGCCCACCTTGGACTGGCGGACGTCCTT 1035
SEQIDNO_50-M.tuberculosis_KZN1     CGGGAGAGGCTGGTCACGGTGTCGCCCACCTTGGACTGGCGGACGTCCTT 1035
SEQIDNO_51-M.tuberculosis_CDC1     CGGGAGAGGCTGGTCACGGTGTCGCCCACCTTGGACTGGCGGACGTCCTT 1035
SEQIDNO_52-M.tuberculosis_Haar     CGGGAGAGGCTGGTCACGGTGTCGCCCACCTTGGACTGGCGGACGTCCTT 1035
SEQIDNO_53-M.tuberculosis_C        CGGGAGAGGCTGGTCACGGTGTCGCCCACCTTGGACTGGCGGACGTCCTT 1035
SEQIDNO_54-M.bovisAF2122/97        CGGGAGAGGCTGGTCACGGTGTCGCCCACCTTGGACTGGCGGACGTCCTT 1035
SEQIDNO_55-M.bovisBCG_Pasteur1     CGGGAGAGGCTGGTCACGGTGTCGCCCACCTTGGACTGGCGGACGTCCTT 1035
SEQIDNO_56-M.bovisBCG_Tokyo172     CGGGAGAGGCTGGTCACGGTGTCGCCCACCTTGGACTGGCGGACGTCCTT 1035
SEQIDNO_57-M.microtti              CGGGAGAGGCTGGTCACGGTGTCGCCCACCTTGGACTGGCGGACGTCCTT 1035
SEQIDNO_58-M.canetti_CIPT14001     CGGGAGAGGCTGGTCACGGTGTCGCCCACCTTGGACTGGCGGACGTCCTT 1035
SEQIDNO_59-M.africanum_GM04118     --------------------------------------------------
SEQIDNO_76-M.capraeRIVM2006_19     --------------------------------------------------
SEQIDNO_60-M.avium_subsp_Parat     --------GCTGGTGACGGTGTCGCCCACTTTGGACTGGCGGACGTCCTT 1026
SEQIDNO_61-M.leprae_cosmid_B19     --------CGTCGTTACAGTGTCGCCGACTTTGGATTGGCGGACGTCTTT 1026
SEQIDNO_62-M.ulcerans_Agy99        --------GGTCGTGACGGTGTCGCCGACCTTGGACTGCCACACGTCCTT 1026
SEQIDNO_63-M.avium_104             --------GCTGGTCACGGTGTCGCCCACTTTGGACTGGCGGACGTCCTT 1026
SEQIDNO_64-M.vanbaalenii_PYR-1     --------CGTCGTCACCGTGTCGCCGACCTTGGACTGGCGCACGTCCTT 1026
SEQIDNO_65-M.gilvum_PYR-GCK        --------CGTCGTCACCGTGTCGCCGACCTTGGACTGACGCACGTCCTT 1026
SEQIDNO_66-M.abscessus             --------GGCGGTGACGGTGTCACCGACCTTCGACTGGCGCACATCCTT 1038
SEQIDNO_67-M.marinum_M             --------GGTCGTGACCGTGTCGCCGACCTTGGACTGCCGCACGTCCTT 1026
SEQIDNO_68-M.smegmatis             --------CGTGGTCACCGTGTCACCGACCTTCGACTGGCGGACGTCCTT 1026

SEQIDNO_47-M.tuberculosis_H37R     GACGCCGGTGATCAGGTAACCCACCTCGCCGACACCGAGGCCCTCACACG 1085
SEQIDNO_48-M.tuberculosis_H37R     GACGCCGGTGATCAGGTAACCCACCTCGCCGACACCGAGGCCCTCACACG 1085
SEQIDNO_49-M.tuberculosis_F11      GACGCCGGTGATCAGGTAACCCACCTCGCCGACACCGAGGCCCTCACACG 1085
SEQIDNO_50-M.tuberculosis_KZN1     GACGCCGGTGATCAGGTAACCCACCTCGCCGACACCGAGGCCCTCACACG 1085
SEQIDNO_51-M.tuberculosis_CDC1     GACGCCGGTGATCAGGTAACCCACCTCGCCGACACCGAGGCCCTCACACG 1085
SEQIDNO_52-M.tuberculosis_Haar     GACGCCGGTGATCAGGTAACCCACCTCGCCGACACCGAGGCCCTCACACG 1085
SEQIDNO_53-M.tuberculosis_C        GACGCCGGTGATCAGGTAACCCACCTCGCCGACACCGAGGCCCTCACACG 1085
SEQIDNO_54-M.bovisAF2122/97        GACGCCGGTGATCAGGTAACCCACCTCGCCGACACCGAGGCCCTCACACG 1085
SEQIDNO_55-M.bovisBCG_Pasteur1     GACGCCGGTGATCAGGTAACCCACCTCGCCGACACCGAGGCCCTCACACG 1085
SEQIDNO_56-M.bovisBCG_Tokyo172     GACGCCGGTGATCAGGTAACCCACCTCGCCGACACCGAGGCCCTCACACG 1085
SEQIDNO_57-M.microtti              GACGCCGGTGATCAGGTAACCCACCTCGCCGACACCGAGGCCCTCACACG 1085
SEQIDNO_58-M.canetti_CIPT14001     GACGCCGGTGATCAGGTAACCCACCTCGCCGACACCGAGGCCCTCACACG 1085
SEQIDNO_59-M.africanum_GM04118     --------------------------------------------------
SEQIDNO_76-M.capraeRIVM2006_19     --------------------------------------------------
SEQIDNO_60-M.avium_subsp_Parat     CACCCCGGTGATCAGGTAGCCCACCTCGCCGACGCCAAGGCCGTCGCTGG 1076
SEQIDNO_61-M.leprae_cosmid_B19     AACCCCAGTAATCAGGTAGCCCACCTCCCCCACGCCCAGGCCCGCGCTGG 1076
SEQIDNO_62-M.ulcerans_Agy99        GACCCCGGTGATAAGATAACCCACCTCGCCGACACCAAGGCCGTCGCTGG 1076
SEQIDNO_63-M.avium_104             CACCCCGGTGATCAGGTAGCCCACCTCGCCGACGCCCAGGCCGTCGCTGG 1076
SEQIDNO_64-M.vanbaalenii_PYR-1     CACACCGGTGATGAGGTAGCCGACCTCGCCGACGCCGAGGCCGTCGGAGG 1076
SEQIDNO_65-M.gilvum_PYR-GCK        CACGCCGGTGATCAGGTAGCCGACCTCGCCGACACCGAGACCGACCGAAG 1076
SEQIDNO_66-M.abscessus             CACGCCGGTGATCAGGTAGCCCACCTCGCCGACCCCGAGTCCCGCGGAGG 1088
SEQIDNO_67-M.marinum_M             GACCCCGGTGATCAGATAACCCACCTCGCCGACACCAAGGCCGTCGCTGG 1076
SEQIDNO_68-M.smegmatis             CACACCCGTGATCAGGTAACCGACCTCACCGACGCCCAGGCCCGCACTGG 1076

SEQIDNO_47-M.tuberculosis_H37R     GTTTCGGCTCGGGTGAGACGATGCCGACCTCAAGCAGCTCGTGGGTGGCG 1135
SEQIDNO_48-M.tuberculosis_H37R     GTTTCGGCTCGGGTGAGACGATGCCGACCTCAAGCAGCTCGTGGGTGGCG 1135
SEQIDNO_49-M.tuberculosis_F11      GTTTCGGCTCGGGTGAGACGATGCCGACCTCAAGCAGCTCGTGGGTGGCG 1135
SEQIDNO_50-M.tuberculosis_KZN1     GTTTCGGCTCGGGTGAGACGATGCCGACCTCAAGCAGCTCGTGGGTGGCG 1135
SEQIDNO_51-M.tuberculosis_CDC1     GTTTCGGCTCGGGTGAGACGATGCCGACCTCAAGCAGCTCGTGGGTGGCG 1135
SEQIDNO_52-M.tuberculosis_Haar     GTTTCGGCTCGGGTGAGACGATGCCGACCTCAAGCAGCTCGTGGGTGGCG 1135
SEQIDNO_53-M.tuberculosis_C        GTTTCGGCTCGGGTGAGACGATGCCGACCTCAAGCAGCTCGTGGGTGGCG 1135
SEQIDNO_54-M.bovisAF2122/97        GTTTCGGCTCGGGTGAGACGATGCCGACCTCAAGCAGCTCGTGGGTGGCG 1135
SEQIDNO_55-M.bovisBCG_Pasteur1     GTTTCGGCTCGGGTGAGACGATGCCGACCTCAAGCAGCTCGTGGGTGGCG 1135
SEQIDNO_56-M.bovisBCG_Tokyo172     GTTTCGGCTCGGGTGAGACGATGCCGACCTCAAGCAGCTCGTGGGTGGCG 1135
SEQIDNO_57-M.microtti              GTTTCGGCTCGGGTGAGACGATGCCGACCTCAAGCAGCTCGTGGGTGGCG 1135
SEQIDNO_58-M.canetti_CIPT14001     GTTTCGGCTCGGGTGAGACGATGCCGACCTCAAGCAGCTCGTGGGTGGCG 1135
SEQIDNO_59-M.africanum_GM04118     --------------------------------------------------
SEQIDNO_76-M.capraeRIVM2006_19     --------------------------------------------------
SEQIDNO_60-M.avium_subsp_Parat     CCTTCGGCTCGGGTGAGACGATGCCGACCTCGAGCAGTTCGTGGGTGGCG 1126
SEQIDNO_61-M.leprae_cosmid_B19     CCTTCGGTTCAGGCGACACGATGCCGACCTCGAGCAGTTCGTACGTCGCA 1126
SEQIDNO_62-M.ulcerans_Agy99        CCTTGGGTTCGGGTGAGACGATGCCGACCTCGAGCAGTTCGTGGGTGGCG 1126
SEQIDNO_63-M.avium_104             CCTTCGGCTCGGGTGAGACGATGCCGACTTCGAGCAGTTCGTGGGTGGCG 1126
SEQIDNO_64-M.vanbaalenii_PYR-1     GCTTGGGCTCGGGTGAGACGATTCCCACCTCGAGCAGTTCGTGGGTGGCG 1126
SEQIDNO_65-M.gilvum_PYR-GCK        GCTTGGGGTCCGGCGAGACGATGCCCACTTCGAGGAGTTCGTGCGTCGCG 1126
SEQIDNO_66-M.abscessus             GTTTGGGCTCCGGCGAGACGATGCCCACTTCCAGCAGTTCGTGGGTGGCG 1138
SEQIDNO_67-M.marinum_M             CCTTGGGTTCGGGTGAGACGATGCCGACCTCGAGCAGTTCGTGGGTGGCG 1126
SEQIDNO_68-M.smegmatis             CCTTCGGTTCCGGTGAGACGATGCCGACCTCGAGCAGTTCATGGGTGGCG 1126

SEQIDNO_47-M.tuberculosis_H37R     CCGGTGGACATCATCATGATGCGCTCACGGGGGCTGATCTTGCCGTCGAC 1185
SEQIDNO_48-M.tuberculosis_H37R     CCGGTGGACATCATCATGATGCGCTCACGGGGGCTGATCTTGCCGTCGAC 1185
SEQIDNO_49-M.tuberculosis_F11      CCGGTGGACATCATCATGATGCGCTCACGGGGGCTGATCTTGCCGTCGAC 1185
SEQIDNO_50-M.tuberculosis_KZN1     CCGGTGGACATCATCATGATGCGCTCACGGGGGCTGATCTTGCCGTCGAC 1185
SEQIDNO_51-M.tuberculosis_CDC1     CCGGTGGACATCATCATGATGCGCTCACGGGGGCTGATCTTGCCGTCGAC 1185
SEQIDNO_52-M.tuberculosis_Haar     CCGGTGGACATCATCATGATGCGCTCACGGGGGCTGATCTTGCCGTCGAC 1185
SEQIDNO_53-M.tuberculosis_C        CCGGTGGACATCATCATGATGCGCTCACGGGGGCTGATCTTGCCGTCGAC 1185
```

Figure 2 (cont)

```
SEQIDNO_54-M.bovisAF2122/97         CCGGTGGACATCATCATGATGCGCTCACGGGGGCTGATCTTGCCGTCGAC 1185
SEQIDNO_55-M.bovisBCG_Pasteur1      CCGGTGGACATCATCATGATGCGCTCACGGGGGCTGATCTTGCCGTCGAC 1185
SEQIDNO_56-M.bovisBCG_Tokyo172      CCGGTGGACATCATCATGATGCGCTCACGGGGGCTGATCTTGCCGTCGAC 1185
SEQIDNO_57-M.microtti               CCGGTGGACATCATCATGATGCGCTCACGGGGGCTGATCTTGCCGTCGAC 1185
SEQIDNO_58-M.canetti_CIPT14001      CCGGTGGACATCATCATGATGCGCTCACGGGGGCTGATCTTGCCGTCGAC 1185
SEQIDNO_59-M.africanum_GM04118      --------------------------------------------------
SEQIDNO_76-M.capraeRIVM2006_19      --------------------------------------------------
SEQIDNO_60-M.avium_subsp_Parat      CCGGTGGACATCATCGCGATGCGTTCGCGCGGGGTGATCTTGCCGTCGAC 1176
SEQIDNO_61-M.leprae_cosmid_B19      CCGGTGGACATCATCGCGATGCGCTCACGCGGGCTGATCTTGCCGTCGAC 1176
SEQIDNO_62-M.ulcerans_Agy99         CCGGTGGACATCATGGCGATGCGCTCGCGGGGGGTGATCTTGCCGTCGAC 1176
SEQIDNO_63-M.avium_104              CCGGTGGACATCATCGCGATGCGTTCGCGCGGGGTGATCTTGCCGTCGAC 1176
SEQIDNO_64-M.vanbaalenii_PYR-1      CCGGTCGACATCATCGCGATGCGCTCGCGCGGGGTGATCTTCCCGTCCAC 1176
SEQIDNO_65-M.gilvum_PYR-GCK         CCGGTCGACATCATCGCGATGCGCTCACGCGGGGTGATCCTGCCGTCGAC 1176
SEQIDNO_66-M.abscessus              CCCGTCGACATCATCGCGATCTTCTCGCGCGGAGTGATCTTGCCGTCCAC 1188
SEQIDNO_67-M.marinum_M              CCGGTGGACATCATGGCGATGCGCTCGCGGGGGGTGATCTTGCCGTCGAC 1176
SEQIDNO_68-M.smegmatis              CCGGTGGACATCATCGCGATGCGTTCGCGCGGCACGATCTTGCCGTCGAC 1176

SEQIDNO_47-M.tuberculosis_H37R      GACGCGGACGTAGGTCACCACTCCGCGGTAGATGTCGTAAACGGAGTCGA 1235
SEQIDNO_48-M.tuberculosis_H37R      GACGCGGACGTAGGTCACCACTCCGCGGTAGATGTCGTAAACGGAGTCGA 1235
SEQIDNO_49-M.tuberculosis_F11       GACGCGGACGTAGGTCACCACTCCGCGGTAGATGTCGTAAACGGAGTCGA 1235
SEQIDNO_50-M.tuberculosis_KZN1      GACGCGGACGTAGGTCACCACTCCGCGGTAGATGTCGTAAACGGAGTCGA 1235
SEQIDNO_51-M.tuberculosis_CDC1      GACGCGGACGTAGGTCACCACTCCGCGGTAGATGTCGTAAACGGAGTCGA 1235
SEQIDNO_52-M.tuberculosis_Haar      GACGCGGACGTAGGTCACCACTCCGCGGTAGATGTCGTAAACGGAGTCGA 1235
SEQIDNO_53-M.tuberculosis_C         GACGCGGACGTAGGTCACCACTCCGCGGTAGATGTCGTAAACGGAGTCGA 1235
SEQIDNO_54-M.bovisAF2122/97         GACGCGGACGTAGGTCACCACTCCGCGGTAGATGTCGTAAACGGAGTCGA 1235
SEQIDNO_55-M.bovisBCG_Pasteur1      GACGCGGACGTAGGTCACCACTCCGCGGTAGATGTCGTAAACGGAGTCGA 1235
SEQIDNO_56-M.bovisBCG_Tokyo172      GACGCGGACGTAGGTCACCACTCCGCGGTAGATGTCGTAAACGGAGTCGA 1235
SEQIDNO_57-M.microtti               GACGCGGACGTAGGTCACCACTCCGCGGTAGATGTCGTAAACGGAGTCGA 1235
SEQIDNO_58-M.canetti_CIPT14001      GACGCGGACGTAGGTCACCACTCCGCGGTAGATGTCGTAAACGGAGTCGA 1235
SEQIDNO_59-M.africanum_GM04118      --------------------------------------------------
SEQIDNO_76-M.capraeRIVM2006_19      --------------------------------------------------
SEQIDNO_60-M.avium_subsp_Parat      CACCCGCACGTAGGTCACCACGCCGCGGTAGATGTCGTAGACCGAGTCGA 1226
SEQIDNO_61-M.leprae_cosmid_B19      CACACGGACGTAGGTGACCACGCCTCGGTAGATGTCGTAGACGGAGTCGA 1226
SEQIDNO_62-M.ulcerans_Agy99         GACGCGGACGTAGGTGACCACACCGCGGTAGATGTCATAGACGGAGTCGA 1226
SEQIDNO_63-M.avium_104              CACCCGCACGTAGGTCACCACGCCGCGGTAGATGTCGTAGACCGAGTCGA 1226
SEQIDNO_64-M.vanbaalenii_PYR-1      CACCCGCACGTAGGTCACCACGCCGCGGTAGATGTCGTAGACCGAGTCGA 1226
SEQIDNO_65-M.gilvum_PYR-GCK         GACGCGCACATAGGTGACGACGCCGCGGTAGATGTCGTACACCGAGTCGA 1226
SEQIDNO_66-M.abscessus              GACGCGCACGTAGGTGACCACACCGCGGTAGATGTCGTAGACCGAGTCGA 1238
SEQIDNO_67-M.marinum_M              GACGCGGACGTAGGTGACCACACCGCGGTAGATGTCATAGACGGAGTCGA 1226
SEQIDNO_68-M.smegmatis              CACACGGACGTAGGTCACCACGCCGCGGTAGATGTCGTACACGGAGTCGA 1226

SEQIDNO_47-M.tuberculosis_H37R      AAATCATTGCGCGGGTAGGTGCCTCGGCGTCGCCCTGAGGGGGCGGCACC 1285
SEQIDNO_48-M.tuberculosis_H37R      AAATCATTGCGCGGGTAGGTGCCTCGGCGTCGCCCTGAGGGGGCGGCACC 1285
SEQIDNO_49-M.tuberculosis_F11       AAATCATTGCGCGGGTAGGTGCCTCGGCGTCGCCCTGAGGGGGCGGCACC 1285
SEQIDNO_50-M.tuberculosis_KZN1      AAATCATTGCGCGGGTAGGTGCCTCGGCGTCGCCCTGAGGGGGCGGCACC 1285
SEQIDNO_51-M.tuberculosis_CDC1      AAATCATTGCGCGGGTAGGTGCCTCGGCGTCGCCCTGAGGGGGCGGCACC 1285
SEQIDNO_52-M.tuberculosis_Haar      AAATCATTGCGCGGGTAGGTGCCTCGGCGTCGCCCTGAGGGGGCGGCACC 1285
SEQIDNO_53-M.tuberculosis_C         AAATCATTGCGCGGGTAGGTGCCTCGGCGTCGCCCTGAGGGGGCGGCACC 1285
SEQIDNO_54-M.bovisAF2122/97         AAATCATTGCGCGGGTAGGTGCCTCGGCGTCGCCCTGAGGGGGCGGCACC 1285
SEQIDNO_55-M.bovisBCG_Pasteur1      AAATCATTGCGCGGGTAGGTGCCTCGGCGTCGCCCTGAGGGGGCGGCACC 1285
SEQIDNO_56-M.bovisBCG_Tokyo172      AAATCATTGCGCGGGTAGGTGCCTCGGCGTCGCCCTGAGGGGGCGGCACC 1285
SEQIDNO_57-M.microtti               AAATCATTGCGCGGGTAGGTGCCTCGGCGTCGCCCTGAGGGGGCGGCACC 1285
SEQIDNO_58-M.canetti_CIPT14001      AAATCATTGCGCGGGTACGTGCCTCGGCGTCGCCCTGCGGGGGCGGCACC 1285
SEQIDNO_59-M.africanum_GM04118      --------------------------------------------------
SEQIDNO_76-M.capraeRIVM2006_19      --------------------------------------------------
SEQIDNO_60-M.avium_subsp_Parat      AGATCATCGCGCGCAGCGGCGCATCGGCCTGCCCCTGCGGCGGCGGCACC 1276
SEQIDNO_61-M.leprae_cosmid_B19      AGATCATCGCGCGGGTAGGCGCATCAGGGTCACCTTGCGGATGCGGCACC 1276
SEQIDNO_62-M.ulcerans_Agy99         AGATCATTGCGCGAGTGGGTGCGTCGGCATCGCCCTGCGGTGGCGGCACC 1276
SEQIDNO_63-M.avium_104              AGATCATCGCGCGCAGCGGCGCATCGGCCTGCCCCTGCGGCGGCGGCACC 1276
SEQIDNO_64-M.vanbaalenii_PYR-1      AGATCATCGCGCGGGCAGGCGCGTCCGGGTCGCCCTGCGGCGCCGGGATC 1276
SEQIDNO_65-M.gilvum_PYR-GCK         AGATCATCGCGCGCGCCGGAGCGTCCGGGTCGCCCTGCGGCGGCGGGATC 1276
SEQIDNO_66-M.abscessus              AGATCATCGCCCGCGCCGGCGCATCCGGATCACCTTGCGGCGCTGGGATG 1288
SEQIDNO_67-M.marinum_M              AGATCATTGCGCGAGTGGGTGCGTCGGCATCGCCCTGCGGTGGCGGCACC 1276
SEQIDNO_68-M.smegmatis              AGATCATCGCGCGCGTCGGGGCGTCGGGGTCACCGACCGGCGGCGGCACC 1276

SEQIDNO_47-M.tuberculosis_H37R      TGTCGGACCACCTCGTCGAGCAGGTCGGACACGCCTTCGCCGGTTTTGCC 1335
SEQIDNO_48-M.tuberculosis_H37R      TGTCGGACCACCTCGTCGAGCAGGTCGGACACGCCTTCGCCGGTTTTGCC 1335
SEQIDNO_49-M.tuberculosis_F11       TGTCGGACCACCTCGTCGAGCAGGTCGGACACGCCTTCGCCGGTTTTGCC 1335
SEQIDNO_50-M.tuberculosis_KZN1      TGTCGGACCACCTCGTCGAGCAGGTCGGACACGCCTTCGCCGGTTTTGCC 1335
SEQIDNO_51-M.tuberculosis_CDC1      TGTCGGACCACCTCGTCGAGCAGGTCGGACACGCCTTCGCCGGTTTTGCC 1335
SEQIDNO_52-M.tuberculosis_Haar      TGTCGGACCACCTCGTCGAGCAGGTCGGACACGCCTTCGCCGGTTTTGCC 1335
SEQIDNO_53-M.tuberculosis_C         TGTCGGACCACCTCGTCGAGCAGGTCGGACACGCCTTCGCCGGTTTTGCC 1335
SEQIDNO_54-M.bovisAF2122/97         TGTCGGACCACCTCGTCGAGCAGGTCGGACACGCCTTCGCCGGTTTTGCC 1335
SEQIDNO_55-M.bovisBCG_Pasteur1      TGTCGGACCACCTCGTCGAGCAGGTCGGACACGCCTTCGCCGGTTTTGCC 1335
SEQIDNO_56-M.bovisBCG_Tokyo172      TGTCGGACCACCTCGTCGAGCAGGTCGGACACGCCTTCGCCGGTTTTGCC 1335
SEQIDNO_57-M.microtti               TGTCGGACCACCTCGTCGAGCAGGTCGGACACGCCTTCGCCGGTTTTGCC 1335
SEQIDNO_58-M.canetti_CIPT14001      TGTCGGACCACCTCGTCGAGCAGGTCGGACACGCCTTCGCCGGTTTTGCC 1335
SEQIDNO_59-M.africanum_GM04118      --------------------------------------------------
SEQIDNO_76-M.capraeRIVM2006_19      --------------------------------------------------
SEQIDNO_60-M.avium_subsp_Parat      TGGCGCACCACCTCGTCGAGCAGCCGCGCCACGCCCTCCCCGGTTTTGCC 1326
SEQIDNO_61-M.leprae_cosmid_B19      CGACGGACCACCTCGTCAAGAAGGTCAGAAACCCCCTCGCCGGTTTTGCC 1326
SEQIDNO_62-M.ulcerans_Agy99         TCGCGCACCACGTGGTCGAGCAGGTCTGCGACGCCTTCCCCGGTTTTGCC 1326
SEQIDNO_63-M.avium_104              TGGCGCACCACCTCGTCGAGCAGCCGCGCCACGCCCTCCCCGGTTTTGCC 1326
SEQIDNO_64-M.vanbaalenii_PYR-1      TCCCGCACCACGTGGTCGAGCAGCTCGGCCACACCCTCACCCGTCTTGCC 1326
SEQIDNO_65-M.gilvum_PYR-GCK         TCCCGGACGACGTGGTCGAGCAGGTCGCCGACGCCGGCGCCGGTCTTGCC 1326
```

Figure 2 (cont)

```
SEQIDNO_66-M.abscessus           AGCCGCACCACCTCGTCGAGCAGCGCCGCGACGCCCTCCCCGGTCTTACC 1338
SEQIDNO_67-M.marinum_M           TCGCGCACCACGTGGTCGAGCAGGTCTGCGACGCCTTCCCCGGTTTTGCC 1326
SEQIDNO_68-M.smegmatis           TTACGCACCACCTCGTCGAGCAGCTCGGCCACGCCTTCGCCGGTCTTGCC 1326

SEQIDNO_47-M.tuberculosis_H37R   GGACACCCGCAACACCTCGGCCGGCTCGCAGCCGATGATGTGTGCCATCT 1385
SEQIDNO_48-M.tuberculosis_H37R   GGACACCCGCAACACCTCGGCCGGCTCGCAGCCGATGATGTGTGCCATCT 1385
SEQIDNO_49-M.tuberculosis_F11    GGACACCCGCAACACCTCGGCCGGCTCGCAGCCGATGATGTGTGCCATCT 1385
SEQIDNO_50-M.tuberculosis_KZN1   GGACACCCGCAACACCTCGGCCGGCTCGCAGCCGATGATGTGTGCCATCT 1385
SEQIDNO_51-M.tuberculosis_CDC1   GGACACCCGCAACACCTCGGCCGGCTCGCAGCCGATGATGTGTGCCATCT 1385
SEQIDNO_52-M.tuberculosis_Haar   GGACACCCGCAACACCTCGGCCGGCTCGCAGCCGATGATGTGTGCCATCT 1385
SEQIDNO_53-M.tuberculosis_C      GGACACCCGCAACACCTCGGCCGGCTCGCAGCCGATGATGTGTGCCATCT 1385
SEQIDNO_54-M.bovisAF2122/97      GGACACCCGCAACACCTCGGCCGGCTCGCAGCCGATGATGTGTGCCATCT 1385
SEQIDNO_55-M.bovisBCG_Pasteur1   GGACACCCGCAACACCTCGGCCGGCTCGCAGCCGATGATGTGTGCCATCT 1385
SEQIDNO_56-M.bovisBCG_Tokyo172   GGACACCCGCAACACCTCGGCCGGCTCGCAGCCGATGATGTGTGCCATCT 1385
SEQIDNO_57-M.microtti            GGACACCCGCAACACCTCGGCCGGCTCGCAGCCGATGATGTGTGCCATCT 1385
SEQIDNO_58-M.canetti_CIPT14001   GGACACCCGCAACACCTCGGCCGGCTCGCAGCCGATGATGTGTGCCATCT 1385
SEQIDNO_59-M.africanum_GM04118   --------------------------------------------------
SEQIDNO_76-M.capraeRIVM2006_19   --------------------------------------------------
SEQIDNO_60-M.avium_subsp_Parat   GGACACCCACAGCACGTCGTCGGGTTCGCACCCGATGATGTGGGCGAGCT 1376
SEQIDNO_61-M.leprae_cosmid_B19   GGACACCCGAAGCACATCGCCTGACTCATAACCAATGATGTGGGCGATCT 1376
SEQIDNO_62-M.ulcerans_Agy99      GGAAACCCGCAGCACGTCGCCGGGCTCGCAGCCGATGATGTGAGCAATCT 1376
SEQIDNO_63-M.avium_104           GGACACCCGCAGCACGTCGTCGGGTTCGCACCCGATGATGTGGGCGAGCT 1376
SEQIDNO_64-M.vanbaalenii_PYR-1   CGACACCCGCAACACGTCCTCGGGCTCGCAGCCGATGATGTGGGCGATCT 1376
SEQIDNO_65-M.gilvum_PYR-GCK      CGACACCCGCAGCACATCCTCCGGTTCGCAGCCGATGATGTGCGCGATCT 1376
SEQIDNO_66-M.abscessus           GGACACCCGCAGCACATCGGAGGGCTCGCAGCCGATGATGTGCGCGATCT 1388
SEQIDNO_67-M.marinum_M           GGAAACCCGCAGCACGTCGCCGGGCTCGCAGCCGATGATGTGAGCAATCT 1376
SEQIDNO_68-M.smegmatis           CGAGACACGCAGCACGTCCGACGGCTCACACCCGATGATGTGGGCGAGCT 1376

SEQIDNO_47-M.tuberculosis_H37R   CGGCGGCGTAACGGTCCGGGTCGGCCGCGGGCAGGTCGATCTTGTTGAGC 1435
SEQIDNO_48-M.tuberculosis_H37R   CGGCGGCGTAACGGTCCGGGTCGGCCGCGGGCAGGTCGATCTTGTTGAGC 1435
SEQIDNO_49-M.tuberculosis_F11    CGGCGGCGTAACGGTCCGGGTCGGCCGCGGGCAGGTCGATCTTGTTGAGC 1435
SEQIDNO_50-M.tuberculosis_KZN1   CGGCGGCGTAACGGTCCGGGTCGGCCGCGGGCAGGTCGATCTTGTTGAGC 1435
SEQIDNO_51-M.tuberculosis_CDC1   CGGCGGCGTAACGGTCCGGGTCGGCCGCGGGCAGGTCGATCTTGTTGAGC 1435
SEQIDNO_52-M.tuberculosis_Haar   CGGCGGCGTAACGGTCCGGGTCGGCCGCGGGCAGGTCGATCTTGTTGAGC 1435
SEQIDNO_53-M.tuberculosis_C      CGGCGGCGTAACGGTCCGGGTCGGCCGCGGGCAGGTCGATCTTGTTGAGC 1435
SEQIDNO_54-M.bovisAF2122/97      CGGCGGCGTAACGGTCCGGGTCGGCCGCGGGCAGGTCGATCTTGTTGAGC 1435
SEQIDNO_55-M.bovisBCG_Pasteur1   CGGCGGCGTAACGGTCCGGGTCGGCCGCGGGCAGGTCGATCTTGTTGAGC 1435
SEQIDNO_56-M.bovisBCG_Tokyo172   CGGCGGCGTAACGGTCCGGGTCGGCCGCGGGCAGGTCGATCTTGTTGAGC 1435
SEQIDNO_57-M.microtti            CGGCGGCGTAACGGTCCGGGTCGGCCGCGGGCAGGTCGATCTTGTTGAGC 1435
SEQIDNO_58-M.canetti_CIPT14001   CGGCGGCGTAACGGTCCGGGTCGGCCGCAGGCAGGTCGATCTTGTTGAGC 1435
SEQIDNO_59-M.africanum_GM04118   --------------------------------------------------
SEQIDNO_76-M.capraeRIVM2006_19   --------------------------------------------------
SEQIDNO_60-M.avium_subsp_Parat   CGCCGGCGTAGCGATCCGGGTCGGCGGCCGGCAGGTCGATCTTGTTGAGG 1426
SEQIDNO_61-M.leprae_cosmid_B19   CAGCGGCGTAACGGTCCGGATCGGCAGCCGGCAGGTCGATTTTGTTTAGC 1426
SEQIDNO_62-M.ulcerans_Agy99      CGCCCGCGTAGCGGTCCGGGTCGGCGGCCGGCAGGTCGATCTTGTTCAGC 1426
SEQIDNO_63-M.avium_104           CGCCGGCGTACCGGTCCGGGTCGGCGGCCGGCAGGTCGATCTTGTTGAGG 1426
SEQIDNO_64-M.vanbaalenii_PYR-1   CGGCGGCGTACCGGTCCGGGTCTGCGGCGGGCAGATCGATCTTGTTCAGC 1426
SEQIDNO_65-M.gilvum_PYR-GCK      CACCGGCGTAGCGGTCGGGGTCGGCGGCGGGCAGGTCGATCTTGTTGAGC 1426
SEQIDNO_66-M.abscessus           CCTCGGCGTAACGCTCCGGATCGGCCGCGGGCAGGTCGATCTTGTTCAGG 1438
SEQIDNO_67-M.marinum_M           CGCCCGCGTAGCGGTCCGGGTCGGCGGCCGGCAGGTCGATCTTGTTCAGC 1426
SEQIDNO_68-M.smegmatis           CGTCGGCATAGCGGTCCGGGTCAGCGGCGGGCAGGTCGATCTTGTTGAGC 1426

SEQIDNO_47-M.tuberculosis_H37R   ACCGGGATGATGTGCAGGTCGCGGTCCAACGCCAGGTAGAGGTTCGCCAG 1485
SEQIDNO_48-M.tuberculosis_H37R   ACCGGGATGATGTGCAGGTCGCGGTCCAACGCCAGGTAGAGGTTCGCCAG 1485
SEQIDNO_49-M.tuberculosis_F11    ACCGGGATGATGTGCAGGTCGCGGTCCAACGCCAGGTAGAGGTTCGCCAG 1485
SEQIDNO_50-M.tuberculosis_KZN1   ACCGGGATGATGTGCAGGTCGCGGTCCAACGCCAGGTAGAGGTTCGCCAG 1485
SEQIDNO_51-M.tuberculosis_CDC1   ACCGGGATGATGTGCAGGTCGCGGTCCAACGCCAGGTAGAGGTTCGCCAG 1485
SEQIDNO_52-M.tuberculosis_Haar   ACCGGGATGATGTGCAGGTCGCGGTCCAACGCCAGGTAGAGGTTCGCCAG 1485
SEQIDNO_53-M.tuberculosis_C      ACCGGGATGATGTGCAGGTCGCGGTCCAACGCCAGGTAGAGGTTCGCCAG 1485
SEQIDNO_54-M.bovisAF2122/97      ACCGGGATGATGTGCAGGTCGCGGTCCAACGCCAGGTAGAGGTTCGCCAG 1485
SEQIDNO_55-M.bovisBCG_Pasteur1   ACCGGGATGATGTGCAGGTCGCGGTCCAACGCCAGGTAGAGGTTCGCCAG 1485
SEQIDNO_56-M.bovisBCG_Tokyo172   ACCGGGATGATGTGCAGGTCGCGGTCCAACGCCAGGTAGAGGTTCGCCAG 1485
SEQIDNO_57-M.microtti            ACCGGGATGATGTGCAGGTCGCGGTCCAACGCCAGGTAGAGGTTCGCCAG 1485
SEQIDNO_58-M.canetti_CIPT14001   ACCGGGATGATGTGCAGGTCGCGGTCCAACGCCAGGTAGAGGTTCGCCAG 1485
SEQIDNO_59-M.africanum_GM04118   --------------------------------------------------
SEQIDNO_76-M.capraeRIVM2006_19   --------------------------------------------------
SEQIDNO_60-M.avium_subsp_Parat   ACCGGGATGATGGTCAGATCGCGGTCCAGCGCCAGGTAGAGGTTGGCCAG 1476
SEQIDNO_61-M.leprae_cosmid_B19   ACCGGAATAATCGTCAAGTCACGCTCCAGAGCGAGATAGAGATTGGCCAA 1476
SEQIDNO_62-M.ulcerans_Agy99      ACCGGAATGATGTGCAGGTCGCGGTCCAGTGCCAGGTAGAGGTTGGCCAG 1476
SEQIDNO_63-M.avium_104           ACCGGGATGATGGTCAGATCGCGGTCCAGCGCCAGGTAGAGGTTGGCCAG 1476
SEQIDNO_64-M.vanbaalenii_PYR-1   ACCGGGATGATCGTCAGGTCGCGGTCCAGCGCCAGATACAGGTTCGCCAG 1476
SEQIDNO_65-M.gilvum_PYR-GCK      ACCGGGATGATTGTCAGGTCGCGATCCAGCGCCAGGTACAGGTTCGCCAG 1476
SEQIDNO_66-M.abscessus           ACCGGGATGATCGTCAGGTCCTTGTCCAGCGCCAGGTACAGGTTGGCCAG 1488
SEQIDNO_67-M.marinum_M           ACCGGAATGATGTGCAGGTCGCGGTCCAGTGCCAGGTAGAGGTTGGCCAG 1476
SEQIDNO_68-M.smegmatis           ACCGGGATGATCGCCAGGTCGCGGTCCAGCGCCAGGTACAGGTTGGCCAG 1476

SEQIDNO_47-M.tuberculosis_H37R   CGTCTGCGCCTCGATGCCTTGCGCGGCATCGACCAACAGCACCGCACCCT 1535
SEQIDNO_48-M.tuberculosis_H37R   CGTCTGCGCCTCGATGCCTTGCGCGGCATCGACCAACAGCACCGCACCCT 1535
SEQIDNO_49-M.tuberculosis_F11    CGTCTGCGCCTCGATGCCTTGCGCGGCATCGACCAACAGCACCGCACCCT 1535
SEQIDNO_50-M.tuberculosis_KZN1   CGTCTGCGCCTCGATGCCTTGCGCGGCATCGACCAACAGCACCGCACCCT 1535
SEQIDNO_51-M.tuberculosis_CDC1   CGTCTGCGCCTCGATGCCTTGCGCGGCATCGACCAACAGCACCGCACCCT 1535
SEQIDNO_52-M.tuberculosis_Haar   CGTCTGCGCCTCGATGCCTTGCGCGGCATCGACCAACAGCACCGCACCCT 1535
SEQIDNO_53-M.tuberculosis_C      CGTCTGCGCCTCGATGCCTTGCGCGGCATCGACCAACAGCACCGCACCCT 1535
SEQIDNO_54-M.bovisAF2122/97      CGTCTGCGCCTCGATGCCTTGCGCGGCATCGACCAACAGCACCGCACCCT 1535
```

Figure 2 (cont)

SEQIDNO_55-M.bovisBCG_Pasteur1 CGTCTGCGCCTCGATGCCTTGCGCGGCATCGACCAACAGCACCGCACCCT 1535
SEQIDNO_56-M.bovisBCG_Tokyo172 CGTCTGCGCCTCGATGCCTTGCGCGGCATCGACCAACAGCACCGCACCCT 1535
SEQIDNO_57-M.microtti CGTCTGCGCCTCGATGCCTTGCGCGGCATCGACCAACAGCACCGCACCCT 1535
SEQIDNO_58-M.canetti_CIPT14001 CGTCTGCGCCTCGATGCCTTGCGCGGCATCGACCAACAGCACCGCACCCT 1535
SEQIDNO_59-M.africanum_GM04118 --------------------------------------------------
SEQIDNO_76-M.capraeRIVM2006_19 --------------------------------------------------
SEQIDNO_60-M.avium_subsp_Parat CGTCTGGGCCTCGATGCCCTGCGCGGCGTCGACCAGCAGCACGGCACCTT 1526
SEQIDNO_61-M.leprae_cosmid_B19 GGTCTGAGCTTCGATGCCCTGGACGGCGTCTACCAGCAGCACCGCACCCT 1526
SEQIDNO_62-M.ulcerans_Agy99 CGTCTGGGCCTCGATGCCCTGGGCGGCGTCAACCAGCAGCACCGCGCCCT 1526
SEQIDNO_63-M.avium_104 CGTCTGGGCCTCGATGCCCTGCGCGGCGTCGACCAGCAGCACGGCACCTT 1526
SEQIDNO_64-M.vanbaalenii_PYR-1 CGTCTGCGCTTCGATGCCCTGGGCGGCGTCGACCAGCAGCACCGCGCCCT 1526
SEQIDNO_65-M.gilvum_PYR-GCK GGTCTGCGCCTCGATGCCCTGGGCGGCGTCGACCAGCAGCACCGCACCCT 1526
SEQIDNO_66-M.abscessus CGTCTGCGCTTCGATGCCCTGCGCGGCGTCGACCAGCAGCACTGCCCCCT 1538
SEQIDNO_67-M.marinum_M CGTCTGGGCCTCGATGCCCTGGGCGGCGTCAACCAGCAGCACCGCGCCCT 1526
SEQIDNO_68-M.smegmatis CGTCTGCGCCTCGATGCCCTGCGCCGCGTCGACCAGCAGCACCGCGCCCT 1526

SEQIDNO_47-M.tuberculosis_H37R CGCAAGCCTCCAGCGCACGCGAGACTTCGTAGGTGAAGTCGACATGGCCC 1585
SEQIDNO_48-M.tuberculosis_H37R CGCAAGCCTCCAGCGCACGCGAGACTTCGTAGGTGAAGTCGACATGGCCC 1585
SEQIDNO_49-M.tuberculosis_F11 CGCAAGCCTCCAGCGCACGCGAGACTTCGTAGGTGAAGTCGACATGGCCC 1585
SEQIDNO_50-M.tuberculosis_KZN1 CGCAAGCCTCCAGCGCACGCGAGACTTCGTAGGTGAAGTCGACATGGCCC 1585
SEQIDNO_51-M.tuberculosis_CDC1 CGCAAGCCTCCAGCGCACGCGAGACTTCGTAGGTGAAGTCGACATGGCCC 1585
SEQIDNO_52-M.tuberculosis_Haar CGCAAGCCTCCAGCGCACGCGAGACTTCGTAGGTGAAGTCGACATGGCCC 1585
SEQIDNO_53-M.tuberculosis_C CGCAAGCCTCCAGCGCACGCGAGACTTCGTAGGTGAAGTCGACATGGCCC 1585
SEQIDNO_54-M.bovisAF2122/97 CGCAAGCCTCCAGCGCACGCGAGACTTCGTAGGTGAAGTCGACATGGCCC 1585
SEQIDNO_55-M.bovisBCG_Pasteur1 CGCAAGCCTCCAGCGCACGCGAGACTTCGTAGGTGAAGTCGACATGGCCC 1585
SEQIDNO_56-M.bovisBCG_Tokyo172 CGCAAGCCTCCAGCGCACGCGAGACTTCGTAGGTGAAGTCGACATGGCCC 1585
SEQIDNO_57-M.microtti CGCAAGCCTCCAGCGCACGCGAGACTTCGTAGGTGAAGTCGACATGGCCC 1585
SEQIDNO_58-M.canetti_CIPT14001 CGCAAGCCTCCAGCGCACGCGAGACTTCGTAGGTGAAGTCGACATGGCCC 1585
SEQIDNO_59-M.africanum_GM04118 --------------------------------------------------
SEQIDNO_76-M.capraeRIVM2006_19 --------------------------------------------------
SEQIDNO_60-M.avium_subsp_Parat CGCAGGCCTCCAGTGCGCGCGACACCTCGTAGGTGAAGTCGACGTGGCCC 1576
SEQIDNO_61-M.leprae_cosmid_B19 CACAGGCTTCCAATGCTCGCGATACCTCGTAGGTGAAGTCCACATGGCCG 1576
SEQIDNO_62-M.ulcerans_Agy99 CGCAGGCCTCCAGCGCACGTGACACCTCGTAGGTGAAGTCGACGTGTCCT 1576
SEQIDNO_63-M.avium_104 CGCAGGCCTCCAGTGCGCGCGACACCTCGTAGGTGAAGTCGACGTGGCCC 1576
SEQIDNO_64-M.vanbaalenii_PYR-1 CGCACGCCTCCAGCGCGCGGGACACCTCATAGGTGAAATCAACATGGCCG 1576
SEQIDNO_65-M.gilvum_PYR-GCK CGCAGGCCTCCAGCGCGCGCGACACCTCGTAGGTGAAATCGACGTGGCCA 1576
SEQIDNO_66-M.abscessus CGCACGCCTCCAGGGCGCGCGACACCTCGTAGGTGAAGTCGACGTGCCCG 1588
SEQIDNO_67-M.marinum_M CGCAGGCCTCCAGCGCACGTGACACCTCGTAGGTGAAGTCGACGTGTCCT 1576
SEQIDNO_68-M.smegmatis CGCAGGCCTCCAGCGCGCGCGACACCTCGTAGGTGAAGTCGACGTGGCCC 1576

SEQIDNO_47-M.tuberculosis_H37R GGGGTGTCGATCAGATGCAGCACGTA------------------GTCGGT 1617
SEQIDNO_48-M.tuberculosis_H37R GGGGTGTCGATCAGATGCAGCACGTA------------------GTCGGT 1617
SEQIDNO_49-M.tuberculosis_F11 GGGGTGTCGATCAGATGCAGCACGTA------------------GTCGGT 1617
SEQIDNO_50-M.tuberculosis_KZN1 GGGGTGTCGATCAGATGCAGCACGTA------------------GTCGGT 1617
SEQIDNO_51-M.tuberculosis_CDC1 GGGGTGTCGATCAGATGCAGCACGTA------------------GTCGGT 1617
SEQIDNO_52-M.tuberculosis_Haar GGGGTGTCGATCAGATGCAGCACGTA------------------GTCGGT 1617
SEQIDNO_53-M.tuberculosis_C GGGGTGTCGATCAGATGCAGCACGTA------------------GTCGGT 1617
SEQIDNO_54-M.bovisAF2122/97 GGGGTGTCGATCAGATGCAGCACGTA------------------GTCGGT 1617
SEQIDNO_55-M.bovisBCG_Pasteur1 GGGGTGTCGATCAGATGCAGCACGTA------------------GTCGGT 1617
SEQIDNO_56-M.bovisBCG_Tokyo172 GGGGTGTCGATCAGATGCAGCACGTA------------------GTCGGT 1617
SEQIDNO_57-M.microtti GGGGTGTCGATCAGATGCAGCACGTA------------------GTCGGT 1617
SEQIDNO_58-M.canetti_CIPT14001 GGGGTGTCGATCAGATGCAGCACGTA------------------GTCGGT 1617
SEQIDNO_59-M.africanum_GM04118 --------------------------------------------------
SEQIDNO_76-M.capraeRIVM2006_19 --------------------------------------------------
SEQIDNO_60-M.avium_subsp_Parat GGGGTGTCGATCAGGTGCAGGACAAATTCT------TTGCCGGCGTCCTC 1620
SEQIDNO_61-M.leprae_cosmid_B19 GGGGTGTCGATCAAGTGCAACACATAA-----------------TTCTCA 1609
SEQIDNO_62-M.ulcerans_Agy99 GGCGTGTCGATGAGATGCAGGACGTA------------------CTCGGT 1608
SEQIDNO_63-M.avium_104 GGGGTGTCGATCAGGTGCAGGACAAATTCT------TTGCCGGCGTCCTC 1620
SEQIDNO_64-M.vanbaalenii_PYR-1 GGCGTGTCAATCAAATGCAGCACGAA------------------CTCCTC 1608
SEQIDNO_65-M.gilvum_PYR-GCK GGGGTGTCGATCAGATGCAGGACGAA------------------CTCTTC 1608
SEQIDNO_66-M.abscessus GGGGTGTCGATCAGGTGTAGCACATG------------------GTCCTG 1620
SEQIDNO_67-M.marinum_M GGCGTGTCGATGAGATGCAGGACGTA------------------CTCGGT 1608
SEQIDNO_68-M.smegmatis GGGGTGTCGATCAGGTGCAGCACGTAATCACCCGCGTCCGCGCCGTCTTG 1626

SEQIDNO_47-M.tuberculosis_H37R CTTGTCG----ACCCG-------CCAGGGTAGCCGCACATTCTGGGCCTT 1656
SEQIDNO_48-M.tuberculosis_H37R CTTGTCG----ACCCG-------CCAGGGTAGCCGCACATTCTGGGCCTT 1656
SEQIDNO_49-M.tuberculosis_F11 CTTGTCG----ACCCG-------CCAGGGTAGCCGCACATTCTGGGCCTT 1656
SEQIDNO_50-M.tuberculosis_KZN1 CTTGTCG----ACCCG-------CCAGGGTAGCCGCACATTCTGGGCCTT 1656
SEQIDNO_51-M.tuberculosis_CDC1 CTTGTCG----ACCCG-------CCAGGGTAGCCGCACATTCTGGGCCTT 1656
SEQIDNO_52-M.tuberculosis_Haar CTTGTCG----ACCCG-------CCAGGGTAGCCGCACATTCTGGGCCTT 1656
SEQIDNO_53-M.tuberculosis_C CTTGTCG----ACCCG-------CCAGGGTAGCCGCACATTCTGGGCCTT 1656
SEQIDNO_54-M.bovisAF2122/97 CTTGTCG----ACCCG-------CCAGGGTAGCCGCACATTCTGGGCCTT 1656
SEQIDNO_55-M.bovisBCG_Pasteur1 CTTGTCG----ACCCG-------CCAGGGTAGCCGCACATTCTGGGCCTT 1656
SEQIDNO_56-M.bovisBCG_Tokyo172 CTTGTCG----ACCCG-------CCAGGGTAGCCGCACATTCTGGGCCTT 1656
SEQIDNO_57-M.microtti CTTGTCG----ACCCG-------CCAGGGTAGCCGCACATTCTGGGCCTT 1656
SEQIDNO_58-M.canetti_CIPT14001 CTTGTCG----ACCCG-------CCAGGGTAGCCGCACATTCTGGGCCTT 1656
SEQIDNO_59-M.africanum_GM04118 --------------------------------------------------
SEQIDNO_76-M.capraeRIVM2006_19 --------------------------------------------------
SEQIDNO_60-M.avium_subsp_Parat GCCGCCGGAG-ACCTG-------CCAGGGCAGCCGCACGTTCTGCGCCTT 1662
SEQIDNO_61-M.leprae_cosmid_B19 GTCGTCCCACCAGCTGTGACACTCCAAGACAGCCGCACGTTCTGCGCTTT 1659
SEQIDNO_62-M.ulcerans_Agy99 TCCATCG----AGCTG-------CCAGGGCAGCCGCACATTCTGCGCCTT 1647
SEQIDNO_63-M.avium_104 GCCGCCGGAG-ACCTG-------CCAGGGCAGCCGCACGTTCTGCGCCTT 1662
SEQIDNO_64-M.vanbaalenii_PYR-1 ACCGTTG----ACCAC-------CCACGGCAGCCGCACGTTCTGCGCCTT 1647
SEQIDNO_65-M.gilvum_PYR-GCK GCCGTTG----ACGAC-------CCACGGCAGGCGCACGTTCTGCGCCTT 1647
SEQIDNO_66-M.abscessus GCCATTG----AGCTG-------CCACGGCAGCCGCACGTTCTGTGCCTT 1659

Figure 2 (cont)

```
SEQIDNO_67-M.marinum_M             TCCATCG----AGCTG-------CCAGGGCAGCCGCACATTCTGCGCCTT 1647
SEQIDNO_68-M.smegmatis             GCCGTCCTTC-AGCGT-------CCACGGAAGCCGGACGTTCTGAGCCTT 1668

SEQIDNO_47-M.tuberculosis_H37R     GATGGTGATGCCGCGTTCCCGCTCGATGTCCATCCGATCCAAGTACTGGG 1706
SEQIDNO_48-M.tuberculosis_H37R     GATGGTGATGCCGCGTTCCCGCTCGATGTCCATCCGATCCAAGTACTGGG 1706
SEQIDNO_49-M.tuberculosis_F11      GATGGTGATGCCGCGTTCCCGCTCGATGTCCATCCGATCCAAGTACTGGG 1706
SEQIDNO_50-M.tuberculosis_KZN1     GATGGTGATGCCGCGTTCCCGCTCGATGTCCATCCGATCCAAGTACTGGG 1706
SEQIDNO_51-M.tuberculosis_CDC1     GATGGTGATGCCGCGTTCCCGCTCGATGTCCATCCGATCCAAGTACTGGG 1706
SEQIDNO_52-M.tuberculosis_Haar     GATGGTGATGCCGCGTTCCCGCTCGATGTCCATCCGATCCAAGTACTGGG 1706
SEQIDNO_53-M.tuberculosis_C        GATGGTGATGCCGCGTTCCCGCTCGATGTCCATCCGATCCAAGTACTGGG 1706
SEQIDNO_54-M.bovisAF2122/97        GATGGTGATGCCGCGTTCCCGCTCGATGTCCATCCGATCCAAGTACTGGG 1706
SEQIDNO_55-M.bovisBCG_Pasteur1     GATGGTGATGCCGCGTTCCCGCTCGATGTCCATCCGATCCAAGTACTGGG 1706
SEQIDNO_56-M.bovisBCG_Tokyo172     GATGGTGATGCCGCGTTCCCGCTCGATGTCCATCCGATCCAAGTACTGGG 1706
SEQIDNO_57-M.microtti              GATGGTGATGCCGCGTTCCCGCTCGATGTCCATCCGATCCAAGTACTGGG 1706
SEQIDNO_58-M.canetti_CIPT14001     GATGGTGATGCCGCGTTCCCGCTCGATGTCCATCCGATCCAAGTACTGGG 1706
SEQIDNO_59-M.africanum_GM04118     --------------------------------------------------
SEQIDNO_76-M.capraeRIVM2006_19     --------------------------------------------------
SEQIDNO_60-M.avium_subsp_Parat     GATGGTGATGCCGCGCTCCCGCTCGATGTCCATCCGGTCCAGGTACTGGG 1712
SEQIDNO_61-M.leprae_cosmid_B19     AATCGTGATTCCGCGCTCACGTTCGATGTCCATCCGGTCCAGGTACTGGG 1709
SEQIDNO_62-M.ulcerans_Agy99        GATGGTGATCCCGCGTTCGCGTTCGATATCCATCCGGTCCAGGTACTGGG 1697
SEQIDNO_63-M.avium_104             GATGGTGATGCCGCGCTCCCGCTCGATGTCCATCCGGTCCAGGTACTGGG 1712
SEQIDNO_64-M.vanbaalenii_PYR-1     GATCGTGATCCCGCGCTCACGCTCGATGTCCATCCGGTCCAGGTACTGCG 1697
SEQIDNO_65-M.gilvum_PYR-GCK        GATCGTGATGCCGCGTTCCCGCTCGATGTCCATCCGGTCCAGGTACTGCG 1697
SEQIDNO_66-M.abscessus             GATGGTGATGCCGCGCTCACGCTCGATATCCATGCGATCCAGGTACTGCG 1709
SEQIDNO_67-M.marinum_M             GATGGTGATCCCGCGTTCGCGTTCGATATCCATCCGGTCCAGGTACTGGG 1697
SEQIDNO_68-M.smegmatis             GATGGTGATCCCGCGCTCACGTTCGATGTCCATGCGGTCGAGGTACTGGG 1718

SEQIDNO_47-M.tuberculosis_H37R     CCCGCATAGAGCGTTCGTC---GACCACGCCGGTGAGCTGCAGCATCCGG 1753
SEQIDNO_48-M.tuberculosis_H37R     CCCGCATAGAGCGTTCGTC---GACCACGCCGGTGAGCTGCAGCATCCGG 1753
SEQIDNO_49-M.tuberculosis_F11      CCCGCATAGAGCGTTCGTC---GACCACGCCGGTGAGCTGCAGCATCCGG 1753
SEQIDNO_50-M.tuberculosis_KZN1     CCCGCATAGAGCGTTCGTC---GACCACGCCGGTGAGCTGCAGCATCCGG 1753
SEQIDNO_51-M.tuberculosis_CDC1     CCCGCATAGAGCGTTCGTC---GACCACGCCGGTGAGCTGCAGCATCCGG 1753
SEQIDNO_52-M.tuberculosis_Haar     CCCGCATAGAGCGTTCGTC---GACCACGCCGGTGAGCTGCAGCATCCGG 1753
SEQIDNO_53-M.tuberculosis_C        CCCGCATAGAGCGTTCGTC---GACCACGCCGGTGAGCTGCAGCATCCGG 1753
SEQIDNO_54-M.bovisAF2122/97        CCCGCATAGAGCGTTCGTC---GACCACTCCGGTGAGCTGCAGCATCCGG 1753
SEQIDNO_55-M.bovisBCG_Pasteur1     CCCGCATAGAGCGTTCGTC---GACCACTCCGGTGAGCTGCAGCATCCGG 1753
SEQIDNO_56-M.bovisBCG_Tokyo172     CCCGCATAGAGCGTTCGTC---GACCACTCCGGTGAGCTGCAGCATCCGG 1753
SEQIDNO_57-M.microtti              CCCGCATAGAGCGTTCGTC---GACCACTCCGGTGAGCTGCAGCATCCGG 1753
SEQIDNO_58-M.canetti_CIPT14001     CCCGCATAGAGCGTTCGTC---GACCACGCCGGTGAGCTGCAGCATCCGG 1753
SEQIDNO_59-M.africanum_GM04118     --------------------------------------------------
SEQIDNO_76-M.capraeRIVM2006_19     --------------------------------------------------
SEQIDNO_60-M.avium_subsp_Parat     CGCGCATCGACCGCTCGTC---GACGACGCCGGTGAGCTGCAGCATCCGG 1759
SEQIDNO_61-M.leprae_cosmid_B19     CACGCATCGACCGCTCATC---GACGACACCAGTCAGCTGAAGCATCCGG 1756
SEQIDNO_62-M.ulcerans_Agy99        CCCGCATCGAGCGCTCGTC---AACGACCCCGGTCAACTGCAGCAT---- 1740
SEQIDNO_63-M.avium_104             CGCGCATCGACCGCTCGTC---GACGACGCCGGTGAGCTGCAGCATCCGG 1759
SEQIDNO_64-M.vanbaalenii_PYR-1     CCCGCATCGAGCGCTCGTC---GACCACACCGGTGAGCTGCAGCATCCGG 1744
SEQIDNO_65-M.gilvum_PYR-GCK        CCCGCAT---GTCCCTGTCCGCGACCACACCGGTGAGCTGCAGCATCCGA 1744
SEQIDNO_66-M.abscessus             CGCGCATGGAACGCTCGTC---GACCACACCGGTCAGCTGCAGCATCCGG 1756
SEQIDNO_67-M.marinum_M             CCCGCATCGAGCGCTCGTC---AACGACCCCGGTCAACTGCAGCATTCGG 1744
SEQIDNO_68-M.smegmatis             CCCGCATCGACCGCTCATC---GACAACACCGGTGAGCTGCAGCATCCGG 1765

SEQIDNO_47-M.tuberculosis_H37R     TCGGCCAACGTTGACTTGCCGTGGTCGATGTGGGCGATGATGCAAAAGTT 1803
SEQIDNO_48-M.tuberculosis_H37R     TCGGCCAACGTTGACTTGCCGTGGTCGATGTGGGCGATGATGCAAAAGTT 1803
SEQIDNO_49-M.tuberculosis_F11      TCGGCCAACGTTGACTTGCCGTGGTCGATGTGGGCGATGATGCAAAAGTT 1803
SEQIDNO_50-M.tuberculosis_KZN1     TCGGCCAACGTTGACTTGCCGTGGTCGATGTGGGCGATGATGCAAAAGTT 1803
SEQIDNO_51-M.tuberculosis_CDC1     TCGGCCAACGTTGACTTGCCGTGGTCGATGTGGGCGATGATGCAAAAGTT 1803
SEQIDNO_52-M.tuberculosis_Haar     TCGGCCAACGTTGACTTGCCGTGGTCGATGTGGGCGATGATGCAAAAGTT 1803
SEQIDNO_53-M.tuberculosis_C        TCGGCCAACGTTGACTTGCCGTGGTCGATGTGGGCGATGATGCAAAAGTT 1803
SEQIDNO_54-M.bovisAF2122/97        TCGGCCAACGTTGACTTGCCGTGGTCGATGTGGGCGATGATGCAAAAGTT 1803
SEQIDNO_55-M.bovisBCG_Pasteur1     TCGGCCAACGTTGACTTGCCGTGGTCGATGTGGGCGATGATGCAAAAGTT 1803
SEQIDNO_56-M.bovisBCG_Tokyo172     TCGGCCAACGTTGACTTGCCGTGGTCGATGTGGGCGATGATGCAAAAGTT 1803
SEQIDNO_57-M.microtti              TCGGCCAACGTTGACTTGCCGTGGTCGATGTGGGCGATGATGCAAAAGTT 1803
SEQIDNO_58-M.canetti_CIPT14001     TCGGCCAACGTTGACTTGCCGTGGTCGATGTGGGCGATGATGCAAAAGTT 1803
SEQIDNO_59-M.africanum_GM04118     --------------------------------------------------
SEQIDNO_76-M.capraeRIVM2006_19     --------------------------------------------------
SEQIDNO_60-M.avium_subsp_Parat     TCGGCCAGCGTCGACTTGCCGTGATCGATGTGGGCGATGATGCAGAAGTT 1809
SEQIDNO_61-M.leprae_cosmid_B19     TCCGCCAGCGTGGATTTGCCGTGATCAATATGAGCGATTATGCAGAAGTT 1806
SEQIDNO_62-M.ulcerans_Agy99        --------------------------------------------------
SEQIDNO_63-M.avium_104             TCGGCCAGCGTCGACTTGCCGTGATCGATGTGGGCGATGATGCAGAAGTT 1809
SEQIDNO_64-M.vanbaalenii_PYR-1     TCGGCCAGGGTGGACTTTCCGTGGTCGATGTGGGCGATGATGCAGAAGTT 1794
SEQIDNO_65-M.gilvum_PYR-GCK        TCGGCCAGGGTGGACTTGCCGTGGTCGATGTCGGCGATGATGCAGAAGTT 1794
SEQIDNO_66-M.abscessus             TCGGCCAGGGTCGACTTCCCGTGGTCGATGTGGGCGATGATGCAGAAGTT 1806
SEQIDNO_67-M.marinum_M             TCCGCCAGCGTCGACTTTCCGTGGTCGATGTCAGCGATGATGCAGAAGTT 1794
SEQIDNO_68-M.smegmatis             TCGGCCAGCGTCGACTTGCCGTGGTCGATGTGGGCGATGATGCAGAAGTT 1815

SEQIDNO_47-M.tuberculosis_H37R     CCTAATCTGCGCCGGCGCAGTGAAGGTTTTGTCGGCGAAACTGCTGATGG 1853
SEQIDNO_48-M.tuberculosis_H37R     CCTAATCTGCGCCGGCGCAGTGAAGGTTTTGTCGGCGAAACTGCTGATGG 1853
SEQIDNO_49-M.tuberculosis_F11      CCTAATCTGCGCCGGCGCAGTGAAGGTTTTGTCGGCGAAACTGCTGATGG 1853
SEQIDNO_50-M.tuberculosis_KZN1     CCTAATCTGCGCCGGCGCAGTGAAGGTTTTGTCGGCGAAACTGCTGATGG 1853
SEQIDNO_51-M.tuberculosis_CDC1     CCTAATCTGCGCCGGCGCAGTGAAGGTTTTGTCGGCGAAACTGCTGATGG 1853
SEQIDNO_52-M.tuberculosis_Haar     CCTAATCTGCGCCGGCGCAGTGAAGGTTTTGTCGGCGAAACTGCTGATGG 1853
SEQIDNO_53-M.tuberculosis_C        CCTAATCTGCGCCGGCGCAGTGAAGGTTTTGTCGGCGAAACTGCTGATGG 1853
SEQIDNO_54-M.bovisAF2122/97        CCTAATCTGCGCCGGCGCAGTGAAGGTTTTGTCGGCGAAACTGCTGATGG 1853
SEQIDNO_55-M.bovisBCG_Pasteur1     CCTAATCTGCGCCGGCGCAGTGAAGGTTTTGTCGGCGAAACTGCTGATGG 1853
```

Figure 2 (cont)

```
SEQIDNO_56-M.bovisBCG_Tokyo172        CCTAATCTGCGCCGGCGCAGTGAAGGTTTTGTCGGCGAAACTGCTGATGG 1853
SEQIDNO_57-M.microtti                 CCTAATCTGCGCCGGCGCAGTGAAGGTTTTGTCGGCGAAACTGCTGATGG 1853
SEQIDNO_58-M.canetti_CIPT14001        CCTAATCTGCGCCGGCGCAGTGAAGGTTTTGTCGGCGAAACTGCTGATGG 1853
SEQIDNO_59-M.africanum_GM04118        --------------------------------------------------
SEQIDNO_76-M.capraeRIVM2006_19        --------------------------------------------------
SEQIDNO_60-M.avium_subsp_Parat        GCGAATCTGCGCCGGCGCGGTGAAGGTCTTGTCGGCGAAACTGCTGATGG 1859
SEQIDNO_61-M.leprae_cosmid_B19        CCTAATCTGCGCCGGCGCGGTAAAGGTCTTGTCAGCGAAACTGCTGATGG 1856
SEQIDNO_62-M.ulcerans_Agy99           --------------------------------------------------
SEQIDNO_63-M.avium_104                GCGAATCTGCGCCGGCGCGGTGAAGGTCTTGTCGGCGAAACTGCTGATGG 1859
SEQIDNO_64-M.vanbaalenii_PYR-1        CCGAATCTGCGCCGGCGCAGTGAACGTCTTGTCGGCGAAGCTGCTGATGG 1844
SEQIDNO_65-M.gilvum_PYR-GCK           CCTGATCTGCGCCGGCGCAGTGAACGTCTTGTCGGCGAAGCTGGCGATGG 1844
SEQIDNO_66-M.abscessus                ACGAATCAGCGCCGGATCCGTGAACGTCGTGTCGGCAAAACT-----TGG 1851
SEQIDNO_67-M.marinum_M                CCGAATCTGCGCCGGCGGGGTGAAGGTTTTGTCGGCGAAACTGCTGATGG 1844
SEQIDNO_68-M.smegmatis                CCGAATCTGCGCCGGCGCAGTGAACGTCTTGTCGGCGAAGCTGCTGATGG 1865

SEQIDNO_47-M.tuberculosis_H37R        GAATCTCCTGG-------AG--CGGGGGTTGACGGGTA------------ 1882
SEQIDNO_48-M.tuberculosis_H37R        GAATCTCCTGG-------AG--CGGGGGTTGACGGGTA------------ 1882
SEQIDNO_49-M.tuberculosis_F11         GAATCTCCTGG-------AG--CGGGGGTTGACGGGTA------------ 1882
SEQIDNO_50-M.tuberculosis_KZN1        GAATCTCCTGG-------AG--CGGGGGTTGACGGGTA------------ 1882
SEQIDNO_51-M.tuberculosis_CDC1        GAATCTCCTGG-------AG--CGGGGGTTGACGGGTA------------ 1882
SEQIDNO_52-M.tuberculosis_Haar        GAATCTCCTGG-------AG--CGGGGGTTGACGGGTA------------ 1882
SEQIDNO_53-M.tuberculosis_C           GAATCTCCTGG-------AG--CGGGGGTTGACGGGTA------------ 1882
SEQIDNO_54-M.bovisAF2122/97           GAATCTCCTGG-------AG--CGGGGGTTGACGGGTA------------ 1882
SEQIDNO_55-M.bovisBCG_Pasteur1        GAATCTCCTGG-------AG--CGGGGGTTGACGGGTA------------ 1882
SEQIDNO_56-M.bovisBCG_Tokyo172        GAATCTCCTGG-------AG--CGGGGGTTGACGGGTA------------ 1882
SEQIDNO_57-M.microtti                 GAATCTCCTGG-------AG--CGGGGGTTGACGGGTA------------ 1882
SEQIDNO_58-M.canetti_CIPT14001        GAATCTCCTGG-------AG--CGGGGGTTGACGGGTA------------ 1882
SEQIDNO_59-M.africanum_GM04118        --------------------------------------------------
SEQIDNO_76-M.capraeRIVM2006_19        --------------------------------------------------
SEQIDNO_60-M.avium_subsp_Parat        GTATCTCCTGG-------T---CCGGGCCTGCTAGACGGCGGTTCGCAAG 1899
SEQIDNO_61-M.leprae_cosmid_B19        GAATCTCCTGGGCTCCAGTTACTAGAGAATGTTTGAACGGCGATT-CGCC 1905
SEQIDNO_62-M.ulcerans_Agy99           --------------------------------------------------
SEQIDNO_63-M.avium_104                GTATCTCCTGG-------T---CCGGGCCTGCTAGACGGCGGTTCGCAAG 1899
SEQIDNO_64-M.vanbaalenii_PYR-1        GAATCTCCTGG-------TGAGCGGGTCGTGGCGGCCTGAA-----CAGG 1882
SEQIDNO_65-M.gilvum_PYR-GCK           GAATCTCCTGG-------TGAGCGGGGTCTGTCGGCCTGAG-----CAGG 1882
SEQIDNO_66-M.abscessus                --------------------------------------------------
SEQIDNO_67-M.marinum_M                GACTCTCCTGA-------AG--CGGGGGTTTGCGGGTT------------ 1873
SEQIDNO_68-M.smegmatis                GAATCTCCTGG-------T-----GAGCGTGG------------------ 1885

SEQIDNO_47-M.tuberculosis_H37R        ----TCCAGGGTATCC-GCGTCGGGCAGCTGCGACCCAATCGCGCTCGGT 1927
SEQIDNO_48-M.tuberculosis_H37R        ----TCCAGGGTATCC-GCGTCGGGCAGCTGCGACCCAATCGCGCTCGGT 1927
SEQIDNO_49-M.tuberculosis_F11         ----TCCAGGGTATCC-GCGTCGGGCAGCTGCGACCCAATCGCGCTCGGT 1927
SEQIDNO_50-M.tuberculosis_KZN1        ----TCCAGGGTATCC-GCGTCGGGCAGCTGCGACCCAATCGCGCTCGGT 1927
SEQIDNO_51-M.tuberculosis_CDC1        ----TCCAGGGTATCC-GCGTCGGGCAGCTGCGACCCAATCGCGCTCGGT 1927
SEQIDNO_52-M.tuberculosis_Haar        ----TCCAGGGTATCC-GCGTCGGGCAGCTGCGACCCAATCGCGCTCGGT 1927
SEQIDNO_53-M.tuberculosis_C           ----TCCAGGGTATCC-GCGTCGGGCAGCTGCGACCCAATCGCGCTCGGT 1927
SEQIDNO_54-M.bovisAF2122/97           ----TCCAGGGTATCC-GCGTCGGGCAGCTGCGACCCAATCGCGCTCGGT 1927
SEQIDNO_55-M.bovisBCG_Pasteur1        ----TCCAGGGTATCC-GCGTCGGGCAGCTGCGACCCAATCGCGCTCGGT 1927
SEQIDNO_56-M.bovisBCG_Tokyo172        ----TCCAGGGTATCC-GCGTCGGGCAGCTGCGACCCAATCGCGCTCGGT 1927
SEQIDNO_57-M.microtti                 ----TCCAGGGTATCC-GCGTCGGGCAGCTGCGACCCAATCGCGCTCGGT 1927
SEQIDNO_58-M.canetti_CIPT14001        ----TCCAGGGTATCC-GCGTCGGGCAGCTGCGACCCAATCGCGCTCGGT 1927
SEQIDNO_59-M.africanum_GM04118        --------------------------------------------------
SEQIDNO_76-M.capraeRIVM2006_19        --------------------------------------------------
SEQIDNO_60-M.avium_subsp_Parat        TGTGTCCAGCGTATCG-GCGCGGCCGGACTGCGGCACAATCGGCGCGTCT 1948
SEQIDNO_61-M.leprae_cosmid_B19        GGTGTCCGGCTTATCC-ACGCGAAGTGACCAAGACAC------------- 1941
SEQIDNO_62-M.ulcerans_Agy99           --------------------------------------------------
SEQIDNO_63-M.avium_104                TGTGTCCAGCGTATCG-GCGCGGCCGGACTGCGGCAC------------- 1935
SEQIDNO_64-M.vanbaalenii_PYR-1        CCTGTCCAGAGTATCGAGCGCA-CACCCCCGCGACACAATCGAGCCGTGA 1931
SEQIDNO_65-M.gilvum_PYR-GCK           CCAGTCCAGAGTATCGAGCGCA-T-------------------------- 1905
SEQIDNO_66-M.abscessus                --------------------CA-C-------------------------- 1854
SEQIDNO_67-M.marinum_M                ----TCCAGCCTATCT-GTGCAGCGCCGCCCGGACCTACTTGAGGCCAA- 1917
SEQIDNO_68-M.smegmatis                ------------GTCAAGCGCA-C-------------------------- 1896

SEQIDNO_47-M.tuberculosis_H37R        CGATCGCGTCTATGCTGCGAGCATGGCGTCCGCAC--------- 1962
SEQIDNO_48-M.tuberculosis_H37R        CGATCGCGTCTATGCTGCGAGCATGGCGTCCGCAC--------- 1962
SEQIDNO_49-M.tuberculosis_F11         CGATCGCGTCTATGCTGCGAGCATGGCGTCCGCAC--------- 1962
SEQIDNO_50-M.tuberculosis_KZN1        CGATCGCGTCTATGCTGCGAGCATGGCGTCCGCAC--------- 1962
SEQIDNO_51-M.tuberculosis_CDC1        CGATCGCGTCTATGCTGCGAGCATGGCGTCCGCAC--------- 1962
SEQIDNO_52-M.tuberculosis_Haar        CGATCGCGTCTATGCTGCGAGCATGGCGTCCGCAC--------- 1962
SEQIDNO_53-M.tuberculosis_C           CGATCGCGTCTATGCTGCGAGCATGGCGTCCGCACGGAAGTCAC 1971
SEQIDNO_54-M.bovisAF2122/97           CGATCGCGTCTATGCTGCGAGCATGGCGTCCGCAC--------- 1962
SEQIDNO_55-M.bovisBCG_Pasteur1        CGATCGCGTCTATGCTGCGAGCATGGCGTCCGCAC--------- 1962
SEQIDNO_56-M.bovisBCG_Tokyo172        CGATCGCGTCTATGCTGCGAGCATGGCGTCCGCAC--------- 1962
SEQIDNO_57-M.microtti                 CGATCGCGTCTATGCTGCGAGCATGGCGTCCGCAC--------- 1962
SEQIDNO_58-M.canetti_CIPT14001        CGATCGCGTCTATGCTGCGAGCATGGCGTCCGCAC--------- 1962
SEQIDNO_59-M.africanum_GM04118        --------------------------------------------
SEQIDNO_76-M.capraeRIVM2006_19        --------------------------------------------
SEQIDNO_60-M.avium_subsp_Parat        ATGCTGCGAATATGGCGTCCGGCCGGAAGTCGCAG--------- 1983
SEQIDNO_61-M.leprae_cosmid_B19        --------------------------------------------
SEQIDNO_62-M.ulcerans_Agy99           --------------------------------------------
SEQIDNO_63-M.avium_104                --------------------------------------------
SEQIDNO_64-M.vanbaalenii_PYR-1        TCGAGGCGGCTTCGGGGCACCGGGGCAC---------------- 1959
SEQIDNO_65-M.gilvum_PYR-GCK           --------------------------------------------
SEQIDNO_66-M.abscessus                --------------------------------------------
SEQIDNO_67-M.marinum_M                --------------------------------------------
```

Figure 2 (cont)

SEQIDNO_68-M.smegmatis ------------------------------------------------

Figure 3 (A)

```
M.tuberculosis_H37Rv                --------------------------------------------------
M.tuberculosis_F11                  --------------------------------------------------
M.tuberculosis_H37Ra                --------------------------------------------------
M.tuberculosis_CDC1551              --------------------------------------------------
M.bovisBCG_Tokyo172                 CTAGGCTAACCCATGGCTACTGCATTGGGGAAATTCGATCCTTGTGAGCT 50
M.bovisBCG_Pasteur1173P2            CTAGGCTAACCCATGGCTACTGCATTGGGGAAATTCGATCCTTGTGAGCT 50
M.bovis_AF2122/97                   CTAGGCTAACCCATGGCTACTGCATTGGGGAAATTCGATCCTTGTGAGCT 50
M.africanumC2__GM04118              --------------------------------------------------
M.africanumC1_CPHL_A                --------------------------------------------------
M.canettii_CIPT14001                --------------------------------------------------
M.microti                           --------------------------------------------------
M.avium                             --------------------------------------------------
M.avium_paratuberculosis_k10        --------------------------------------------------
M.leprae_Br4923                     --------------------------------------------------
M.marinum_M                         --------------------------------------------------
M.ulcerans_Agy99                    --------------------------------------------------

M.tuberculosis_H37Rv                ---------------------------------TTACTTTGCCGCGACGA 17
M.tuberculosis_F11                  ---------------------------------TTACTTTGCCGCGACGA 17
M.tuberculosis_H37Ra                ---------------------------------TTACTTTGCCGCGACGA 17
M.tuberculosis_CDC1551              ---------------------------------TTACTTTGCCGCGACGA 17
M.bovisBCG_Tokyo172                 GCTCGGATAGCTGTGCCCCAACCGTGCGGACAATTACTTTGCCGCGACGA 100
M.bovisBCG_Pasteur1173P2            GCTCGGATAGCTGTGCCCCAACCGTGCGGACAATTACTTTGCCGCGACGA 100
M.bovis_AF2122/97                   GCTCGGATAGCTGTGCCCCAACCGTGCGGACAATTACTTTGCCGCGACGA 100
M.africanumC2__GM04118              ---------------------------------TTACTTTGCCGCGACGA 17
M.africanumC1_CPHL_A                ---------------------------------TTACTTTGCCGCGACGA 17
M.canettii_CIPT14001                ---------------------------------TTACTTTGCCGCGACGA 17
M.microti                           ---------------------------------TTACTTTGCCGCGACGA 17
M.avium                             ---------------------------------CTACTTCGCCGCCACCA 17
M.avium_paratuberculosis_k10        ---------------------------------CTACTTCGCCGCCACCA 17
M.leprae_Br4923                     ---------------------------------TTACTTGGGGGCGACGA 17
M.marinum_M                         ---------------------------------TCACTTCACCGCAACCA 17
M.ulcerans_Agy99                    ---------------------------------TCACTTCACCGCAACCA 17
                                                                      ****    ** ** *

M.tuberculosis_H37Rv                CGAATCCGGCGATGATCGCCTCGATGTCGGAAGCGTGCTT-GACGGCCTC 66
M.tuberculosis_F11                  CGAATCCGGCGATGATCGCCTCGATGTCGGAAGCGTGCTT-GACGGCCTC 66
M.tuberculosis_H37Ra                CGAATCCGGCGATGATCGCCTCGATGTCGGAAGCGTGCTT-GACGGCCTC 66
M.tuberculosis_CDC1551              CGAATCCGGCGATGATCGCCTCGATGTCGGAAGCGTGCTT-GACGGCCTC 66
M.bovisBCG_Tokyo172                 CGAATCCGGCGATGATCGCCTCGATGTCGGAAGCGTGCTT-GACGGCCTC 149
M.bovisBCG_Pasteur1173P2            CGAATCCGGCGATGATCGCCTCGATGTCGGAAGCGTGCTT-GACGGCCTC 149
M.bovis_AF2122/97                   CGAATCCGGCGATGATCGCCTCGATGTCGGAAGCGTGCTT-GACGGCCTC 149
M.africanumC2__GM04118              CGAATCCGGCGATGATCGCCTCGATGTCGGAAGCGTGCTT-GACGGCCTC 66
M.africanumC1_CPHL_A                CGAATCCGGCGATGATCGCCTCGATGTCGGAAGCGTGCTT-GACGGCCTC 66
M.canettii_CIPT14001                CGAATCCGGCGATGATCGCCTCGATGTCGGAAGCGTGCTT-GACGGCCTC 66
M.microti                           CGAATCCGGCGATGATCGCCTCGATGTCGGAAGCGTGCTT-GACGGCCTC 66
M.avium                             CGAAGCCGTGGATGATCGCCTCGATGTCGGTCGACTCCGC-GGCGGCCTG 66
M.avium_paratuberculosis_k10        CGAAGCCGTGGATGATCGCCTCGATGTCGGTCGACTCCGC-GGCGGCCTG 66
M.leprae_Br4923                     CAAAGCCGCGGATGATAGCCTCGATATCGTTTGATTGTGC-GACCGCCTC 66
M.marinum_M                         CGAATCCGTTGATGATCGACTCGATGTCGGATG-CGCTGCCGGCGGCCTG 66
M.ulcerans_Agy99                    CGAATCCGTTGATGATCGACTCGATGTCGGATG-CGCTGCCGGCGGCCTG 66
                                    * ** ***  ****** * ****** ***   *        * * ****

M.tuberculosis_H37Rv                GTTGGCCAGACTCGTGATGGTGAGCTGCACCAGGTAGCGCTGCTTGGCCG 116
M.tuberculosis_F11                  GTTGGCCAGACTCGTGATGGTGAGCTGCACCAGGTAGCGCTGCTTGGCCG 116
M.tuberculosis_H37Ra                GTTGGCCAGACTCGTGATGGTGAGCTGCACCAGGTAGCGCTGCTTGGCCG 116
M.tuberculosis_CDC1551              GTTGGCCAGACTCGTGATGGTGAGCTGCACCAGGTAGCGCTGCTTGGCCG 116
M.bovisBCG_Tokyo172                 GTTGGCCAGACTCGTGATGGTGAGCTGCACCAGGTAGCGCTGCTTGGCCG 199
M.bovisBCG_Pasteur1173P2            GTTGGCCAGACTCGTGATGGTGAGCTGCACCAGGTAGCGCTGCTTGGCCG 199
M.bovis_AF2122/97                   GTTGGCCAGACTCGTGATGGTGAGCTGCACCAGGTAGCGCTGCTTGGCCG 199
M.africanumC2__GM04118              GTTGGCCAGACTCGTGATGGTGAGCTGCACCAGGTAGCGCTGCTTGGCCG 116
M.africanumC1_CPHL_A                GTTGGCCAGACTCGTGATGGTGAGCTGCACCAGGTAGCGCTGCTTGGCCG 116
M.canettii_CIPT14001                GTTGGCCAGACTCGTGATGGTGAGCTGCACCAGGTAGCGCTGCTTGGCCG 116
M.microti                           GTTGGCCAGACTCGTGATGGTGAGCTGCACCAGGTAGCGCTGCTTGGCCG 116
M.avium                             ATCGGCCAGGCTGGTGATCGTGAGCTGCACCAGATAGCGCTGATGCGCCG 116
M.avium_paratuberculosis_k10        ATCGGCCAGGCTGGTGATCGTGAGCTGCACCAGATAGCGCTGATGCGCCG 116
M.leprae_Br4923                     GTTGGCCAAGCTGGTAATGGTGAGCTGAACGAGATACTGTTGCTTAGAGG 116
M.marinum_M                         ACTGGCCAGGCTGGTGATGGTCAGTTGGACCAGATACCGCTGATTGTCCG 116
M.ulcerans_Agy99                    ACTGGCCAGGCTGGTGATGGTCAGTTGGACCAGATACCGCTGGTTGTCCG 116
                                       *****  ** ** ** ** ** ** ** ** ** **  * ** *     *

M.tuberculosis_H37Rv                GCGGTGCGCCGGTTGGGAAGACGATCCGGTTCCAGGTGTGCAGTCGCCTG 166
M.tuberculosis_F11                  GCGGTGCGCCGGTTGGGAAGACGATCCGGTTCCAGGTGTGCAGTCGCCTG 166
M.tuberculosis_H37Ra                GCGGTGCGCCGGTTGGGAAGACGATCCGGTTCCAGGTGTGCAGTCGCCTG 166
M.tuberculosis_CDC1551              GCGGTGCGCCGGTTGGGAAGACGATCCGGTTCCAGGTGTGCAGTCGCCTG 166
M.bovisBCG_Tokyo172                 -----GCGCCGGTTGGGAAGACGATCCGGTTCCAGGTGTGCAGTCGCCTG 244
M.bovisBCG_Pasteur1173P2            -----GCGCCGGTTGGGAAGACGATCCGGTTCCAGGTGTGCAGTCGCCTG 244
M.bovis_AF2122/97                   -----GCGCCGGTTGGGAAGACGATCCGGTTCCAGGTGTGCAGTCGCCTG 244
M.africanumC2__GM04118              GCGGTGCGCCGGTTGGGAAGACGATCCGGTTCCAGGTGTGCAGTCGCCTG 166
M.africanumC1_CPHL_A                GCGGTGCGCCGGTTGGGAAGACGATCCGGTTCCAGGTGTGCAGTCGCCTG 166
M.canettii_CIPT14001                GCGGTGCGCCGGTTGGGAAGACGATCCGGTTCCAGGTGTGCAGTCGCCTG 166
M.microti                           GCGGTGCGCCGGTTGGGAAGACGATCCGGTTCCAGGTGTGCAGTCGCCTG 166
M.avium                             GCGGCGATCCGGTGGCGATGACGATCCGGTTCCAGCTGTGCAGCCGCATG 166
```

Figure 3A (cont)

```
M.avium_paratuberculosis_k10      GCGGCGATCCGGTGGCGATGACGATCCGGTTCCAGCTGTGCAGCCGCATG 166
M.leprae_Br4923                   GTGGTGGACCGGTGGGGATCACGATTCGGTTCCAGGCATGTAGTCGCCTG 166
M.marinum_M                       GCGGCGGCCCGGTGGGAATGACGATCCGATTCCAGCTGTGCATGCGGGCA 166
M.ulcerans_Agy99                  GCGGCGGCCCGGTGGGAATGACGATCCGATTCCAGCTGTGCATGCGGGCA 166
                                        *  *****  *   *   *****  **  ******     **  *   **

M.tuberculosis_H37Rv              CCGTGCAGGTCATAACTGCCCTGAATCATCGAGGACGGAAACCCGTTGAA 216
M.tuberculosis_F11                CCGTGCAGGTCATAACTGCCCTGAATCATCGAGGACGGAAACCCGTTGAA 216
M.tuberculosis_H37Ra              CCGTGCAGGTCATAACTGCCCTGAATCATCGAGGACGGAAACCCGTTGAA 216
M.tuberculosis_CDC1551            CCGTGCAGGTCATAACTGCCCTGAATCATCGAGGACGGAAACCCGTTGAA 216
M.bovisBCG_Tokyo172               CCGTGCAGGTCATAACTGCCCTGAATCATCGAGGACGGAAACCCGTTGAA 294
M.bovisBCG_Pasteur1173P2          CCGTGCAGGTCATAACTGCCCTGAATCATCGAGGACGGAAACCCGTTGAA 294
M.bovis_AF2122/97                 CCGTGCAGGTCATAACTGCCCTGAATCATCGAGGACGGAAACCCGTTGAA 294
M.africanumC2__GM04118            CCGTGCAGGTCATAACTGCCCTGAATCATCGAGGACGGAAACCCGTTGAA 216
M.africanumC1_CPHL_A              CCGTGCAGGTCATAACTGCCCTGAATCATCGAGGACGGAAACCCGTTGAA 216
M.canettii_CIPT14001              CCGTGCAGGTCATAACTGCCCTGAATCATCGAGGACGGAAACCCGTTGAA 216
M.microti                         CCGTGCAGGTCATAACTGCCCTGAATCATCGAGGACGGAAACCCGTTGAA 216
M.avium                           CCGTCCAGGTCGTAGCTGCCCTGGATCATCGACGAGGGAAAGCCGTTGTA 216
M.avium_paratuberculosis_k10      CCGTCCAGGTCGTAGCTGCCCTGGATCATCGACGAGGGAAAGCCGTTGTA 216
M.leprae_Br4923                   CCCTCGAGGTCATAGCTGCCTTGGATCATTGCCGACGGAAAACCGTTGTA 216
M.marinum_M                       CCCTCGAGGTCGTAGCTGCCCTGCATCATCGACGAGGGAAAACCGTGAAA 216
M.ulcerans_Agy99                  CCCTCGAGGTCGTAGCTGCCCTGCATCATCGACGAGGGAAAACCGTGAAA 216
                                  ** *  ***** ** ***** ** ***** *   ** ***** ****   *

M.tuberculosis_H37Rv              --GTCTGCCGTCGAGGAGTCCAATTCGGTGAAGTTCGTCGACAGCCGGGC 264
M.tuberculosis_F11                --GTCTGCCGTCGAGGAGTCCAATTCGGTGAAGTTCGTCGACAGCCGGGC 264
M.tuberculosis_H37Ra              --GTCTGCCGTCGAGGAGTCCAATTCGGTGAAGTTCGTCGACAGCCGGGC 264
M.tuberculosis_CDC1551            --GTCTGCCGTCGAGGAGTCCAATTCGGTGAAGTTCGTCGACAGCCGGGC 264
M.bovisBCG_Tokyo172               --GTCTGCCGTCGAGGAGTCCAATTCGGTGAAGTTCGTCGACAGCCGGGC 342
M.bovisBCG_Pasteur1173P2          --GTCTGCCGTCGAGGAGTCCAATTCGGTGAAGTTCGTCGACAGCCGGGC 342
M.bovis_AF2122/97                 --GTCTGCCGTCGAGGAGTCCAATTCGGTGAAGTTCGTCGACAGCCGGGC 342
M.africanumC2__GM04118            --GTCTGCCGTCGAGGAGTCCAATTCGGTGAAGTTCGTCGACAGCCGGGC 264
M.africanumC1_CPHL_A              --GTCTGCCGTCGAGGAGTCCAATTCGGTGAAGTTCGTCGACAGCCGGGC 264
M.canettii_CIPT14001              --GTCTGCCGTCGAGGAGTCCAATTCGGTGAAGTTCGTCGACAGCCGGGC 264
M.microti                         --GTCTGCCGTCGAGGAGTCCAATTCGGTGAAGTTCGTCGACAGCCGGGC 264
M.avium                           CGGGGCGCCG--GACGCGTCCAGCTGCTTGAAGTTCTCGAACAGCTGCGC 264
M.avium_paratuberculosis_k10      CGGGGCGCCG--GACGCGTCCAGCTGCTTGAAGTTCTCGAACAGCTGCGC 264
M.leprae_Br4923                   --GTTTGCCGTCGAAACGTCCAGCTGCCTGAAGTTCTCGAAGAGTTGGGC 264
M.marinum_M                       --GTCTGCCGACGAGGCGTCCAGCTGTTTGAAGTTCTCGAACAGTTGCGC 264
M.ulcerans_Agy99                  --GTCTGCCGATGAGGCGTCCAGCTGTTTGAAGTTCTCGAACAGTTGCGC 264
                                     *   ****  **   *****  *  ********    * **  * **

M.tuberculosis_H37Rv              ATCGGCAGTGCCATGCTTGAGCGCTTCGGCGATATCGAAGTCCCGGTGCA 314
M.tuberculosis_F11                ATCGGCAGTGCCATGCTTGAGCGCTTCGGCGATATCGAAGTCCCGGTGCA 314
M.tuberculosis_H37Ra              ATCGGCAGTGCCATGCTTGAGCGCTTCGGCGATATCGAAGTCCCGGTGCA 314
M.tuberculosis_CDC1551            ATCGGCAGTGCCATGCTTGAGCGCTTCGGCGATATCGAAGTCCCGGTGCA 314
M.bovisBCG_Tokyo172               ATCGGCAGTGCCATGCTTGAGCGCTTCGGCGATATCGAAGTCCCGGTGCA 392
M.bovisBCG_Pasteur1173P2          ATCGGCAGTGCCATGCTTGAGCGCTTCGGCGATATCGAAGTCCCGGTGCA 392
M.bovis_AF2122/97                 ATCGGCAGTGCCATGCTTGAGCGCTTCGGCGATATCGAAGTCCCGGTGCA 392
M.africanumC2__GM04118            ATCGGCAGTGCCATGCTTGAGCGCTTCGGCGATATCGAAGTCCCGGTGCA 314
M.africanumC1_CPHL_A              ATCGGCAGTGCCATGCTTGAGCGCTTCGGCGATATCGAAGTCCCGGTGCA 314
M.canettii_CIPT14001              ATCGGCAGTGCCATGCTTGAGCGCTTCGGCGATATCGAAGTCCCGGTGCA 314
M.microti                         ATCGGCAGTGCCATGCTTGAGCGCTTCGGCGATATCGAAGTCCCGGTGCA 314
M.avium                           GTCGTCGTTGCCGTGCTTGATGACTTGGGCCGGGTCGAAATCGCCGCTCA 314
M.avium_paratuberculosis_k10      GTCGTCGTTGCCGTGCTTGATGACTTGGGCCGGGTCGAAATCGCCGCTCA 314
M.leprae_Br4923                   ATCGTCGTTCCCGTGTTTGATGACTTGGGTTGGGTCGAAGTCTCCGCGCA 314
M.marinum_M                       GTCGTCGTTGCCGCGCCTGGCGACGTCGGCGGGGTCGAAGTTCCCGCGCA 314
M.ulcerans_Agy99                  GTCGTCGTTGCCGCGCCTGGCGACGTCGGCGGGGTCGAAGTTCCCGCGCA 314
                                   *** *  * **  *  **    * * **      ***** *  * *  **

M.tuberculosis_H37Rv              GCTTGAACACCATGAGCATGGCCGTTGGATAGCTTTCGCCCTTGGCGATC 364
M.tuberculosis_F11                GCTTGAACACCATGAGCATGGCCGTTGGATAGCTTTCGCCCTTGGCGATC 364
M.tuberculosis_H37Ra              GCTTGAACACCATGAGCATGGCCGTTGGATAGCTTTCGCCCTTGGCGATC 364
M.tuberculosis_CDC1551            GCTTGAACACCATGAGCATGGCCGTTGGATAGCTTTCGCCCTTGGCGATC 364
M.bovisBCG_Tokyo172               GCTTGAACACCATGAGCATGGCCGTTGGATAGCTTTCGCCCTTGGCGATC 442
M.bovisBCG_Pasteur1173P2          GCTTGAACACCATGAGCATGGCCGTTGGATAGCTTTCGCCCTTGGCGATC 442
M.bovis_AF2122/97                 GCTTGAACACCATGAGCATGGCCGTTGGATAGCTTTCGCCCTTGGCGATC 442
M.africanumC2__GM04118            GCTTGAACACCATGAGCATGGCCGTTGGATAGCTTTCGCCCTTGGCGATC 364
M.africanumC1_CPHL_A              GCTTGAACACCATGAGCATGGCCGTTGGATAGCTTTCGCCCTTGGCGATC 364
M.canettii_CIPT14001              GCTTGAACACCATGAGCATGGCCGTTGGATAGCTTTCGCCCTTGGCGATC 364
M.microti                         GCTTGAACACCATGAGCATGGCCGTTGGATAGCTTTCGCCCTTGGCGATC 364
M.avium                           GCTTGAAGACCACCAGCCGCGCCGTGGGGAACTTGCCGCCCTTGGAGATC 364
M.avium_paratuberculosis_k10      GCTTGAAGACCACCAGCCGCGCCGTGGGGAACTTGCCGCCCTTGGAGATC 364
M.leprae_Br4923                   GCTTGAACGCTACGAGCCTTGCCGTCGGGTACTTGCCGCTTTTGGCGATG 364
M.marinum_M                       GCAAGAACACGACCAGTCTGGCCGTGGGGTAGTGGCCGCCCTTGGAGATG 364
M.ulcerans_Agy99                  GCAAGAACACGACCAGTCTGGCCGTGGGGTAGTGGCCGCCCTTGGAGATG 364
                                  **   ***   * *  **     ***** **  *       ***  **** ***

M.tuberculosis_H37Rv              ATCTCCGTGTTCGGGGTGATGTTCGGATTTTTCATCGGTGCCCAGCCCGG 414
M.tuberculosis_F11                ATCTCCGTGTTCGGGGTGATGTTCGGATTTTTCATCGGTGCCCAGCCCGG 414
M.tuberculosis_H37Ra              ATCTCCGTGTTCGGGGTGATGTTCGGATTTTTCATCGGTGCCCAGCCCGG 414
M.tuberculosis_CDC1551            ATCTCCGTGTTCGGGGTGATGTTCGGATTTTTCATCGGTGCCCAGCCCGG 414
M.bovisBCG_Tokyo172               ATCTCCGTGTTCGGGGTGATGTTCGGATTTTTCATCGGTGCCCAGCCCGG 492
M.bovisBCG_Pasteur1173P2          ATCTCCGTGTTCGGGGTGATGTTCGGATTTTTCATCGGTGCCCAGCCCGG 492
M.bovis_AF2122/97                 ATCTCCGTGTTCGGGGTGATGTTCGGATTTTTCATCGGTGCCCAGCCCGG 492
M.africanumC2__GM04118            ATCTCCGTGTTCGGGGTGATGTTCGGATTTTTCATCGGTGCCCAGCCCGG 414
M.africanumC1_CPHL_A              ATCTCCGTGTTCGGGGTGATGTTCGGATTTTTCATCGGTGCCCAGCCCGG 414
M.canettii_CIPT14001              ATCTCCGTGTTCGGGGTGATGTTCGGATTTTTCATCGGTGCCCAGCCCGG 414
```

Figure 3A (cont)

```
M.microti                           ATCTCCGTGTTCGGGGTGATGTTCGGATTTTTCATCGGTGCCCAGCCCGG 414
M.avium                             ATCACCGTCTGCGGGCTGATGTTCGGGCTGCTGAACGGCGCCCAGCCCGG 414
M.avium_paratuberculosis_k10        ATCACCGTCTGCGGGCTGATGTTCGGGCTGCTGAACGGCGCCCAGCCCGG 414
M.leprae_Br4923                     ATCAGCGTCTCCGGTGTGATGTTCGGATTGCTATACGGCGACCAGCCCGG 414
M.marinum_M                         ATCACCGTTTCCGGATTGATCTTCGGGCCCTCGTAGGGGGACCAGCCCGG 414
M.ulcerans_Agy99                    ATCACCGTTTCCGGGTTGATCTTCGGGCCCTCGTAGGGGGACCAGCCCGG 414
                                    ***  *** * ***  **** *****         ** * *********

M.tuberculosis_H37Rv                TGGTGTCGGAATCGACACGGTCAGGTCGGTCAG-GCTGCTCGGTGCCACC 463
M.tuberculosis_F11                  TGGTGTCGGAATCGACACGGTCAGGTCGGTCAG-GCTGCTCGGTGCCACC 463
M.tuberculosis_H37Ra                TGGTGTCGGAATCGACACGGTCAGGTCGGTCAG-GCTGCTCGGTGCCACC 463
M.tuberculosis_CDC1551              TGGTGTCGGAATCGACACGGTCAGGTCGGTCAG-GCTGCTCGGTGCCACC 463
M.bovisBCG_Tokyo172                 TGGTGTCGGAATCGACACGGTCAGGTCGGTCAG-GCTGCTCGGTGCCACC 541
M.bovisBCG_Pasteur1173P2            TGGTGTCGGAATCGACACGGTCAGGTCGGTCAG-GCTGCTCGGTGCCACC 541
M.bovis_AF2122/97                   TGGTGTCGGAATCGACACGGTCAGGTCGGTCAG-GCTGCTCGGTGCCACC 541
M.africanumC2__GM04118              TGGTGTCGGAATCGACACGGTCAGGTCGGTCAG-GCTGCTCGGTGCCACC 463
M.africanumC1_CPHL_A                TGGTGTCGGAATCGACACGGTCAGGTCGGTCAG-GCTGCTCGGTGCCACC 463
M.canettii_CIPT14001                TGGTGTCGGAATCGACACGGTCAGGTCGGTCAG-GCTGCTCGGTGCCACC 463
M.microti                           TGGTGTCGGAATCGACACGGTCAGGTCGGTCAG-GCTGCTCGGTGCCACC 463
M.avium                             CGGGGTCGGGATCGACACCGTCAGATCCGGCAGCGACGC-CGGGGCCACC 463
M.avium_paratuberculosis_k10        CGGGGTCGGGATCGACACCGTCAGATCCGGCAGCGACGC-CGGGGCCACC 463
M.leprae_Br4923                     TGGGGTCGGTATCGACACGGTCAGACCGGGCAG-GGAGCTCGGCGCCACC 463
M.marinum_M                         TGGTGTCGGGATCGACACGGTAAGGCCTTTGAG-GTCGCTCGGCGCGATC 463
M.ulcerans_Agy99                    TGGTGTCGGGATCGATACGGTAAGGCCTTTGAG-GTCGCTCGGCGCGATC 463
                                     ** ***** ***** ** ** **  *     ** *   ** *** ** * *

M.tuberculosis_H37Rv                GGCTCTCCGGTGACGCCGACGCTTTCCAGATACTTCCACAGCGGGACCGG 513
M.tuberculosis_F11                  GGCTCTCCGGTGACGCCGACGCTTTCCAGATACTTCCACAGCGGGACCGG 513
M.tuberculosis_H37Ra                GGCTCTCCGGTGACGCCGACGCTTTCCAGATACTTCCACAGCGGGACCGG 513
M.tuberculosis_CDC1551              GGCTCTCCGGTGACGCCGACGCTTTCCAGATACTTCCACAGCGGGACCGG 513
M.bovisBCG_Tokyo172                 GGCTCTCCGGTGACGCCGACGCTTTCCAGATACTTCCACAGCGGGACCGG 591
M.bovisBCG_Pasteur1173P2            GGCTCTCCGGTGACGCCGACGCTTTCCAGATACTTCCACAGCGGGACCGG 591
M.bovis_AF2122/97                   GGCTCTCCGGTGACGCCGACGCTTTCCAGATACTTCCACAGCGGGACCGG 591
M.africanumC2__GM04118              GGCTCTCCGGTGACGCCGACGCTTTCCAGATACTTCCACAGCGGGACCGG 513
M.africanumC1_CPHL_A                GGCTCTCCGGTGACGCCGACGCTTTCCAGATACTTCCACAGCGGGACCGG 513
M.canettii_CIPT14001                GGCTCTCCGGTGACGCCGACGCTTTCCAGATACTTCCACAGCGGGACCGG 513
M.microti                           GGCTCTCCGGTGACGCCGACGCTTTCCAGATACTTCCACAGCGGGACCGG 513
M.avium                             TGCTGCCCGGTGACACCGATGCTCTGCAGATACTGCGACAGCGGGACCGG 513
M.avium_paratuberculosis_k10        TGCTGCCCGGTGACACCGATGCTCTGCAGATACTGCGACAGCGGGACCGG 513
M.leprae_Br4923                     TGCTGCCCGGTGACGCCGATACTTTCCAGATATTGCGGCAAAGGGATGGG 513
M.marinum_M                         TGCTTTCCGCTGACCCCGATGCTTTCCAGGTACTGCGACAGCGGCACGGG 513
M.ulcerans_Agy99                    TGCTTTCCGCTGACCCCGATGCTTTCCAGGTACTGCGACAGCGGCACGGG 513
                                     ***   *** **** ****   ** * *** ** * *   **   ** *   **

M.tuberculosis_H37Rv                CACTTCCGTCGTGGTCGAGACGGCGCTGGTGGTTG--GGC-TCGTGGACA 560
M.tuberculosis_F11                  CACTTCCGTCGTGGTCGAGACGGCGCTGGTGGTTG--GGC-TCGTGGACA 560
M.tuberculosis_H37Ra                CACTTCCGTCGTGGTCGAGACGGCGCTGGTGGTTG--GGC-TCGTGGACA 560
M.tuberculosis_CDC1551              CACTTCCGTCGTGGTCGAGACGGCGCTGGTGGTTG--GGC-TCGTGGACA 560
M.bovisBCG_Tokyo172                 CACTTCCGTCGTGGTCGAGACGGCGCTGGTGGTTG--GGC-TCGTGGACA 638
M.bovisBCG_Pasteur1173P2            CACTTCCGTCGTGGTCGAGACGGCGCTGGTGGTTG--GGC-TCGTGGACA 638
M.bovis_AF2122/97                   CACTTCCGTCGTGGTCGAGACGGCGCTGGTGGTTG--GGC-TCGTGGACA 638
M.africanumC2__GM04118              CACTTCCGTCGTGGTCGAGACGGCGCTGGTGGTTG--GGC-TCGTGGACA 560
M.africanumC1_CPHL_A                CACTTCCGTCGTGGTCGAGACGGCGCTGGTGGTTG--GGC-TCGTGGACA 560
M.canettii_CIPT14001                CACTTCCGTCGTGGTCGAGACGGCGCTGGTGGTTG--GGC-TCGTGGACA 560
M.microti                           CACTTCCGTCGTGGTCGAGACGGCGCTGGTGGTTG--GGC-TCGTGGACA 560
M.avium                             CTTCGCCGTGGCGCTGG---TGGTGGTGGTCGTCGTCGGCGTCTTCGACA 560
M.avium_paratuberculosis_k10        CTTCGCCGTGGCGCTGG---TGGTGGTGGTCGTCGTCGGCGTCTTCGACA 560
M.leprae_Br4923                     CTTGTCGGGTGTGGTCG------TAGTGGTTGTAG--AAC-TTTTCGACA 554
M.marinum_M                         TGGGGCGGTGGTGGCGG---TGGTGCTGGTTGTTGC--GC-TCGTGGTCC 557
M.ulcerans_Agy99                    CGGGGCGGTGGTGGCGG---TGGTGCTGGTTGTTGC--GC-TCGTGGTCC 557
                                         * *  * *  *         **** ** *    * *  * * *

M.tuberculosis_H37Rv                AAATCGACTGGAAGTCAGGCGATTTCGGTCCGCAAGCGACCGCTGACATT 610
M.tuberculosis_F11                  AAATCGACTGGAAGTCAGGCGATTTCGGTCCGCAAGCGACCGCTGACATT 610
M.tuberculosis_H37Ra                AAATCGACTGGAAGTCAGGCGATTTCGGTCCGCAAGCGACCGCTGACATT 610
M.tuberculosis_CDC1551              AAATCGACTGGAAGTCAGGCGATTTCGGTCCGCAAGCGACCGCTGACATT 610
M.bovisBCG_Tokyo172                 AAATCGACTGGAAGTCAGGCGATTTCGGTCCGCAAGCGACCGCTGACATT 688
M.bovisBCG_Pasteur1173P2            AAATCGACTGGAAGTCAGGCGATTTCGGTCCGCAAGCGACCGCTGACATT 688
M.bovis_AF2122/97                   AAATCGACTGGAAGTCAGGCGATTTCGGTCCGCAAGCGACCGCTGACATT 688
M.africanumC2__GM04118              AAATCGACTGGAAGTCAGGCGATTTCGGTCCGCAAGCGACCGCTGACATT 610
M.africanumC1_CPHL_A                AAATCGACTGGAAGTCAGGCGATTTCGGTCCGCAAGCGACCGCTGACATT 610
M.canettii_CIPT14001                AAATCGACTGGAAGTCAGGCGATTTCGGTCCGCAAGCGACCGCTGACATT 610
M.microti                           AAATCGACTGGAAGTCAGGCGATTTCGGTCCGCAAGCGACCGCTGACATT 610
M.avium                             GGATCGATTGGTAGTCGGGCGGTTTCGGTGCGCAGCCGGCGGTGGCCACG 610
M.avium_paratuberculosis_k10        GGATCGATTGGTAGTCGGGCGGTTTCGGTGCGCAGCCGGCGGTGGCCACG 610
M.leprae_Br4923                     GGATTAATTGGTAGTCAGGGGTTTTCGTCCCGCAGGAGACCGCGGATATG 604
M.marinum_M                         AGATGGATTTGTAGTCAGGGGGCTCGGGTGTGCTGCAGGCAACCGCC--- 604
M.ulcerans_Agy99                    AGATGGATTTGTAGTCAGGGGGCTCGGGTGTGCTGCAGGCAACCGCC--- 604
                                      **   * * * **** ** *   *   *     **     * *     *

M.tuberculosis_H37Rv                GCCAGCGTGGCTAC---CGCGACCGCGACCGCCAAGGGTCTCACAGAATC 657
M.tuberculosis_F11                  GCCAGCGTGGCTAC---CGCGACCGCGACCGCCAAGGGTCTCACAGAATC 657
M.tuberculosis_H37Ra                GCCAGCGTGGCTAC---CGCGACCGCGACCGCCAAGGGTCTCACAGAATC 657
M.tuberculosis_CDC1551              GCCAGCGTGGCTAC---CGCGACCGCGACCGCCAAGGGTCTCACAGAATC 657
M.bovisBCG_Tokyo172                 GCCAGCGTGGCTAC---CGCGACCGCGACCGCCAAGGGTCTCACAGAATC 735
M.bovisBCG_Pasteur1173P2            GCCAGCGTGGCTAC---CGCGACCGCGACCGCCAAGGGTCTCACAGAATC 735
M.bovis_AF2122/97                   GCCAGCGTGGCTAC---CGCGACCGCGACCGCCAAGGGTCTCACAGAATC 735
M.africanumC2__GM04118              GCCAGCCTGGCTAC---CGCGACCGCGACCGCCAAGGGTCTCACAGAATC 657
```

Figure 3A (cont)

```
M.africanumC1_CPHL_A                GCCAGCGTGGCTAC---CGCGACCGCGACCGCCAAGGGTCTCACAGAATC 657
M.canettii_CIPT14001                GCCAGCGTGGCTAC---CGCGACCGCGACCGCCAAGGGTCTCACAGAATC 657
M.microti                           GCCAGCGTGGCTAC---CGCGACCGCGACCGCCAAGGGTCTCACAGAATC 657
M.avium                             GCCAGTGCAACCGC---CGCGGCGACG------------GCCGC-GCAG- 643
M.avium_paratuberculosis_k10        GCCAGTGCAACCGC---TGCGGCGACT------------GCCGC-GCAG- 643
M.leprae_Br4923                     CTCAGCGTGACTAC---CGCGGCAGCG----------GTGT-GCAG---C 637
M.marinum_M                         GGCATCGTGACCGCGAGTGAAACGACG------------GCCGCTGCGAT 642
M.ulcerans_Agy99                    GGCATCGTGACCGCGAGTGAAACGACG------------GCCGCTGCGAT 642
                                      **  *   *  *    *   *  *                 * *

M.tuberculosis_H37Rv                TTGCGGACAGCGTCGACCGGCCAA 681
M.tuberculosis_F11                  TTGCGGACAGCGTCGACCGGCCAA 681
M.tuberculosis_H37Ra                TTGCGGACAGCGTCGACCGGCCAA 681
M.tuberculosis_CDC1551              TTGCGGACAGCGTCGACCGGCCAA 681
M.bovisBCG_Tokyo172                 TTGCGGACAGCGTCGACCGGCCAA 759
M.bovisBCG_Pasteur1173P2            TTGCGGACAGCGTCGACCGGCCAA 759
M.bovis_AF2122/97                   TTGCGGACAGCGTCGACCGGCCAA 759
M.africanumC2__GM04118              TTGCGGACAGCGTCGACCGGCCAA 681
M.africanumC1_CPHL_A                TTGCGGACAGCGTCGACCGGCCAA 681
M.canettii_CIPT14001                TTGCGGACAGCGTCGACCGGCCAA 681
M.microti                           TTGCGGACAGCGTCGACCGGCCAA 681
M.avium                             CCGCGGA----GTCGGTT---CAC 660
M.avium_paratuberculosis_k10        CCGCGGA----GTCGGTT---CAC 660
M.leprae_Br4923                     CCG-AGACGG-ATTGCCTG--CAT 657
M.marinum_M                         CCGGCGA----GCTG--T---CAC 657
M.ulcerans_Agy99                    CCGGCGA----GCTG--T---CAC 657
                                      *  **        *      **
```

Figure 3(B)

```
M.caprae_RIVM2006_1960      TTACTTTGCCGCGACGACGAATCCGGCGATGATCGCCTCGATGTCGGAAG 50
M.caprae_RIVM2007-0039      TTACTTTGCCGCGACGACGAATCCGGCGATGATCGCCTCGATGTCGGAAG 50
M.africanum                 TTACTTTGCCGCGACGACGAATCCGGCGATGATCGCCTCGATGTCGGAAG 50
M.microti_RIVM15274         TTACTTTGCCGCGACGACGAATCCGGCGATGATCGCCTCGATGTCGGAAG 50
M.pinnipedii_RIVM76         TTACTTTGCCGCGACGACGAATCCGGCGATGATCGCCTCGATGTCGGAAG 50
                            **************************************************

M.caprae_RIVM2006_1960      CGTGCTTGACGGCCTCGTTGGCCAGACTCGTGATGGTGAGCTGCACCAGG 100
M.caprae_RIVM2007-0039      CGTGCTTGACGGCCTCGTTGGCCAGACTCGTGATGGTGAGCTGCACCAGG 100
M.africanum                 CGTGCTTGACGGCCTCGTTGGCCAGACTCGTGATGGTGAGCTGCACCAGG 100
M.microti_RIVM15274         CGTGCTTGACGGCCTCGTTGGCCAGACTCGTGATGGTGAGCTGCACCAGG 100
M.pinnipedii_RIVM76         CGTGCTTGACGGCCTCGTTGGCCAGACTCGTGATGGTGAGCTGCACCAGG 100
                            **************************************************

M.caprae_RIVM2006_1960      TAGCGCTGCTTGGCCGGCC-----CCGGTTGGGAAGACGATCCGGTTCCA 145
M.caprae_RIVM2007-0039      TAGCGCTGCTTGGCCGGCC-----CCGGTTGGGAAGACGATCCGGTTCCA 145
M.africanum                 TAGCGCTGCTTGGCCGGCGGTGCGCCGGTTGGGAAGACGATCCGGTTCCA 150
M.microti_RIVM15274         TAGCGCTGCTTGGCCGGCGGTGCGCCGGTTGGGAAGACGATCCGGTTCCA 150
M.pinnipedii_RIVM76         TAGCGCTGCTTGGCCGGCGGTGCGCCGGTTGGGAAGACGATCCGGTTCCA 150
                            ******************      **************************

M.caprae_RIVM2006_1960      GGTGTGCAGTCGCCTGCCGTGCAGGTCATAACTGCCCTGAATCATCGAGG 195
M.caprae_RIVM2007-0039      GGTGTGCAGTCGCCTGCCGTGCAGGTCATAACTGCCCTGAATCATCGAGG 195
M.africanum                 GGTGTGCAGTCGCCTGCCGTGCAGGTCATAACTGCCCTGAATCATCGAGG 200
M.microti_RIVM15274         GGTGTGCAGTCGCCTGCCGTGCAGGTCATAACTGCCCTGAATCATCGAGG 200
M.pinnipedii_RIVM76         GGTGTGCAGTCGCCTGCCGTGCAGGTCATAACTGCCCTGAATCATCGAGG 200
                            **************************************************

M.caprae_RIVM2006_1960      ACGGAAACCCGTTGAAGTCTGCCGTCGAGGAGTCCAATTCGGTGAAGTTC 245
M.caprae_RIVM2007-0039      ACGGAAACCCGTTGAAGTCTGCCGTCGAGGAGTCCAATTCGGTGAAGTTC 245
M.africanum                 ACGGAAACCCGTTGAAGTCTGCCGTCGAGGAGTCCAATTCGGTGAAGTTC 250
M.microti_RIVM15274         ACGGAAACCCGTTGAAGTCTGCCGTCGAGGAGTCCAATTCGGTGAAGTTC 250
M.pinnipedii_RIVM76         ACGGAAACCCGTTGAAGTCTGCCGTCGAGGAGTCCAATTCGGTGAAGTTC 250
                            **************************************************

M.caprae_RIVM2006_1960      GTCGACAGCCGGGCATCGGCAGTGCCATGCTTGAGCGCTTCGGCGATATC 295
M.caprae_RIVM2007-0039      GTCGACAGCCGGGCATCGGCAGTGCCATGCTTGAGCGCTTCGGCGATATC 295
M.africanum                 GTCGACAGCCGGGCATCGGCAGTGCCATGCTTGAGCGCTTCGGCGATATC 300
M.microti_RIVM15274         GTCGACAGCCGGGCATCGGCAGTGCCATGCTTGAGCGCTTCGGCGATATC 300
M.pinnipedii_RIVM76         GTCGACAGCCGGGCATCGGCAGTGCCATGCTTGAGCGCTTCGGCGATATC 300
                            **************************************************

M.caprae_RIVM2006_1960      GAAGTCCCGGTGCAGCTTGAACACCATGAGCATGGCCGTTGGATAGCTTT 345
M.caprae_RIVM2007-0039      GAAGTCCCGGTGCAGCTTGAACACCATGAGCATGGCCGTTGGATAGCTTT 345
M.africanum                 GAAGTCCCGGTGCAGCTTGAACACCATGAGCATGGCCGTTGGATAGCTTT 350
M.microti_RIVM15274         GAAGTCCCGGTGCAGCTTGAACACCATGAGCATGGCCGTTGGATAGCTTT 350
M.pinnipedii_RIVM76         GAAGTCCCGGTGCAGCTTGAACACCATGAGCATGGCCGTTGGATAGCTTT 350
                            **************************************************

M.caprae_RIVM2006_1960      CGCCCTTGGCGATCATCTCCGTGTTCGGGGTGATGTTCGGATTTTTCATC 395
M.caprae_RIVM2007-0039      CGCCCTTGGCGATCATCTCCGTGTTCGGGGTGATGTTCGGATTTTTCATC 395
M.africanum                 CGCCCTTGGCGATCATCTCCGTGTTCGGGGTGATGTTCGGATTTTTCATC 400
M.microti_RIVM15274         CGCCCTTGGCGATCATCTCCGTGTTCGGGGTGATGTTCGGATTTTTCATC 400
M.pinnipedii_RIVM76         CGCCCTTGGCGATCATCTCCGTGTTCGGGGTGATGTTCGGATTTTTCATC 400
                            **************************************************

M.caprae_RIVM2006_1960      GGTGCCCAGCCCGGTGGTGTCGGAATCGACACGGTCAGGTCGGTCAGGCT 445
M.caprae_RIVM2007-0039      GGTGCCCAGCCCGGTGGTGTCGGAATCGACACGGTCAGGTCGGTCAGGCT 445
M.africanum                 GGTGCCCAGCCCGGTGGTGTCGGAATCGACACGGTCAGGTCGGTCAGGCT 450
M.microti_RIVM15274         GGTGCCCAGCCCGGTGGTGTCGGAATCGACACGGTCAGGTCGGTCAGGCT 450
M.pinnipedii_RIVM76         GGTGCCCAGCCCGGTGGTGTCGGAATCGACACGGTCAGGTCGGTCAGGCT 450
                            **************************************************

M.caprae_RIVM2006_1960      GCTCGGTGCCACCGGCTCTCCGGTGACGCCGACGCTTTCCAGATACTTCC 495
M.caprae_RIVM2007-0039      GCTCGGTGCCACCGGCTCTCCGGTGACGCCGACGCTTTCCAGATACTTCC 495
M.africanum                 GCTCGGTGCCACCGGCTCTCCGGTGACGCCGACGCTTTCCAGATACTTCC 500
M.microti_RIVM15274         GCTCGGTGCCACCGGCTCTCCGGTGACGCCGACGCTTTCCAGATACTTCC 500
M.pinnipedii_RIVM76         GCTCGGTGCCACCGGCTCTCCGGTGACGCCGACGCTTTCCAGATACTTCC 500
                            **************************************************

M.caprae_RIVM2006_1960      ACAGCGGGACCGGCACTTCCGTCGTGGTCGAGACGGCGCTGGTGGTTGGG 545
M.caprae_RIVM2007-0039      ACAGCGGGACCGGCACTTCCGTCGTGGTCGAGACGGCGCTGGTGGTTGGG 545
M.africanum                 ACAGCGGGACCGGCACTTCCGTCGTGGTCGAGACGGCGCTGGTGGTTGGG 550
M.microti_RIVM15274         ACAGCGGGACCGGCACTTCCGTCGTGGTCGAGACGGCGCTGGTGGTTGGG 550
M.pinnipedii_RIVM76         ACAGCGGGACCGGCACTTCCGTCGTGGTCGAGACGGCGCTGGTGGTTGGG 550
                            **************************************************

M.caprae_RIVM2006_1960      CTCGTGGACAAAATCGACTGGAAGTCAGGCGATTTCGGTCCGCAAGCGAC 595
M.caprae_RIVM2007-0039      CTCGTGGACAAAATCGACTGGAAGTCAGGCGATTTCGGTCCGCAAGCGAC 595
M.africanum                 CTCGTGGACAAAATCGACTGGAAGTCAGGCGATTTCGGTCCGCAAGCGAC 600
M.microti_RIVM15274         CTCGTGGACAAAATCGACTGGAAGTCAGGCGATTTCGGTCCGCAAGCGAC 600
M.pinnipedii_RIVM76         CTCGTGGACAAAATCGACTGGAAGTCAGGCGATTTCGGTCCGCAAGCGAC 600
                            **************************************************

M.caprae_RIVM2006_1960      CGCTGACATTGCCAGCGTGGCTACCGCGACCGCGACCGCCA 636
```

Figure 3B (cont)

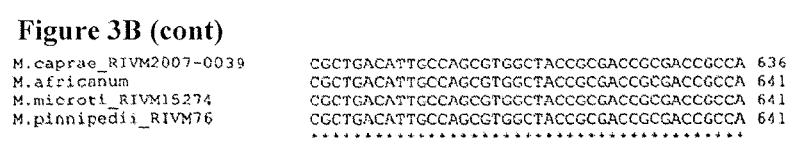

```
M.caprae_RIVM2007-0039      CGCTGACATTGCCAGCGTGGCTACCGCGACCGCGACCGCCA 636
M.africanum                 CGCTGACATTGCCAGCGTGGCTACCGCGACCGCGACCGCCA 641
M.microti_RIVM15274         CGCTGACATTGCCAGCGTGGCTACCGCGACCGCGACCGCCA 641
M.pinnipedii_RIVM76         CGCTGACATTGCCAGCGTGGCTACCGCGACCGCGACCGCCA 641
                            *****************************************
```

Figure 4

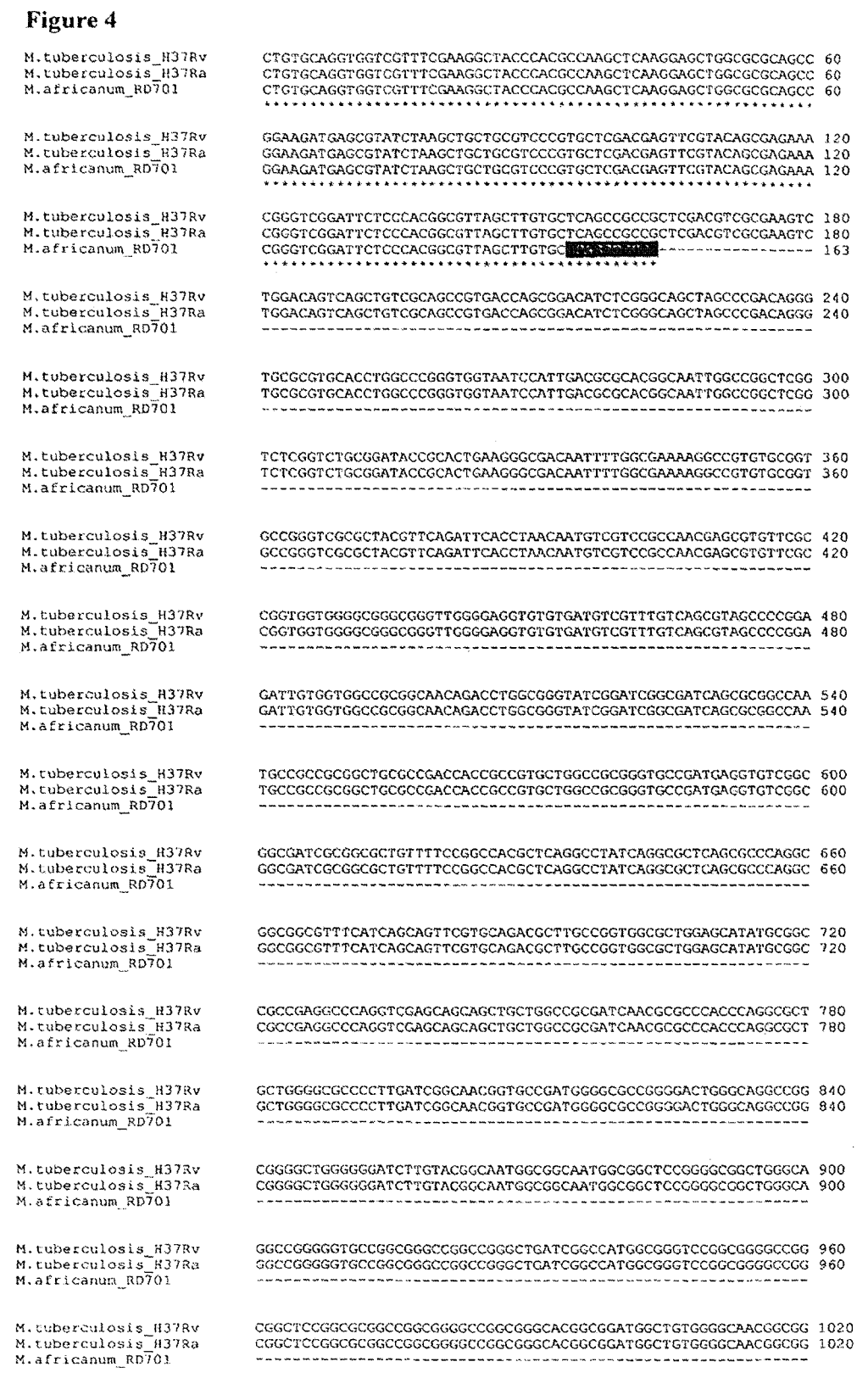

```
M.tuberculosis_H37Rv     CTGTGCAGGTGGTCGTTTCGAAGGCTACCCACGCCAAGCTCAAGGAGCTGGCGCGCAGCC 60
M.tuberculosis_H37Ra     CTGTGCAGGTGGTCGTTTCGAAGGCTACCCACGCCAAGCTCAAGGAGCTGGCGCGCAGCC 60
M.africanum_RD701        CTGTGCAGGTGGTCGTTTCGAAGGCTACCCACGCCAAGCTCAAGGAGCTGGCGCGCAGCC 60
                         ************************************************************

M.tuberculosis_H37Rv     GGAAGATGAGCGTATCTAAGCTGCTGCGTCCCGTGCTCGACGAGTTCGTACAGCGAGAAA 120
M.tuberculosis_H37Ra     GGAAGATGAGCGTATCTAAGCTGCTGCGTCCCGTGCTCGACGAGTTCGTACAGCGAGAAA 120
M.africanum_RD701        GGAAGATGAGCGTATCTAAGCTGCTGCGTCCCGTGCTCGACGAGTTCGTACAGCGAGAAA 120
                         ************************************************************

M.tuberculosis_H37Rv     CGGGTCGGATTCTCCCACGGCGTTAGCTTGTGCTCAGCCGCCGCTCGACGTCGCGAAGTC 180
M.tuberculosis_H37Ra     CGGGTCGGATTCTCCCACGGCGTTAGCTTGTGCTCAGCCGCCGCTCGACGTCGCGAAGTC 180
M.africanum_RD701        CGGGTCGGATTCTCCCACGGCGTTAGCTTGTGC[illegible]----------------- 163
                         *******************************************

M.tuberculosis_H37Rv     TGGACAGTCAGCTGTCGCAGCCGTGACCAGCGGACATCTCGGGCAGCTAGCCCGACAGGG 240
M.tuberculosis_H37Ra     TGGACAGTCAGCTGTCGCAGCCGTGACCAGCGGACATCTCGGGCAGCTAGCCCGACAGGG 240
M.africanum_RD701        ------------------------------------------------------------

M.tuberculosis_H37Rv     TGCGCGTGCACCTGGCCCGGGTGGTAATCCATTGACGCGCACGGCAATTGGCCGGCTCGG 300
M.tuberculosis_H37Ra     TGCGCGTGCACCTGGCCCGGGTGGTAATCCATTGACGCGCACGGCAATTGGCCGGCTCGG 300
M.africanum_RD701        ------------------------------------------------------------

M.tuberculosis_H37Rv     TCTCGGTCTGCGGATACCGCACTGAAGGGCGACAATTTTGGCGAAAAGGCCGTGTGCGGT 360
M.tuberculosis_H37Ra     TCTCGGTCTGCGGATACCGCACTGAAGGGCGACAATTTTGGCGAAAAGGCCGTGTGCGGT 360
M.africanum_RD701        ------------------------------------------------------------

M.tuberculosis_H37Rv     GCCGGGTCGCGCTACGTTCAGATTCACCTAACAATGTCGTCCGCCAACGAGCGTGTTCGC 420
M.tuberculosis_H37Ra     GCCGGGTCGCGCTACGTTCAGATTCACCTAACAATGTCGTCCGCCAACGAGCGTGTTCGC 420
M.africanum_RD701        ------------------------------------------------------------

M.tuberculosis_H37Rv     CGGTGGTGGGGCGGGCGGGTTGGGGAGGTGTGTGATGTCGTTTGTCAGCGTAGCCCCGGA 480
M.tuberculosis_H37Ra     CGGTGGTGGGGCGGGCGGGTTGGGGAGGTGTGTGATGTCGTTTGTCAGCGTAGCCCCGGA 480
M.africanum_RD701        ------------------------------------------------------------

M.tuberculosis_H37Rv     GATTGTGGTGGCCGCGGCAACAGACCTGGCGGGTATCGGATCGGCGATCAGCGCGGCCAA 540
M.tuberculosis_H37Ra     GATTGTGGTGGCCGCGGCAACAGACCTGGCGGGTATCGGATCGGCGATCAGCGCGGCCAA 540
M.africanum_RD701        ------------------------------------------------------------

M.tuberculosis_H37Rv     TGCCGCCGCGGCTGCGCCGACCACCGCCGTGCTGGCCGCGGGTGCCGATGAGGTGTCGGC 600
M.tuberculosis_H37Ra     TGCCGCCGCGGCTGCGCCGACCACCGCCGTGCTGGCCGCGGGTGCCGATGAGGTGTCGGC 600
M.africanum_RD701        ------------------------------------------------------------

M.tuberculosis_H37Rv     GGCGATCGCGGCGCTGTTTTCCGGCCACGCTCAGGCCTATCAGGCGCTCAGCGCCCAGGC 660
M.tuberculosis_H37Ra     GGCGATCGCGGCGCTGTTTTCCGGCCACGCTCAGGCCTATCAGGCGCTCAGCGCCCAGGC 660
M.africanum_RD701        ------------------------------------------------------------

M.tuberculosis_H37Rv     GGCGGCGTTTCATCAGCAGTTCGTGCAGACGCTTGCCGGTGGCGCTGGAGCATATGCGGC 720
M.tuberculosis_H37Ra     GGCGGCGTTTCATCAGCAGTTCGTGCAGACGCTTGCCGGTGGCGCTGGAGCATATGCGGC 720
M.africanum_RD701        ------------------------------------------------------------

M.tuberculosis_H37Rv     CGCCGAGGCCCAGGTCGAGCAGCAGCTGCTGGCCGCGATCAACGCGCCCACCCAGGCGCT 780
M.tuberculosis_H37Ra     CGCCGAGGCCCAGGTCGAGCAGCAGCTGCTGGCCGCGATCAACGCGCCCACCCAGGCGCT 780
M.africanum_RD701        ------------------------------------------------------------

M.tuberculosis_H37Rv     GCTGGGGCGCCCCTTGATCGGCAACGGTGCCGATGGGGCGCCGGGGACTGGGCAGGCCGG 840
M.tuberculosis_H37Ra     GCTGGGGCGCCCCTTGATCGGCAACGGTGCCGATGGGGCGCCGGGGACTGGGCAGGCCGG 840
M.africanum_RD701        ------------------------------------------------------------

M.tuberculosis_H37Rv     CGGGGCTGGGGGGATCTTGTACGGCAATGGCGGCAATGGCGGCTCCGGGGCGGCTGGGCA 900
M.tuberculosis_H37Ra     CGGGGCTGGGGGGATCTTGTACGGCAATGGCGGCAATGGCGGCTCCGGGGCGGCTGGGCA 900
M.africanum_RD701        ------------------------------------------------------------

M.tuberculosis_H37Rv     GGCCGGGGGTGCCGGCGGGCCGGCCGGGCTGATCGGCCATGGCGGGTCCGGCGGGGCCGG 960
M.tuberculosis_H37Ra     GGCCGGGGGTGCCGGCGGGCCGGCCGGGCTGATCGGCCATGGCGGGTCCGGCGGGGCCGG 960
M.africanum_RD701        ------------------------------------------------------------

M.tuberculosis_H37Rv     CGGCTCCGGCGCGGCCGGCGGGGCCGGCGGGCACGGCGGATGGCTGTGGGGCAACGGCGG 1020
M.tuberculosis_H37Ra     CGGCTCCGGCGCGGCCGGCGGGGCCGGCGGGCACGGCGGATGGCTGTGGGGCAACGGCGG 1020
M.africanum_RD701        ------------------------------------------------------------
```

Figure 4 (cont)

```
M.tuberculosis_H37Rv     CGTCGGCGGATCCGGCGGGGCGGGTGTCGGCGCAGGCGTGGCTGGCGGTCACGGCGGTGC 1080
M.tuberculosis_H37Ra     CGTCGGCGGATCCGGCGGGGCGGGTGTCGGCGCAGGCGTGGCTGGCGGTCACGGCGGTGC 1080
M.africanum_RD701        ------------------------------------------------------------

M.tuberculosis_H37Rv     GGGCGGTGCCGCCGGGCTGTGGGGCGCCGGCGGCGGCGGTGGCAATGGCGGGAACGGCGC 1140
M.tuberculosis_H37Ra     GGGCGGTGCCGCCGGGCTGTGGGGCGCCGGCGGCGGCGGTGGCAATGGCGGGAACGGCGC 1140
M.africanum_RD701        ------------------------------------------------------------

M.tuberculosis_H37Rv     CGATGCCAACATCGTCAGCGGTGGAGACGGTGGCCTCGGCGGTGCCGGTGGCGGTGGCGG 1200
M.tuberculosis_H37Ra     CGATGCCAACATCGTCAGCGGTGGAGACGGTGGCCTCGGCGGTGCCGGTGGCGGTGGCGG 1200
M.africanum_RD701        ------------------------------------------------------------

M.tuberculosis_H37Rv     ATGGCTCTACGGCGACGGCGGGGCCGGCGGACACGGCGGACAAGGCGCAATCGGCCTCGG 1260
M.tuberculosis_H37Ra     ATGGCTCTACGGCGACGGCGGGGCCGGCGGACACGGCGGACAAGGCGCAATCGGCCTCGG 1260
M.africanum_RD701        ------------------------------------------------------------

M.tuberculosis_H37Rv     CGGCGGCGCCGGCGGCGACGGGGCCCAGGGCGGCGCCGGCCGCGGACTGTGGGGTACTGG 1320
M.tuberculosis_H37Ra     CGGCGGCGCCGGCGGCGACGGGGCCCAGGGCGGCGCCGGCCGCGGACTGTGGGGTACTGG 1320
M.africanum_RD701        ------------------------------------------------------------

M.tuberculosis_H37Rv     CGGCGCCGGCGGACACGGCGGGCAAGGCGGTGGTACCGGGGGCCCACCGCTGCCCGGTCA 1380
M.tuberculosis_H37Ra     CGGCGCCGGCGGACACGGCGGGCAAGGCGGTGGTACCGGGGGCCCACCGCTGCCCGGTCA 1380
M.africanum_RD701        ------------------------------------------------------------

M.tuberculosis_H37Rv     GGCAGGCATGGGCGCCGCGGGTGGCGCCGGTGGGCTGATCGGCAACGGCGGGGCCGGCGG 1440
M.tuberculosis_H37Ra     GGCAGGCATGGGCGCCGCGGGTGGCGCCGGTGGGCTGATCGGCAACGGCGGGGCCGGCGG 1440
M.africanum_RD701        ------------------------------------------------------------

M.tuberculosis_H37Rv     CGACGGCGGTGTCGGCGCGTCCGGCGGGGTCGCCGGAGTAGGCGGTGCCGGCGGGAACGC 1500
M.tuberculosis_H37Ra     CGACGGCGGTGTCGGCGCGTCCGGCGGGGTCGCCGGAGTAGGCGGTGCCGGCGGGAACGC 1500
M.africanum_RD701        ------------------------------------------------------------

M.tuberculosis_H37Rv     CATGCTGATCGGGCACGGCGGCGCCGGCGGCGCCGGCGGAGACAGCAGTTTCGCTAATGG 1560
M.tuberculosis_H37Ra     CATGCTGATCGGGCACGGCGGCGCCGGCGGCGCCGGCGGAGACAGCAGTTTCGTTAATGG 1560
M.africanum_RD701        ------------------------------------------------------------

M.tuberculosis_H37Rv     CGCGGCCGGCGGCGCGGGCGGTGCCGGAGGGCACCTCTTCGGCAATGGCGGGTCCGGCGG 1620
M.tuberculosis_H37Ra     CGCGGCCGGCGGCGCGGGCGGTGCCGGAGGGCACCTCTTCGGCAATGGCGGGTCCGGCGG 1620
M.africanum_RD701        ------------------------------------------------------------

M.tuberculosis_H37Rv     CCACGGCGGAGCCGTCACGGCCGGCAACACCGGTATCGGTGGCGCCGGCGGCGTCGGTGG 1680
M.tuberculosis_H37Ra     CCACGGCGGAGCCGTCACGGCCGGCAACACCGGTATCGGTGGCGCCGGCGGCGTCGGTGG 1680
M.africanum_RD701        ------------------------------------------------------------

M.tuberculosis_H37Rv     GGACGCCAGGCTGATCGGCCACGGTGGCGCCGGCGGTGCCGGCGGGGACCGCGCCGGAGC 1740
M.tuberculosis_H37Ra     GGACGCCAGGCTGATCGGCCACGGTGGCGCCGGCGGTGCCGGCGGGGACCGCGCCGGAGC 1740
M.africanum_RD701        ------------------------------------------------------------

M.tuberculosis_H37Rv     CTTGGTTGGCCGTGACGGCGGGCCCGGTGGGAACGGGGGCGCTGGCGGCCAGCTATACGG 1800
M.tuberculosis_H37Ra     CTTGGTTGGCCGTGACGGCGGGCCCGGTGGGAACGGGGGCGCTGGCGGCCAGCTATACGG 1800
M.africanum_RD701        ------------------------------------------------------------

M.tuberculosis_H37Rv     CAACGGCGGCGACGGCGCCCCCGGCACCGGCGGAACACTGCAGGCGGCGGTGAGCGGATT 1860
M.tuberculosis_H37Ra     CAACGGCGGCGACGGCGCCCCCGGCACCGGCGGAACACTGCAGGCGGCGGTGAGCGGATT 1860
M.africanum_RD701        ------------------------------------------------------------

M.tuberculosis_H37Rv     GGTGACGGCTTTGTTCGGTGCACCCGGCCAACCCGGCGACACCGGCCAACCCGGCTAGCC 1920
M.tuberculosis_H37Ra     GGTGACGGCTTTGTTCGGTGCACCCGGCCAACCCGGCGACACCGGCCAACCCGGCTAGCC 1920
M.africanum_RD701        ---------------------------------------------[redacted]CGGCTAGCC 179
                                                                      ***************

M.tuberculosis_H37Rv     CCGATCAACGAGGGTTTCGGTGCCGGTCCGGGGCATGGCCATCCGCTGAGCTGGCGATCT 1980
M.tuberculosis_H37Ra     CCGATCAACGAGGGTTTCGGTGCCGGTCCGGGGCATGGCCATCCGCTGAGCTGGCGATCT 1980
M.africanum_RD701        CCGATCAACGAGGGTTTCGGTGCCGGTCCGGGGCATGGCCATCCGCTGAGCTGGCGATCT 239
                         ************************************************************

M.tuberculosis_H37Rv     GGACTACGTTGGTGTAGAAAAATCCTGCCGCCCGGACCCTTAAGGCTGGGACAATTTCTG 2040
M.tuberculosis_H37Ra     GGACTACGTTGGTGTAGAAAAATCCTGCCGCCCGGACCCTTAAGGCTGGGACAATTTCTG 2040
M.africanum_RD701        GGACTACGTTGGTGTAGAAAAATCCTGCCGCCCGGACCCTTAAGGCTGGGACAATTTCTG 299
                         ************************************************************

M.tuberculosis_H37Rv     ATAGCTACCCCGACACAGGAGGTTACGGGATGAGCAATTCG 2081
M.tuberculosis_H37Ra     ATAGCTACCCCGACACAGGAGGTTACGGGATGAGCAATTCG 2081
M.africanum_RD701        ATAGCTACCCCGACACAGGAGGTTACGGGATGAGCAATTCG 340
```

```
M.africanumC1      CCATCTGCGCTTTCGGTGCTTCTTCAGCTCTTGCTGGAACTTCTGGTAATGCTCCAGCGC 60
M.tuberculosis     CCATCTGCGCTTTCGGTGCTTCTTCAGCTCTTGCTGGAACTTCTGGTAATGCTCCAGCGC 60
                   ************************************************************

M.africanumC1      GAATCGCTCTTCCAAAGCCCCAAGGGCGTTAATGACCTCCAGGTGC--GA----AAGGAG 114
M.tuberculosis     GAATCGCTCTTCCAAAGCCCCAAGGGCGTTAATGACCTCGGGATCTTTGACCCCAGGGGT 120
                   ***************************************  * *    **    * **

M.africanumC1      GAGCAGCCCAT-TCAA-CTGAAGGACTTGTTCGGGACCAGTTGGCACGTTCCGTCCGTCC 172
M.tuberculosis     CGATGGCCAATCTCAGGTTGGTAAA-----TCGGG--TGCTCAGATCGGCCCTCCGGACC 173
                        *** ** ***   **    *    *****   *  *  **  **  * * **

M.africanumC1      TCGGTGTTGGCCAGCAAGAAGT-----CGCGGAGCGCCTGGCTGCTGGTCA---TACGCT 224
M.tuberculosis     AGGTTGTCGCCTGGGCAGATGTGCGCTCGCTAACCGCCAACTCACTT-TCAAACTACGCT 232
                     * *** * *  *  *** **     ***  * ****      **  ***   ******

M.africanumC1      -CGGG---GATCTTCATCTGCCGCAA---GACGGTGGCGATGTCGGGGTCGGTC-ACCA 275
M.tuberculosis     GCGAGTTGTGAGCGTAATGT-CAGTGATCTGACGGCAAAGGTCACGGATTTCGTCGAGCA 291
                    ** *     ** * * ** * * *  *   *****    * *  ***  *  *** * **

M.africanumC1      CAC---CTCTCCTTCGCTAA--------CGAG-TAGTAGCGCAAGCGTAAGAGACCGCTC 323
M.tuberculosis     GATGGACGGTATTTCGCGAAAAGCGGTTCGACCTACTGGCTCCTG-GTGTGTGGCC--TC 348
                    *    *  *  ***** **        ***  ** * ** *  * **  * * **  **

M.africanumC1      CCAGGC-------CTACGG--------ATGGGTCTG--GGGCTACG-GCCGT-----GAC 360
M.tuberculosis     CCAGGGTGCTGGGCTGCGGTTTCGCCAACCAACCTGCTGGTCGGCGCGCCGTATTCTGAA 408
                   *****        ** ***        *      ***  ** *  ** *****     **

M.africanumC1      AGCGAAAGCAACGAAAAGTAACGAGTTGAACGTCGCGGGCG---GCTAC-----GCCAAG 412
M.tuberculosis     GACCGGACCAACGAGGGG-ACCGAGCC--ATGTCTCAGACACCCGCTACAACCCGCAAAA 465
                     *   * ******  * * ****     * *** * * *    *****    ** **

M.africanumC1      CGCTCACCA-------CT---GGGC-TGGTCGCGCCG-GTCTTCCGGGTCCTTGTCATCC 460
M.tuberculosis     CGTTTCCCGAGATCAGCTCAAGAGCGTGGGAGCACCCCGCCGACCGGACCGCCCTT-TCC 524
                   ** *  **        **   * ** ***  ** **  * *  ****  *    * ***

M.africanumC1      TCGTC-CGCCGGCCCGGTGGCCGAGACCAGCCCT----GCT----TTGGAGCTGCCGC-- 509
M.tuberculosis     GCGCTGCGCCGGCTCAAAGGCTTCGACCAGATCTTGAAGCTGATGTCGGGGATGTTGCGG 584
                    **   ******* *    ***   ******  **    ***    * ** * **  **

M.africanumC1      ------------CGGCTGGCGTTCC-GGCCCCCATTCCGCTGCCCA--CCGGGGCAG--- 551
M.tuberculosis     GAACGGCAGCACCGGCTGCTGTACCTGGCCAGCGCGGCACGGGTCGGGCCGCGGCAGTTC 644
                               ****** ** ** ****   *     * * *  *   *** *****

M.africanumC1      ------CTCCACTCATCGCCG-ACGA-TCCG--------------GCGTTAGCGG---C 585
M.tuberculosis     GCCGACCTCGACGCGCTGCTGGACGAATGCGTGGATGTGCTGGACGCGTCGGCGAAACCC 704
                         *** ** *   ** * **** * **              ****  ***    *

M.africanumC1      GGTC-------GATGCCATCGGCGA----GGATGCCCCCTCCAACAAC-----TGAGCCA 629
M.tuberculosis     GAACTCTACGTGATGCAGTCACCAATCGCGGATGCCTTCACCATCGGCATGGGCAAGCCA 764
                   *  *       *****  **  * *    ******* * *** *  *      *****

M.africanumC1      T-CAGCGGGGT-GC----GCGCCGC-CGATCCGGC-------------------TTCGC- 662
M.tuberculosis     TTCACCGTGATCACCTCGGGGCTGTACGACCTGGTGACACACGACGAGATGCGGTTCGTG 824
                   * ** ** * *  *    * ** *  *** * **                    ****

M.africanumC1      -CGGGCAGCGATCCCG--CGCGCATCA--------------GTCCCGCAC---------- 695
M.tuberculosis     ATGGGCCACGAGCTCGGCCACGCACTGTCCGGCCACGCGGTGTACCGCACGATGATGATG 884
                     **** *** * **  * ****                  ** ******

M.africanumC1      ------CTGCGCTTGCGCCCGACCCACCCGCG-----------AGCGGGTGG------CG 732
M.tuberculosis     CATCTGCTGCGGTTG-GCCCGGTCATTCGGCGTCTTGCCGGTTGGCGGCTGGGCGCTGCG 943
                         ***** *** *****  *     * ***           **** ***        **

M.africanumC1      CGATGTCA-GGCCG-GCTCC--GATCGTCAACGCA--------------------CCCGC 768
M.tuberculosis     CGCAATCGTGGCTGCGCTGCTGGAATGGCAGCGCAAATCGGAGCTGTCCGGCGATCGCGC 1003
                   **   **  *** * *** *   **  * ** ****                  * ***

M.africanumC1      CGCATTGTCAT-----CGGTATCCCCATAC---ATCCGAG-------CGATGTCCGTCAA 813
M.tuberculosis     TGGGTTGCTGTGCGCGCAGGATTTGGACACCGCGCTCAGGGTGGAGATGAAGCTCGCTGG 1063
                    *  ***    *      * * **   * **      *  *             ** *  **

M.africanumC1      CG-CTGTCCCC-------GCTCGCATC--AGCTCCTCTTGAGCT---GCC---------- 850
M.tuberculosis     CGGCTGCCGGCTGGACAAGCTGGACTCGGAGGCCTTCTTG-GCTCAGGCCCGGGAATACG 1122
                   ** *** *  *        *** *  **  **  * ***** ***   ***

M.africanumC1      --------------------------GTGTTCGAAGCGATCA--TTGAAGCGGC------ 876
M.tuberculosis     AGACATCCGGCGATATGCGCGACGGGGTGCTCAAGCTGCTCAACCTGGAGCTGCAGACCC 1182
                                             *** ** *    * ***    ** *** **

M.africanumC1      -------CTCCGT--CGCGAAC-GCCATCACAGC---CTGCGCGGACACCT----CTTCG 919
M.tuberculosis     ATCCGTTCTCTGTGCTGCGGGCTGCCGCCTTGACTCACTGGGTGGACACCGGCGGCTATG 1242
                          *** **   *** * *** *   *     *   *** * *******     ** *

M.africanumC1      CCC---------CCCGCGGGTACCAGC--CCGGTCATGGTCGGCATCGTCG--------- 959
```

Figure 5A (cont)

```
M.tuberculosis      CCAAGGTGATAGCCGGCGAGTACCCGCGTCGGGCCGACGACGGCAACGCCAAATTTGCAG 1302
                      **   ** ***  ***** *  **  **  *  ****  ** 

M.africanumC1       -CCGCGTTGCCG--GCCGCCAGG------CC---ACGGCT---ACCGATCT--CGACCAGT 1003
M.tuberculosis      ACGACCTTGGCGCGGCCGCCCGGTACTACCGGGACGGCTTCGACCAGTCCAACGACCCGC 1362
                      *  * *** **  ******  **    **   ******  ***  **  *****  *

M.africanumC1       TGC---------------GATCCGATG---TCGCCA------------------------ 1021
M.tuberculosis      TGATCAAAGGTATCCGCGACGGATTCGGTGGCATCGTCGAGGGCGTGGGACGGGCAGCCT 1422
                    ** *                 ***  ** **   ***   *

M.africanumC1       -----GCGGCCGGATCGT---GTGACAAG------GAAT---------CCATCTG-GTTAT 1058
M.tuberculosis      CGAACGCGGCCGATTCATTGGGCCGCAAGATCACCGAGTGCCGGCAGCCCTCGAAGTGAC 1482
                         ******* **  * * ***  ***      ** *         **  **  **  *

M.africanumC1       TGCTCCTGTGT-----------GTTTGTGCG-----CGGACTCGAACGCTTG--TGACGC 1100
M.tuberculosis      GGCCCCTCTGCTACGTAGCTAAGCACGCGCGACCGGCGGGCTGGGGAGCCCGGTCAGCGG 1542
                     **  *** **           *   * ***    ***  **  *    **    **

M.africanumC1       CCCCGTAGCAATCCC---CGCGGAAAGCCGG----------------------------- 1128
M.tuberculosis      TCTCATAGCATTGCGAACACGGGACGTCGAGAGGGGAAGAGCTGCCATGGGTGAGGCGAA 1602
                      *  ****** *      * ***   *   *    *  *

M.africanumC1       ----CGCGA-----CTACCGCCGCAAAGCC------CGGTCCGGCTGCGCC--GGACAAT 1171
M.tuberculosis      CATCCGCGAGCAGGCGATCGCCACGATGCCACGGGGTGGCCCCGACGCGTCTTGGCTGGA 1662
                        *****     * * *** **  * **       *** *  *** ** **

M.africanumC1       AAGACAATTCTAGACC--CGCTGCGGGTTAGCAGACCCGCGAAG------CCG------- 1216
M.tuberculosis      TCGTCGATTCCAGACCGACGCACTGGAGTACCTCGACCGCGACGATGTGCCCGATGAGGT 1722
                    *  *  **** *****    **  ***   *  ** *****      * * ***

M.africanumC1       ----CAGAAATACGTTTG------CAGCCA---------CCTGACC---TTGCGC----- 1249
M.tuberculosis      CAAACAGAAGATCATCGGGGTGCTCGACCGGGTGGGCACCCTGACCAACCTGCACGAGAA 1782
                        ****  *  *  *       *** *          ********   ***

M.africanumC1       -------CGGATCGCCCTG---------------------TGCGAAGGTCGGAACC 1277
M.tuberculosis      GTACGCCCGGATAGCCCTGAAACTTGTTTCTGACATTCCCAACCCGCGAATCCTGGAACT 1842
                           ***** ******                      **     **  **

M.africanumC1       ---------------AGCGTTGCTCGAAGGT------GATGCACCCAGCCGCAA--GT 1312
M.tuberculosis      TGGTGCGGGCCATGGCAAGCTCTCAGCGAAAATCCTCGAGCTACACCCGACAGCGACGGT 1902
                                    *   ** *   ****      **  ***** **  *  **

M.africanumC1       GTCGACCTATTGCGCAAATCACACTGCGGCA-----------CGCGGT----CTG----C 1353
M.tuberculosis      GACGATCAGCGATCTAGATCCCACCTCGGTGGCCAACATCGCCGCGGGAGAGCTGGGAAC 1962
                    * *** *      *  *** **** * **            **** *    ***   *

M.africanumC1       CTGCCCGTGGGACCGAACACAA-CGAACGA--------------AACGGTCA--GTCGCAC 1397
M.tuberculosis      ACATCCGCGAGCACGCACCCAAGTGATCGACGCCACCGCAATCGACGGCCACGACCACAG 2022
                      * ***  *    * ** *** **  **              * * *   *  * **

M.africanumC1       CCCTGAGTT--CGGTCT------------------------------------------- 1412
M.tuberculosis      CTATGACCTGGCGGTCTTCGCGCTGGCATTTCACCACCTGCCGCCTACGGTCGCCTGCAA 2082
                      *  ***   ******

M.africanumC1       GGCAAACACCGAAAC------------------------AATCATGCCGATCT--GCCGGA 1446
M.tuberculosis      AGCGATCGCCGAGGCCACCCGGGTGGGGAAGCGCTTTCTGATCAT-CGACCTCAAACGGC 2141
                     ** * * *****                          ****** **   *    ***

M.africanumC1       ATAAATAGCTATT-----------------TGCAAC--ACT------TTCACATGC----- 1477
M.tuberculosis      AGAAACCGCTGTCGTTCACGCTCTCTTCGGTGCTGCTACTGCCGCTCCACCTACTGCTGC 2201
                    * ***  ****       *                 ***  ***    **** **

M.africanumC1       -GTAATGAAAGTTGG-GCG-TCAAACAAAAGCTAAGGC---GTACGCAAATTCCATGCCG 1531
M.tuberculosis      TGCCATGGTCGTCGATGCGCTCGAGCATGCACGGACGGCTTTATCAGCGGCACTACGTGCCT 2261
                     *  ***   ** *  ***   * *  *   *    *     *  ***  *     *****

M.africanumC1       GGGCTCGGCCGACTGTGTC-ACACCTGCCATCGCGGGCG----GGGAA-GC--------- 1576
M.tuberculosis      ACAGTCCCTCGGCGTTGCAGACGCTTGCCCGCGCCGCCGGATCCGGGAATGCAGGTTGAAA 2321
                      * *    **   **  ** ** ****   *** **    *****  **

M.africanumC1       ---------------------------------------CGCCGTTGTGTC------TTCGG 1593
M.tuberculosis      TCTTGCCCGCACCGACCAGGCTATTCCCGCCATCGCTCGCCGTTGTGTTCTCCCGTTCGA 2381
                                                           ********** *     ****

M.africanumC1       CCGCAATGCCGCGCTGAACGCTAATGTGTAC---GGCGA----CACCCCGGTGG-CGATG 1645
M.tuberculosis      GCTCAGCGCCA-ACGGAAT-CTAGCGAGTGCTCGGCCGATCGCCAACCCGGCGAATGATT 2439
                     *  ** ***   * *** ** ***  *  *    **** **   * ********

M.africanumC1       CGGACGCCGCGCAGACCGGCC--CGCGGG------GAGGAGCACGAATTGCGGTT----C 1693
M.tuberculosis      CGGTAGTAGTGCAGATAAGCCATCGCCGGTACCACGACGAACGTGA-TCACGATCAAAGC 2498
                    ***   *  * *****  ***  ***  **      *  ** **       ** *

M.africanumC1       AATCG-------GTTCAG-------CGC-------------------GTC------CAC 1713
M.tuberculosis      AATCGAGAAGTAGTTCGGACCACCCCGCACTAGAAAGATGCAGCGGTAGTCGTAGGACAC 2558
                    *****        ****       ***                    ***      ***

M.africanumC1       ----AGCTCGGCCG---------------------------TGCTGATGGATA-ACC 1738
```

Figure 5A (cont)

```
M.tuberculosis      TGCCAGCCCAACCGAGACCACGATCGCAACAAGCGGTAACACCTTGTCGGTGAACGCATT 2618
                        *** *  ***                              **   *** *   *

M.africanumC1       TCG------AGCGGC----TTCGTGGTC----ACCTTTTCGAT-CGGTGAT-GCG-TTGG 1781
M.tuberculosis      TCGCCGCACAGCAGCATGTTCTACTGCCTGAGACCTCGCCAATGCGATGAGAGCGATCGG 2678
                    ***      *** **    *     * *    ****   * ** ** ***  *** * **

M.africanumC1       CCAGCTAGTACACCG--------------TCACCG--AGAGCGAT-AGGTGCTATTTCCC 1824
M.tuberculosis      CACGATGATGAACTGGACGAATCGGGCGATCACCGCCAGGCCGGTCAGGTGCAGGTTGTC 2738
                    *  * *  *  ** *              ******  **  ** * ******   **  *

M.africanumC1       ---TTGCCGTGCT-----------GGGCGCCTGCGGTGC---------------GGCC-- 1853
M.tuberculosis      GAACCGCAGCGCCAACGGGAATGCGAGCGCCAACGACGCCGTAATTGCGAAGGAGACCAT 2798
                         ** * **            * *****  **  **               * **

M.africanumC1       ------------TTGGTGCT---------------------GACCGCGCCGCCGGCCAA 1879
M.tuberculosis      CGGCACGTCGTATTGGTTCTTGCGTGACAAGCGTGTCGGCAGAACCCCGCTGTCCGCTAA 2858
                                ***** **                       *** *** * * ** **

M.africanumC1       CCAGGCCCGA-GCCGCGGCGAGCC---TGCTGTCACGAT---------CGAAC-------T 1920
M.tuberculosis      CGCGGTCCAAAGCCGCGGTGCACCGAACGAGGCCGCGACATTGATGCCGAACATCGATAT 2918
                    *  ** ** * ******* *  **    *  * * ***         *****       *

M.africanumC1       GGGTGCTCGCCACTGCGTTGCCCGCCAGTCAGG--ACGTCCCGGCCGATTGGGGCTACTC 1978
M.tuberculosis      CAGGGCTC-CGACGACGATGATCGTTCGGAAGGTAGCGTTTCCGATGGCCGCGGCCAGTT 2977
                      * **** * **  ** **  **   *  ***   ***  * *  *   * *** * *

M.africanumC1       -------GTTGACCG----GGCGGT----TGCGA--CGAGCGGTCTCGCCA--------- 2012
M.tuberculosis      TCACGGTGTCGTCCGACGCGGCGATCTTGTTCGATCCGAGCAGCATCGCTACCGTTAGGG 3037
                           ** * ***    **** *    * ***  ***** *  **** *

M.africanumC1       --AGCA------CCGTGCCGCC------GGCCGCGCT--GCCTAACAC------------ 2044
M.tuberculosis      TGAGCAAGTAGATCGCGCCAACCGAGAAGATCGCGATCGGTATAGCTCTCGGCAGGTTCC 3097
                      ****       ** ***  *      *  **** *  *  ** * *

M.africanumC1       GAGCCGA-GCAGCCGTCTATTCGCCGGC---------TGGATGCGGAA------------ 2082
M.tuberculosis      GGTCCGGCGCGTCCATTTCTTCGGCGGCGTTCGCGATCGATTCGAAACCGGTGAATGCGT 3157
                    *  ***  **  ** * * **** ****        * *** ** **

M.africanumC1       ACATTCCGAAAATCCTGGAC-------CACTCCAG----------CGCCGACTT-GGC-- 2122
M.tuberculosis      ACAACGCGACAATCGTGGCCAGCGCCATACTCGAGAACGTGCCCTTGCCAATTTCGGCGA 3217
                    ***   *** **** *** *        **** **           *** * ** ***

M.africanumC1       CGCC----------TATG---------TCCAGATAGACCGCGACGT---GCAGGTGTTC- 2159
M.tuberculosis      CGCCAAGCAACGAGTACGGGGTCGCGCTGTATGCCGACCACGCCGTTGCGTAGTTGTTCA 3277
                    ****          ** *         *  *    **** ** ***   * ** *****

M.africanumC1       ------GGGCAA-GATG-----CGCCCC---------TGGATGCTGC---CGCGA------ 2190
M.tuberculosis      CGTGCTGGGTGGTGATGATCCACAGCCCGCCGACAATGAATGCCGAGAGCGCGAATGCCT 3337
                          ***    ****     *  ***        ** **** *    *****

M.africanumC1       ---------------------------------------------CCGGGGAAAGCGATG- 2205
M.tuberculosis      TGCCTACCGTTGACGTTCCGTTGGCCCACTTGATCGCCCGGTTGCCGAAGAGGTTGATGG 3397
                                                                ***  **    ****

M.africanumC1       -----AGCGCG------GACCC----AACGCCCGCTTCG-CACTCTGGGCCGTTGC---- 2245
M.tuberculosis      CCAACAGCACGCCGATAAAGCCGAGAAACGTCAGCGTCTTCACACTGAACACTTGCTCGG 3457
                         *** **       * **    **** * ** **  *** ***  * *****

M.africanumC1       CGACGGCCCGG-------CGCGGA-------TCGC------------------------- 2266
M.tuberculosis      CGTCGGCCCAGGCCTTGTCGGGGAAGGCCACTCGCAACAGCGTCGAGACGAAAAAAGAAG 3517
                    ** ****** *       ** ***       ****

M.africanumC1       -CAACTACC---------TGGAC-------TGGC---------------TAAA------ 2287
M.tuberculosis      CCAACACCCCCCAAGCGATGGACGCGGTAATGGCGTGGGTGACACCGACATAGATGCCGA 3577
                     ****  **         *****       ****                ** *

M.africanumC1       -CCGG--------TGCGGTTCTTAC-CAGGT--------CACCAACCACTTT-------- 2321
M.tuberculosis      TCCGGCGCCCAAATGCGGCCGTTGTGTAGGCGTAGGAGGCACCGTTTGTTCTGACGTACC 3637
                     ****        *****   **    ***         ****      * *

M.africanumC1       TTG-------------GACG----------------GAA-----CGGTCAAGA------ 2340
M.tuberculosis      TTGCCGCCGTCGCGAAGACGATCGCCACGACACCCGCGAAAATGCCAGCTAAAACATAGG 3697
                    ***             ****                 ***     * *  ** *

M.africanumC1       ---------ACGAA---------CGAACC--GTCACC--ACC--GAGGTGGAA--------G 2370
M.tuberculosis      CCATCGCCGCGAAGGGTCCTGCGAGCCCGATCACCTCACCTGGAGTTAGGAAGATACCGG 3757
                             ****        *** **   *****  ***  *** * * *        *

M.africanumC1       CGC----TTTCGG-------CCGGCGGTGCCGACGCCGC--------------------- 2398
M.tuberculosis      CGCCGATTATCGAGTTGATCCCGAGCATGACGACGCTGCAGAAACCCAGCTTGTGGATCG 3817
                    ***    * ***        ***    ** ****** **

M.africanumC1       ----------C[redacted]T--------AATCCTCTA 2428
M.tuberculosis      CATATCCTCTC[redacted]CTAGCAGGGAATCCTCTA 3877
                              **** ****      ***      ****  **         *********

M.africanumC1       ACGCACCATAGATTCTCTAGCGACCATTCTTGAGCTCCCGGCCTGTCGATGCCGGCGCTG 2498
```

Figure 5A (cont)

```
M.tuberculosis      ACGCACCATAGATTCTCTAGCGACGATTCTTGAGCTCCCGGCCTGTCGATGCCGGCGCTG 3937
                    ************************************************************

M.africanumCl       CAGGTGAGTCACCGCAGTGGGCGCACCGAACACTCACTTCCGCCGCCCCAAATCCGCGCA 2548
M.tuberculosis      CAGGTGAGTCACCGCAGTGGGCGCACCGAACACTCATTTCCGCCGCCCCAAATCCGCGCA 3997
                    ************************************ ***********************

M.africanumCl       GTGACCACCGCGCGGTCCTCGCGAGTCTAGGCCAGCATCGAGTCGATCGCGGAACGTGGG 2608
M.tuberculosis      GTGACCACCGCGCGGTCCTCGCGAGTCTAGGCCAGCATCGAGTCGATCGCGGAACGTGGG 4057
                    ************************************************************

M.africanumCl       ACCAATACCTGGGTTGGGCCGGCTGCTTCGGGCAGCAACTCCCCCGGGTTGAAGAAGAAA 2668
M.tuberculosis      ACCAATACCTGGGTTGGGCCGGCTGCTTCGGGCAGCAACTCCCCCGGGTTGAAGAAGAAA 4117
                    ************************************************************

M.africanumCl       ATCACCCCGTCGTTCGTGACTGCGAAGTTCTGATAATTCACCGGGTCCAAGCCGGCATTC 2728
M.tuberculosis      ATCACCCCGTCGTTCGTGACTGCGAAGTTCTGATAATTCACCGGGTCCAAGCCGGCATTC 4177
                    ************************************************************

M.africanumCl       GGCGCTATCGATACCTGTTGTCCGGTCTGCTTGCTCAGTTCACCTTGCACAATGGGGAAG 2788
M.tuberculosis      GGCGCTATCGATACCTGTTGTCCGGTCTGCTTGCTCAGTTCACCTTGCACAATGGGGAAG 4237
                    ************************************************************

M.africanumCl       ACGACTGGCAG 2799
M.tuberculosis      ACGACTGGCAG 4248
                    ***********
```

Figure 5 (B)

```
M.africanumCl_1449_02       GCCGTGCTGGGCGCCTGCGGTGCGGCCTTGGTGCTGACCGCGCCGCCGGC 50
M.africanumCl_10473_01      GCCGTGCTGGGCGCCTGCGGTGCGGCCTTGGTGCTGACCGCGCCGCCGGC 50
                            **************************************************

M.africanumCl_1449_02       CAACCAGGCCCGAGCCGCGGCGAGCCTGCTGTCACGATCGAACTGGGTGC 100
M.africanumCl_10473_01      CAACCAGGCCCGAGCCGCGGCGAGCCTGCTGTCACGATCGAACTGGGTGC 100
                            **************************************************

M.africanumCl_1449_02       TCGCCACTGCGTTGCCCGCCAGTCAGGACGTCCCGGCCGATTGGGGCTAC 150
M.africanumCl_10473_01      TCGCCACTGCGTTGCCCGCCAGTCAGGACGTCCCGGCCGATTGGGGCTAC 150
                            **************************************************

M.africanumCl_1449_02       TCGTTGACCGGGCGGTTGCGACGAGCGGTCTCGCCAAGCACCGTGCCGCC 200
M.africanumCl_10473_01      TCGTTGACCGGGCGGTTGCGACGAGCGGTCTCGCCAAGCACCGTGCCGCC 200
                            **************************************************

M.africanumCl_1449_02       GGCCGCGCTGCCTAACACGAGCCGAGCAGCCGTCTATTCGCCGGCTGGAT 250
M.africanumCl_10473_01      GGCCGCGCTGCCTAACACGAGCCGAGCAGCCGTCTATTCGCCGGCTGGAT 250
                            **************************************************

M.africanumCl_1449_02       GCGGAAACATTCCGAAAATCCTGGACCACTCCAGCGCCGACTTGGCCGCC 300
M.africanumCl_10473_01      GCGGAAACATTCCGAAAATCCTGGACCACTCCAGCGCCGACTTGGCCGCC 300
                            **************************************************

M.africanumCl_1449_02       TATGTCCAGATAGACCGCGACGTGCAGGTGTTCGGGCAAGATGCGCCCCT 350
M.africanumCl_10473_01      TATGTCCAGATAGACCGCGACGTGCAGGTGTTCGGGCAAGATGCGCCCCT 350
                            **************************************************

M.africanumCl_1449_02       GGATGCTGCCGCGACCGGGGAAAGCGATGAGCGCGGACCCAACGCCCGCT 400
M.africanumCl_10473_01      GGATGCTGCCGCGACCGGGGAAAGCGATGAGCGCGGACCCAACGCCCGCT 400
                            **************************************************

M.africanumCl_1449_02       TCGCACTCTGGGCCGTTGCCGACGGCCCGGCGCGGATCGCCAACTACCTG 450
M.africanumCl_10473_01      TCGCACTCTGGGCCGTTGCCGACGGCCCGGCGCGGATCGCCAACTACCTG 450
                            **************************************************

M.africanumCl_1449_02       GACTGGCTAAACCGGTGCGGTTCTTACCAGGTCACCAACCACTTTTTGGA 500
M.africanumCl_10473_01      GACTGGCTAAACCGGTGCGGTTCTTACCAGGTCACCAACCACTTTTTGGA 500
                            **************************************************

M.africanumCl_1449_02       CGGAACGGTCAAGAACGAACGAACCGTCACCACCGAGGTGGAAGCGCTTT 550
M.africanumCl_10473_01      CGGAACGGTCAAGAACGAACGAACCGTCACCACCGAGGTGGAAGCGCTTT 550
                            **************************************************

M.africanumCl_1449_02       CGGCCGGCGGTGCCGACGCCGCCGTCGCGGTCACAAGGACGTTAATCCTC 600
M.africanumCl_10473_01      CGGCCGGCGGTGCCGACGCCGCCGTCGCGGTCACAAGGACGTTAATCCTC 600
                            **************************************************

M.africanumCl_1449_02       TAACGCACCATAGATTCTCTAGCGACGATTCTTGAGCTCCCGGCCTGTCG 650
M.africanumCl_10473_01      TAACGCACCATAGATTCTCTAGCGACGATTCTTGAGCTCCCGGCCTGTCG 650
                            **************************************************

M.africanumCl_1449_02       ATGCCGGCGCTGCAGGTGAGTCACCGCAGTGGGCGCACCGAACACTCACT 700
M.africanumCl_10473_01      ATGCCGGCGCTGCAGGTGAGTCACCGCAGTGGGCGCACCGAACACTCACT 700
                            **************************************************

M.africanumCl_1449_02       TCCGCCGCCCCAAATCCGCGCAGTGACCACCGCGCGGTCCTCGCGAGTCT 750
M.africanumCl_10473_01      TCCGCCGCCCCAAATCCGCGCAGTGACCACCGCGCGGTCCTCGCGAGTCT 750
                            **************************************************

M.africanumCl_1449_02       AGGCCAGCATCGAGTCGATCGCGGAACGTGGGACCAATACCTGGGTTGGG 800
M.africanumCl_10473_01      AGGCCAGCATCGAGTCGATCGCGGAACGTGGGACCAATACCTGGGTTGGG 800
                            **************************************************

M.africanumCl_1449_02       CCGGCTGCTTCGGGCAGCAACTCCCCCGGGTTGAAGAAGAAAATCACCCC 850
M.africanumCl_10473_01      CCGGCTGCTTCGGGCAGCAACTCCCCCGGGTTGAAGAAGAAAATCACCCC 850
                            **************************************************

M.africanumCl_1449_02       GTCGTTCGTGACTGCGAAGTTCTGATAATTCACCGGGTCCAAGCCGGCAT 900
M.africanumCl_10473_01      GTCGTTCGTGACTGCGAAGTTCTGATAATTCACCGGGTCCAAGCCGGCAT 900
                            **************************************************

M.africanumCl_1449_02       TCGGCGCTATCGATACCTGTTGT 923
M.africanumCl_10473_01      TCGGCGCTATCGATACCTGTTGT 923
                            ***********************
```

Figure 6 (A)

```
M.tuberculosis_KZN2407      ATGGCGGCCGACTACGACAAGCTCTTCCGGCCGCACGAAGGTATGGAAGC 50
M.tuberculosis_KZN1435      ATGGCGGCCGACTACGACAAGCTCTTCCGGCCGCACGAAGGTATGGAAGC 50
M.tuberculosis_H37RV        ATGGCGGCCGACTACGACAAGCTCTTCCGGCCGCACGAAGGTATGGAAGC 50
M.tuberculosis_H37Ra        ATGGCGGCCGACTACGACAAGCTCTTCCGGCCGCACGAAGGTATGGAAGC 50
M.tuberculosis_F11          ATGGCGGCCGACTACGACAAGCTCTTCCGGCCGCACGAAGGTATGGAAGC 50
M.tuberculosis_CDC1551      ATGGCGGCCGACTACGACAAGCTCTTCCGGCCGCACGAAGGTATGGAAGC 50
M.bovis_AF2122/97           ATGGCGGCCGACTACGACAAGCTCTTCCGGCCGCACGAAGGTATGGAAGC 50
M.africanum                 ATGGCGGCCGACTACGACAAGCTCTTCCGGCCGCACGAAGGTATGGAAGC 50
M.canettii                  ATGGCGGCCGACTACGACAAGCTCTTCCGGCCGCACGAAGGTATGGAAGC 50
                            **************************************************

M.tuberculosis_KZN2407      TCCGGACGATATGGCAGCGCAGCCGTTCTTCGACCCCAGTGCTTCGTTTC 100
M.tuberculosis_KZN1435      TCCGGACGATATGGCAGCGCAGCCGTTCTTCGACCCCAGTGCTTCGTTTC 100
M.tuberculosis_H37RV        TCCGGACGATATGGCAGCGCAGCCGTTCTTCGACCCCAGTGCTTCGTTTC 100
M.tuberculosis_H37Ra        TCCGGACGATATGGCAGCGCAGCCGTTCTTCGACCCCAGTGCTTCGTTTC 100
M.tuberculosis_F11          TCCGGACGATATGGCAGCGCAGCCGTTCTTCGACCCCAGTGCTTCGTTTC 100
M.tuberculosis_CDC1551      TCCGGACGATATGGCAGCGCAGCCGTTCTTCGACCCCAGTGCTTCGTTTC 100
M.bovis_AF2122/97           TCCGGACGATATGGCAGCGCAGCCGTTCTTCGACCCCAGTGCTTCGTTTC 100
M.africanum                 TCCGGACGATATGGCAGCGCAGCCGTTCTTCGACCCCAGTGCTTCGTTTC 100
M.canettii                  TCCGGACGATACGGCAGCGCAGCCGTTCTTCGACCCCAGTGCTTCGTTTC 100
                            *********** **************************************

M.tuberculosis_KZN2407      CGCCGGCGCCCGCATCGGCAAACCTACCGAAGCCCAACGGCCAGACTCCG 150
M.tuberculosis_KZN1435      CGCCGGCGCCCGCATCGGCAAACCTACCGAAGCCCAACGGCCAGACTCCG 150
M.tuberculosis_H37RV        CGCCGGCGCCCGCATCGGCAAACCTACCGAAGCCCAACGGCCAGACTCCG 150
M.tuberculosis_H37Ra        CGCCGGCGCCCGCATCGGCAAACCTACCGAAGCCCAACGGCCAGACTCCG 150
M.tuberculosis_F11          CGCCGGCGCCCGCATCGGCAAACCTACCGAAGCCCAACGGCCAGACTCCG 150
M.tuberculosis_CDC1551      CGCCGGCGCCCGCATCGGCAAACCTACCGAAGCCCAACGGCCAGACTCCG 150
M.bovis_AF2122/97           CGCCGGCGCCCGCATCGGCAAACCTACCGAAGCCCAACGGCCAGACTCCG 150
M.africanum                 CGCCGGCGCCCGCATCGGCAAACCTACCGAAGCCCAACGGCCAGACTCCG 150
M.canettii                  CGCCGGCGCCCGCATCGGCAAACCTACCGAAGCCCAACGGCCAGACTCCG 150
                            **************************************************

M.tuberculosis_KZN2407      CCCCCGACGTCCGACGACCTGTCGGAGCGGTTCGTGTCGGCCCCGCCGCC 200
M.tuberculosis_KZN1435      CCCCCGACGTCCGACGACCTGTCGGAGCGGTTCGTGTCGGCCCCGCCGCC 200
M.tuberculosis_H37RV        CCCCCGACGTCCGACGACCTGTCGGAGCGGTTCGTGTCGGCCCCGCCGCC 200
M.tuberculosis_H37Ra        CCCCCGACGTCCGACGACCTGTCGGAGCGGTTCGTGTCGGCCCCGCCGCC 200
M.tuberculosis_F11          CCCCCGACGTCCGACGACCTGTCGGAGCGGTTCGTGTCGGCCCCGCCGCC 200
M.tuberculosis_CDC1551      CCCCCGACGTCCGACGACCTGTCGGAGCGGTTCGTGTCGGCCCCGCCGCC 200
M.bovis_AF2122/97           CCCCCGACGTCCGACGACCTGTCGGAGCGGTTCGTGTCGGCCCCGCCGCC 200
M.africanum                 CCCCCGACGTCCGACGACCTGTCGGAGCGGTTCGTGTCGGCCCCGCCGCC 200
M.canettii                  CCCCCGACGTCCGACGGCCTGTCGGAGCGGTTCGTGTCGGCCCCGCCGCC 200
                            **************** *********************************

M.tuberculosis_KZN2407      GCCACCCCCACCCCCACCTCCGCCTCCGCCAACTCCGATGCCGATCGCCG 250
M.tuberculosis_KZN1435      GCCACCCCCACCCCCACCTCCGCCTCCGCCAACTCCGATGCCGATCGCCG 250
M.tuberculosis_H37RV        GCCACCCCCACCCCCACCTCCGCCTCCGCCAACTCCGATGCCGATCGCCG 250
M.tuberculosis_H37Ra        GCCACCCCCACCCCCACCTCCGCCTCCGCCAACTCCGATGCCGATCGCCG 250
M.tuberculosis_F11          GCCACCCCCACCCCCACCTCCGCCTCCGCCAACTCCGATGCCGATCGCCG 250
M.tuberculosis_CDC1551      GCCACCCCCACCCCCACCTCCGCCTCCGCCAACTCCGATGCCGATCGCCG 250
M.bovis_AF2122/97           GCCACCCCCACCCCCACCTCCGCCTCCGCCAACTCCGATGCCGATCGCCG 250
M.africanum                 GCCACCCCCACCCCCACCTCCGCCTCCGCCAACTCCGATGCCGATCGCCG 250
M.canettii                  ACCACCCCCACCCCCACCTCCGCCTCCGCCAACTCCGATGCCGATCGCCG 250
                             *************************************************

M.tuberculosis_KZN2407      CAGGAGAGCCGCCCTCGCCGGAACCGGCCGCATCTAAACCACCCACACCC 300
M.tuberculosis_KZN1435      CAGGAGAGCCGCCCTCGCCGGAACCGGCCGCATCTAAACCACCCACACCC 300
M.tuberculosis_H37RV        CAGGAGAGCCGCCCTCGCCGGAACCGGCCGCATCTAAACCACCCACACCC 300
M.tuberculosis_H37Ra        CAGGAGAGCCGCCCTCGCCGGAACCGGCCGCATCTAAACCACCCACACCC 300
M.tuberculosis_F11          CAGGAGAGCCGCCCTCGCCGGAACCGGCCGCATCTAAACCACCCACACCC 300
M.tuberculosis_CDC1551      CAGGAGAGCCGCCCTCGCCGGAACCGGCCGCATCTAAACCACCCACACCC 300
M.bovis_AF2122/97           CAGGAGAGCCGCCCTCGCCGGAACCGGCCGCATCTAAACCACCCACACCC 300
M.africanum                 CAGGAGAGCCGCCCTCGCCGGAACCGGCCGCATCTAAACCACCCACACCC 300
M.canettii                  CAGGAGAGCCGCCCTCGCCGGAACCGGCCGCATCTAAACCACCCACACCC 300
                            **************************************************

M.tuberculosis_KZN2407      CCCATGCCCATCGCCGGACCCGAACCGGCCCCACCCAAACCACCCACACC 350
M.tuberculosis_KZN1435      CCCATGCCCATCGCCGGACCCGAACCGGCCCCACCCAAACCACCCACACC 350
M.tuberculosis_H37RV        CCCATGCCCATCGCCGGACCCGAACCGGCCCCACCCAAACCACCCACACC 350
M.tuberculosis_H37Ra        CCCATGCCCATCGCCGGACCCGAACCGGCCCCACCCAAACCACCCACACC 350
M.tuberculosis_F11          CCCATGCCCATCGCCGGACCCGAACCGGCCCCACCCAAACCACCCACACC 350
M.tuberculosis_CDC1551      CCCATGCCCATCGCCGGACCCGAACCGGCCCCACCCAAACCACCCACACC 350
M.bovis_AF2122/97           CCCATGCCCATCGCCGGACCCGAACCGGCCCCACCCAAACCACCCACACC 350
M.africanum                 CCCATGCCCATCGCCGGACCCGAACCGGCCCCACCCAAACCACCCACACC 350
M.canettii                  CCCATGCCCATCGCCGGACCCGAA-------------------------- 324
                            ************************

M.tuberculosis_KZN2407      CCCCATGCCCATCGCCGGACCCGAACCGGCCCCACCCAAACCACCCACAC 400
M.tuberculosis_KZN1435      CCCCATGCCCATCGCCGGACCCGAACCGGCCCCACCCAAACCACCCACAC 400
M.tuberculosis_H37RV        CCCCATGCCCATCGCCGGACCCGAACCGGCCCCACCCAAACCACCCACAC 400
M.tuberculosis_H37Ra        CCCCATGCCCATCGCCGGACCCGAACCGGCCCCACCCAAACCACCCACAC 400
M.tuberculosis_F11          CCCCATGCCCATCGCCGGACCCGAACCGGCCCCACCCAAACCACCCACAC 400
M.tuberculosis_CDC1551      CCCCATGCCCATCGCCGGACCCGAACCGGCCCCACCCAAACCACCCACAC 400
M.bovis_AF2122/97           CCCCATGCCCATCGCCGGACCCGAACCGGCCCCACCCAAACCACCCACAC 400
M.africanum                 CCCCATGCCCATCGCCGGACCCGAACCGGCCCCACCCAAACCACCCACAC 400
```

Figure 6A (cont)

```
M.canettii                  -------------------------CCGGCCCCACCCAAACCACCCGCAC 349
                                                     ********************* ***

M.tuberculosis_KZN2407      CTCCGATGCCCATCGCCGGACCTGCACCCACCCCAACCGAATCCCAGTTG 450
M.tuberculosis_KZN1435      CTCCGATGCCCATCGCCGGACCTGCACCCACCCCAACCGAATCCCAGTTG 450
M.tuberculosis_H37RV        CTCCGATGCCCATCGCCGGACCTGCACCCACCCCAACCGAATCCCAGTTG 450
M.tuberculosis_H37Ra        CTCCGATGCCCATCGCCGGACCTGCACCCACCCCAACCGAATCCCAGTTG 450
M.tuberculosis_F11          CTCCGATGCCCATCGCCGGACCTGCACCCACCCCAACCGAATCCCAGTTG 450
M.tuberculosis_CDC1551      CTCCGATGCCCATCGCCGGACCTGCACCCACCCCAACCGAATCCCAGTTG 450
M.bovis_AF2122/97           CTCCGATGCCCATCGCCGGACCTGCACCCACCCCAACCGAATCCCAGTTG 450
M.africanum                 CTCCGATGCCCATCGCCGGACCTGCACCCACCCCAACCGAATCCCAGTTG 450
M.canettii                  CTCCGATGCCCATCGCCGGACCTGCACCCACCCCAACCGAATCCCAGTTG 399
                            **************************************************

M.tuberculosis_KZN2407      GCGCCCCCCAGACCACCGACACCACAAACGCCAACCGGAGCGCCGCAGCA 500
M.tuberculosis_KZN1435      GCGCCCCCCAGACCACCGACACCACAAACGCCAACCGGAGCGCCGCAGCA 500
M.tuberculosis_H37RV        GCGCCCCCCAGACCACCGACACCACAAACGCCAACCGGAGCGCCGCAGCA 500
M.tuberculosis_H37Ra        GCGCCCCCCAGACCACCGACACCACAAACGCCAACCGGAGCGCCGCAGCA 500
M.tuberculosis_F11          GCGCCCCCCAGACCACCGACACCACAAACGCCAACCGGAGCGCCGCAGCA 500
M.tuberculosis_CDC1551      GCGCCCCCCAGACCACCGACACCACAAACGCCAACCGGAGCGCCGCAGCA 500
M.bovis_AF2122/97           GCGCCCCCCAGACCACCGACACCACAAACGCCAACCGGAGCGCCGCAGCA 500
M.africanum                 GCGCCCCCCAGACCACCGACACCACAAACGCCAACCGGAGCGCCGCAGCA 500
M.canettii                  GCGCCCCCCAGACCACCGACACCACAAACGCCAACCGGAGCGCCGCAGCA 449
                            **************************************************

M.tuberculosis_KZN2407      ACCGGAATCACCGGCGCCCCACGTACCCTCGCACGGGCCACATCAACCCC 550
M.tuberculosis_KZN1435      ACCGGAATCACCGGCGCCCCACGTACCCTCGCACGGGCCACATCAACCCC 550
M.tuberculosis_H37RV        ACCGGAATCACCGGCGCCCCACGTACCCTCGCACGGGCCACATCAACCCC 550
M.tuberculosis_H37Ra        ACCGGAATCACCGGCGCCCCACGTACCCTCGCACGGGCCACATCAACCCC 550
M.tuberculosis_F11          ACCGGAATCACCGGCGCCCCACGTACCCTCGCACGGGCCACATCAACCCC 550
M.tuberculosis_CDC1551      ACCGGAATCACCGGCGCCCCACGTACCCTCGCACGGGCCACATCAACCCC 550
M.bovis_AF2122/97           ACCGGAATCACCGGCGCCCCACGTACCCTCGCACGGGCCACATCAACCCC 550
M.africanum                 ACCGGAATCACCGGCGCCCCACGTACCCTCGCACGGGCCACATCAACCCC 550
M.canettii                  ACCGGAATCACCGGCGCCCCACGTACCCTCGCACGGGCCACAACAACCCC 499
                            ****************************************** *******

M.tuberculosis_KZN2407      GGCGCACCGCACCAGCACCGCCCTGGGCAAAGATGCCAATCGGCGAACCC 600
M.tuberculosis_KZN1435      GGCGCACCGCACCAGCACCGCCCTGGGCAAAGATGCCAATCGGCGAACCC 600
M.tuberculosis_H37RV        GGCGCACCGCACCAGCACCGCCCTGGGCAAAGATGCCAATCGGCGAACCC 600
M.tuberculosis_H37Ra        GGCGCACCGCACCAGCACCGCCCTGGGCAAAGATGCCAATCGGCGAACCC 600
M.tuberculosis_F11          GGCGCACCGCACCAGCACCGCCCTGGGCAAAGATGCCAATCGGCGAACCC 600
M.tuberculosis_CDC1551      GGCGCACCGCACCAGCACCGCCCTGGGCAAAGATGCCAATCGGCGAACCC 600
M.bovis_AF2122/97           GGCGCACCGCACCAGCACCGCCCTGGGCAAAGATGCCAATCGGCGAACCC 600
M.africanum                 GGCGCACCGCACCAGCACCGCCCTGGGCAAAGATGCCAATCGGCGAACCC 600
M.canettii                  GGCGCACCGCACCCGCACCGCCCTGGGCAAAGATGCCTATCGGCGAACCC 549
                            ************* *********************** ************

M.tuberculosis_KZN2407      CCGCCCGCTCCGTCCAGACCGTCTGCGTCCCCGGCCGAACCACCGACCCG 650
M.tuberculosis_KZN1435      CCGCCCGCTCCGTCCAGACCGTCTGCGTCCCCGGCCGAACCACCGACCCG 650
M.tuberculosis_H37RV        CCGCCCGCTCCGTCCAGACCGTCTGCGTCCCCGGCCGAACCACCGACCCG 650
M.tuberculosis_H37Ra        CCGCCCGCTCCGTCCAGACCGTCTGCGTCCCCGGCCGAACCACCGACCCG 650
M.tuberculosis_F11          CCGCCCGCTCCGTCCAGACCGTCTGCGTCCCCGGCCGAACCACCGACCCG 650
M.tuberculosis_CDC1551      CCGCCCGCTCCGTCCAGACCGTCTGCGTCCCCGGCCGAACCACCGACCCG 650
M.bovis_AF2122/97           CCGCCCGCTCCGTCCAGACCGTCTGCGTCCCCGGCCGAACCACCGACCCG 650
M.africanum                 CCGCCCGCTCCGTCCAGACCGTCTGCGTCCCCGGCCGAACCACCGACCCG 650
M.canettii                  CCGCCCGCTCCGTCCAGACCGTTTGCGTCCCCGGCCGAACCACCGACCCG 599
                            ********************** ***************************

M.tuberculosis_KZN2407      GCCTGCCCCCCAACACTCCCGACGTGCGCGCCGGGGTCACCGCTATCGCA 700
M.tuberculosis_KZN1435      GCCTGCCCCCCAACACTCCCGACGTGCGCGCCGGGGTCACCGCTATCGCA 700
M.tuberculosis_H37RV        GCCTGCCCCCCAACACTCCCGACGTGCGCGCCGGGGTCACCGCTATCGCA 700
M.tuberculosis_H37Ra        GCCTGCCCCCCAACACTCCCGACGTGCGCGCCGGGGTCACCGCTATCGCA 700
M.tuberculosis_F11          GCCTGCCCCCCAACACTCCCGACGTGCGCGCCGGGGTCACCGCTATCGCA 700
M.tuberculosis_CDC1551      GCCTGCCCCCCAACACTCCCGACGTGCGCGCCGGGGTCACCGCTATCGCA 700
M.bovis_AF2122/97           GCCTGCCCCCCAACACTCCCGACGTGCGCGCCGGGGTCACCGCTATCGCA 700
M.africanum                 GCCTGCCCCCCAACACTCCCGACGTGCGCGCCGGGGTCACCGCTATCGCA 700
M.canettii                  GCCTGCCCCCCAACACTCCCGACGTGCGCGCCGGGGTCACCGCTATCGCA 649
                            **************************************************

M.tuberculosis_KZN2407      CAGACACCGAACGAAACGTCGGGAAGGTAGCAACTGGTCCATCCATCCAG 750
M.tuberculosis_KZN1435      CAGACACCGAACGAAACGTCGGGAAGGTAGCAACTGGTCCATCCATCCAG 750
M.tuberculosis_H37RV        CAGACACCGAACGAAACGTCGGGAAGGTAGCAACTGGTCCATCCATCCAG 750
M.tuberculosis_H37Ra        CAGACACCGAACGAAACGTCGGGAAGGTAGCAACTGGTCCATCCATCCAG 750
M.tuberculosis_F11          CAGACACCGAACGAAACGTCGGGAAGGTAGCAACTGGTCCATCCATCCAG 750
M.tuberculosis_CDC1551      CAGACACCGAACGAAACGTCGGGAAGGTAGCAACTGGTCCATCCATCCAG 750
M.bovis_AF2122/97           CAGACACCGAACGAAACGTCGGGAAGGTAGCAACTGGTCCATCCATCCAG 750
M.africanum                 CAGACACCGAACGAAACGTCGGGAAGGTAGCAACTGGTCCATCCATCCAG 750
M.canettii                  CAGACACCGAACGAAACGTCGGGAAGGTAGCAACTGGTCCATCCATCCAA 699
                            ************************************************* 

M.tuberculosis_KZN2407      GCGCGGCTGCGGGCAGAGGAAGCATCCGGCGCGCAGCTCGCCCCCGGAAC 800
M.tuberculosis_KZN1435      GCGCGGCTGCGGGCAGAGGAAGCATCCGGCGCGCAGCTCGCCCCCGGAAC 800
M.tuberculosis_H37RV        GCGCGGCTGCGGGCAGAGGAAGCATCCGGCGCGCAGCTCGCCCCCGGAAC 800
M.tuberculosis_H37Ra        GCGCGGCTGCGGGCAGAGGAAGCATCCGGCGCGCAGCTCGCCCCCGGAAC 800
M.tuberculosis_F11          GCGCGGCTGCGGGCAGAGGAAGCATCCGGCGCGCAGCTCGCCCCCGGAAC 800
M.tuberculosis_CDC1551      GCGCGGCTGCGGGCAGAGGAAGCATCCGGCGCGCAGCTCGCCCCCGGAAC 800
M.bovis_AF2122/97           GCGCGGCTGCGGGCAGAGGAAGCATCCGGCGCGCAGCTCGCCCCCGGAAC 800
M.africanum                 GCGCGGCTGCGGGCAGAGGAAGCATCCGGCGCGCAGCTCGCCCCCGGAAC 800
```

Figure 6A (cont)

```
M.canettii                     GCGCGGCTGCGGGCAGAGGAAGCATCCGGCGCGCAGCTCGCCCCCGGAAC 749
                               **************************************************

M.tuberculosis_KZN2407         GGAGCCCTCGCCAGCGCCGTTGGGCCAACCGAGATCGTATCTGGCTCCGC 850
M.tuberculosis_KZN1435         GGAGCCCTCGCCAGCGCCGTTGGGCCAACCGAGATCGTATCTGGCTCCGC 850
M.tuberculosis_H37RV           GGAGCCCTCGCCAGCGCCGTTGGGCCAACCGAGATCGTATCTGGCTCCGC 850
M.tuberculosis_H37Ra           GGAGCCCTCGCCAGCGCCGTTGGGCCAACCGAGATCGTATCTGGCTCCGC 850
M.tuberculosis_F11             GGAGCCCTCGCCAGCGCCGTTGGGCCAACCGAGATCGTATCTGGCTCCGC 850
M.tuberculosis_CDC1551         GGAGCCCTCGCCAGCGCCGTTGGGCCAACCGAGATCGTATCTGGCTCCGC 850
M.bovis_AF2122/97              GGAGCCCTCGCCAGCGCCGTTGGGCCAACCGAGATCGTATCTGGCTCCGC 850
M.africanum                    GGAGCCCTCGCCAGCGCCGTTGGGCCAACCGAGATCGTATCTGGCTCCGC 850
M.canettii                     GGAGCCCTCGCCGGCGCCGTTGGGCCAACCGAGATCGTATCTGGCTCCGC 799
                               ************ *************************************

M.tuberculosis_KZN2407         CCACCCGCCCCGCGCCGACAGAACCTCCCCCAGCCCCTCGCCGCAGCGC 900
M.tuberculosis_KZN1435         CCACCCGCCCCGCGCCGACAGAACCTCCCCCAGCCCCTCGCCGCAGCGC 900
M.tuberculosis_H37RV           CCACCCGCCCCGCGCCGACAGAACCTCCCCCAGCCCCTCGCCGCAGCGC 900
M.tuberculosis_H37Ra           CCACCCGCCCCGCGCCGACAGAACCTCCCCCAGCCCCTCGCCGCAGCGC 900
M.tuberculosis_F11             CCACCCGCCCCGCGCCGACAGAACCTCCCCCAGCCCCTCGCCGCAGCGC 900
M.tuberculosis_CDC1551         CCACCCGCCCCGCGCCGACAGAACCTCCCCCAGCCCCTCGCCGCAGCGC 900
M.bovis_AF2122/97              CCACCCGCCCCGCGCCGACAGAACCTCCCCCAGCCCCTCGCCGCAGCGC 900
M.africanum                    CCACCCGCCCCGCGCCGACAGAACCTCCCCCAGCCCCTCGCCGCAGCGC 900
M.canettii                     CCACCCGTCCCGCCTCGACAGAACCTCCCCCAGCCCCGCGCCGCAGCGC 849
                               ******* *****  ********************** ***********

M.tuberculosis_KZN2407         AACTCCGGTCGGCGTGCCGAGCGACGCGTCCACCCCGATTTAGCCGCCCA 950
M.tuberculosis_KZN1435         AACTCCGGTCGGCGTGCCGAGCGACGCGTCCACCCCGATTTAGCCGCCCA 950
M.tuberculosis_H37RV           AACTCCGGTCGGCGTGCCGAGCGACGCGTCCACCCCGATTTAGCCGCCCA 950
M.tuberculosis_H37Ra           AACTCCGGTCGGCGTGCCGAGCGACGCGTCCACCCCGATTTAGCCGCCCA 950
M.tuberculosis_F11             AACTCCGGTCGGCGTGCCGAGCGACGCGTCCACCCCGATTTAGCCGCCCA 950
M.tuberculosis_CDC1551         AACTCCGGTCGGCGTGCCGAGCGACGCGTCCACCCCGATTTAGCCGCCCA 950
M.bovis_AF2122/97              AACTCCGGTCGGCGTGCCGAGCGACGCGTCCACCCCGATTTAGCCGCCCA 950
M.africanum                    AACTCCGGTCGGCGTGCCGAGCGACGCGTCCACCCCGATTTAGCCGCCCA 950
M.canettii                     GACTCCGGTCGGCGTGCCGAGCGACGCGTCCACCCCGACTTAGCCGCTCA 899
                                ************************************* ******** **

M.tuberculosis_KZN2407         ACATGCCGCGGCGCAACCTGATTCAATTACGGCCGCAACCACTGGCGGTC 1000
M.tuberculosis_KZN1435         ACATGCCGCGGCGCAACCTGATTCAATTACGGCCGCAACCACTGGCGGTC 1000
M.tuberculosis_H37RV           ACATGCCGCGGCGCAACCTGATTCAATTACGGCCGCAACCACTGGCGGTC 1000
M.tuberculosis_H37Ra           ACATGCCGCGGCGCAACCTGATTCAATTACGGCCGCAACCACTGGCGGTC 1000
M.tuberculosis_F11             ACATGCCGCGGCGCAACCTGATTCAATTACGGCCGCAACCACTGGCGGTC 1000
M.tuberculosis_CDC1551         ACATGCCGCGGCGCAACCTGATTCAATTACGGCCGCAACCACTGGCGGTC 1000
M.bovis_AF2122/97              ACATGCCGCGGCGCAACCTGATTCAATTACGGCCGCAACCACTGGCGGTC 1000
M.africanum                    ACATGCCGCGGCGCAACCTGATTCAATTACGGCCGCAACCACTGGCGGTC 1000
M.canettii                     ACATGCTGCGGCTCAACCTGATTCGATTACGGCCGCAACCACTGGCGGTC 949
                               ****** ***** *********** *************************

M.tuberculosis_KZN2407         GTCGCCGCAAGCGTGCAGCGCCGGATCTCGACGCGACACAGAAATCCTTA 1050
M.tuberculosis_KZN1435         GTCGCCGCAAGCGTGCAGCGCCGGATCTCGACGCGACACAGAAATCCTTA 1050
M.tuberculosis_H37RV           GTCGCCGCAAGCGTGCAGCGCCGGATCTCGACGCGACACAGAAATCCTTA 1050
M.tuberculosis_H37Ra           GTCGCCGCAAGCGTGCAGCGCCGGATCTCGACGCGACACAGAAATCCTTA 1050
M.tuberculosis_F11             GTCGCCGCAAGCGTGCAGCGCCGGATCTCGACGCGACACAGAAATCCTTA 1050
M.tuberculosis_CDC1551         GTCGCCGCAAGCGTGCAGCGCCGGATCTCGACGCGACACAGAAATCCTTA 1050
M.bovis_AF2122/97              GTCGCCGCAAGCGTGCAGCGCCGGATCTCGACGCGACACAGAAATCCTTA 1050
M.africanum                    GTCGCCGCAAGCGTGCAGCGCCGGATCTCGACGCGACACAGAAATCCTTA 1050
M.canettii                     GTCGCCGCAAGCGCGCAGCGCCCGATCTCGACGCGACACAGAAATCCTTA 999
                               ************* ******** ***************************

M.tuberculosis_KZN2407         AGGCCGGCGGCCAAGGGGCCGAAGGTGAAGAAGGTGAAGCCCCAGAAACC 1100
M.tuberculosis_KZN1435         AGGCCGGCGGCCAAGGGGCCGAAGGTGAAGAAGGTGAAGCCCCAGAAACC 1100
M.tuberculosis_H37RV           AGGCCGGCGGCCAAGGGGCCGAAGGTGAAGAAGGTGAAGCCCCAGAAACC 1100
M.tuberculosis_H37Ra           AGGCCGGCGGCCAAGGGGCCGAAGGTGAAGAAGGTGAAGCCCCAGAAACC 1100
M.tuberculosis_F11             AGGCCGGCGGCCAAGGGGCCGAAGGTGAAGAAGGTGAAGCCCCAGAAACC 1100
M.tuberculosis_CDC1551         AGGCCGGCGGCCAAGGGGCCGAAGGTGAAGAAGGTGAAGCCCCAGAAACC 1100
M.bovis_AF2122/97              AGGCCGGCGGCCAAGGGGCCGAAGGTGAAGAAGGTGAAGCCCCAGAAACC 1100
M.africanum                    AGGCCGGCGGCCAAGGGGCCGAAGGTGAAGAAGGTGAAGCCCCAGAAACC 1100
M.canettii                     AGGCCGGCGGCCAAGGGGCCGAAGGTTAAGAAGGTGAAGCCCCAGAAACC 1049
                               ************************** ***********************

M.tuberculosis_KZN2407         GAAGGCCACGAAGCCGCCCAAAGTGGTGTCGCAGCGCGGCTGGCGACATT 1150
M.tuberculosis_KZN1435         GAAGGCCACGAAGCCGCCCAAAGTGGTGTCGCAGCGCGGCTGGCGACATT 1150
M.tuberculosis_H37RV           GAAGGCCACGAAGCCGCCCAAAGTGGTGTCGCAGCGCGGCTGGCGACATT 1150
M.tuberculosis_H37Ra           GAAGGCCACGAAGCCGCCCAAAGTGGTGTCGCAGCGCGGCTGGCGACATT 1150
M.tuberculosis_F11             GAAGGCCACGAAGCCGCCCAAAGTGGTGTCGCAGCGCGGCTGGCGACATT 1150
M.tuberculosis_CDC1551         GAAGGCCACGAAGCCGCCCAAAGTGGTGTCGCAGCGCGGCTGGCGACATT 1150
M.bovis_AF2122/97              GAAGGCCACGAAGCCGCCCAAAGTGGTGTCGCAGCGCGGCTGGCGACATT 1150
M.africanum                    GAAGGCCACGAAGCCGCCCAAAGTGGTGTCGCAGCGCGGCTGGCGACATT 1150
M.canettii                     GAAGGCCACGAAGCCGCCCAAAGTGGTGTCGCAGCGCGGCTGGCGACATT 1099
                               **************************************************

M.tuberculosis_KZN2407         GGGTGCATGCGTTGACGCGAATCAACCTGGGCCTGTCACCCGACGAGAAG 1200
M.tuberculosis_KZN1435         GGGTGCATGCGTTGACGCGAATCAACCTGGGCCTGTCACCCGACGAGAAG 1200
M.tuberculosis_H37RV           GGGTGCATGCGTTGACGCGAATCAACCTGGGCCTGTCACCCGACGAGAAG 1200
M.tuberculosis_H37Ra           GGGTGCATGCGTTGACGCGAATCAACCTGGGCCTGTCACCCGACGAGAAG 1200
M.tuberculosis_F11             GGGTGCATGCGTTGACGCGAATCAACCTGGGCCTGTCACCCGACGAGAAG 1200
M.tuberculosis_CDC1551         GGGTGCATGCGTTGACGCGAATCAACCTGGGCCTGTCACCCGACGAGAAG 1200
M.bovis_AF2122/97              GGGTGCATGCGTTGACGCGAATCAACCTGGGCCTGTCACCCGACGAGAAG 1200
M.africanum                    GGGTGCATGCGTTGACGCGAATCAACCTGGGCCTGTCACCCGACGAGAAG 1200
```

Figure 6A (cont)

```
M.canettii                     GGGTGCATGCGTTGACGCGAATCAACCTGGGCCTGTCACCCGACGAGAAG 1149
                               **************************************************

M.tuberculosis_KZN2407         TACGAGCTGGACCTGCACGCTCGAGTCCGCCGCAATCCCCGCGGGTCGTA 1250
M.tuberculosis_KZN1435         TACGAGCTGGACCTGCACGCTCGAGTCCGCCGCAATCCCCGCGGGTCGTA 1250
M.tuberculosis_H37RV           TACGAGCTGGACCTGCACGCTCGAGTCCGCCGCAATCCCCGCGGGTCGTA 1250
M.tuberculosis_H37Ra           TACGAGCTGGACCTGCACGCTCGAGTCCGCCGCAATCCCCGCGGGTCGTA 1250
M.tuberculosis_F11             TACGAGCTGGACCTGCACGCTCGAGTCCGCCGCAATCCCCGCGGGTCGTA 1250
M.tuberculosis_CDC1551         TACGAGCTGGACCTGCACGCTCGAGTCCGCCGCAATCCCCGCGGGTCGTA 1250
M.bovis_AF2122/97              TACGAGCTGGACCTGCACGCTCGAGTCCGCCGCAATCCCCGCGGGTCGTA 1250
M.africanum                    TACGAGCTGGACCTGCACGCTCGAGTCCGCCGCAATCCCCGCGGGTCGTA 1250
M.canettii                     TACGAGCTGGACCTGCACGCTCGAGTCCGCCGCAATCCCCGCGGGTCGTA 1199
                               **************************************************

M.tuberculosis_KZN2407         TCAGATCGCCGTCGTCGGTCTCAAAGGTGGGGCTGGCAAAACCACGCTGA 1300
M.tuberculosis_KZN1435         TCAGATCGCCGTCGTCGGTCTCAAAGGTGGGGCTGGCAAAACCACGCTGA 1300
M.tuberculosis_H37RV           TCAGATCGCCGTCGTCGGTCTCAAAGGTGGGGCTGGCAAAACCACGCTGA 1300
M.tuberculosis_H37Ra           TCAGATCGCCGTCGTCGGTCTCAAAGGTGGGGCTGGCAAAACCACGCTGA 1300
M.tuberculosis_F11             TCAGATCGCCGTCGTCGGTCTCAAAGGTGGGGCTGGCAAAACCACGCTGA 1300
M.tuberculosis_CDC1551         TCAGATCGCCGTCGTCGGTCTCAAAGGTGGGGCTGGCAAAACCACGCTGA 1300
M.bovis_AF2122/97              TCAGATCGCCGTCGTCGGTCTCAAAGGTGGGGCTGGCAAAACCACGCTGA 1300
M.africanum                    TCAGATCGCCGTCGTCGGTCTCAAAGGTGGGGCTGGCAAAACCACGCTGA 1300
M.canettii                     TCAGATCGCCGTCGTCGGTCTCAAAGGTGGGGCTGGCAAAACCACGCTGA 1249
                               **************************************************

M.tuberculosis_KZN2407         CAGCAGCGTTGGGGTCGACGTTGGCTCAGGTGCGGGCCGACCGGATCCTG 1350
M.tuberculosis_KZN1435         CAGCAGCGTTGGGGTCGACGTTGGCTCAGGTGCGGGCCGACCGGATCCTG 1350
M.tuberculosis_H37RV           CAGCAGCGTTGGGGTCGACGTTGGCTCAGGTGCGGGCCGACCGGATCCTG 1350
M.tuberculosis_H37Ra           CAGCAGCGTTGGGGTCGACGTTGGCTCAGGTGCGGGCCGACCGGATCCTG 1350
M.tuberculosis_F11             CAGCAGCGTTGGGGTCGACGTTGGCTCAGGTGCGGGCCGACCGGATCCTG 1350
M.tuberculosis_CDC1551         CAGCAGCGTTGGGGTCGACGTTGGCTCAGGTGCGGGCCGACCGGATCCTG 1350
M.bovis_AF2122/97              CAGCAGCGTTGGGGTCGACGTTGGCTCAGGTGCGGGCCGACCGGATCCTG 1350
M.africanum                    CAGCAGCGTTGGGGTCGACGTTGGCTCAGGTGCGGGCCGACCGGATCCTG 1350
M.canettii                     CAGCAGCGTTGGGGTCGACGTTGGCTCAGGTGCGGGCCGACCGGATCCTG 1299
                               **************************************************

M.tuberculosis_KZN2407         GCTCTAGACGCGGATCCAGGCGCCGGAAACCTCGCCGATCGGGTAGGGCG 1400
M.tuberculosis_KZN1435         GCTCTAGACGCGGATCCAGGCGCCGGAAACCTCGCCGATCGGGTAGGGCG 1400
M.tuberculosis_H37RV           GCTCTAGACGCGGATCCAGGCGCCGGAAACCTCGCCGATCGGGTAGGGCG 1400
M.tuberculosis_H37Ra           GCTCTAGACGCGGATCCAGGCGCCGGAAACCTCGCCGATCGGGTAGGGCG 1400
M.tuberculosis_F11             GCTCTAGACGCGGATCCAGGCGCCGGAAACCTCGCCGATCGGGTAGGGCG 1400
M.tuberculosis_CDC1551         GCTCTAGACGCGGATCCAGGCGCCGGAAACCTCGCCGATCGGGTAGGGCG 1400
M.bovis_AF2122/97              GCTCTAGACGCGGATCCAGGCGCCGGAAACCTCGCCGATCGGGTAGGGCG 1400
M.africanum                    GCTCTAGACGCGGATCCAGGCGCCGGAAACCTCGCCGATCGGGTAGGGCG 1400
M.canettii                     GCTCTAGACGCGGATCCAGGCGCCGGAAACCTCGCCGATCGGGTAGGGCG 1349
                               **************************************************

M.tuberculosis_KZN2407         ACAATCGGGCGCGACCATCGCTGATGTGCTTGCAGAAAAAGAGCTGTCGC 1450
M.tuberculosis_KZN1435         ACAATCGGGCGCGACCATCGCTGATGTGCTTGCAGAAAAAGAGCTGTCGC 1450
M.tuberculosis_H37RV           ACAATCGGGCGCGACCATCGCTGATGTGCTTGCAGAAAAAGAGCTGTCGC 1450
M.tuberculosis_H37Ra           ACAATCGGGCGCGACCATCGCTGATGTGCTTGCAGAAAAAGAGCTGTCGC 1450
M.tuberculosis_F11             ACAATCGGGCGCGACCATCGCTGATGTGCTTGCAGAAAAAGAGCTGTCGC 1450
M.tuberculosis_CDC1551         ACAATCGGGCGCGACCATCGCTGATGTGCTTGCAGAAAAAGAGCTGTCGC 1450
M.bovis_AF2122/97              ACAATCGGGCGCGACCATCGCTGATGTGCTTGCAGAAAAAGAGCTGTCGC 1450
M.africanum                    ACAATCGGGCGCGACCATCGCTGATGTGCTTGCAGAAAAAGAGCTGTCGC 1450
M.canettii                     ACAATCGGGCGCGACCATCGCTGATGTGCTTGCAGAAAAAGAGCTGTCGC 1399
                               **************************************************

M.tuberculosis_KZN2407         ACTACAACGACATCCGCGCAC[redacted]ATCTGGAA 1500
M.tuberculosis_KZN1435         ACTACAACGACATCCGCGCACACACTAGCGTCAATGCGGTCAATCTGGAA 1500
M.tuberculosis_H37RV           ACTACAACGACATCCGCGCACACACTAGCGTCAATGCGGTCAATCTGGAA 1500
M.tuberculosis_H37Ra           ACTACAACGACATCCGCGCACACACTAGCGTCAATGCGGTCAATCTGGAA 1500
M.tuberculosis_F11             ACTACAACGACATCCGCGCACACACTAGCGTCAATGCGGTCAATCTGGAA 1500
M.tuberculosis_CDC1551         ACTACAACGACATCCGCGCACACACTAGCGTCAATGCGGTCAATCTGGAA 1500
M.bovis_AF2122/97              ACTACAACGACATCCGCGCACACACTAGCGTCAATGCGGTCAATCTGGAA 1500
M.africanum                    ACTACAACGACATCCGCGCACACACTAGCGTCAATGCGGTCAATCTGGAA 1500
M.canettii                     ACTACAACGACATCCGCGCACACACCAGTGTCAATGCGGTCAATCTGGAA 1449
                               ************************* ** *********************

M.tuberculosis_KZN2407         GTGCTGCCGGCACCGGAATACAGCTCGGCGCAGCGCGCGCTCAGCGACGC 1550
M.tuberculosis_KZN1435         GTGCTGCCGGCACCGGAATACAGCTCGGCGCAGCGCGCGCTCAGCGACGC 1550
M.tuberculosis_H37RV           GTGCTGCCGGCACCGGAATACAGCTCGGCGCAGCGCGCGCTCAGCGACGC 1550
M.tuberculosis_H37Ra           GTGCTGCCGGCACCGGAATACAGCTCGGCGCAGCGCGCGCTCAGCGACGC 1550
M.tuberculosis_F11             GTGCTGCCGGCACCGGAATACAGCTCGGCGCAGCGCGCGCTCAGCGACGC 1550
M.tuberculosis_CDC1551         GTGCTGCCGGCACCGGAATACAGCTCGGCGCAGCGCGCGCTCAGCGACGC 1550
M.bovis_AF2122/97              GTGCTGCCGGCACCGGAATACAGCTCGGCGCAGCGCGCGCTCAGCGACGC 1550
M.africanum                    GTGCTGCCGGCACCGGAATACAGCTCGGCGCAGCGCGCGCTCAGCGACGC 1550
M.canettii                     GTGCTGCCGGCACCGGAATACAGCTCGGCGCAGCGCGCGCTCAGCGACGC 1499
                               **************************************************

M.tuberculosis_KZN2407         CGACTGGCATTTCATCGCCGATCCTGCGTCGAGGTTTTACAACCTCGTCT 1600
M.tuberculosis_KZN1435         CGACTGGCATTTCATCGCCGATCCTGCGTCGAGGTTTTACAACCTCGTCT 1600
M.tuberculosis_H37RV           CGACTGGCATTTCATCGCCGATCCTGCGTCGAGGTTTTACAACCTCGTCT 1600
M.tuberculosis_H37Ra           CGACTGGCATTTCATCGCCGATCCTGCGTCGAGGTTTTACAACCTCGTCT 1600
M.tuberculosis_F11             CGACTGGCATTTCATCGCCGATCCTGCGTCGAGGTTTTACAACCTCGTCT 1600
M.tuberculosis_CDC1551         CGACTGGCATTTCATCGCCGATCCTGCGTCGAGGTTTTACAACCTCGTCT 1600
M.bovis_AF2122/97              CGACTGGCATTTCATCGCCGATCCTGCGTCGAGGTTTTACAACCTCGTCT 1600
M.africanum                    CGACTGGCATTTCATCGCCGATCCTGCGTCGAGGTTTTACAACCTCGTCT 1600
```

Figure 6A (cont)

```
M.canettii                    CGACTGGCATTTCATCGCCGATCCGGCGTCGAGGTTTTACAACCTCGTCT 1549
                              ********************** ***************************

M.tuberculosis_KZN2407        TGGCTGATTGTGGGGCCGGCTTCTTCGACCCGCTGACCCGCGGCGTGCTG 1650
M.tuberculosis_KZN1435        TGGCTGATTGTGGGGCCGGCTTCTTCGACCCGCTGACCCGCGGCGTGCTG 1650
M.tuberculosis_H37RV          TGGCTGATTGTGGGGCCGGCTTCTTCGACCCGCTGACCCGCGGCGTGCTG 1650
M.tuberculosis_H37Ra          TGGCTGATTGTGGGGCCGGCTTCTTCGACCCGCTGACCCGCGGCGTGCTG 1650
M.tuberculosis_F11            TGGCTGATTGTGGGGCCGGCTTCTTCGACCCGCTGACCCGCGGCGTGCTG 1650
M.tuberculosis_CDC1551        TGGCTGATTGTGGGGCCGGCTTCTTCGACCCGCTGACCCGCGGCGTGCTG 1650
M.bovis_AF2122/97             TGGCTGATTGTGGGGCCGGCTTCTTCGACCCGCTGACCCGCGGCGTGCTG 1650
M.africanum                   TGGCTGATTGTGGGGCCGGCTTCTTCGACCCGCTGACCCGCGGCGTGCTG 1650
M.canettii                    TGGCTGATTGTGGGGCCGGCTTCTTCGACCCGCTGACCCGCGGCGTGCTG 1599
                              **************************************************

M.tuberculosis_KZN2407        TCCACGGTGTCTGGTGTCGTGGTCGTGGCAAGTGTCTCAATCGACGGCGC 1700
M.tuberculosis_KZN1435        TCCACGGTGTCTGGTGTCGTGGTCGTGGCAAGTGTCTCAATCGACGGCGC 1700
M.tuberculosis_H37RV          TCCACGGTGTCCGGTGTCGTGGTCGTGGCAAGTGTCTCAATCGACGGCGC 1700
M.tuberculosis_H37Ra          TCCACGGTGTCCGGTGTCGTGGTCGTGGCAAGTGTCTCAATCGACGGCGC 1700
M.tuberculosis_F11            TCCACGGTGTCCGGTGTCGTGGTCGTGGCAAGTGTCTCAATCGACGGCGC 1700
M.tuberculosis_CDC1551        TCCACGGTGTCCGGTGTCGTGGTCGTGGCAAGTGTCTCAATCGACGGCGC 1700
M.bovis_AF2122/97             TCCACGGTGTCCGGTGTCGTGGTCGTGGCAAGTGTCTCAATCGACGGCGC 1700
M.africanum                   TCCACGGTGTCCGGTGTCGTGGTCGTGGCAAGTGTCTCAATCGACGGCGC 1700
M.canettii                    TCCACGGTGTCCGGTGTCGTGGTCGTGGCAAGTGTCTCAATCGACGGCGC 1649
                              *********** **************************************

M.tuberculosis_KZN2407        ACAACAGGCGTCGGTCGCGTTGGACTGGTTGCGCAACAACGGTTACCAAG 1750
M.tuberculosis_KZN1435        ACAACAGGCGTCGGTCGCGTTGGACTGGTTGCGCAACAACGGTTACCAAG 1750
M.tuberculosis_H37RV          ACAACAGGCGTCGGTCGCGTTGGACTGGTTGCGCAACAACGGTTACCAAG 1750
M.tuberculosis_H37Ra          ACAACAGGCGTCGGTCGCGTTGGACTGGTTGCGCAACAACGGTTACCAAG 1750
M.tuberculosis_F11            ACAACAGGCGTCGGTCGCGTTGGACTGGTTGCGCAACAACGGTTACCAAG 1750
M.tuberculosis_CDC1551        ACAACAGGCGTCGGTCGCGTTGGACTGGTTGCGCAACAACGGTTACCAAG 1750
M.bovis_AF2122/97             ACAACAGGCGTCGGTCGCGTTGGACTGGTTGCGCAACAACGGTTACCAAG 1750
M.africanum                   ACAACAGGCGTCGGTCGCGTTGGACTGGTTGCGCAACAACGGTTACCAAG 1750
M.canettii                    ACAGCAAGCCTCGGTCGCGTTGGACTGGTTGCGCAACAACGGTTACCAAG 1699
                              *** ** ** ****************************************

M.tuberculosis_KZN2407        ATTTGGCGAGCCGCGCATGCGTGGTCATCAATCACATCATGCCGGGAGAA 1800
M.tuberculosis_KZN1435        ATTTGGCGAGCCGCGCATGCGTGGTCATCAATCACATCATGCCGGGAGAA 1800
M.tuberculosis_H37RV          ATTTGGCGAGCCGCGCATGCGTGGTCATCAATCACATCATGCCGGGAGAA 1800
M.tuberculosis_H37Ra          ATTTGGCGAGCCGCGCATGCGTGGTCATCAATCACATCATGCCGGGAGAA 1800
M.tuberculosis_F11            ATTTGGCGAGCCGCGCATGCGTGGTCATCAATCACATCATGCCGGGAGAA 1800
M.tuberculosis_CDC1551        ATTTGGCGAGCCGCGCATGCGTGGTCATCAATCACATCATGCCGGGAGAA 1800
M.bovis_AF2122/97             ATTTGGCGAGCCGCGCATGCGTGGTCATCAATCACATCATGCCGGGAGAA 1800
M.africanum                   ATTTGGCGAGCCGCGCATGCGTGGTCATCAATCACATCATGCCGGGAGAA 1800
M.canettii                    ATTTGGCGAGCCGCGCATGCGTGGTCATCAATCACATCATGCCGGGAGAA 1749
                              **************************************************

M.tuberculosis_KZN2407        CCCAATGTCGCAGTTAAAGACCTGGTGCGGCATTTCGAACAGCAAGTTCA 1850
M.tuberculosis_KZN1435        CCCAATGTCGCAGTTAAAGACCTGGTGCGGCATTTCGAACAGCAAGTTCA 1850
M.tuberculosis_H37RV          CCCAATGTCGCAGTTAAAGACCTGGTGCGGCATTTCGAACAGCAAGTTCA 1850
M.tuberculosis_H37Ra          CCCAATGTCGCAGTTAAAGACCTGGTGCGGCATTTCGAACAGCAAGTTCA 1850
M.tuberculosis_F11            CCCAATGTCGCAGTTAAAGACCTGGTGCGGCATTTCGAACAGCAAGTTCA 1850
M.tuberculosis_CDC1551        CCCAATGTCGCAGTTAAAGACCTGGTGCGGCATTTCGAACAGCAAGTTCA 1850
M.bovis_AF2122/97             CCCAATGTCGCAGTTAAAGACCTGGTGCGGCATTTCGAACAGCAAGTTCA 1850
M.africanum                   CCCAATGTCGCAGTTAAAGACCTGGTGCGGCATTTCGAACAGCAAGTTCA 1850
M.canettii                    CCCAATGTCGCAGTTAAAGACCTGGTGCGGCATTTCGAACAGCAAGTTCA 1799
                              **************************************************

M.tuberculosis_KZN2407        ACCCGGCCGGGTCGTGGTCATGCCGTGGGACAGGCACATTGCGGCCGGAA 1900
M.tuberculosis_KZN1435        ACCCGGCCGGGTCGTGGTCATGCCGTGGGACAGGCACATTGCGGCCGGAA 1900
M.tuberculosis_H37RV          ACCCGGCCGGGTCGTGGTCATGCCGTGGGACAGGCACATTGCGGCCGGAA 1900
M.tuberculosis_H37Ra          ACCCGGCCGGGTCGTGGTCATGCCGTGGGACAGGCACATTGCGGCCGGAA 1900
M.tuberculosis_F11            ACCCGGCCGGGTCGTGGTCATGCCGTGGGACAGGCACATTGCGGCCGGAA 1900
M.tuberculosis_CDC1551        ACCCGGCCGGGTCGTGGTCATGCCGTGGGACAGGCACATTGCGGCCGGAA 1900
M.bovis_AF2122/97             ACCCGGCCGGGTCGTGGTCATGCCGTGGGACAGGCACATTGCGGCCGGAA 1900
M.africanum                   ACCCGGCCGGGTCGTGGTCATGCCGTGGGACAGGCACATTGCGGCCGGAA 1900
M.canettii                    ACCCGGCCGGGTCGTGGTCATGCCGTGGGACAGGCACATTGCGGCCGGAA 1849
                              **************************************************

M.tuberculosis_KZN2407        CCGAGATTTCACTCGACTTGCTCGACCCTATCTACAAGCGCAAGGTCCTC 1950
M.tuberculosis_KZN1435        CCGAGATTTCACTCGACTTGCTCGACCCTATCTACAAGCGCAAGGTCCTC 1950
M.tuberculosis_H37RV          CCGAGATTTCACTCGACTTGCTCGACCCTATCTACAAGCGCAAGGTCCTC 1950
M.tuberculosis_H37Ra          CCGAGATTTCACTCGACTTGCTCGACCCTATCTACAAGCGCAAGGTCCTC 1950
M.tuberculosis_F11            CCGAGATTTCACTCGACTTGCTCGACCCTATCTACAAGCGCAAGGTCCTC 1950
M.tuberculosis_CDC1551        CCGAGATTTCACTCGACTTGCTCGACCCTATCTACAAGCGCAAGGTCCTC 1950
M.bovis_AF2122/97             CCGAGATTTCACTCGACTTGCTCGACCCTATCTACAAGCGCAAGGTCCTC 1950
M.africanum                   CCGAGATTTCACTCGACTTGCTCGACCCTATCTACAAGCGCAAGGTCCTC 1950
M.canettii                    CCGAGATTTCACTCGACTTGCTCGACCCTATCTACAAGCGCAAGGTCCTC 1899
                              **************************************************

M.tuberculosis_KZN2407        GAATTGGCCGCAGCGCTATCCGACGATTTCGAGAGGGCTGGACGTCGTTG 2000
M.tuberculosis_KZN1435        GAATTGGCCGCAGCGCTATCCGACGATTTCGAGAGGGCTGGACGTCGTTG 2000
M.tuberculosis_H37RV          GAATTGGCCGCAGCGCTATCCGACGATTTCGAGAGGGCTGGACGTCGTTG 2000
M.tuberculosis_H37Ra          GAATTGGCCGCAGCGCTATCCGACGATTTCGAGAGGGCTGGACGTCGTTG 2000
M.tuberculosis_F11            GAATTGGCCGCAGCGCTATCCGACGATTTCGAGAGGGCTGGACGTCGTTG 2000
M.tuberculosis_CDC1551        GAATTGGCCGCAGCGCTATCCGACGATTTCGAGAGGGCTGGACGTCGTTG 2000
M.bovis_AF2122/97             GAATTGGCCGCAGCGCTATCCGACGATTTCGAGAGGGCTGGACGTCGTTG 2000
M.africanum                   GAATTGGCCGCAGCGCTATCCGACGATTTCGAGAGGGCTGGACGTCGTTG 2000
```

Figure 6A (cont)

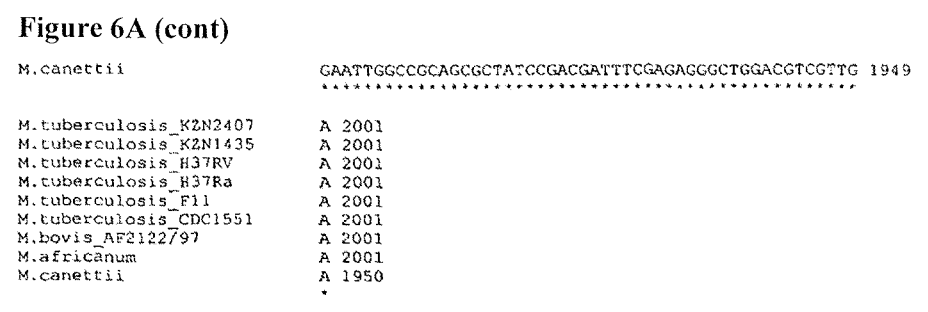

```
M.canettii                       GAATTGGCCGCAGCGCTATCCGACGATTTCGAGAGGGCTGGACGTCGTTG 1949
                                 **************************************************

M.tuberculosis_KZN2407           A 2001
M.tuberculosis_KZN1435           A 2001
M.tuberculosis_H37RV             A 2001
M.tuberculosis_H37Ra             A 2001
M.tuberculosis_F11               A 2001
M.tuberculosis_CDC1551           A 2001
M.bovis_AF2122797                A 2001
M.africanum                      A 2001
M.canettii                       A 1950
                                 *
```

Figure 6 (B)

```
M.africanumCl_1449_02     AGAAAAAGAGCTGTCGCACTACAACGACATCCGCGCACACACTAGCGTCA 50
M.caprae_                 AGAAAAAGAGCTGTCGCACTACAACGACATCCGCGCACACACTAGCGTCA 50
M.canettii_1997-1549      AGAAAAAGAGCTGTCGCACTACAACGACATCCGCGCACACACTAGCGTCA 50
M.pinnipedii_RIVM76       AGAAAAAGAGCTGTCGCACTACAACGACATCCGCGCACACACTAGCGTCA 50
                          **************************************************

M.africanumCl_1449_02     ATGCGGTCAATCTGGAAGTGCTGCCGGCACCGGAATACAGCTCGGCGC 98
M.caprae_                 ATGCGGTCAATCTGGAAGTGCTGCCGGCACCGGAATACAGCTCGGCGC 98
M.canettii_1997-1549      ATGCGGTCAATCTGGAAGTGCTGCCGGCACCGGAATACAGCTCGGCGC 98
M.pinnipedii_RIVM76       ATGCGGTCAATCTGGAAGTGCTGCCGGCACCGGAATACAGCTCGGCGC 98
                          ************************************************
```

DIAGNOSTIC METHOD

BACKGROUND TO THE INVENTION

Tuberculosis (TB) is the leading cause of death worldwide from an infectious agent (Flint et al., 2004), with the WHO estimating that one third of the global population are infected with TB. In a global report from the WHO (2009), it was estimated that there were 9.27 million cases of TB in 2007, with 2 million associated deaths. TB in mammals is caused by members of the *Mycobacterium tuberculosis* Complex (MTC). The eight closely related species in the complex have a wide range of natural hosts including humans hosts (*M. tuberculosis M. africanum M. canetti*), bovine hosts (*M. bovis*), caprine hosts (*M. caprae*), rodent hosts (*M. microti*) and pinniped hosts (*M. pinnipedii*) along with the attenuated *M. bovis* strain BCG (Bacillus Calmette-Guérin), the commonly used vaccine strain. While there are a number of natural hosts, each member of the MTC has been implicated in human infection (Brosch et al., 2002; Kiers et al., 2008a).

Traditionally, diagnosis of TB relies on culture techniques and a battery of biochemical tests which are time consuming, labour intensive and often yield insensitive results (Huard et al., 2003). Nucleic Acid Diagnostics (NAD), in particular real-time PCR, offer a rapid, reliable and highly sensitive alternative diagnostic tool for many infectious agents (Malhotra-Kumar et al., 2008; Yang & Rothman, 2004). Advances in real-time PCR such as the availability of multiple fluorophores, along with the development of non-fluorescent quenchers has facilitated multiplexing, allowing for the simultaneous detection and discrimination of multiple targets, along with internal controls, in one reaction (Arya et al., 2005).

While significant advances have been made in the diagnosis of TB using NAD (Huard et al., 2006), the differentiation of members of the MTC to the species level is not routinely performed. Conventional PCR and real-time PCR assays for the rapid diagnosis of the MTC have been described (Huard et al., 2003; Parsons et al., 2002). Also, commercially available real-time PCR kits for the diagnosis of TB are available, such as AMPLIFIED MTD (Gen-Probe, San Diego, Calif.), Xpert MTB/RIF (Cepheid, Sunnyvale, Calif.) and AMPLICOR MTB (Roche, Branchburg, N.J.). These kits identify the MTC, but not individual species.

The high degree of nucleotide sequence homology between members of the complex makes discrimination of species challenging, which may explain why it is not routinely carried out (Pinsky & Banaei, 2008). Comparative genomics revealed that *M. tuberculosis* and *M. bovis* genomes are 99.95% similar (Garnier et al., 2003), with whole genome DNA microarrays identifying 16 regions of difference (RD 1-16). (Behr et al., 1999). These RDs represent regions of the genome deleted in *M. bovis* BCG which are present in *M. tuberculosis* and have been used for the differentiation of members of the MTC. One RD commonly targeted for the specific detection of *M. tuberculosis* is RD9 (Pinsky & Banaei, 2008), however this RD is also present in *M. canettii* (Brosch et al., 2000). There is currently no real-time PCR test which can diagnose TB, whilst identifying the exact causative agent of infection.

Differentiation of the MTC allows health care professionals to determine the most appropriate course of treatment for infected patients and also provides valuable epidemiological information with relation to prevalence, transmission and geographical distribution of the neglected members of the MTC including members associated with zoonotic TB infection in humans. There is currently one molecular based kit commercially available for differentiation of the MTC, the GenoType MTBC (Hain Lifesciences GmbH, Nehren, Germany). However this kit is unable to differentiate between *M. tuberculosis* and *M. canettii* or between the two clades of *M. africanum*, and the target used in this kit for the detection of *M. africanum* also crossreacts with *M. pinnipedii.*

*M. tuberculosis* is the most important human pathogen in the MTC and is thought to be responsible for 95% of human cases of TB, yet rarely causes disease in other mammals (Brosch et al., 2000; Das et al., 2007). While drug resistant strains of *M. tuberculosis* are emerging, it is considered sensitive to anti-tuberculosis drugs such as Pyrazinamide (PZA), a first line antibiotic that reduces patient treatment time from 9 months to 6 months (Niemann et al., 2000; Somoskovi et al., 2006).

*M. canettii* is thought to be the most phylogenetically distant member of the MTC and is considered the species from which other members of the complex may have evolved (Brosch et al., 2002). *M. canettii* is phenotypically characterised by its smooth glossy white colonies, however a small number of these colonies have been shown to revert to rough colony variants when individual colonies are replated (van Soolingen et al., 1997). Smooth colonies are uncharacteristic of the MTC and are due to the presence of large amounts of lipooligosaccharides in the *M. canettii* cell wall (Pfyffer et al., 1998). Like *M. tuberculosis, M. canettii* contains all the RDs with the exception of RD12 *canettii* ($RD12^{can}$) which has been targeted for the specific detection of *M. canettii* in a complicated conventional PCR approach (Huard et al., 2003). The method provided by Huard et al. requires time-consuming multiple reactions and produces results that require detailed interpretation. To achieve the limited distinction that the methods of Huard et al. and other methods of the prior art offer, detailed analysis of gels must be undertaken. This requires that polyacrylamide gels, for example, are prepared and run and then analysed by eye.

While infection with *M. canettii* is thought to be rare, there is a lack of rapid diagnostic tests available to differentiate between *M. tuberculosis* and *M. canettii*. Also recent reports have suggested that the true cases of TB caused by *M. canettii* may in fact be underrepresented (Goh et al., 2001; Somoskovi et al., 2009). While differentiation between *M. tuberculosis* and *M. canettii* is useful from an epidemiological point of view, it is also important for indicating the therapeutic approach to treatment as *M. tuberculosis* is sensitive to PZA, whereas *M. canettii* is resistant (Somoskovi et al., 2009).

The major ethologic agents of zoonotic TB in humans are the phylogenetically related species *M. bovis* and *M. caprae*. These species occur worldwide and there are indications which suggest the true prevalence of zoonotic human TB infection may be underrepresented (Ojo et al., 2008; Cicero et al., 2009; Allix-Beguec et al. 2010). In developed countries it has been suggested that the burden of bovine TB in humans ranges from 0.5 to 7.2% of TB cases, while in developing countries, where very little data are available, this figure may be up to 15% (de la Rua-Domenech, 2006; Kubica et al., 2003). Recent reports have identified TB in humans caused by *M. bovis* in countries officially free from bovine TB and suggest that the true prevalence of zoonotic TB may be underestimated clinically (Cicero et al., 2009; Allix-Beguec et al., 2010). Moreover, zoonotic TB remains a significant threat to human health in developing countries where its prevalence is currently unknown, as speciation of the MTC is not routinely performed (de la Rua-Domenech, 2006). *M. bovis* and *M. bovis* BCG are intrinsically resistant to pyrazinamide (PZA), and this important first line drug for treating disease caused by *M. tuberculosis* and *M. caprae* infection should not be used for treating *M. bovis*, or *M. bovis* BCG infection. It is therefore important to distinguish between these members of the MTC in order to provide a useful treatment regimen.

This invention provides a multiplex in vitro nucleic acid amplification assay using novel nucleic acid targets which can diagnose TB from clinical isolates by detecting the MTC while simultaneously differentiating between the different species that are members of the MTC.

DESCRIPTION OF THE INVENTION

This invention provides a multiplex in vitro nucleic acid amplification method for identifying a species of the *Mycobacterium tuberculosis* complex (MTC) present in a sample, wherein the method comprises detecting the presence or absence of a plurality of nucleic acid molecule targets in the sample in one reaction, wherein at least one of the nucleic acid molecule targets is present in the genome of one or more, but not all, of the species of the *Mycobacterium tuberculosis* complex.

Previous methods for the detection of the MTC have not been capable of identifying the specific members of the MTC that are present in a manner that is practically useful. This means that diagnosis and treatment provision is not tailored to the specific species present unless extensive experimentation is carried out. This requires significant time and effort that is incompatible with rapid and effective diagnosis and treatment. This invention, for the first time, provides a method that is able to identify different members of the MTC in a rapid and easily-interpretable manner. The inventors have surprisingly found that there is sufficient variation between species yet sufficient conservation between isolates of the same species to identify specific species of the MTC in a single reaction multiplex nucleic acid amplification assay. By identifying and characterising a series of sequences that are either shared or not shared between the different members of the MTC, the present invention thus allows the use of multiplex nucleic acid amplification methods to detect specific individual members of the MTC.

The species that make up the MTC are closely related but differ significantly in their pathology and susceptibility to certain treatments. Therefore, although it is important to be able to distinguish between the different species, it has previously not been possible to do this in any straightforward way that is amenable to use in rapid diagnosis. The different members of the MTC share a significant proportion of their genetic material. The present invention has successfully identified sufficient differences between the genomes of the members of the MTC to be able to distinguish between them in multiplex in vitro nucleic acid amplification assays. In contrast to the methods of the prior art, the methods of the present invention allow a single multiplex reaction to be performed that gives clear signals to identify which species is present in the tested sample. It is not necessary to run gels or to undertake complex interpretation of the results.

In addition to providing the first methods for discriminating between the different members of the MTC in a rapid and effective manner and the first methods for specifically identifying *M. tuberculosis*, the present invention additionally provides the first methods for specifically identifying *M. canettii, M. africanum* clade 1 and *M. africanum* clade 2. These members may be identified in a second multiplex reaction. Further, the present invention provides the first method for specifically identifying *M. pinnipedii*. This member of the MTC may be identified by combining the results of a first and second multiplex reaction.

There is a clinical need to differentiate between *M. tuberculosis* and *M. canettii* and between *M. caprae* and *M. bovis* and *M. bovis* BCG as they require different therapeutic treatment regimes (Somoskovi et al., 2009).

Infection by *M. canettii* is considered to be rare and confined to Africa and it is not considered to be a significant concern for healthcare professionals. However, in the absence of methods for specifically identifying *M. canettii*, it is possible that the number of cases of *M. canettii* has been underestimated (Gob et al., 2001). Therefore, the present invention identifies that there is a need to be able to identify *M. canettii* specifically, and in particular to distinguish it from *M. tuberculosis*. The present invention also provides methods that are able to achieve such differentiation as well as to distinguish between other members of the MTC in order to provide a suitable treatment profile.

For monitoring of zoonotic TB in humans it is also important to accurately identify *M. pinnipedii* and *M. microti* as causes of infection. While these members of the MTC are rare, outbreaks of human TB caused by these members of the MTC have been observed (Kiers et al., 2008b; Panteix et al., 2010). Accurate identification of these members of the MTC is important for tracing source exposure (Djelouadji et al., 2008).

*M. africanum* has been shown to cause unto 50% of human TB cases in certain regions in Africa, yet is rarely observed elsewhere (de Jong et al., 2010). Since the reclassification of *M. africanum* into two distinct lineages *M. africanum* clade 1 and *M. africanum* clade 2, little is known as to the prevalence of TB caused by each lineage (Vasconcellos et al., 2010) as there is currently no commercially available diagnostic kit with the capability to differentiate between these clades. The capability to accurately differentiate between these clades of *M. africanum* will be important for epidemiological studies.

The present inventors have surprisingly found that it is possible to identify species of the MTC, despite the high sequence homology that exists between the members of the MTC. In particular, the present invention provides a multiplex in vitro nucleic acid amplification assay that is capable of identifying species of the MTC, such as *Mycobacterium tuberculosis* and *Mycobacterium canettii* in a single reaction. The inventors have also discovered that *Mycobacterium africanum* clade 1 can also be identified in the same single reaction. Furthermore, the inventors have devised a method for discriminating other members of the MTC, including *Mycobacterium bovis, Mycobacterium bovis* BCG, *Mycobacterium caprae* and *Mycobacterium africanum* clade 2. Preferably, these members are identified in a second multiplex reaction. In one embodiment the method of the invention may be performed in a stepwise manner, for example, with two separate multiplex steps, with *Mycobacterium tuberculosis, Mycobacterium canettii* and *Mycobacterium africanum* clade 1 distinguished in a first multiplex reaction (Multiplex 1) and *Mycobacterium bovis, Mycobacterium bovis* BCG, *Mycobacterium caprae*, and *Mycobacterium africanum* clade 2 distinguished in a second multiplex reaction (Multiplex 2). The inventors have also discovered that combining the results of Multiplex 1 with the results of Multiplex 2 allows the identification of *Mycobacterium pinnipedii* and *Mycobacterium microti.*

Prior to this invention, it was not expected that such assays could be developed or that any nucleic acid sequences necessary for such assays existed or could be identified.

Assay Components

As indicated above, the multiplex in vitro nucleic acid amplification assay used in the methods of the invention utilises genomic differences between members of the MTC to determine which member is present in a sample. Generally, this is achieved by incorporating one or more pairs of primers specific for target nucleic acid sequences which are uniquely present or absent in a particular member of the MTC into a sample and using a probe to determine which target nucleic acid sequences are present in the sample. The target nucleic acid sequences used in the methods of the present invention are described below.

Identification of the MTC

In certain embodiments, the method of the present invention comprises detecting the presence or absence of the MTC in a sample. This is preferably performed by detecting the presence or absence of MTC lepA in a sample. In certain embodiments, the method comprises the use of primers or probes specific for MTC lepA, SEQ ID NO: 47.

In one embodiment lepA may be amplified using primers comprising or consisting of SEQ ID NOs: 164 and 165.

The presence or absence of the MTC may be determined using a probe comprising or consisting of SEQ ID NO: 173. The probe is preferably labelled and the label may be a fluorescent label. In one embodiment the label may be HEX.

In certain preferred embodiments, the method comprises the use of more than one probe specific for MTC lepA. In such embodiments, the lepA probes are labelled with different fluorescent labels.

In certain embodiments, at least one of the probes specific for MTC lepA does not significantly bind to nucleic acid amplified from a member of the *Mycobacterium tuberculosis* complex.

This is the first description of a real-time PCR diagnostics assay using the MTC lepA gene as the diagnostics target. This gene has demonstrated promising potential as a candidate for nucleic acid diagnostics as it exhibits 5' and 3' flanking sequence conservation, but also internal sequence variability which enables the design of genus and species-specific NAD assays (O'Grady et al., 2008).

The MTC lepA region is defined by SED ID NO: 47. Any part of the MTC lepA region could be used to identify the MTC. Therefore, this invention contemplates the use of primers, probes and arrays directed to any part of the MTC lepA region. Preferably, the primers, probes or arrays are suitably designed according to methods known in the art so that they bind specifically to the MTC lepA region, and not to regions outside this sequence.

Internal Amplification Control (IAC)

In one embodiment the multiplex in vitro nucleic acid amplification method of the invention includes the use of an Internal Amplification Control (IAC).

The use of an IAC gives the assay greater reliability as false negative results are reduced. Without an IAC, if amplification fails in an individual reaction, no signals will be produced. There is a danger that this will be incorrectly interpreted as a negative result indicating the absence of a species of the MTC in a sample. However, by adding a control sample to each aliquot and detecting its amplification using an IAC probe, it can be checked that amplification is successful. If only the IAC signal is detected, no MTC species are present in a sample. However, if no signals at all are detected, amplification failed and the test must be repeated. The present invention has developed an IAC target that is also used for the simultaneous detection of the MTC, reducing the complexity of the multiplex PCR assay. One set of primers and two different probes are used to detect species of the MTC and to check that amplification is successful.

In one embodiment the IAC may be lepA, SEQ ID NO: 84. This gene has demonstrated promising potential as a candidate for nucleic acid diagnostics as it exhibits 5' and 3' flanking sequence conservation, but also internal sequence variability which enables the design of genus and species-specific NAD assays (O'Grady et al., 2008). This surprising feature of the lepA sequence has allowed an internal amplification control (IAC) to be incorporated into the multiplex assay, according to the guidelines set out in a review by Hoorfar et al. (2004). The lepA gene is present in all bacteria sequenced to date and codes for one of the most conserved proteins in bacteria. Surprisingly, however, there is enough sequence heterogeneity between the *M. smegmatis* (or any other species to be used as a control) and the MTC lepA sequences for the design of independent, specific probes to detect either members of the MTC or the internal amplification control, here *M. smegmatis*. The 5' and 3' homology allows the design of a single pair of primers for the amplification of both the IAC and the target, therefore reducing the complexity of the multiplex assay and aiding its effectiveness.

In certain embodiments, the IAC lepA may be amplified using primers which comprise or consist of SEQ NOs 164 and 165.

The presence or absence of the IAC lepA may be determined using a probe comprising or consisting of SEQ ID NO: 107. The probe is preferably labelled and may be a fluorescent label. In one embodiment the label may be Cy5.

The present invention additionally contemplates assays which do not use lepA or which do not use an IAC.

In another embodiment the IAC may be MSMEG_0660. In certain embodiments, the method comprises the use of primers or probes specific for MSMEG_600, SEQ ID NO: 135.

The MSMEG_0660 gene was chosen as the target for the IAC because this gene is present only in *M. smegmatis*. This gene is thought to code for an extracellular solute-binding protein.

In one embodiment the IAC MSMEG_0660 may be amplified using primers comprising or consisting of SEQ ID NOs: 155 and 156.

The presence or absence of the IAC MSMEG_0660 may be determined using a probe comprising or consisting of SEQ ID NO: 157. The probe is preferably labelled and may be a fluorescent label. In one embodiment the label may be Cy5.

If the internal control is not detected, the result is considered invalid and must be repeated (Floorfar et al., 2004; O'Grady et al., 2008).

Identification of *M. canettii*

In certain embodiments of the invention, the multiplex in vitro nucleic acid amplification method is for identifying *M. canettii*. In certain embodiments, the method of the present invention comprises detecting a plurality of nucleic acid molecules which, in combination, are unique in their presence or absence to *Mycobacterium canettii*.

*M. canettii* and *M. tuberculosis* are considered to be the most closely related members of the MTC (Brosch et al., 2002). Of the 16 RDs identified between members of the MTC, none have been capable of differentiating between *M. canettii* and *M. tuberculosis*, highlighting the high degree of evolutionary constraint between the two species. Therefore, it is surprising that the present inventors have been able to develop an assay that can distinguish between them.

It has been proposed that *M. canettii* is the most phylogenetically distinct member of the MTC, with other MTC members evolving from an *M. canettii*-like organism (Brosch et al., 2002; Huard et al., 2006). An *M. canettii* RD has previously been described by Huard et al. (2003) which represents a region of the genome flanking RD12 which is deleted in *M. canettii* but present in *M. tuberculosis*. A conventional PCR was performed for differentiation between *M. tuberculosis* and *M. canettii* based on the PCR product size. If a particular PCR product size was observed for both RD 9 and a region of RD 12, *M. tuberculosis* was present. If the same PCR product was observed for RD 9 but not RD 12, *M. canettii* was present. Interpretation of these results is complex as the particular region which was not amplified for *M. canettii* was also not amplified in *M. bovis* or *M. bovis* BCG. This invention, in contrast, provides a new RD which is present in *M. canettii* but deleted in *M. tuberculosis* and all other members of the MTC. As this region is only present in *M. canettii*, the interpretation of results becomes less complex, thus avoiding false reporting of the organism present. Therefore, the present invention has surprisingly found that there are sequences that allow the specific identification of *M. canettii*.

The method of the present invention may includes the use of primers and probes specific for a plurality of nucleic acid molecules which are unique in their presence or absence to *Mycobacterium canettii*.

In certain embodiments, the method of the invention includes the use of primers or probes specific for a nucleic acid that is present in *M. canettii* but is not present in *M. tuberculosis*, and optionally is also not present in *M. africanum* clade 2, *M. bovis. M. bovis* BCG, *M. caprae, M. pinnipedii*, and *M. microti.*

In certain embodiments, the method of the present invention comprises detecting the presence or absence of $RD^{canetti1}$ in a sample. In such embodiments, the method of the present invention comprises the use of primers or probes that are specific for a region of $RD^{canetti1}$, SEQ ID NO: 78.

In certain embodiments $RD^{canetti1}$ may be amplified using primers which comprise or consist of SEQ ID NOs 103 and 105.

In certain embodiments, the presence or absence of $RD^{canetti1}$ may be detected using a probe which comprises or consists of SEQ ID NO: 104. The probe is preferably labelled and the label may be a fluorescent label. In one embodiment the label may be ROX.

*M. canettii* is present in a sample if lepA, wbbl1, $RD^{canetti1}$ and the IAC (lepA or MSMEG_0660) diagnostics assays generate a positive signal, but the RD713 diagnostics assay (described below) does not generate a positive signal.

In a specific embodiment *M. canettii* is present if the HEX labelled MTC lepA, the FAM labelled wbbl1, the ROX labelled $RD^{canetti1}$ and the Cy5 labelled IAC MSMEG_0660 diagnostics assays generate a positive signal, but the Cyan 500 labelled RD713 diagnostics assay (described below) does not generate a positive signal.

The present invention provides the use of this $RD^{canetti1}$ region in identifying members of the MTC, either in the methods of the invention described above or in any other methods. The $RD^{canetti1}$ region is the first to be identified that is unique to *M. canettii*. By allowing the discrimination of *M. canettii* from *M. tuberculosis* and all the other members of the MTC, the $RD^{canetti1}$ region allows both *M. canettii* and *M. tuberculosis* to be identified in a simple multiplex nucleic acid amplification assay. In one embodiment the $RD^{canetti1}$ region allows both *M. canettii* and *M. tuberculosis* to be identified in a single multiplex nucleic acid amplification assay.

Vitally, the $RD^{canetti1}$ region is not only absent in all of the other members of the MTC, it is present in all of the *M. canettii* isolates tested. Therefore, it allows the specific and unambiguous identification of *M. canettii*. Due to the high similarity between *M. canettii* and *M. tuberculosis*, it is surprising that such a sequence exists. Furthermore, due to the variability between isolates of *M. canettii*, it is surprising that the region is conserved between isolates. Other *M. canettii* sequences that have been characterised have shown significant variability and polymorphisms, for example gyrB (Goh et al. 2003), pncA (Somoskovi et al. 2007) and hsp65 (Fabre et al. 2004).

The $RD^{canetti1}$ region is defined by SED ID NO: 78. Any part of the $RD^{canetti1}$ region could be used to identify *M. canettii* or to identify *M. tuberculosis* by distinguishing it from *M. canettii*. Therefore, this invention contemplates the use of primers, probes and arrays directed to any part of the $RD^{canetti1}$ region. Preferably, the primers, probes or arrays are suitably designed according to methods known in the art so that they bind specifically to the $RD^{canetti1}$ region, and not to regions outside this sequence.

Identification of *M. tuberculosis*

In certain embodiments of the invention, the multiplex in vitro nucleic acid amplification method is for identifying *M. tuberculosis*. In certain embodiments, the method comprises detecting a plurality of nucleic acid molecules which, in combination, are unique in their presence or absence to *Mycobacterium tuberculosis.*

The majority of human cases of tuberculosis are caused by *Mycobacterium tuberculosis*. However, significant numbers of cases are caused by other pathogens such as *M. canettii* (Gob et al 2001). Therefore, assays are required that are able to distinguish *Mycobacterium tuberculosis* from other members of the MTC. The methods of the present invention are the first to achieve this. The present invention has identified and characterised types of sequences that, by virtue of their presence or absence in the genome of *M. tuberculosis* and the other members of the MTC, allow *M. tuberculosis* to be identified in a simple multiplex in vitro nucleic acid amplification assay. This may be achieved in a single multiplex in vitro nucleic acid amplification assay.

In certain embodiments, the method of the invention detects the presence or absence of a gene region that is present in *M. tuberculosis, M. canettii*, and *M. africanum* clade 1, but optionally is also not present in *M. africanum* clade 2, *M. bovis, M. bovis* BCG, *M. caprae, M. pinnipedii*, and *M. microti.*

In certain embodiments, the method of the present invention detects the presence or absence of wbbl1 in a sample. In certain embodiments, the method comprises the use of primers or probes specific for a region of wbbl1, SEQ ID NO: 1.

This novel molecular target, identified and evaluated in this study, is based on the wbbl1 gene which enables the simultaneous detection of *M. tuberculosis* and *M. canettii*, a target with the same properties as the widely used RD9 region for *M. tuberculosis* identification. As the aim of this study was to identify novel nucleic acid diagnostic targets for the detection of tuberculosis, this wbbl1 target may be used in the multiplex assay described. In certain embodiments, RD9 could be used in conjunction with any of the assays outlined below.

Therefore, this invention contemplates the use of primers, probes and arrays directed to any part of the region of wbbl1 represented by SEQ ID NO: 1. Preferably, the primers, probes or arrays are suitably designed according to methods known in the art so that they bind specifically to this region, and not to regions outside this sequence.

In certain embodiments wbb1 may be amplified using primers which comprise or consist of SEQ ID NOs 97 and 99.

In certain embodiments the presence or absence of wbbl1 may be determined using a probe which comprises or consists of SEQ ID NO: 98. The probe is preferably labelled and the label may be a fluorescent label. In one embodiment the label may be FAM.

*M. tuberculosis* is present in a sample if MTC lepA, wbbl1 and the IAC (lepA or MSMEG_0660) diagnostics assays generate a positive signal, but RD713 (discussed below) and $RD^{canetti1}$ diagnostics assays do not generate positive signals in these channels.

In a specific embodiment *M. tuberculosis* is present if the HEX labelled MTC lepA, the FAM labelled wbbl1 and the Cy5 labelled IAC MSMEG_0660 diagnostics assays generate a positive signal but the Cyan 500 labelled RD713 and the ROX labelled $RD^{canetti1}$ diagnostics assays do not generate positive signals.

Identification of *M. africanum* Clade 1

In certain embodiments of the invention, the multiplex in vitro nucleic acid amplification method is for identifying *M. africanum* clade 1. In certain embodiments, the method of the present invention comprises detecting a plurality of nucleic acid molecules which, in combination, are unique in their presence or absence to *Mycobacterium africanum* clade 1.

*M. africanum* is a member of the MTC originally thought to have a natural host in humans. In certain geographical regions, *M. africanum* is thought to cause up to half the cases of human TB infection (de Jong et al., 2010). Prior to 2004, *M. africanum* was divided into two subgroups, namely *M. africanum* subtype 1 and *M. africanum* subtype 2. Differentiation between these species was difficult owing to the variable biochemical test results observed. Based on genomic analysis studies *M. africanum* subtype 2 was reclassified as *M. tuberculosis* (Mostowy et al., 2004).

Recent studies have subsequently further classified *M. africanum* subtype 1 into two distinct lineages namely *M. africanum* West African-1 (clade 1) and *M. africanum* West African-2 (clade 2) (de Jong et al., 2010 & Vasconcellos et al., 2010). *M. africanum* clade 1 appears to be closely related to *M. tuberculosis* whereas africanum clade 2 is phylogenetically more closely related to animal isolates of the MTC (de Jong et al., 2010). These recent studies have discovered robust molecular markers for each lineage of *M. africanum* based on deletions and single nucleotide polymorphisms (SNP). However, there is currently no commercially available method or diagnostics kit with the capability of differentiating between these described clades of *M. africanum*. The present invention provides such methods and kits.

In certain embodiments, the invention identities *M. africanum* using a set of primers and probes specific for a plurality of nucleic acid molecules which are unique in their presence or absence to *Mycobacterium africanum* clade 1.

In certain embodiments, the invention provides the use of primers or probes specific for a nucleic acid that is present in *M. africanum* clade 1 but is not present in *M. canettii* or *M. tuberculosis*, and optionally not present in *M. bovis, M. bovis* BCG, *M. caprae, M. africanum* clade 2, *M. pinnipedii* and *M. microti*.

In certain embodiments, *M. africanum* clade 1 is identified by detecting the presence or absence of RD713.

The presence or absence of RD713 may be determined using primers or probes specific for a region of RD713, SEQ ID NO: 137.

In certain embodiments, RD713 may be amplified using primers which comprise or consist of SEQ ID NOs 167 and 168.

The presence or absence of RD713 may be detecting using a probe which comprises or consists of SEQ ID NO: 169. The probe is preferably labelled and the label may be a fluorescent label. In one embodiment the label is Cyan 500.

*M. africanum* clade 1 is present if the MTC lepA, wbbl1, RD713 and IAC (lepA or MSMEG_0660) diagnostics assays generate a positive signal, but the $RD^{canetti1}$ diagnostics assay does not generate a positive signal.

In a specific embodiment, *M. africanum* is present if the HEX labelled MTC lepA, the FAM labelled wbbl1, the Cyan 500 labelled RD713 and the Cy5 labelled IAC MSMEG_0660 diagnostics assay generate a positive signal, but the ROX labelled $RD^{canetti1}$ diagnostics assay does not generate a positive signal.

Identification of *M. bovis*

In certain embodiments of the invention, the multiplex in vitro nucleic acid amplification method is for identifying *M. bovis*. In certain embodiments, the method of the present invention comprises detecting a plurality of nucleic acid molecules which, in combination, are unique in their presence or absence to *Mycobacterium bovis*.

In certain embodiments, the method uses primers or probes specific for a nucleic acid that is present in *M. bovis, M. bovis* BCG and *M. caprae* but is not present in *M. africanum* clade 2, *M. pinnipedii* and *M. microti*, and optionally is not present in *M. tuberculosis* and *M. canettii*.

In certain embodiments, the identification of *M. bovis* is determined using primers or probes specific for a region of lpqT, SEQ ID NO: 109.

In certain embodiments, lpqT is amplified using primers which comprise or consist of SEQ ID NOs 158 and 159.

In certain embodiments, the presence or absence of lpqT is determined using a probe which comprises or consists of SEQ ID NO: 160. The probe is preferably labelled and the label may be fluorescent. In one embodiment the label may be FAM.

In one embodiment, *M. bovis* is present if the MTC lepA and IAC (lepA or MSMEG_0660) diagnostics assays generate a positive signal, but the wbbl1, the $RD^{canetti1}$ and the RD713 diagnostics assays do not generate positive signals, and the lpqT, RD1 and the IAC (lepA or MSMEG_0660) diagnostics assay generate positive signals, but the *M. caprae* lepA (described below) and the RD701 (described below) diagnostics assays do not generate positive signals.

In a specific embodiment, *M. bovis* is present if in the first multiplex the HEX labelled MTC lepA and Cy5 labelled IAC MSMEG_0660 diagnostics assays generate a positive signal, but the FAM labelled wbbl1, the ROX labelled $RD^{canetti1}$ and the Cyan 500 labelled RD713 diagnostics assays do not generate positive signals. This indicates that a member of the MTC other than *M. tuberculosis, M. canettii* and *M. africanum* clade 1 is present in the sample and the user should proceed to the second multiplex real-time PCR disclosed in this invention. The second multiplex indicates that *M. bovis* is present if a positive signal is observed in the FAM labelled lpqT, the HEX labelled RD1 and the Cy5 labelled IAC MSMEG_0660 diagnostics assay, but the Cyan500 labelled *M. caprae* lepA and the ROX labelled RD701 diagnostics assays do not generate positive signals.

Identification of *M. bovis* BCG

In certain embodiments of the invention, the multiplex in vitro nucleic acid amplification method is for identifying *M. bovis* BCG. In certain embodiments, the method of the present invention comprises detecting a plurality of nucleic acid molecules which, in combination, are unique in their presence or absence to *Mycobacterium bovis* BCG.

In certain embodiments, the method uses primers or probes specific for a nucleic acid that is deleted in *M. bovis* BCG and *M. microti* but is present in *M. bovis, M. caprae, M. africanum* clade 2, and *M. pinnipedii*, and optionally is present in *M. tuberculosis* and *M. canettii*.

In certain embodiments, the presence or absence of *M. bovis* BCG is determined using primers or probes specific for a region of RD1, SEQ ID NO: 141.

In certain embodiments, RD1 is amplified using primers which comprise or consist of SEQ ID NOs 161 and 162.

In certain embodiments, the presence or absence of RD1 is determined using a probe which comprises or consists of SEQ ID NO: 163.

In one embodiment, *M. bovis* BCG is present if the MTC lepA and Cy5 labelled IAC (lepA or MSMEG_0660) diagnostics assays generate a positive signal, but the wbbl1, $RD^{canetti1}$ and the RD713 diagnostics assays do not generate positive signals, and the lpqT and the IAC (lepA or MSMEG_0660) diagnostics assays generate positive signals but the *M. caprae* lepA (discussed below), the RD1 and RD701 (discussed below) diagnostics assays do not generate positive signals.

In a specific embodiment. *M. bovis* BCG is present if in the first multiplex the HEX labelled MTC lepA and Cy5 labelled IAC MSMEG_0660 diagnostics assays generate a positive signal, but the FAM labelled wbbl1, the ROX labelled $RD^{canetti1}$ and the Cyan 500 labelled RD713 diagnostics assays do not generate positive signals. This indicates that a member of the MTC other than *M. tuberculosis, M. canettii* and *M. africanum* clade 1 is present in the sample and the user should now proceed to the second multiplex real-time PCR disclosed in this invention.

Using multiplex 2, *M. bovis* BCG is present if a positive signal is observed in the FAM labelled lpqT and the Cy5 labelled IAC MSMEG_0660 diagnostics assays, but the Cyan 500 labelled *M. caprae* lepA (discussed below), the HEX labelled RD1 and the ROX labelled RD701 (discussed below) diagnostics assays do not generate positive signals.

identification of *M. caprae*

In certain embodiments of the invention, the multiplex in vitro nucleic acid amplification method is for identifying *M. caprae*. In certain embodiments, the method of the present invention comprises detecting a plurality of nucleic acid molecules which, in combination, are unique in their presence or absence to *Mycobacterium caprae.*

In certain embodiments, the method of the invention uses primers or probes specific for a nucleic acid that is present in *M. caprae* but is not present in *M. bovis, M. bovis* BCG. *M. africanum* clade 2, *M. pinnipedii* or *M. microtti*, and optionally is not present in *M. tuberculosis* and *M. canettii.*

In certain embodiments, *M. caprae* may be identified using primers or probes specific for a region of *M. caprae* lepA, SEQ ID NO: 76.

As discussed above, MTC lepA (encoded by SEQ ID NO: 47) is used to identify the presence of the MTC and lepA (encoded by SEQ ID NO; 84) may be used as an IAC. However, the inventors have surprisingly identified an SNP in the lepA gene of *M. caprae* which allows this gene to simultaneously be used to detect the presence or absence of *M. caprae*. The use of the same gene for these two or three identification purposes will simplify the diagnostic assay by reducing the number of primers required. It is surprising that this SNP is conserved between all isolates of *M. caprae* tested, but is not present in any of the other members of the MTC, despite the high level of sequence homology between the genomes of all members of the MTC.

In certain embodiments, *M. caprae* lepA may be amplified using primers which comprise or consist of SEQ ID NOs 164 and 165. These are the same primers which are used to amplify the lepA sequence which identified the presence of the MTC, and which may be used as an IAC. This reduces the numbers of primers required to perform the diagnostic assay and therefore reduces the complexity of the assay.

In certain embodiments, the presence or absence of *M. caprae* lepA may be determined using a probe which comprises or consists of SEQ ID NO: 166. This probe differs from the probe which is used to determine the presence of the MTC or as an IAC as it binds to the region of the lepA gene which includes the *M. caprae* specific SNP. The probe is preferably labelled and the label may be fluorescent. In one embodiment the label may be Cyan 500.

If the MTC lepA and IAC (lepA or MSMEG_0660) diagnostics assays generate a positive signal, but the wbbl1, $RD^{canetti1}$ and RD713 diagnostics assays do not generate positive signals, and a positive signal is observed for the *M. caprae* lepA, lpqT, RD1 and IAC (lepA or MSMEG_0660) diagnostics assay, but the RD701 diagnostics assay does not generate a positive signal, *M. caprae* is present in the sample.

In one specific embodiment, *M. caprae* is present if in the first multiplex the HEX labelled MTC lepA and Cy5 labelled IAC MSMEG_0660 diagnostics assays generate a positive signal, but the FAM labelled wbbl1, the ROX labelled $RD^{canetti1}$ and the Cyan 500 labelled RD713 diagnostics assays do not generate positive signals. This indicates that a member of the MTC other than *M. tuberculosis, M. canettii* and *M. africanum* clade 1 is present in the sample and the user should now proceed to the second multiplex real-time PCR disclosed in this invention.

Using multiplex 2, *M. caprae* is present if a positive signal is observed for the Cyan 500 labelled *M. caprae* lepA, the FAM labelled lpqT, the HEX labelled RD1 and the Cy5 labelled IAC MSMEG_0660 diagnostics assay, but the ROX labelled RD701 diagnostics assay does not generate a positive signal.

Identification of *M. africanum* Clade 2

In certain embodiments of the invention, the multiplex in vitro nucleic acid amplification method is for identifying *M. africanum* clade 2. In certain embodiments, the method of the present invention comprises detecting a plurality of nucleic acid molecules which, in combination, are unique in their presence or absence to *Mycobacterium africanum* clade 2.

In certain embodiments, the invention uses primers or probes specific for a nucleic acid that is present in *M. africanum* clade 2 but is not present in *M. bovis, M. bovis* BCG, *M. caprae, M. pinnipedii*, and *M. microti*, and optionally is not present in *M. tuberculosis* and *M. canettii.*

In certain embodiments, the presence or absence of *M. africanum* clade 2 is identified using primers or probes specific for a region of RD701, SEQ ID NO: 132.

In certain embodiments, RD701 is amplified using primers which comprise or consist of SEQ ID NOs 170 and 171.

In certain embodiments, presence or absence of RD701 is determined using a probe which comprises or consists of SEQ ID NO: 172. The probe is preferably labelled and the label may be fluorescent. In one embodiment the label is ROX.

In certain embodiments, *M. africanum* clade 2 is present if the MTC lepA and IAC (lepA or MSMEG_0660) diagnostics assays generate a positive signal, but the wbbl1, the $RD^{canetti1}$ and the RD713 diagnostics assays do not generate positive signals, and the RD701, the RD1 and the IAC (lepA or MSMEG_0660) diagnostics assays generate positive signals, but the *M. caprae* lepA and the lpqT diagnostics assays do not generate positive signals.

In one specific embodiment, *M. africanum* clade 2 is present if in multiplex 1, the HEX labelled MTC lepA and Cy5 labelled IAC MSMEG_21660 diagnostics assays generate a positive signal, but the FAM labelled wbbl1, the ROX labelled $RD^{canetti1}$ and the Cyan 500 labelled RD713 diagnostics assays do not generate positive signals. This indicates that a member of the MTC other than *M. tuberculosis, M. canettii* and *M. africanum* clade 1 is present in the sample and the user should proceed to the second multiplex real-time PCR disclosed in this invention.

Using multiplex 2, *M. africanum* clade 2 is present if a positive signal is observed in the ROX labelled RD701, the HEX labelled RD1 and the Cy5 labelled IAC MSMEG_0660 diagnostics assays, but the Cyan500 labelled *M. caprae* lepA and the FAM labelled lpqT diagnostics assays do not generate positive signals.

Identification of *M. pinnipedii*

In certain embodiments of the invention, the multiplex in vitro nucleic acid amplification method is for identifying *M. pinnipedii*. In certain embodiments, the method of the present invention comprises detecting a plurality of nucleic acid molecules which, in combination, are unique in their presence or absence to *Mycobacterium pinnipedii*.

In certain embodiments, *M. pinnipedii* is present if a positive signal is observed for the MTC lepA, IAC (lepA or MSMEG_0660) and RD1 diagnostics assays and no further positive signals are identified.

In one specific embodiment, *M. pinnipedii* is present if a positive signal is observed in the HEX labelled MTC lepA and the Cy5 labelled IAC MSMEG_0660 diagnostics assay in multiplex 1 and no positive signal is observed for all other assays in multiplex 1 and multiplex 2, with the exception of a positive signal in the HEX labelled RD1 and the Cy5 labelled MSMEG_0660 diagnostics assays in multiplex 2.

Identification of *M. microtii*

In certain preferred embodiments of the invention, the multiplex in vitro nucleic acid amplification method is for identifying *M. microtii*. In certain embodiments, the method of the present invention comprises detecting a plurality of nucleic acid molecules which, in combination, are unique in their presence or absence to *Mycobacterium microti*.

In certain embodiments *M. microti* is present if a positive signal is observed in the MTC lepA and the IAC (lepA or MSMEG_0660) diagnostics assays and no other positive signal is observed.

In one specific example, *M. microti* is present if a positive signal is observed in the HEX labelled MTC lepA and the Cy5 labelled IAC MSMEG_0660 diagnostics assay in Multiplex 1 and a positive signal is observed in the Cy5 labelled IAC MSMEG_0660 diagnostics assay in Multiplex 2.

Assay Methods

The method of the present invention preferably comprises the steps of DNA isolation, amplification and detection. DNA isolation can be performed using any technique known in the art from whichever sample is to be tested. DNA amplification is preferably performed with the use of primers and the polymerase chain reaction (PCR). Other methods of amplification will be apparent to those skilled in the art. One or more pairs of primers is designed to anneal to each nucleic acid molecule target and DNA polymerases are used to amplify the nucleic acid sequence between the primer annealing sites during thermal cycling. The presence of the amplified nucleic acid molecule targets is then detected. This can be done through the use of gel electrophoresis but in preferred embodiments of the invention, detection is performed with the use of labelled probes specific for the amplified nucleic acid molecule targets. Preferably, fluorescent probes are used in detection. A wide range of fluorescent probes are available and include FAM, HEX, ROX, CY5, JOE, VIC and Texas Red and many more will be known to those skilled in the art. Quencher dyes such as Black Hole Quenchers are preferably used in conjunction with the fluorescent probes. As detailed below, in the multiplex assays of the present invention, each probe preferably uses a different fluorescent marker with a different output wavelength so that amplification of all the different nucleic acid molecule targets can be detected at the same time, in the single reaction.

The methods of the invention utilise multiplex PCR assays wherein more than one nucleic acid molecule target is amplified and detected in a single PCR reaction with the use of a plurality of probes and sets of primers. Multiple sets of primers are used; each specific for a different nucleic acid molecule target. Multiple different probes are used; each specific for an amplified nucleic acid molecule targets. Preferably, each probe is labelled differently, for example with different fluorophores, so that amplification of each target can be detected independently but at the same time in the single multiplex reactions, for example through the use of different colour channels. In the detection phase, the presence or lack of a signal in the different channels, indicating the presence or absence of amplification of the different nucleic acid molecule targets, is used to determine the identity of the species in a sample.

The present invention contemplates the use of any appropriate method for amplification of target molecules. Preferably, the method of amplification is multiplex PCR. However, the teaching of the present invention and the sequences identified herein as allowing the identification of specific members of the MTC can be used with any appropriate method of amplification.

Also contemplated for use in the present invention is Nucleic Acid Sequence Based Amplification (NASBA). Nucleic acid sequence-based amplification (NASBA) is an isothermal amplification technique which uses three enzymes—RNase H, AMV reverse transcriptase and T7 RNA polymerase—working in concert at a low isothermal temperature (generally 41° C.). The product of a NASBA reaction is mainly single-stranded RNA, which can be detected by gel electrophoresis, enzyme-linked gel assay (ELGA) or electrochemiluminescent detection (ECL). Alternatively, NASBA products can be detected in real time using molecular beacons included in the reaction (Rodríguez-Lázaro et al, 2004). In microbial diagnostics, NASBA has been successfully combined with electrochemiluminescent (ECL), ELISA labelled dendrimer and molecular beacon-based methods to detect and identify viral and bacterial pathogens. (Scheler et al., 2009).

Also contemplated for use in the present invention is Rolling Circle Amplification (RCA). RCA describes a process of unidirectional nucleic acid replication that can rapidly synthesize multiple copies of circular molecules of DNA or RNA. RCA is a technology that is adaptable to an on-chip signal amplification format. RCA is well suited to solid phase formats such as microarrays for generating localized signals at specific microarray locations. This distinctive property of RCA should allow many assays to be performed simultaneously (multiplexing) without interference (Nallur et al., 2001).

Also contemplated for use in the present invention is the Ligase Chain Reaction (LCR). LCR uses two complementary pairs of probes which, when the correct template is available, hybridize next to each other and then are ligated together. These ligated probes plus the original template serve as the template for the next cycle of hybridization and ligation. As subsequent cycles are performed, the amplification proceeds exponentially (Dille et al., 1993). A commercially available kit using this technology is the LCx *M. tuberculosis* complex specific kit available from Abbott Diagnostics (Tortoli et al., 1997).

Further isothermal amplification technologies that are contemplated for use with the present invention are provided in Gill and Ghaemi, 2007 and include signal mediated amplification of RNA technology (SMART), strand displacement amplification (SDA), loop mediated isothermal amplification (LAMP), isothermal multiple displacement amplification (IMDA), helicase-dependent amplification (FIDA), single primer isothermal amplification (SIPA) and circular helicase dependent amplification (cHDA). As exemplified by SMART, the amplification method used with the invention may comprise signal amplification rather than target amplification.

Also contemplated for use in the present invention is Next Generation Sequencing (NGS). Next generation sequencing is a relatively new field of sequencing which allows for the rapid high throughput process. NGS has the capacity to generate gigabases of nucleotide sequence, depending on the instrument used, in a single run (Voelkerding et al., 2009). A recently described assay combines the use of real-time PCR in combination with pyrosequencing which allows for the rapid detection of MTC DNA in addition to sequencing of an 81-bp core region of the rpoB gene associated with rifampin resistance (Halse et al.)

Multiplex Assay Formats

As discussed above, the methods of the present invention utilise different nucleic acid molecule targets to identify species of the MTC in a multiplex in vitro nucleic acid amplification assay.

In certain embodiments one or more multiplex in vitro nucleic acid amplification assays each utilising one or more nucleic acid molecule targets are performed sequentially in order to fully characterise the MTC member present in a sample.

In preferred embodiments of the invention, the initial multiplex in vitro nucleic acid amplification assay (Multiplex 1) utilises a target that is present in all members of the MTC, a target that is present in only two members of the MTC and a target that is present in only one of these two members. In preferred embodiments, lepA is used to identify the MTC, wbbl11 is used to identify *M. tuberculosis* and *M. canettii* and $RD^{canetti1}$ is used to identify *M. canettii*. This allows the identification of the MTC in general, and also specific evaluation of the presence or absence of *M. tuberculosis* and *M. canettii*.

In alternative preferred embodiments of the invention, the initial multiplex in vitro nucleic acid amplification assay (Multiplex 1) utilises a target that is present in all members of the MTC, a target that is present in only three members of the MTC and two targets that are present in only one of these three members. lepA may be used to identify the MTC, wbbl11 may be used to identify *M. tuberculosis, M. canettii* and *M. africanum* clade 1. $RD^{canetti1}$ may be used to identify *M. canettii* and RD713 may be used to identify *M. africanum* clade 1. This allows the identification of the MTC in general, and also specific evaluation of the presence or absence of *M. tuberculosis, M. canettii* and *M. africanum* clade 1. It will be appreciated that when performing the Multiplex 1 assay that any of the nucleic acid molecule targets, primers and probes described in the various embodiments of the invention presented above may be utilised.

A second multiplex in vitro nucleic acid amplification assay may be performed if additional characterisation is required. In particular, a second multiplex in vitro nucleic acid amplification assay may be performed if Multiplex 1 indicates that a member of the MTC other than *M. tuberculosis* or *M. canettii* or other than *M. tuberculosis, M. canettii* or *M. africanum* clade 1 is present.

In further preferred embodiments on the invention, a second multiplex in vitro nucleic acid amplification assay (Multiplex 2) utilises a target that is present in only three members of the MTC, a target that is present in only one of these three members, a target which is deleted in only one of these three members and one additional member, and a target which is only present in one additional member.

lpqT may be used to identify *M. bovis, M. bovis*. BCG and *M. caprae. M. caprae* lepA may be used to identify *M. caprae*. Deletion of RD1 may be used to identify *M. bovis* BCG and *M. microti*. RD701 may be used to identify *M. africanum* clade 2. *M. pinnipedii* can subsequently be identified by a positive result for RD1 only. It will be appreciated that when performing Multiplex 2, any of the nucleic acid molecule targets, primers and probes described in any of the embodiments of the invention presented above, may be utilised.

Those skilled in the art will appreciate how using different selections of sequences will allow different species to be identified. For example, it is not essential to use a target to identify the MTC in Multiplex 1 if it is desired only to confirm the presence or absence of, for example, *M. tuberculosis* and *M. canettii*. Therefore, in certain embodiments of the invention, only one or two nucleic acid molecule targets are used. It will also be appreciated that either Multiplex 1 or Multiplex 2 can be performed independently, or that Multiplex 1 and Multiplex 2 can be performed sequentially in any order. It will also be appreciated that if Multiplex 1 identifies the member of the MTC, performance of Multiplex 2 may not be required.

In addition to the nucleic acid molecule targets discussed for each multiplex above, an IAC may be included in the multiplex reaction. In one embodiment the IAC may be lepA or MSMEG_0660, and the primers and probes discussed above for this nucleic acid molecule target may be used.

It will be apparent to the skilled person that the invention is not restricted to the detection of members of the MTC in a two step multiplex assay format, and the invention therefore encompasses the use of any number of the nucleic acid molecule targets and methods described above in a single multiplex assay. In one embodiment all of the nucleic acid molecule targets described above may be used in a single multiplex assay. In alternative embodiments 3, 4, 5, 6, 7, 8, 9 or 10 targets are used, to allow identification of more species, and potentially with more confidence.

The use of a number of different multiplex in vitro nucleic acid amplification assays of the invention allows identification of a greater number of species of the MTC. Different multiplex assays, each using a certain combination of primers and probes to identify different species of the MTC, may be performed on a series of aliquots of a sample or a group of samples, either in parallel or sequentially.

Uses of the Invention

The methods and kits of the present invention can be used to perform various analyses. The invention therefore provides, in general, the use of a method or kit as disclosed herein to analyse the nucleic acids present in a sample. Some of the types of analyses envisaged by the inventors are described below.

In one embodiment, the invention provides the use of a method or kit as disclosed herein to identify the type of cell(s) present in a biological sample (such as a sample taken from a patient). For example, the invention provides a method for identifying the type of cell(s) present in a biological sample, the method comprising analysing a sample nucleic acid obtained from the biological sample using an analysis method as described herein, and using the results of the analysis to identify the type of cell(s) present in the biological sample.

The invention provides the use of a method or kit as disclosed herein to analyse a sample taken from a human patient, such as a sputum sample, a pus sample, a lung fluid sample, a lymph node sample, a pleural fluid sample, a pleural tissue sample, a blood sample, a plasma sample, a serum sample, a urine sample, a tissue sample, or a saliva sample.

In another embodiment, the invention provides the use of a method or kit as disclosed herein to diagnose a disease or condition in a patient (e.g. a human patient). Preferably, the disease is tuberculosis or a related condition. For example, the invention provides a method for diagnosing a disease or condition in a patient, comprising analysing the nucleic acid in a sample obtained from the patient using an analysis method as described herein, and using the results of the analysis to diagnose a disease or condition in the patient. In some embodiments, methods of diagnosis as described herein are performed in vitro on a sample taken from a patient.

In another embodiment, the invention provides the use of a method or kit as disclosed herein to select a therapeutic strategy or treatment regimen for treating a disease or condition in a patient. For example, the invention provides a method for selecting a therapeutic strategy or treatment regimen for treating a disease or condition in a patient (e.g. a human patient), comprising analysing a sample nucleic acid obtained from the patient using an analysis method as described herein, identifying the presence of a pathogenic species and using the results of the analysis to select a therapeutic strategy or treatment regimen for treating the disease or condition. These methods may be performed in vitro on a sample taken from a patient.

In a further embodiment, the invention provides the use of a method or kit as disclosed herein to monitor progression or status of a disease or condition in a patient, e.g. to monitor a patient's response to treatment.

The invention also provides the use of a method or kit as disclosed herein for biosurveillance, e.g. to detect pathogens in samples, such as water, food or soil samples.

As discussed above, the assays provided in the present invention and the sequences disclosed and characterised herein are useful for the identification of species of the MTC and allow a rapid and specific identification that is not achieved with the methods of the prior art and which would not be possible with the sequences that have been previously identified and characterised. The methods, assays and sequences of the present invention will be useful in diagnosis of disease. As discussed above, the different members of the MTC respond differently to treatment and differ in their pathology. Therefore, it is essential that medical professionals are able to identify which species are present to make an accurate diagnosis and provide suitable treatment.

The methods, assays and sequences of the present invention will also be useful in a range of other applications. The simple and effective nature of the multiplex assays that are made possible with the types of sequences identified and characterised herein mean that the assays are suitable for routine screening and diagnosis of not only patients with tuberculosis symptoms but also patients potentially at risk, such as HIV patients and patients who have spent time in certain risk areas, for example.

The methods, assays and sequences of the present invention will also be useful in maintenance of research stocks of MTC species. Due to the high similarity between different species, it was not easy, prior to the present invention, to identify or confirm the identity of MTC species kept as stocks in, for example, research laboratory situations.

The present invention will also be useful in other research situations, including monitoring the growth and survival of different MTC species and, for example, the effectiveness of drug treatments and development of drug resistance.

The individual sequences identified and characterised herein and primers and probes directed to these sequences will also be useful a range of other applications, including, as discussed below, the development and use of microarray platforms. Also, the $RD^{canetti1}$ region in particular, which is herein identified and characterised as unique to *M. canettii*, is currently not annotated. Therefore, primers and probes directed to the region will be useful in further characterising the region, identifying genes present in the region and in analysis of expression of the region.

Alternative Methods of MTC Member Identification

In addition to the methods described above, this invention contemplates the use of some of or all of the sequences provided in alternative methods for the identification of species of the MTC.

The present invention provides the use of hybridisation techniques using probes specific for $RD^{canetti1}$, wbbl1, MTC lepA, RD713, *M. caprae* lepA, lpqT, RD1 and RD701 either individually or in combination and preferably as part of an array comprising a plurality of probes which can specifically detect a number of different members of the MTC.

Preferably the present invention provides the use of hybridisation techniques using probes specific for one or more of $RD^{canetti1}$, wbbl1, MTC lepA and RD713 in combination and preferably as part of an array comprising a plurality of probes which can specifically detect *M. canettii. M. tuberculosis*, any member of the MTC and *M. africanum* clade 1, respectively. More preferably the invention provides the use of hybridisation techniques using probes specific for all of $RD^{canetti1}$, wbbl1, lepA and RD713 in combination and preferably as part of an array.

Preferably the present invention provides the use of hybridisation techniques using probes specific for *M. caprae* lepA, lpqT, RD1 and RD701, either individually or in combination and preferably as part of an array comprising a plurality of probes which can specifically detect *M. caprae, M. bovis*, bolls BCG, and *M. africanum* clade 2, respectively. More preferably the invention provides the use of hybridisation techniques using probes specific for all of *M. caprae* lepA, lpqT, RD1 and RD701 in combination and preferably as part of an array.

In one embodiment hybridisation techniques may be used with probes specific for the two groups of nucleic acid molecule targets described below in combination and preferably as part of an array. The two groups of nucleic acid molecule targets may be arrange as a single array with the two groups positioned apart from one another at spaced locations, or as two separate arrays.

Such arrays will allow the high-throughput screening of samples and rapid diagnosis of specific pathogens. The properties of the sequences provided herein, as described above, make them suitable for use in such microarray platforms and screening methods. Due to their specific presence or absence in the different species of the MTC, the sequences provided herein are suitable for use in a range of different hybridisation techniques and microarray applications.

The multiplex real-time PCR developed in this study is the first description of a hydrolysis probe based diagnostic tool capable of rapid detection of the MTC, combined with the detection and differentiation of members of the MTC using novel targets. As exemplified herein, this rapid, specific and sensitive multiplex real-time PCR assay takes approximately 50 minutes after DNA extraction. Depending on the number of samples and the extraction methods used the total assay time may be approximately 2-3 hours. This assay has been tested on Mycobacteria DNA from clinical isolates. Testing of TB positive and negative patient samples, for example sputum and bronchial lavage, will further validate the assay in due course. The multiplex real-time PCR assay presented here may be used in the hospital laboratory for the routine detection of the MTC and detection of the member of the MTC present, including simultaneous differentiation of *M. tuberculosis* and *M. canettii*.

Kits

The present invention additionally provides kits suitable for use in the methods provided herein. The invention provides a kit comprising sets of primers and probes which are specific for a plurality of nucleic acid molecule targets, wherein at least one of the nucleic acid molecule targets is present in the genome of one or more, but not all, of the species of the *Mycobacterium tuberculosis* complex.

In certain embodiments, the invention provides a kit comprising sets of primers and probes specific for a plurality of nucleic acid molecules which are unique in their presence or absence to *Mycobacterium tuberculosis*.

In certain embodiments, the invention provides a kit comprising sets of primers and probes specific for a plurality of nucleic acid molecules which are unique in their presence or absence to *Mycobacterium canettii*.

In certain embodiments, the invention provides a kit comprising primers or probes specific for a nucleic acid that is not present in both *M. tuberculosis* and *M. canettii*.

In certain embodiments, the invention provides a kit comprising primers or probes specific for a nucleic acid that is present in *M. canettii* but is not present in *M. tuberculosis*, and optionally is also not present in *M. africanum* clade 2, *M. bovis, M. bovis* BCG, *M. caprae, M. pinnipedii*, and *M. microti*.

In certain embodiments, the invention provides a kit comprising primers or probes specific for a region of $RD^{canetti1}$, SEQ ID NO: 78.

In certain embodiments, the invention provides a kit wherein the primers comprise or consist of SEQ ID NOs 103 and 105.

In certain embodiments, the invention provides a kit wherein the probe comprises or consists of SEQ ID NO: 104.

In certain embodiments, the invention provides a kit comprising primers or probes specific for a nucleic acid that is present in both *M. tuberculosis* and *M. canettii*, but is not present in *M. africanum* clade 1 and optionally is not present in *M. africanum* clade 2, *M. bovis, M. bovis* BCG, *M. caprae, M. pinnipedii*, and *M. microti*.

In certain embodiments, the invention provides a kit comprising primers or probes specific for wbbl1, SEQ ID NO: 1.

In certain embodiments, the invention provides a kit wherein the primers comprise or consist of SEQ ID NOs 97 and 99.

In certain embodiments, the invention provides a kit wherein the probe comprises or consists of SEQ ID NO: 98.

In certain embodiments, the invention provides a kit comprising sets of primers and probes specific for a plurality of nucleic acid molecules which are unique in their presence or absence to *Mycobacterium africanum* clade 1.

In certain embodiments, the invention provides a kit comprising primers or probes specific for a nucleic acid that is present in *M. africanum* clade 1 but is not present in *M. canettii* or *M. tuberculosis*, and optionally is also not present in *M. africanum* clade 2, *M. bovis. M. bovis* BCG, *M. caprae, M. pinnipedii*, and *M. microti*.

In certain embodiments, the invention provides a kit comprising primers or probes specific for a region of RD713, SEQ ID NO: 137.

In certain embodiments, the invention provides a kit wherein the primers comprise or consist of SEQ ID NOs 167 and 168.

In certain embodiments, the invention provides a kit wherein the probe comprises or consists of SEQ ID NO: 169.

In certain embodiments, the invention provides a kit comprising primers or probes specific for a nucleic acid that is present in *M. bovis, M. bovis* BCG and *M. caprae* but is not present in *M. africanum* clade 2, *M. pinnipedii* and *M. microti*, and optionally is not present in *M. tuberculosis* and *M. canettii* or *M. africanum* clade 1.

In certain embodiments, the invention provides a kit comprising primers or probes specific for a region of lpqT, SEQ ID NO: 109.

In certain embodiments, the invention provides a kit wherein the primers comprise or consist of SEQ NOs 158 and 159.

In certain embodiments, the invention provides a kit wherein the probe comprises or consists of SEQ ID NO: 160.

In certain embodiments, the invention provides a kit comprising sets of primers and probes specific for a plurality of nucleic acid molecules which are unique in their presence or absence to *Mycobacterium bovis*.

In certain embodiments, the invention provides a kit comprising sets of primers and probes specific for a plurality of nucleic acid molecules which are unique in their presence or absence to *Mycobacterium caprae*.

In certain embodiments, the invention provides a kit comprising primers or probes specific for a nucleic acid that is present in *M. caprae* but is not present in *M. bovis, M. bovis* BCG. *M. africanum* clade 2, *M. pinnipedii* or *M. microtti*, and optionally is not present in *M. tuberculosis* and *M. canettii*.

In certain embodiments, the invention provides a kit comprising primers or probes specific for a region of *M. caprae* lepA, SEQ ID NO: 76.

In certain embodiments, the invention provides a kit wherein the primers comprise or consist of SEQ ID NOs 164 and 165.

In certain embodiments, the invention provides a kit wherein the probe comprises or consists of SEQ ID NO: 166.

In certain embodiments, the invention provides a kit comprising sets of primers and probes specific for a plurality of nucleic acid molecules which are unique in their presence or absence to *Mycobacterium bovis* BCG.

In certain embodiments, the invention provides a kit comprising sets of primers and probes specific for a plurality of nucleic acid molecules which are unique in their presence or absence to *Mycobacterium microti*.

In certain embodiments, the invention provides a kit comprising primers or probes specific for a nucleic acid that is deleted in *M. bovis* BCG and *M. microti* but is present in *M. bovis, M. caprae, M. africanum* clade 2, and *M. pinnipedii*, and optionally is present in *M. tuberculosis* and *M. canettii* and *M. africanum* clade 1.

In certain embodiments, the invention provides a kit comprising primers or probes specific for a region of RD1, SEQ ID NO: 141.

In certain embodiments, the invention provides a kit wherein the primers comprise or consist of SEQ ID NOs 161 and 162.

In certain embodiments, the invention provides a kit wherein the probe comprises or consists of SEQ ID NO: 163.

In certain embodiments, the invention provides a kit comprising sets of primers and probes specific for a plurality of nucleic acid molecules which are unique in their presence or absence to *Mycobacterium africanum* clade 2.

In certain embodiments, the invention provides a kit comprising primers or probes specific for a nucleic acid that is present in *M. africanum* clade 2 but is not present in *M. bovis, M. bovis* BCG, *M. caprae, M. pinnipedii*, and *M. microti*, and optionally is not present in *M. tuberculosis. M. canettii* and *M. africanum* clade 1.

In certain embodiments, the invention provides a kit comprising primers or probes specific for a region of RD701, SEQ ID NO: 132.

In certain embodiments, the invention provides a kit wherein the primers comprise or consist of SEQ ID NOs 170 and 171.

In certain embodiments, the invention provides a kit wherein the probe comprises or consists of SEQ ID NO: 172.

In certain embodiments, the invention provides a kit comprising sets of primers and probes specific for a plurality of nucleic acid molecules which are unique in their presence or absence to *Mycobacterium pinnipedii*.

In one embodiment, the invention comprises a kit comprising primers or probes which allow differentiation between *M. tuberculosis* and *M. canettii*. Such a kit may comprise primers comprising or consisting of SEQ ID NOs: 103 and 105 and 97 and 99. Such a kit may also comprise probes comprising or consisting of SEQ ID NOs: 104 and 98.

In one embodiment, the invention comprises a kit comprising primers or probes which allow differentiation between *M. tuberculosis, M. canettii*, and *M. africanum* clade 1. Such a kit may comprise primers comprising or consisting of SEQ ID NOs: 103 and 105, 97 and 99, and 167 and 168. Such a kit may also comprise probes comprising or consisting of SEQ ID NOs: 104, 98 and 169.

In a further embodiment, the invention comprises a kit comprising primers or probes which allow differentiation between *M. caprae. M. bovis, M. bovis* BCG, *M. africanum* clade 2, *M. pinnipedii* and *M. micoti*. Such a kit may comprise primers comprising or consisting of SEQ ID NOs: 164 and 165, 158 and 159, 161 and 162, and 170 and 171. Such a kit may also comprise probes comprising or consisting of SEQ ID NOs: 166, 160, 163 and 172.

In one embodiment any of the kits described above may additionally comprise primers and probes specific for the identification of a member of the MTC. In certain embodiments, the invention provides a kit comprising primers or probes specific for a region of MTC lepA, SEQ ID NO: 47.

In certain embodiments, the invention provides a kit wherein the primers comprise or consist of SEQ ID NOs 164 and 165.

In certain embodiments, the invention provides a kit wherein the probe comprises or consists of SEQ ID NO: 173.

In another embodiment any of the kits described above may additionally comprise primers and probes specific for an IAC.

In certain embodiments, the invention provides a kit comprising primers or probes specific for a region of lepA, SEQ ID NO:84.

In certain embodiments, the invention provides a kit wherein the primers comprise or consist of SEQ ID NOs 164 and 165.

In certain embodiments, the invention provides a kit wherein the probe comprises or consists of SEQ ID NO: 107.

In certain embodiments, the invention provides a kit comprising primers or probes specific for a region of MSMEG_0660, SEQ ID NO: 135.

In certain embodiments, the invention provides a kit wherein the primers comprise or consist of SEQ ID NOs 155 and 156.

In certain embodiments, the invention provides a kit wherein the probe comprises or consists of SEQ ID NO: 157.

Additionally, the invention provides one or more nucleic acid molecules comprising a sequence selected from the group consisting of SEQ ID NOs: 1-78 and 109-154 and sequences complementary to SEQ ID NOs: 1-78 and 109-154, for use in identifying a species of the *Mycobacterium tuberculosis* complex.

Preferably, the one or more nucleic acid molecules correspond to the species of the MTC that is to be identified (for example, *Mycobacterium tuberculosis*—SEQ ID NOs:1-5, 15-39 and 47-53, *M. canettii* SEQ ID NOs: 40-44, 58, 71, 72 and 78-83, *M. bovis*—115 and 148, *M. bovis* BCG—113, 114, *M. caprae* 128, 129, 151 and 152. *M. africanum* clade 1—137, 139, 140, *M. africanum* clade 2—132-134).

DEFINITIONS

As used herein, the following terms and phrases shall have the meanings set forth below. Unless defined otherwise, all technical and scientific terms used herein have the same meaning as commonly understood by one of ordinary skill in the art to which this invention belongs.

The articles "a" and "an" refer to one or to more than one (i.e., to at least one) of the grammatical object of the article. By way of example, "an element" means one element or more than one element.

The terms "comprise" and "comprising" are used in the inclusive, open sense, meaning that additional elements may be included.

The terms "consists" and "consisting of" are used in the exclusive, closed sense, meaning that no additional elements may be included.

The term "including" is used herein to mean "including but not limited to". "Including" and "including but not limited to" are used interchangeably.

A "patient", "subject" or "host" to be tested by the method of the invention may mean either a human or non-human animal and is preferably a mammal, more preferably a human. The human may be a child or an adult.

The *Mycobacterium tuberculosis* complex (MTC) includes species that are known to cause tuberculosis in humans or animals.

The term "nucleic acid molecule target" is used herein to mean a nucleic acid molecule that is specifically amplified and detected to identify species of the MTC. Preferably, the target is a genomic DNA sequence.

By the term "specific for" is meant that primers or probes hybridize to a particular target nucleic acid sequence in preference to other nucleic acid sequences, particularly in preference to another gene implicated in the MTC. A probe or primer which is "specific for" a target sequence preferentially hybridises to that sequence and a primer or probe is considered to be "specific for" a target sequence if it binds to that sequence with greater affinity than a sequence from another gene implicated in the MTC. For example, the probe or primer may bind with 2-fold, 3-fold, 4-fold, 5-fold, six-fold, seven-fold, eight-fold, nine-fold, 10-fold, 15-fold, 20-fold, 30-fold, 30-fold, 40-fold, 50-fold, 60-fold, 70-fold, 80-fold, 90-fold, 100-fold, 200-fold, 300-fold, 400-fold, 500-fold, or 1000-fold greater affinity to the target sequence which it is "specific for" than to a sequence from another gene implicated in the MTC.

The term "primer" is used herein to mean a pair of nucleic acid molecules for use in assisting amplification of specific nucleic acid molecules. Primers hybridize specifically to their target sequence and are "specific for" that sequence. Primers are preferably 100% complementary to the sequence to which they are targeted. However, primers may be less than completely complementary in sequence, and may be, for example, 99%, 98%, 97%, 96% 95%, 94%, 93%, 92%, 91%, 90%, 89%, 88%, 87%, 86%, 85%, 84%, 83% 82%, 81%, 80%, 79%, 78%, 77%, 76%, 75%, 74%, 73%, 72% 71%, 70% or less complementary to the sequence to which they are targeted. Primers are preferably between 1 and 100 base pairs long, more preferably 5-50 base pairs long and even more preferably, between 10 and 30 base pairs long such as 10, 11, 12, 13, 14, 15, 16, 17, 18, 19, 20, 21, 22, 23, 24, 25, 26, 27, 28, 29 or 30 base pairs long.

The term "probe" is used herein to mean nucleic acid molecules for the detection of specific nucleic acid molecules. Probes hybridize specifically to their target sequence and are "specific for" that sequence. Probes are preferably 100% complementary to the sequence to which they are targeted. However, probes may be less than completely complementary in sequence, and may be, for example, 99%, 98%, 97%, 96% 95%, 94%, 93%, 92%, 91%, 90%, 89%, 88%, 87%, 86%, 85%, 84%, 83% 82%, 81%, 80%. 79%, 78%, 77%, 76%, 75%, 74%, 73%, 72%, 71%, 70% or less complementary to the sequence to which they are targeted. Probes are preferably between 1 and 100 base pairs long, more preferably 5-50 base pairs long and even more preferably, between 10 and 30 base pairs long, such as 10, 11, 12, 13, 14, 15, 16, 17, 18, 19, 20, 21, 22, 23, 24, 25, 26, 27, 28, 29 or 30 base pairs long.

Probes are preferably labelled to assist detection. Preferably, they are labelled with a fluorescent dye. Preferably they also comprise a quencher.

The term "sample" is used herein to mean any substance in which a member of the MTC may be found. Preferably the sample is taken from a patient or subject. For example, the sample may be a sputum sample, a pus sample, a lung fluid sample, a lymph node sample, a pleural fluid sample, a pleural tissue sample, a blood sample, a plasma sample, a serum sample, a urine sample, a tissue sample, or a saliva sample.

The term "multiplex in vitro nucleic acid amplification assay" is used herein to mean a single reaction wherein two or more different nucleic acid molecules are amplified and preferably detected. In a multiplex PCR assay, this is a polymerase chain reaction and this is achieved with the use of more than one set of primers. The multiplex assays of the invention may amplify and detect a plurality of nucleic acid molecule targets. A "plurality" means more than 1 and includes, for example, 2, 3, 4, 5, 6, 7, 8, 9, 10, 11, 12, 13, 14, 15 or more targets. In certain embodiments the invention may require the performance of one or more separate "multiplex in vitro nucleic acid amplification assays".

When referring to nucleic acid molecule targets, the term "present in" is used herein to mean found in the genome of the organism in question. Preferably the genomic sequence is identical to the target but it may be 100-95%, 100-90%, 100-80%, 100-70%, 100-60% or 100-50% identical to the target.

"Microarrays" are a collection of small microscopic features (DNA/RNA/Proteins) which are usually probed with target molecules to produce data. Some examples of Microarrays are printed microarrays, in situ-synthesized oligonucleotide microarrays, high density bead arrays and electronic microarrays (Miller & Tang, 2009). Whole genome microarrays have been carried out in relation to *M. tuberculosis* and *M. bovis* BCG which identified the initial Regions of Difference (RD's) (Behr et al., 1999), which are now used for identifying particular members of the *Mycobacterium Tuberculosis* Complex (Pinsky & Banaei, 2008).

BRIEF DESCRIPTION OF THE FIGURES

FIG. 1—(A) an alignment of publicly available wbbl1 sequences identifying the region of wbbl1 unique to *M. tuberculosis* and *M. canettii*. (B) Sequencing analysis and alignment of the wbbl1 region unique to *M. tuberculosis* and *M. canettii*.

FIG. 2—an alignment of publicly available lepA sequences with the forward and reverse primers and the MTC, IAC and *M. caprae* lepA probes annotated. Bases that differ from the primers or the MTC probe are highlighted in black. Bases that differ from the IAC probe are highlighted in black and italicised.

FIG. 3—(A) An alignment of publicly available lpqT sequences identifying the region of lpqT which is deleted in *M. bovis, M. bovis* BCG and *M. caprae*. (B) Sequencing analysis and alignment of the lpqT deletion in *M. bovis, M. bovis* BCG and *M. caprae.*

FIG. 4—An alignment of publicly available RD701 sequences identifying the region uniquely deleted from *M. africanum* clade 2. Where intact this is a 2081 bp region of sequence. In *M. africanum* clade 2 where the deletion is present this is 320 bp region. Alignment is complicated because, while there are 100% homology to members of the MTC, this region inserts in different areas of the genome and PE proteins affect alignments.

FIG. 5—(A) An alignment of publicly available RD713 sequences identifying the RD713 region unique to *M. africanum* clade 1. (B) Sequencing analysis and alignment of the RD713 region unique to *M. africanum* clade 1.

FIG. 6—(A) An alignment of publicly available RD1 sequences identifying the region present in *M. caprae* and *M. bovis* but not in *M. bovis* BCG. (B) Sequencing and alignment of the RD1 region present in *M. caprae* and *M. bovis* but not in *M. bovis* BCG.

EXAMPLES

General Techniques

Figure 7A:
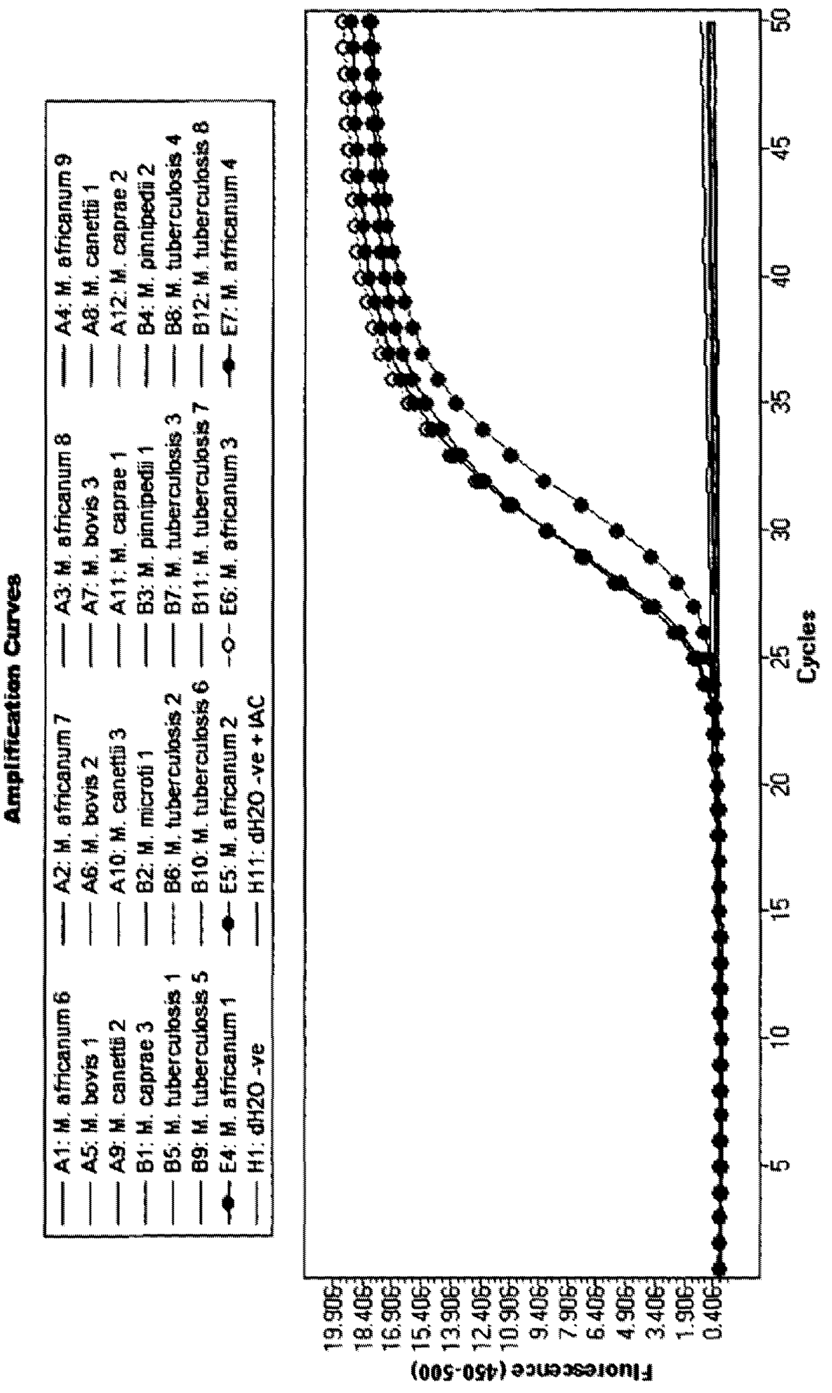
FIG. 7—(A) Amplification curves for *M. africanum* clade 1 (circle) using a region of RD 713 in Cyan 500 channel (450-500); (B) Amplification curves for *M. africanum* clade 1 (circle), *M. tuberculosis* (triangle) and *M. canettii* (rectangle) using the wbbl1 gene in FAM channel (483-533); (C) Amplification curves for all MTC using the lepA gene in HEX channel (523-568), with the non-template control highlighted with stars through line; (D) Amplification curves for *M. canettii* specific assay in ROX channel (558-610), with *M. canettii* strains depicted with rectangles; (E) Amplification curves for IAC in Cy5 channel (615-670) with the non-template control highlighted with stars through line.

Bacteriol Strains, Culture Media and Growth Conditions

One hundred and nineteen MTC isolates (60 *M. tuberculosis,* 14 *M. bovis,* 7 *M. bovis* BCG (of which 2 were from DSMZ and cultured in this study), 8 *M. canettii,* 5 *M. caprae,*

14 *M. africanum*, 6 *M. microti* and 5 *M. pinnipedii*), 44 NTM and 17 other bacteria were used in this study (Tables 2 and 3). Of the 119 MTC, 36 strains previously characterised by spoligotyping, were provided by the National Institute for Health and the Environment, RIVM the Netherlands and 56 strains were provided from the National Reference centre for Mycobacteria, Borstel, Germany. All other MTC strains, provided by Mario Vaneechoutte, were clinical isolates which had been previously characterised to species level, with the exception of the 2 *M. bovis* BCG which were purchased from DSMZ. All NTM were purchased from culture collections (DSMZ) and grown on middlebook agar/broth at either 30° C. or 37° C. or DNA was supplied by Mario Vaneechoutte. Mycobacteria considered fast growers were cultured for 3-6 days, whereas slow growers were incubated for six weeks, or until sufficient growth was visible. All media were purchased from BD Biosciences (Oxford, United Kingdom). For all other bacterial species tested, DNA was provided from stocks held within this laboratory.

DNA Isolation and Quantification

Genomic DNA from NTM and 2 *M. bovis* BCG cultures was isolated from 1 ml of culture (Middlebrook 7H9 broth, Becton Dickenson), using a modified procedure combining mechanical lysis (IDI lysiskit, GeneOhm, Quebec, Canada) and purification using a DNeasy Blood and Tissue kit (Qiagen, Hilden, Germany). Briefly 1 ml culture was centrifuged in a benchtop centrifuge (Microcentrifuge 5415, Eppendorf) at 13,000 rpm for 3 min. The supernatant was discarded and the pellet resuspended in 250 μl GeneOhm sample buffer. The suspension was transferred to a GeneOhm lysis tube and bead beaten (Mini-Bead-Beater-16™, Stratech, UK) for 3 min. After bead-beating 200 μl was transferred to a sterile microcentrifuge tube and steps 3-8 (add 200 μl of buffer AL and 200 μl ethanol and mix gently by vortexing) for purification of total DNA from animal tissue using the DNeasy Blood and Tissue kit were followed according to the manufacturer's instructions. DNA concentrations were determined using the PicoGreen dsDNA Quantitation Kit (Molecular Probes, Eugene, Oreg., USA) and the TBS-380 mini-fluorometer (Invitrogen Corporation, California, USA). All DNA samples were stored at −20° C.

Conventional and Real-Time PCR Primers and Hydrolysis Probes

Oligonucleotide primers and hydrolysis probes were designed in accordance with the general recommendations and guidelines outlined (Dorak, 2006; Robertson & Walsh-Weller, 1998). All primers and probes (Table 4) used in this study were supplied by MWG-BIOTECH AG (Essenberg, Germany). Sequence data for real-time PCR assay design was generated in-house or was obtained from the National Centre for Biotechnology Information (NCBI) along with BLAST searches carried out on the Sanger website, where partial sequences for *M. canettii*, *M. africanum* and *M. microti* were available. The primers used for the real-time PCR assays were also used in conventional PCR for generating sequence information for each of the assays used in this study. In addition, sequencing primers were designed to span the full 2869 bp *M. canettii* specific sequence identified in this study to evaluate if this region is conserved in all *M. canettii* strains in addition to identifying regions which are 100% homologous in each strain.

PCR products were generated as discussed below, followed by purification using high pure PCR product purification kit (Roche Diagnostics Ltd., West Sussex, United Kingdom). The purified products were sent for sequencing externally (Sequiserve, Vaterstetten, Germany).

Conventional PCR

Conventional PCR was performed using the sequencing primers outlined in Table 4 on the iCycler iQ thermal cycler (Bio-Rad Laboratories Inc., California, USA). All reactions were carried out in a final volume of 50 μl, containing 5 μl 10× buffer (15 mM $MgCl_2$), 1 μl forward and reverse primers (10 μM), 2 μl Taq DNA polymerase (1 U/μl, Roche Diagnostics, Mannheim, Germany), 1 μl dNTP mix (10 mM: deoxynucleoside triphosphate set, Roche), 2 μl of template DNA, 38 μl Nuclease free water (Applied Biosystems/Ambion, Texas, USA). The cycling parameters consisted of initial denaturation 95° C. for 5 mins, followed by 35 cycles of denaturation 94° C. (1 min), amplification 55° C. (1 min), and extension 72° C. (1 min), followed by a final elongation at 72° C. for 10 min.

Development of an Internal Amplification Control (IAC) for Real-Time PCR

An internal control was designed and incorporated in the multiplex assay designed to monitor for PCR inhibition and PCR efficiency. The MSMEG_0660 gene was chosen as the target for the IAC because this gene is present only in *M. smegmatis*. This gene is thought to code for an extracellular solute-binding protein. Titrations of MTC and IAC DNA were performed to determine the optimum concentration of IAC target per reaction such that the IAC is always detected without impacting on detection of the primary MTC target. An internal control concentration of 100 genome equivalents per reaction allowed for the detection of the IAC all real-time PCR experiments performed.

As this is a non-competitive IAC, in order for a result to be considered valid using this assay, a positive signal must be obtained in the Cy5 detection channels on the LightCycler 480. If the internal control is not detected, the result is considered invalid and must be repeated (Hoorfar et al., 2004; O'Grady et al., 2008). *M. smegmatis* could also be used as a process control to monitor for DNA extraction efficiency from biological samples.

Real-Time PCR

Monoplex real-time PCR was performed on the LightCycler 2.0 Instrument (Roche Diagnostics) using the LightCycler® TaqMan Master kit (Roche Diagnostics). A final volume of 20 μl was used in each reaction, containing Master mix 5×, forward and reverse primers (0.5 mM final conc.), FAM labelled probe (0.2 mM final conc.), template DNA (2 μl) and the volume adjusted to 20 μl with the addition of nuclease free $dH_2O$. The cycling parameters consisted of incubation for 10 min at 95° C. to activate enzymes and DNA denaturation followed by 50 cycles of 95° C. for 10 s and 60° C. for 30 s, followed by a cooling step at 40° C. for 10 s. The temperature transition rate for all cycling steps was 20° C./s.

Multiplex real-time PCR reactions were carried out on the LightCycler 480 using LightCycler® 480 Probes Master kit (Roche Diagnostics). A final volume of 40 μl was used for each multiplex experiment. The optimised master mix contained 2× LightCycler 480 Probes Master (6.4 mM $MgCl_2$), forward and reverse primer (0.5 mM final conc.), FAM labelled probe (0.4 μM final conc.), HEX, ROX and CY5 labelled dyes (0.2 μM final conc.), template DNA (MTC 2 μl, IAC DNA 2 μl, NTM 10 μl) and the volume adjusted to 40 μl with the addition of nuclease free $dH_2O$. The internal control DNA was diluted to contain 500 genome equivalents per 2 μl and the NTM contained 10,000 genome equivalents per 10 μl.

The cycling parameters used were the same as those used in the LightCycler 2.0, however the temperature transition rate, referred to as the ramp rate on the LightCycler 480 were variable, for the initial incubation the ramp rate was 4.8° C./s, during the 50 cycles at 95° C., the ramp rate was 4.8° C./s and at 60° C. 2.5° C./s and the final cooling step had a ramp rate of 2.0° C./s. Prior to experimental analysis on the LightCycler 480, a colour compensation file was generated using the technical note outlined in the Advanced Software Functionalities of the operator manual.

Example 1

Diagnostics Target Identification

A number of approaches were used to search for and identify sequences that would allow the differentiation of the members of the MTC. To identify targets suitable for the detection of *M. tuberculosis* and other species of the MTC and that are suitable for use in a multiplex in vitro nucleic acid amplification assay, approximately 3000 genes were evaluated in in silico analysis.

It was necessary to identify genomic regions that are deleted in certain species of the MTC but present in others. Potential target regions were identified using the Mycobacterial Genome Divergence Database (MGDD) (http://mirna-.jnu.ac.in/mgdd/), which allowed for identification of insertions, deletions and single nucleotide polymorphisms between *M. tuberculosis, M. bovis* and *M. bovis* BCG. Potential target regions were also identified using the web based version of the Artemis comparison tool, WebACT (http://www.webact.org/WebACT/home). Sequence information was retrieved from the *M. africanum* and *M. microti* genomes currently being sequenced by the Welcome Trust Sanger Institute (using the Basic Local Alignment Search Tool (BLAST) tool available on the Sanger website) to determine if the candidate regions identified for *M. tuberculosis* detection were specific, based on in silico analysis. Sequence information for the remaining members of the complex, namely, *M. canettii, M. caprae* and *M. pinnipedii*, is not available, so specificity of potential targets was determined empirically and further validated through sequencing.

Specific parameters were employed for the in silico analysis. Insertions or deletions were preferred as such genomic events are considered to be unidirectional events. Therefore, insertions and deletions are more likely to be unique to an individual species of the MTC. Single nucleotide polymorphisms (SNPs) were only accepted when insertions or deletions could not be identified. This allows for the potential geographical nucleotide sequence variation which is often observed. Nucleic acid diagnostics targets had to be specific for the species of the MTC to be identified. As described above, empirical sequencing analysis then had to be carried out for *M. canettii, M. caprae* and *M. pinnipedii.*

For each putative target identified, alignments were carried out using clustalW multiple sequence alignment programme (http://www.ebi.ac.uk/Tools/clustalw2/index.htm and PCR primers and probes were designed (Table 4).

Of the approximately 3000 genes analysed in this study, very few met the criteria imposed and were suitable for use in multiplex in vitro nucleic acid amplification assays capable of identifying species of the MTC. The vast majority of the sequences studied with the in silica and empirical sequencing analyses were not found to be unique to a species of the MTC. Of the few that were initially found to be unique, a number were later found to not be conserved between clinical isolates when PCR assays were developed and so the assays did not successfully detect all the isolates.

Diagnostic Target Identification—wbbl1

For the specific detection of *M. tuberculosis* and *M. canettii*, the wbbl1 gene (RV 3265c) was selected. Although present in all members of the MTC, it has surprisingly been identified that there is a 12 base pair region present in *M. tuberculosis* and *M. canettii* which has been deleted in other members of the MTC. Therefore, this gene allows for the specific detection of *M. tuberculosis* and *M. canettii*. The wbbl1 gene encodes rhamnosyl transferase, which inserts rhamnose into the cell wall and is thought to be essential for Mycobacterial viability (Ma et al., 2002). Nucleotide sequence analysis of members of the MTC surprisingly revealed a 12 base pair region of the wbbl1 gene present only in *M. tuberculosis* and *M. canettii*, which has been deleted in all other members of the MTC.

As demonstrated in FIG. 1A, in silica analysis revealed a region deleted in all the species tested other than *M. tuberculosis*. Sequencing analysis, as detailed in FIG. 1B, confirmed that this region is specific to *M. tuberculosis* and *M. canettii* and is deleted in *M. caprae* and *M. pinnipedii.*

Diagnostic Target Identification—$RD^{canetti1}$

To identify MI tuberculosis and *M. canettii* specifically and to distinguish between them, a novel target specific for *M. canettii* was also required as the target wbbl1 was empirically determined to detect both *M. tuberculosis* and *M. canettii*. When sequence information became publicly available on the Sanger website for *M. canettii*, a number of block sequence regions available were evaluated. These blocks of sequence information were BLAST (NCBI http://www.ncbi.nlm.nih-.gov/) analysed to identify a potential specific target for *M. canettii.*

The *M. canettii* specific diagnostic target identified herein is a region of the genome that appears to be deleted in all other members of MTC. This 2869 bp region was discovered while mapping $RD12^{can}$ to the unfinished genome sequence of *M. canettii* available on the Sanger website. This region appears to be a novel RD specific for *M. canettii*. The *M. canettii* genome is not annotated to date; therefore the function of the gene/s in this region are unknown.

To be able to distinguish *M. canettii* from *M. tuberculosis* and the other members of the MTC, and therefore allow the specific diagnosis of *M. canettii* and *M. tuberculosis*, the selected region should preferably be shared by all *M. canettii* isolates. To identify whether this was true for $RD^{canetti1}$, the region was sequenced using the primers listed in Table 4 for the 5 *M. canettii* strains used in this study. Sequence analysis revealed 100% homology between the 5 strains and the sequence available on the Sanger website (compare SEQ ID NOs 78-83). As this sequence is present in the 5 *M. canettii* strains and is 100% homologous, we propose this to be a novel RD (RD) that allows the discrimination of *M. canettii* from *M. tuberculosis* and the other members of the MTC and therefore allows the specific diagnosis of *M. canettii* and *M. tuberculosis.*

Diagnostic Target Identification—MTC lepA

In order to identify a target for collective detection of the MTC, a number of housekeeping genes which are highly conserved throughout the *Mycobacterium* genus were evaluated.

The diagnostic target gene used in this study for detection of the MTC along with detection of the internal amplification control was lepA (Rv2404c). LepA is an elongation factor required for accurate and efficient protein synthesis capable of inducing back-translocation of mistranslocated tRNA's. The LepA gene is present in all bacteria sequenced to date and codes for one of the most conserved proteins in bacteria (55-68% amino acid sequence homology between bacteria), with a homologue (Guf1) found in higher organisms (Qin et al., 2006).

As shown in the alignments of FIG. 2, analysis of the publicly available lepA sequences and the sequences generated by the inventors revealed that enough sequence heterogeneity exists between the species of the MTC and other species to be used as a internal amplification control (here *M. smegmatis*) for the design of independent, specific probes. There is also enough homology present, flanking these probe regions, to allow the design a single set of primers to amplify both the MTC and internal amplification control targets. This allows a reduction in the complexity of the multiplex PCR assay with a reduction in the number of primer pairs required.

The techniques and methods described in the Example above surprisingly demonstrate that sufficient genetic variation exists between the members of the MTC to identify specific species of the MTC in a multiplex in vitro nucleic acid amplification assay. The teaching provided herein above could be used to identify other similar sequences that also allow the discrimination of the different members of the MTC.

Diagnostic Target Identification—RD713

For identification of the newly defined *M. africanum* clade 1 isolates RD713 was selected. In-silico analysis, in addition to literature describing this RD, demonstrated its potential for the specific identification of *M. africanum* clade 1 isolates (de Jong et al., 2010; Vasconcellos et al., 2010). While another RD, RD711, has been described for specific detection of *M. africanum* clade 1, this RD is not present in all *M. africanum* clade 1 strains. RD713 relates to a 2799 bp region of *M. africanum* clade 1. In other members of the MTC such as *M. tuberculosis* H37Rv, where this deletion is not present, this region relates to a 4248 bp region of nucleotide sequence. In other members of the MTC, owing to the complex region incorporated in this RD, no amplification will be observed for this region (Vasconcellos et al., 2010). As shown in FIG. 5 (A) RD713 contains a region unique to *M. africanum* clade 1, which is also conserved between *M. africanum* clade 1 isolates.

Diagnostic Target Identification—*M. caprae* lepA

It was discovered that *M. caprae* contains an SNP which allows its differentiation from all other members of the MTC. As seen in FIG. 2, there is a C to T substitution at position 691 of the lepA gene nucleotide sequence specific for *M. caprae*. The probe for identifying *M. caprae* lepA targets this SNP.

Diagnostic Target Identification—lpqT lpqT (Rv1016c) was selected to identify the presence of *M. bovis, M. bovis* BCG and *M. caprae*. While the lpqT gene is present in all members of the MTC, it was surprising to observe from in silica analysis, that a 5 bp deletion was present in *M. bovis* and *M. bovis* BCG. Sequence analysis of nucleotide sequence generated in this study revealed that this deletion was also present in the phylogenetically related *M. caprae*. lpqT belongs to a group of proteins known al lipoproteins (Garnier et al., 2003) which are present in all bacteria (Rezwan et al., 2007). FIG. 3 A shows that a region of lpqT is deleted in *M. bovis, M. bovis* BCG and *M. caprae.*

Diagnostic Target Identification—RD1

A region of RD1 was selected to identify the presence of *M. bovis* BCG in a sample. In all *M. bovis* BCG strains RD1, which contains the genes Rv 3871-3879c, is deleted (Behr et al., 1999). The loss of RD1 has been proposed to be associated with the attenuation of this strain (Pym et al., 2002). Interestingly, regions of RD1 are also deleted in *M. microti*, such as the region targeted in this invention to differentiate *M. bovis* and *M. caprae* from *M. bovis* BCG. RD1 is present in all other members of the MTC, however sequence heterogeneity is observed from the publicly available *M. canetti* sequence as demonstrated in FIG. 6 (A). FIG. 6 (A) shows a region of RD1 which is present in *M. caprae* and *M. bovis* but not in *M. bovis* BCG.

Diagnostic Target Identification—RD701

For the specific detection of *M. africanum* clade 2 isolates, two RDs could potentially have be used, namely RD701 and RD702. RD701 was selected to identify the presence of *M. africanum* clade 2. Where intact this is a 2081 bp region of sequence. In *M. africanum* chide 2 where the deletion is present this is 320 bp region. Where RD702 is intact a PCR product of 2101 bp is observed in members of the MTC, whereas this region is 732 bp in *M. africanum* clade 2 (Vasconcellos et al., 2010). In this invention RD701 was chosen for the specific detection of *M. africanum* clade 2 isolates as a previous study has shown an *M. africanum* like organism which has RD702, RD711 and RD713 present (Vasconcellos et al., 2010). In this instance the use of RD702 may in fact misclassify the *M. africanum* clade present. FIG. 4 highlights a region of RD701 which is uniquely deleted from *M. africanum* clade 2.

Example 2

Assay Design and Development for Multiplex 1

Nucleotide sequences generated in-house and publicly available sequences from GenBank were aligned for primer and probe design for real-time PCR assays.

TaqMan probes were designed to be specific for each assay following design guidelines.

MTC Assay—lepA

For the MTC assay, PCR primers MTC_Fw (SEQ ID NOs: 164) and MTC_Rv (SEQ ID NO: 165), were designed to amplify a 155 bp fragment of the lepA gene for all members of the MTC. The MTC_Fw primer was located at positions 618-634 bp and the MTC_Rv primer located at positions 755-772 bp of the *M. tuberculosis* H37RV lepA gene.

*M. tuberculosis, M. canettii* and *M. africanum* Clade 1 Assay—wbbl1

For the *M. tuberculosis, M. canettii* and *M. africanum* clade 1 assay, wbbl1_Fw (SEQ ID NO: 97) and wbbl1_Rv (SEQ ID NO: 99) were designed to amplify a 146 bp fragment of the wbbl1 gene. The wbbl1_Fw primer was located at positions 16-34 bp and the wbbl1_Rv primer located at positions 141-161 bp of the *M. tuberculosis* H37RV wbbl1 gene.

*M. canettii* Assay—$RD^{canetti1}$

The *M. canettii* specific assay was designed to amplify a 128 bp fragment of a 2869 bp region of the genome identified in this study as specific to *M. canettii*. This 2869 bp region of the genome has been mapped to the *M. tuberculosis* H37Rv genome and is inserted between Rv0150c (hypothetical protein) and Rv0151c (gene name PE1, a PE family protein) at position 177,445 bp on the *M. tuberculosis* H37Rv genome.

*M. africanum* Clade 1 Assay—RD713

For the *M. africanum* clade 1 specific assay, PCR primers RD713_Fw (SEQ ID NO: 167) and RD713 Rv (SEQ ID NO: 168), were designed to amplify a 138 bp fragment of RD713 (2800 bp in *M. africanum* clade 1 and 4248 bp in *M. tuberculosis*_H37Rv). Based on the publicly available *M. africanum* clade 1 RD713 nucleotide sequence the RD713_Fw primer is located at positions 2326-2342 bp and the RD713 RV primer is located at positions 2446-2463 bp.

All real-time PCR assays were initially tested in a monoplex format, to evaluate their specificity, using probes labelled with FAM and Black Hole Quencher 1 (BHQ1). All primers used in this study were designed to have a melting temperature (Tm) of between 58-61° C., with all probes designed to have a Tm of 4-7 degrees higher. These parameters were adhered to during the design of monoplex assays so that the assays could be easily multiplexed after specificity and sensitivity testing was complete. After the monoplex real-time PCR assays were optimised, four of the five assay probes were labelled with different fluorescent dyes to allow for multiplex real-time PCR. The MTC probe was labelled with HEX and BHQ1, the *M. canettii* specific probe with ROX and BHQ2, the *M. africanum* clade 1 with Cyan 500 and BBQ and the IAC probe with Cy5 and BHQ2. While the guidelines for primer and probe design were adhered to as closely as possible, the high GC content (60-65%) of the *Mycobacterium* species did have an impact on assay design. The wbbl1 specific probe was based on a region present in *M. tuberculosis, M. canettii* and *M. africanum* clade 1 which is deleted in other MTC, that is very G/C rich making probe design difficult. This probe was labelled with FAM and double the standard probe concentration (0.4 μM/reaction) was used to improve the endpoint fluorescence, sensitivity and robustness of the assay. For optimal performance of the multiplex the half the standard probe concentration (0.1 μM/reaction) was required for the HEX labelled MTC assay.

Example 3

Assay Design and Development for Multiplex 2

Nucleotide sequences generated in-house and publicly available sequences from GenBank were aligned for primer and probe design for real-time PCR assays.

TaqMan probes were designed to be specific for each assay following design guidelines.

*M. caprae, M. bovis* & *M. bovis* BCG Assay—lpqT lpqT_FW (SEQ ID NO: 158) and lpqT_RV (SEQ ID NO: 159) were designed to amplify a 141 bp fragment of the lpqT gene for the identification of *M. bovis, M. bovis* BCG and *M. caprae* (positions 100-117 bp and 224-240 bp of the *M. bovis* AF2122/97 lpqT gene).

*M. caprae* Assay—lepA

The *M. caprae* specific assay PCR primers, MTC_Fw (SEQ ID NO: 164; position 618-634 bp of the lepA gene of *M. tuberculosis* H37Rv) and MTC_Rv (SEQ ID NO: 165; position 754-772 bp), were designed to amplify a 155 bp fragment of the lepA gene.

*M. bovis* BCG Assay—RD1

The RD1 assay was designed to amplify a 117 bp region of the Rv3876 gene, a conserved hypothetical protein, part of RD1, absent in all *M. bovis* BCG strains. The RD1_Fw primer (SEQ ID NO: 161) was located at position 1416-1433 bp and the reverse primer RD1_Rv (SEQ ID NO: 162) between 1516-1532 bp of the *M. tuberculosis* H37 Rv 3876 gene.

*M. africanum* Clade 2 Assay—RD701

The *M. africanum* clade 2 specific assay was designed to amplify a 81 bp region of the publicly available RD701 nucleotide sequence (320 bp region in *M. africanum* clade 2, 2081 bp region in *M. tuberculosis*_H37Rv). Based on the publicly available *M. africanum* clade 2 RD701 nucleotide sequence the RD701_Fw primer (SEQ ID NO: 170) is located at positions 119-135 bp and the RD701_RV (SEQ ID NO: 172) primer is located at positions 182-199 bp.

While the guidelines for primer and probe design were adhered to as closely as possible, the high G/C content *Mycobacterium* species had an impact on assay design. The lpqT specific probe was designed spanning the deletion junction of a region deleted in *M. bovis. M. bovis* BCG and *M. caprae* and present in the other members of the MTC, that was very G/C rich, making probe design difficult. The lpqT probe, therefore, had a relatively high Tm, but this did not impact on assay performance. The *M. caprae* specific probe targeted an SNP in the lepA gene. Avoiding cross reaction of the *M. caprae* probe with other members of the MTC proved challenging. A number of probes were designed and tested and the optimum probe was chosen empirically based on specificity and sensitivity results. The optimum probe was designed complementary to the + strand of the lepA gene as the resulting G/A mismatch, that occurred in the presence of non-target MTC DNA, was more destabilising to the probe than the C/T mismatch, hence improving specificity. The probe was designed to have a Tm of 60.1° C., only slightly above the annealing temperature of the assay (60° C.), allowing the probe to hybridise to exactly matched sequence only, therefore maximising the specificity effect of the SNP. This did, however, slightly reduce probe binding efficiency, leading to a small reduction in sensitivity.

Example 3

Internal Control (IAC)

An internal control was designed and incorporated in both of the multiplex assays. It was designed to monitor for PCR inhibition and PCR efficiency. The lepA gene was chosen as the target for the IAC because enough sequence heterogeneity exists between the *M. smegmatis* and MTC lepA gene sequences for the design of independent, specific probes. There was also enough homology present, flanking these probe regions, to design one set of primers to amplify both MTC and IAC targets. This resulted in less primer pairs being required in the multiplex PCR reducing assay complexity.

For the IAC assay, PCR primers, IAC_Fw (SEQ ID NO: 155) and IAC_Rv (SEQ ID NO: 156), were designed to amplify a 157 bp region of the *M. smegmatis* MSMEG__0660 gene. The IAC_Fw primer was located at positions 497-513 bp and the reverse primer between positions 636-653 bp of the publicly available *M. smegmatis*_MC2__155 MSMEG__0660 gene.

Titrations of MTC and IAC DNA were performed to determine the optimum concentration of IAC target per reaction such that it is always detected without impacting on detection of the primary MTC target. An internal control concentration of 500 genome equivalents per reaction allowed for the detection of the IAC at low concentrations or the absence of primary target.

In order for a result to be considered valid using this assay, a positive signal must be obtained in at least one of the four detection channels on the LightCycler 480. If none of the assay targets or the internal control are detected, the result is considered invalid and must be repeated (Hoorfar et al., 2004; O Grady et al., 2008). *M. smegmatis* could also be used as a process control to monitor for DNA extraction efficiency from biological samples.

Example 4

Sensitivity and Specificity of the Assays

Figure 7:
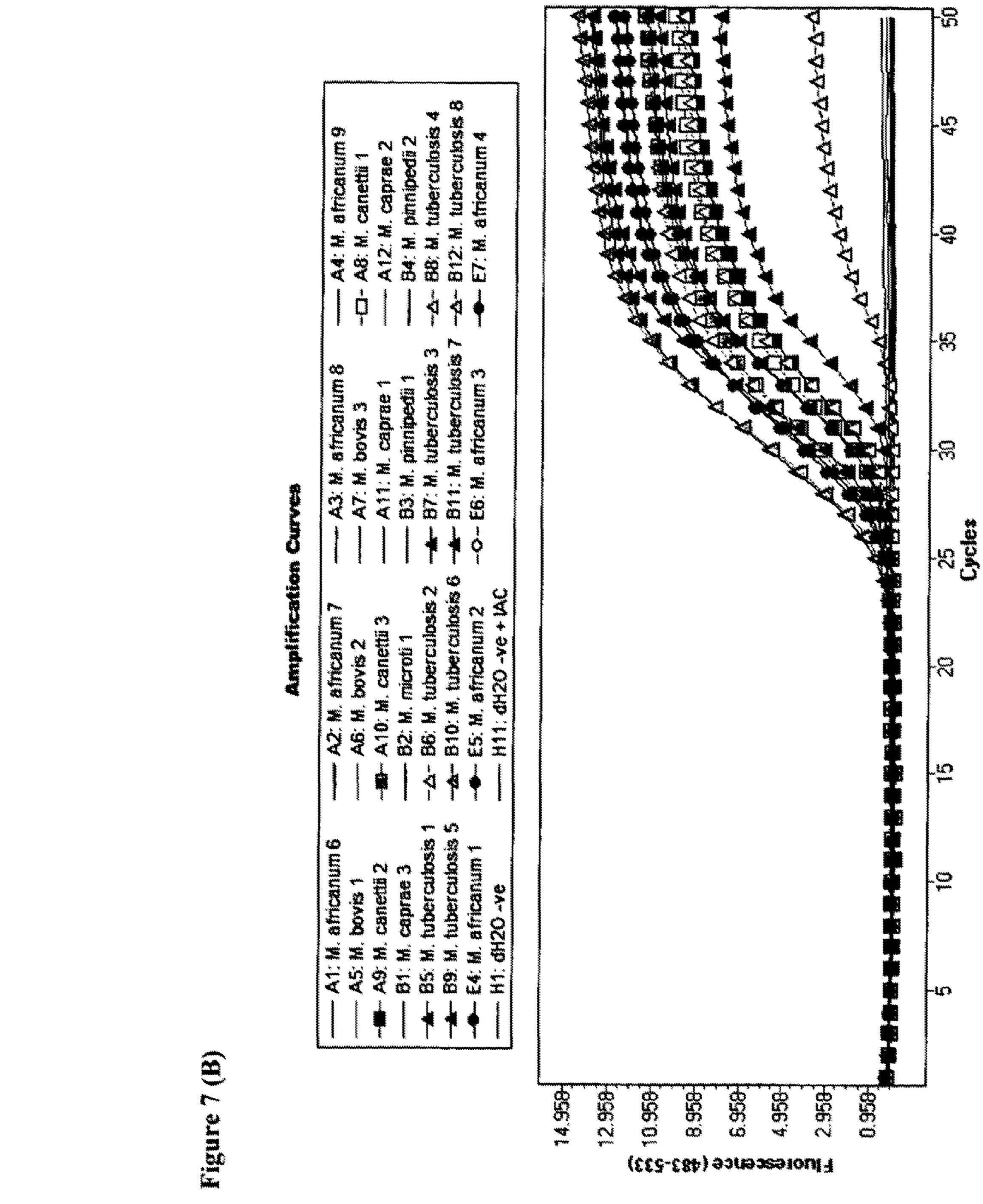
Figure 7:
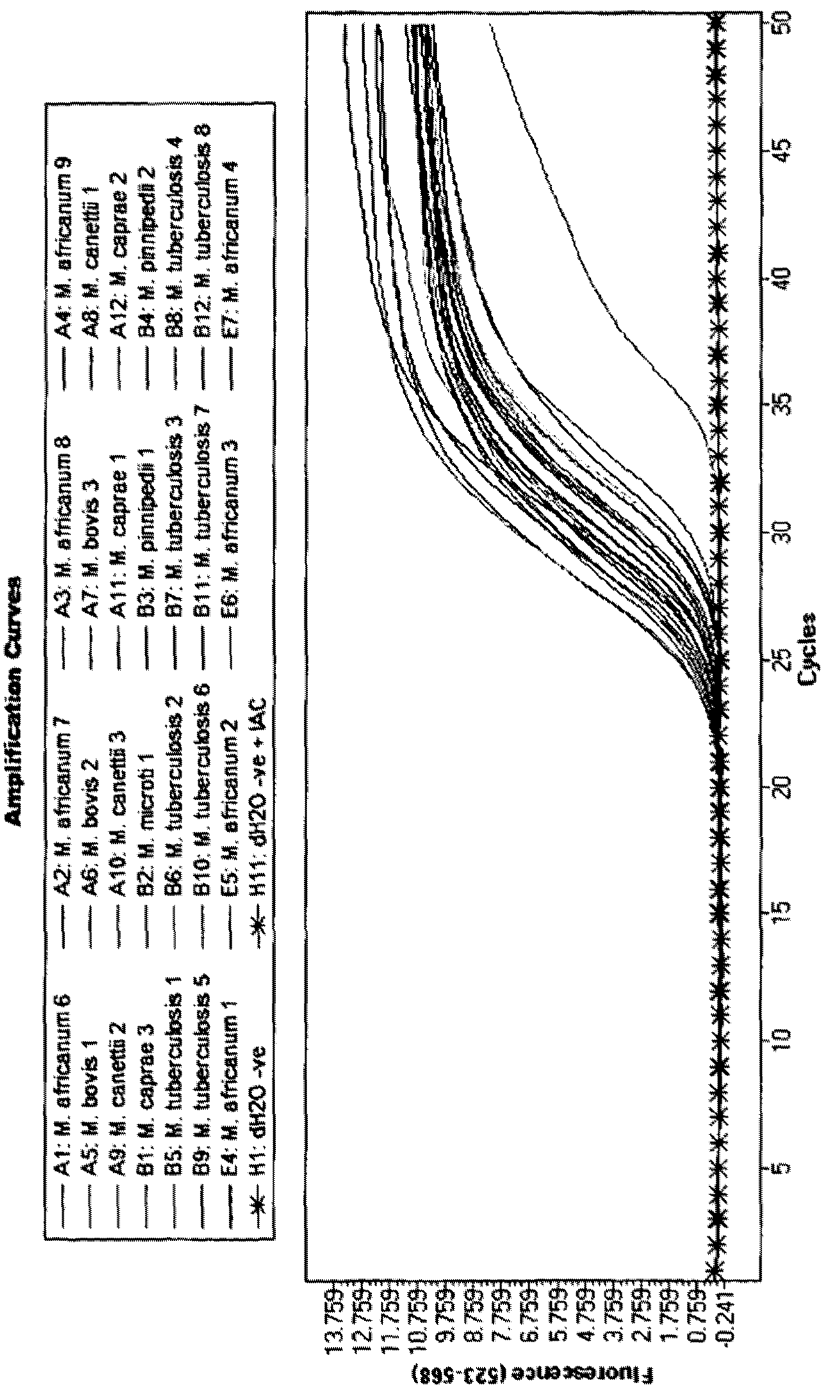
Figure 7:
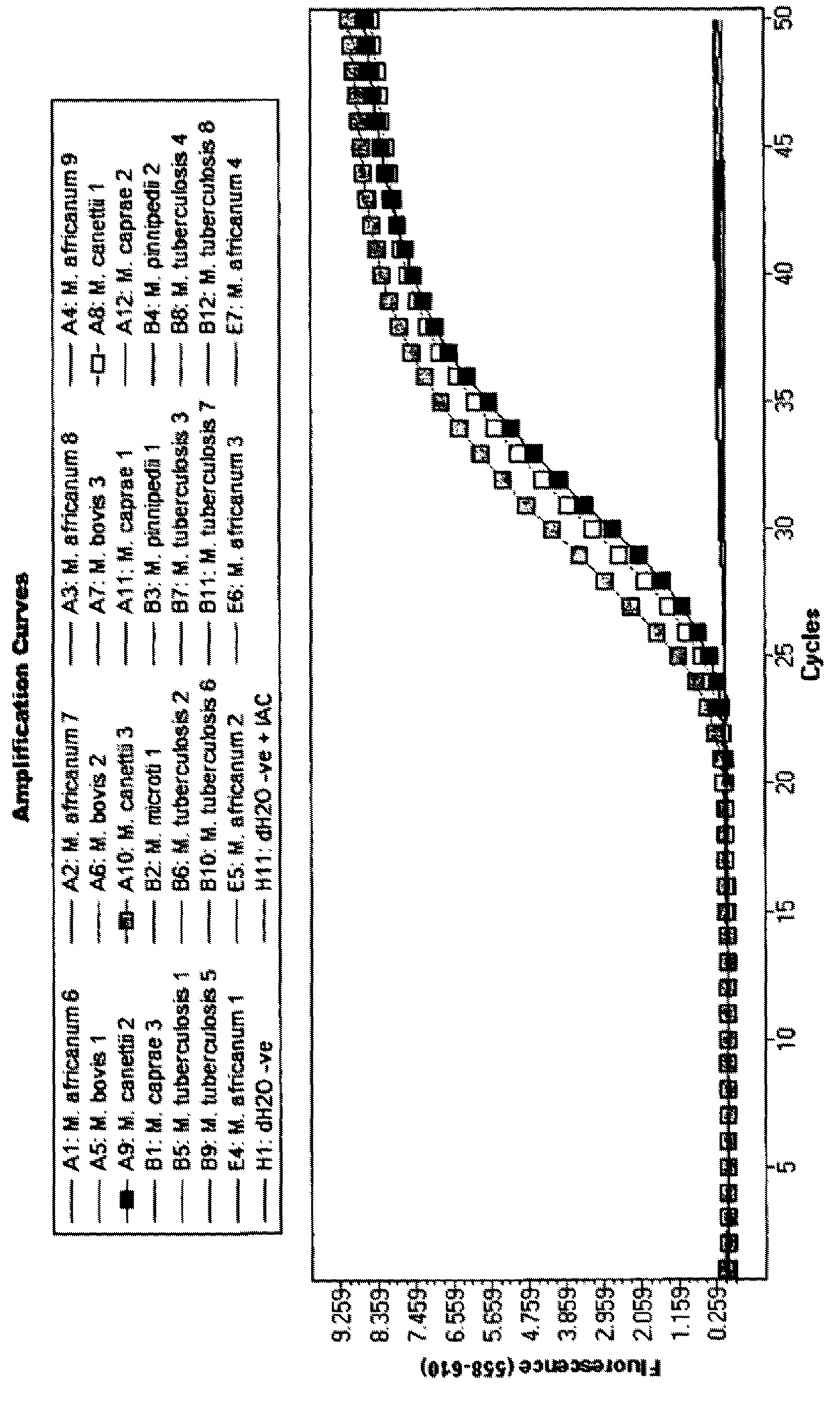
Figure 7:
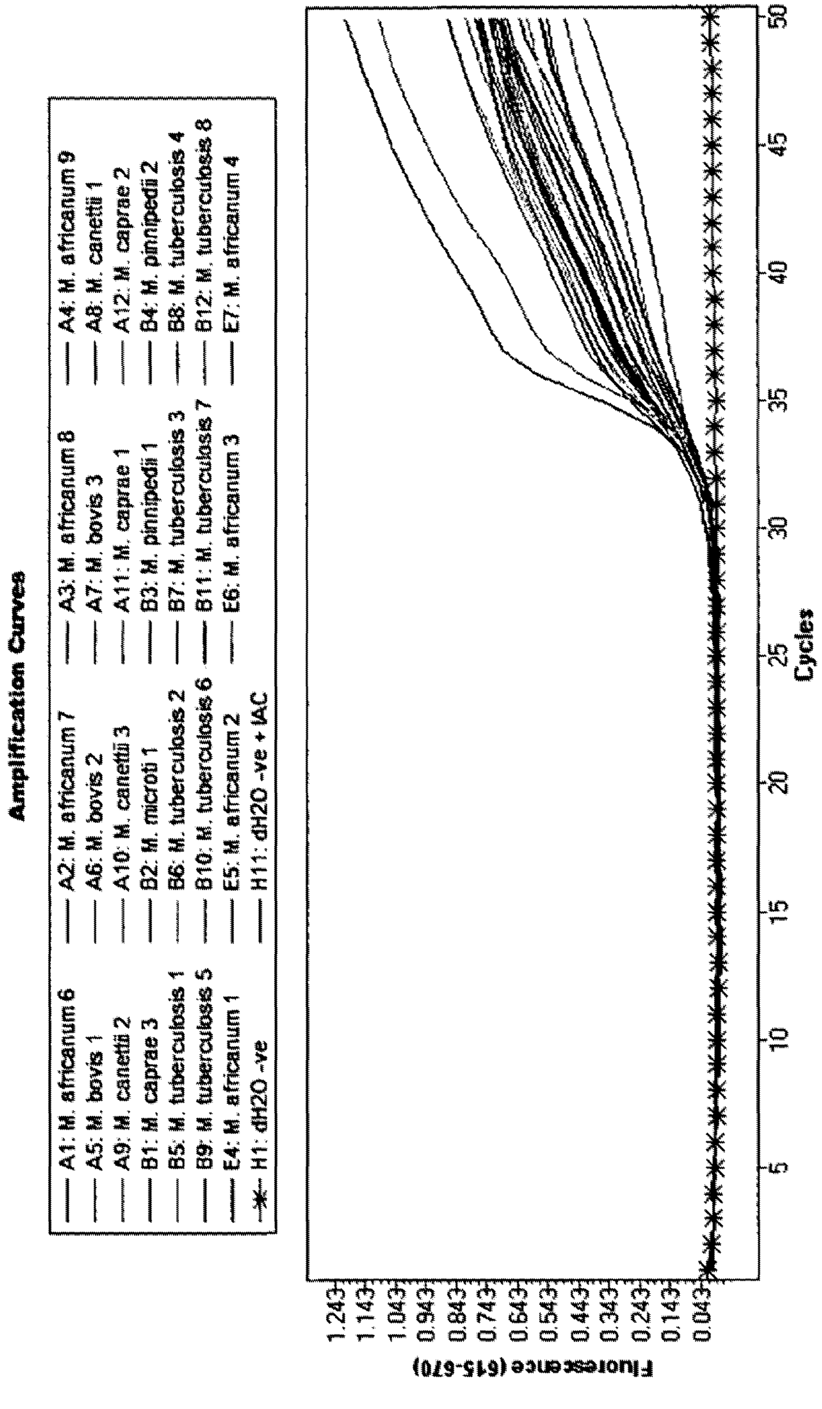

The specificity of each real-time PCR assay was confirmed both in monoplex and multiplex formats using the specificity panel listed in Tables 2 and 3. Using multiplex 1, the 119 MTC strains were all detected in the MTC assay, a representation of this can be seen in FIG. 7 (C) and 44 NTM and 17 other bacterial species were not detected. The wbbl1 assay was specific for the detection of the 60 *M. tuberculosis* the 8 *M. canettii* and 5 *M. africanum* clade 1 strains. A representation of this can be seen in FIG. 7 (B), with 8 *M. tuberculosis* strains (triangle) 3 *M. canettii* strains (rectangle) and 4 *M. africanum* clade 1 (circle). The remaining members of the MTC, the NTM and closely related species were not detected. The *M. canettii* assay was specific for the *M. canettii* isolates and did not cross-react with the specificity panel. A representation of this can be seen in FIG. 7 (D) with 3 *M. canettii* represented with rectangles. The *M. africanum* clade 1 specific assay targeting a region of RI) 713 was specific for the detection of *M. africanum* clade 1 isolates. A representation of this can be seen in FIG. 7 (A) with 4 *M. africanum* isolates represented with circles. The specificity of the IAC assay was tested using the full specificity panel and was specific for *M. smegmatis* DNA. As the IAC assay is designed using a non competitive approach, when spiked into the master mix a positive signal should always be observed in the Cy5 channel. A representation of this can be seen in FIG. 7 (E) with the no template control highlighted with stars.

Figure 8:
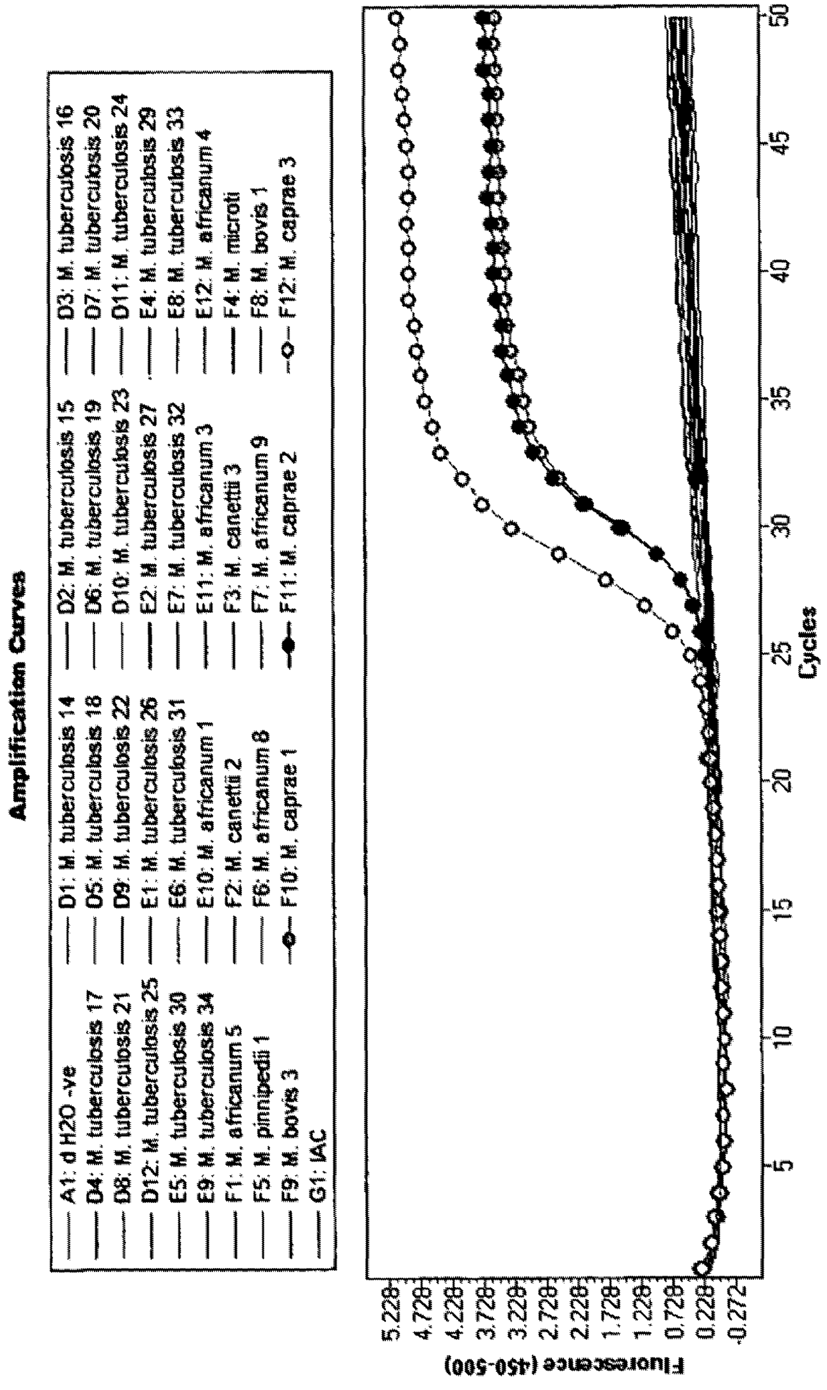
FIG. 8—(A) Amplification curves for *M. caprae* (circle) using lepA in Cyan 500 channel (450-500); (B) Amplification curves for *M. caprae* (circle) and *M. bovis* (triangle) using the lpqT gene in FAM channel (483-533); (C) Amplification curves for *M. caprae* (circle), *M. bovis* (triangle), *M. pinnipedii* (star) and *M. microti* (diamond) using a region of RD1 in HEX channel (523-568); (D) Amplification curves for *M. africanum* clade 2 (star) specific assay using a region of RD 701 in ROX channel (558-610); (E) Amplification curves for IAC in Cy5 channel (615-670) with the non-template control highlighted with stars through line.
Figure 8:
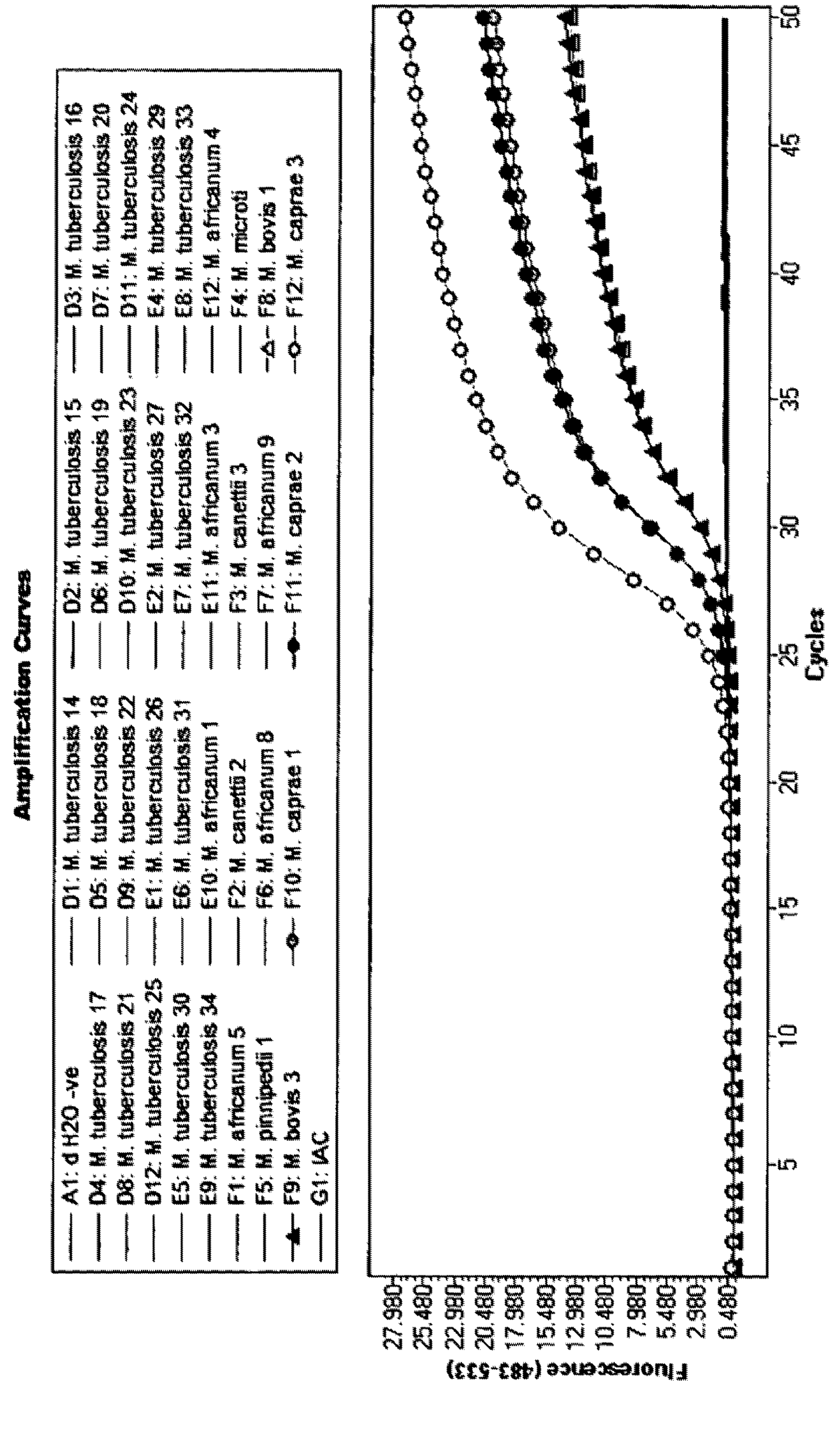
Figure 8:
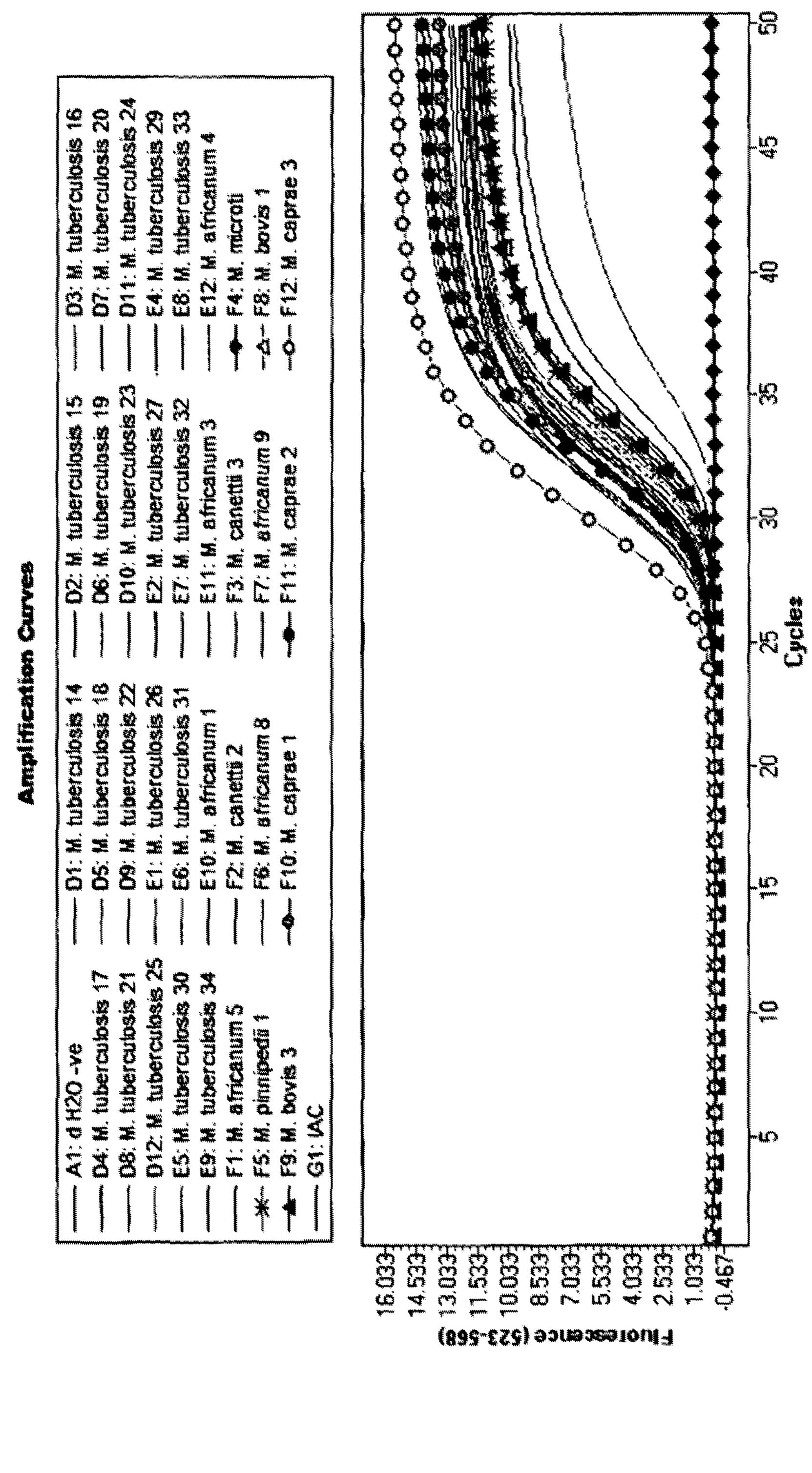
Figure 8:
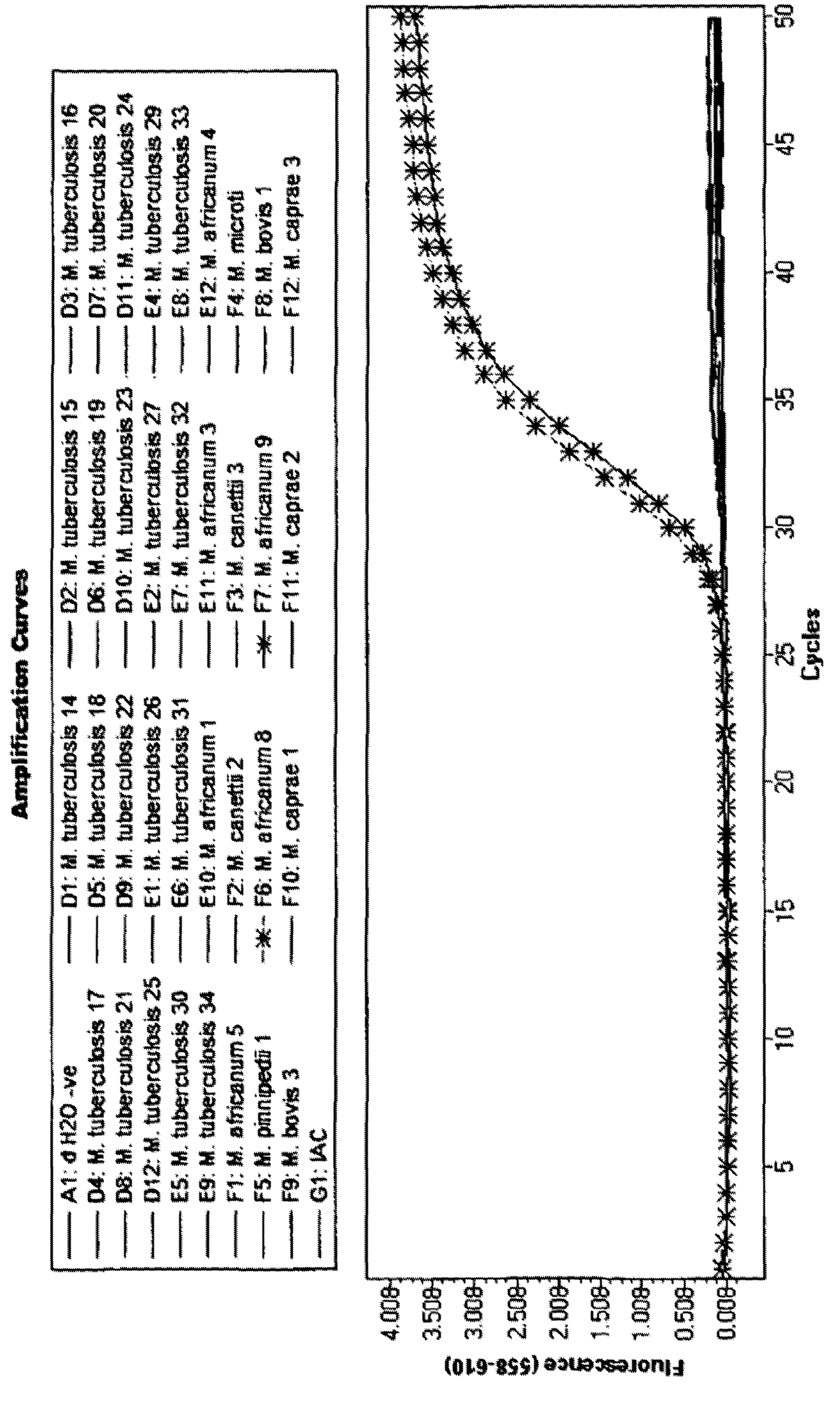
Figure 8:
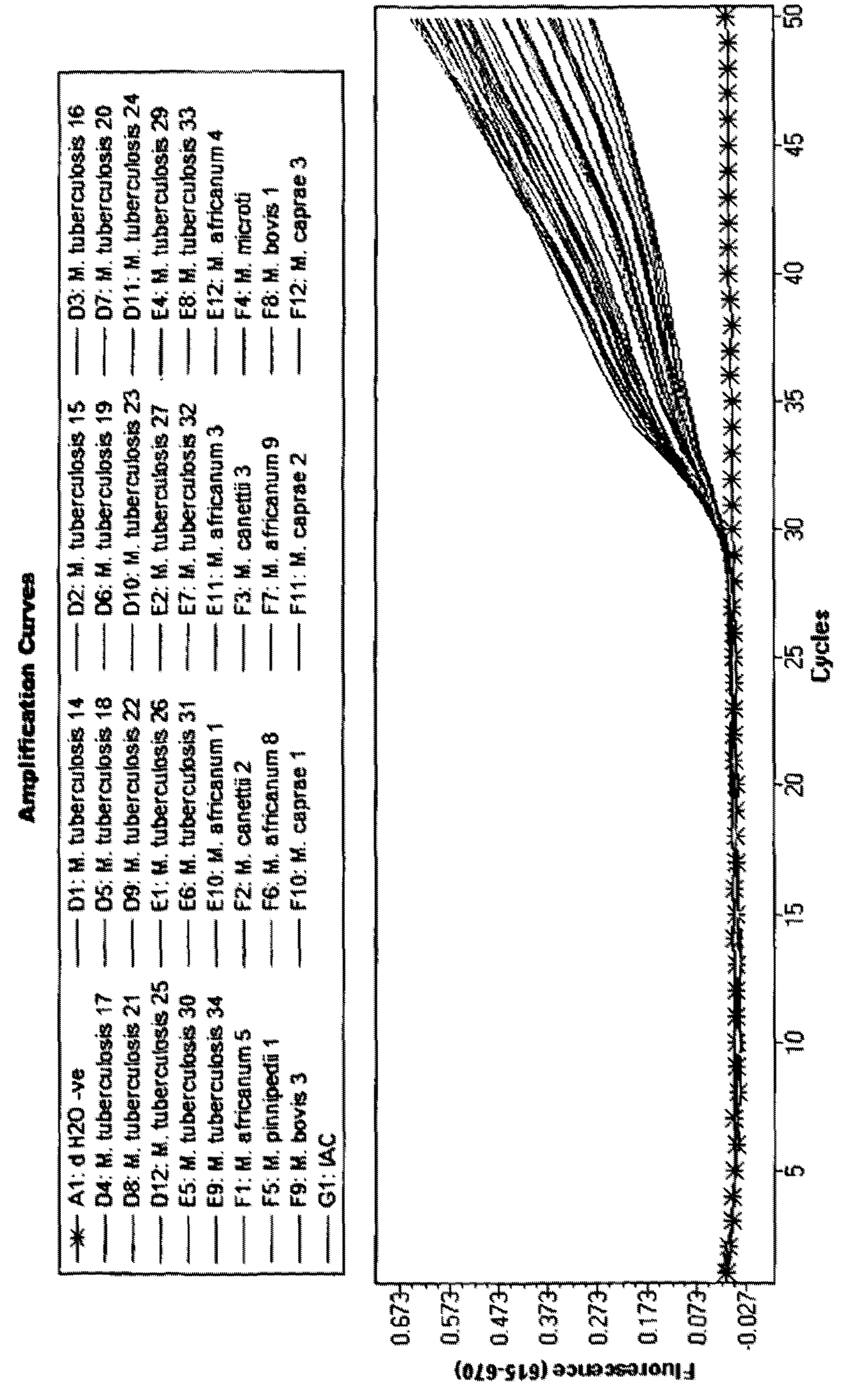

Using multiplex 2, the 5 *M. caprae* isolates were detected using the *M. caprae* lepA assay. The remaining members of the MTC, NTM and other bacteria tested for were not detected, a representation of this can bee seen in FIG. 8 (A). The lpqT assay was specific for the detection of 14 *M. bovis,* 7 *M. bovis* BCG and 5 *M. caprae*. A representation of this can be seen in FIG. 8 (B) with 3 *M. bovis* (triangle) and 3 caprae (circles) highlighted. The remaining members of the MTC, the NTM and other bacteria were not detected. For the purpose of multiplex 2, the RD1 assay detected the 14 *M. bovis* and 5 *M. caprae* isolates but not the 7 *M. bovis* BCG. A representation pf this can be seen in FIG. 8 (C) with 3 *M. caprae* depicted with circles and 2 *M. bovis* depicted with triangles. Additionally the 5 *M. pinnipedii* strains tested for are detected by the RD 1 based assay, whereas the 5 *M. microti* strains were not. A representation of this is seen in FIG. 8 (C) with 1 *M. pinnipedii* (star) and 1 *M. microti* (diamond). The IAC was the same as that used in multiplex 1, a representation can be seen in FIG. 8 (E) with the no template control again highlighted with stars.

The limit of detection (LOD) of each assay was evaluated in a monoplex real-time PCR format. Genomic DNA was quantified and serial dilutions were prepared from 200,000 to 2 genome equivalents of *M. canettii, M. africanum* clade 1, *M. caprae* and *M. africanum* clade 2, equating to approximately 5 fg DNA per cell. These members of the MTC were required to evaluate the sensitivity of all assays described.

In a monoplex format, the dilution series was run in duplicate and a sensitivity of 2-20 genome equivalents was determined for each assay. In multiplex format, multiple sensitivity experiments were performed to optimise primer, probe and IAC concentrations. After optimisation of the multiplex, the lower limit of detection was established using probit regression analysis. In multiplex 1, 12 replicates of each of 20, 15, 12, 10, 7.5, 4, 2, 0.2 genome equivalents of *M. canettii* and *M. africanum* clade 1 were evaluated. For ease of use and to avoid the possibility of cross talk between channels, a manual bandwidth was set at 1.2 fluorescent units for the primary assays. LOD's of 5.89, 9.04, 0.4 and 5.09 genome equivalents for the *M. canetti/M. tuberculosis/M. africanum* clade 1, MTC and *M. canettii* specific and *M. africanum* clade 1 assays respectively were determined with 95% probability. The IAC at a concentration of 100 genome equivalents per reaction was detected in all samples tested.

In multiplex 2, 12 replicates of each of 20, 15, 12, 10, 7.5, 4, 2, 0.2 genome equivalents of *M. caprae* and *M. africanum* clade 2 were evaluated. For ease of use and to avoid the possibility of cross talk between channels, a manual bandwidth was set at 1.3 fluorescent units for the primary assays. LOD's of 5.66, 6.05, 24.9 genome equivalents for the *M. bovis/M. bovis* BCG/*M. caprae*, the *M. bovis/M. caprae* and *M. africanum* clade 2 assays respectively were determined with 95% probability. The IAC at a concentration of 100 genome equivalents per reaction was detected in all samples tested. For the *M. caprae* specific assay the dilution series above was not sufficient for analysis, a further dilution series of 200, 100, 80, 60, 50, 40, 20 and 10 genome equivalents of *M. caprae* were evaluated. An LOD of 98.28 genome equivalents was determined with 95% probability.

Example 5

Diagnostics Algorithm

For determination of the identification of each specific member of the MTC using the two multiplex real-time PCR diagnostics assays outlined the user must take into account the combination of results observed for each channel of the real-time in vitro amplification instrument. This are set out in Table 1 below and explained below.

TABLE 1

Result of multiplex PCRs associated with each diagnosis

| Test | Multiplex 1 | | | | | |
|---|---|---|---|---|---|---|
| Analysis Channel (Target) | Cyan 500 (RD713) | FAM (wbbll) | HEX (MTC lepA) | ROX ($RD^{canettii1}$) | Cy5 (IAC MSMEG_0660) | Result Interpretation |
| | X | ● | ● | X | ● | *M. tuberculosis* |
| | X | ● | ● | ● | ● | *M. canettii* |
| | ● | ● | ● | X | ● | *M. africanum* clade 1 |
| | X | X | ● | X | ● | MTC—perform second multiplex |
| | X | X | X | X | ● | Not member of MTC |
| | X | X | X | X | X | Result invalid, test must be repeated |
| **Test** | **Multiplex 2 (taking multiplex 1 result into account)** | | | | | |
| Analysis Channel (Target) | Cyan 500 (*M. caprae* lepA) | FAM (lpqT) | HEX (RD1 ) | ROX (RD701 ) | Cy5 (IAC MSMEG_0660) | Result Interpretation |
| | X | ● | ● | X | ● | *M. bovis* |
| | X | ● | X | X | ● | *M. bovis BCG* |

TABLE 1-continued

| Result of multiplex PCRs associated with each diagnosis | | | | | |
|---|---|---|---|---|---|
| ● | ● | ● | X | ● | *M. caprae* |
| X | X | ● | ● | ● | *M. africanum* clade 2 |
| X | X | ● | X | ● | *M. pinnipedii* |
| X | X | X | X | ● | *M. microti* |
| X | X | X | X | X | Result invalid, test must be repeated |

● Positive signal obtained in this channel
X Negative result in this channel

Multiplex 1

Result Scenario for the Identification of *M. tuberculosis*

Using multiplex 1, if the HEX labelled MTC lepA, the FAM labelled wbbl1 and the Cy5 labelled IAC MSMEG_0660 diagnostics assays generate a positive signal in each of these channels, but the Cyan 500 labelled RD713 and the ROX labelled $RD^{canetti1}$ diagnostics assays do not generate positive signals in these channels the result indicates *M. tuberculosis* is present in the sample.

Result Scenario for the Identification of *M. Canettii*

Using multiplex 1, if the HEX labelled MTC lepA, the FAM labelled wbbl1, the ROX labelled $RD^{canetti1}$ and the Cy5 labelled IAC MSMEG_0660 diagnostics assays generate a positive signal in each of these channels, but the Cyan 500 labelled RD713 diagnostics assay does not generate a positive signal in this channel, the result indicates *M. canettii* is present in the sample.

Result Scenario for the Identification of *M. africanum* Clade

Using multiplex 1, if the HEX labelled MTC lepA, the FAM labelled wbbl1, the Cyan 500 labelled RD713 and the Cy5 labelled IAC MSMEG_0660 diagnostics assay generate a positive signal in each of these channels, but the ROX labelled $RD^{canetti1}$ diagnostics assay does not generate a positive signal in this channel, the result indicates that *M. africanum* clade 1 is present in the samples.

Result Scenario for Other Members of the AMC Other than *M. tuberculosis, M. canettii* and *M. africanum* Clade 1

Using multiplex 1, if the HEX labelled MTC lepA and Cy5 labelled IAC MSMEG_0660 diagnostics assays generate a positive signal in each of these channels, but the PAM labelled wbbl1, the ROX labelled $RD^{canetti1}$ and the Cyan 500 labelled RD713 diagnostics assays do not generate positive signals in each of these channels, the result indicates that a member of the MTC other than *M. tuberculosis, M. canettii* and *M. africanum* clade 1 is present in the sample and the user of the test should now proceed to the second multiplex real-time PCR disclosed in this invention.

Result Scenario if No Member of MTC not Present

Using multiplex 1, if a positive signal observed in the Cy5 labelled IAC MSMEG_0660 diagnostics assay, but the HEX labelled MTC lepA, the FAM labelled wbbl1, the ROX labelled $RD^{canetti1}$ and the Cyan 500 labelled RD713 diagnostics assays do not generate positive signals in each of these channels, the result indicates that a member of the MTC is not present in the sample being tested for.

Result Scenario for Invalid Result

Using multiplex 1, if no positive signal is observed for any diagnostics assay tested for, including the Cy5 labelled IAC MSMEG_0660 diagnostics assay, the result is considered invalid and must be repeated.

Multiplex 2

If from multiplex 1 it is known that a member of the MTC is present, other than *M. tuberculosis, M. canettii* or *M. africanum* clade 1, the user will perform the second multiplex real-time PCR diagnostics assay disclosed in this invention.

Result Scenario for the Identification of *M. caprae*

Using multiplex 2, if a positive signal is observed for the Cyan 500 labelled *M. caprae* lepA, the FAM labelled lpqT, the HEX labelled RD1 and the Cy5 labelled IAC MSMEG_0660 diagnostics assay, but the ROX labelled RD701 diagnostics assay does not generate a positive signal in this channel, the result indicates that *M. caprae* is present in the sample.

Result Scenario for the Identification of *M. Bovis*

Using multiplex 2, if a positive signal is observed in the FAM labelled lpqT, the HEX labelled RD1 and the Cy5 labelled IAC MSMEG_0660 diagnostics assay, but the Cyan500 labelled *M. caprae* lepA and the ROX labelled RD701 diagnostics assays do not generate positive signals in these channels, the result indicated that *M. bovis* is present in the sample.

Result Scenario for the Identification of *M. bovis* BCG

Using multiplex 2, if a positive signal is observed in the FAM labelled lpqT and the Cy5 labelled IAC MSMEG_0660 diagnostics assays, but the Cyan 500 labelled *M. caprae* lepA, the HEX labelled RD1 and the ROX labelled RD701 diagnostics assays do not generate positive signals in these channels, the result indicates that *M. bovis* BCG is present in the sample.

Result Scenario for the Identification of *M. africanum* Clade 2

Using multiplex 2, if a positive signal is observed in the ROX labelled RD701, the HEX labelled RD1 and the Cy5 labelled IAC MSMEG_0660 diagnostics assays, but the Cyan500 labelled *M. caprae* lepA and the FAM labelled lpqT diagnostics assays do not generate positive signals in these channels, the result indicates that *M. africanum* clade 2 is present in the sample.

Result Scenario for Invalid Result

Using multiplex 2, if no positive signal is observed for any assay tested in this multiplex, the result is considered invalid and must be repeated.

Combined Results of Multiplex 1 and Multiplex 2

If the results from both multiplex real-time PCR assays described are taken into account it is also possible to accurately identify the remaining members of the MTC, namely *M. microti* and *M. pinnipedii.*

Result Scenario for the Identification of *M. microti*

If a positive signal is observed in the HEX labelled MTC lepA and the Cy5 labelled IAC MSMEG_0660 diagnostics assay in multiplex 1 and no other positive signal is observed in any of the other diagnostics assays channels in multiplex 1 and multiplex 2 with the exception of a positive signal in the Cy5 labelled IAC MSMEG_0660 diagnostics assay in multiplex 2 the result indicates that *M. microti* is present in the sample.

Result Scenario for the Identification of *M. Pinnipedii*

If taking the results from both multiplex real-time PCR assays described into account and a positive signal is observed in the HEX labelled MTC lepA and the Cy5 labelled IAC MSMEG_0660 diagnostics assay in multiplex 1 and no positive signal is observed for all other assays in multiplex 1 and multiplex 2, with the exception of a positive signal in the HEX labelled RD1 and the Cy5 labelled MSMEG_0660 diagnostics assays in multiplex 2 the result indicates that *M. pinnipedii* is present in the sample.

TABLE 2

*Mycobacterium tuberculosis* complex isolates used in this study

| Species | Strain | Country of Isolation | Origin | Remarks |
|---|---|---|---|---|
| *M. tuberculosis* | 22 | Mongolia | RIVM | Beijing lineage |
| *M. tuberculosis* | 53 | Argentina | RIVM | Haarlem lineage |
| *M. tuberculosis* | 112 | The Netherlands | RIVM | CAS lineage |
| *M. tuberculosis* | 67 | Comoro Islands | RIVM | EAI lineage |
| *M. tuberculosis* | 41 | Chile | RIVM | LAM lineage |
| *M. tuberculosis* | 103 | China | RIVM | T-family lineage |
| *M. tuberculosis* | 12594_02 | Former Soviet Union | Borstel | Beijing lineage |
| *M. tuberculosis* | 1500_03 | Former Soviet Union | Borstel | Beijing lineage |
| *M. tuberculosis* | 1934_03 | Former Soviet Union | Borstel | Beijing lineage |
| *M. tuberculosis* | 1428_02 | Ghana | Borstel | Cameroon lineage |
| *M. tuberculosis* | 5390_02 | Ghana | Borstel | Cameroon lineage |
| *M. tuberculosis* | 5400_02 | Ghana | Borstel | Cameroon lineage |
| *M. tuberculosis* | 2637_02 | Germany | Borstel | Delhi/CAS lineage |
| *M. tuberculosis* | 7936_01 | Germany | Borstel | Delhi/CAS lineage |
| *M. tuberculosis* | 1797_03 | Germany | Borstel | EAI lineage |
| *M. tuberculosis* | 4850_03 | Germany | Borstel | EAI lineage |
| *M. tuberculosis* | 947_01 | Germany | Borstel | EAI lineage |
| *M. tuberculosis* | 2336_02 | Germany | Borstel | Haarlem lineage |
| *M. tuberculosis* | 9532_03 | Germany | Borstel | Haarlem lineage |
| *M. tuberculosis* | 7968_03 | Germany | Borstel | LAM lineage |
| *M. tuberculosis* | 8885_03 | Germany | Borstel | LAM lineage |
| *M. tuberculosis* | 946_03 | Germany | Borstel | LAM lineage |
| *M. tuberculosis* | 2151_03 | Germany | Borstel | S-type lineage |
| *M. tuberculosis* | 2318_06 | Germany | Borstel | S-type lineage |
| *M. tuberculosis* | 10469_01 | NA[b] | Borstel | Ghana lineage |
| *M. tuberculosis* | 10493_01 | NA[b] | Borstel | Ghana lineage |
| *M. tuberculosis* | 2570_02 | NA[b] | Borstel | Ghana lineage |
| *M. tuberculosis* | 2201_99 | Uganda | Borstel | Uganda I lineage |
| *M. tuberculosis* | 2333_99 | Uganda | Borstel | Uganda I lineage |
| *M. tuberculosis* | 2176_99 | Uganda | Borstel | Uganda II lineage |
| *M. tuberculosis* | 2191_99 | Uganda | Borstel | Uganda II lineage |
| *M. tuberculosis* | 4412_04 | Germany | Borstel | X-type lineage |
| *M. tuberculosis* | 9953_04 | Germany | Borstel | X-type lineage |
| *M. tuberculosis* | 11313_03 | Germany | Borstel | Tur lineage |
| *M. tuberculosis* | 1657_03 | Germany | Borstel | Ural lineage |
| *M. tuberculosis* | 10264_03 | Germany | Borstel | Tur lineage |
| *M. tuberculosis* | 10529_03 | Germany | Borstel | Tur lineage |
| *M. tuberculosis* | 8431_03 | Germany | Borstel | Ural lineage |
| *M. tuberculosis* | 3493_07 | | Borstel | Hamburg lineage |
| *M. tuberculosis* | 10707_07 | | Borstel | Hamburg lineage |
| *M. tuberculosis* H37Rv | 9679_00 | NA[b] | Borstel | Laboratory strain ATCC |
| *M. tuberculosis* (19 clinical isolates) | — | NA[b] | Mario Vaneechoutte | Clinical isolates |
| *M. canettii* | 116 | Somalia | RIVM | Smooth growing strain described by van Soolingen et al. 1997 |
| *M. canettii* | 1997-1549 | Switzerland | RIVM | Swiss isolate described in Pfyffer et al. 1998 |
| *M. canettii* | NLA000701671 | Somalia | RIVM | Characterised on the basis of their spoligotype, IS6110 RFLP type and smooth growth as |
| *M. canettii* | NLA000200937 | Eritrea | RIVM | Characterised on the basis of their spoligotype, IS6110 RFLP type and smooth growth |
| *M. canettii* | 1996-46 | France | RIVM | *Canetti* strain |
| *M. canettii* | 3040_99 | The Netherlands | Borstel | |
| *M. canettii* | 3151_08 | NA[b] | Borstel | |
| *M. canettii* | 3041_99 | The Netherlands | Borstel | |
| *M. bovis* | 117 | Argentina | RIVM | See Kremer et al. 2005 |
| *M. bovis* | 126 | Argentina | RIVM | See Kremer et al. 2005 |
| *M. bovis* | 73 | The Netherlands | RIVM | See Kremer et al. 2005 |
| *M. bovis* | 130 | The Netherlands | RIVM | See Kremer et al. 2005 |
| *M. bovis* | 24 | Saudi Arabia | RIVM | Isolated from an oryx, Antelope clade, see also Smith et al. 2006 |

TABLE 2-continued

| Mycobacterium tuberculosis complex isolates used in this study | | | | |
|---|---|---|---|---|
| Species | Strain | Country of Isolation | Origin | Remarks |
| *M. bovis* | 4258_00 | Germany | Borstel | |
| *M. bovis* | 751_01 | Germany | Borstel | |
| *M. bovis* | 7540_01 | Germany | Borstel | |
| *M. bovis* (6 isolates) | — | NA[b] | Mario Vaneechoutte | Clinical isolates |
| *M. bovis* BCG | 48 (2) | The Netherlands | RIVM | See Kremer et al. 2005 |
| *M. bovis* BCG | 71 | Japan | RIVM | See Kremer et al. 2005 |
| *M. bovis* BCG | 83 | Russia | RIVM | See Kremer et al. 2005 |
| *M. bovis* BCG | 2008-714[a] | NA[b] | RIVM | identified on basis of characteristic IS6110/IS1081 RFLP patterns according to van Soolingen et al. 1992 |
| *M. bovis* BCG | 2008-1601[a] | NA[b] | RIVM | Identified on basis of characteristic IS6110/IS1081 RFLP patterns according to van Soolingen et al. 1992 |
| *M. bovis* BCG | DSM 43990 | NA[b] | DSMZ | *Mycobacterium bovis* Karlson and Lessel 1970<br>BCG, Chicago 1 |
| *M. bovis* BCG | DSM 45071 | NA[b] | DSMZ | *Mycobacterium bovis* Karlson and Lessel 1970 |
| *M. caprae* | 2006-1960[a] | The Netherlands | RIVM | Characterised using Hain genotype MTBC kit |
| *M. caprae* | 2007-0039[a] | The Netherlands | RIVM | Characterised using Hain genotype MTBC kit |
| *M. caprae* | 1694_00 | Germany | Borstel | |
| *M. caprae* | 8986_99 | Germany | Borstel | |
| *M. caprae* | 9577_99 | Germany | Borstel | |
| *M. microti* | 62 | United Kingdom | RIVM | see van Soolingen et al. 1998 |
| *M. microti* | 25 | United Kingdom | RIVM | see van Soolingen et al. 1998 |
| *M. microti* | 15274[a] | United Kingdom | RIVM | see van Soolingen et al. 1998 |
| *M. microti* | 15912[a] | Belgium | RIVM | see van Soolingen et al. 1998 |
| *M. microti* | 15911[a] | Netherlands | RIVM | see van Soolingen et al. 1998 |
| *M. microti* | 417/01 | Germany | | Liama lineage |
| *M. pinnipedii* | 76 | Argentina | RIVM | See Kremer et al. 2005 |
| *M. pinnipedii* | 81 | Argentina | RIVM | See Kremer et al. 2005 |
| *M. pinnipedii* | 101 | Argentina | RIVM | See Kremer et al. 2005 |
| *M. pinnipedii* | 7011_02 | Germany | Borstel | |
| *M. pinnipedii* | 7739_01 | Germany | Borstel | |
| *M. africanum* | 6 | The Netherlands | RIVM | *M. africanum* clade 2 |
| *M. africanum* | 128 (85) | The Netherlands | RIVM | *M. africanum* clade 2 |
| *M. africanum* | 2007-1386[a] | The Netherlands | RIVM | *M. africanum* clade 2 |
| *M. africanum* | 2007-1154[a] | The Netherlands | RIVM | *M. africanum* clade 2 |
| *M. africanum* | 2007-1073[a] | The Netherlands | RIVM | *M. africanum* clade 2 |
| *M. africanum* | 1449_02 | Ghana | Borstel | *M. africanum* clade 1 |
| *M. africanum* | 1473_02 | Ghana | Borstel | *M. africanum* clade 1 |
| *M. africanum* | 10473_01 | Ghana | Borstel | *M. africanum* clade 1 |
| *M. africanum* | 10494_01 | Ghana | Borstel | *M. africanum* clade 1 |
| *M. africanum* | 1443_02 | Ghana | Borstel | *M. africanum* clade 1 |
| *M. africanum* | 10476_01 | Ghana | Borstel | *M. africanum* clade 2 |
| *M. africanum* | 10514_01 | Ghana | Borstel | *M. africanum* clade 2 |
| *M. africanum* | 5468_02 | Ghana | Borstel | *M. africanum* clade 2 |
| *M. africanum* | 9550_99 | Ghana | Borstel | *M. africanum* clade 2 ATCC |

[a]Represent RIVM strains not previously described in literature, however have been characterised to the species level using techniques outlined in references supplied as remark.
[b]This information was not available.

TABLE 3

| Non-tuberculosis *Mycobacterium* and Non-*Mycobacterium* species used in this study | | |
|---|---|---|
| Non tuberculosis mycobacteria | Strain designation[a] | Remark |
| *Mycobacterium aichiense* | DSM 44147 | Type strain, isolated from soil |
| *Mycobacterium alvei* | DSM 44176 | Type strain, isolated from water sample |
| *Mycobacterium arupense* | DSM 44942 | Type strain, isolated from a tendon |
| *Mycobacterium asiaticum* | ITG 8182 | |
| *Mycobactertum avium* | ITG 7886 | |
| *Mycobacterium boenickei* | DSM 44677 | Type strain, isolated from a leg wound |
| *Mycobacterium branderi* | DSM 44624 | Type strain, isolated from human sputum |
| *Mycobacterium brisbanense* | DSM 44680 | Type strain, isolated from a sinus |
| *Mycobacterium brumae* | DSM 44177 | Type strain, isolated from water sample |
| *Mycobacterium canariasense* | DSM 44828 | Type strain, isolated from human blood |
| *Mycobacterium celatum* | ITG 6147 | |
| *Mycobactertum chelonae* | ITG 4975 | |

TABLE 3-continued

Non-tuberculosis *Mycobacterium* and Non-*Mycobacterium* species used in this study

| | | |
|---|---|---|
| *Mycobacterium chelonae* subsp. *abscessus* | DSM 44196 | Type strain |
| *Mycobacterium confluentis* | DSM 44017 | Type strain, isolated from human sputum |
| *Mycobacterium conspicuum* | DSM 44136 | Type strain, isolated from patient with disseminated infection |
| *Mycobacterium flavescens* | VUB A016 | |
| *Mycobacterium fortuitum* | ITG 8020 | |
| *Mycobacterium genavense* | ITG 97-102 | |
| *Mycobacterium gilvum* | DSM 9487 | Isolated from soil |
| *Mycobacterium goodii* | DSM 44492 | Type strain |
| *Mycobacterium gordonae* | ITG 7704 | |
| *Mycobacterium heckeshornense* | DSM 44428 | Type strain, isolated from human respiratory tract |
| *Mycobacterium houstonense* | DSM 44676 | Type strain, isolated from a facial abscess |
| *Mycobacterium intracellulare* | DSM 43223 | Type strain |
| *Mycobacterium kansasii* | ITG 7727 | |
| *Mycobacterium kubiciae* | DSM 44627 | Type strain, isolated from human sputum |
| *Mycobacterium lacus* | DSM 44577 | Type strain, isolated from human elbow |
| *Mycobacterium mageritense* | DSM 44476 | Type strain, isolated from human sputum |
| *Mycobacterium malmoense* | ITG 940611 | |
| *Mycobacterium marinum* | ITG 1727 | |
| *Mycobacterium massiliense* | DSM 45103 | Type strain, isolated from human blood |
| *Mycobacterium moriokaense* | DSM 44221 | Type strain, isolated from soil |
| *Mycobacterium mucogenicum* | DSM 44625 | Type strain, isolated from human cyst |
| *Mycobacterium nebraskense* | DSM 44803 | Type strain, isolated from human sputum |
| *Mycobacterium neworleansense* | DSM 44679 | Type strain, isolated from human scalp |
| *Mycobacterium paratuberculosis* | ITG 2666 | |
| *Mycobacterium scrofulaceum* | DSM 43992 | Type strain, isolated from human cervical lymph node |
| *Mycobacterium shimoidei* | DSM 44152 | Type strain, isolated from sputum of patient with tuberculosis-like disease |
| *Mycobacterium simiae* | ITG 4485 | |
| *Mycobacterium smegmatis* | DSM 43756 | Type strain |
| *Mycobacterium szulgai* | ITG 4979 | |
| *Mycobacterium tusciae* | DSM 44338 | Type strain, isolated from human cervical lymph node |
| *Mycobacterium ulcerans* | ITG 96-1439 | |
| *Mycobacterium xenopi* | ITG 4986 | |

| Other bacteria | Strain designation | Remark |
|---|---|---|
| *Staphylococcus aureus* | DSM 20231 | Type strain, isolated from human pleural fluid |
| *Listeria monocytogenes* | DSM 20600 | Type strain, isolated from a rabbit |
| *Escherichia coli* | DSM 301 | Disinfectant test strain |
| *Klebsiella oxytoca* | ATCC 43086 | |
| *Enterococcus faecalis* | DSM 20371 | Isolated from pleural fluid |
| *Proteus mirabilis* | DSM 4479 | Type strain |
| *Bacillus cereus* | DSM 31 | Type strain |
| *Bordetella pertussis* | CCUG 13475 | Isolated from patient suffering from whooping cough |
| *Streptococcus agalactiae* | DSM 2134 | Type strain |
| *Rhodococcus equi* | DSM 20307 | Type strain, isolated from lung abscess of foal |
| *Streptomyces albidoflavus* | DSM 40455 | Type strain |
| *Nocardioides* sp. | DSM 17401 | Proposed type strain, isolated from marine sediment |
| *Nocardia salmonicida* | DSM 40472 | Type strain, isolated from blueback salmon |
| *Nocardia asiatica* | clinical isolate | Isolated from human wound |
| *Nocardia nova* | clinical isolate | Isolated from human abscess |
| *Nocardia cyriacigeorgica* | clinical isolate | Isolated from human bronchial aspirate |
| *Nocardia farcinica* | clinical isolate | Isolated from human abscess |

[a]RIVM = National Tuberculosis Reference Laboratory, National Institute for Public Health and the Environment, Bilthoven, The Netherlands;
Borstel = National Reference Center for Mycobacteria, Borstel, Germany:
DSM = The German Collection of Microorganisms;
ATCC = American Type Culture Collection;
ITG = Institute of Tropical Medicine, Antwerp, Germany;
CCUG = Culture Collection, University of Goteborg, Sweden;
VUB = Department of Microbiology. Academic Hospital of the Free University of Brussels, Brussels, Belgium.
[b]This information was not available (NA) for this study.

TABLE 4

Oligonucleotide primers and probes used in this study

| Name | Function | Sequence 5'→3' |
|---|---|---|
| MTC_IAC Fw | Forward Sequencing primer, forward MTC and internal control real-time PCR assay primer | AGACCGTGCGGATCTTG (SEQ ID NO: 100/106) |

TABLE 4-continued

Oligonucleotide primers and probes used in this study

| Name | Function | Sequence 5'→3' |
|---|---|---|
| MTC_IAC Rv | Reverse Sequencing primer, Reverse MTC and internal control real-time PCR assay primer | CATGGAGATCACCCGTGA (SEQ ID NO: 102/108) |
| MTC Probe | MTC probe | HEX-ACGGATTGGTCACCCGGATT-BHQ1 (SEQ ID NO: 101) |
| IAC probe | Internal control probe | CY5-ACGACCTTCTCGGAACCGT-BHQ2 (SEQ ID NO: 107) |
| wbbl1_Fw | Forward sequencing primer, Forward real-time PCR assay primer | TACCAGCTTCAGTTTCCGT (SEQ ID NO: 97) |
| wbbl1_Rv | Reverse sequencing primer, Reverse real-time PCR assay primer | GCACCTATATCTTCTTAGCCG (SEQ ID NO: 99) |
| wbbl1 probe | wbbl1 probe | FAM-ATGGTGCGCAGTTCACTGC-BHQ1 (SEQ ID NO: 98) |
| *M. canetti* sp Fw | Forward *M. canetti* specific primer | ATGTGGTTTCAGTACGACTTC (SEQ ID NO: 103) |
| *M. canetti* sp Rv | Reverse *M. canetti* specific primer | GATGGCAGTGTCTTATCCAA (SEQ ID NO: 105) |
| *M. canetti* sp probe | *M. canetti* specific probe | ROX-TGAGAGGTGTTGGCACGCAA-BHQ2 (SEQ ID NO: 104) |
| *M. canetti* seq 1.a | Forward sequencing primer 1 | TGTCGGCGGCCACGT (SEQ ID NO: 89) |
| *M. canetti* seq 1.b | Reverse sequencing primer 1 | GAAGTCCAGCATCTTGGCGTT (SEQ ID NO: 90) |
| *M. canetti* seq 2.a | Forward sequencing primer 1 | TGTCGGCGGCCACGT (SEQ ID NO: 91) |
| *M. canetti* seq 2.b | Reverse sequencing primer 2 | ATCGTGCAGTGCGGCCA (SEQ ID NO: 92) |
| *M. canetti* seq 3.a | Forward sequencing primer 3 | GCAGCATTGTGGTTGACCGA (SEQ ID NO: 93) |
| *M. canetti* seq 3.b | Reverse sequencing primer 3 | TCCCAGCGTTGCGCCTT (SEQ ID NO: 94) |
| *M. canetti* seq 4.a | Forward sequencing primer 4 | TGATGCGGCTGCTCAAGC (SEQ ID NO: 95) |
| *M. canetti* seq 4.b | Reverse sequencing primer 4 | TGTCAAGGGACATGGGGAACT (SEQ ID NO: 96) |
| lpqT_Fw[1] | Forward sequencing primer, Forward real-time PCR assay primer | ACGAATCCGGCGATGATC (SEQ ID NO: 158) |
| lpqT_Rv | Reverse sequencing primer, Reverse real time PCR assay primer | CGACTGCACACCTGGAA (SEQ ID NO: 159) |
| lpqT probe | lpqT Probe | FAM-TTGGCCGGCGCCGGTT-BHQ1 (SEQ ID NO: 160) |
| RD1_Fw | Forward sequencing primer, Forward real-time PCR assay primer | CATCGCTGATGTGCTTGC (SEQ ID NO: 161) |
| RD1_Rv | Reverse sequencing primer, Reverse real-time PCR assay primer | TGCGCCGAGCTGTATTC (SEQ ID NO: 162) |
| RD1_probe | RD1 Probe | ROX-ACACTAGCGTCAATGCGGTCA-BHQ2 (SEQ ID NO: 163) |
| *M. caprae* lepA_Fw | Forward sequencing primer, Forward real-time PCR assay primer | AGACCGTGCGGATCTTG (SEQ ID NO: 164) |
| *M. caprae* lepA_Rv | Reverse sequencing primer, Reverse real-time PCR assay primer | CATGGAGATCACCCGTGA (SEQ ID NO: 165) |
| *M. caprae* lepA probe | *M. caprae* lepA Probe | Cyan 500-TATCGGGTACACAAAGACGA-BBQ (SEQ ID NO: 166) |
| RD713_Fw | Forward sequencing primer, Forward real-time PCR assay primer | ACGGAACGGTCAAGAAC (SEQ ID NO: 167) |

TABLE 4-continued

| Oligonucleotide primers and probes used in this study | | |
|---|---|---|
| Name | Function | Sequence 5'→3' |
| RD713_Rv | Reverse sequencing primer, Reverse real-time PCR assay primer | GCTCAAGAATCGTCGCTA (SEQ ID NO: 168) |
| RD713 probe | RD 713 Probe | Cyan 500-ACGTCCTTGTGACCGCGAC-BBQ (SEQ ID NO: 169) |
| RD701_Fw | Forward sequencing primer, Forward real-time PCR assay primer | AACGGGTCGGATTCTCC (SEQ ID NO: 170) |
| RD701_Rv | Reverse sequencing primer | CCGAAACCCTCGTTGATC (SEQ ID NO: 171) |
| RD701 probe | RD 701 Probe | ROX-TCAGCCGCCGGCCAACC-BHQ2 (SEQ ID NO: 172) |
| MTC_FW | Forward sequencing primer | AGACCGTGCGGATCTTG (SEQ ID NO: 164) |
| MTC_Rv | Reverse sequencing primer | CATGGAGATCACCCGTGA (SEQ ID NO: 165) |
| MTC probe | MTC lepA Probe | HEX-ATTGGTCACCCGGATTTCGGT-BHQ1 (SEQ ID NO: 173) |
| IAC MSMEG_0660_Fw | Forward sequencing primer, Forward real-time PCR assay primer | TCACCGACCATGTCCAG(SEQ ID NO: 155) |
| IAC MSMEG_0660_Rv | Reverse sequencing primer, Reverse real-time PCR assay primer | CGTTGCCCAATCCGTATG (SEQ ID NO: 156) |
| IAC MSMEG_0660 probe | IAC MSMEG_0660 probe | Cy5-CAGCAGTACCATCGCCATCG-BHQ2 (SEQ ID NO: 157) |

REFERENCES

Al-Attiyah, R. & Mustafa, A. S. (2008). Characterization of Human Cellular Immune Responses to Novel *Mycobacterium tuberculosis* Antigens Encoded by Genomic Regions Absent in *Mycobacterium bovis* BCG. *Infect Immun* 76, 4190-4198.

Arya, M., Shergill, I. S., Williamson, M., Gornmersall, L., Arya, N. & Patel, H. R. (2005). Basic principles of real-time quantitative PCR. *Expert Review of Molecular Diagnostics* 5, 209-219.

Behr, M. A., Wilson, M. A., Gill, W. P., Salmon, H., Schoolnik, G. K., Rane, S. & Small, P. M. (1999). Comparative Genomics of BCG Vaccines by Whole-Genome DNA Microarray. *Science* 284, 1520-1523.

Brosch, R., Gordon, S. V., Pym, A., Eiglmeier, K., Garnier, T. & Cole, S. T. (2000). Comparative genomics of the mycobacteria. *Int J Med Microbiol* 290, 143-152.

Broseh, R., Gordon, S. V., Marmiesse, M. & other authors (2002). A new evolutionary scenario for the *Mycobacterium tuberculosis* complex. *Proceedings of the National Academy of Sciences of the United States of America* 99, 3684-3689, Das, S., Das, S. C. & Verma, R. (2007). Occurrence of RD9 region and 500 bp fragment among clinical isolates of *Mycobacterium tuberculosis* and *Mycobacterium bovis. Microbiol Immunol* 51, 231-234.

de Jong, B. C., Antonio, M. & Gagneux, S. (2010). *Mycobacterium africanum*—Review of an Important Cause of Human Tuberculosis in West Africa. *PLoS Negl Trop Dis* 4, e744.

Dille, B. J., Butzen, C. C. & Birkenmeyer, L. G. (1993). Amplification of Chlamydia trachomatis DNA by ligase chain reaction. *J Clin Microbiol* 31, 729-73

Djelouadji, Z., Raoult, D., Daffé, M. & Drancourt, M. (2008). A Single-Step Sequencing Method for the Identification of *Mycobacterium tuberculosis* Complex Species. *PLoS Negl Trop Dis* 2, e253.

Dorak, M. T. (2006). In M. T. Dorak (ED.), Real-time PCR, <http://www.dorak.info/genetics/realtime.html>.

Flint, J. L., Kowalski, J. C., Karnati, P. K. & Derbyshire, K. M. (2004). The RD1 virulence locus of *Mycobacterium tuberculosis* regulates DNA transfer in *Mycobacterium smegmatis. Proceedings of the National Academy of Sciences of the United States of America* 101, 12598-12603.

Garnier, T., Eiglmeier, K., Cams, J.-C. & other authors (2003). The complete genome sequence of *Mycobacterium bovis. Proceedings of the National Academy of Sciences of the United States of America* 100, 7877-7882.

Goh, K. S., Legrand, E., Sola, C. & Rastogi, N. (2001). Rapid Differentiation of "*Mycobacterium canettii*" from Other *Mycobacterium tuberculosis* Complex Organisms by PCR-Restriction Analysis of the hsp65 Gene. *J Clin Microbiol* 39, 3705-3708.

Halse, T. A., Edwards, J., Cunningham, P. L., Wolfgang, W. J., Dumas, N. B., Escuyer, V. E. & Musser, K. A. Combined Real-Time PCR and rpoB Gene Pyrosequencing for Rapid Identification of *Mycobacterium tuberculosis* and Determination of Rifampin Resistance Directly in Clinical Specimens. *J Clin Microbiol* 48, 1182-1188.

Hoorfar, J., Malorny, B., Abdulmawjood, A., Cook, N., Wagner, M. & Fach, P. (2004). Practical Considerations in Design of Internal Amplification Controls for Diagnostic PCR Assays. *J Clin Microbiol* 42, 1863-1868.

Huard, R. C., de Oliveira Lazzarini, L. C., Butler, W. R., van Soolingen, D. & Ho, J. L. (2003). PCR-Based Method To Differentiate the Subspecies of the *Mycobacterium tuberculosis* Complex on the Basis of Genomic Deletions. *J Clin Microbiol* 41, 1637-1650.

Huard, R. C., Fabre, M., de Haas, P., Claudio Oliveira Lazzarini, L., van Soolingen, D., Cousins, D. & Ho, J. L. (2006). Novel Genetic Polymorphisms That Further Delineate the Phylogeny of the *Mycobacterium tuberculosis* Complex. *J Bacteriol* 188, 4271-4287.

Kiers, A., Klarenbeek, A., Mendelts, B., Van Soolingen, D., Ko & ter, G. (2008a). Transmission of *Mycobacterium pinnipedii* to humans in a zoo with marine mammals. *The International Journal of Tuberculosis and Lung Disease* 12, 1469-1473.

Kiers, A., Klarenbeek, A., Mendelts, B., Van Soolingen, D. & Koëter, G. (2008b). Transmission of *Mycobacterium pinnipedii* to humans in a zoo with marine mammals. *The International Journal of Tuberculosis and Lung Disease* 12, 1469-1473.

Ma, Y., Pan, F. & McNeil, M. (2002). Formation of dTDP-Rhamnose Is Essential for Growth of Mycobacteria. *J Bacteriol* 184, 3392-3395.

Malbotra-Kumar, S., Haccuria, K., Michiels, M., leven, M., Poyart, C., Hryniewicz, W., Goossens, H. & on behalf of the MOSAR WP2 Study Team (2008). Current Trends in Rapid Diagnostics for Methicillin-Resistant Staphylococcus aureus and Glycopeptide-Resistant *Enterococcus* Species. *J Clin Microbiol* 46, 1577-1587.

Miller, M. B. & Tang, Y.-W. (2009). Basic Concepts of Microarrays and Potential Applications in Clinical Microbiology. *Clin Microbiol Rev* 22, 611-633.

Nallur, G., Luo, C., Fang, L. & other authors (2001). Signal amplification by rolling circle amplification on DNA microarrays. Nucl Acids Res 29, e118-.

Niemann, S., Richter, E. & Rusch-Gerdes, S. (2000). Differentiation among Members of the *Mycobacterium tuberculosis* Complex by Molecular and Biochemical Features: Evidence for Two Pyrazinamide-Susceptible Subtypes *M. bovis*. *J Clin Microbiol* 38, 152-157.

O'Grady, J., Sedano-Balbás, S., Maher, M., Smith, T. & Barry, T. (2008). Rapid real-time PCR detection of *Listeria monocytogenes* in enriched food samples based on the ssrA gene, a novel diagnostic target. *Food Microbiology* 25, 75-84.

Panteix, G., Gutierrez, M. C., Boschiroli, M. L. & other authors (2010). Pulmonary tuberculosis due to *Mycobacterium microti*: a study of six recent cases in France. *J Med Microbiol* 59, 984-989.

Parsons, L. M., Brosch, R., Cole, S. T., Somoskovi, A., Loder, A., Bretzel, G., van Soolingen, D., Hale, Y. M. & Salfinger, M. (2002). Rapid and Simple Approach for Identification of *Mycobacterium tuberculosis* Complex Isolates by PCR-Based Genomic Deletion Analysis. *J Microbiol* 40, 2339-2345.

Pfyffer, G. E., Auckenthaler, R., van Embden, J. D. & van Soolingen, D. (1998). *Mycobacterium canettii*, the smooth variant of *M. tuberculosis*, isolated from a Swiss patient exposed in Africa. *Emerg Infect Dis* 4, 631-634.

Pinsky, B. A. & Banaei, N. (2008). Multiplex Real-Time PCR Assay for Rapid Identification of *Mycobacterium tuberculosis* Complex Members to the Species Level. *J Clin Microbiol* 46, 2241-2246.

Pym, A. S., Brodin, P., Brosch, R., Huerre, N. & Cole, S. T. (2002). Loss of RD1 contributed to the attenuation of the live tuberculosis vaccines *Mycobacterium bovis* BCG and *Mycobacterium microti. Molecular Microbiology* 46, 709-717.

Qin, Y., Polacek, N., Vesper, O., Staub, E., Einfeldt, E., Wilson, D. N. & Nierhaus, K. H. (2006). The Highly Conserved LepA Is a Ribosomal Elongation Factor that Back-Translocates the Ribosome. *Cell* 127, 721-733.

Rezwan, M., Grau, T., Tschumi, A. & Sander, P. (2007). Lipoprotein synthesis in mycobacteria. *Microbiology* 153, 652-658.

Robertson, J. M. & Walsh-Weller, J. (1998). An Introduction to PCR Primer Design and Optimization of Amplification Reactions. In *Forensic DNA Profiling Protocols*, pp. 121-154.

Rodríguez-Lázaro, D., Lloyd, J., Herrewegh, A., Ikonomopoulos, J., D'Agostino, M., Pla, M. & Cook, N. (2004). A molecular beacon-based real-time NASBA assay for detection of <i>*Mycobacterium avium*<i> subsp. <i>paratuberculosis<i> in water and milk. *FEMS Microbiology Letters* 237, 119-126.

Scheler, O., Glynn, B., Parkel, S., Palta, P., borne, K., Kaplinski, L., Remm, M., Maher, M. & Kurg, A. (2009). Fluorescent labeling of NASBA amplified tmRNA molecules for microarray applications. *BMC Biotechnology* 9, 45.

Somoskovi, A., Dormandy, J., Parsons, L. M., Kaswa, M., Goh, K. S., Rastogi, N. & Salfinger, M. (2006). Sequencing of the pncA gene in members of the *Mycobacterium tuberculosis* complex has important diagnostic applications: Identification of a species-specific pncA Mutation in *Mycobacterium canettii*, and the Reliable and Rapid Predictor of Pyrazinamide Resistance. *J Clin Microbiol, JCM.* 01454-01406.

Somoskovi, A., Dormandy, J., Mayrer, A. R., Carter, M., Hooper, N. & Salfinger, M. (2009). "*Mycobacterium canettii*" Isolated from a Human Immunodeficiency Virus-Positive Patient: First Case Recognized in the United States. *J Clin Microbiol* 47, 255-257.

Tortoli, E., Lavinia, F. & Simonetti, M. (1997). Evaluation of a commercial ligase chain reaction kit (Abbott LCx) for direct detection of *Mycobacterium tuberculosis* in pulmonary and extrapulmonary specimens. *J Clin Microbiol* 35, 2424-2426.

van Soolingen, D., Hoogenboezem, T., Be Haas, P. E. W. & other authors (1997). A Novel Pathogenic Taxon of the *Mycobacterium tuberculosis* Complex, *Canetti*: Characterization of an Exceptional Isolate from Africa. *Int J Syst Bacteriol* 47, 1236-1245.

Vasconcellos, S., Huard, R., Niemann, S., Kremer, K., Santos, A., Suffys, P. & Ho, J. (2010). Distinct genotypic profiles of the two major clades of *Mycobacterium africanum. BMC Infectious Diseases* 10, 80.

Voelkerding, K. V., Barnes, S. A. & Durtschi, J. D. (2009). Next-Generation Sequencing: From Basic Research to Diagnostics. *Clin Chem* 55, 641-658.

Yang, S. & Rothman, R. E. (2004). PCR-based diagnostics for infectious diseases: uses, limitations, and future applications in acute-care settings. *The Lancet Infectious Diseases* 4, 337-348.

The invention claimed is:

1. A multiplex in vitro nucleic acid amplification method for identifying *Mycobacterium canettii* present in a sample, wherein the method comprises:

(i) performing a multiplex in vitro nucleic acid amplification using multiple sets of primers that are suitable for amplifying a plurality of nucleic acid molecule targets in the sample in one reaction, and (ii) detecting the presence or absence of a plurality of nucleic acid molecule targets in the sample in one reaction, wherein the plurality of nucleic acid molecule targets, in combination, are unique in their presence or absence to *Mycobacterium canettii*, and wherein primers or probes comprise a sequence of at least 16 contiguous nucleotides of SEQ ID NO:78, or the sequence complementary thereto, said primers or probes are specific for a nucleic acid sequence that is present in *M. canettii*, but is not present in *M. tuberculosis* and comprises a region of $RD^{canetti1}$, SEQ ID NO: 78, and are used in the amplification and/or detection step.

2. The multiplex in vitro nucleic acid amplification method of claim 1 wherein the method comprises a multiplex PCR.

3. The method of claim 1 wherein:

a) the primers comprise SEQ ID NO: 103 and SEQ ID NO: 105; and/or b) the probe comprises SEQ ID NO: 104.

4. The method of claim 1, further comprising amplifying and/or detecting a nucleic acid sequence that is present in both *M. tuberculosis* and *M. canettii* using primers or probes specific for the nucleic acid sequence that is present in both *M. tuberculosis* and *M. canettii.*

5. The method of claim 4 wherein the nucleic acid sequence that is present in both *M. tuberculosis* and *M. canettii* comprises a region of wbbl1, SEQ ID NO: 1.

6. The method of claim 5 wherein:

a) the primers comprise SEQ ID NO: 97 and SEQ ID NO: 99; and/or b) the probe comprises SEQ ID NO: 98.

7. The method of claim 1, further comprising amplifying and/or detecting a nucleic acid sequence that is present in *M. africanum* clade 1 but is not present in *M. tuberculosis* or *M. canettii* using primers or probes specific for the nucleic acid sequence that is present in *M. africanum* clade 1 but not present in *M. tuberculosis* or *M. canettii.*

8. The method of claim 7 wherein the nucleic acid sequence that is present in *M. africanum* clade 1 but is not present in *M. tuberculosis* or *M. canettii* comprises a region of RD713, SEQ ID NO: 137.

9. The method of claim 8 wherein:

a) the primers comprise SEQ ID NOs: 167 and 168; and/or b) the probe comprises SEQ ID NO: 169.

10. The method of claim 1 further comprising amplifying and/or detecting lepA, SEQ ID NO: 47, using primers or probes specific for lepA, SEQ ID NO: 47, to detect the presence or absence of the *Mycobacterium tuberculosis* complex.

11. The method of claim 1, further comprising amplifying and/or detecting a nucleic acid sequence that is present in both *M. tuberculosis* and *M. canettii* using primers or probes specific for a nucleic acid sequence that is present in both *M. tuberculosis* and *M. canettii* and amplifying and/or detecting a nucleic acid sequence that is present in all members of the *Mycobacterium tuberculosis* complex using primers or probes specific for a nucleic acid sequence that is present in all members of the *Mycobacterium tuberculosis* complex.

12. The method of claim 1 further comprising a multiplex in vitro nucleic acid amplification comprising:

(i) detecting a plurality of nucleic acid molecules which, in combination, are unique in their presence or absence to *Mycobacterium bovis,*

(ii) detecting a plurality of nucleic acid molecules which, in combination, are unique in their presence or absence to *Mycobacterium bovis* BCG, (iii) detecting a plurality of nucleic acid molecules which, in combination, are unique in their presence or absence to *Mycobacterium caprae,*

(iv) detecting a plurality of nucleic acid molecules which, in combination, are unique in their presence or absence to *Mycobacterium africanum* clade 2, (v) detecting a plurality of nucleic acid molecules which, in combination, are unique in their presence or absence to *Mycobacterium pinnipedii* or (vi) detecting a plurality of nucleic acid molecules which, in combination, are unique in their presence or absence to *Mycobacterium microti.*

13. The method of claim 11 further comprising a multiplex in vitro nucleic acid amplification comprising:

(i) detecting a plurality of nucleic acid molecules which, in combination, are unique in their presence or absence to *Mycobacterium bovis,*

(ii) detecting a plurality of nucleic acid molecules which, in combination, are unique in their presence or absence to *Mycobacterium bovis* BCG, (iii) detecting a plurality of nucleic acid molecules which, in combination, are unique in their presence or absence to *Mycobacterium caprae,*

(iv) detecting a plurality of nucleic acid molecules which, in combination, are unique in their presence or absence to *Mycobacterium africanum* clade 2, (v) detecting a plurality of nucleic acid molecules which, in combination, are unique in their presence or absence to *Mycobacterium pinnipedii* or (vi) detecting a plurality of nucleic acid molecules which, in combination, are unique in their presence or absence to *Mycobacterium microti*.

14. The method of claim 12 comprising amplifying and/or detecting a nucleic acid sequence that is present in all three of *M. bovis, M. bovis* BCG and *M. caprae* using primers or probes that are specific for the nucleic acid sequence that is present in all three of *M. bovis, M. bovis* BCG and *M. caprae*.

15. The method of claim 12 comprising amplifying and/or detecting a nucleic acid sequence that is present in *M. caprae* but is not present in *M. bovis* or *M. bovis* BCG using primers or probes that are specific for the nucleic acid sequence that is present in *M. caprae* but is not present in *M. bovis* or *M. bovis* BCG.

16. The method of claim 12 comprising amplifying and/or detecting a nucleic acid sequence that is deleted in *M. bovis* BCG and *M. microti* but is present in *M. bovis, M. caprae* and *M. pinnipedii* using primers or probes that are specific for the nucleic acid sequence that is deleted in *M. bovis* BCG and *M. microti* but is present in *M. bovis, M. caprae* and *M. pinnipedii*.

17. The method of claim 12 comprising amplifying and/or detecting a nucleic acid sequence that is present in *M. africanum* clade 2 but is not present in *M. bovis, M. bovis* BCG, *M. caprae, M. microti* or *M. pinnipedii* using primers or probes that are specific for the nucleic acid sequence that is present in *M. africanum* clade 2 but is not present in *M. bovis, M. bovis* BCG, *M. caprae, M. microti* or *M. pinnipedii*.

18. A multiplex in vitro nucleic acid amplification method for identifying a species of the *Mycobacterium tuberculosis* complex present in a sample, comprising:

(i) a multiplex in vitro nucleic acid amplification method for identifying *Mycobacterium canettii* present in a sample wherein the method comprises (a) performing a multiplex in vitro nucleic acid amplification using multiple sets of primers that are suitable for amplifying a plurality of nucleic acid molecule targets in the sample in one reaction, and (b) detecting the presence or absence of a plurality of nucleic acid molecule targets in the sample in one reaction, wherein the plurality of nucleic acid molecule targets, in combination, are unique in their presence or absence to *Mycobacterium canettii*, and wherein primers or probes comprise a sequence of at least 16 contiguous nucleotides of SEQ ID NO:78, or the sequence complementary thereto, said primers or probes are specific for a nucleic acid sequence that is present in *M. canettii*, but is not present in *M. tuberculosis* and comprises a region of $RD^{canetti1}$, SEQ ID NO: 78, and are used in the amplification and/or detection step and subsequently (ii) a multiplex in vitro nucleic acid amplification comprising detecting a plurality of nucleic acid molecules which, in combination, are unique in their presence or absence to *Mycobacterium bovis*, detecting a plurality of nucleic acid molecules which, in combination, are unique in their presence or absence to *Mycobacterium bovis* BCG, detecting a plurality of nucleic acid molecules which, in combination, are unique in their presence or absence to *Mycobacterium caprae*, detecting a plurality of nucleic acid molecules which, in combination, are unique in their presence or absence to *Mycobacterium africanum* clade 2, detecting a plurality of nucleic acid molecules which, in combination, are unique in their presence or absence to *Mycobacterium pinnipedii* or detecting a plurality of nucleic acid molecules which, in combination, are unique in their presence or absence to *Mycobacterium microti*.

19. A multiplex in vitro nucleic acid amplification method for identifying a species of the *Mycobacterium tuberculosis* complex present in a sample, comprising:

(i) a multiplex in vitro nucleic acid amplification method for identifying *Mycobacterium canettii* present in a sample wherein the method comprises (a) performing a multiplex in vitro nucleic acid amplification using multiple sets of primers that are suitable for amplifying a plurality of nucleic acid molecule targets in the sample in one reaction, and (b) detecting the presence or absence of a plurality of nucleic acid molecule targets in the sample in one reaction, wherein the plurality of nucleic acid molecule targets, in combination, are unique in their presence or absence to *Mycobacterium canettii*, and wherein primers or probes comprise a sequence of at least 16 contiguous nucleotides of SEQ ID NO:78, or the sequence complementary thereto, said primers or probes are specific for a nucleic acid sequence that is present in *M. canettii*, but is not present in *M. tuberculosis* and comprises a region of $RD^{canetti1}$, SEQ ID NO: 78, and are used in the amplification and/or detection step, and primers or probes specific for a nucleic acid sequence that is present in both *M. tuberculosis* and *M. canettii* and primers or probes specific for a nucleic acid sequence that is present in all members of the *Mycobacterium tuberculosis* complex are used in the amplification and/or detection step, and subsequently (ii) a multiplex in vitro nucleic acid amplification comprising detecting a plurality of nucleic acid molecules which, in combination, are unique in their presence or absence to *Mycobacterium bovis*, detecting a plurality of nucleic acid molecules which, in combination, are unique in their presence or absence to *Mycobacterium bovis* BCG, detecting a plurality of nucleic acid molecules which, in combination, are unique in their presence or absence to *Mycobacterium caprae*, detecting a plurality of nucleic acid molecules which, in combination, are unique in their presence or absence to *Mycobacterium africanum* clade 2, detecting a plurality of nucleic acid molecules which, in combination, are unique in their presence or absence to *Mycobacterium pinnipedii* or detecting a plurality of nucleic acid molecules which, in combination, are unique in their presence or absence to *Mycobacterium microti*.

20. The method of claim 1 further comprising amplifying and/or detecting an internal amplification control (IAC) using primers or probes specific for the IAC.

21. A diagnostic technique for identifying *Mycobacterium canettii* comprising hybridising sample nucleic acid molecules to one or more nucleic acid molecules which comprise or are complementary to a region of at least 16 contiguous nucleotides of $RD^{canetti1}$ (SEQ ID NO:78) and which are specific for a nucleic acid sequence that is present in *M. canettii* but is not present in *M. tuberculosis*.

22. The diagnostic technique of claim 21 wherein the sample nucleic acid molecules are further hybridised to at least one nucleic acid molecule that comprises or is complementary to a) a region of wbbl1 (SEQ ID NOs: 1-46), and which is present in both *M. tuberculosis* and *M. canettii;* b) a region of lepA (SEQ ID NOs: 47-77);

c) a region of RD713 (SEQ ID NO: 137), and which is present in *M. africanum* clade 1 but is not present in *M. tuberculosis* or *M. canettii;* d) a region of lpqT (SEQ ID NO: 109), and which is present in all three of *M. bovis, M. bovis* BCG and *M. caprae;* e) a region of *M. caprae* lepA (SEQ ID NO: 76) and which is specific for a nucleic acid sequence that is present in *M. caprae* but is not present in *M. bovis* or *M. bovis* BCG;

f) a region of RD1 (SEQ ID NO: 141) and which is specific for a nucleic acid sequence that is deleted in *M. bovis* BCG and *M. microti* but present in *M. bovis, M. caprae* and *M. pinnipedii*; and/or g) a region of RD701 (SEQ ID NO: 132) and which is specific for a nucleic acid sequence that is present in *M. africanum* clade 2 but is not present in *M. bovis, M. bovis* BCG, *M. caprae, M. microti* or *M. pinnipedii.*

23. The method of claim 1, wherein said primers or probe comprise a sequence of 16 to 30 contiguous nucleotides of SEQ ID NO:78, or the sequence complementary thereto.

24. The method of claim 18, wherein said primers or probe comprise a sequence of 16 to 30 contiguous nucleotides of SEQ ID NO:78, or the sequence complementary thereto.

25. The method of claim 19, wherein said primers or probe comprise a sequence of 16 to 30 contiguous nucleotides of SEQ ID NO:78, or the sequence complementary thereto.

26. The diagnostic technique of claim 21, wherein said nucleic acid molecules comprise a sequence of 16 to 30 contiguous nucleotides of SEQ ID NO:78, or the sequence complementary thereto.

* * * * *

SEQUENCE LISTING

<160> NUMBER OF SEQ ID NOS: 173

<210> SEQ ID NO 1

<211> LENGTH: 906
<212> TYPE: DNA
<213> ORGANISM: Mycobacterium tuberculosis

<400> SEQUENCE: 1

```
tcagtgccgc ccttctacca gcttcagttt ccgtctgcgg gacctgcgca gtgaactgcg     60
caccatgagg tgggaacgca gcgccagtga tccccgcagg gtccagcgca gcggagcccg    120
ccaccaacca gaatgtcggt cggctaagaa gatataggtg cttttgtgat gggcggccag    180
atggcttgcc gggtcgcgac ccgtcgaatg cgccttgtgg tgcagaacct cggctgacgg    240
cacatacacc gacagccaac cggctttgcc aagccggtcg ccaaggtcga cgtcctccat    300
gtacatgaag taacgttcgt cgaatccgcc gacctggcca aacgccgacc ggcgcaccag    360
taggcaagac cccgacaacc aacccaccgg ccgttcactg ggctccagcc gctcctgccg    420
gtaggccgtc gtccacggat tgcgcggcca gaacggcccg agcactgcgt gcatgccgcc    480
gcggatcagg ctgggcatct gccgcgccga cgggtacacc gacccgtcgg ggtcccgaat    540
cagcgggccc agcgcgcccg cgcggggcca gcgggaggcg gcgtccagta gtgcatcgat    600
actgcccggg ccccattgca cgtccgggtt ggccacgatc acccagtcat cgacccaggg    660
ttcgccggca tcgcccgcca tttcaccgag ctgggcgatc gtccgattca ccgcggttcc    720
gtacccgagg ttggcccctg tgggcagcag ccgcacgttg gggtagcgct gcaccgcggc    780
ctgcggggtg ccgtcggtgg agccgttgtc tgccaacagc acgctgaccg gccgctcggt    840
ggccagcgac aacgacgcca ggaaccgctc tagatggggc cccggcgagt aggtcaccgc    900
taccac                                                               906
```

<210> SEQ ID NO 2
<211> LENGTH: 906
<212> TYPE: DNA
<213> ORGANISM: Mycobacterium tuberculosis

<400> SEQUENCE: 2

```
tcagtgccgc ccttctacca gcttcagttt ccgtctgcgg gacctgcgca gtgaactgcg     60
caccatgagg tgggaacgca gcgccagtga tccccgcagg gtccagcgca gcggagcccg    120
ccaccaacca gaatgtcggt cggctaagaa gatataggtg cttttgtgat gggcggccag    180
atggcttgcc gggtcgcgac ccgtcgaatg cgccttgtgg tgcagaacct cggctgacgg    240
cacatacacc gacagccaac cggctttgcc aagccggtcg ccaaggtcga cgtcctccat    300
gtacatgaag taacgttcgt cgaatccgcc gacctggcca aacgccgacc ggcgcaccag    360
taggcaagac cccgacaacc aacccaccgg ccgttcactg ggctccagcc gctcctgccg    420
gtaggccgtc gtccacggat tgcgcggcca gaacggcccg agcactgcgt gcatgccgcc    480
gcggatcagg ctgggcatct gccgcgccga cgggtacacc gacccgtcgg ggtcccgaat    540
cagcgggccc agcgcgcccg cgcggggcca gcgggaggcg gcgtccagta gtgcatcgat    600
actgcccggg ccccattgca cgtccgggtt ggccacgatc acccagtcat cgacccaggg    660
ttcgccggca tcgcccgcca tttcaccgag ctgggcgatc gtccgattca ccgcggttcc    720
gtacccgagg ttggcccctg tgggcagcag ccgcacgttg gggtagcgct gcaccgcggc    780
ctgcggggtg ccgtcggtgg agccgttgtc tgccaacagc acgctgaccg gccgctcggt    840
ggccagcgac aacgacgcca ggaaccgctc tagatggggc cccggcgagt aggtcaccgc    900
taccac                                                               906
```

-continued

<210> SEQ ID NO 3
<211> LENGTH: 906
<212> TYPE: DNA
<213> ORGANISM: Mycobacterium tuberculosis

<400> SEQUENCE: 3
tcagtgccgc ccttctacca gcttcagttt ccgtctgcgg gacctgcgca gtgaactgcg 60
caccatgagg tgggaacgca gcgccagtga tccccgcagg gtccagcgca gcggagcccg 120
ccaccaacca gaatgtcggt cggctaagaa gatataggtg cttttgtgat gggcggccag 180
atggcttgcc gggtcgcgac ccgtcgaatg cgccttgtgg tgcagaacct cggctgacgg 240
cacatacacc gacagccaac cggctttgcc aagccggtcg ccaaggtcga cgtcctccat 300
gtacatgaag taacgttcgt cgaatccgcc gacctggcca aacgccgacc ggcgcaccag 360
taggcaagac cccgacaacc aacccaccgg ccgttcactg ggctccagcc gctcctgccg 420
gtaggccgtc gtccacggat tgcgcggcca gaacggcccg agcactgcgt gcatgccgcc 480
gcggatcagg ctgggcatct gccgcgccga cgggtacacc gacccgtcgg ggtcccgaat 540
cagcgggccc agcgcgcccg cgcggggcca gcgggaggcg gcgtccagta gtgcatcgat 600
actgcccggg ccccattgca cgtccgggtt ggccacgatc acccagtcat cgacccaggg 660
ttcgccggca tcgcccgcca tttcaccgag ctgggcgatc gtccgattca ccgcggttcc 720
gtacccgagg ttggcccctg tgggcagcag ccgcacgttg ggtagcgct gcaccgcggc 780 ctgcggggtg ccgtcggtgg agccgttgtc tgccaacagc acgctgaccg gccgctcggt 840
ggccagcgac aacgacgcca ggaaccgctc tagatggggc cccggcgagt aggtcaccgc 900
taccac 906

<210> SEQ ID NO 4
<211> LENGTH: 924
<212> TYPE: DNA
<213> ORGANISM: Mycobacterium tuberculosis

<400> SEQUENCE: 4
tcagtgccgc ccttctacca gcttcagttt ccgtctgcgg gacctgcgca gtgaactgcg 60
caccatgagg tgggaacgca gcgccagtga tccccgcagg gtccagcgca gcggagcccg 120
ccaccaacca gaatgtcggt cggctaagaa gatataggtg cttttgtgat gggcggccag 180
atggcttgcc gggtcgcgac ccgtcgaatg cgccttgtgg tgcagaacct cggctgacgg 240
cacatacacc gacagccaac cggctttgcc aagccggtcg ccaaggtcga cgtcctccat 300
gtacatgaag taacgttcgt cgaatccgcc gacctggcca aacgccgacc ggcgcaccag 360
taggcaagac cccgacaacc aacccaccgg ccgttcactg ggctccagcc gctcctgccg 420
gtaggccgtc gtccacggat tgcgcggcca gaacggcccg agcactgcgt gcatgccgcc 480
gcggatcagg ctgggcatct gccgcgccga cgggtacacc gacccgtcgg ggtcccgaat 540
cagcgggccc agcgcgcccg cgcggggcca gcgggaggcg gcgtccagta gtgcatcgat 600
actgcccggg ccccattgca cgtccgggtt ggccacgatc acccagtcat cgacccaggg 660
ttcgccggca tcgcccgcca tttcaccgag ctgggcgatc gtccgattca ccgcggttcc 720
gtacccgagg ttggcccctg tgggcagcag ccgcacgttg ggtagcgct gcaccgcggc 780 ctgcggggtg ccgtcggtgg agccgttgtc tgccaacagc acgctgaccg gccgctcggt 840
ggccagcgac aacgacgcca ggaaccgctc tagatggggc cccggcgagt aggtcaccgc 900
taccaccggc aggacgtcag tcac 924

-continued

<210> SEQ ID NO 5
<211> LENGTH: 906
<212> TYPE: DNA
<213> ORGANISM: Mycobacterium tuberculosis

<400> SEQUENCE: 5
tcagtgccgc ccttctacca gcttcagttt ccgtctgcgg gacctgcgca gtgaactgcg 60
caccatgagg tgggaacgca gcgccagtga tccccgcagg gtccagcgca gcggagcccg 120
ccaccaacca gaatgtcggt cggctaagaa gatataggtg cttttgtgat gggcggccag 180
atggcttgcc gggtcgcgac ccgtcgaatg cgccttgtgg tgcagaacct cggctgacgg 240
cacatacacc gacagccaac cggctttgcc aagccggtcg ccaaggtcga cgtcctccat 300
gtacatgaag taacgttcgt cgaatccgcc gacctggcca aacgccgacc ggcgcaccag 360
taggcaagac cccgacaacc aacccaccgg ccgttcactg ggctccagcc gctcctgccg 420
gtaggccgtc gtccacggat tgcgcggcca gaacggcccg agcactgcgt gcatgccgcc 480
gcggatcagg ctgggcatct gccgcgccga cgggtacacc gacccgtcgg ggtcccgaat 540
cagcgggccc agcgcgcccg cgcggggcca gcgggaggcg gcgtccagta gtgcatcgat 600
actgcccggg ccccattgca cgtccgggtt ggccacgatc acccagtcat cgacccaggg 660
ttcgccggca tcgcccgcca tttcaccgag ctgggcgatc gtccgattca ccgcggttcc 720
gtacccgagg ttggcccctg tgggcagcag ccgcacgttg ggtagcgcgt gcaccgcggc 780
ctgcggggtg ccgtcggtgg agccgttgtc tgccaacagc acgctgaccg gccgctcggt 840
ggccagcgac aacgacgcca ggaaccgctc tagatggggc cccggcgagt aggtcaccgc 900
taccac 906

<210> SEQ ID NO 6
<211> LENGTH: 894
<212> TYPE: DNA
<213> ORGANISM: Mycobacterium bovis BCG

<400> SEQUENCE: 6
tcagtgccgc ccttctacca gcttcagttt ccgtctgcgg gacctgcgca ccatgaggtg 60
ggaacgcagc gccagtgatc cccgcagggt ccagcgcagc ggagcccgcc accaaccaga 120
atgtcggtcg gctaagaaga tataggtgct tttgtgatgg gcggccagat ggcttgccgg 180
gtcgcgaccc gtcgaatgcg ccttgtggtg cagaacctcg gctgacggca catacaccga 240
cagccaaccg gctttgccaa gccggtcgcc aaggtcgacg tcctccatgt acatgaagta 300
acgttcgtcg aatccgccga cctggccaaa cgccgaccgg cgcaccagta ggcaagaccc 360
cgacaaccaa cccaccggcc gttcactggg ctccagccgc tcctgccggt aggccgtcgt 420
ccacggattg cgcggccaga acggcccgag cactgcgtgc atgccgccgc ggatcaggct 480
gggcatctgc cgcgccgacg ggtacaccga cccgtcgggg tcccgaatca gcgggcccag 540
cgcgcccgcg cggggccagc gggaggcggc gtccagtagt gcatcgatac tgcccgggcc 600
ccattgcacg tccgggttgg ccacgatcac ccagtcatcg acccagggtt cgccggcatc 660
gcccgccatt tcaccgagct gggcgatcgt ccgattcacc gcggttccgt acccgaggtt 720
ggcccctgtg ggcagcagcc gcacgttggg gtagcgctgc accgcggcct gcggggtgcc 780
gtcggtggag ccgttgtctg ccaacagcac gctgaccggc cgctcggtgg ccagcgacaa 840
cgacgccagg aaccgctcta gatggggccc cggcgagtag gtcaccgcta ccac 894

-continued

<210> SEQ ID NO 7
<211> LENGTH: 894
<212> TYPE: DNA
<213> ORGANISM: Mycobacterium bovis BCG

<400> SEQUENCE: 7
tcagtgccgc ccttctacca gcttcagttt ccgtctgcgg gacctgcgca ccatgaggtg 60
ggaacgcagc gccagtgatc cccgcagggt ccagcgcagc ggagcccgcc accaaccaga 120
atgtcggtcg gctaagaaga tataggtgct tttgtgatgg gcggccagat ggcttgccgg 180
gtcgcgaccc gtcgaatgcg ccttgtggtg cagaacctcg gctgacggca catacaccga 240
cagccaaccg gctttgccaa gccggtcgcc aaggtcgacg tcctccatgt acatgaagta 300
acgttcgtcg aatccgccga cctggccaaa cgccgaccgg cgcaccagta ggcaagaccc 360
cgacaaccaa cccaccggcc gttcactggg ctccagccgc tcctgccggt aggccgtcgt 420
ccacggattg cgcggccaga acggcccgag cactgcgtgc atgccgccgc ggatcaggct 480
gggcatctgc cgcgccgacg ggtacaccga cccgtcgggg tcccgaatca gcgggcccag 540
cgcgcccgcg cggggccagc gggaggcggc gtccagtagt gcatcgatac tgcccgggcc 600
ccattgcacg tccgggttgg ccacgatcac ccagtcatcg acccagggtt cgccggcatc 660
gcccgccatt tcaccgagct gggcgatcgt ccgattcacc gcggttccgt acccgaggtt 720
ggcccctgtg ggcagcagcc gcacgttggg gtagcgctgc accgcggcct gcggggtgcc 780
gtcggtggag ccgttgtctg ccaacagcac gctgaccggc cgctcggtgg ccagcgacaa 840
cgacgccagg aaccgctcta gatggggccc cggcgagtag gtcaccgcta ccac 894

<210> SEQ ID NO 8
<211> LENGTH: 894
<212> TYPE: DNA
<213> ORGANISM: Mycobacterium bovis

<400> SEQUENCE: 8
tcagtgccgc ccttctacca gcttcagttt ccgtctgcgg gacctgcgca ccatgaggtg 60
ggaacgcagc gccagtgatc cccgcagggt ccagcgcagc ggagcccgcc accaaccaga 120
atgtcggtcg gctaagaaga tataggtgct tttgtgatgg gcggccagat ggcttgccgg 180
gtcgcgaccc gtcgaatgcg ccttgtggtg cagaacctcg gctgacggca catacaccga 240
cagccaaccg gctttgccaa gccggtcgcc aaggtcgacg tcctccatgt acatgaagta 300
acgttcgtcg aatccgccga cctggccaaa cgccgaccgg cgcaccagta ggcaagaccc 360
cgacaaccaa cccaccggcc gttcactggg ctccagccgc tcctgccggt aggccgtcgt 420
ccacggattg cgcggccaga acggcccgag cactgcgtgc atgccgccgc ggatcaggct 480
gggcatctgc cgcgccgacg ggtacaccga cccgtcgggg tcccgaatca gcgggcccag 540
cgcgcccgcg cggggccagc gggaggcggc gtccagtagt gcatcgatac tgcccgggcc 600
ccattgcacg tccgggttgg ccacgatcac ccagtcatcg acccagggtt cgccggcatc 660
gcccgccatt tcaccgagct gggcgatcgt ccgattcacc gcggttccgt acccgaggtt 720
ggcccctgtg ggcagcagcc gcacgttggg gtagcgctgc accgcggcct gcggggtgcc 780
gtcggtggag ccgttgtctg ccaacagcac gctgaccggc cgctcggtgg ccagcgacaa 840
cgacgccagg aaccgctcta gatggggccc cggcgagtag gtcaccgcta ccac 894

<210> SEQ ID NO 9
<211> LENGTH: 881
<212> TYPE: DNA

-continued

<213> ORGANISM: Mycobacterium africanum

<400> SEQUENCE: 9

```
tcagtgccgc ccttctacca gcttcagttt ccgtctgcgg gacctgcgca ccatgaggtg      60
ggaacgcagc gccagtgatc cccgcagggt ccagcgcagc ggagcccgcc accaaccaga     120
atgtcggtcg gctaagaaga tataggtgct tttgtgatgg gcggccagat ggcttgccgg     180
gtcgcgaccc gtcgaatgcg ccttgtggtg cagaacctcg gctgacggca catacaccga     240
cagccaaccg gctttgccaa gccggtcgcc aaggtcgacg tcctccatgt acatgaagta     300
acgttcgtcg aatccgccga cctggccaaa cgccgaccgg cgcaccagta ggcaagaccc     360
cgacaaccaa cccaccggcc gttcactggg ctccagccgc tcctgccggt aggccgtcgt     420
ccacggattg cgcggccaga acggcccgag cactgcgtgc atgccgccgc ggatcaggct     480
gggcatctgc cgcgccgacg ggtacaccga cccgtcgggg tcccgaatca gcgggcccag     540
cgcgcccgcg cggggccagc gggaggcggc gtccagtagt gcatcgatac tgcccgggcc     600
ccattgcacg tccgggttgg ccacgatcac ccagtcatcg acccagggtt cgccggcatc     660
gcccgccatt tcaccgagct gggcgatcgt ccgattcacc gcggttccgt acccgaggtt     720
ggcccctgtg ggcagcagcc gcacgttggg gtagcgctgc accgcggcct gcggggtgcc     780
gtcggtggag ccgttgtctg ccaacagcac gctgaccggc cgctcggtgg ccagcgacaa     840
cgacgccagg aaccgctcta gatggggccc cggcgagtag g                         881
```

<210> SEQ ID NO 10
<211> LENGTH: 905
<212> TYPE: DNA
<213> ORGANISM: Mycobacterium microti

<400> SEQUENCE: 10

```
tcagtgccgc ccttctacca gcttcagttt ccgtctgcgg gacctgcgca ccatgaggtg      60
ggaacgcagc gccagtgatc cccgcagggt ccagcgcagc ggagcccgcc accaaccaga     120
atgtcggtcg gctaagaaga tataggtgct tttgtgatgg gcggccagat ggcttgccgg     180
gtcgcgaccc gtcgaatgcg ccttgtggtg cagaacctcg gctgacggca catacaccga     240
cagccaaccg gctttgccaa gccggtcgcc aaggtcgacg tcctccatgt acatgaagta     300
acgttcgtcg aatccgccga cctggccaaa cgccgaccgg cgcaccagta ggcaagaccc     360
cgacaaccaa cccaccggcc gttcactggg ctccagccgc tcctgccggt aggccgtcgt     420
ccacggattg cgcggccaga acggcccgag cactgcgtgc atgccgccgc ggatcaggct     480
gggcatctgc cgcgccgacg ggtacaccga cccgtcgggg tcccgaatca gcgggcccag     540
cgcgcccgcg cggggccagc gggaggcggc gtccagtagt gcatcgatac tgcccgggcc     600
ccattgcacg tccgggttgg ccacgatcac ccagtcatcg acccagggtt cgccggcatc     660
gcccgccatt tcaccgagct gggcgatcgt ccgattcacc gcggttccgt acccgaggtt     720
ggcccctgtg ggcagcagcc gcacgttggg gtagcgctgc accgcggcct gcggggtgcc     780
gtcggtggag ccgttgtctg ccaacagcac gctgaccggc cgctcggtgg ccagcgacaa     840
cgacgccagg aaccgctcta gatggggccc cggcgagtag gtcaccgcta ccacaccgct     900
accac                                                                905
```

<210> SEQ ID NO 11
<211> LENGTH: 876
<212> TYPE: DNA
<213> ORGANISM: Mycobacterium avium -continued

<400> SEQUENCE: 11

```
tcagtgccgc ccttctaccc gccgcccgga ctcgcgcagc gcgctgcgca ccatcagccg     60
ggcgcgcacc gccagcgacg cgcgcagcgc ccagcgcagc ggcgcgcgca tccaaccgga    120
ataccggtcg gccagaaaca tataggtgct gcggtggtgg gcggccaggt ggctggccgg    180
gtcggccccg gtggagtggc ccttgtggtg cagcacctcg gccgacggca cgtagaccga    240
cagccagccg gccttgccca gccggtcgcc gaggtcgacg tcctccatgt acatgaagta    300
gcgctcgtcg aacccgccga cccgctcgaa tgccgagcgg cgcaccagca ggcacgaacc    360
cgacagccag cccaccggcc gctcgctggg ctccagccgc tcctggcgat aggccgtcga    420
ccacgggttg ttcttccaga acggcccgac gaccgcgtgc atgccgccgc gcaccaggct    480
gggcaggtgc cgcgccgacg ggtacaccga cccgtcgggg tcgcgcacca gcgggcccag    540
cgcgccggcc cgcggccagc gcgccgcggc gtccagcagc gcgtcgatgc tgccgggccc    600
ccactgcacg tccgggttgg cgacgatcac ccactcgccg ccgcgatcca gctgtgccac    660
agcacgattc accgcggtgc cgtagccgag gttggcgccg gtgtgaaaca gccgcacgtt    720
ggggtagcgc tcgacggcgg cctgcggcgt cccgtcggtg gagccgttgt cggccagcag    780
cacgcacacc tcgcgttcgg tggccagcga cagcgacgcc aggaagcgct ccaggtgcgg    840
gcccggtgaa taggtcaccg tcaccaccgg cagcac                               876
```

<210> SEQ ID NO 12
<211> LENGTH: 867
<212> TYPE: DNA
<213> ORGANISM: Mycobacterium avium

<400> SEQUENCE: 12

```
tcagtgccgc ccttctaccc gccgcccgga ctcgcgcagc gcgctgcgca ccatcagccg     60
ggcgcgcacc gccagcgacg cgcgcagcgc ccagcgcagc ggcgcgcgca tccaaccgga    120
ataccggtcg gccagaaaca tataggtgct gcggtggtgg gcggccaggt ggctggccgg    180
gtcggccccg gtggagtggc ccttgtggtg cagcacctcg gccgacggca cgtagaccga    240
cagccagccg gccttgccca gccggtcgcc gaggtcgacg tcctccatgt acatgaagta    300
gcgctcgtcg aacccgccga cccgctcgaa tgccgagcgg cgcaccagca ggcacgaacc    360
cgacagccag cccaccggcc gctcgctggg ctccagccgc tcctggcggt aggccgtcga    420
ccacgggttg ttcttccaga acggcccgac gaccgcgtgc atgccgccgc gcaccaggct    480
gggcaggtgc cgcgccgacg ggtacaccga cccgtcgggg tcgcgcacca gcgggcccag    540
cgcgccggcc cgcggccagc gcgccgcggc gtccagcagc gcgtcgatgc tgccgggccc    600
ccactgcacg tccgggttgg cgacgatcac ccactcgccg ccgcgatcca gctgtgccac    660
agcacgattc accgcggtgc cgtagccgag gttggcgccg gtgtgaaaca gccgcacgtt    720
ggggtagcgc tcgacggcgg cctgcggcgt cccgtcggtg gagccgttgt cggccagcag    780
cacgcacacc tcgcgttcgg tggccagcga cagcgacgcc aggaagcgct ccaggtgcgg    840
gcccggtgaa taggtcaccg tcaccac                                         867
```

<210> SEQ ID NO 13
<211> LENGTH: 885
<212> TYPE: DNA
<213> ORGANISM: Mycobacterium marinum

<400> SEQUENCE: 13

```
tcagtgccgc ccttctacca gctttcggcg cgaactgcgc accatcagac gggagcgtac     60

cgccagcgat ccccgcaaag tccagcgcaa tggggcccgc caccagccgg catggcgatc    120

cgccaggaaa atgtaggtgc ttcggtggtg tgccgccagg tgattggccg gatcgcgtcc    180

ggtggagtgg cctttgtggt gcagcacttc cgccgacggc acatagacgc tgagccagcc    240

ggcctggccc agccggtcgc cgaggtccac gtcttccata tacatgaagt agcgctcgtc    300

gaaaccgccg atctggcgga acgcggagcg gcgcaccaac aggcacgaac ccgatagcca    360

gcccaccggc cgttcgctgg gctcgaggtg ttcctggcga taggccttgg tccagggatt    420

gcggggccat accggcccga gcaccgcgtg cataccgccg cggaccaggc tgggcagatg    480

gcgcgccgag ggtacaccg atccatcggg atcgcggatc agcgggccca acgccccggc    540

ctggggccag cgctcgacgg cctcgagcag cgcgtcgatg ctgcccggac cccactgcac    600

gtccgggttg gccacgatca gccagtcgtc tggctccggt tgttcggtga gctgggcgac    660

ggcccggttc accgcggtgc catacccgag gttggccccg gtgtggaaga tccgcacgtt    720

ggggtagcgc tcgacagccg cctgaggtgt tccgtcggtg gagccgttgt cggccagcag    780

cacactcacc ggacggtcgg tggccagcga caaagacgcc aagaagcgct ccaggtgggg    840

gcccggcgag taggtcaccg ccacgaccgg caggacgtca gtcac                    885
```

<210> SEQ ID NO 14
<211> LENGTH: 885
<212> TYPE: DNA
<213> ORGANISM: Mycobacterium ulcerans

<400> SEQUENCE: 14

```
tcagtgccgc ccttctacca gctttcggcg cgaactgcgc accatcagac gggagcgtac     60

cgccagcgat ccccgcaaag tccagcgcaa tggggcccgc caccagccgg catggcgatc    120

cgccaggaaa atgtaggtgc ttcggtggtg taccgccagg tgagtggccg gatcgcgtcc    180

ggtggagtgg cctttgtggt gcagcacttc cgccgacggc acatagacgc tgagccagcc    240

ggcctggccc agccggtcgc cgaggtccac gtcttccata tacatgaagt agcgctcgtc    300

gaaaccgccg atctggcgga acgcggagcg gcgcaccaac aggcacgaac ccgatagcca    360

gcccaccggc cgttcgctgg gctcgaggtg ttcctggcga taggccttgg tccagggatt    420

gcggggccat accggcccga gcaccgcgtg cataccgccg cggaccaggc tgggcagatg    480

gcgcgccgag ggtacaccg atccatcggg atcgcggatc agcgggccca acgccccggc    540

ctggggccag cgctcgacgg cctcgagcag cgcgtcgatg ctgcccggac cccactgcac    600

gtccgggttg gccacgatca gccagtcgtc tggctccggt tgttcggtga gttgggcgac    660

ggcccggttc accgcggtgc cgtacccgag gttggccccg gtgtggaaga tccgcacgtt    720

ggggtagcgc tcgacggccg cctgaggtgt tccgtcggtg gagccgttgt cggccagcag    780

cacactcacc ggacggtcgg tggccagcga caaagacgcc aagaagcgct ccaagtgggg    840

gcccggcgag taggtcaccg ccacgaccgg caggacgtca gtcac                    885
```

<210> SEQ ID NO 15
<211> LENGTH: 125
<212> TYPE: DNA
<213> ORGANISM: Artificial Sequence
<220> FEATURE:
<223> OTHER INFORMATION: Mycobacterium tuberculosis DNA fragment

<400> SEQUENCE: 15

```
taccagcttc agtttccgtc tgcgggacct gcgcagtgaa ctgcgcacca tgaggtggga     60
```

acgcagcgcc agtgatcccc gcagggtcca gcgcagcgga gcccgccacc aaccagaatg 120
tcggt 125

<210> SEQ ID NO 16
<211> LENGTH: 125
<212> TYPE: DNA
<213> ORGANISM: Artificial Sequence
<220> FEATURE:
<223> OTHER INFORMATION: Mycobacterium tuberculosis DNA fragment

<400> SEQUENCE: 16
taccagcttc agtttccgtc tgcgggacct gcgcagtgaa ctgcgcacca tgaggtggga 60
acgcagcgcc agtgatcccc gcagggtcca gcgcagcgga gcccgccacc aaccagaatg 120
tcggt 125

<210> SEQ ID NO 17
<211> LENGTH: 125
<212> TYPE: DNA
<213> ORGANISM: Artificial Sequence
<220> FEATURE:
<223> OTHER INFORMATION: Mycobacterium tuberculosis DNA fragment

<400> SEQUENCE: 17
taccagcttc agtttccgtc tgcgggacct gcgcagtgaa ctgcgcacca tgaggtggga 60
acgcagcgcc agtgatcccc gcagggtcca gcgcagcgga gcccgccacc aaccagaatg 120
tcggt 125

<210> SEQ ID NO 18
<211> LENGTH: 125
<212> TYPE: DNA
<213> ORGANISM: Artificial Sequence
<220> FEATURE:
<223> OTHER INFORMATION: Mycobacterium tuberculosis DNA fragment

<400> SEQUENCE: 18
taccagcttc agtttccgtc tgcgggacct gcgcagtgaa ctgcgcacca tgaggtggga 60
acgcagcgcc agtgatcccc gcagggtcca gcgcagcgga gcccgccacc aaccagaatg 120
tcggt 125

<210> SEQ ID NO 19
<211> LENGTH: 125
<212> TYPE: DNA
<213> ORGANISM: Artificial Sequence
<220> FEATURE:
<223> OTHER INFORMATION: Mycobacterium tuberculosis DNA fragment

<400> SEQUENCE: 19
taccagcttc agtttccgtc tgcgggacct gcgcagtgaa ctgcgcacca tgaggtggga 60
acgcagcgcc agtgatcccc gcagggtcca gcgcagcgga gcccgccacc aaccagaatg 120
tcggt 125

<210> SEQ ID NO 20
<211> LENGTH: 125
<212> TYPE: DNA
<213> ORGANISM: Artificial Sequence
<220> FEATURE:
<223> OTHER INFORMATION: Mycobacterium tuberculosis DNA fragment

<400> SEQUENCE: 20
taccagcttc agtttccgtc tgcgggacct gcgcagtgaa ctgcgcacca tgaggtggga 60
acgcagcgcc agtgatcccc gcagggtcca gcgcagcgga gcccgccacc aaccagaatg 120
tcggt 125

<210> SEQ ID NO 21
<211> LENGTH: 125
<212> TYPE: DNA
<213> ORGANISM: Artificial Sequence
<220> FEATURE:
<223> OTHER INFORMATION: Mycobacterium tuberculosis DNA fragment

<400> SEQUENCE: 21
taccagcttc agtttccgtc tgcgggacct gcgcagtgaa ctgcgcacca tgaggtggga 60
acgcagcgcc agtgatcccc gcagggtcca gcgcagcgga gcccgccacc aaccagaatg 120
tcggt 125

<210> SEQ ID NO 22
<211> LENGTH: 125
<212> TYPE: DNA
<213> ORGANISM: Artificial Sequence
<220> FEATURE:
<223> OTHER INFORMATION: Mycobacterium tuberculosis DNA fragment

<400> SEQUENCE: 22
taccagcttc agtttccgtc tgcgggacct gcgcagtgaa ctgcgcacca tgaggtggga 60
acgcagcgcc agtgatcccc gcagggtcca gcgcagcgga gcccgccacc aaccagaatg 120
tcggt 125

<210> SEQ ID NO 23
<211> LENGTH: 125
<212> TYPE: DNA
<213> ORGANISM: Artificial Sequence
<220> FEATURE:
<223> OTHER INFORMATION: Mycobacterium tuberculosis DNA fragment

<400> SEQUENCE: 23
taccagcttc agtttccgtc tgcgggacct gcgcagtgaa ctgcgcacca tgaggtggga 60
acgcagcgcc agtgatcccc gcagggtcca gcgcagcgga gcccgccacc aaccagaatg 120
tcggt 125

<210> SEQ ID NO 24
<211> LENGTH: 125
<212> TYPE: DNA
<213> ORGANISM: Artificial Sequence
<220> FEATURE:
<223> OTHER INFORMATION: Mycobacterium tuberculosis DNA fragment

<400> SEQUENCE: 24
taccagcttc agtttccgtc tgcgggacct gcgcagtgaa ctgcgcacca tgaggtggga 60
acgcagcgcc agtgatcccc gcagggtcca gcgcagcgga gcccgccacc aaccagaatg 120
tcggt 125

<210> SEQ ID NO 25
<211> LENGTH: 125
<212> TYPE: DNA
<213> ORGANISM: Artificial Sequence
<220> FEATURE:
<223> OTHER INFORMATION: Mycobacterium tuberculosis DNA fragment

<400> SEQUENCE: 25
taccagcttc agtttccgtc tgcgggacct gcgcagtgaa ctgcgcacca tgaggtggga 60
acgcagcgcc agtgatcccc gcagggtcca gcgcagcgga gcccgccacc aaccagaatg 120
tcggt 125

<210> SEQ ID NO 26
<211> LENGTH: 125
<212> TYPE: DNA
<213> ORGANISM: Artificial Sequence
<220> FEATURE:
<223> OTHER INFORMATION: Mycobacterium tuberculosis DNA fragment

<400> SEQUENCE: 26
taccagcttc agtttccgtc tgcgggacct gcgcagtgaa ctgcgcacca tgaggtggga 60
acgcagcgcc agtgatcccc gcagggtcca gcgcagcgga gcccgccacc aaccagaatg 120
tcggt 125

<210> SEQ ID NO 27
<211> LENGTH: 125
<212> TYPE: DNA
<213> ORGANISM: Artificial Sequence
<220> FEATURE:
<223> OTHER INFORMATION: Mycobacterium tuberculosis DNA fragment

<400> SEQUENCE: 27
taccagcttc agtttccgtc tgcgggacct gcgcagtgaa ctgcgcacca tgaggtggga 60
acgcagcgcc agtgatcccc gcagggtcca gcgcagcgga gcccgccacc aaccagaatg 120
tcggt 125

<210> SEQ ID NO 28
<211> LENGTH: 125
<212> TYPE: DNA
<213> ORGANISM: Artificial Sequence
<220> FEATURE:
<223> OTHER INFORMATION: Mycobacterium tuberculosis DNA fragment

<400> SEQUENCE: 28
taccagcttc agtttccgtc tgcgggacct gcgcagtgaa ctgcgcacca tgaggtggga 60
acgcagcgcc agtgatcccc gcagggtcca gcgcagcgga gcccgccacc aaccagaatg 120
tcggt 125

<210> SEQ ID NO 29
<211> LENGTH: 125
<212> TYPE: DNA
<213> ORGANISM: Artificial Sequence
<220> FEATURE:
<223> OTHER INFORMATION: Mycobacterium tuberculosis DNA fragment

<400> SEQUENCE: 29
taccagcttc agtttccgtc tgcgggacct gcgcagtgaa ctgcgcacca tgaggtggga 60
acgcagcgcc agtgatcccc gcagggtcca gcgcagcgga gcccgccacc aaccagaatg 120
tcggt 125

<210> SEQ ID NO 30
<211> LENGTH: 125
<212> TYPE: DNA
<213> ORGANISM: Artificial Sequence
<220> FEATURE:
<223> OTHER INFORMATION: Mycobacterium tuberculosis DNA fragment

<400> SEQUENCE: 30
taccagcttc agtttccgtc tgcgggacct gcgcagtgaa ctgcgcacca tgaggtggga 60
acgcagcgcc agtgatcccc gcagggtcca gcgcagcgga gcccgccacc aaccagaatg 120
tcggt 125

<210> SEQ ID NO 31
<211> LENGTH: 125
<212> TYPE: DNA
<213> ORGANISM: Artificial Sequence
<220> FEATURE:
<223> OTHER INFORMATION: Mycobacterium tuberculosis DNA fragment

<400> SEQUENCE: 31
taccagcttc agtttccgtc tgcgggacct gcgcagtgaa ctgcgcacca tgaggtggga 60
acgcagcgcc agtgatcccc gcagggtcca gcgcagcgga gcccgccacc aaccagaatg 120
tcggt 125

<210> SEQ ID NO 32
<211> LENGTH: 125
<212> TYPE: DNA
<213> ORGANISM: Artificial Sequence
<220> FEATURE:
<223> OTHER INFORMATION: Mycobacterium tuberculosis DNA fragment

<400> SEQUENCE: 32
taccagcttc agtttccgtc tgcgggacct gcgcagtgaa ctgcgcacca tgaggtggga 60
acgcagcgcc agtgatcccc gcagggtcca gcgcagcgga gcccgccacc aaccagaatg 120
tcggt 125

<210> SEQ ID NO 33
<211> LENGTH: 125
<212> TYPE: DNA
<213> ORGANISM: Artificial Sequence
<220> FEATURE:
<223> OTHER INFORMATION: Mycobacterium tuberculosis DNA fragment

<400> SEQUENCE: 33
taccagcttc agtttccgtc tgcgggacct gcgcagtgaa ctgcgcacca tgaggtggga 60
acgcagcgcc agtgatcccc gcagggtcca gcgcagcgga gcccgccacc aaccagaatg 120
tcggt 125

<210> SEQ ID NO 34
<211> LENGTH: 125
<212> TYPE: DNA
<213> ORGANISM: Artificial Sequence
<220> FEATURE:
<223> OTHER INFORMATION: Mycobacterium tuberculosis DNA fragment

<400> SEQUENCE: 34
taccagcttc agtttccgtc tgcgggacct gcgcagtgaa ctgcgcacca tgaggtggga 60
acgcagcgcc agtgatcccc gcagggtcca gcgcagcgga gcccgccacc aaccagaatg 120
tcggt 125

<210> SEQ ID NO 35
<211> LENGTH: 125
<212> TYPE: DNA
<213> ORGANISM: Artificial Sequence
<220> FEATURE:
<223> OTHER INFORMATION: Mycobacterium tuberculosis DNA fragment

<400> SEQUENCE: 35
taccagcttc agtttccgtc tgcgggacct gcgcagtgaa ctgcgcacca tgaggtggga 60
acgcagcgcc agtgatcccc gcagggtcca gcgcagcgga gcccgccacc aaccagaatg 120
tcggt 125

<210> SEQ ID NO 36
<211> LENGTH: 125
<212> TYPE: DNA
<213> ORGANISM: Artificial Sequence
<220> FEATURE:
<223> OTHER INFORMATION: Mycobacterium tuberculosis DNA fragment

<400> SEQUENCE: 36
taccagcttc agtttccgtc tgcgggacct gcgcagtgaa ctgcgcacca tgaggtggga 60
acgcagcgcc agtgatcccc gcagggtcca gcgcagcgga gcccgccacc aaccagaatg 120
tcggt 125

<210> SEQ ID NO 37
<211> LENGTH: 125
<212> TYPE: DNA
<213> ORGANISM: Artificial Sequence
<220> FEATURE:
<223> OTHER INFORMATION: Mycobacterium tuberculosis DNA fragment

<400> SEQUENCE: 37
taccagcttc agtttccgtc tgcgggacct gcgcagtgaa ctgcgcacca tgaggtggga 60
acgcagcgcc agtgatcccc gcagggtcca gcgcagcgga gcccgccacc aaccagaatg 120
tcggt 125

<210> SEQ ID NO 38
<211> LENGTH: 125
<212> TYPE: DNA
<213> ORGANISM: Artificial Sequence
<220> FEATURE:
<223> OTHER INFORMATION: Mycobacterium tuberculosis DNA fragment

<400> SEQUENCE: 38
taccagcttc agtttccgtc tgcgggacct gcgcagtgaa ctgcgcacca tgaggtggga 60
acgcagcgcc agtgatcccc gcagggtcca gcgcagcgga gcccgccacc aaccagaatg 120
tcggt 125

<210> SEQ ID NO 39
<211> LENGTH: 125
<212> TYPE: DNA
<213> ORGANISM: Artificial Sequence
<220> FEATURE:
<223> OTHER INFORMATION: Mycobacterium tuberculosis DNA fragment

<400> SEQUENCE: 39
taccagcttc agtttccgtc tgcgggacct gcgcagtgaa ctgcgcacca tgaggtggga 60
acgcagcgcc agtgatcccc gcagggtcca gcgcagcgga gcccgccacc aaccagaatg 120
tcggt 125

<210> SEQ ID NO 40
<211> LENGTH: 125
<212> TYPE: DNA
<213> ORGANISM: Artificial Sequence
<220> FEATURE:

<223> OTHER INFORMATION: Mycobacterium canettii DNA fragment

<400> SEQUENCE: 40
taccagcttc agtttccgtc tgcgggacct gcgcagtgaa ctgcgcacca tgaggtggga 60
acgcagcgcc agtgatcccc gcagggtcca gcgcagcgga gcccgccacc aaccagaatg 120
tcggt 125

<210> SEQ ID NO 41
<211> LENGTH: 125
<212> TYPE: DNA
<213> ORGANISM: Artificial Sequence
<220> FEATURE:
<223> OTHER INFORMATION: Mycobacterium canettii DNA fragment

<400> SEQUENCE: 41
taccagcttc agtttccgtc tgcgggacct gcgcagtgaa ctgcgcacca tgaggtggga 60
acgcagcgcc agtgatcccc gcagggtcca gcgcagcgga gcccgccacc aaccagaatg 120
tcggt 125

<210> SEQ ID NO 42
<211> LENGTH: 125
<212> TYPE: DNA
<213> ORGANISM: Artificial Sequence
<220> FEATURE:
<223> OTHER INFORMATION: Mycobacterium canettii DNA fragment

<400> SEQUENCE: 42
taccagcttc agtttccgtc tgcgggacct gcgcagtgaa ctgcgcacca tgaggtggga 60
acgcagcgcc agtgatcccc gcagggtcca gcgcagcgga gcccgccacc aaccagaatg 120
tcggt 125

<210> SEQ ID NO 43
<211> LENGTH: 125
<212> TYPE: DNA
<213> ORGANISM: Artificial Sequence
<220> FEATURE:
<223> OTHER INFORMATION: Mycobacterium canettii DNA fragment

<400> SEQUENCE: 43
taccagcttc agtttccgtc tgcgggacct gcgcagtgaa ctgcgcacca tgaggtggga 60
acgcagcgcc agtgatcccc gcagggtcca gcgcagcgga gcccgccacc aaccagaatg 120
tcggt 125

<210> SEQ ID NO 44
<211> LENGTH: 125
<212> TYPE: DNA
<213> ORGANISM: Artificial Sequence
<220> FEATURE:
<223> OTHER INFORMATION: Mycobacterium canettii DNA fragment

<400> SEQUENCE: 44
taccagcttc agtttccgtc tgcgggacct gcgcagtgaa ctgcgcacca tgaggtggga 60
acgcagcgcc agtgatcccc gcagggtcca gcgcagcgga gcccgccacc aaccagaatg 120
tcggt 125

<210> SEQ ID NO 45
<211> LENGTH: 113
<212> TYPE: DNA
<213> ORGANISM: Artificial Sequence
<220> FEATURE:
<223> OTHER INFORMATION: Mycobacterium pinnipedii DNA fragment

<400> SEQUENCE: 45
taccagcttc agtttccgtc tgcgggacct gcgcaccatg aggtgggaac gcagcgccag 60
tgatccccgc agggtccagc gcagcggagc ccgccaccaa ccagaatgtc ggt 113

<210> SEQ ID NO 46
<211> LENGTH: 113
<212> TYPE: DNA
<213> ORGANISM: Artificial Sequence
<220> FEATURE:
<223> OTHER INFORMATION: Mycobacterium caprae DNA fragment

<400> SEQUENCE: 46
taccagcttc agtttccgtc tgcgggacct gcgcaccatg aggtgggaac gcagcgccag 60
tgatccccgc agggtccagc gcagcggagc ccgccaccaa ccagaatgtc ggt 113

<210> SEQ ID NO 47
<211> LENGTH: 1962
<212> TYPE: DNA
<213> ORGANISM: Mycobacterium tuberculosis

<400> SEQUENCE: 47
tcacttcttg cctttgtccc cggcggcatc ggtggacaat gccgcgacga aagcctcctg 60
tggcacctcg acgcgcccga tggtcttcat ccgcttcttg ccttccttct gcttctccag 120
cagcttgcgt ttgcgcgtga tgtcgccgcc gtagcacttg gacaacacgt ccttgcggat 180
cgcgcggatg ttttcgcggg caatgatttt cgatccgatg gcggcctgca ccggcacctc 240
gaactgctgg cgcgggatca gctccttgag tttggtggtc atcttgttgc cgtaggcata 300
cgccgtgtcc ttgtgcacga tcgcgctgaa cgcatccacc gcctcgccct gcagcaggat 360
gtcgaccttg accagcgcgg cctcctgttc gccggcctcc tcgtagtcga ggctggcata 420
gccgcgggtg cgcgatttca gtgcgtcgaa gaagtcgaag atgatctcgc cgagcggcat 480
ggtgtagcgc agttccaccc gctcggggga gagatagtcc atgccgccca actcgccgcg 540
gcgcgactgg cacagctcca tgatggtgcc gatgaactcg ctgggcgcga tgatggtggt 600
cttgacgacg ggctcgtaga ccgtgcggat cttgccctcc ggccagtccg acggattggt 660
cacccggatt tcggtgccgt cgtctttgtg cacccgatac accacattgg gtgaggtcga 720
gatcaggtcc aggccgaact cgcgctcaag gcgctcacgg gtgatctcca tgtgcagcag 780
gcccaagaaa ccgcaccgga acccaaaacc cagcgccacc gaggtttccg gctcataggt 840
caaggccgcg tcgttgagct gcagcttgtc cagggcgtcg cgcaggttcg ggtagtccga 900
accgtcgacc ggatacaacc ccgagtagac catcggtttg ggctcacggt agccggtcaa 960
cgcttcggcg gcagccccgc gggcccggga gaggctggtc acggtgtcgc ccaccttgga 1020
ctggcggacg tccttgacgc cggtgatcag gtaacccacc tcgccgacac cgaggccctc 1080
acacggtttc ggctcgggtg agacgatgcc gacctcaagc agctcgtggg tggcgccggt 1140
ggacatcatc atgatgcgct cacgggggct gatcttgccg tcgacgacgc ggacgtaggt 1200
caccactccg cggtagatgt cgtaaacgga gtcgaaaatc attgcgcggg taggtgcctc 1260
ggcgtcgccc tgagggggcg gcacctgtcg gaccacctcg tcgagcaggt cggacacgcc 1320
ttcgccggtt ttgccggaca cccgcaacac ctcggccggc tcgcagccga tgatgtgtgc 1380
catctcggcg gcgtaacggt ccgggtcggc cgcgggcagg tcgatcttgt tgagcaccgg 1440

-continued

```
gatgatgtgc aggtcgcggt ccaacgccag gtagaggttc gccagcgtct gcgcctcgat   1500

gccttgcgcg gcatcgacca acagcaccgc accctcgcaa gcctccagcg cacgcgagac   1560

ttcgtaggtg aagtcgacat ggcccggggt gtcgatcaga tgcagcacgt agtcggtctt   1620

gtcgacccgc cagggtagcc gcacattctg ggccttgatg gtgatgccgc gttcccgctc   1680

gatgtccatc cgatccaagt actgggcccg catagagcgt tcgtcgacca cgccggtgag   1740

ctgcagcatc cggtcggcca acgttgactt gccgtggtcg atgtgggcga tgatgcaaaa   1800

gttcctaatc tgcgccggcg cagtgaaggt tttgtcggcg aaactgctga tgggaatctc   1860

ctggagcggg ggttgacggg tatccagggt atccgcgtcg ggcagctgcg acccaatcgc   1920

gctcggtcga tcgcgtctat gctgcgagca tggcgtccgc ac                      1962
```

<210> SEQ ID NO 48
<211> LENGTH: 1962
<212> TYPE: DNA
<213> ORGANISM: Mycobacterium tuberculosis

<400> SEQUENCE: 48

```
tcacttcttg cctttgtccc cggcggcatc ggtggacaat gccgcgacga aagcctcctg     60

tggcacctcg acgcgcccga tggtcttcat ccgcttcttg ccttccttct gcttctccag    120

cagcttgcgt ttgcgcgtga tgtcgccgcc gtagcacttg gacaacacgt ccttgcggat    180

cgcgcggatg ttttcgcggg caatgatttt cgatccgatg gcggcctgca ccggcacctc    240

gaactgctgg cgcgggatca gctccttgag tttggtggtc atcttgttgc cgtaggcata    300

cgccgtgtcc ttgtgcacga tcgcgctgaa cgcatccacc gcctcgccct gcagcaggat    360

gtcgaccttg accagcgcgg cctcctgttc gccggcctcc tcgtagtcga ggctggcata    420

gccgcgggtg cgcgatttca gtgcgtcgaa gaagtcgaag atgatctcgc cgagcggcat    480

ggtgtagcgc agttccaccc gctcggggga gagatagtcc atgccgccca actcgccgcg    540

gcgcgactgg cacagctcca tgatggtgcc gatgaactcg ctgggcgcga tgatggtggt    600

cttgacgacg ggctcgtaga ccgtgcggat cttgccctcc ggccagtccg acggattggt    660

cacccggatt tcggtgccgt cgtctttgtg cacccgatac accacattgg gtgaggtcga    720

gatcaggtcc aggccgaact cgcgctcaag gcgctcacgg gtgatctcca tgtgcagcag    780

gcccaagaaa ccgcaccgga acccaaaacc cagcgccacc gaggtttccg gctcataggt    840

caaggccgcg tcgttgagct gcagcttgtc cagggcgtcg cgcaggttcg ggtagtccga    900

accgtcgacc ggatacaacc ccgagtagac catcggtttg ggctcacggt agccggtcaa    960

cgcttcggcg gcagccccgc gggcccggga gaggctggtc acggtgtcgc ccaccttgga   1020

ctggcggacg tccttgacgc cggtgatcag gtaacccacc tcgccgacac cgaggccctc   1080

acacggtttc ggctcgggtg agacgatgcc gacctcaagc agctcgtggg tggcgccggt   1140

ggacatcatc atgatgcgct cacgggggct gatcttgccg tcgacgacgc ggacgtaggt   1200

caccactccg cggtagatgt cgtaaacgga gtcgaaaatc attgcgcggg taggtgcctc   1260

ggcgtcgccc tgagggggcg gcacctgtcg gaccacctcg tcgagcaggt cggacacgcc   1320

ttcgccggtt ttgccggaca cccgcaacac ctcggccggc tcgcagccga tgatgtgtgc   1380

catctcggcg gcgtaacggt ccgggtcggc cgcgggcagg tcgatcttgt tgagcaccgg   1440

gatgatgtgc aggtcgcggt ccaacgccag gtagaggttc gccagcgtct gcgcctcgat   1500

gccttgcgcg gcatcgacca acagcaccgc accctcgcaa gcctccagcg cacgcgagac   1560

ttcgtaggtg aagtcgacat ggcccggggt gtcgatcaga tgcagcacgt agtcggtctt   1620
```

gtcgacccgc cagggtagcc gcacattctg ggccttgatg gtgatgccgc gttcccgctc 1680
gatgtccatc cgatccaagt actgggcccg catagagcgt tcgtcgacca cgccggtgag 1740
ctgcagcatc cggtcggcca acgttgactt gccgtggtcg atgtgggcga tgatgcaaaa 1800
gttcctaatc tgcgccggcg cagtgaaggt tttgtcggcg aaactgctga tgggaatctc 1860
ctggagcggg ggttgacggg tatccagggt atccgcgtcg ggcagctgcg acccaatcgc 1920
gctcggtcga tcgcgtctat gctgcgagca tggcgtccgc ac 1962

<210> SEQ ID NO 49
<211> LENGTH: 1962
<212> TYPE: DNA
<213> ORGANISM: Mycobacterium tuberculosis

<400> SEQUENCE: 49
tcacttcttg cctttgtccc cggcggcatc ggtggacaat gccgcgacga aagcctcctg 60
tggcacctcg acgcgcccga tggtcttcat ccgcttcttg ccttccttct gcttctccag 120
cagcttgcgt ttgcgcgtga tgtcgccgcc gtagcacttg gacaacacgt ccttgcggat 180
cgcgcggatg ttttcgcggg caatgatttt cgatccgatg gcggcctgca ccggcacctc 240
gaactgctgg cgcgggatca gctccttgag tttggtggtc atcttgttgc cgtaggcata 300
cgccgtgtcc ttgtgcacga tcgcgctgaa cgcatccacc gcctcgccct gcagcaggat 360
gtcgaccttg accagcgcgg cctcctgttc gccggcctcc tcgtagtcga ggctggcata 420
gccgcgggtg cgcgatttca gtgcgtcgaa gaagtcgaag atgatctcgc cgagcggcat 480
ggtgtagcgc agttccaccc gctcggggga gagatagtcc atgccgccca actcgccgcg 540
gcgcgactgg cacagctcca tgatggtgcc gatgaactcg ctgggcgcga tgatggtggt 600
cttgacgacg ggctcgtaga ccgtgcggat cttgccctcc ggccagtccg acggattggt 660
cacccggatt tcggtgccgt cgtctttgtg cacccgatac accacattgg gtgaggtcga 720
gatcaggtcc aggccgaact cgcgctcaag gcgctcacgg gtgatctcca tgtgcagcag 780
gcccaagaaa ccgcaccgga acccaaaacc cagcgccacc gaggtttccg gctcataggt 840
caaggccgcg tcgttgagct gcagcttgtc cagggcgtcg cgcaggttcg ggtagtccga 900
accgtcgacc ggatacaacc ccgagtagac catcggtttg ggctcacggt agccggtcaa 960
cgcttcggcg gcagccccgc gggcccggga gaggctggtc acggtgtcgc ccaccttgga 1020
ctggcggacg tccttgacgc cggtgatcag gtaacccacc tcgccgacac cgaggccctc 1080
acacggtttc ggctcgggtg agacgatgcc gacctcaagc agctcgtggg tggcgccggt 1140
ggacatcatc atgatgcgct cacgggggct gatcttgccg tcgacgacgc ggacgtaggt 1200
caccactccg cggtagatgt cgtaaacgga gtcgaaaatc attgcgcggg taggtgcctc 1260
ggcgtcgccc tgagggggcg gcacctgtcg gaccacctcg tcgagcaggt cggacacgcc 1320
ttcgccggtt ttgccggaca cccgcaacac ctcggccggc tcgcagccga tgatgtgtgc 1380
catctcggcg gcgtaacggt ccgggtcggc cgcgggcagg tcgatcttgt tgagcaccgg 1440
gatgatgtgc aggtcgcggt ccaacgccag gtagaggttc gccagcgtct gcgcctcgat 1500
gccttgcgcg gcatcgacca acagcaccgc accctcgcaa gcctccagcg cacgcgagac 1560
ttcgtaggtg aagtcgacat ggcccggggt gtcgatcaga tgcagcacgt agtcggtctt 1620
gtcgacccgc cagggtagcc gcacattctg ggccttgatg gtgatgccgc gttcccgctc 1680
gatgtccatc cgatccaagt actgggcccg catagagcgt tcgtcgacca cgccggtgag 1740

```
ctgcagcatc cggtcggcca acgttgactt gccgtggtcg atgtgggcga tgatgcaaaa   1800

gttcctaatc tgcgccggcg cagtgaaggt tttgtcggcg aaactgctga tgggaatctc   1860

ctggagcggg ggttgacggg tatccagggt atccgcgtcg ggcagctgcg acccaatcgc   1920

gctcggtcga tcgcgtctat gctgcgagca tggcgtccgc ac                       1962
```

```
<210> SEQ ID NO 50
<211> LENGTH: 1962
<212> TYPE: DNA
<213> ORGANISM: Mycobacterium tuberculosis

<400> SEQUENCE: 50
```

```
tcacttcttg cctttgtccc cggcggcatc ggtggacaat gccgcgacga aagcctcctg     60

tggcacctcg acgcgcccga tggtcttcat ccgcttcttg ccttccttct gcttctccag    120

cagcttgcgt ttgcgcgtga tgtcgccgcc gtagcacttg gacaacacgt ccttgcggat    180

cgcgcggatg ttttcgcggg caatgatttt cgatccgatg gcggcctgca ccggcacctc    240

gaactgctgg cgcgggatca gctccttgag tttggtggtc atcttgttgc cgtaggcata    300

cgccgtgtcc ttgtgcacga tcgcgctgaa cgcatccacc gcctcgccct gcagcaggat    360

gtcgaccttg accagcgcgg cctcctgttc gccggcctcc tcgtagtcga ggctggcata    420

gccgcgggtg cgcgatttca gtgcgtcgaa gaagtcgaag atgatctcgc cgagcggcat    480

ggtgtagcgc agttccaccc gctcggggga gagatagtcc atgccgccca actcgccgcg    540

gcgcgactgg cacagctcca tgatggtgcc gatgaactcg ctgggcgcga tgatggtggt    600

cttgacgacg ggctcgtaga ccgtgcggat cttgccctcc ggccagtccg acggattggt    660

cacccggatt tcggtgccgt cgtctttgtg cacccgatac accacattgg gtgaggtcga    720

gatcaggtcc aggccgaact cgcgctcaag gcgctcacgg gtgatctcca tgtgcagcag    780

gcccaagaaa ccgcaccgga acccaaaacc cagcgccacc gaggtttccg gctcataggt    840

caaggccgcg tcgttgagct gcagcttgtc cagggcgtcg cgcaggttcg ggtagtccga    900

accgtcgacc ggatacaacc ccgagtagac catcggtttg ggctcacggt agccggtcaa    960

cgcttcggcg gcagccccgc gggcccggga gaggctggtc acggtgtcgc ccaccttgga   1020

ctggcggacg tccttgacgc cggtgatcag gtaacccacc tcgccgacac cgaggccctc   1080

acacggtttc ggctcgggtg agacgatgcc gacctcaagc agctcgtggg tggcgccggt   1140

ggacatcatc atgatgcgct cacgggggct gatcttgccg tcgacgacgc ggacgtaggt   1200

caccactccg cggtagatgt cgtaaacgga gtcgaaaatc attgcgcggg taggtgcctc   1260

ggcgtcgccc tgagggggcg gcacctgtcg gaccacctcg tcgagcaggt cggacacgcc   1320

ttcgccggtt ttgccggaca cccgcaacac ctcggccggc tcgcagccga tgatgtgtgc   1380

catctcggcg gcgtaacggt ccgggtcggc cgcgggcagg tcgatcttgt tgagcaccgg   1440

gatgatgtgc aggtcgcggt ccaacgccag gtagaggttc gccagcgtct gcgcctcgat   1500

gccttgcgcg gcatcgacca acagcaccgc accctcgcaa gcctccagcg cacgcgagac   1560

ttcgtaggtg aagtcgacat ggcccggggt gtcgatcaga tgcagcacgt agtcggtctt   1620

gtcgacccgc cagggtagcc gcacattctg ggccttgatg gtgatgccgc gttcccgctc   1680

gatgtccatc cgatccaagt actgggcccg catagagcgt tcgtcgacca cgccggtgag   1740

ctgcagcatc cggtcggcca acgttgactt gccgtggtcg atgtgggcga tgatgcaaaa   1800

gttcctaatc tgcgccggcg cagtgaaggt tttgtcggcg aaactgctga tgggaatctc   1860

ctggagcggg ggttgacggg tatccagggt atccgcgtcg ggcagctgcg acccaatcgc   1920
```

-continued

```
gctcggtcga tcgcgtctat gctgcgagca tggcgtccgc ac                    1962
```

<210> SEQ ID NO 51
<211> LENGTH: 1962
<212> TYPE: DNA
<213> ORGANISM: Mycobacterium tuberculosis

<400> SEQUENCE: 51

```
tcacttcttg cctttgtccc cggcggcatc ggtggacaat gccgcgacga aagcctcctg     60
tggcacctcg acgcgcccga tggtcttcat ccgcttcttg ccttccttct gcttctccag    120
cagcttgcgt ttgcgcgtga tgtcgccgcc gtagcacttg gacaacacgt ccttgcggat    180
cgcgcggatg ttttcgcggg caatgatttt cgatccgatg gcggcctgca ccggcacctc    240
gaactgctgg cgcgggatca gctccttgag tttggtggtc atcttgttgc cgtaggcata    300
cgccgtgtcc ttgtgcacga tcgcgctgaa cgcatccacc gcctcgccct gcagcaggat    360
gtcgaccttg accagcgcgg cctcctgttc gccggcctcc tcgtagtcga ggctggcata    420
gccgcgggtg cgcgatttca gtgcgtcgaa gaagtcgaag atgatctcgc cgagcggcat    480
ggtgtagcgc agttccaccc gctcggggga gagatagtcc atgccgccca actcgccgcg    540
gcgcgactgg cacagctcca tgatggtgcc gatgaactcg ctgggcgcga tgatggtggt    600
cttgacgacg ggctcgtaga ccgtgcggat cttgccctcc ggccagtccg acggattggt    660
cacccggatt tcggtgccgt cgtctttgtg cacccgatac accacattgg gtgaggtcga    720
gatcaggtcc aggccgaact cgcgctcaag gcgctcacgg gtgatctcca tgtgcagcag    780
gcccaagaaa ccgcaccgga acccaaaacc cagcgccacc gaggtttccg gctcataggt    840
caaggccgcg tcgttgagct gcagcttgtc cagggcgtcg cgcaggttcg ggtagtccga    900
accgtcgacc ggatacaacc ccgagtagac catcggtttg ggctcacggt agccggtcaa    960
cgcttcggcg gcagccccgc gggcccggga gaggctggtc acggtgtcgc ccaccttgga   1020
ctggcggacg tccttgacgc cggtgatcag gtaacccacc tcgccgacac cgaggccctc   1080
acacggtttc ggctcgggtg agacgatgcc gacctcaagc agctcgtggg tggcgccggt   1140
ggacatcatc atgatgcgct cacgggggct gatcttgccg tcgacgacgc ggacgtaggt   1200
caccactccg cggtagatgt cgtaaacgga gtcgaaaatc attgcgcggg taggtgcctc   1260
ggcgtcgccc tgagggggcg gcacctgtcg gaccacctcg tcgagcaggt cggacacgcc   1320
ttcgccggtt ttgccggaca cccgcaacac ctcggccggc tcgcagccga tgatgtgtgc   1380
catctcggcg gcgtaacggt ccgggtcggc cgcgggcagg tcgatcttgt tgagcaccgg   1440
gatgatgtgc aggtcgcggt ccaacgccag gtagaggttc gccagcgtct gcgcctcgat   1500
gccttgcgcg gcatcgacca acagcaccgc accctcgcaa gcctccagcg cacgcgagac   1560
ttcgtaggtg aagtcgacat ggcccggggt gtcgatcaga tgcagcacgt agtcggtctt   1620
gtcgacccgc cagggtagcc gcacattctg ggccttgatg gtgatgccgc gttcccgctc   1680
gatgtccatc cgatccaagt actgggcccg catagagcgt tcgtcgacca cgccggtgag   1740
ctgcagcatc cggtcggcca acgttgactt gccgtggtcg atgtgggcga tgatgcaaaa   1800
gttcctaatc tgcgccggcg cagtgaaggt tttgtcggcg aaactgctga tgggaatctc   1860
ctggagcggg ggttgacggg tatccagggt atccgcgtcg ggcagctgcg acccaatcgc   1920
gctcggtcga tcgcgtctat gctgcgagca tggcgtccgc ac                    1962
```

<210> SEQ ID NO 52

<211> LENGTH: 1962
<212> TYPE: DNA
<213> ORGANISM: Mycobacterium tuberculosis

<400> SEQUENCE: 52
tcacttcttg cctttgtccc cggcggcatc ggtggacaat gccgcgacga aagcctcctg 60
tggcacctcg acgcgcccga tggtcttcat ccgcttcttg ccttccttct gcttctccag 120
cagcttgcgt ttgcgcgtga tgtcgccgcc gtagcacttg gacaacacgt ccttgcggat 180
cgcgcggatg ttttcgcggg caatgatttt cgatccgatg gcggcctgca ccggcacctc 240
gaactgctgg cgcgggatca gctccttgag tttggtggtc atcttgttgc cgtaggcata 300
cgccgtgtcc ttgtgcacga tcgcgctgaa cgcatccacc gcctcgccct gcagcaggat 360
gtcgaccttg accagcgcgg cctcctgttc gccggcctcc tcgtagtcga ggctggcata 420
gccgcgggtg cgcgatttca gtgcgtcgaa gaagtcgaag atgatctcgc cgagcggcat 480
ggtgtagcgc agttccaccc gctcggggga gagatagtcc atgccgccca actcgccgcg 540
gcgcgactgg cacagctcca tgatggtgcc gatgaactcg ctgggcgcga tgatggtggt 600
cttgacgacg ggctcgtaga ccgtgcggat cttgccctcc ggccagtccg acggattggt 660
cacccggatt tcggtgccgt cgtctttgtg cacccgatac accacattgg gtgaggtcga 720
gatcaggtcc aggccgaact cgcgctcaag gcgctcacgg gtgatctcca tgtgcagcag 780
gcccaagaaa ccgcaccgga acccaaaacc cagcgccacc gaggtttccg gctcataggt 840
caaggccgcg tcgttgagct gcagcttgtc cagggcgtcg cgcaggttcg ggtagtccga 900
accgtcgacc ggatacaacc ccgagtagac catcggtttg ggctcacggt agccggtcaa 960
cgcttcggcg gcagccccgc gggcccggga gaggctggtc acggtgtcgc ccaccttgga 1020
ctggcggacg tccttgacgc cggtgatcag gtaacccacc tcgccgacac cgaggccctc 1080
acacggtttc ggctcgggtg agacgatgcc gacctcaagc agctcgtggg tggcgccggt 1140
ggacatcatc atgatgcgct cacgggggct gatcttgccg tcgacgacgc ggacgtaggt 1200
caccactccg cggtagatgt cgtaaacgga gtcgaaaatc attgcgcggg taggtgcctc 1260
ggcgtcgccc tgagggggcg gcacctgtcg gaccacctcg tcgagcaggt cggacacgcc 1320
ttcgccggtt ttgccggaca cccgcaacac ctcggccggc tcgcagccga tgatgtgtgc 1380
catctcggcg gcgtaacggt ccgggtcggc cgcgggcagg tcgatcttgt tgagcaccgg 1440
gatgatgtgc aggtcgcggt ccaacgccag gtagaggttc gccagcgtct gcgcctcgat 1500
gccttgcgcg gcatcgacca acagcaccgc accctcgcaa gcctccagcg cacgcgagac 1560
ttcgtaggtg aagtcgacat ggcccggggt gtcgatcaga tgcagcacgt agtcggtctt 1620
gtcgacccgc cagggtagcc gcacattctg ggccttgatg gtgatgccgc gttcccgctc 1680
gatgtccatc cgatccaagt actgggcccg catagagcgt tcgtcgacca cgccggtgag 1740
ctgcagcatc cggtcggcca acgttgactt gccgtggtcg atgtgggcga tgatgcaaaa 1800
gttcctaatc tgcgccggcg cagtgaaggt tttgtcggcg aaactgctga tgggaatctc 1860
ctggagcggg ggttgacggg tatccagggt atccgcgtcg ggcagctgcg acccaatcgc 1920
gctcggtcga tcgcgtctat gctgcgagca tggcgtccgc ac 1962

<210> SEQ ID NO 53
<211> LENGTH: 1971
<212> TYPE: DNA
<213> ORGANISM: Mycobacterium tuberculosis

<400> SEQUENCE: 53

-continued

```
tcacttcttg cctttgtccc cggcggcatc ggtggacaat gccgcgacga aagcctcctg     60
tggcacctcg acgcgcccga tggtcttcat ccgcttcttg ccttccttct gcttctccag    120
cagcttgcgt ttgcgcgtga tgtcgccgcc gtagcacttg gacaacacgt ccttgcggat    180
cgcgcggatg ttttcgcggg caatgatttt cgatccgatg gcggcctgca ccggcacctc    240
gaactgctgg cgcgggatca gctccttgag tttggtggtc atcttgttgc cgtaggcata    300
cgccgtgtcc ttgtgcacga tcgcgctgaa cgcatccacc gcctcgccct gcagcaggat    360
gtcgaccttg accagcgcgg cctcctgttc gccggcctcc tcgtagtcga ggctggcata    420
gccgcgggtg cgcgatttca gtgcgtcgaa gaagtcgaag atgatctcgc cgagcggcat    480
ggtgtagcgc agttccaccc gctcggggga gagatagtcc atgccgccca actcgccgcg    540
gcgcgactgg cacagctcca tgatggtgcc gatgaactcg ctgggcgcga tgatggtggt    600
cttgacgacg ggctcgtaga ccgtgcggat cttgccctcc ggccagtccg acggattggt    660
cacccggatt tcggtgccgt cgtctttgtg cacccgatac accacattgg gtgaggtcga    720
gatcaggtcc aggccgaact cgcgctcaag gcgctcacgg gtgatctcca tgtgcagcag    780
gcccaagaaa ccgcaccgga acccaaaacc cagcgccacc gaggtttccg gctcataggt    840
caaggccgcg tcgttgagct gcagcttgtc cagggcgtcg cgcaggttcg ggtagtccga    900
accgtcgacc ggatacaacc ccgagtagac catcggtttg ggctcacggt agccggtcaa    960
cgcttcggcg gcagccccgc gggcccggga gaggctggtc acggtgtcgc ccaccttgga   1020
ctggcggacg tccttgacgc cggtgatcag gtaacccacc tcgccgacac cgaggccctc   1080
acacggtttc ggctcgggtg agacgatgcc gacctcaagc agctcgtggg tggcgccggt   1140
ggacatcatc atgatgcgct cacgggggct gatcttgccg tcgacgacgc ggacgtaggt   1200
caccactccg cggtagatgt cgtaaacgga gtcgaaaatc attgcgcggg taggtgcctc   1260
ggcgtcgccc tgagggggcg gcacctgtcg gaccacctcg tcgagcaggt cggacacgcc   1320
ttcgccggtt ttgccggaca cccgcaacac ctcggccggc tcgcagccga tgatgtgtgc   1380
catctcggcg gcgtaacggt ccgggtcggc cgcgggcagg tcgatcttgt tgagcaccgg   1440
gatgatgtgc aggtcgcggt ccaacgccag gtagaggttc gccagcgtct gcgcctcgat   1500
gccttgcgcg gcatcgacca acagcaccgc accctcgcaa gcctccagcg cacgcgagac   1560
ttcgtaggtg aagtcgacat ggcccggggt gtcgatcaga tgcagcacgt agtcggtctt   1620
gtcgacccgc cagggtagcc gcacattctg ggccttgatg gtgatgccgc gttcccgctc   1680
gatgtccatc cgatccaagt actgggcccg catagagcgt tcgtcgacca cgccggtgag   1740
ctgcagcatc cggtcggcca acgttgactt gccgtggtcg atgtgggcga tgatgcaaaa   1800
gttcctaatc tgcgccggcg cagtgaaggt tttgtcggcg aaactgctga tgggaatctc   1860
ctggagcggg ggttgacggg tatccagggt atccgcgtcg ggcagctgcg acccaatcgc   1920
gctcggtcga tcgcgtctat gctgcgagca tggcgtccgc acggaagtca c            1971
```

<210> SEQ ID NO 54
<211> LENGTH: 1962
<212> TYPE: DNA
<213> ORGANISM: Mycobacterium bovis

<400> SEQUENCE: 54

```
tcacttcttg cctttgtccc cggcggcatc ggtggacaat gccgcgacga aagcctcctg     60
tggcacctcg acgcgcccga tggtcttcat ccgcttcttg ccttccttct gcttctccag    120
```

```
cagcttgcgt ttgcgcgtga tgtcgccgcc gtagcacttg gacaacacgt ccttgcggat    180
cgcgcggatg ttttcgcggg caatgatttt cgatccgatg gcggcctgca ccggcacctc    240
gaactgctgg cgcgggatca gctccttgag tttggtggtc atcttgttgc cgtaggcata    300
cgccgtgtcc ttgtgcacga tcgcgctgaa cgcatccacc gcctcgccct gcagcaggat    360
gtcgaccttg accagcgcgg cctcctgttc gccggcctcc tcgtagtcga ggctggcata    420
gccgcgggtg cgcgatttca gtgcgtcgaa gaagtcgaag atgatctcgc cgagcggcat    480
ggtgtagcgc agttccaccc gctcggggga gagatagtcc atgccgccca actcgccgcg    540
gcgcgactgg cacagctcca tgatggtgcc gatgaactcg ctgggcgcga tgatggtggt    600
cttgacgacg ggctcgtaga ccgtgcggat cttgccctcc ggccagtccg acggattggt    660
cacccggatt tcggtgccgt cgtctttgtg cacccgatac accacattgg gtgaggtcga    720
gatcaggtcc aggccgaact cgcgctcaag gcgctcacgg gtgatctcca tgtgcagcag    780
gcccaagaaa ccgcaccgga acccaaaacc cagcgccacc gaggtttccg gctcataggt    840
caaggccgcg tcgttgagct gcagcttgtc cagggcgtcg cgcaggttcg ggtagtccga    900
accgtcgacc ggatacaacc ccgagtagac catcggtttg ggctcacggt agccggtcaa    960
cgcttcggcg gcagccccgc gggcccggga gaggctggtc acggtgtcgc ccaccttgga   1020
ctggcggacg tccttgacgc cggtgatcag gtaacccacc tcgccgacac cgaggccctc   1080
acacggtttc ggctcgggtg agacgatgcc gacctcaagc agctcgtggg tggcgccggt   1140
ggacatcatc atgatgcgct cacgggggct gatcttgccg tcgacgacgc ggacgtaggt   1200
caccactccg cggtagatgt cgtaaacgga gtcgaaaatc attgcgcggg taggtgcctc   1260
ggcgtcgccc tgagggggcg gcacctgtcg gaccacctcg tcgagcaggt cggacacgcc   1320
ttcgccggtt ttgccggaca cccgcaacac ctcggccggc tcgcagccga tgatgtgtgc   1380
catctcggcg gcgtaacggt ccgggtcggc cgcgggcagg tcgatcttgt tgagcaccgg   1440
gatgatgtgc aggtcgcggt ccaacgccag gtagaggttc gccagcgtct gcgcctcgat   1500
gccttgcgcg gcatcgacca acagcaccgc accctcgcaa gcctccagcg cacgcgagac   1560
ttcgtaggtg aagtcgacat ggcccggggt gtcgatcaga tgcagcacgt agtcggtctt   1620
gtcgacccgc cagggtagcc gcacattctg ggccttgatg gtgatgccgc gttcccgctc   1680
gatgtccatc cgatccaagt actgggcccg catagagcgt tcgtcgacca ctccggtgag   1740
ctgcagcatc cggtcggcca acgttgactt gccgtggtcg atgtgggcga tgatgcaaaa   1800
gttcctaatc tgcgccggcg cagtgaaggt tttgtcggcg aaactgctga tgggaatctc   1860
ctggagcggg ggttgacggg tatccagggt atccgcgtcg ggcagctgcg acccaatcgc   1920
gctcggtcga tcgcgtctat gctgcgagca tggcgtccgc ac                      1962
```

<210> SEQ ID NO 55
<211> LENGTH: 1962
<212> TYPE: DNA
<213> ORGANISM: Mycobacterium bovis BCG

<400> SEQUENCE: 55

```
tcacttcttg cctttgtccc cggcggcatc ggtggacaat gccgcgacga aagcctcctg     60
tggcacctcg acgcgcccga tggtcttcat ccgcttcttg ccttccttct gcttctccag    120
cagcttgcgt ttgcgcgtga tgtcgccgcc gtagcacttg gacaacacgt ccttgcggat    180
cgcgcggatg ttttcgcggg caatgatttt cgatccgatg gcggcctgca ccggcacctc    240
gaactgctgg cgcgggatca gctccttgag tttggtggtc atcttgttgc cgtaggcata    300
```

cgccgtgtcc ttgtgcacga tcgcgctgaa cgcatccacc gcctcgccct gcagcaggat 360
gtcgaccttg accagcgcgg cctcctgttc gccggcctcc tcgtagtcga ggctggcata 420
gccgcgggtg cgcgatttca gtgcgtcgaa gaagtcgaag atgatctcgc cgagcggcat 480
ggtgtagcgc agttccaccc gctcggggga gagatagtcc atgccgccca actcgccgcg 540
gcgcgactgg cacagctcca tgatggtgcc gatgaactcg ctgggcgcga tgatggtggt 600
cttgacgacg ggctcgtaga ccgtgcggat cttgccctcc ggccagtccg acggattggt 660
cacccggatt tcggtgccgt cgtctttgtg cacccgatac accacattgg gtgaggtcga 720
gatcaggtcc aggccgaact cgcgctcaag gcgctcacgg gtgatctcca tgtgcagcag 780
gcccaagaaa ccgcaccgga acccaaaacc cagcgccacc gaggtttccg gctcataggt 840
caaggccgcg tcgttgagct gcagcttgtc cagggcgtcg cgcaggttcg ggtagtccga 900
accgtcgacc ggatacaacc ccgagtagac catcggtttg ggctcacggt agccggtcaa 960
cgcttcggcg gcagccccgc gggcccggga gaggctggtc acggtgtcgc ccaccttgga 1020
ctggcggacg tccttgacgc cggtgatcag gtaacccacc tcgccgacac cgaggccctc 1080
acacggtttc ggctcgggtg agacgatgcc gacctcaagc agctcgtggg tggcgccggt 1140
ggacatcatc atgatgcgct cacgggggct gatcttgccg tcgacgacgc ggacgtaggt 1200
caccactccg cggtagatgt cgtaaacgga gtcgaaaatc attgcgcggg taggtgcctc 1260
ggcgtcgccc tgagggggcg gcacctgtcg gaccacctcg tcgagcaggt cggacacgcc 1320
ttcgccggtt ttgccggaca cccgcaacac ctcggccggc tcgcagccga tgatgtgtgc 1380
catctcggcg gcgtaacggt ccgggtcggc cgcgggcagg tcgatcttgt tgagcaccgg 1440
gatgatgtgc aggtcgcggt ccaacgccag gtagaggttc gccagcgtct gcgcctcgat 1500
gccttgcgcg gcatcgacca acagcaccgc accctcgcaa gcctccagcg cacgcgagac 1560
ttcgtaggtg aagtcgacat ggcccggggt gtcgatcaga tgcagcacgt agtcggtctt 1620
gtcgacccgc cagggtagcc gcacattctg ggccttgatg gtgatgccgc gttcccgctc 1680
gatgtccatc cgatccaagt actgggcccg catagagcgt tcgtcgacca ctccggtgag 1740
ctgcagcatc cggtcggcca acgttgactt gccgtggtcg atgtgggcga tgatgcaaaa 1800
gttcctaatc tgcgccggcg cagtgaaggt tttgtcggcg aaactgctga tgggaatctc 1860
ctggagcggg ggttgacggg tatccagggt atccgcgtcg ggcagctgcg acccaatcgc 1920
gctcggtcga tcgcgtctat gctgcgagca tggcgtccgc ac 1962

<210> SEQ ID NO 56
<211> LENGTH: 1962
<212> TYPE: DNA
<213> ORGANISM: Mycobacterium bovis BCG

<400> SEQUENCE: 56
tcacttcttg cctttgtccc cggcggcatc ggtggacaat gccgcgacga aagcctcctg 60
tggcacctcg acgcgcccga tggtcttcat ccgcttcttg ccttccttct gcttctccag 120
cagcttgcgt ttgcgcgtga tgtcgccgcc gtagcacttg gacaacacgt ccttgcggat 180
cgcgcggatg ttttcgcggg caatgatttt cgatccgatg gcggcctgca ccggcacctc 240
gaactgctgg cgcgggatca gctccttgag tttggtggtc atcttgttgc cgtaggcata 300
cgccgtgtcc ttgtgcacga tcgcgctgaa cgcatccacc gcctcgccct gcagcaggat 360
gtcgaccttg accagcgcgg cctcctgttc gccggcctcc tcgtagtcga ggctggcata 420

-continued gccgcgggtg cgcgatttca gtgcgtcgaa gaagtcgaag atgatctcgc cgagcggcat 480
ggtgtagcgc agttccaccc gctcggggga gagatagtcc atgccgccca actcgccgcg 540
gcgcgactgg cacagctcca tgatggtgcc gatgaactcg ctgggcgcga tgatggtggt 600
cttgacgacg ggctcgtaga ccgtgcggat cttgccctcc ggccagtccg acggattggt 660
cacccggatt tcggtgccgt cgtctttgtg cacccgatac accacattgg gtgaggtcga 720
gatcaggtcc aggccgaact cgcgctcaag gcgctcacgg gtgatctcca tgtgcagcag 780
gcccaagaaa ccgcaccgga acccaaaacc cagcgccacc gaggtttccg gctcataggt 840
caaggccgcg tcgttgagct gcagcttgtc cagggcgtcg cgcaggttcg ggtagtccga 900
accgtcgacc ggatacaacc ccgagtagac catcggtttg ggctcacggt agccggtcaa 960
cgcttcggcg gcagccccgc gggcccggga gaggctggtc acggtgtcgc ccaccttgga 1020
ctggcggacg tccttgacgc cggtgatcag gtaacccacc tcgccgacac cgaggccctc 1080
acacggtttc ggctcgggtg agacgatgcc gacctcaagc agctcgtggg tggcgccggt 1140
ggacatcatc atgatgcgct cacgggggct gatcttgccg tcgacgacgc ggacgtaggt 1200
caccactccg cggtagatgt cgtaaacgga gtcgaaaatc attgcgcggg taggtgcctc 1260
ggcgtcgccc tgagggggcg gcacctgtcg gaccacctcg tcgagcaggt cggacacgcc 1320
ttcgccggtt ttgccggaca cccgcaacac ctcggccggc tcgcagccga tgatgtgtgc 1380
catctcggcg gcgtaacggt ccgggtcggc cgcgggcagg tcgatcttgt tgagcaccgg 1440
gatgatgtgc aggtcgcggt ccaacgccag gtagaggttc gccagcgtct gcgcctcgat 1500
gccttgcgcg gcatcgacca acagcaccgc accctcgcaa gcctccagcg cacgcgagac 1560
ttcgtaggtg aagtcgacat ggcccggggt gtcgatcaga tgcagcacgt agtcggtctt 1620
gtcgacccgc cagggtagcc gcacattctg ggccttgatg gtgatgccgc gttcccgctc 1680
gatgtccatc cgatccaagt actgggcccg catagagcgt tcgtcgacca ctccggtgag 1740
ctgcagcatc cggtcggcca acgttgactt gccgtggtcg atgtgggcga tgatgcaaaa 1800
gttcctaatc tgcgccggcg cagtgaaggt tttgtcggcg aaactgctga tgggaatctc 1860
ctggagcggg ggttgacggg tatccagggt atccgcgtcg ggcagctgcg acccaatcgc 1920
gctcggtcga tcgcgtctat gctgcgagca tggcgtccgc ac 1962

<210> SEQ ID NO 57
<211> LENGTH: 1962
<212> TYPE: DNA
<213> ORGANISM: Mycobacterium microti

<400> SEQUENCE: 57
tcacttcttg cctttgtccc cggcggcatc ggtggacaat gccgcgacga aagcctcctg 60
tggcacctcg acgcgcccga tggtcttcat ccgcttcttg ccttccttct gcttctccag 120
cagcttgcgt ttgcgcgtga tgtcgccgcc gtagcacttg gacaacacgt ccttgcggat 180
cgcgcggatg ttttcgcggg caatgatttt cgatccgatg gcggcctgca ccggcacctc 240
gaactgctgg cgcgggatca gctccttgag tttggtggtc atcttgttgc cgtaggcata 300
cgccgtgtcc ttgtgcacga tcgcgctgaa cgcatccacc gcctcgccct gcagcaggat 360
gtcgaccttg accagcgcgg cctcctgttc gccggcctcc tcgtagtcga ggctggcata 420
gccgcgggtg cgcgatttca gtgcgtcgaa gaagtcgaag atgatctcgc cgagcggcat 480
ggtgtagcgc agttccaccc gctcggggga gagatagtcc atgccgccca actcgccgcg 540
gcgcgactgg cacagctcca tgatggtgcc gatgaactcg ctgggcgcga tgatggtggt 600

```
cttgacgacg ggctcgtaga ccgtgcggat cttgccctcc ggccagtccg acggattggt    660

cacccggatt tcggtgccgt cgtctttgtg cacccgatac accacattgg gtgaggtcga    720

gatcaggtcc aggccgaact cgcgctcaag gcgctcacgg gtgatctcca tgtgcagcag    780

gcccaagaaa ccgcaccgga acccaaaacc cagcgccacc gaggtttccg gctcataggt    840

caaggccgcg tcgttgagct gcagcttgtc cagggcgtcg cgcaggttcg ggtagtccga    900

accgtcgacc ggatacaacc ccgagtagac catcggtttg ggctcacggt agccggtcaa    960

cgcttcggcg gcagccccgc gggcccggga gaggctggtc acggtgtcgc ccaccttgga   1020

ctggcggacg tccttgacgc cggtgatcag gtaacccacc tcgccgacac cgaggccctc   1080

acacggtttc ggctcgggtg agacgatgcc gacctcaagc agctcgtggg tggcgccggt   1140

ggacatcatc atgatgcgct cacgggggct gatcttgccg tcgacgacgc ggacgtaggt   1200

caccactccg cggtagatgt cgtaaacgga gtcgaaaatc attgcgcggg taggtgcctc   1260

ggcgtcgccc tgagggggcg gcacctgtcg gaccacctcg tcgagcaggt cggacacgcc   1320

ttcgccggtt ttgccggaca cccgcaacac ctcggccggc tcgcagccga tgatgtgtgc   1380

catctcggcg gcgtaacggt ccgggtcggc cgcgggcagg tcgatcttgt tgagcaccgg   1440

gatgatgtgc aggtcgcggt ccaacgccag gtagaggttc gccagcgtct gcgcctcgat   1500

gccttgcgcg gcatcgacca acagcaccgc accctcgcaa gcctccagcg cacgcgagac   1560

ttcgtaggtg aagtcgacat ggcccggggt gtcgatcaga tgcagcacgt agtcggtctt   1620

gtcgacccgc cagggtagcc gcacattctg ggccttgatg gtgatgccgc gttcccgctc   1680

gatgtccatc cgatccaagt actgggcccg catagagcgt tcgtcgacca ctccggtgag   1740

ctgcagcatc cggtcggcca acgttgactt gccgtggtcg atgtgggcga tgatgcaaaa   1800

gttcctaatc tgcgccggcg cagtgaaggt tttgtcggcg aaactgctga tgggaatctc   1860

ctggagcggg ggttgacggg tatccagggt atccgcgtcg ggcagctgcg acccaatcgc   1920

gctcggtcga tcgcgtctat gctgcgagca tggcgtccgc ac                      1962
```

<210> SEQ ID NO 58
<211> LENGTH: 1962
<212> TYPE: DNA
<213> ORGANISM: Mycobacterium canettii

<400> SEQUENCE: 58

```
tcacttcttg cctttgtccc cggcggcatc ggtggacaat gccgcgacga aagcctcctg     60

tggcacctcg acgcgcccga tggtcttcat ccgcttcttg ccttccttct gcttctccag    120

cagcttgcgt ttgcgcgtga tgtcgccgcc gtagcacttg gacaacacgt ccttgcggat    180

cgcgcggatg ttttcgcggg caatgatttt cgatccgatg gcggcctgca ccggcacctc    240

gaactgctgg cgcgggatca gctccttgag tttggtggtc atcttgttgc cgtaggcata    300

cgccgtatcc ttgtgcacga tcgcgctgaa cgcatccacc gcctcgccct gcagcaggat    360

gtcgaccttg accagcgcgg cctcctgttc gccggcctcc tcgtagtcga ggctggcata    420

gccgcgggtg cgcgatttca gtgcgtcgaa gaagtcgaag atgatctcgc cgagcggcat    480

ggtgtagcgc agttccaccc gctcggggga gagatagtcc atgccgccca actcgccgcg    540

gcgcgactgg cacagctcca tgatggtgcc gatgaactcg ctgggcgcga tgatggtggt    600

cttgacgacg ggctcgtaga ccgtgcggat cttgccctcc ggccagtccg acggattggt    660

cacccggatt tcggtgccgt cgtctttgtg cacccggtac accacattgg gtgaagtcga    720
```

```
gatcaggtcc aggccgaact cgcgctcaag gcgctcacgg gtgatctcca tgtgcagcag     780
gcccaagaaa ccgcaccgga acccaaaacc cagcgccacc gaggtttccg gctcataggt     840
caaggccgcg tcgttgagct gcagcttgtc cagggcgtcg cgcaggttcg ggtagtccga     900
accgtcgacc ggatacaacc ccgagtagac catcggtttg ggctcacggt agccggtcaa     960
cgcttcggct gcagccccgc gggcccggga gaggctggtc acggtgtcgc ccaccttgga    1020
ctggcggacg tccttgacgc cggtgatcag gtaacccacc tcgccgacac cgaggccctc    1080
acacggtttc ggctcgggtg agacgatgcc gacctcaagc agctcgtggg tggcgccggt    1140
ggacatcatc atgatgcgct cacgggggct gatcttgccg tcgacgacgc ggacgtaggt    1200
caccactccg cggtagatgt cgtaaacgga gtcgaaaatc attgcgcggg taggtgcctc    1260
ggcgtcgccc tgcgggggcg gcacctgtcg gaccacctcg tcgagcaggt cggacacgcc    1320
ttcgccggtt ttgccggaca cccgcaacac ctcggccggc tcgcagccga tgatgtgtgc    1380
catctcggcg gcgtaacggt ccgggtcggc cgcaggcagg tcgatcttgt tgagcaccgg    1440
gatgatgtgc aggtcgcggt ccaacgccag gtagaggttc gccagcgtct gcgcctcgat    1500
gccttgcgcg gcatcgacca acagcaccgc accctcgcaa gcctccagcg cacgcgagac    1560
ttcgtaggtg aagtcgacat ggcccggggt gtcgatcaga tgcagcacgt agtcggtctt    1620
gtcgacccgc cagggtagcc gcacattctg ggccttgatg gtgatgccgc gttcccgctc    1680
gatgtccatc cgatccaagt actgggcccg catagagcgt tcgtcgacca cgccggtgag    1740
ctgcagcatc cggtcggcca acgttgactt gccgtggtcg atgtgggcga tgatgcaaaa    1800
gttcctaatc tgcgccggcg cagtgaaggt tttgtcggcg aaactgctga tgggaatctc    1860
ctggagcggg ggttgacggg tatccagggt atccgcgtcg ggcagctgcg acccaatcgc    1920
gctcggtcga tcgcgtctat gctgcgagca tggcgtccgc ac                       1962
```

<210> SEQ ID NO 59
<211> LENGTH: 627
<212> TYPE: DNA
<213> ORGANISM: Mycobacterium africanum

<400> SEQUENCE: 59

```
catccaccgc ctcgccctgc agcaggatgt cgaccttgac cagcgcggca tcctgttcgc      60
cggcctccta gtagtcgagg ctggcatagc cgcgggtgcg cgatttcagt gcatcgaaga     120
agtcgaagat gatctcgccg agcggcatgg tgtagcgcag ttccacccgc tcggcggaga     180
gatagtccat gccgcccaac tcgccgcggc gcgactggca cagctccatg atggtgccga     240
tgaactcgct gggcgcgatg atggtggtct caacgacggg ctcgtagacc ttgcggatct     300
tgccctccgg accagtccga cggattggtc acccggattt cggtgccgtc gtcttggtgc     360
acccgataca ccacattggg tgaggtcgag atcaggtcca ggccgaactc gcgctcaagg     420
cgctcacggg tgatctccat gtgcatgcag gcccaagaaa ccgcaccgga acccaaaacc     480
cagcgccacc gaggtttccg gctcataggt caaggccgcg tcgttgagct gcagcttgtc     540
cagggcgtcg cgcaggttcg ggtagtccga accgtcgacc ggatacaacc ccgagtagac     600
catcggtttg ggctcacggt agccggg                                         627
```

<210> SEQ ID NO 60
<211> LENGTH: 1983
<212> TYPE: DNA
<213> ORGANISM: Mycobacterium avium

<400> SEQUENCE: 60
ttacttcttg gatttgtcgc ccgcggcgtc ggcggacagc gcggcgacga acgcctcctg 60
cggcacgtcg acccggccga tggtcttcat ccgcttcttg ccctccttct gcttttccag 120
aagtttgcgc ttgcgggtga tgtcaccgcc gtaacacttg gacagcacgt ccttgcggat 180
ggcccgaatg ttctcgcggg caatgatttt cgagccgatc gcggcctgga cgggcacctc 240
gaactgctgg cgcgggatca gctccttgag cttggtggtc atcttgttgc cgtacgcgaa 300
cgccgcatcc ttgtgcacga tcgcgctgaa cgcgtcgacg gcctccccct gcaacaggat 360
gtccaccttg accagctggg cctcctgctc gccggcctcc tcgtagtcca ggctggcgta 420
gccgcgggtc cgcgacttca gcgagtcgaa gaagtcgaag atgatctcgc ccaacggcat 480
ggtgtagcgc agctcaaccc gttccggcga caggtaatcc atgccgccca gctcgccgcg 540
gcgggactgg cacagctcca tgatggtgcc gatgaattcg ctgggcgcga tgatggtggt 600
cttgaccacc ggctcgtaca ccgtgcgcac cttgccctcg ggccagtccg acgggttggt 660
caccacgatc tcggtgccgt cctctttgat cacccggtac accacgttgg gcgacgtcga 720
gatcaggtcg aggtcgaact cgcgctccag gcgctcgcgg gtgatctcca tgtgcagcaa 780
acccaaaaag ccacaacgga atccgcagcc cagcgccacc gatgtctccg gttcgtaggt 840
gagcgcggcg tcgttgagcc gcagccggtc cagcgcgtcg cgcagatccg gatagtccga 900
gccgtccacc ggatacagac ccgaatagac catcggcttg ggttcgcggt atccggtcag 960
cgcctcttgc gcgccgtggc gcgcgctggt gacggtgtcg cccactttgg actggcggac 1020
gtccttcacc ccggtgatca ggtagcccac ctcgccgacg ccaaggccgt cgctggcctt 1080
cggctcgggt gagacgatgc cgacctcgag cagttcgtgg gtggcgccgg tggacatcat 1140
cgcgatgcgt tcgcgcgggg tgatcttgcc gtcgaccacc cgcacgtagg tcaccacgcc 1200
gcggtagatg tcgtagaccg agtcgaagat catcgcgcgc agcggcgcat cggcctgccc 1260
ctgcggcggc ggcacctggc gcaccacctc gtcgagcagc cgcgccacgc cctccccggt 1320
tttgccggac acccacagca cgtcgtcggg ttcgcacccg atgatgtggg cgagctcgcc 1380
ggcgtagcga tccgggtcgg cggccggcag gtcgatcttg ttgaggaccg ggatgatggt 1440
cagatcgcgg tccagcgcca ggtagaggtt ggccagcgtc tgggcctcga tgccctgcgc 1500
ggcgtcgacc agcagcacgg caccttcgca ggcctccagt gcgcgcgaca cctcgtaggt 1560
gaagtcgacg tggcccgggg tgtcgatcag gtgcaggaca aattctttgc cggcgtcctc 1620
gccgccggag acctgccagg gcagccgcac gttctgcgcc ttgatggtga tgccgcgctc 1680
ccgctcgatg tccatccggt ccaggtactg ggcgcgcatc gaccgctcgt cgacgacgcc 1740
ggtgagctgc agcatccggt cggccagcgt cgacttgccg tgatcgatgt gggcgatgat 1800
gcagaagttg cgaatctgcg ccggcgcggt gaaggtcttg tcggcgaaac tgctgatggg 1860
tatctcctgg tccgggcctg ctagacggcg gttcgcaagt gtgtccagcg tatcggcgcg 1920
gccggactgc ggcacaatcg gcgcgtctat gctgcgaata tggcgtccgg ccggaagtcg 1980
cag 1983

<210> SEQ ID NO 61
<211> LENGTH: 1941
<212> TYPE: DNA
<213> ORGANISM: Mycobacterium leprae

<400> SEQUENCE: 61
ttatttcttg tccttgtctc ctgcggcatc ggcggacaac gcggcgacaa acgcttcctg 60

-continued

```
cggcacctcg acccgcccaa tggtcttcat ccgtttcttg ccttccttct gcttttccag    120

aagcttacgt ttgcgggtga tatcgccgcc ataacatttc gacagcacat ccttgcgtat    180

cgccctaata ttttcgcgcg caatgacttt cgatccaata gccgcctgta ctggcacctc    240

aaactgctga cgtgggatca gttctttgag cttgttggtc atcttgttgc cataggcaga    300

ggctgaatcc ttgtgcacaa tcgcgctgaa tgcgtcgacg gcctcgcctt gcagcaggat    360

gtcaaccttg accagttggg cctcctgctc gccagcctcc tcatagtcga ggctagcgta    420

gccccgggtg cgtgacttca gcgaatcgaa gaaatcgaag atgatttccc cgagcggcat    480

aatgtagcgt aactcgactc gctcaggtga aagatagtcc atgccaccta attcgccacg    540

gcgcgactgg cacagctcca tgatcgttcc gatgaactcg ctgggcgcaa tgatggtgat    600

cttcaccact ggctcgtaca ccgttcggat cttgccctcc ggccagtctg acgggttggt    660

caccacaatc tcggtgttat cttctgtcac cacacggtat acgacgttgg gcgacgtgga    720

gatcaggtcc aggtcgaact cgcgctctaa gcgttcgcgg gttatatcta tgtgcagcaa    780

accgaggaag ccgcaccggt acccaacgcc cagcgccacc gatgtttccg gctcgtaggt    840

cagcgccgcg tcgttgagct gtaacttacc tagagcgtca cgcaaactcg ggtagtccga    900

actgtcgacg ggatacagcc cggagtacac catgggcttg ggttctcggt agccagttaa    960

cggttcagtg gcaccataac gaaccgtcgt tacagtgtcg ccgactttgg attggcggac   1020

gtctttaacc ccagtaatca ggtagcccac ctcccccacg cccaggcccg cgctggcctt   1080

cggttcaggc gacacgatgc cgacctcgag cagttcgtac gtcgcaccgg tggacatcat   1140

cgcgatgcgc tcacgcgggc tgatcttgcc gtcgaccaca cggacgtagg tgaccacgcc   1200

tcggtagatg tcgtagacgg agtcgaagat catcgcgcgg gtaggcgcat cagggtcacc   1260

ttgcggatgc ggcacccgac ggaccacctc gtcaagaagg tcagaaaccc cctcgccggt   1320

tttgccggac acccgaagca catcgcctga ctcataacca atgatgtggg cgatctcagc   1380

ggcgtaacgg tccggatcgg cagccggcag gtcgattttg tttagcaccg gaataatcgt   1440

caagtcacgc tccagagcga gatagagatt ggccaaggtc tgagcttcga tgccctggac   1500

ggcgtctacc agcagcaccg caccctcaca ggcttccaat gctcgcgata cctcgtaggt   1560

gaagtccaca tggccggggg tgtcgatcaa gtgcaacaca taattctcag tcgtcccacc   1620

agctgtgaca ctccaagaca gccgcacgtt ctgcgcttta atcgtgattc cgcgctcacg   1680

ttcgatgtcc atccggtcca ggtactgggc acgcatcgac cgctcatcga cgacaccagt   1740

cagctgaagc atccggtccg ccagcgtgga tttgccgtga tcaatatgag cgattatgca   1800

gaagttccta atctgcgccg gcgcggtaaa ggtcttgtca gcgaaactgc tgatgggaat   1860

ctcctgggct ccagttacta gagaatgttt gaacggcgat tcgccggtgt ccggcttatc   1920

cacgcgaagt gaccaagaca c                                             1941
```

<210> SEQ ID NO 62
<211> LENGTH: 1740
<212> TYPE: DNA
<213> ORGANISM: Mycobacterium ulcerans

<400> SEQUENCE: 62

```
ctacttcttg cccttatccc ccgcggcgtc ggtggacagt gccgcgacaa acgcctcctg     60

cggcacctcg acccggccga tggacttcat ccgcttcttg ccctctttct gcttttccag    120

cagcttgcgt ttgcgggtga tgtcaccgcc gtagcacttc gacaacacat ccttgaggat    180

cgcgcggatg ttctcgcgcg cgatgatctt ggaaccgatg gccgcctgca ccggcacctc    240
```

-continued gaactgctga cgcggaatca gctccttgag cttggtggtc atcttgttgc cgtaggcgaa 300
cgccgaatcc ttgtggacga tagcgctgaa cgcatcgacg gcctcgcctt gcagcaggat 360
gtcgaccttg accagttggg cttcctgctc gccggactcc tcgtaatcga gactggcgta 420
gccacgggtc cgcgatatga gcgagtcgaa gaagtcaaag atgatctccc ccaacggcat 480
tgtgtatcgc agttccaccc gttcgggcga caaatagtcc atgcccccca gctcgccgcg 540
ccgcgactgg cacagctcca tgatggtgcc gatgaattcg ctgggcgcga tgatggtggt 600
cttcaccacc ggctcgtaga cggtgcggat cttgccctcg ggccagtccg acgggttggt 660
cacctgcatt tcggtgccgt cgtccttgat gacgcggtac acgacgttgg gcgaggtcga 720
gatcaggtcg aggtcgaact cgcgctccag acgttcccga ctgatctcca tgtgcagcag 780
gcccaggaag ccgcaccgga atccgaaacc cagcgccacc gacgtttcgg gctcataggt 840
cagggccgcg tcgttgagct gcagcttgtc cagggcgtcc cgcaggttcg gatagtccga 900
tccgtcaacg ggatacagtc ccgaatacac catcggcttg ggttcgcggt agccggtcag 960
tgcctcggtg gcacctttc gggcggtcgt gacggtgtcg ccgaccttgg actgccacac 1020
gtccttgacc ccggtgataa gataacccac ctcgccgaca ccaaggccgt cgctggcctt 1080
gggttcgggt gagacgatgc cgacctcgag cagttcgtgg gtggcgccgg tggacatcat 1140
ggcgatgcgc tcgcgggggg tgatcttgcc gtcgacgacg cggacgtagg tgaccacacc 1200
gcggtagatg tcatagacgg agtcgaagat cattgcgcga gtgggtgcgt cggcatcgcc 1260
ctgcggtggc ggcacctcgc gcaccacgtg gtcgagcagg tctgcgacgc cttccccggt 1320
tttgccggaa acccgcagca cgtcgccggg ctcgcagccg atgatgtgag caatctcgcc 1380
cgcgtagcgg tccgggtcgg cggccggcag gtcgatcttg ttcagcaccg gaatgatgtg 1440
caggtcgcgg tccagtgcca ggtagaggtt ggccagcgtc tgggcctcga tgccctgggc 1500
ggcgtcaacc agcagcaccg cgccctcgca ggcctccagc gcacgtgaca cctcgtaggt 1560
gaagtcgacg tgtcctggcg tgtcgatgag atgcaggacg tactcggttc catcgagctg 1620
ccagggcagc cgcacattct gcgccttgat ggtgatcccg cgttcgcgtt cgatatccat 1680
ccggtccagg tactgggccc gcatcgagcg ctcgtcaacg accccggtca actgcagcat 1740

<210> SEQ ID NO 63
<211> LENGTH: 1935
<212> TYPE: DNA
<213> ORGANISM: Mycobacterium avium

<400> SEQUENCE: 63
ttacttcttg gatttgtcgc ccgcggcgtc ggcggacagc gccgcgacga acgcctcctg 60
cggcacgtcg acccggccga tggtcttcat ccgcttcttg ccctccttct gcttttccag 120
aagtttgcgc ttacgggtga tgtcaccgcc gtaacacttg gacagcacgt ccttgcggat 180
ggcccgaatg ttctcgcggg caatgatttt cgagccgatc gcggcctgga cgggcacctc 240
gaactgctga cgggggatca gctccttgag cttggtggtc atcttgttgc cgtaggcgaa 300
cgccgcatcc ttgtgcacga tcgcgctgaa cgcgtcgacg gcctccccct gcaacaggat 360
gtccaccttg accagctggg cctcctgctc gccggcctcc tcgtagtcca ggctggcgta 420
gccgcgggtc cgcgacttca gcgagtcgaa gaagtcgaag atgatctcgc ccaacggcat 480
ggtgtagcgc agctcgaccc gttccggcga caggtaatcc atgccgccca gctcgccgcg 540
gcgggactgg cacagctcca tgatggtgcc gatgaattcg ctgggcgcga tgatggtggt 600

```
cttgaccacc ggctcgtaca ccgtgcgcac cttgccctcg ggccagtccg acgggttggt    660
caccacgatc tcggtgccgt cctctttgat cacccggtac accacgttgg gcgacgtcga    720
gatcaggtcg aggtcgaact cgcgctccag gcgctcgcgg gtgatctcca tgtgcagcaa    780
acccaaaaag ccgcaacgga atccgaagcc cagcgccacc gacgtctccg gttcgtaggt    840
gagcgcggcg tcgttgagcc gcagccggtc cagcgcgtcg cgcagatccg gatagtccga    900
gccgtccacc ggatacagac ccgaatagac catcggcttg ggttcgcgat atccggtcag    960
cgcctcttgc gcgccgtggc gcgcgctggt cacggtgtcg cccactttgg actggcggac   1020
gtccttcacc ccggtgatca ggtagcccac ctcgccgacg cccaggccgt cgctggcctt   1080
cggctcgggt gagacgatgc cgacttcgag cagttcgtgg gtggcgccgg tggacatcat   1140
cgcgatgcgt tcgcgcgggg tgatcttgcc gtcgaccacc cgcacgtagg tcaccacgcc   1200
gcggtagatg tcgtagaccg agtcgaagat catcgcgcgc agcggcgcat cggcctgccc   1260
ctgcggcggc ggcacctggc gcaccacctc gtcgagcagc cgcgccacgc cctccccggt   1320
tttgccggac acccgcagca cgtcgtcggg ttcgcacccg atgatgtggg cgagctcgcc   1380
ggcgtaccgg tccgggtcgg cggccggcag gtcgatcttg ttgaggaccg ggatgatggt   1440
cagatcgcgg tccagcgcca ggtagaggtt ggccagcgtc tgggcctcga tgccctgcgc   1500
ggcgtcgacc agcagcacgg caccttcgca ggcctccagt gcgcgcgaca cctcgtaggt   1560
gaagtcgacg tggcccgggg tgtcgatcag gtgcaggaca aattctttgc cggcgtcctc   1620
gccgccggag acctgccagg gcagccgcac gttctgcgcc ttgatggtga tgccgcgctc   1680
ccgctcgatg tccatccggt ccaggtactg ggcgcgcatc gaccgctcgt cgacgacgcc   1740
ggtgagctgc agcatccggt cggccagcgt cgacttgccg tgatcgatgt gggcgatgat   1800
gcagaagttg cgaatctgcg ccggcgcggt gaaggtcttg tcggcgaaac tgctgatggg   1860
tatctcctgg tccgggcctg ctagacggcg gttcgcaagt gtgtccagcg tatcggcgcg   1920
gccggactgc ggcac                                                    1935
```

<210> SEQ ID NO 64
<211> LENGTH: 1959
<212> TYPE: DNA
<213> ORGANISM: Mycobacterium vanbaalenii

<400> SEQUENCE: 64

```
tcatttcttc ggcttgtccg cggtggattc ggtggacagc gcggcgacga aggcctcctg     60
cgggacgtcg acccggccga tggtcttcat ccgcttcttg ccttccttct gcttttccag    120
cagcttgcgc ttacgggtga tgtcaccgcc gtagcacttg gacagcacat ccttgcggat    180
cgcccgaatg ttctcgcggg caatgattct cgagccgacg gcggcctgca cgggcacctc    240
gaactgctgg cgcgggatga gctccttgag cttggtggtc atcttgttgc cgtaggccga    300
ggccccgtcc ttgtgcacga tcgccgagaa cgcgtcgacg gcctcgccct gcagcaggat    360
gtcgaccttg accaggtcgg cctcctgctc gcctgcctcc tcgtagtcca ggctggcgta    420
gccgcgggtg cgcgatttca gcgagtcgaa gaagtcgaag atgatctcgc ccagcggcat    480
ggtgtagcgc agctcgacgc gctcgggcga caggtagtcc attccgccga gttcaccgcg    540
ccgcgactgg cacagctcca tgatcgtgcc gatgaactcg ctgggcgcga tcaccgtcgt    600
cttgaccacc ggctcgaaca ccgatcgcac cttgccctcg ggccagtccg aggggttggt    660
gacgatgatc tcggacccgt cgtccttgac gacgcggtag accacgttgg gcgcggtcga    720
gatcaggtcc aggttgaact cgcgctccag gcgttcccgg gtgatctcca tgtgcagcag    780
```

cccgaggaac ccgcagcgga acccgaaccc gagcgccacc gacgtctcgg gttcgtacgt 840
cagcgccgcg tcgttgagtt gcagcttgtc cagcgcctcg cgcagcaccg ggtagtccga 900
gccgtcgacc ggatacaggc ccgagtagac catcggcctg ggctcccggt agccggtcaa 960
cgcttccttg gcaccgttac gcgccgtcgt caccgtgtcg ccgaccttgg actggcgcac 1020
gtccttcaca ccggtgatga ggtagccgac ctcgccgacg ccgaggccgt cggagggctt 1080
gggctcgggt gagacgattc ccacctcgag cagttcgtgg gtggcgccgg tcgacatcat 1140
cgcgatgcgc tcgcgcgggg tgatcttccc gtccaccacc cgcacgtagg tcaccacgcc 1200
gcggtagatg tcgtagaccg agtcgaagat catcgcgcgg gcaggcgcgt ccgggtcgcc 1260
ctgcggcgcc gggatctccc gcaccacgtg gtcgagcagc tcggccacac cctcacccgt 1320
cttgcccgac acccgcaaca cgtcctcggg ctcgcagccg atgatgtggg cgatctcggc 1380
ggcgtaccgg tccgggtctg cggcgggcag atcgatcttg ttcagcaccg ggatgatcgt 1440
caggtcgcgg tccagcgcca gatacaggtt cgccagcgtc tgcgcttcga tgccctgggc 1500
ggcgtcgacc agcagcaccg cgccctcgca cgcctccagc gcgcgggaca cctcataggt 1560
gaaatcaaca tggccgggcg tgtcaatcaa atgcagcacg aactcctcac cgttgaccac 1620
ccacggcagc cgcacgttct gcgccttgat cgtgatcccg cgctcacgct cgatgtccat 1680
ccggtccagg tactgcgccc gcatcgagcg ctcgtcgacc acaccggtga gctgcagcat 1740
ccggtcggcc agggtggact ttccgtggtc gatgtgggcg atgatgcaga agttccgaat 1800
ctgcgccggc gcagtgaacg tcttgtcggc gaagctgctg atgggaatct cctggtgagc 1860
gggtcgtggc ggcctgaaca ggcctgtcca gagtatcgag cgcacacccc cgcgacacaa 1920
tcgagccgtg atcgaggcgg cttcggggca ccggggcac 1959

<210> SEQ ID NO 65
<211> LENGTH: 1905
<212> TYPE: DNA
<213> ORGANISM: Mycobacterium gilvum

<400> SEQUENCE: 65
ctacttcttc ggcttgtccg cggcggactc ggtcgacagt gccgcgacga aggcctcctg 60
cggcacctcg acccggccga tcgtcttcat ccgcttcttg ccttccttct gcttctccag 120
cagcttgcgc ttacgagtga tgtcaccgcc gtagcacttc gacagcacgt ccttgcggat 180
cgcccggatg ttctctcgcg caatgattct cgagccgatc gcggcctgca cgggcacctc 240
gaactgctgg cgtgggatca gttccttcag cttggtcgtc atcttgttgc cgtacgccgc 300
ggcaccgtcc ttgtggacga tggcgctgaa cgcgtcgacg gcttcgccct gcagcaggat 360
gtcgaccttg accaggtcgg cctcctgctc gcccgcctcc tcgtagtcga ggctcgcgta 420
gccgcgggtg cgggacttca gcgagtcgaa gaagtcgaag atgatctcgc ccagcggcat 480
cgtgtagcgc agctcgaccc gctcgggtga caggtagtcc atgccgccga gctcgccacg 540
gcgcgactgg cacagctcca tgatcgttcc gatgaactca ctcggcgcga tcaccgtcgt 600
cttgacgacc ggctcgaaca ccgaacggac cttgccctcg ggccagtccg acgggttggt 660
gaccgtgagc tcgctgttgt cctctttgat gacgcggtag acgacgttgg gcgcggtcga 720
gatcaggtcg aggttgaact cgcgttcgag ccgctcgcgc gtgatctcca tgtgcagcaa 780
gcccaggaag ccgcagcgga agccgaaccc gagcgcgacc gacgtctccg gctcgtaagt 840
cagtgccgcg tcgttcagct gcagtttgtc gagcgcctcg cgcaacaccg ggtagtcgga 900

```
accgtccacg ggatacaggc ccgagtagac catcggcttg ggctcgcggt agccggtcag    960
cgcttcggtg gcacccttgc gtgccgtcgt caccgtgtcg ccgaccttgg actgacgcac   1020
gtccttcacg ccggtgatca ggtagccgac ctcgccgaca ccgagaccga ccgaaggctt   1080
ggggtccggc gagacgatgc ccacttcgag gagttcgtgc gtcgcgccgg tcgacatcat   1140
cgcgatgcgc tcacgcgggg tgatcctgcc gtcgacgacg cgcacatagg tgacgacgcc   1200
gcggtagatg tcgtacaccg agtcgaagat catcgcgcgc gccggagcgt ccgggtcgcc   1260
ctgcggcggc gggatctccc ggacgacgtg gtcgagcagg tcgccgacgc cggcgccggt   1320
cttgcccgac acccgcagca catcctccgg ttcgcagccg atgatgtgcg cgatctcacc   1380
ggcgtagcgg tcggggtcgg cggcgggcag gtcgatcttg ttgagcaccg ggatgattgt   1440
caggtcgcga tccagcgcca ggtacaggtt cgccagggtc tgcgcctcga tgccctgggc   1500
ggcgtcgacc agcagcaccg caccctcgca ggcctccagc gcgcgcgaca cctcgtaggt   1560
gaaatcgacg tggccagggg tgtcgatcag atgcaggacg aactcttcgc cgttgacgac   1620
ccacggcagg cgcacgttct gcgccttgat cgtgatgccg cgttcccgct cgatgtccat   1680
ccggtccagg tactgcgccc gcatgtccct gtccgcgacc acaccggtga gctgcagcat   1740
ccgatcggcc agggtggact tgccgtggtc gatgtgggcg atgatgcaga agttcctgat   1800
ctgcgccggc gcagtgaacg tcttgtcggc gaagctggcg atgggaatct cctggtgagc   1860
ggggtctgtc ggcctgagca ggccagtcca gagtatcgag cgcat                   1905
```

<210> SEQ ID NO 66
<211> LENGTH: 1854
<212> TYPE: DNA
<213> ORGANISM: Mycobacterium abscessus

<400> SEQUENCE: 66

```
ctacttcttc ggtttgtccg ccgtcgactc ggtggacagt gccgccacaa acgcctcctg     60
cggcacctcg acgcgaccga tggtcttcat gcgcttcttg ccctccttct gcttctcgag    120
cagcttgcgc ttacgggtga tatcaccgcc gtagcacttg gagagcacat ccttacggat    180
ggcccgaata ttctcgcgcg caatgattct cgatccgaca gcggcctgca ccggcacctc    240
gaactgctgg cgcgggatga gttccttgag cttgacggtc atcttgttgc cataggccga    300
ggccccgtcc ttgtggacga tggcgctgaa cgcgtcgacc gcctcgccct gcagcaggat    360
gtcgaccttg accagatcgg cctcctgctc gccggcctcc tcgtaatcca ggctggcgta    420
gccgcgcgta cgcgacttca acgagtcgaa gaagtcgaag atgatctcgc ccaacggcat    480
cgtgtagcgc agctcgacgc gttcgggtga caggtagtcc atgccgccga gctcgccgcg    540
ccgcgattgg cacagctcca tgatcgaacc gatgaattca ctcggcgcga tcaccgtcgt    600
cttgaccacc ggctcgaaca ccgaccggat cttgccctcg ggccagatgg acggattggt    660
caccatcatc cctggatcat cggccgtcat tccttcggta atcacccggt acaccacgtt    720
gggagccgtc gagatgaggt cgaggttgaa ctcgcgttcg aggcgctcac gggtgatctc    780
catgtgcagc aatcccagga agccacaacg gaatccgaag cccagcgcca ccgaggtctc    840
cggctcgtag gtgagcgcgg cgtcgttgag ctggagtttg tccagcgcct cgcgcaggtt    900
cgggtagtcg gatccgtcca ccgggtacag cccggaatag accatcggct tgggttcgcg    960
gtagccggtc agcggctcct tggcgccgtt gcgcgcggcg gtgacggtgt caccgacctt   1020
cgactggcgc acatccttca cgccggtgat caggtagccc acctcgccga ccccgagtcc   1080
cgcggagggt ttgggctccg gcgagacgat gcccacttcc agcagttcgt gggtggcgcc   1140
```

```
cgtcgacatc atcgcgatct tctcgcgcgg agtgatcttg ccgtccacga cgcgcacgta   1200

ggtgaccaca ccgcggtaga tgtcgtagac cgagtcgaag atcatcgccc gcgccggcgc   1260

atccggatca ccttgcggcg ctgggatgag ccgcaccacc tcgtcgagca gcgccgcgac   1320

gccctccccg gtcttaccgg acacccgcag cacatcggag ggctcgcagc cgatgatgtg   1380

cgcgatctcc tcggcgtaac gctccggatc ggccgcgggc aggtcgatct tgttcaggac   1440

cgggatgatc gtcaggtcct tgtccagcgc caggtacagg ttggccagcg tctgcgcttc   1500

gatgccctgc gcggcgtcga ccagcagcac tgccccctcg cacgcctcca gggcgcgcga   1560

cacctcgtag gtgaagtcga cgtgcccggg ggtgtcgatc aggtgtagca catggtcctg   1620

gccattgagc tgccacggca gccgcacgtt ctgtgccttg atggtgatgc cgcgctcacg   1680

ctcgatatcc atgcgatcca ggtactgcgc gcgcatggaa cgctcgtcga ccacaccggt   1740

cagctgcagc atccggtcgg ccagggtcga cttcccgtgg tcgatgtggg cgatgatgca   1800

gaagttacga atcagcgccg gatccgtgaa cgtcgtgtcg gcaaaacttg gcac         1854
```

<210> SEQ ID NO 67
<211> LENGTH: 1917
<212> TYPE: DNA
<213> ORGANISM: Mycobacterium marinum

<400> SEQUENCE: 67

```
ctacttcttg cccttatccc ccgcggcgtc ggtggacagt gccgcgacaa acgcctcctg     60

cggcacctcg acccggccga tggtcttcat ccgcttcttg ccctctttct gcttttccag    120

cagcttgcgt ttgcgggtga tgtcaccgcc gtagcacttc gacaacacat ccttgcggat    180

cgcgcggatg ttctcgcgcg cgatgatctt ggaaccgatg gccgcctgca ccggcacctc    240

gaactgctga cgcggaatca gctccttgag cttggtggtc atcttgttgc cgtaggcgaa    300

cgccgaatcc ttgtggacga tagcgctgaa cgcatcgacg gcctcgcctt gcagcaggat    360

gtcgaccttg accagttggg cttcctgctc gccggactcc tcgtaatcga gactggcgta    420

gccacgggtc cgcgacttga gcgagtcgaa gaagtcaaag atgatctccc ccaacggcat    480

tgtgtatcgc agttccaccc gttcgggcga caaatagtcc atgcccccca gctcgccgcg    540

ccgcgactgg cacagctcca tgatggtgcc gatgaattcg ctgggcgcga tgatggtggt    600

cttcaccacc ggctcgtaga cggtgcggat cttgccctcg ggccagtccg acgggttggt    660

cacctgcatt tcggtgccgt cgtccttgat gacgcggtac acgacgttgg gcgaggtcga    720

gatcaggtcg aggtcgaact cgcgctccag acgttcccga ctgatctcca tgtgcagcag    780

gcccaggaag ccgcaccgga atccgaaacc cagcgccacc gacgtttcgg gctcataggt    840

cagggccgcg tcgttgagct gcagcttgtc cagggcgtcc cgcaggttcg gatagtccga    900

tccgtcaacg ggatacagtc ccgaatacac catcggcttg ggttcgcggt agccggtcag    960

tgcctcggtg gcaccttttc gggcggtcgt gacggtgtcg ccgaccttgg actgccgcac   1020

gtccttgacc ccggtgatca gataacccac ctcgccgaca ccaaggccgt cgctggcctt   1080

gggttcgggt gagacgatgc cgacctcgag cagttcgtgg gtggcgccgg tggacatcat   1140

ggcgatgcgc tcgcgggggg tgatcttgcc gtcgacgacg cggacgtagg tgaccacacc   1200

gcggtagatg tcatagacgg agtcgaagat cattgcgcga gtgggtgcgt cggcatcgcc   1260

ctgcggtggc ggcacctcgc gcaccacgtg gtcgagcagg tctgcgacgc cttccccggt   1320

tttgccggaa acccgcagca cgtcgccggg ctcgcagccg atgatgtgag caatctcgcc   1380
```

-continued cgcgtagcgg tccgggtcgg cggccggcag gtcgatcttg ttcagcaccg gaatgatgtg 1440
caggtcgcgg tccagtgcca ggtagaggtt ggccagcgtc tgggcctcga tgccctgggc 1500
ggcgtcaacc agcagcaccg cgccctcgca ggcctccagc gcacgtgaca cctcgtaggt 1560
gaagtcgacg tgtcctggcg tgtcgatgag atgcaggacg tactcggttc catcgagctg 1620
ccagggcagc cgcacattct gcgccttgat ggtgatcccg cgttcgcgtt cgatatccat 1680
ccggtccagg tactgggccc gcatcgagcg ctcgtcaacg accccggtca actgcagcat 1740
tcggtccgcc agcgtcgact ttccgtggtc gatgtgagcg atgatgcaga agttccgaat 1800
ctgcgccggc ggggtgaagg ttttgtcggc gaaactgctg atgggactct cctgaagcgg 1860
gggtttgcgg gtttccagcc tatctgtgca gcgccgcccg gacctacttg aggccaa 1917

<210> SEQ ID NO 68
<211> LENGTH: 1896
<212> TYPE: DNA
<213> ORGANISM: Mycobacterium smegmatis

<400> SEQUENCE: 68
ctacttcttg ggcttgtcgc ccgccgcgtc ggtggacagc gccgcgacga atgcctcctg 60
cggcacgtcg acccggccga tcgtcttcat gcgcttcttg ccctctttct gcttctcgag 120
cagcttgcgc ttacgggtga tgtcaccgcc gtagcacttc gagagcacgt ccttgcggat 180
ggcccggatg ttttcgcgcg caatgattct cgagccgatc gcggcctgca ccgggacctc 240
gaactgctgt cgcgggatca gttctttgag cttggaggtc atcttgttgc cgtaggccga 300
cgcaccgtcc ttgtggacga tagccgagaa cgcgtcgacg gcctcgccct gcagcaggat 360
gtcgaccttg accagatcgg cctcctgctc accggcctcc tcgtagtcga ggctcgcgta 420
gccgcgggtg cgggacttca gcgagtcgaa gaagtcgaag atgatctcgc ccaacggcat 480
gatgtagcgc agttcgacac gctcgggcga caggtagtcc atgccctgca gttcgccgcg 540
acgggactgg cacagctcca tgatggtgcc gatgaactcg ctgggcgcga tgatcgtggt 600
cttcacgacg ggctcgaaca ccgtgcggat cttgccttcc ggccagtccg acgggttcgt 660
cacgaccttc tcggaaccgt cgtcctgcac gacgcggtac accacgttgg gtgaggtgga 720
gatcaggtcc aggccgaact cgcgctccag gcgttcacgg gtgatctcca tgtgcagcag 780
tccgaggaag ccgcagcgga acccgaagcc cagggccacc gaggtctccg gctcatacgt 840
cagtgcggcg tcgttgagtt gcagcttgtc cagcgcgtca cgcagatccg ggtagtccga 900
accgtcgacg ggatacaggc ccgagtacac catcggcttg ggctcgcgat aacccgtgag 960
cgcctcggtc gcgcccttgc gcgccgtggt caccgtgtca ccgaccttcg actggcggac 1020
gtccttcaca cccgtgatca ggtaaccgac ctcaccgacg cccaggcccg cactggcctt 1080
cggttccggt gagacgatgc cgacctcgag cagttcatgg gtggcgccgg tggacatcat 1140
cgcgatgcgt tcgcgcggca cgatcttgcc gtcgaccaca cggacgtagg tcaccacgcc 1200
gcggtagatg tcgtacacgg agtcgaagat catcgcgcgc gtcggggcgt cggggtcacc 1260
gaccggcggc ggcaccttac gcaccacctc gtcgagcagc tcggccacgc cttcgccggt 1320
cttgcccgag acacgcagca cgtccgacgg ctcacacccg atgatgtggg cgagctcgtc 1380
ggcatagcgg tccgggtcag cggcgggcag gtcgatcttg ttgagcaccg ggatgatcgc 1440
caggtcgcgg tccagcgcca ggtacaggtt ggccagcgtc tgcgcctcga tgccctgcgc 1500
cgcgtcgacc agcagcaccg cgccctcgca ggcctccagc gcgcgcgaca cctcgtaggt 1560
gaagtcgacg tggcccgggg tgtcgatcag gtgcagcacg taatcacccg cgtccgcgcc 1620

-continued gtcttggccg tccttcagcg tccacggaag ccggacgttc tgagccttga tggtgatccc 1680
gcgctcacgt tcgatgtcca tgcggtcgag gtactgggcc cgcatcgacc gctcatcgac 1740
aacaccggtg agctgcagca tccggtcggc cagcgtcgac ttgccgtggt cgatgtgggc 1800
gatgatgcag aagttccgaa tctgcgccgg cgcagtgaac gtcttgtcgg cgaagctgct 1860
gatgggaatc tcctggtgag cgtgggtcaa gcgcac 1896

<210> SEQ ID NO 69
<211> LENGTH: 475
<212> TYPE: DNA
<213> ORGANISM: Artificial Sequence
<220> FEATURE:
<223> OTHER INFORMATION: Mycobacterium tuberculosis DNA fragment

<400> SEQUENCE: 69
cggcatggtg tagcgcagtt ccacccgctc gggggagaga tagtccatgc cgcccaactc 60
gccgcggcgc gactggcaca gctccatgat ggtgccgatg aactcgctgg gcgcgatgat 120
ggtggtcttg acgacgggct cgtagaccgt gcggatcttg ccctccggcc agtccgacgg 180
attggtcacc cggatttcgg tgccgtcgtc tttgtgcacc cgatacacca cattgggtga 240
ggtcgagatc aggtccaggc cgaactcgcg ctcaaggcgc tcacgggtga tctccatgtg 300
cagcaggccc aagaaaccgc accggaaccc aaaacccagc gccaccgagg tttccggctc 360
ataggtcaag gccgcgtcgt tgagctgcag cttgtccagg gcgtcgcgca ggttcgggta 420
gtccgaaccg tcgaccggat acaaccccga gtagaccatc ggtttgggct cacgg 475

<210> SEQ ID NO 70
<211> LENGTH: 475
<212> TYPE: DNA
<213> ORGANISM: Artificial Sequence
<220> FEATURE:
<223> OTHER INFORMATION: Mycobacterium bovis DNA fragment

<400> SEQUENCE: 70
cggcatggtg tagcgcagtt ccacccgctc gggggagaga tagtccatgc cgcccaactc 60
gccgcggcgc gactggcaca gctccatgat ggtgccgatg aactcgctgg gcgcgatgat 120
ggtggtcttg acgacgggct cgtagaccgt gcggatcttg ccctccggcc agtccgacgg 180
attggtcacc cggatttcgg tgccgtcgtc tttgtgcacc cgatacacca cattgggtga 240
ggtcgagatc aggtccaggc cgaactcgcg ctcaaggcgc tcacgggtga tctccatgtg 300
cagcaggccc aagaaaccgc accggaaccc aaaacccagc gccaccgagg tttccggctc 360
ataggtcaag gccgcgtcgt tgagctgcag cttgtccagg gcgtcgcgca ggttcggata 420
gtccgaaccg tcgaccggat acnaccccga gtagaccatc ggtttgggct cacgg 475

<210> SEQ ID NO 71
<211> LENGTH: 475
<212> TYPE: DNA
<213> ORGANISM: Artificial Sequence
<220> FEATURE:
<223> OTHER INFORMATION: Mycobacterium canettii DNA fragment

<400> SEQUENCE: 71
cggcatggtg tagcgcagtt ccacccgctc gggggagaga tagtccatgc cgcccaactc 60
gccgcggcgc gactggcaca gctccatgat ggtgccgatg aactcgctgg gcgcgatgat 120
ggtggtcttg acgacgggct cgtagaccgt gcggatcttg ccctccggcc agtccgacgg 180

```
attggtcacc cggatttcgg tgccgtcgtc tttgtgcacc cgatacacca cattgggtga    240

ggtcgagatc aggtccaggc cgaactcgcg ctcaaggcgc tcacgggtga tctccatgtg    300

cagcaggccc aagaaaccgc accggaaccc aaaacccagc gccaccgagg tttccggctc    360

ataggtcaag gccgcgtcgt tgagctgcag cttgtccagg gcgtcgcgca ggttcgggta    420

gtccgaaccg tcgaccggat acaaccccga gtagaccatc ggtttgggct cacgg         475


<210> SEQ ID NO 72
<211> LENGTH: 475
<212> TYPE: DNA
<213> ORGANISM: Artificial Sequence
<220> FEATURE:
<223> OTHER INFORMATION: Mycobacterium canettii DNA fragment

<400> SEQUENCE: 72

cggcatggtg tagcgcagtt ccacccgctc gggggagaga tagtccatgc cgcccaactc     60

gccgcggcgc gactggcaca gctccatgat ggtgccgatg aactcgctgg gcgcgatgat    120

ggtggtcttg acgacgggct cgtagaccgt gcggatcttg ccctccggcc agtccgacgg    180

attggtcacc cggatttcgg tgccgtcgtc tttgtgcacc cgatacacca cattgggtga    240

ggtcgagatc aggtccaggc cgaactcgcg ctcaaggcgc tcacgggtga tctccatgtg    300

cagcaggccc aagaaaccgc accggaaccc aaaacccagc gccaccgagg tttccggctc    360

ataggtcaag gccgcgtcgt tgagctgcag cttgtccagg gcgtcgcgca ggttcgggta    420

gtccgaaccg tcgaccggat acaaccccga gtagaccatc ggtttgggct cacgg         475


<210> SEQ ID NO 73
<211> LENGTH: 475
<212> TYPE: DNA
<213> ORGANISM: Artificial Sequence
<220> FEATURE:
<223> OTHER INFORMATION: Mycobacterium africanum DNA fragment

<400> SEQUENCE: 73

cggcatggtg tagcgcagtt ccacccgctc gggggagaga tagtccatgc cgcccaactc     60

gccgcggcgc gactggcaca gctccatgat ggtgccgatg aactcgctgg gcgcgatgat    120

ggtggtcttg acgacgggct cgtagaccgt gcggatcttg ccctccggcc agtccgacgg    180

attggtcacc cggatttcgg tgccgtcgtc tttgtgcacc cgatacacca cattgggtga    240

ggtcgagatc aggtccaggc cgaactcgcg ctcaaggcgc tcacgggtga tctccatgtg    300

cagcaggccc aagaaaccgc accggaaccc aaaacccagc gccaccgagg tttccggctc    360

ataggtcaag gccgcgtcgt tgagctgcag cttgtccagg gcgtcgcgca ggttcgggta    420

gtccgaaccg tcgaccggat acaaccccga gtagaccatc ggtttgggct cacgg         475


<210> SEQ ID NO 74
<211> LENGTH: 475
<212> TYPE: DNA
<213> ORGANISM: Artificial Sequence
<220> FEATURE:
<223> OTHER INFORMATION: Mycobacterium microti DNA fragment

<400> SEQUENCE: 74

cggcatggtg tagcgcagtt ccacccgctc gggggagaga tagtccatgc cgcccaactc     60

gccgcggcgc gactggcaca gctccatgat ggtgccgatg aactcgctgg gcgcgatgat    120

ggtggtcttg acgacgggct cgtagaccgt gcggatcttg ccctccggcc agtccgacgg    180

attggtcacc cggatttcgg tgccgtcgtc tttgtgcacc cgatacacca cattgggtga    240
```

ggtcgagatc aggtccaggc cgaactcgcg ctcaaggcgc tcacgggtga tctccatgtg 300
cagcaggccc aagaaaccgc accggaaccc aaaacccagc gccaccgagg tttccggctc 360
ataggtcaag gccgcgtcgt tgagctgcag cttgtccagg gcgtcgcgca ggttcgggta 420
gtccgaaccg tcgaccggat acaaccccga gtagaccatc ggtttgggct cacgg 475

<210> SEQ ID NO 75
<211> LENGTH: 475
<212> TYPE: DNA
<213> ORGANISM: Artificial Sequence
<220> FEATURE:
<223> OTHER INFORMATION: Mycobacterium pinipedii DNA fragment

<400> SEQUENCE: 75
cggcatggtg tagcgcagtt ccacccgctc gggggagaga tagtccatgc cgcccaactc 60
gccgcggcgc gactggcaca gctccatgat ggtgccgatg aactcgctgg gcgcgatgat 120
ggtggtcttg acgacgggct cgtagaccgt gcggatcttg ccctccggcc agtccgacgg 180
attggtcacc cggatttcgg tgccgtcgtc tttgtgcacc cgatacacca cattgggtga 240
ggtcgagatc aggtccaggc cgaactcgcg ctcaaggcgc tcacgggtga tctccatgtg 300
cagcaggccc aagaaaccgc accggaaccc aaaacccagc gccaccgagg tttccggctc 360
ataggtcaag gccgcgtcgt tgagctgcag cttgtccagg gcgtcgcgca ggttcgggta 420
gtccgaaccg tcgaccggat acaaccccga gtagaccatc ggtttgggct cacgg 475

<210> SEQ ID NO 76
<211> LENGTH: 475
<212> TYPE: DNA
<213> ORGANISM: Artificial Sequence
<220> FEATURE:
<223> OTHER INFORMATION: Mycobacterium caprae DNA fragment

<400> SEQUENCE: 76
cggcatggtg tagcgcagtt ccacccgctc gggggagaga tagtccatgc cgcccaactc 60
gccgcggcgc gactggcaca gctccatgat ggtgccgatg aactcgctgg gcgcgatgat 120
ggtggtcttg acgacgggct cgtagaccgt gcggatcttg ccctccggcc agtccgacgg 180
attggtcacc cggatttcgg tgccgtcgtc tttgtgtacc cgatacacca cattgggtga 240
ggtcgagatc aggtccaggc cgaactcgcg ctcaaggcgc tcacgggtga tctccatgtg 300
cagcaggccc aagaaaccgc accggaaccc aaaacccagc gccaccgagg tttccggctc 360
ataggtcaag gccgcgtcgt tgagctgcag cttgtccagg gcgtcgcgca ggttcgggta 420
gtccgaaccg tcgaccggat acaaccccga gtagaccatc ggtttgggct cacgg 475

<210> SEQ ID NO 77
<211> LENGTH: 475
<212> TYPE: DNA
<213> ORGANISM: Artificial Sequence
<220> FEATURE:
<223> OTHER INFORMATION: Mycobacterium caprae DNA fragment

<400> SEQUENCE: 77
cggcatggtg tagcgcagtt ccacccgctc gggggagaga tagtccatgc cgcccaactc 60
gccgcggcgc gactggcaca gctccatgat ggtgccgatg aactcgctgg gcgcgatgat 120
ggtggtcttg acgacgggct cgtagaccgt gcggatcttg ccctccggcc agtccgacgg 180
attggtcacc cggatttcgg tgccgtcgtc tttgtgtacc cgatacacca cattgggtga 240
ggtcgagatc aggtccaggc cgaactcgcg ctcaaggcgc tcacgggtga tctccatgtg 300
cagcaggccc aagaaaccgc accggaaccc aaaacccagc gccaccgagg tttccggctc 360
ataggtcaag gccgcgtcgt tgagctgcag cttgtccagg gcgtcgcgca ggttcgggta 420
gtccgaaccg tcgaccggat acaaccccga gtagaccatc ggtttgggct cacgg 475

<210> SEQ ID NO 78
<211> LENGTH: 2869
<212> TYPE: DNA
<213> ORGANISM: Mycobacterium canettii

<400> SEQUENCE: 78
tgtcggcggc cacgtcagac tgcccagtga tggccatata agtgcccgct ggcggtcatg 60
aaaactgccc gctggcggtc acgagatctg cccagttgat ttgttcgtcc cgcgtgcctg 120
cgaggtgcgg gggcccctcc tcgggtgcgc tgaacggtgc caaccgttgt tcagctcccg 180
aggaggggtg aagtgaagtc tgccgaggag atcatggaaa ttctggaagc ctacgatttg 240
accggttcgt tgcgtgatgc ggcggaactg gcggggtgct cgcatcacac ggtcgccgag 300
tatgtggccg cgcgggagcg gggcgagttg acgcccgggc gcgcggcgcg gcgggagatg 360
ctggtggatc cgtatctgga caagctcgag gagtgggtcg accgctcgcg gggcaaggtc 420
cgcggcgatg tcgcccacga gaagctggtc gcgttggggt atgcgggttc gcagcgtacg 480
acacggcggg cggtcgccga ggtcaaggca gcgtatcggg cggggcgacg gcgggtgcac 540
cgtccgtgga tcaccgagcc ggggatgtgg tttcagtacg acttcgggga tggcccgcgc 600
gtgagaggtg ttggcacgca attgttttgc gcgtggctgg cgtggtgccg gtttagggtg 660
gtgctggcgc ttttggataa gacactgcca tcggtgatgg ccgcgatcga tacaacgcta 720
cgcgtcttcg gtggggtgcc cacctacgcg ttgaccgata acgagaagac cgtgaccagc 780
gagcatgtcg cggggatacc ggtgcgcaac gccaagatgc tggacttcgc ccgccattac 840
gggctcacga tcgccacctg cgtgccggcc gatccggcca gcaagggcgg ctcggaaaac 900
gcggtcaaga tcgccaaggc cgatctggtg ccctgtgagg ccaacctgct accggaatac 960
cacagtttcg ccgagctgca agcggcgtgc gcgacgtttt gccagcaggt caacaatcgc 1020
ccgcatcggg tcacgcggcg catcccggcg gagatgctgg ccgaggaacg cgcccggtta 1080
cacccgttac ccgcccatcc ctacaccgcg gcgttcgggg tgacccgcac ggtgccgccc 1140
aacaccgcga tgatcacctt tgagcacggg tcgtattcgg tgccgcacac cttgtgcggg 1200
cagacggtgt gggtgcgggc ccacgaccag caggtagtgg tcgtgcacct cggccatgcc 1260
ggcccagtcg aagtcgcccg ccaccagcgc accacgccgg gtaacccgcg ggtggatgac 1320
gcgcatttcc caccccggcc caaggggccg ctgggccgaa caccacgcgc gaaaactgtt 1380
gctgaggcgc agtttttggc tctcggtgac ggggcagcat tgtggttgac cgaggccgcc 1440
gccgcgggat gctcgcggat tcgggccaag atggccgggg cggtcgattt ggccgcactg 1500
cacgatcggg gcagcgtgga ccgcgccttg ggccaagccg cgaccgcggg ccggttcggc 1560
cacggcgatc tggccgccat cgtggcccat caggccggcg accccgacca ccacagcgcc 1620
tcgcagcccg cccacgcggg cgagtacaac agcctggccc aaggcaccgg tggctgggcg 1680
aagctcggtg agcaggaggc caactaacga tggcctacct cgacatctcc tttaagacca 1740
catcgatcct gctcaacacc tgcggcgccg acgatcccga ccaactggtc ggcgtggccg 1800
ccgcagaact gttccagtgg gcgtggctga tcggcgagct cgccagctgg ctcgccgacg 1860
ctgacgagca cacccacgcc gacttcgacc ggttcttcag cagctaccgc ggcgtcgaca 1920
agaccgcagg gttggccacc cacatcgcgc agcgcatcgc cgcgctgctc gacggggacc 1980
ggagccagcc atgagcacaa caacaccgcc accaccaccg ctagacgacg agctgatgcg 2040
gctgctcaag cggatgcggc tgccttacat ccgcaacgcc gcacccgagc tgctggccac 2100
cgccaaggcg caacgctggg accctgccga ggtgctcaaa gcgcttctga ccgaagaggt 2160
caacgggcga gaccgctccg cgctggccat ccgccgcacg cgggccggtt ttcccaccgg 2220
taagaccttc gccgcgtggg accccgcact gtcgtccatc cccgcaccca cccaggccgc 2280
gttgcgcacc ctggaatgga tccaccgacg cgaaaacctg gtggtctgcg ggccgtcggg 2340
caccggcaag acgttcctgc tcgaagccct cggccaacaa gccgtcgaaa ccgggctcca 2400
cgtcgcgtgg tttagcctcg aacaactcgg cgccctggtg cgccggcacc gcgccgacga 2460
caccgtcacc aaagccatca gccgtatcct gcgtgccgat ctggtcgcgg ttgatgacat 2520
cggcctgctg ccggtcggca ccgacgccgc cgaagggctc taccggcttg tcgacgccgc 2580
ttacgagaaa cgctccatcg cactatcaag caatcttcac ccggcaggat tcgacgagtt 2640
gatgcccaag acactggcca ccgccaccgt cgaccggctc ctgcaccacg cccacgtctg 2700
ccagaccagt ggcgacagca tccgacttac ccaagccatg gccggcaagg gggtgaacgc 2760
cttgacctaa cccccagcca cgtctggtgg ccgccagcag gcagatctcg tggccgccag 2820
cgggcagttc tcatgaccgc cactgggcag ttccccatgt cccttgaca 2869

<210> SEQ ID NO 79
<211> LENGTH: 2832
<212> TYPE: DNA
<213> ORGANISM: Artificial Sequence
<220> FEATURE:
<223> OTHER INFORMATION: Mycobacterium canetti DNA fragment

<400> SEQUENCE: 79
tataagtgcc cgctggcggt catgaaaact gcccgctggc ggtcacgaga tctgcccagt 60
tgatttgttc gtcccgcgtg cctgcgaggt gcgggggccc ctcctcgggt gcgctgaacg 120
gtgccaaccg ttgttcagct cccgaggagg ggtgaagtga agtctgccga ggagatcatg 180
gaaattctgg aagcctacga tttgaccggt tcgttgcgtg atgcggcgga actggcgggg 240
tgctcgcatc acacggtcgc cgagtatgtg gccgcgcggg agcggggcga gttgacgccc 300
gggcgcgcgg cgcggcggga gatgctggtg gatccgtatc tggacaagct cgaggagtgg 360
gtcgaccgct cgcggggcaa ggtccgcggc gatgtcgccc acgagaagct ggtcgcgttg 420
gggtatgcgg gttcgcagcg tacgacacgg cgggcggtcg ccgaggtcaa ggcagcgtat 480
cgggcggggc gacggcgggt gcaccgtccg tggatcaccg agccggggat gtggtttcag 540
tacgacttcg gggatggccc gcgcgtgaga ggtgttggca cgcaattgtt ttgcgcgtgg 600
ctggcgtggt gccggtttag ggtggtgctg gcgcttttgg ataagacact gccatcggtg 660
atggccgcga tcgatacaac gctacgcgtc ttcggtgggg tgcccaccta cgcgttgacc 720
gataacgaga agaccgtgac cagcgagcat gtcgcgggga taccggtgcg caacgccaag 780
atgctggact tcgcccgcca ttacgggctc acgatcgcca cctgcgtgcc ggccgatccg 840
gccagcaagg gcggctcgga aaacgcggtc aagatcgcca aggccgatct ggtgccctgt 900
gaggccaacc tgctaccgga ataccacagt ttcgccgagc tgcaagcggc gtgcgcgacg 960
ttttgccagc aggtcaacaa tcgcccgcat cgggtcacgc ggcgcatccc ggcggagatg 1020
ctggccgagg aacgcgcccg gttacacccg ttacccgccc atccctacac cgcggcgttc 1080
ggggtgaccc gcacggtgcc gcccaacacc gcgatgatca cctttgagca cgggtcgtat 1140
tcggtgccgc acaccttgtg cgggcagacg gtgtgggtgc gggcccacga ccagcaggta 1200
gtggtcgtgc acctcggcca tgccggccca gtcgaagtcg cccgccacca gcgcaccacg 1260
ccgggtaacc cgcgggtgga tgacgcgcat ttcccacccc ggcccaaggg gccgctgggc 1320
cgaacaccac gcgcgaaaac tgttgctgag gcgcagtttt tggctctcgg tgacggggca 1380
gcattgtggt tgaccgaggc cgccgccgcg ggatgctcgc ggattcgggc caagatggcc 1440
ggggcggtcg atttggccgc actgcacgat cggggcagcg tggaccgcgc cttgggccaa 1500
gccgcgaccg cgggccggtt cggccacggc gatctggccg ccatcgtggc ccatcaggcc 1560
ggcgaccccg accaccacag cgcctcgcag cccgcccacg cgggcgagta caacagcctg 1620
gcccaaggca ccggtggctg ggcgaagctc ggtgagcagg aggccaacta acgatggcct 1680
acctcgacat ctcctttaag accacatcga tcctgctcaa cacctgcggc gccgacgatc 1740
ccgaccaact ggtcggcgtg gccgccgcag aactgttcca gtgggcgtgg ctgatcggcg 1800
agctcgccag ctggctcgcc gacgctgacg agcacaccca cgccgacttc gaccggttct 1860
tcagcagcta ccgcggcgtc gacaagaccg cagggttggc cacccacatc gcgcagcgca 1920
tcgccgcgct gctcgacggg gaccggagcc agccatgagc acaacaacac cgccaccacc 1980
accgctagac gacgagctga tgcggctgct caagcggatg cggctgcctt acatccgcaa 2040
cgccgcaccc gagctgctgg ccaccgccaa ggcgcaacgc tgggaccctg ccgaggtgct 2100
caaagcgctt ctgaccgaag aggtcaacgg gcgagaccgc tccgcgctgg ccatccgccg 2160
cacgcgggcc ggttttccca ccggtaagac cttcgccgcg tgggaccccg cactgtcgtc 2220
catccccgca cccacccagg ccgcgttgcg caccctggaa tggatccacc gacgcgaaaa 2280
cctggtggtc tgcgggccgt cgggcaccgg caagacgttc ctgctcgaag ccctcggcca 2340
acaagccgtc gaaaccgggc tccacgtcgc gtggtttagc ctcgaacaac tcggcgccct 2400
ggtgcgccgg caccgcgccg acgacaccgt caccaaagcc atcagccgta tcctgcgtgc 2460
cgatctggtc gcggttgatg acatcggcct gctgccggtc ggcaccgacg ccgccgaagg 2520
gctctaccgg cttgtcgacg ccgcttacga gaaacgctcc atcgcactat caagcaatct 2580
tcacccggca ggattcgacg agttgatgcc caagacactg gccaccgcca ccgtcgaccg 2640
gctcctgcac cacgcccacg tctgccagac cagtggcgac agcatccgac ttacccaagc 2700
catggccggc aagggggtga acgccttgac ctaaccccca gccacgtctg gtggccgcca 2760
gcaggcagat ctcgtggccg ccagcgggca gttctcatga ccgccactgg gcagttcccc 2820
atgtcccttg ac 2832

<210> SEQ ID NO 80
<211> LENGTH: 2832
<212> TYPE: DNA
<213> ORGANISM: Artificial Sequence
<220> FEATURE:
<223> OTHER INFORMATION: Mycobacterium canettii DNA fragment

<400> SEQUENCE: 80
tataagtgcc cgctggcggt catgaaaact gcccgctggc ggtcacgaga tctgcccagt 60
tgatttgttc gtcccgcgtg cctgcgaggt gcgggggccc ctcctcgggt gcgctgaacg 120
gtgccaaccg ttgttcagct cccgaggagg ggtgaagtga agtctgccga ggagatcatg 180
gaaattctgg aagcctacga tttgaccggt tcgttgcgtg atgcggcgga actggcgggg 240
tgctcgcatc acacggtcgc cgagtatgtg gccgcgcggg agcggggcga gttgacgccc 300

-continued

```
gggcgcgcgg cgcggcggga gatgctggtg gatccgtatc tggacaagct cgaggagtgg    360
gtcgaccgct cgcggggcaa ggtccgcggc gatgtcgccc acgagaagct ggtcgcgttg    420
gggtatgcgg gttcgcagcg tacgacacgg cgggcggtcg ccgaggtcaa ggcagcgtat    480
cgggcggggc gacggcgggt gcaccgtccg tggatcaccg agccggggat gtggtttcag    540
tacgacttcg ggatggcccc gcgcgtgaga ggtgttggca cgcaattgtt ttgcgcgtgg    600
ctggcgtggt gccggtttag ggtggtgctg gcgcttttgg ataagacact gccatcggtg    660
atggccgcga tcgatacaac gctacgcgtc ttcggtgggg tgcccaccta cgcgttgacc    720
gataacgaga agaccgtgac cagcgagcat gtcgcgggga taccggtgcg caacgccaag    780
atgctggact tcgcccgcca ttacgggctc acgatcgcca cctgcgtgcc ggccgatccg    840
gccagcaagg gcggctcgga aaacgcggtc aagatcgcca aggccgatct ggtgccctgt    900
gaggccaacc tgctaccgga ataccacagt ttcgccgagc tgcaagcggc gtgcgcgacg    960
ttttgccagc aggtcaacaa tcgcccgcat cgggtcacgc ggcgcatccc ggcggagatg   1020
ctggccgagg aacgcgcccg gttacacccg ttacccgccc atccctacac cgcggcgttc   1080
ggggtgaccc gcacggtgcc gcccaacacc gcgatgatca cctttgagca cgggtcgtat   1140
tcggtgccgc acaccttgtg cgggcagacg gtgtgggtgc gggcccacga ccagcaggta   1200
gtggtcgtgc acctcggcca tgccggccca gtcgaagtcg cccgccacca gcgcaccacg   1260
ccgggtaacc cgcgggtgga tgacgcgcat ttcccacccc ggcccaaggg gccgctgggc   1320
cgaacaccac gcgcgaaaac tgttgctgag gcgcagtttt tggctctcgg tgacggggca   1380
gcattgtggt tgaccgaggc cgccgccgcg ggatgctcgc ggattcgggc caagatggcc   1440
ggggcggtcg atttggccgc actgcacgat cggggcagcg tggaccgcgc cttgggccaa   1500
gccgcgaccg cgggccggtt cggccacggc gatctggccg ccatcgtggc ccatcaggcc   1560
ggcgaccccg accaccacag cgcctcgcag cccgcccacg cgggcgagta caacagcctg   1620
gcccaaggca ccggtggctg ggcgaagctc ggtgagcagg aggccaacta acgatggcct   1680
acctcgacat ctcctttaag accacatcga tcctgctcaa cacctgcggc gccgacgatc   1740
ccgaccaact ggtcggcgtg gccgccgcag aactgttcca gtgggcgtgg ctgatcggcg   1800
agctcgccag ctggctcgcc gacgctgacg agcacaccca cgccgacttc gaccggttct   1860
tcagcagcta ccgcggcgtc gacaagaccg cagggttggc cacccacatc gcgcagcgca   1920
tcgccgcgct gctcgacggg gaccggagcc agccatgagc acaacaacac cgccaccacc   1980
accgctagac gacgagctga tgcggctgct caagcggatg cggctgcctt acatccgcaa   2040
cgccgcaccc gagctgctgg ccaccgccaa ggcgcaacgc tgggaccctg ccgaggtgct   2100
caaagcgctt ctgaccgaag aggtcaacgg gcgagaccgc tccgcgctgg ccatccgccg   2160
cacgcgggcc ggttttccca ccggtaagac cttcgccgcg tgggaccccg cactgtcgtc   2220
catccccgca cccacccagg ccgcgttgcg caccctggaa tggatccacc gacgcgaaaa   2280
cctggtggtc tgcgggccgt cgggcaccgg caagacgttc ctgctcgaag ccctcggcca   2340
acaagccgtc gaaaccgggc tccacgtcgc gtggtttagc ctcgaacaac tcggcgccct   2400
ggtgcgccgg caccgcgccg acgacaccgt caccaaagcc atcagccgta tcctgcgtgc   2460
cgatctggtc gcggttgatg acatcggcct gctgccggtc ggcaccgacg ccgccgaagg   2520
gctctaccgg cttgtcgacg ccgcttacga gaaacgctcc atcgcactat caagcaatct   2580
tcacccggca ggattcgacg agttgatgcc caagacactg gccaccgcca ccgtcgaccg   2640
```

gctcctgcac cacgcccacg tctgccagac cagtggcgac agcatccgac ttacccaagc 2700
catggccggc aagggggtga acgccttgac ctaaccccca gccacgtctg gtggccgcca 2760
gcaggcagat ctcgtggccg ccagcgggca gttctcatga ccgccactgg gcagttcccc 2820
atgtcccttg ac 2832

<210> SEQ ID NO 81
<211> LENGTH: 2832
<212> TYPE: DNA
<213> ORGANISM: Artificial Sequence
<220> FEATURE:
<223> OTHER INFORMATION: Mycobacterium canettii DNA fragment

<400> SEQUENCE: 81
tataagtgcc cgctggcggt catgaaaact gcccgctggc ggtcacgaga tctgcccagt 60
tgatttgttc gtcccgcgtg cctgcgaggt gcgggggccc ctcctcgggt gcgctgaacg 120
gtgccaaccg ttgttcagct cccgaggagg ggtgaagtga agtctgccga ggagatcatg 180
gaaattctgg aagcctacga tttgaccggt tcgttgcgtg atgcggcgga actggcgggg 240
tgctcgcatc acacggtcgc cgagtatgtg gccgcgcggg agcggggcga gttgacgccc 300
gggcgcgcgg cgcggcggga gatgctggtg gatccgtatc tggacaagct cgaggagtgg 360
gtcgaccgct cgcggggcaa ggtccgcggc gatgtcgccc acgagaagct ggtcgcgttg 420
gggtatgcgg gttcgcagcg tacgacacgg cgggcggtcg ccgaggtcaa ggcagcgtat 480
cgggcggggc gacggcgggt gcaccgtccg tggatcaccg agccggggat gtggtttcag 540
tacgacttcg gggatggccc gcgcgtgaga ggtgttggca cgcaattgtt ttgcgcgtgg 600
ctggcgtggt gccggtttag ggtggtgctg gcgcttttgg ataagacact gccatcggtg 660
atggccgcga tcgatacaac gctacgcgtc ttcggtgggg tgcccaccta cgcgttgacc 720
gataacgaga agaccgtgac cagcgagcat gtcgcgggga taccggtgcg caacgccaag 780
atgctggact tcgcccgcca ttacgggctc acgatcgcca cctgcgtgcc ggccgatccg 840
gccagcaagg gcggctcgga aaacgcggtc aagatcgcca aggccgatct ggtgccctgt 900
gaggccaacc tgctaccgga ataccacagt ttcgccgagc tgcaagcggc gtgcgcgacg 960
ttttgccagc aggtcaacaa tcgcccgcat cgggtcacgc ggcgcatccc ggcggagatg 1020
ctggccgagg aacgcgcccg gttacacccg ttacccgccc atccctacac cgcggcgttc 1080
ggggtgaccc gcacggtgcc gcccaacacc gcgatgatca cctttgagca cgggtcgtat 1140
tcggtgccgc acaccttgtg cggcagacg gtgtgggtgc gggcccacga ccagcaggta 1200
gtggtcgtgc acctcggcca tgccggccca gtcgaagtcg cccgccacca gcgcaccacg 1260
ccgggtaacc cgcgggtgga tgacgcgcat ttcccacccc ggcccaaggg gccgctgggc 1320
cgaacaccac gcgcgaaaac tgttgctgag gcgcagtttt tggctctcgg tgacggggca 1380
gcattgtggt tgaccgaggc cgccgccgcg ggatgctcgc ggattcgggc caagatggcc 1440
ggggcggtcg atttggccgc actgcacgat cggggcagcg tggaccgcgc cttgggccaa 1500
gccgcgaccg cgggccggtt cggccacggc gatctggccg ccatcgtggc ccatcaggcc 1560
ggcgaccccg accaccacag cgcctcgcag cccgcccacg cgggcgagta caacagcctg 1620
gcccaaggca ccggtggctg ggcgaagctc ggtgagcagg aggccaacta acgatggcct 1680
acctcgacat ctcctttaag accacatcga tcctgctcaa cacctgcggc gccgacgatc 1740
ccgaccaact ggtcggcgtg gccgccgcag aactgttcca gtgggcgtgg ctgatcggcg 1800
agctcgccag ctggctcgcc gacgctgacg agcacaccca cgccgacttc gaccggttct 1860

```
tcagcagcta ccgcggcgtc gacaagaccg cagggttggc cacccacatc gcgcagcgca   1920

tcgccgcgct gctcgacggg gaccggagcc agccatgagc acaacaacac cgccaccacc   1980

accgctagac gacgagctga tgcggctgct caagcggatg cggctgcctt acatccgcaa   2040

cgccgcaccc gagctgctgg ccaccgccaa ggcgcaacgc tgggaccctg ccgaggtgct   2100

caaagcgctt ctgaccgaag aggtcaacgg gcgagaccgc tccgcgctgg ccatccgccg   2160

cacgcgggcc ggttttccca ccggtaagac cttcgccgcg tgggaccccg cactgtcgtc   2220

catccccgca cccacccagg ccgcgttgcg caccctggaa tggatccacc gacgcgaaaa   2280

cctggtggtc tgcgggccgt cgggcaccgg caagacgttc ctgctcgaag ccctcggcca   2340

acaagccgtc gaaaccgggc tccacgtcgc gtggtttagc ctcgaacaac tcggcgccct   2400

ggtgcgccgg caccgcgccg acgacaccgt caccaaagcc atcagccgta tcctgcgtgc   2460

cgatctggtc gcggttgatg acatcggcct gctgccggtc ggcaccgacg ccgccgaagg   2520

gctctaccgg cttgtcgacg ccgcttacga gaaacgctcc atcgcactat caagcaatct   2580

tcacccggca ggattcgacg agttgatgcc caagacactg gccaccgcca ccgtcgaccg   2640

gctcctgcac cacgcccacg tctgccagac cagtggcgac agcatccgac ttacccaagc   2700

catggccggc aagggggtga acgccttgac ctaaccccca gccacgtctg gtggccgcca   2760

gcaggcagat ctcgtggccg ccagcgggca gttctcatga ccgccactgg gcagttcccc   2820

atgtcccttg ac                                                       2832
```

<210> SEQ ID NO 82
<211> LENGTH: 2832
<212> TYPE: DNA
<213> ORGANISM: Artificial Sequence
<220> FEATURE:
<223> OTHER INFORMATION: Mycobacterium canettii DNA fragment

<400> SEQUENCE: 82

```
tataagtgcc cgctggcggt catgaaaact gcccgctggc ggtcacgaga tctgcccagt     60

tgatttgttc gtcccgcgtg cctgcgaggt gcgggggccc ctcctcgggt gcgctgaacg    120

gtgccaaccg ttgttcagct cccgaggagg ggtgaagtga agtctgccga ggagatcatg    180

gaaattctgg aagcctacga tttgaccggt tcgttgcgtg atgcggcgga actggcgggg    240

tgctcgcatc acacggtcgc cgagtatgtg gccgcgcggg agcggggcga gttgacgccc    300

gggcgcgcgg cgcggcggga gatgctggtg gatccgtatc tggacaagct cgaggagtgg    360

gtcgaccgct cgcggggcaa ggtccgcggc gatgtcgccc acgagaagct ggtcgcgttg    420

gggtatgcgg gttcgcagcg tacgacacgg cgggcggtcg ccgaggtcaa ggcagcgtat    480

cgggcggggc gacggcgggt gcaccgtccg tggatcaccg agccggggat gtggtttcag    540

tacgacttcg gggatggccc gcgcgtgaga ggtgttggca cgcaattgtt ttgcgcgtgg    600

ctggcgtggt gccggtttag ggtggtgctg gcgcttttgg ataagacact gccatcggtg    660

atggccgcga tcgatacaac gctacgcgtc ttcggtgggg tgcccaccta cgcgttgacc    720

gataacgaga agaccgtgac cagcgagcat gtcgcgggga taccggtgcg caacgccaag    780

atgctggact tcgcccgcca ttacgggctc acgatcgcca cctgcgtgcc ggccgatccg    840

gccagcaagg gcggctcgga aaacgcggtc aagatcgcca aggccgatct ggtgccctgt    900

gaggccaacc tgctaccgga ataccacagt ttcgccgagc tgcaagcggc gtgcgcgacg    960

ttttgccagc aggtcaacaa tcgcccgcat cgggtcacgc ggcgcatccc ggcggagatg   1020
```

```
ctggccgagg aacgcgcccg gttacacccg ttacccgccc atccctacac cgcggcgttc   1080
ggggtgaccc gcacggtgcc gcccaacacc gcgatgatca cctttgagca cgggtcgtat   1140
tcggtgccgc acaccttgtg cgggcagacg gtgtgggtgc gggcccacga ccagcaggta   1200
gtggtcgtgc acctcggcca tgccggccca gtcgaagtcg cccgccacca gcgcaccacg   1260
ccgggtaacc cgcgggtgga tgacgcgcat ttcccacccc ggcccaaggg gccgctgggc   1320
cgaacaccac gcgcgaaaac tgttgctgag gcgcagtttt tggctctcgg tgacggggca   1380
gcattgtggt tgaccgaggc cgccgccgcg ggatgctcgc ggattcgggc caagatggcc   1440
ggggcggtcg atttggccgc actgcacgat cggggcagcg tggaccgcgc cttgggccaa   1500
gccgcgaccg cgggccggtt cggccacggc gatctggccg ccatcgtggc ccatcaggcc   1560
ggcgaccccg accaccacag cgcctcgcag cccgcccacg cgggcgagta caacagcctg   1620
gcccaaggca ccggtggctg ggcgaagctc ggtgagcagg aggccaacta acgatggcct   1680
acctcgacat ctcctttaag accacatcga tcctgctcaa cacctgcggc gccgacgatc   1740
ccgaccaact ggtcggcgtg gccgccgcag aactgttcca gtgggcgtgg ctgatcggcg   1800
agctcgccag ctggctcgcc gacgctgacg agcacaccca cgccgacttc gaccggttct   1860
tcagcagcta ccgcggcgtc gacaagaccg cagggttggc cacccacatc gcgcagcgca   1920
tcgccgcgct gctcgacggg gaccggagcc agccatgagc acaacaacac cgccaccacc   1980
accgctagac gacgagctga tgcggctgct caagcggatg cggctgcctt acatccgcaa   2040
cgccgcaccc gagctgctgg ccaccgccaa ggcgcaacgc tgggaccctg ccgaggtgct   2100
caaagcgctt ctgaccgaag aggtcaacgg gcgagaccgc tccgcgctgg ccatccgccg   2160
cacgcgggcc ggttttccca ccggtaagac cttcgccgcg tggacccccg cactgtcgtc   2220
catccccgca cccacccagg ccgcgttgcg caccctggaa tggatccacc gacgcgaaaa   2280
cctggtggtc tgcgggccgt cgggcaccgg caagacgttc ctgctcgaag ccctcggcca   2340
acaagccgtc gaaaccgggc tccacgtcgc gtggtttagc ctcgaacaac tcggcgccct   2400
ggtgcgccgg caccgcgccg acgacaccgt caccaaagcc atcagccgta tcctgcgtgc   2460
cgatctggtc gcggttgatg acatcggcct gctgccggtc ggcaccgacg ccgccgaagg   2520
gctctaccgg cttgtcgacg ccgcttacga gaaacgctcc atcgcactat caagcaatct   2580
tcacccggca ggattcgacg agttgatgcc caagacactg gccaccgcca ccgtcgaccg   2640
gctcctgcac cacgcccacg tctgccagac cagtggcgac agcatccgac ttacccaagc   2700
catggccggc aagggggtga acgccttgac ctaaccccca gccacgtctg gtggccgcca   2760
gcaggcagat ctcgtggccg ccagcgggca gttctcatga ccgccactgg gcagttcccc   2820
atgtcccttg ac                                                       2832
```

<210> SEQ ID NO 83
<211> LENGTH: 2832
<212> TYPE: DNA
<213> ORGANISM: Artificial Sequence
<220> FEATURE:
<223> OTHER INFORMATION: Mycobacterium canettii DNA fragment

<400> SEQUENCE: 83

```
tataagtgcc cgctggcggt catgaaaact gcccgctggc ggtcacgaga tctgcccagt     60
tgatttgttc gtcccgcgtg cctgcgaggt gcgggggccc ctcctcgggt gcgctgaacg    120
gtgccaaccg ttgttcagct cccgaggagg ggtgaagtga agtctgccga ggagatcatg    180
gaaattctgg aagcctacga tttgaccggt tcgttgcgtg atgcggcgga actggcgggg    240
```

```
tgctcgcatc acacggtcgc cgagtatgtg gccgcgcggg agcggggcga gttgacgccc    300
gggcgcgcgg cgcggcggga gatgctggtg gatccgtatc tggacaagct cgaggagtgg    360
gtcgaccgct cgcggggcaa ggtccgcggc gatgtcgccc acgagaagct ggtcgcgttg    420
gggtatgcgg gttcgcagcg tacgacacgg cgggcggtcg ccgaggtcaa ggcagcgtat    480
cgggcggggc gacggcgggt gcaccgtccg tggatcaccg agccggggat gtggtttcag    540
tacgacttcg gggatggccc gcgcgtgaga ggtgttggca cgcaattgtt ttgcgcgtgg    600
ctggcgtggt gccggtttag ggtggtgctg gcgcttttgg ataagacact gccatcggtg    660
atggccgcga tcgatacaac gctacgcgtc ttcggtgggg tgcccaccta cgcgttgacc    720
gataacgaga agaccgtgac cagcgagcat gtcgcgggga taccggtgcg caacgccaag    780
atgctggact tcgcccgcca ttacgggctc acgatcgcca cctgcgtgcc ggccgatccg    840
gccagcaagg gcggctcgga aaacgcggtc aagatcgcca aggccgatct ggtgccctgt    900
gaggccaacc tgctaccgga ataccacagt ttcgccgagc tgcaagcggc gtgcgcgacg    960
ttttgccagc aggtcaacaa tcgcccgcat cgggtcacgc ggcgcatccc ggcggagatg   1020
ctggccgagg aacgcgcccg gttacacccg ttacccgccc atccctacac cgcggcgttc   1080
ggggtgaccc gcacggtgcc gcccaacacc gcgatgatca cctttgagca cgggtcgtat   1140
tcggtgccgc acaccttgtg cgggcagacg gtgtgggtgc gggcccacga ccagcaggta   1200
gtggtcgtgc acctcggcca tgccggccca gtcgaagtcg cccgccacca gcgcaccacg   1260
ccgggtaacc cgcgggtgga tgacgcgcat ttcccacccc ggcccaaggg gccgctgggc   1320
cgaacaccac gcgcgaaaac tgttgctgag gcgcagtttt tggctctcgg tgacggggca   1380
gcattgtggt tgaccgaggc cgccgccgcg ggatgctcgc ggattcgggc caagatggcc   1440
ggggcggtcg atttggccgc actgcacgat cggggcagcg tggaccgcgc cttgggccaa   1500
gccgcgaccg cgggccggtt cggccacggc gatctggccg ccatcgtggc ccatcaggcc   1560
ggcgaccccg accaccacag cgcctcgcag cccgcccacg cgggcgagta caacagcctg   1620
gcccaaggca ccggtggctg ggcgaagctc ggtgagcagg aggccaacta acgatggcct   1680
acctcgacat ctcctttaag accacatcga tcctgctcaa cacctgcggc gccgacgatc   1740
ccgaccaact ggtcggcgtg gccgccgcag aactgttcca gtgggcgtgg ctgatcggcg   1800
agctcgccag ctggctcgcc gacgctgacg agcacaccca cgccgacttc gaccggttct   1860
tcagcagcta ccgcggcgtc gacaagaccg cagggttggc cacccacatc gcgcagcgca   1920
tcgccgcgct gctcgacggg gaccggagcc agccatgagc acaacaacac cgccaccacc   1980
accgctagac gacgagctga tgcggctgct caagcggatg cggctgcctt acatccgcaa   2040
cgccgcaccc gagctgctgg ccaccgccaa ggcgcaacgc tgggaccctg ccgaggtgct   2100
caaagcgctt ctgaccgaag aggtcaacgg gcgagaccgc tccgcgctgg ccatccgccg   2160
cacgcgggcc ggttttccca ccggtaagac cttcgccgcg tgggaccccg cactgtcgtc   2220
catccccgca cccacccagg ccgcgttgcg caccctggaa tggatccacc gacgcgaaaa   2280
cctggtggtc tgcgggccgt cgggcaccgg caagacgttc ctgctcgaag ccctcggcca   2340
acaagccgtc gaaaccgggc tccacgtcgc gtggtttagc ctcgaacaac tcggcgccct   2400
ggtgcgccgg caccgcgccg acgacaccgt caccaaagcc atcagccgta tcctgcgtgc   2460
cgatctggtc gcggttgatg acatcggcct gctgccggtc ggcaccgacg ccgccgaagg   2520
gctctaccgg cttgtcgacg ccgcttacga gaaacgctcc atcgcactat caagcaatct   2580
```

tcacccggca ggattcgacg agttgatgcc caagacactg gccaccgcca ccgtcgaccg 2640
gctcctgcac cacgcccacg tctgccagac cagtggcgac agcatccgac ttacccaagc 2700
catggccggc aagggggtga acgccttgac ctaaccccca gccacgtctg gtggccgcca 2760
gcaggcagat ctcgtggccg ccagcgggca gttctcatga ccgccactgg gcagttcccc 2820
atgtcccttg ac 2832

<210> SEQ ID NO 84
<211> LENGTH: 1896
<212> TYPE: DNA
<213> ORGANISM: Mycobacterium smegmatis

<400> SEQUENCE: 84
ctacttcttg ggcttgtcgc ccgccgcgtc ggtggacagc gccgcgacga atgcctcctg 60
cggcacgtcg acccggccga tcgtcttcat gcgcttcttg ccctctttct gcttctcgag 120
cagcttgcgc ttacgggtga tgtcaccgcc gtagcacttc gagagcacgt ccttgcggat 180
ggcccggatg ttttcgcgcg caatgattct cgagccgatc gcggcctgca ccgggacctc 240
gaactgctgt cgcgggatca gttctttgag cttggaggtc atcttgttgc cgtaggccga 300
cgcaccgtcc ttgtggacga tagccgagaa cgcgtcgacg gcctcgccct gcagcaggat 360
gtcgaccttg accagatcgg cctcctgctc accggcctcc tcgtagtcga ggctcgcgta 420
gccgcgggtg cgggacttca gcgagtcgaa gaagtcgaag atgatctcgc ccaacggcat 480
gatgtagcgc agttcgacac gctcgggcga caggtagtcc atgccctgca gttcgccgcg 540
acgggactgg cacagctcca tgatggtgcc gatgaactcg ctgggcgcga tgatcgtggt 600
cttcacgacg ggctcgaaca ccgtgcggat cttgccttcc ggccagtccg acgggttcgt 660
cacgaccttc tcggaaccgt cgtcctgcac gacgcggtac accacgttgg gtgaggtgga 720
gatcaggtcc aggccgaact cgcgctccag gcgttcacgg gtgatctcca tgtgcagcag 780
tccgaggaag ccgcagcgga acccgaagcc cagggccacc gaggtctccg gctcatacgt 840
cagtgcggcg tcgttgagtt gcagcttgtc cagcgcgtca cgcagatccg ggtagtccga 900
accgtcgacg ggatacaggc ccgagtacac catcggcttg ggctcgcgat aacccgtgag 960
cgcctcggtc gcgcccttgc gcgccgtggt caccgtgtca ccgaccttcg actggcggac 1020
gtccttcaca cccgtgatca ggtaaccgac ctcaccgacg cccaggcccg cactggcctt 1080
cggttccggt gagacgatgc cgacctcgag cagttcatgg gtggcgccgg tggacatcat 1140
cgcgatgcgt tcgcgcggca cgatcttgcc gtcgaccaca cggacgtagg tcaccacgcc 1200
gcggtagatg tcgtacacgg agtcgaagat catcgcgcgc gtcggggcgt cggggtcacc 1260
gaccggcggc ggcaccttac gcaccacctc gtcgagcagc tcggccacgc cttcgccggt 1320
cttgcccgag acacgcagca cgtccgacgg ctcacacccg atgatgtggg cgagctcgtc 1380
ggcatagcgg tccgggtcag cggcgggcag gtcgatcttg ttgagcaccg ggatgatcgc 1440
caggtcgcgg tccagcgcca ggtacaggtt ggccagcgtc tgcgcctcga tgccctgcgc 1500
cgcgtcgacc agcagcaccg cgccctcgca ggcctccagc gcgcgcgaca cctcgtaggt 1560
gaagtcgacg tggcccgggg tgtcgatcag gtgcagcacg taatcacccg cgtccgcgcc 1620
gtcttggccg tccttcagcg tccacggaag ccggacgttc tgagccttga tggtgatccc 1680
gcgctcacgt tcgatgtcca tgcggtcgag gtactgggcc cgcatcgacc gctcatcgac 1740
aacaccggtg agctgcagca tccggtcggc cagcgtcgac ttgccgtggt cgatgtgggc 1800
gatgatgcag aagttccgaa tctgcgccgg cgcagtgaac gtcttgtcgg cgaagctgct 1860
gatgggaatc tcctggtgag cgtgggtcaa gcgcac 1896

<210> SEQ ID NO 85
<211> LENGTH: 19
<212> TYPE: DNA
<213> ORGANISM: Artificial Sequence
<220> FEATURE:
<223> OTHER INFORMATION: Primer

<400> SEQUENCE: 85
taccagcttc agtttccgt 19

<210> SEQ ID NO 86
<211> LENGTH: 21
<212> TYPE: DNA
<213> ORGANISM: Artificial Sequence
<220> FEATURE:
<223> OTHER INFORMATION: Primer

<400> SEQUENCE: 86
gcacctatat cttcttagcc g 21

<210> SEQ ID NO 87
<211> LENGTH: 18
<212> TYPE: DNA
<213> ORGANISM: Artificial Sequence
<220> FEATURE:
<223> OTHER INFORMATION: Primer

<400> SEQUENCE: 87
ggatgtcgac cttgacca 18

<210> SEQ ID NO 88
<211> LENGTH: 17
<212> TYPE: DNA
<213> ORGANISM: Artificial Sequence
<220> FEATURE:
<223> OTHER INFORMATION: Primer

<400> SEQUENCE: 88
ctgatcaccg gcgtcaa 17

<210> SEQ ID NO 89
<211> LENGTH: 15
<212> TYPE: DNA
<213> ORGANISM: Artificial Sequence
<220> FEATURE:
<223> OTHER INFORMATION: Primer

<400> SEQUENCE: 89
tgtcggcggc cacgt 15

<210> SEQ ID NO 90
<211> LENGTH: 21
<212> TYPE: DNA
<213> ORGANISM: Artificial Sequence
<220> FEATURE:
<223> OTHER INFORMATION: Primer

<400> SEQUENCE: 90
gaagtccagc atcttggcgt t 21

<210> SEQ ID NO 91
<211> LENGTH: 15
<212> TYPE: DNA

<213> ORGANISM: Artificial Sequence
<220> FEATURE:
<223> OTHER INFORMATION: Primer

<400> SEQUENCE: 91
tgtcggcggc cacgt 15

<210> SEQ ID NO 92
<211> LENGTH: 17
<212> TYPE: DNA
<213> ORGANISM: Artificial Sequence
<220> FEATURE:
<223> OTHER INFORMATION: Primer

<400> SEQUENCE: 92
atcgtgcagt gcggcca 17

<210> SEQ ID NO 93
<211> LENGTH: 20
<212> TYPE: DNA
<213> ORGANISM: Artificial Sequence
<220> FEATURE:
<223> OTHER INFORMATION: Primer

<400> SEQUENCE: 93
gcagcattgt ggttgaccga 20

<210> SEQ ID NO 94
<211> LENGTH: 17
<212> TYPE: DNA
<213> ORGANISM: Artificial Sequence
<220> FEATURE:
<223> OTHER INFORMATION: Primer

<400> SEQUENCE: 94
tcccagcgtt gcgcctt 17

<210> SEQ ID NO 95
<211> LENGTH: 18
<212> TYPE: DNA
<213> ORGANISM: Artificial Sequence
<220> FEATURE:
<223> OTHER INFORMATION: Primer

<400> SEQUENCE: 95
tgatgcggct gctcaagc 18

<210> SEQ ID NO 96
<211> LENGTH: 21
<212> TYPE: DNA
<213> ORGANISM: Artificial Sequence
<220> FEATURE:
<223> OTHER INFORMATION: Primer

<400> SEQUENCE: 96
tgtcaaggga catggggaac t 21

<210> SEQ ID NO 97
<211> LENGTH: 19
<212> TYPE: DNA
<213> ORGANISM: Artificial Sequence
<220> FEATURE:
<223> OTHER INFORMATION: Primer

<400> SEQUENCE: 97
taccagcttc agtttccgt 19

<210> SEQ ID NO 98
<211> LENGTH: 19
<212> TYPE: DNA
<213> ORGANISM: Artificial Sequence
<220> FEATURE:
<223> OTHER INFORMATION: Probe

<400> SEQUENCE: 98
atggtgcgca gttcactgc 19

<210> SEQ ID NO 99
<211> LENGTH: 21
<212> TYPE: DNA
<213> ORGANISM: Artificial Sequence
<220> FEATURE:
<223> OTHER INFORMATION: Probe

<400> SEQUENCE: 99
gcacctatat cttcttagcc g 21

<210> SEQ ID NO 100
<211> LENGTH: 17
<212> TYPE: DNA
<213> ORGANISM: Artificial Sequence
<220> FEATURE:
<223> OTHER INFORMATION: Primer

<400> SEQUENCE: 100
agaccgtgcg gatcttg 17

<210> SEQ ID NO 101
<211> LENGTH: 20
<212> TYPE: DNA
<213> ORGANISM: Artificial Sequence
<220> FEATURE:
<223> OTHER INFORMATION: Probe

<400> SEQUENCE: 101
acggattggt cacccggatt 20

<210> SEQ ID NO 102
<211> LENGTH: 18
<212> TYPE: DNA
<213> ORGANISM: Artificial Sequence
<220> FEATURE:
<223> OTHER INFORMATION: Primer

<400> SEQUENCE: 102
catggagatc acccgtga 18

<210> SEQ ID NO 103
<211> LENGTH: 21
<212> TYPE: DNA
<213> ORGANISM: Artificial Sequence
<220> FEATURE:
<223> OTHER INFORMATION: Primer

<400> SEQUENCE: 103
atgtggtttc agtacgactt c 21

<210> SEQ ID NO 104
<211> LENGTH: 20
<212> TYPE: DNA
<213> ORGANISM: Artificial Sequence
<220> FEATURE:

<223> OTHER INFORMATION: Probe

<400> SEQUENCE: 104
tgagaggtgt tggcacgcaa 20

<210> SEQ ID NO 105
<211> LENGTH: 20
<212> TYPE: DNA
<213> ORGANISM: Artificial Sequence
<220> FEATURE:
<223> OTHER INFORMATION: Primer

<400> SEQUENCE: 105
gatggcagtg tcttatccaa 20

<210> SEQ ID NO 106
<211> LENGTH: 17
<212> TYPE: DNA
<213> ORGANISM: Artificial Sequence
<220> FEATURE:
<223> OTHER INFORMATION: Primer

<400> SEQUENCE: 106
agaccgtgcg gatcttg 17

<210> SEQ ID NO 107
<211> LENGTH: 19
<212> TYPE: DNA
<213> ORGANISM: Artificial Sequence
<220> FEATURE:
<223> OTHER INFORMATION: Probe

<400> SEQUENCE: 107
acgaccttct cggaaccgt 19

<210> SEQ ID NO 108
<211> LENGTH: 18
<212> TYPE: DNA
<213> ORGANISM: Artificial Sequence
<220> FEATURE:
<223> OTHER INFORMATION: Primer

<400> SEQUENCE: 108
catggagatc acccgtga 18

<210> SEQ ID NO 109
<211> LENGTH: 681
<212> TYPE: DNA
<213> ORGANISM: Mycobacterium tuberculosis

<400> SEQUENCE: 109
ttactttgcc gcgacgacga atccggcgat gatcgcctcg atgtcggaag cgtgcttgac 60
ggcctcgttg gccagactcg tgatggtgag ctgcaccagg tagcgctgct tggccggcgg 120
tgcgccggtt gggaagacga tccggttcca ggtgtgcagt cgcctgccgt gcaggtcata 180
actgccctga atcatcgagg acggaaaccc gttgaagtct gccgtcgagg agtccaattc 240
ggtgaagttc gtcgacagcc gggcatcggc agtgccatgc ttgagcgctt cggcgatatc 300
gaagtcccgg tgcagcttga acaccatgag catggccgtt ggatagcttt cgcccttggc 360
gatcatctcc gtgttcgggg tgatgttcgg atttttcatc ggtgcccagc ccggtggtgt 420
cggaatcgac acggtcaggt cggtcaggct gctcggtgcc accggctctc cggtgacgcc 480
gacgctttcc agatacttcc acagcgggac cggcacttcc gtcgtggtcg agacggcgct 540

-continued

```
ggtggttggg ctcgtggaca aaatcgactg gaagtcaggc gatttcggtc cgcaagcgac    600

cgctgacatt gccagcgtgg ctaccgcgac cgcgaccgcc aagggtctca cagaatcttg    660

cggacagcgt cgaccggcca a                                               681
```

<210> SEQ ID NO 110
<211> LENGTH: 681
<212> TYPE: DNA
<213> ORGANISM: Mycobacterium tuberculosis

<400> SEQUENCE: 110

```
ttactttgcc gcgacgacga atccggcgat gatcgcctcg atgtcggaag cgtgcttgac     60

ggcctcgttg gccagactcg tgatggtgag ctgcaccagg tagcgctgct tggccggcgg    120

tgcgccggtt gggaagacga tccggttcca ggtgtgcagt cgcctgccgt gcaggtcata    180

actgccctga atcatcgagg acggaaaccc gttgaagtct gccgtcgagg agtccaattc    240

ggtgaagttc gtcgacagcc gggcatcggc agtgccatgc ttgagcgctt cggcgatatc    300

gaagtcccgg tgcagcttga acaccatgag catggccgtt ggatagcttt cgcccttggc    360

gatcatctcc gtgttcgggg tgatgttcgg atttttcatc ggtgcccagc ccggtggtgt    420

cggaatcgac acggtcaggt cggtcaggct gctcggtgcc accggctctc cggtgacgcc    480

gacgctttcc agatacttcc acagcgggac cggcacttcc gtcgtggtcg agacggcgct    540

ggtggttggg ctcgtggaca aaatcgactg gaagtcaggc gatttcggtc cgcaagcgac    600

cgctgacatt gccagcgtgg ctaccgcgac cgcgaccgcc aagggtctca cagaatcttg    660

cggacagcgt cgaccggcca a                                               681
```

<210> SEQ ID NO 111
<211> LENGTH: 681
<212> TYPE: DNA
<213> ORGANISM: Mycobacterium tuberculosis

<400> SEQUENCE: 111

```
ttactttgcc gcgacgacga atccggcgat gatcgcctcg atgtcggaag cgtgcttgac     60

ggcctcgttg gccagactcg tgatggtgag ctgcaccagg tagcgctgct tggccggcgg    120

tgcgccggtt gggaagacga tccggttcca ggtgtgcagt cgcctgccgt gcaggtcata    180

actgccctga atcatcgagg acggaaaccc gttgaagtct gccgtcgagg agtccaattc    240

ggtgaagttc gtcgacagcc gggcatcggc agtgccatgc ttgagcgctt cggcgatatc    300

gaagtcccgg tgcagcttga acaccatgag catggccgtt ggatagcttt cgcccttggc    360

gatcatctcc gtgttcgggg tgatgttcgg atttttcatc ggtgcccagc ccggtggtgt    420

cggaatcgac acggtcaggt cggtcaggct gctcggtgcc accggctctc cggtgacgcc    480

gacgctttcc agatacttcc acagcgggac cggcacttcc gtcgtggtcg agacggcgct    540

ggtggttggg ctcgtggaca aaatcgactg gaagtcaggc gatttcggtc cgcaagcgac    600

cgctgacatt gccagcgtgg ctaccgcgac cgcgaccgcc aagggtctca cagaatcttg    660

cggacagcgt cgaccggcca a                                               681
```

<210> SEQ ID NO 112
<211> LENGTH: 681
<212> TYPE: DNA
<213> ORGANISM: Mycobacterium tuberculosis

<400> SEQUENCE: 112

-continued

```
ttactttgcc gcgacgacga atccggcgat gatcgcctcg atgtcggaag cgtgcttgac     60

ggcctcgttg gccagactcg tgatggtgag ctgcaccagg tagcgctgct tggccggcgg    120

tgcgccggtt gggaagacga tccggttcca ggtgtgcagt cgcctgccgt gcaggtcata    180

actgccctga atcatcgagg acggaaaccc gttgaagtct gccgtcgagg agtccaattc    240

ggtgaagttc gtcgacagcc gggcatcggc agtgccatgc ttgagcgctt cggcgatatc    300

gaagtcccgg tgcagcttga acaccatgag catggccgtt ggatagcttt cgcccttggc    360

gatcatctcc gtgttcgggg tgatgttcgg atttttcatc ggtgcccagc ccggtggtgt    420

cggaatcgac acggtcaggt cggtcaggct gctcggtgcc accggctctc cggtgacgcc    480

gacgctttcc agatacttcc acagcgggac cggcacttcc gtcgtggtcg agacggcgct    540

ggtggttggg ctcgtggaca aaatcgactg gaagtcaggc gatttcggtc cgcaagcgac    600

cgctgacatt gccagcgtgg ctaccgcgac cgcgaccgcc aagggtctca cagaatcttg    660

cggacagcgt cgaccggcca a                                              681
```

```
<210> SEQ ID NO 113
<211> LENGTH: 759
<212> TYPE: DNA
<213> ORGANISM: Mycobacterium bovis BCG

<400> SEQUENCE: 113

ctaggctaac ccatggctac tgcattgggg aaattcgatc cttgtgagct gctcggatag     60

ctgtgcccca accgtgcgga caattacttt gccgcgacga cgaatccggc gatgatcgcc    120

tcgatgtcgg aagcgtgctt gacggcctcg ttggccagac tcgtgatggt gagctgcacc    180

aggtagcgct gcttggccgg cgccggttgg gaagacgatc cggttccagg tgtgcagtcg    240

cctgccgtgc aggtcataac tgccctgaat catcgaggac ggaaacccgt tgaagtctgc    300

cgtcgaggag tccaattcgg tgaagttcgt cgacagccgg gcatcggcag tgccatgctt    360

gagcgcttcg gcgatatcga agtcccggtg cagcttgaac accatgagca tggccgttgg    420

atagctttcg cccttggcga tcatctccgt gttcggggtg atgttcggat tttcatcgg    480

tgcccagccc ggtggtgtcg gaatcgacac ggtcaggtcg gtcaggctgc tcggtgccac    540

cggctctccg gtgacgccga cgctttccag atacttccac agcgggaccg gcacttccgt    600

cgtggtcgag acggcgctgg tggttgggct cgtggacaaa atcgactgga agtcaggcga    660

tttcggtccg caagcgaccg ctgacattgc cagcgtggct accgcgaccg cgaccgccaa    720

gggtctcaca gaatcttgcg gacagcgtcg accggccaa                           759
```

```
<210> SEQ ID NO 114
<211> LENGTH: 759
<212> TYPE: DNA
<213> ORGANISM: Mycobacterium bovis BCG

<400> SEQUENCE: 114

ctaggctaac ccatggctac tgcattgggg aaattcgatc cttgtgagct gctcggatag     60

ctgtgcccca accgtgcgga caattacttt gccgcgacga cgaatccggc gatgatcgcc    120

tcgatgtcgg aagcgtgctt gacggcctcg ttggccagac tcgtgatggt gagctgcacc    180

aggtagcgct gcttggccgg cgccggttgg gaagacgatc cggttccagg tgtgcagtcg    240

cctgccgtgc aggtcataac tgccctgaat catcgaggac ggaaacccgt tgaagtctgc    300

cgtcgaggag tccaattcgg tgaagttcgt cgacagccgg gcatcggcag tgccatgctt    360

gagcgcttcg gcgatatcga agtcccggtg cagcttgaac accatgagca tggccgttgg    420
```

```
atagctttcg cccttggcga tcatctccgt gttcggggtg atgttcggat ttttcatcgg    480

tgcccagccc ggtggtgtcg gaatcgacac ggtcaggtcg gtcaggctgc tcggtgccac    540

cggctctccg gtgacgccga cgctttccag atacttccac agcgggaccg gcacttccgt    600

cgtggtcgag acggcgctgg tggttgggct cgtggacaaa atcgactgga agtcaggcga    660

tttcggtccg caagcgaccg ctgacattgc cagcgtggct accgcgaccg cgaccgccaa    720

gggtctcaca gaatcttgcg gacagcgtcg accggccaa                           759
```

<210> SEQ ID NO 115
<211> LENGTH: 759
<212> TYPE: DNA
<213> ORGANISM: Mycobacterium bovis

<400> SEQUENCE: 115

```
ctaggctaac ccatggctac tgcattgggg aaattcgatc cttgtgagct gctcggatag     60

ctgtgcccca accgtgcgga caattacttt gccgcgacga cgaatccggc gatgatcgcc    120

tcgatgtcgg aagcgtgctt gacggcctcg ttggccagac tcgtgatggt gagctgcacc    180

aggtagcgct gcttggccgg cgccggttgg gaagacgatc cggttccagg tgtgcagtcg    240

cctgccgtgc aggtcataac tgccctgaat catcgaggac ggaaacccgt tgaagtctgc    300

cgtcgaggag tccaattcgg tgaagttcgt cgacagccgg gcatcggcag tgccatgctt    360

gagcgcttcg gcgatatcga agtcccggtg cagcttgaac accatgagca tggccgttgg    420

atagctttcg cccttggcga tcatctccgt gttcggggtg atgttcggat ttttcatcgg    480

tgcccagccc ggtggtgtcg gaatcgacac ggtcaggtcg gtcaggctgc tcggtgccac    540

cggctctccg gtgacgccga cgctttccag atacttccac agcgggaccg gcacttccgt    600

cgtggtcgag acggcgctgg tggttgggct cgtggacaaa atcgactgga agtcaggcga    660

tttcggtccg caagcgaccg ctgacattgc cagcgtggct accgcgaccg cgaccgccaa    720

gggtctcaca gaatcttgcg gacagcgtcg accggccaa                           759
```

<210> SEQ ID NO 116
<211> LENGTH: 681
<212> TYPE: DNA
<213> ORGANISM: Mycobacterium africanum

<400> SEQUENCE: 116

```
ttactttgcc gcgacgacga atccggcgat gatcgcctcg atgtcggaag cgtgcttgac     60

ggcctcgttg gccagactcg tgatggtgag ctgcaccagg tagcgctgct tggccggcgg    120

tgcgccggtt gggaagacga tccggttcca ggtgtgcagt cgcctgccgt gcaggtcata    180

actgccctga atcatcgagg acggaaaccc gttgaagtct gccgtcgagg agtccaattc    240

ggtgaagttc gtcgacagcc gggcatcggc agtgccatgc ttgagcgctt cggcgatatc    300

gaagtcccgg tgcagcttga acaccatgag catggccgtt ggatagcttt cgcccttggc    360

gatcatctcc gtgttcgggg tgatgttcgg atttttcatc ggtgcccagc ccggtggtgt    420

cggaatcgac acggtcaggt cggtcaggct gctcggtgcc accggctctc cggtgacgcc    480

gacgctttcc agatacttcc acagcgggac cggcacttcc gtcgtggtcg agacggcgct    540

ggtggttggg ctcgtggaca aaatcgactg gaagtcaggc gatttcggtc cgcaagcgac    600

cgctgacatt gccagcgtgg ctaccgcgac cgcgaccgcc aagggtctca cagaatcttg    660

cggacagcgt cgaccggcca a                                              681
```

<210> SEQ ID NO 117
<211> LENGTH: 681
<212> TYPE: DNA
<213> ORGANISM: Mycobacterium africanum

<400> SEQUENCE: 117
ttactttgcc gcgacgacga atccggcgat gatcgcctcg atgtcggaag cgtgcttgac 60
ggcctcgttg gccagactcg tgatggtgag ctgcaccagg tagcgctgct tggccggcgg 120
tgcgccggtt gggaagacga tccggttcca ggtgtgcagt cgcctgccgt gcaggtcata 180
actgccctga atcatcgagg acggaaaccc gttgaagtct gccgtcgagg agtccaattc 240
ggtgaagttc gtcgacagcc gggcatcggc agtgccatgc ttgagcgctt cggcgatatc 300
gaagtcccgg tgcagcttga acaccatgag catggccgtt ggatagcttt cgcccttggc 360
gatcatctcc gtgttcgggg tgatgttcgg atttttcatc ggtgcccagc ccggtggtgt 420
cggaatcgac acggtcaggt cggtcaggct gctcggtgcc accggctctc cggtgacgcc 480
gacgctttcc agatacttcc acagcgggac cggcacttcc gtcgtggtcg agacggcgct 540
ggtggttggg ctcgtggaca aaatcgactg gaagtcaggc gatttcggtc cgcaagcgac 600
cgctgacatt gccagcgtgg ctaccgcgac cgcgaccgcc aagggtctca cagaatcttg 660
cggacagcgt cgaccggcca a 681

<210> SEQ ID NO 118
<211> LENGTH: 681
<212> TYPE: DNA
<213> ORGANISM: Mycobacterium canettii

<400> SEQUENCE: 118
ttactttgcc gcgacgacga atccggcgat gatcgcctcg atgtcggaag cgtgcttgac 60
ggcctcgttg gccagactcg tgatggtgag ctgcaccagg tagcgctgct tggccggcgg 120
tgcgccggtt gggaagacga tccggttcca ggtgtgcagt cgcctgccgt gcaggtcata 180
actgccctga atcatcgagg acggaaaccc gttgaagtct gccgtcgagg agtccaattc 240
ggtgaagttc gtcgacagcc gggcatcggc agtgccatgc ttgagcgctt cggcgatatc 300
gaagtcccgg tgcagcttga acaccatgag catggccgtt ggatagcttt cgcccttggc 360
gatcatctcc gtgttcgggg tgatgttcgg atttttcatc ggtgcccagc ccggtggtgt 420
cggaatcgac acggtcaggt cggtcaggct gctcggtgcc accggctctc cggtgacgcc 480
gacgctttcc agatacttcc acagcgggac cggcacttcc gtcgtggtcg agacggcgct 540
ggtggttggg ctcgtggaca aaatcgactg gaagtcaggc gatttcggtc cgcaagcgac 600
cgctgacatt gccagcgtgg ctaccgcgac cgcgaccgcc aagggtctca cagaatcttg 660
cggacagcgt cgaccggcca a 681

<210> SEQ ID NO 119
<211> LENGTH: 681
<212> TYPE: DNA
<213> ORGANISM: Mycobacterium microti

<400> SEQUENCE: 119
ttactttgcc gcgacgacga atccggcgat gatcgcctcg atgtcggaag cgtgcttgac 60
ggcctcgttg gccagactcg tgatggtgag ctgcaccagg tagcgctgct tggccggcgg 120
tgcgccggtt gggaagacga tccggttcca ggtgtgcagt cgcctgccgt gcaggtcata 180
actgccctga atcatcgagg acggaaaccc gttgaagtct gccgtcgagg agtccaattc 240
ggtgaagttc gtcgacagcc gggcatcggc agtgccatgc ttgagcgctt cggcgatatc 300
gaagtcccgg tgcagcttga acaccatgag catggccgtt ggatagcttt cgcccttggc 360
gatcatctcc gtgttcgggg tgatgttcgg atttttcatc ggtgcccagc ccggtggtgt 420
cggaatcgac acggtcaggt cggtcaggct gctcggtgcc accggctctc cggtgacgcc 480
gacgctttcc agatacttcc acagcgggac cggcacttcc gtcgtggtcg agacggcgct 540
ggtggttggg ctcgtggaca aaatcgactg gaagtcaggc gatttcggtc cgcaagcgac 600
cgctgacatt gccagcgtgg ctaccgcgac cgcgaccgcc aagggtctca cagaatcttg 660
cggacagcgt cgaccggcca a 681

<210> SEQ ID NO 120
<211> LENGTH: 660
<212> TYPE: DNA
<213> ORGANISM: Mycobacterium avium

<400> SEQUENCE: 120
ctacttcgcc gccaccacga agccgtggat gatcgcctcg atgtcggtcg actccgcggc 60
ggcctgatcg gccaggctgg tgatcgtgag ctgcaccaga tagcgctgat gcgccggcgg 120
cgatccggtg gcgatgacga tccggttcca gctgtgcagc cgcatgccgt ccaggtcgta 180
gctgccctgg atcatcgacg agggaaagcc gttgtacggg gcgccggacg cgtccagctg 240
cttgaagttc tcgaacagct gcgcgtcgtc gttgccgtgc ttgatgactt gggccgggtc 300
gaaatcgccg ctcagcttga agaccaccag ccgcgccgtg gggaacttgc cgcccttgga 360
gatcatcacc gtctgcgggc tgatgttcgg gctgctgaac ggcgcccagc ccggcggggt 420
cgggatcgac accgtcagat ccggcagcga cgccggggcc acctgctgcc cggtgacacc 480
gatgctctgc agatactgcg acagcgggac cggcttcgcc gtggcgctgg tggtggtggt 540
cgtcgtcggc gtcttcgaca ggatcgattg gtagtcgggc ggtttcggtg cgcagccggc 600
ggtggccacg gccagtgcaa ccgccgcggc gacggccgcg cagccgcgga gtcggttcac 660

<210> SEQ ID NO 121
<211> LENGTH: 660
<212> TYPE: DNA
<213> ORGANISM: Mycobacterium avium

<400> SEQUENCE: 121
ctacttcgcc gccaccacga agccgtggat gatcgcctcg atgtcggtcg actccgcggc 60
ggcctgatcg gccaggctgg tgatcgtgag ctgcaccaga tagcgctgat gcgccggcgg 120
cgatccggtg gcgatgacga tccggttcca gctgtgcagc cgcatgccgt ccaggtcgta 180
gctgccctgg atcatcgacg agggaaagcc gttgtacggg gcgccggacg cgtccagctg 240
cttgaagttc tcgaacagct gcgcgtcgtc gttgccgtgc ttgatgactt gggccgggtc 300
gaaatcgccg ctcagcttga agaccaccag ccgcgccgtg gggaacttgc cgcccttgga 360
gatcatcacc gtctgcgggc tgatgttcgg gctgctgaac ggcgcccagc ccggcggggt 420
cgggatcgac accgtcagat ccggcagcga cgccggggcc acctgctgcc cggtgacacc 480
gatgctctgc agatactgcg acagcgggac cggcttcgcc gtggcgctgg tggtggtggt 540
cgtcgtcggc gtcttcgaca ggatcgattg gtagtcgggc ggtttcggtg cgcagccggc 600
ggtggccacg gccagtgcaa ccgctgcggc gactgccgcg cagccgcgga gtcggttcac 660

<210> SEQ ID NO 122

<211> LENGTH: 657
<212> TYPE: DNA
<213> ORGANISM: Mycobacterium leprae

<400> SEQUENCE: 122

```
ttacttgggg gcgacgacaa agccgcggat gatagcctcg atatcgtttg attgtgcgac     60
cgcctcgttg gccaagctgg taatggtgag ctgaacgaga tactgttgct tagagggtgg    120
tggaccggtg gggatcacga ttcggttcca ggcatgtagt cgcctgccct cgaggtcata    180
gctgccttgg atcattgccg acggaaaacc gttgtagttt gccgtcgaaa cgtccagctg    240
cctgaagttc tcgaagagtt gggcatcgtc gttcccgtgt ttgatgactt gggttgggtc    300
gaagtctccg cgcagcttga acgctacgag ccttgccgtc gggtacttgc cgcttttggc    360
gatgatcagc gtctccggtg tgatgttcgg attgctatac ggcgaccagc ccggtggggt    420
cggtatcgac acggtcagac cgggcaggga gctcggcgcc acctgctgcc cggtgacgcc    480
gatactttcc agatattgcg gcaaagggat gggcttgtcg ggtgtggtcg tagtggttgt    540
agaacttttc gacaggatta attggtagtc aggggttttc gtcccgcagg agaccgcgga    600
tatgctcagc gtgactaccg cggcagcggt gtgcagcccg agacggattg cctgcat       657
```

<210> SEQ ID NO 123
<211> LENGTH: 657
<212> TYPE: DNA
<213> ORGANISM: Mycobacterium marinum

<400> SEQUENCE: 123

```
tcacttcacc gcaaccacga atccgttgat gatcgactcg atgtcggatg cgctgccggc     60
ggcctgactg gccaggctgg tgatggtcag ttggaccaga taccgctgat tgtccggcgg    120
cggcccggtg ggaatgacga tccgattcca gctgtgcatg cgggcaccct cgaggtcgta    180
gctgccctgc atcatcgacg agggaaaacc gtgaaagtct gccgacgagg cgtccagctg    240
tttgaagttc tcgaacagtt gcgcgtcgtc gttgccgcgc ctggcgacgt cggcggggtc    300
gaagttcccg cgcagcaaga acacgaccag tctggccgtg gggtagtggc cgcccttgga    360
gatgatcacc gtttccggat tgatcttcgg gccctcgtag gggaccagc ccggtggtgt     420
cgggatcgac acggtaaggc ctttgaggtc gctcggcgcg atctgctttc cgctgacccc    480
gatgctttcc aggtactgcg acagcggcac gggtggggcg gtggtggcgg tggtgctggt    540
tgttgcgctc gtggtccaga tggatttgta gtcagggggc tcgggtgtgc tgcaggcaac    600
cgccggcatc gtgaccgcga gtgaaacgac ggccgctgcg atccggcgag ctgtcac       657
```

<210> SEQ ID NO 124
<211> LENGTH: 657
<212> TYPE: DNA
<213> ORGANISM: Mycobacterium ulcerans

<400> SEQUENCE: 124

```
tcacttcacc gcaaccacga atccgttgat gatcgactcg atgtcggatg cgctgccggc     60
ggcctgactg gccaggctgg tgatggtcag ttggaccaga taccgctggt tgtccggcgg    120
cggcccggtg ggaatgacga tccgattcca gctgtgcatg cgggcaccct cgaggtcgta    180
gctgccctgc atcatcgacg agggaaaacc gtgaaagtct gccgatgagg cgtccagctg    240
tttgaagttc tcgaacagtt gcgcgtcgtc gttgccgcgc ctggcgacgt cggcggggtc    300
gaagttcccg cgcagcaaga acacgaccag tctggccgtg gggtagtggc cgcccttgga    360
gatgatcacc gtttccgggt tgatcttcgg gccctcgtag gggaccagc ccggtggtgt     420
```

cgggatcgat acggtaaggc ctttgaggtc gctcggcgcg atctgctttc cgctgacccc 480
gatgctttcc aggtactgcg acagcggcac gggcggggcg gtggtggcgg tggtgctggt 540
tgttgcgctc gtggtccaga tggatttgta gtcagggggc tcgggtgtgc tgcaggcaac 600
cgccggcatc gtgaccgcga gtgaaacgac ggccgctgcg atccggcgag ctgtcac 657

<210> SEQ ID NO 125
<211> LENGTH: 641
<212> TYPE: DNA
<213> ORGANISM: Artificial Sequence
<220> FEATURE:
<223> OTHER INFORMATION: Mycobacterium africanum DNA fragment

<400> SEQUENCE: 125
ttactttgcc gcgacgacga atccggcgat gatcgcctcg atgtcggaag cgtgcttgac 60
ggcctcgttg gccagactcg tgatggtgag ctgcaccagg tagcgctgct tggccggcgg 120
tgcgccggtt gggaagacga tccggttcca ggtgtgcagt cgcctgccgt gcaggtcata 180
actgccctga atcatcgagg acggaaaccc gttgaagtct gccgtcgagg agtccaattc 240
ggtgaagttc gtcgacagcc gggcatcggc agtgccatgc ttgagcgctt cggcgatatc 300
gaagtcccgg tgcagcttga acaccatgag catggccgtt ggatagcttt cgcccttggc 360
gatcatctcc gtgttcgggg tgatgttcgg atttttcatc ggtgcccagc ccggtggtgt 420
cggaatcgac acggtcaggt cggtcaggct gctcggtgcc accggctctc cggtgacgcc 480
gacgctttcc agatacttcc acagcgggac cggcacttcc gtcgtggtcg agacggcgct 540
ggtggttggg ctcgtggaca aaatcgactg gaagtcaggc gatttcggtc cgcaagcgac 600
cgctgacatt gccagcgtgg ctaccgcgac cgcgaccgcc a 641

<210> SEQ ID NO 126
<211> LENGTH: 641
<212> TYPE: DNA
<213> ORGANISM: Artificial Sequence
<220> FEATURE:
<223> OTHER INFORMATION: Mycobacterium microti DNA fragment

<400> SEQUENCE: 126
ttactttgcc gcgacgacga atccggcgat gatcgcctcg atgtcggaag cgtgcttgac 60
ggcctcgttg gccagactcg tgatggtgag ctgcaccagg tagcgctgct tggccggcgg 120
tgcgccggtt gggaagacga tccggttcca ggtgtgcagt cgcctgccgt gcaggtcata 180
actgccctga atcatcgagg acggaaaccc gttgaagtct gccgtcgagg agtccaattc 240
ggtgaagttc gtcgacagcc gggcatcggc agtgccatgc ttgagcgctt cggcgatatc 300
gaagtcccgg tgcagcttga acaccatgag catggccgtt ggatagcttt cgcccttggc 360
gatcatctcc gtgttcgggg tgatgttcgg atttttcatc ggtgcccagc ccggtggtgt 420
cggaatcgac acggtcaggt cggtcaggct gctcggtgcc accggctctc cggtgacgcc 480
gacgctttcc agatacttcc acagcgggac cggcacttcc gtcgtggtcg agacggcgct 540
ggtggttggg ctcgtggaca aaatcgactg gaagtcaggc gatttcggtc cgcaagcgac 600
cgctgacatt gccagcgtgg ctaccgcgac cgcgaccgcc a 641

<210> SEQ ID NO 127
<211> LENGTH: 641
<212> TYPE: DNA
<213> ORGANISM: Artificial Sequence
<220> FEATURE:

<223> OTHER INFORMATION: Mycobacterium pinnipedii DNA fragment

<400> SEQUENCE: 127
ttactttgcc gcgacgacga atccggcgat gatcgcctcg atgtcggaag cgtgcttgac 60
ggcctcgttg gccagactcg tgatggtgag ctgcaccagg tagcgctgct tggccggcgg 120
tgcgccggtt gggaagacga tccggttcca ggtgtgcagt cgcctgccgt gcaggtcata 180
actgccctga atcatcgagg acggaaaccc gttgaagtct gccgtcgagg agtccaattc 240
ggtgaagttc gtcgacagcc gggcatcggc agtgccatgc ttgagcgctt cggcgatatc 300
gaagtcccgg tgcagcttga acaccatgag catggccgtt ggatagcttt cgcccttggc 360
gatcatctcc gtgttcgggg tgatgttcgg atttttcatc ggtgcccagc ccggtggtgt 420
cggaatcgac acggtcaggt cggtcaggct gctcggtgcc accggctctc cggtgacgcc 480
gacgctttcc agatacttcc acagcgggac cggcacttcc gtcgtggtcg agacggcgct 540
ggtggttggg ctcgtggaca aaatcgactg gaagtcaggc gatttcggtc cgcaagcgac 600
cgctgacatt gccagcgtgg ctaccgcgac cgcgaccgcc a 641

<210> SEQ ID NO 128
<211> LENGTH: 636
<212> TYPE: DNA
<213> ORGANISM: Artificial Sequence
<220> FEATURE:
<223> OTHER INFORMATION: Mycobacterium caprae DNA fragment

<400> SEQUENCE: 128
ttactttgcc gcgacgacga atccggcgat gatcgcctcg atgtcggaag cgtgcttgac 60
ggcctcgttg gccagactcg tgatggtgag ctgcaccagg tagcgctgct tggccggcgc 120
cggttgggaa gacgatccgg ttccaggtgt gcagtcgcct gccgtgcagg tcataactgc 180
cctgaatcat cgaggacgga aacccgttga agtctgccgt cgaggagtcc aattcggtga 240
agttcgtcga cagccgggca tcggcagtgc catgcttgag cgcttcggcg atatcgaagt 300
cccggtgcag cttgaacacc atgagcatgg ccgttggata gctttcgccc ttggcgatca 360
tctccgtgtt cggggtgatg ttcggatttt tcatcggtgc ccagcccggt ggtgtcggaa 420
tcgacacggt caggtcggtc aggctgctcg gtgccaccgg ctctccggtg acgccgacgc 480
tttccagata cttccacagc gggaccggca cttccgtcgt ggtcgagacg gcgctggtgg 540
ttgggctcgt ggacaaaatc gactggaagt caggcgattt cggtccgcaa gcgaccgctg 600
acattgccag cgtggctacc gcgaccgcga ccgcca 636

<210> SEQ ID NO 129
<211> LENGTH: 636
<212> TYPE: DNA
<213> ORGANISM: Artificial Sequence
<220> FEATURE:
<223> OTHER INFORMATION: Mycobacterium caprae DNA fragment

<400> SEQUENCE: 129
ttactttgcc gcgacgacga atccggcgat gatcgcctcg atgtcggaag cgtgcttgac 60
ggcctcgttg gccagactcg tgatggtgag ctgcaccagg tagcgctgct tggccggcgc 120
cggttgggaa gacgatccgg ttccaggtgt gcagtcgcct gccgtgcagg tcataactgc 180
cctgaatcat cgaggacgga aacccgttga agtctgccgt cgaggagtcc aattcggtga 240
agttcgtcga cagccgggca tcggcagtgc catgcttgag cgcttcggcg atatcgaagt 300
cccggtgcag cttgaacacc atgagcatgg ccgttggata gctttcgccc ttggcgatca 360
tctccgtgtt cggggtgatg ttcggatttt tcatcggtgc ccagcccggt ggtgtcggaa 420
tcgacacggt caggtcggtc aggctgctcg gtgccaccgg ctctccggtg acgccgacgc 480
tttccagata cttccacagc gggaccggca cttccgtcgt ggtcgagacg gcgctggtgg 540
ttgggctcgt ggacaaaatc gactggaagt caggcgattt cggtccgcaa gcgaccgctg 600
acattgccag cgtggctacc gcgaccgcga ccgcca 636

<210> SEQ ID NO 130
<211> LENGTH: 2081
<212> TYPE: DNA
<213> ORGANISM: Mycobacterium tuberculosis

<400> SEQUENCE: 130
ctgtgcaggt ggtcgtttcg aaggctaccc acgccaagct caaggagctg gcgcgcagcc 60
ggaagatgag cgtatctaag ctgctgcgtc ccgtgctcga cgagttcgta cagcgagaaa 120
cgggtcggat tctcccacgg cgttagcttg tgctcagccg ccgctcgacg tcgcgaagtc 180
tggacagtca gctgtcgcag ccgtgaccag cggacatctc gggcagctag cccgacaggg 240
tgcgcgtgca cctggcccgg gtggtaatcc attgacgcgc acggcaattg gccggctcgg 300
tctcggtctg cggataccgc actgaagggc gacaattttg gcgaaaaggc cgtgtgcggt 360
gccgggtcgc gctacgttca gattcaccta acaatgtcgt ccgccaacga gcgtgttcgc 420
cggtggtggg gcgggcgggt tggggaggtg tgtgatgtcg tttgtcagcg tagccccgga 480
gattgtggtg gccgcggcaa cagacctggc gggtatcgga tcggcgatca gcgcggccaa 540
tgccgccgcg gctgcgccga ccaccgccgt gctggccgcg ggtgccgatg aggtgtcggc 600
ggcgatcgcg gcgctgtttt ccggccacgc tcaggcctat caggcgctca gcgcccaggc 660
ggcggcgttt catcagcagt tcgtgcagac gcttgccggt ggcgctggag catatgcggc 720
cgccgaggcc caggtcgagc agcagctgct ggccgcgatc aacgcgccca cccaggcgct 780
gctggggcgc cccttgatcg gcaacggtgc cgatggggcg ccggggactg ggcaggccgg 840
cggggctggg gggatcttgt acggcaatgg cggcaatggc ggctccgggg cggctgggca 900
ggccgggggt gccggcgggc cggccgggct gatcggccat ggcgggtccg gcggggccgg 960
cggctccggc gcggccggcg gggccggcgg gcacggcgga tggctgtggg gcaacggcgg 1020
cgtcggcgga tccggcgggg cgggtgtcgg cgcaggcgtg gctggcggtc acggcggtgc 1080
gggcggtgcc gccgggctgt ggggcgccgg cggcggcggt ggcaatggcg ggaacggcgc 1140
cgatgccaac atcgtcagcg gtggagacgg tggcctcggc ggtgccggtg gcggtggcgg 1200
atggctctac ggcgacggcg gggccggcgg acacggcgga caaggcgcaa tcggcctcgg 1260
cggcggcgcc ggcggcgacg gggccaggg cggcgccggc cgcggactgt ggggtactgg 1320
cggcgccggc ggacacggcg ggcaaggcgg tggtaccggg ggcccaccgc tgcccggtca 1380
ggcaggcatg ggcgccgcgg gtggcgccgg tgggctgatc ggcaacggcg gggccggcgg 1440
cgacggcggt gtcggcgcgt ccggcggggt cgccggagta ggcggtgccg gcgggaacgc 1500
catgctgatc gggcacggcg gcgccggcgg cgccggcgga gacagcagtt tcgctaatgg 1560
cgcggccggc ggcgcgggcg gtgccggagg gcacctcttc ggcaatggcg ggtccggcgg 1620
ccacggcgga gccgtcacgg ccggcaacac cggtatcggt ggcgccggcg gcgtcggtgg 1680
ggacgccagg ctgatcggcc acggtggcgc cggcggtgcc ggcggggacc gcgccggagc 1740
cttggttggc cgtgacggcg ggcccggtgg gaacgggggc gctggcggcc agctatacgg 1800

-continued

```
caacggcggc gacggcgccc ccggcaccgg cggaacactg caggcggcgg tgagcggatt   1860

ggtgacggct ttgttcggtg cacccggcca acccggcgac accggccaac ccggctagcc   1920

ccgatcaacg agggtttcgg tgccggtccg gggcatggcc atccgctgag ctggcgatct   1980

ggactacgtt ggtgtagaaa aatcctgccg cccggaccct taaggctggg acaatttctg   2040

atagctaccc cgacacagga ggttacggga tgagcaattc g                       2081


<210> SEQ ID NO 131
<211> LENGTH: 2081
<212> TYPE: DNA
<213> ORGANISM: Mycobacterium tuberculosis

<400> SEQUENCE: 131

ctgtgcaggt ggtcgtttcg aaggctaccc acgccaagct caaggagctg gcgcgcagcc     60

ggaagatgag cgtatctaag ctgctgcgtc ccgtgctcga cgagttcgta cagcgagaaa    120

cgggtcggat tctcccacgg cgttagcttg tgctcagccg ccgctcgacg tcgcgaagtc    180

tggacagtca gctgtcgcag ccgtgaccag cggacatctc gggcagctag cccgacaggg    240

tgcgcgtgca cctggcccgg gtggtaatcc attgacgcgc acggcaattg gccggctcgg    300

tctcggtctg cggataccgc actgaagggc gacaattttg gcgaaaaggc cgtgtgcggt    360

gccgggtcgc gctacgttca gattcaccta acaatgtcgt ccgccaacga gcgtgttcgc    420

cggtggtggg gcgggcgggt tggggaggtg tgtgatgtcg tttgtcagcg tagccccgga    480

gattgtggtg gccgcggcaa cagacctggc gggtatcgga tcggcgatca gcgcggccaa    540

tgccgccgcg gctgcgccga ccaccgccgt gctggccgcg ggtgccgatg aggtgtcggc    600

ggcgatcgcg gcgctgtttt ccggccacgc tcaggcctat caggcgctca gcgcccaggc    660

ggcggcgttt catcagcagt tcgtgcagac gcttgccggt ggcgctggag catatgcggc    720

cgccgaggcc caggtcgagc agcagctgct ggccgcgatc aacgcgccca cccaggcgct    780

gctggggcgc cccttgatcg gcaacggtgc cgatggggcg ccggggactg ggcaggccgg    840

cggggctggg gggatcttgt acggcaatgg cggcaatggc ggctccgggg cggctgggca    900

ggccgggggt gccggcgggc cggccgggct gatcggccat ggcgggtccg gcggggccgg    960

cggctccggc gcggccggcg gggccggcgg gcacggcgga tggctgtggg gcaacggcgg   1020

cgtcggcgga tccggcgggg cgggtgtcgg cgcaggcgtg gctggcggtc acggcggtgc   1080

gggcggtgcc gccgggctgt ggggcgccgg cggcggcggt ggcaatggcg ggaacggcgc   1140

cgatgccaac atcgtcagcg gtggagacgg tggcctcggc ggtgccggtg gcggtggcgg   1200

atggctctac ggcgacggcg gggccggcgg acacggcgga caaggcgcaa tcggcctcgg   1260

cggcggcgcc ggcggcgacg gggccaggg cggcgccggc cgcggactgt ggggtactgg   1320

cggcgccggc ggacacggcg ggcaaggcgg tggtaccggg ggcccaccgc tgcccggtca   1380

ggcaggcatg ggcgccgcgg gtggcgccgg tgggctgatc ggcaacggcg gggccggcgg   1440

cgacggcggt gtcggcgcgt ccggcggggt cgccggagta ggcggtgccg gcgggaacgc   1500

catgctgatc gggcacggcg gcgccggcgg cgccggcgga gacagcagtt tcgttaatgg   1560

cgcggccggc ggcgcgggcg gtgccggagg gcacctcttc ggcaatggcg ggtccggcgg   1620

ccacggcgga gccgtcacgg ccggcaacac cggtatcggt ggcgccggcg gcgtcggtgg   1680

ggacgccagg ctgatcggcc acggtggcgc cggcggtgcc ggcggggacc gcgccggagc   1740

cttggttggc cgtgacggcg ggcccggtgg gaacgggggc gctggcggcc agctatacgg   1800

caacggcggc gacggcgccc ccggcaccgg cggaacactg caggcggcgg tgagcggatt   1860
```

ggtgacggct ttgttcggtg cacccggcca acccggcgac accggccaac ccggctagcc 1920
ccgatcaacg agggtttcgg tgccggtccg gggcatggcc atccgctgag ctggcgatct 1980
ggactacgtt ggtgtagaaa aatcctgccg cccggaccct taaggctggg acaatttctg 2040
atagctaccc cgacacagga ggttacggga tgagcaattc g 2081

<210> SEQ ID NO 132
<211> LENGTH: 340
<212> TYPE: DNA
<213> ORGANISM: Mycobacterium africanum

<400> SEQUENCE: 132
ctgtgcaggt ggtcgtttcg aaggctaccc acgccaagct caaggagctg gcgcgcagcc 60
ggaagatgag cgtatctaag ctgctgcgtc ccgtgctcga cgagttcgta cagcgagaaa 120
cgggtcggat tctcccacgg cgttagcttg tgctcagccg ccggccaacc cggctagccc 180
cgatcaacga gggtttcggt gccggtccgg ggcatggcca tccgctgagc tggcgatctg 240
gactacgttg gtgtagaaaa atcctgccgc ccggaccctt aaggctggga caatttctga 300
tagctacccc gacacaggag gttacgggat gagcaattcg 340

<210> SEQ ID NO 133
<211> LENGTH: 340
<212> TYPE: DNA
<213> ORGANISM: Artificial Sequence
<220> FEATURE:
<223> OTHER INFORMATION: Mycobacterium africanum DNA fragment

<400> SEQUENCE: 133
ctgtgcaggt ggtcgtttcg aaggctaccc acgccaagct caaggagctg gcgcgcagcc 60
ggaagatgag cgtatctaag ctgctgcgtc ccgtgctcga cgagttcgta cagcgagaaa 120
cgggtcggat tctcccacgg cgttagcttg tgctcagccg ccggccaacc cggctagccc 180
cgatcaacga gggtttcggt gccggtccgg ggcatggcca tccgctgagc tggcgatctg 240
gactacgttg gtgtagaaaa atcctgccgc ccggaccctt aaggctggga caatttctga 300
tagctacccc gacacaggag gttacgggat gagcaattcg 340

<210> SEQ ID NO 134
<211> LENGTH: 340
<212> TYPE: DNA
<213> ORGANISM: Artificial Sequence
<220> FEATURE:
<223> OTHER INFORMATION: Mycobacterium africanum DNA fragment

<400> SEQUENCE: 134
ctgtgcaggt ggtcgtttcg aaggctaccc acgccaagct caaggagctg gcgcgcagcc 60
ggaagatgag cgtatctaag ctgctgcgtc ccgtgctcga cgagttcgta cagcgagaaa 120
cgggtcggat tctcccacgg cgttagcttg tgctcagccg ccggccaacc cggctagccc 180
cgatcaacga gggtttcggt gccggtccgg ggcatggcca tccgctgagc tggcgatctg 240
gactacgttg gtgtagaaaa atcctgccgc ccggaccctt aaggctggga caatttctga 300
tagctacccc gacacaggag gttacgggat gagcaattcg 340

<210> SEQ ID NO 135
<211> LENGTH: 1275
<212> TYPE: DNA
<213> ORGANISM: Mycobacterium smegmatis

<400> SEQUENCE: 135
tcaggatcct ccggccttga agccacgcca gacgttgtgc cacgcggcgt cgttctcggc 60
gtcgagttcc agcaggcggt atccggcgtc gaagtactcg ggtttgacga tcgccgacgt 120
caggttctcg gggatggttc cgtccgcgac cagggtgtcg ggattgatcg acttctgcgg 180
cggctggtag ccgatctgcg cgaagttctg ttgtgccgac accggatcca gcatgtggtt 240
gaggaacagg tgcgccagca ccgggttctt gccgctcttg aggatgacca tgaggtcgtt 300
gtccaccagg cccttgccat cggccgggaa ccagtactgc aggatctccg gcggggtgtt 360
ctcgggcagg tagccgagcg cctggatgat gtcgcccgac cacatctggg cgaggccgat 420
ctggcctgcg ggcacatcgt tgtacatcgt gatggtgacc ttgggggagg tcgcggccac 480
catctgccgg agttgttcac cgaccatgtc cagatcggtc tgcgacgacg tgttgacatc 540
ggtgataccg ttgcgcagca gtaccatcgc catcgcggtg tgccagtcgt cgatgatcgc 600
ggtcttgttc ttgtatctcg gatcccacag cgcgtcatac ggattgggca acgcgccgat 660
gtcctcgggg acctggtcgg tgcgccaccc gattccggtg gtgtagacgg tgtacggcgt 720
ggtgtagcgc cactccttgt cgtaccacgg gttggtgaac accggccaca cgttctcgat 780
gttcggaatg tagctgtggt tcaacggttt gagcaggcca ccgttgacca gccggctgat 840
ctggtcgtag ctggggaagt agatgtcgta atcgacgttg ccgccgcgga tcttggtgat 900
ggcttcgtcg gtgtcgttga acgtcgagac ctggaccttg gtctggtact tgtcctcgaa 960
cgaggacacc gcgtcgggcg agatgtaatc ggcatagctg tacagctgca gggtggcgcc 1020
cttctcgggt gccagcccgt cggcgatcgg ctcgttgtcg gaggcgatgt cccatgtcac 1080
cgggctgctc ggtgacgcga tggtcaggct gggggccgac gacgacggcg gaccgccctt 1140
ggagcacgcg tcgagcagca cgcccagcgc cggggcggtc gcggcgatca acgcggcacg 1200
cgtcaggaac tgtctacggg tgggcccgga ccggggcatc ccgtgcggca gtgcgtttcc 1260
ggtgggtcca ggcat 1275

<210> SEQ ID NO 136
<211> LENGTH: 156
<212> TYPE: DNA
<213> ORGANISM: Artificial Sequence
<220> FEATURE:
<223> OTHER INFORMATION: Mycobacterium smegmatis DNA fragment

<400> SEQUENCE: 136
caccgaccat gtccagatcg gtctgcgacg acgtgttgac atcggtgata ccgttgcgca 60
gcagtaccat cgccatcgcg gtgtgccagt cgtcgatgat cgcggtcttg ttcttgtatc 120
tcggatccca cagcgcgtca tacggattgg gcaacg 156

<210> SEQ ID NO 137
<211> LENGTH: 2799
<212> TYPE: DNA
<213> ORGANISM: Mycobacterium africanum

<400> SEQUENCE: 137
ccatctgcgc tttcggtgct tcttcagctc ttgctggaac ttctggtaat gctccagcgc 60
gaatcgctct tccaaagccc caagggcgtt aatgacctcc aggtgcgaaa ggaggagcag 120
cccattcaac tgaaggactt gttcgggacc agttggcacg ttccgtccgt cctcggtgtt 180
ggccagcaag aagtcgcgga gcgcctggct gctggtcata cgctcgggga tcttcatctg 240
ccgcaagacg gtggcgatgt cggggtcggt caccacacct ctccttcgct aacgagtagt 300

-continued agcgcaagcg taagagaccg ctcccaggcc tacggatggg tctggggcta cggccgtgac 360
agcgaaagca acgaaaagta acgagttgaa cgtcgcgggc ggctacgcca agcgctcacc 420
actgggctgg tcgcgccggt cttccgggtc cttgtcatcc tcgtccgccg gcccggtggc 480
cgagaccagc cctgctttgg agctgccgcc ggctggcgtt ccggccccca ttccgctgcc 540
caccggggca gctccactca tcgccgacga tccggcgtta gcggcggtcg atgccatcgg 600
cgaggatgcc ccctccaaca actgagccat cagcggggtg cgcgccgccg atccggcttc 660
gccgggcagc gatcccgcgc gcatcagtcc cgcacctgcg cttgcgcccg acccacccgc 720
gagcgggtgg cgcgatgtca ggccggctcc gatcgtcaac gcacccgccg cattgtcatc 780
ggtatcccca tacatccgag cgatgtccgt caacgctgtc cccgctcgca tcagctcctc 840
ttgagctgcc gtgttcgaag cgatcattga agcggcctcc gtcgcgaacg ccatcacagc 900
ctgcgcggac acctcttcgc cccccgcggg taccagcccg gtcatggtcg gcatcgtcgc 960
cgcgttgccg gccgccaggc cacggctacc gatctcgacc agttgcgatc cgatgtcgcc 1020
agcggccgga tcgtgtgaca aggaatccat ctggttattg ctcctgtgtg tttgtgcgcg 1080
gactcgaacg cttgtgacgc ccccgtagca atccccgcgg aaagccggcg cgactaccgc 1140
cgcaaagccc ggtccggctg cgccggacaa taagacaatt ctagacccgc tgcgggttag 1200
cagacccgcg aagccgcaga aatacgtttg cagccacctg accttgcgcc ggatcgccct 1260
gtgcgaaggt cggaaccagc gttgctcgaa ggtgatgcac ccagccgcaa gtgtcgacct 1320
attgcgcaaa tcacactgcg gcacgcggtc tgcctgcccg tgggaccgaa cacaacgaac 1380
gaaacggtca gtcgcacccc tgagttcggt ctggcaaaca ccgaaacaat catgcgatct 1440
gccggaataa atagctattt gcaacacttt cacatgcgta atgaaagttg ggcgtcaaac 1500
aaaagctaag gcgtacgcaa attccatgcc ggggctcggc cgactgtgtc acacctgcca 1560
tcgcgggcgg ggaagccgcc gttgtgtctt cggccgcaat gccgcgctga acgctaatgt 1620
gtacggcgac accccggtgg cgatgcggac gccgcgcaga ccggcccgcg gggaggagca 1680
cgaattgcgg ttcaatcggt tcagcgcgtc cacagctcgg ccgtgctgat ggataacctc 1740
gagcggcttc gtggtcacct tttcgatcgg tgatgcgttg gccagctagt acaccgtcac 1800
cgagagcgat aggtgctatt tcccttgccg tgctgggcgc ctgcggtgcg gccttggtgc 1860
tgaccgcgcc gccggccaac caggcccgag ccgcggcgag cctgctgtca cgatcgaact 1920
gggtgctcgc cactgcgttg cccgccagtc aggacgtccc ggccgattgg ggctactcgt 1980
tgaccgggcg gttgcgacga gcggtctcgc caagcaccgt gccgccggcc gcgctgccta 2040
acacgagccg agcagccgtc tattcgccgg ctggatgcgg aaacattccg aaaatcctgg 2100
accactccag cgccgacttg gccgcctatg tccagataga ccgcgacgtg caggtgttcg 2160
ggcaagatgc gcccctggat gctgccgcga ccggggaaag cgatgagcgc ggacccaacg 2220
cccgcttcgc actctgggcc gttgccgacg gcccggcgcg gatcgccaac tacctggact 2280
ggctaaaccg gtgcggttct taccaggtca ccaaccactt tttggacgga acggtcaaga 2340
acgaacgaac cgtcaccacc gaggtggaag cgctttcggc cggcggtgcc gacgccgccg 2400
tcgcggtcac aaggacgtta atcctctaac gcaccataga ttctctagcg acgattcttg 2460
agctcccggc ctgtcgatgc cggcgctgca ggtgagtcac cgcagtgggc gcaccgaaca 2520
ctcacttccg ccgccccaaa tccgcgcagt gaccaccgcg cggtcctcgc gagtctaggc 2580
cagcatcgag tcgatcgcgg aacgtgggac caatacctgg gttgggccgg ctgcttcggg 2640
cagcaactcc cccgggttga agaagaaaat cacccccgtcg ttcgtgactg cgaagttctg 2700
ataattcacc gggtccaagc cggcattcgg cgctatcgat acctgttgtc cggtctgctt 2760
gctcagttca ccttgcacaa tggggaagac gactggcag 2799

<210> SEQ ID NO 138
<211> LENGTH: 4248
<212> TYPE: DNA
<213> ORGANISM: Mycobacterium tuberculosis

<400> SEQUENCE: 138
ccatctgcgc tttcggtgct tcttcagctc ttgctggaac ttctggtaat gctccagcgc 60
gaatcgctct tccaaagccc caagggcgtt aatgacctcg ggatctttga ccccaggggt 120
cgatggccaa tctcaggttg gtaaatcggg tgctcagatc ggccctccgg accaggttgt 180
cgcctgggca gatgtgcgct cgctaaccgc caactcactt tcaaactacg ctgcgagttg 240
tgagcgtaat gtcagtgatc tgacggcaaa ggtcacggat ttcgtcgagc agatggacgg 300
tatttcgcga aaagcggttc gacctactgg ctcctggtgt gtggcctccc agggtgctgg 360
gctgcggttt cgccaaccaa cctgctggtc ggcgcgccgt attctgaaga ccggaccaac 420
gaggggaccg agccatgtct cagacacccg ctacaacccg caaaacgttt cccgagatca 480
gctcaagagc gtgggagcac ccccgccgacc ggaccgccct ttccgcgctg cgccggctca 540
aaggcttcga ccagatcttg aagctgatgt cggggatgtt gcgggaacgg cagcaccggc 600
tgctgtacct ggccagcgcg gcacgggtcg ggccgcggca gttcgccgac ctcgacgcgc 660
tgctggacga atgcgtggat gtgctggacg cgtcggcgaa acccgaactc tacgtgatgc 720
agtcaccaat cgcggatgcc ttcaccatcg gcatgggcaa gccattcacc gtgatcacct 780
cggggctgta cgacctggtg acacacgacg agatgcggtt cgtgatgggc cacgagctcg 840
gccacgcact gtccggccac gcggtgtacc gcacgatgat gatgcatctg ctgcggttgg 900
cccggtcatt cggcgtcttg ccggttggcg gctgggcgct gcgcgcaatc gtggctgcgc 960
tgctggaatg gcagcgcaaa tcggagctgt ccggcgatcg cgctgggttg ctgtgcgcgc 1020
aggatttgga caccgcgctc agggtggaga tgaagctcgc tggcggctgc cggctggaca 1080
agctggactc ggaggccttc ttggctcagg cccgggaata cgagacatcc ggcgatatgc 1140
gcgacggggt gctcaagctg ctcaacctgg agctgcagac ccatccgttc tctgtgctgc 1200
gggctgccgc cttgactcac tgggtggaca ccggcggcta tgccaaggtg atagccggcg 1260
agtacccgcg tcgggccgac gacggcaacg ccaaatttgc agacgacctt ggcgcggccg 1320
cccggtacta ccgggacggc ttcgaccagt ccaacgaccc gctgatcaaa ggtatccgcg 1380
acggattcgg tggcatcgtc gagggcgtgg gacgggcagc ctcgaacgcg gccgattcat 1440
tgggccgcaa gatcaccgag tggcggcagc cctcgaagtg acggcccctc tgctacgtag 1500
ctaagcacgc gcgaccggcg ggctggggag cccggtcagc ggtctcatag cattgcgaac 1560
acgggacgtc gagaggggaa gagctgccat gggtgaggcg aacatccgcg agcaggcgat 1620
cgccacgatg ccacggggtg gccccgacgc gtcttggctg gatcgtcgat tccagaccga 1680
cgcactggag tacctcgacc gcgacgatgt gcccgatgag gtcaaacaga agatcatcgg 1740
ggtgctcgac cgggtgggca ccctgaccaa cctgcacgag aagtacgccc ggatagccct 1800
gaaacttgtt tctgacattc ccaacccgcg aatcctggaa cttggtgcgg gccatggcaa 1860
gctctcagcg aaaatcctcg agctacaccc gacagcgacg gtgacgatca gcgatctaga 1920
tcccacctcg gtggccaaca tcgccgcggg agagctggga acacatccgc gagcacgcac 1980

```
ccaagtgatc gacgccaccg caatcgacgg ccacgaccac agctatgacc tggcggtctt   2040
cgcgctggca tttcaccacc tgccgcctac ggtcgcctgc aaagcgatcg ccgaggccac   2100
ccgggtgggg aagcgctttc tgatcatcga cctcaaacgg cagaaaccgc tgtcgttcac   2160
gctctcttcg gtgctgctac tgccgctcca cctactgctg ctgccatggt cgtcgatgcg   2220
ctcgagcatg cacgacggct ttatcagcgc actacgtgcc tacagtccct cggcgttgca   2280
gacgcttgcc cgcgccgccg atccgggaat gcaggttgaa atcttgcccg caccgaccag   2340
gctattcccg ccatcgctcg ccgttgtgtt ctcccgttcg agctcagcgc caacggaatc   2400
tagcgagtgc tcggccgatc gccaacccgg cgaatgattc ggtagtagtg cagataagcc   2460
atcgccggta ccacgacgaa cgtgatcacg atcaaagcaa tcgagaagta gttcggacca   2520
ccccgcacta gaaagatgca gcggtagtcg taggacactg ccagcccaac cgagaccacg   2580
atcgcaacaa gcggtaacac cttgtcggtg aacgcatttc gccgcacagc agcatgttct   2640
actgcctgag acctcgccaa tgcgatgaga gcgatcggca cgatgatgaa ctggacgaat   2700
cgggcgatca ccgccaggcc ggtcaggtgc aggttgtcga accgcagcgc caacgggaat   2760
gcgagcgcca acgacgccgt aattgcgaag gagaccatcg gcacgtcgta ttggttcttg   2820
cgtgacaagc gtgtcggcag aaccccgctg tccgctaacg cggtccaaag ccgcggtgca   2880
ccgaacgagg ccgcgacatt gatgccgaac atcgatatca gggctccgac gacgatgatc   2940
gttcggaagg tagcgtttcc gatggccgcg gccagtttca cggtgtcgtc cgacgcggcg   3000
atcttgttcg atccgagcag catcgctacc gttagggtga gcaagtagat cgcgccaacc   3060
gagaagatcg cgatcggtat agctctcggc aggttccggt ccggcgcgtc catttcttcg   3120
gcggcgttcg cgatcgattc gaaaccggtg aatgcgtaca acgcgacaat cgtggccagc   3180
gccatactcg agaacgtgcc cttgccaatt tcggcgacgc caagcaacga gtacggggtc   3240
gcgctgtatg ccgaccacgc cgttgcgtag ttgttcacgt gctgggtggt gatgatccac   3300
agcccgccga caatgaatgc cgagagcgcg aatgccttgc ctaccgttga cgttccgttg   3360
gcccacttga tcgcccggtt gccgaagagg ttgatggcca acagcacgcc gataaagccg   3420
agaaacgtca gcgtcttcac actgaacagt tgctcggcgt cggcccaggc cttgtcgggg   3480
aaggccactc gcaacagcgt cgagacgaaa aaagaagcca acacccccca agcgatggac   3540
gcggtaatgg cgtgggtgac accgacatag atgccgatcc ggcgcccaaa tgcggccgtt   3600
gtgtaggcgt aggaggcacc gtttgttctg acgtaccttg ccgccgtcgc gaagacgatc   3660
gccacgacac ccgcgaaaat gccagctaaa acataggcca tcggcgcgaa gggtcctgcg   3720
agcccgatca cctcacctgg agttaggaag ataccggcgc cgattatcga gttgatcccg   3780
agcatgacga cgctgcagaa acccagcttg tggatcgcat atcctctcgt ccgcgggccg   3840
accaccgcac caaggctgtc tagcagggaa tcctctaacg caccatagat tctctagcga   3900
cgattcttga gctcccggcc tgtcgatgcc ggcgctgcag gtgagtcacc gcagtgggcg   3960
caccgaacac tcatttccgc cgccccaaat ccgcgcagtg accaccgcgc ggtcctcgcg   4020
agtctaggcc agcatcgagt cgatcgcgga acgtgggacc aatacctggg ttgggccggc   4080
tgcttcgggc agcaactccc ccgggttgaa gaagaaaatc accccgtcgt tcgtgactgc   4140
gaagttctga taattcaccg ggtccaagcc ggcattcggc gctatcgata cctgttgtcc   4200
ggtctgcttg ctcagttcac cttgcacaat ggggaagacg actggcag                4248
```

<210> SEQ ID NO 139

<211> LENGTH: 923
<212> TYPE: DNA
<213> ORGANISM: Artificial Sequence
<220> FEATURE:
<223> OTHER INFORMATION: Mycobacterium africanum DNA fragment

<400> SEQUENCE: 139

```
gccgtgctgg gcgcctgcgg tgcggccttg gtgctgaccg cgccgccggc caaccaggcc     60
cgagccgcgg cgagcctgct gtcacgatcg aactgggtgc tcgccactgc gttgcccgcc    120
agtcaggacg tcccggccga ttggggctac tcgttgaccg ggcggttgcg acgagcggtc    180
tcgccaagca ccgtgccgcc ggccgcgctg cctaacacga gccgagcagc cgtctattcg    240
ccggctggat gcggaaacat tccgaaaatc ctggaccact ccagcgccga cttggccgcc    300
tatgtccaga tagaccgcga cgtgcaggtg ttcgggcaag atgcgcccct ggatgctgcc    360
gcgaccgggg aaagcgatga gcgcggaccc aacgcccgct tcgcactctg ggccgttgcc    420
gacggcccgg cgcggatcgc caactacctg gactggctaa accggtgcgg ttcttaccag    480
gtcaccaacc actttttgga cggaacggtc aagaacgaac gaaccgtcac caccgaggtg    540
gaagcgcttt cggccggcgg tgccgacgcc gccgtcgcgg tcacaaggac gttaatcctc    600
taacgcacca tagattctct agcgacgatt cttgagctcc cggcctgtcg atgccggcgc    660
tgcaggtgag tcaccgcagt gggcgcaccg aacactcact tccgccgccc caaatccgcg    720
cagtgaccac cgcgcggtcc tcgcgagtct aggccagcat cgagtcgatc gcggaacgtg    780
ggaccaatac ctgggttggg ccggctgctt cgggcagcaa ctcccccggg ttgaagaaga    840
aaatcacccc gtcgttcgtg actgcgaagt tctgataatt caccgggtcc aagccggcat    900
tcggcgctat cgatacctgt tgt                                            923
```

<210> SEQ ID NO 140
<211> LENGTH: 923
<212> TYPE: DNA
<213> ORGANISM: Artificial Sequence
<220> FEATURE:
<223> OTHER INFORMATION: Mycobacterium africanum DNA fragment

<400> SEQUENCE: 140

```
gccgtgctgg gcgcctgcgg tgcggccttg gtgctgaccg cgccgccggc caaccaggcc     60
cgagccgcgg cgagcctgct gtcacgatcg aactgggtgc tcgccactgc gttgcccgcc    120
agtcaggacg tcccggccga ttggggctac tcgttgaccg ggcggttgcg acgagcggtc    180
tcgccaagca ccgtgccgcc ggccgcgctg cctaacacga gccgagcagc cgtctattcg    240
ccggctggat gcggaaacat tccgaaaatc ctggaccact ccagcgccga cttggccgcc    300
tatgtccaga tagaccgcga cgtgcaggtg ttcgggcaag atgcgcccct ggatgctgcc    360
gcgaccgggg aaagcgatga gcgcggaccc aacgcccgct tcgcactctg ggccgttgcc    420
gacggcccgg cgcggatcgc caactacctg gactggctaa accggtgcgg ttcttaccag    480
gtcaccaacc actttttgga cggaacggtc aagaacgaac gaaccgtcac caccgaggtg    540
gaagcgcttt cggccggcgg tgccgacgcc gccgtcgcgg tcacaaggac gttaatcctc    600
taacgcacca tagattctct agcgacgatt cttgagctcc cggcctgtcg atgccggcgc    660
tgcaggtgag tcaccgcagt gggcgcaccg aacactcact tccgccgccc caaatccgcg    720
cagtgaccac cgcgcggtcc tcgcgagtct aggccagcat cgagtcgatc gcggaacgtg    780
ggaccaatac ctgggttggg ccggctgctt cgggcagcaa ctcccccggg ttgaagaaga    840
aaatcacccc gtcgttcgtg actgcgaagt tctgataatt caccgggtcc aagccggcat    900
```

tcggcgctat cgatacctgt tgt 923

<210> SEQ ID NO 141
<211> LENGTH: 2001
<212> TYPE: DNA
<213> ORGANISM: Mycobacterium tuberculosis

<400> SEQUENCE: 141
atggcggccg actacgacaa gctcttccgg ccgcacgaag gtatggaagc tccggacgat 60
atggcagcgc agccgttctt cgaccccagt gcttcgtttc cgccggcgcc cgcatcggca 120
aacctaccga agcccaacgg ccagactccg cccccgacgt ccgacgacct gtcggagcgg 180
ttcgtgtcgg ccccgccgcc gccacccccca cccccacctc cgcctccgcc aactccgatg 240
ccgatcgccg caggagagcc gccctcgccg gaaccggccg catctaaacc acccacaccc 300
cccatgccca tcgccggacc cgaaccggcc ccacccaaac cacccacacc ccccatgccc 360
atcgccggac ccgaaccggc cccacccaaa ccacccacac ctccgatgcc catcgccgga 420
cctgcaccca ccccaaccga atcccagttg gcgcccccca gaccaccgac accacaaacg 480
ccaaccggag cgccgcagca accggaatca ccggcgcccc acgtaccctc gcacgggcca 540
catcaacccc ggcgcaccgc accagcaccg ccctgggcaa agatgccaat cggcgaaccc 600
ccgcccgctc cgtccagacc gtctgcgtcc ccggccgaac caccgacccg gcctgccccc 660
caacactccc gacgtgcgcg ccggggtcac cgctatcgca cagacaccga acgaaacgtc 720
gggaaggtag caactggtcc atccatccag gcgcggctgc gggcagagga agcatccggc 780
gcgcagctcg cccccggaac ggagccctcg ccagcgccgt tgggccaacc gagatcgtat 840
ctggctccgc ccacccgccc cgcgccgaca gaacctcccc ccagcccctc gccgcagcgc 900
aactccggtc ggcgtgccga gcgacgcgtc caccccgatt tagccgccca acatgccgcg 960
gcgcaacctg attcaattac ggccgcaacc actggcggtc gtcgccgcaa gcgtgcagcg 1020
ccggatctcg acgcgacaca gaaatcctta aggccggcgg ccaaggggcc gaaggtgaag 1080
aaggtgaagc cccagaaacc gaaggccacg aagccgccca aagtggtgtc gcagcgcggc 1140
tggcgacatt gggtgcatgc gttgacgcga atcaacctgg gcctgtcacc cgacgagaag 1200
tacgagctgg acctgcacgc tcgagtccgc cgcaatcccc gcgggtcgta tcagatcgcc 1260
gtcgtcggtc tcaaaggtgg ggctggcaaa accacgctga cagcagcgtt ggggtcgacg 1320
ttggctcagg tgcgggccga ccggatcctg gctctagacg cggatccagg cgccggaaac 1380
ctcgccgatc gggtagggcg acaatcgggc gcgaccatcg ctgatgtgct tgcagaaaaa 1440
gagctgtcgc actacaacga catccgcgca cacactagcg tcaatgcggt caatctggaa 1500
gtgctgccgg caccggaata cagctcggcg cagcgcgcgc tcagcgacgc cgactggcat 1560
ttcatcgccg atcctgcgtc gaggttttac aacctcgtct tggctgattg tggggccggc 1620
ttcttcgacc cgctgacccg cggcgtgctg tccacggtgt ccggtgtcgt ggtcgtggca 1680
agtgtctcaa tcgacggcgc acaacaggcg tcggtcgcgt tggactggtt gcgcaacaac 1740
ggttaccaag atttggcgag ccgcgcatgc gtggtcatca atcacatcat gccgggagaa 1800
cccaatgtcg cagttaaaga cctggtgcgg catttcgaac agcaagttca acccggccgg 1860
gtcgtggtca tgccgtggga caggcacatt gcggccggaa ccgagatttc actcgacttg 1920
ctcgacccta tctacaagcg caaggtcctc gaattggccg cagcgctatc cgacgatttc 1980
gagagggctg gacgtcgttg a 2001

<210> SEQ ID NO 142
<211> LENGTH: 2001
<212> TYPE: DNA
<213> ORGANISM: Mycobacterium tuberculosis

<400> SEQUENCE: 142
atggcggccg actacgacaa gctcttccgg ccgcacgaag gtatggaagc tccggacgat 60
atggcagcgc agccgttctt cgaccccagt gcttcgtttc cgccggcgcc cgcatcggca 120
aacctaccga agcccaacgg ccagactccg cccccgacgt ccgacgacct gtcggagcgg 180
ttcgtgtcgg ccccgccgcc gccacccccca cccccacctc cgcctccgcc aactccgatg 240
ccgatcgccg caggagagcc gccctcgccg gaaccggccg catctaaacc acccacaccc 300
cccatgccca tcgccggacc cgaaccggcc ccacccaaac cacccacacc ccccatgccc 360
atcgccggac ccgaaccggc cccacccaaa ccacccacac ctccgatgcc catcgccgga 420
cctgcaccca ccccaaccga atcccagttg gcgcccccca gaccaccgac accacaaacg 480
ccaaccggag cgccgcagca accggaatca ccggcgcccc acgtaccctc gcacgggcca 540
catcaacccc ggcgcaccgc accagcaccg ccctgggcaa agatgccaat cggcgaaccc 600
ccgcccgctc cgtccagacc gtctgcgtcc ccggccgaac caccgacccg gcctgccccc 660
caacactccc gacgtgcgcg ccggggtcac cgctatcgca cagacaccga acgaaacgtc 720
gggaaggtag caactggtcc atccatccag gcgcggctgc gggcagagga agcatccggc 780
gcgcagctcg cccccggaac ggagccctcg ccagcgccgt tgggccaacc gagatcgtat 840
ctggctccgc ccacccgccc cgcgccgaca gaacctcccc ccagcccctc gccgcagcgc 900
aactccggtc ggcgtgccga gcgacgcgtc caccccgatt tagccgccca acatgccgcg 960
gcgcaacctg attcaattac ggccgcaacc actggcggtc gtcgccgcaa gcgtgcagcg 1020
ccggatctcg acgcgacaca gaaatcctta aggccggcgg ccaaggggcc gaaggtgaag 1080
aaggtgaagc cccagaaacc gaaggccacg aagccgccca aagtggtgtc gcagcgcggc 1140
tggcgacatt gggtgcatgc gttgacgcga atcaacctgg gcctgtcacc cgacgagaag 1200
tacgagctgg acctgcacgc tcgagtccgc cgcaatcccc gcgggtcgta tcagatcgcc 1260
gtcgtcggtc tcaaaggtgg ggctggcaaa accacgctga cagcagcgtt ggggtcgacg 1320
ttggctcagg tgcgggccga ccggatcctg gctctagacg cggatccagg cgccggaaac 1380
ctcgccgatc gggtagggcg acaatcgggc gcgaccatcg ctgatgtgct tgcagaaaaa 1440
gagctgtcgc actacaacga catccgcgca cacactagcg tcaatgcggt caatctggaa 1500
gtgctgccgg caccggaata cagctcggcg cagcgcgcgc tcagcgacgc cgactggcat 1560
ttcatcgccg atcctgcgtc gaggttttac aacctcgtct tggctgattg tggggccggc 1620
ttcttcgacc cgctgacccg cggcgtgctg tccacggtgt ccggtgtcgt ggtcgtggca 1680
agtgtctcaa tcgacggcgc acaacaggcg tcggtcgcgt tggactggtt gcgcaacaac 1740
ggttaccaag atttggcgag ccgcgcatgc gtggtcatca atcacatcat gccgggagaa 1800
cccaatgtcg cagttaaaga cctggtgcgg catttcgaac agcaagttca acccggccgg 1860
gtcgtggtca tgccgtggga caggcacatt gcggccggaa ccgagatttc actcgacttg 1920
ctcgacccta tctacaagcg caaggtcctc gaattggccg cagcgctatc cgacgatttc 1980
gagagggctg gacgtcgttg a 2001

<210> SEQ ID NO 143
<211> LENGTH: 2001

-continued

<212> TYPE: DNA
<213> ORGANISM: Mycobacterium tuberculosis

<400> SEQUENCE: 143

```
atggcggccg actacgacaa gctcttccgg ccgcacgaag gtatggaagc tccggacgat     60
atggcagcgc agccgttctt cgaccccagt gcttcgtttc cgccggcgcc cgcatcggca    120
aacctaccga agcccaacgg ccagactccg cccccgacgt ccgacgacct gtcggagcgg    180
ttcgtgtcgg ccccgccgcc gccacccccca cccccacctc cgcctccgcc aactccgatg   240
ccgatcgccg caggagagcc gccctcgccg gaaccggccg catctaaacc acccacaccc    300
cccatgccca tcgccggacc cgaaccggcc ccacccaaac cacccacacc ccccatgccc    360
atcgccggac ccgaaccggc cccacccaaa ccacccacac ctccgatgcc catcgccgga    420
cctgcaccca ccccaaccga atcccagttg gcgcccccca gaccaccgac accacaaacg    480
ccaaccggag cgccgcagca accggaatca ccggcgcccc acgtaccctc gcacgggcca    540
catcaacccc ggcgcaccgc accagcaccg ccctgggcaa agatgccaat cggcgaaccc    600
ccgcccgctc cgtccagacc gtctgcgtcc ccggccgaac caccgacccg gcctgccccc    660
caacactccc gacgtgcgcg ccggggtcac cgctatcgca cagacaccga acgaaacgtc    720
gggaaggtag caactggtcc atccatccag gcgcggctgc gggcagagga agcatccggc    780
gcgcagctcg cccccggaac ggagccctcg ccagcgccgt tgggccaacc gagatcgtat    840
ctggctccgc ccacccgccc cgcgccgaca gaacctcccc ccagcccctc gccgcagcgc    900
aactccggtc ggcgtgccga gcgacgcgtc caccccgatt tagccgccca acatgccgcg    960
gcgcaacctg attcaattac ggccgcaacc actggcggtc gtcgccgcaa gcgtgcagcg   1020
ccggatctcg acgcgacaca gaaatcctta aggccggcgg ccaaggggcc gaaggtgaag   1080
aaggtgaagc cccagaaacc gaaggccacg aagccgccca aagtggtgtc gcagcgcggc   1140
tggcgacatt gggtgcatgc gttgacgcga atcaacctgg gcctgtcacc cgacgagaag   1200
tacgagctgg acctgcacgc tcgagtccgc cgcaatcccc gcgggtcgta tcagatcgcc   1260
gtcgtcggtc tcaaaggtgg ggctggcaaa accacgctga cagcagcgtt ggggtcgacg   1320
ttggctcagg tgcgggccga ccggatcctg gctctagacg cggatccagg cgccggaaac   1380
ctcgccgatc gggtagggcg acaatcgggc gcgaccatcg ctgatgtgct tgcagaaaaa   1440
gagctgtcgc actacaacga catccgcgca cacactagcg tcaatgcggt caatctggaa   1500
gtgctgccgg caccggaata cagctcggcg cagcgcgcgc tcagcgacgc cgactggcat   1560
ttcatcgccg atcctgcgtc gaggttttac aacctcgtct tggctgattg tggggccggc   1620
ttcttcgacc cgctgacccg cggcgtgctg tccacggtgt ccggtgtcgt ggtcgtggca   1680
agtgtctcaa tcgacggcgc acaacaggcg tcggtcgcgt tggactggtt gcgcaacaac   1740
ggttaccaag atttggcgag ccgcgcatgc gtggtcatca atcacatcat gccgggagaa   1800
cccaatgtcg cagttaaaga cctggtgcgg catttcgaac agcaagttca acccggccgg   1860
gtcgtggtca tgccgtggga caggcacatt gcggccggaa ccgagatttc actcgacttg   1920
ctcgacccta tctacaagcg caaggtcctc gaattggccg cagcgctatc cgacgatttc   1980
gagagggctg gacgtcgttg a                                              2001
```

<210> SEQ ID NO 144
<211> LENGTH: 2001
<212> TYPE: DNA
<213> ORGANISM: Mycobacterium tuberculosis

<400> SEQUENCE: 144

```
atggcggccg actacgacaa gctcttccgg ccgcacgaag gtatggaagc tccggacgat     60
atggcagcgc agccgttctt cgaccccagt gcttcgtttc cgccggcgcc cgcatcggca    120
aacctaccga agcccaacgg ccagactccg cccccgacgt ccgacgacct gtcggagcgg    180
ttcgtgtcgg ccccgccgcc gccacccccca cccccacctc cgcctccgcc aactccgatg    240
ccgatcgccg caggagagcc gccctcgccg gaaccggccg catctaaacc acccacaccc    300
cccatgccca tcgccggacc cgaaccggcc ccacccaaac cacccacacc ccccatgccc    360
atcgccggac ccgaaccggc cccacccaaa ccacccacac ctccgatgcc catcgccgga    420
cctgcaccca ccccaaccga atcccagttg gcgccccccca gaccaccgac accacaaacg    480
ccaaccggag cgccgcagca accggaatca ccggcgcccc acgtaccctc gcacgggcca    540
catcaacccc ggcgcaccgc accagcaccg ccctgggcaa agatgccaat cggcgaaccc    600
ccgcccgctc cgtccagacc gtctgcgtcc ccggccgaac caccgacccg gcctgccccc    660
caacactccc gacgtgcgcg ccggggtcac cgctatcgca cagacaccga acgaaacgtc    720
gggaaggtag caactggtcc atccatccag gcgcggctgc gggcagagga agcatccggc    780
gcgcagctcg cccccggaac ggagccctcg ccagcgccgt tgggccaacc gagatcgtat    840
ctggctccgc ccacccgccc cgcgccgaca gaacctcccc ccagcccctc gccgcagcgc    900
aactccggtc ggcgtgccga gcgacgcgtc caccccgatt tagccgccca acatgccgcg    960
gcgcaacctg attcaattac ggccgcaacc actggcggtc gtcgccgcaa gcgtgcagcg   1020
ccggatctcg acgcgacaca gaaatcctta aggccggcgg ccaaggggcc gaaggtgaag   1080
aaggtgaagc cccagaaacc gaaggccacg aagccgccca aagtggtgtc gcagcgcggc   1140
tggcgacatt gggtgcatgc gttgacgcga atcaacctgg gcctgtcacc cgacgagaag   1200
tacgagctgg acctgcacgc tcgagtccgc cgcaatcccc gcgggtcgta tcagatcgcc   1260
gtcgtcggtc tcaaaggtgg ggctggcaaa accacgctga cagcagcgtt ggggtcgacg   1320
ttggctcagg tgcgggccga ccggatcctg gctctagacg cggatccagg cgccggaaac   1380
ctcgccgatc gggtagggcg acaatcgggc gcgaccatcg ctgatgtgct tgcagaaaaa   1440
gagctgtcgc actacaacga catccgcgca cacactagcg tcaatgcggt caatctggaa   1500
gtgctgccgg caccggaata cagctcggcg cagcgcgcgc tcagcgacgc cgactggcat   1560
ttcatcgccg atcctgcgtc gaggttttac aacctcgtct tggctgattg tggggccggc   1620
ttcttcgacc cgctgacccg cggcgtgctg tccacggtgt ccggtgtcgt ggtcgtggca   1680
agtgtctcaa tcgacggcgc acaacaggcg tcggtcgcgt tggactggtt gcgcaacaac   1740
ggttaccaag atttggcgag ccgcgcatgc gtggtcatca atcacatcat gccgggagaa   1800
cccaatgtcg cagttaaaga cctggtgcgg catttcgaac agcaagttca acccggccgg   1860
gtcgtggtca tgccgtggga caggcacatt gcggccggaa ccgagatttc actcgacttg   1920
ctcgacccta tctacaagcg caaggtcctc gaattggccg cagcgctatc cgacgatttc   1980
gagagggctg gacgtcgttg a                                              2001
```

<210> SEQ ID NO 145
<211> LENGTH: 2001
<212> TYPE: DNA
<213> ORGANISM: Mycobacterium tuberculosis

<400> SEQUENCE: 145

```
atggcggccg actacgacaa gctcttccgg ccgcacgaag gtatggaagc tccggacgat     60
```

-continued

```
atggcagcgc agccgttctt cgaccccagt gcttcgtttc cgccggcgcc cgcatcggca    120
aacctaccga agcccaacgg ccagactccg cccccgacgt ccgacgacct gtcggagcgg    180
ttcgtgtcgg ccccgccgcc gccaccccca cccccacctc cgcctccgcc aactccgatg    240
ccgatcgccg caggagagcc gccctcgccg gaaccggccg catctaaacc acccacaccc    300
cccatgccca tcgccggacc cgaaccggcc ccacccaaac cacccacacc ccccatgccc    360
atcgccggac ccgaaccggc cccacccaaa ccacccacac ctccgatgcc catcgccgga    420
cctgcaccca ccccaaccga atcccagttg gcgcccccca gaccaccgac accacaaacg    480
ccaaccggag cgccgcagca accggaatca ccggcgcccc acgtaccctc gcacgggcca    540
catcaacccc ggcgcaccgc accagcaccg ccctgggcaa agatgccaat cggcgaaccc    600
ccgcccgctc cgtccagacc gtctgcgtcc ccggccgaac caccgacccg gcctgccccc    660
caacactccc gacgtgcgcg ccggggtcac cgctatcgca cagacaccga acgaaacgtc    720
gggaaggtag caactggtcc atccatccag gcgcggctgc gggcagagga agcatccggc    780
gcgcagctcg cccccggaac ggagccctcg ccagcgccgt tgggccaacc gagatcgtat    840
ctggctccgc ccacccgccc cgcgccgaca gaacctcccc ccagcccctc gccgcagcgc    900
aactccggtc ggcgtgccga gcgacgcgtc caccccgatt tagccgccca acatgccgcg    960
gcgcaacctg attcaattac ggccgcaacc actggcggtc gtcgccgcaa gcgtgcagcg   1020
ccggatctcg acgcgacaca gaaatcctta aggccggcgg ccaaggggcc gaaggtgaag   1080
aaggtgaagc cccagaaacc gaaggccacg aagccgccca aagtggtgtc gcagcgcggc   1140
tggcgacatt gggtgcatgc gttgacgcga atcaacctgg gcctgtcacc cgacgagaag   1200
tacgagctgg acctgcacgc tcgagtccgc cgcaatcccc gcgggtcgta tcagatcgcc   1260
gtcgtcggtc tcaaaggtgg ggctggcaaa accacgctga cagcagcgtt ggggtcgacg   1320
ttggctcagg tgcgggccga ccggatcctg gctctagacg cggatccagg cgccggaaac   1380
ctcgccgatc gggtagggcg acaatcgggc gcgaccatcg ctgatgtgct tgcagaaaaa   1440
gagctgtcgc actacaacga catccgcgca cacactagcg tcaatgcggt caatctggaa   1500
gtgctgccgg caccggaata cagctcggcg cagcgcgcgc tcagcgacgc cgactggcat   1560
ttcatcgccg atcctgcgtc gaggttttac aacctcgtct tggctgattg tggggccggc   1620
ttcttcgacc cgctgacccg cggcgtgctg tccacggtgt ccggtgtcgt ggtcgtggca   1680
agtgtctcaa tcgacggcgc acaacaggcg tcggtcgcgt tggactggtt gcgcaacaac   1740
ggttaccaag atttggcgag ccgcgcatgc gtggtcatca atcacatcat gccgggagaa   1800
cccaatgtcg cagttaaaga cctggtgcgg catttcgaac agcaagttca acccggccgg   1860
gtcgtggtca tgccgtggga caggcacatt gcggccggaa ccgagatttc actcgacttg   1920
ctcgacccta tctacaagcg caaggtcctc gaattggccg cagcgctatc cgacgatttc   1980
gagagggctg gacgtcgttg a                                             2001
```

<210> SEQ ID NO 146
<211> LENGTH: 2001
<212> TYPE: DNA
<213> ORGANISM: Mycobacterium tuberculosis

<400> SEQUENCE: 146

```
atggcggccg actacgacaa gctcttccgg ccgcacgaag gtatggaagc tccggacgat     60
atggcagcgc agccgttctt cgaccccagt gcttcgtttc cgccggcgcc cgcatcggca    120
```

```
aacctaccga agcccaacgg ccagactccg cccccgacgt ccgacgacct gtcggagcgg    180
ttcgtgtcgg ccccgccgcc gccacccccca cccccacctc cgcctccgcc aactccgatg    240
ccgatcgccg caggagagcc gccctcgccg gaaccggccg catctaaacc acccacaccc    300
cccatgccca tcgccggacc cgaaccggcc ccacccaaac cacccacacc ccccatgccc    360
atcgccggac ccgaaccggc cccacccaaa ccacccacac ctccgatgcc catcgccgga    420
cctgcaccca ccccaaccga atcccagttg gcgcccccca gaccaccgac accacaaacg    480
ccaaccggag cgccgcagca accggaatca ccggcgcccc acgtaccctc gcacgggcca    540
catcaacccc ggcgcaccgc accagcaccg ccctgggcaa agatgccaat cggcgaaccc    600
ccgcccgctc cgtccagacc gtctgcgtcc ccggccgaac caccgacccg gcctgccccc    660
caacactccc gacgtgcgcg ccggggtcac cgctatcgca cagacaccga acgaaacgtc    720
gggaaggtag caactggtcc atccatccag gcgcggctgc gggcagagga agcatccggc    780
gcgcagctcg cccccggaac ggagccctcg ccagcgccgt tgggccaacc gagatcgtat    840
ctggctccgc ccacccgccc cgcgccgaca gaacctcccc ccagcccctc gccgcagcgc    900
aactccggtc ggcgtgccga gcgacgcgtc caccccgatt tagccgccca acatgccgcg    960
gcgcaacctg attcaattac ggccgcaacc actggcggtc gtcgccgcaa gcgtgcagcg   1020
ccggatctcg acgcgacaca gaaatcctta aggccggcgg ccaaggggcc gaaggtgaag   1080
aaggtgaagc cccagaaacc gaaggccacg aagccgccca aagtggtgtc gcagcgcggc   1140
tggcgacatt gggtgcatgc gttgacgcga atcaacctgg gcctgtcacc cgacgagaag   1200
tacgagctgg acctgcacgc tcgagtccgc cgcaatcccc gcgggtcgta tcagatcgcc   1260
gtcgtcggtc tcaaaggtgg ggctggcaaa accacgctga cagcagcgtt ggggtcgacg   1320
ttggctcagg tgcgggccga ccggatcctg gctctagacg cggatccagg cgccggaaac   1380
ctcgccgatc gggtagggcg acaatcgggc gcgaccatcg ctgatgtgct tgcagaaaaa   1440
gagctgtcgc actacaacga catccgcgca cacactagcg tcaatgcggt caatctggaa   1500
gtgctgccgg caccggaata cagctcggcg cagcgcgcgc tcagcgacgc cgactggcat   1560
ttcatcgccg atcctgcgtc gaggttttac aacctcgtct tggctgattg tggggccggc   1620
ttcttcgacc cgctgacccg cggcgtgctg tccacggtgt ctggtgtcgt ggtcgtggca   1680
agtgtctcaa tcgacggcgc acaacaggcg tcggtcgcgt tggactggtt gcgcaacaac   1740
ggttaccaag atttggcgag ccgcgcatgc gtggtcatca atcacatcat gccgggagaa   1800
cccaatgtcg cagttaaaga cctggtgcgg catttcgaac agcaagttca acccggccgg   1860
gtcgtggtca tgccgtggga caggcacatt gcggccggaa ccgagatttc actcgacttg   1920
ctcgacccta tctacaagcg caaggtcctc gaattggccg cagcgctatc cgacgatttc   1980
gagagggctg gacgtcgttg a                                              2001
```

<210> SEQ ID NO 147
<211> LENGTH: 2001
<212> TYPE: DNA
<213> ORGANISM: Mycobacterium tuberculosis

<400> SEQUENCE: 147

```
atggcggccg actacgacaa gctcttccgg ccgcacgaag gtatggaagc tccggacgat     60
atggcagcgc agccgttctt cgaccccagt gcttcgtttc cgccggcgcc cgcatcggca    120
aacctaccga agcccaacgg ccagactccg cccccgacgt ccgacgacct gtcggagcgg    180
ttcgtgtcgg ccccgccgcc gccaccccca cccccacctc cgcctccgcc aactccgatg    240
```

ccgatcgccg caggagagcc gccctcgccg gaaccggccg catctaaacc acccacaccc 300
cccatgccca tcgccggacc cgaaccggcc ccacccaaac cacccacacc ccccatgccc 360
atcgccggac ccgaaccggc cccacccaaa ccacccacac ctccgatgcc catcgccgga 420
cctgcaccca ccccaaccga atcccagttg gcgcccccca gaccaccgac accacaaacg 480
ccaaccggag cgccgcagca accggaatca ccggcgcccc acgtaccctc gcacgggcca 540
catcaacccc ggcgcaccgc accagcaccg ccctgggcaa agatgccaat cggcgaaccc 600
ccgcccgctc cgtccagacc gtctgcgtcc ccggccgaac caccgacccg gcctgccccc 660
caacactccc gacgtgcgcg ccggggtcac cgctatcgca cagacaccga acgaaacgtc 720
gggaaggtag caactggtcc atccatccag gcgcggctgc gggcagagga agcatccggc 780
gcgcagctcg cccccggaac ggagccctcg ccagcgccgt tgggccaacc gagatcgtat 840
ctggctccgc ccacccgccc cgcgccgaca gaacctcccc ccagcccctc gccgcagcgc 900
aactccggtc ggcgtgccga gcgacgcgtc caccccgatt tagccgccca acatgccgcg 960
gcgcaacctg attcaattac ggccgcaacc actggcggtc gtcgccgcaa gcgtgcagcg 1020
ccggatctcg acgcgacaca gaaatcctta aggccggcgg ccaaggggcc gaaggtgaag 1080
aaggtgaagc cccagaaacc gaaggccacg aagccgccca aagtggtgtc gcagcgcggc 1140
tggcgacatt gggtgcatgc gttgacgcga atcaacctgg gcctgtcacc cgacgagaag 1200
tacgagctgg acctgcacgc tcgagtccgc cgcaatcccc gcgggtcgta tcagatcgcc 1260
gtcgtcggtc tcaaaggtgg ggctggcaaa accacgctga cagcagcgtt ggggtcgacg 1320
ttggctcagg tgcgggccga ccggatcctg gctctagacg cggatccagg cgccggaaac 1380
ctcgccgatc gggtagggcg acaatcgggc gcgaccatcg ctgatgtgct tgcagaaaaa 1440
gagctgtcgc actacaacga catccgcgca cacactagcg tcaatgcggt caatctggaa 1500
gtgctgccgg caccggaata cagctcggcg cagcgcgcgc tcagcgacgc cgactggcat 1560
ttcatcgccg atcctgcgtc gaggttttac aacctcgtct tggctgattg tggggccggc 1620
ttcttcgacc cgctgacccg cggcgtgctg tccacggtgt ctggtgtcgt ggtcgtggca 1680
agtgtctcaa tcgacggcgc acaacaggcg tcggtcgcgt tggactggtt gcgcaacaac 1740
ggttaccaag atttggcgag ccgcgcatgc gtggtcatca atcacatcat gccgggagaa 1800
cccaatgtcg cagttaaaga cctggtgcgg catttcgaac agcaagttca acccggccgg 1860
gtcgtggtca tgccgtggga caggcacatt gcggccggaa ccgagatttc actcgacttg 1920
ctcgacccta tctacaagcg caaggtcctc gaattggccg cagcgctatc cgacgatttc 1980
gagagggctg gacgtcgttg a 2001

<210> SEQ ID NO 148
<211> LENGTH: 2001
<212> TYPE: DNA
<213> ORGANISM: Mycobacterium bovis

<400> SEQUENCE: 148
atggcggccg actacgacaa gctcttccgg ccgcacgaag gtatggaagc tccggacgat 60
atggcagcgc agccgttctt cgaccccagt gcttcgtttc cgccggcgcc cgcatcggca 120
aacctaccga agcccaacgg ccagactccg cccccgacgt ccgacgacct gtcggagcgg 180
ttcgtgtcgg ccccgccgcc gccaccccca cccccacctc cgcctccgcc aactccgatg 240
ccgatcgccg caggagagcc gccctcgccg gaaccggccg catctaaacc acccacaccc 300

-continued

```
cccatgccca tcgccggacc cgaaccggcc ccacccaaac cacccacacc ccccatgccc    360

atcgccggac ccgaaccggc cccacccaaa ccacccacac ctccgatgcc catcgccgga    420

cctgcaccca ccccaaccga atcccagttg gcgcccccca gaccaccgac accacaaacg    480

ccaaccggag cgccgcagca accggaatca ccggcgcccc acgtaccctc gcacgggcca    540

catcaacccc ggcgcaccgc accagcaccg ccctgggcaa agatgccaat cggcgaaccc    600

ccgcccgctc cgtccagacc gtctgcgtcc ccggccgaac caccgacccg gcctgccccc    660

caacactccc gacgtgcgcg ccggggtcac cgctatcgca cagacaccga acgaaacgtc    720

gggaaggtag caactggtcc atccatccag gcgcggctgc gggcagagga agcatccggc    780

gcgcagctcg cccccggaac ggagccctcg ccagcgccgt tgggccaacc gagatcgtat    840

ctggctccgc ccacccgccc cgcgccgaca gaacctcccc ccagcccctc gccgcagcgc    900

aactccggtc ggcgtgccga gcgacgcgtc caccccgatt tagccgccca acatgccgcg    960

gcgcaacctg attcaattac ggccgcaacc actggcggtc gtcgccgcaa gcgtgcagcg   1020

ccggatctcg acgcgacaca gaaatcctta aggccggcgg ccaaggggcc gaaggtgaag   1080

aaggtgaagc cccagaaacc gaaggccacg aagccgccca aagtggtgtc gcagcgcggc   1140

tggcgacatt gggtgcatgc gttgacgcga atcaacctgg gcctgtcacc cgacgagaag   1200

tacgagctgg acctgcacgc tcgagtccgc cgcaatcccc gcgggtcgta tcagatcgcc   1260

gtcgtcggtc tcaaaggtgg ggctggcaaa accacgctga cagcagcgtt ggggtcgacg   1320

ttggctcagg tgcgggccga ccggatcctg gctctagacg cggatccagg cgccggaaac   1380

ctcgccgatc gggtagggcg acaatcgggc gcgaccatcg ctgatgtgct tgcagaaaaa   1440

gagctgtcgc actacaacga catccgcgca cacactagcg tcaatgcggt caatctggaa   1500

gtgctgccgg caccggaata cagctcggcg cagcgcgcgc tcagcgacgc cgactggcat   1560

ttcatcgccg atcctgcgtc gaggttttac aacctcgtct tggctgattg tggggccggc   1620

ttcttcgacc cgctgacccg cggcgtgctg tccacggtgt ccggtgtcgt ggtcgtggca   1680

agtgtctcaa tcgacggcgc acaacaggcg tcggtcgcgt tggactggtt gcgcaacaac   1740

ggttaccaag atttggcgag ccgcgcatgc gtggtcatca atcacatcat gccgggagaa   1800

cccaatgtcg cagttaaaga cctggtgcgg catttcgaac agcaagttca acccggccgg   1860

gtcgtggtca tgccgtggga caggcacatt gcggccggaa ccgagatttc actcgacttg   1920

ctcgacccta tctacaagcg caaggtcctc gaattggccg cagcgctatc cgacgatttc   1980

gagagggctg gacgtcgttg a                                             2001
```

<210> SEQ ID NO 149
<211> LENGTH: 2001
<212> TYPE: DNA
<213> ORGANISM: Mycobacterium africanum

<400> SEQUENCE: 149

```
atggcggccg actacgacaa gctcttccgg ccgcacgaag gtatggaagc tccggacgat     60

atggcagcgc agccgttctt cgaccccagt gcttcgtttc cgccggcgcc cgcatcggca    120

aacctaccga agcccaacgg ccagactccg cccccgacgt ccgacgacct gtcggagcgg    180

ttcgtgtcgg ccccgccgcc gccacccccca cccccacctc cgcctccgcc aactccgatg    240

ccgatcgccg caggagagcc gccctcgccg gaaccggccg catctaaacc acccacaccc    300

cccatgccca tcgccggacc cgaaccggcc ccacccaaac cacccacacc ccccatgccc    360

atcgccggac ccgaaccggc cccacccaaa ccacccacac ctccgatgcc catcgccgga    420
```

-continued cctgcaccca ccccaaccga atcccagttg gcgcccccca gaccaccgac accacaaacg 480
ccaaccggag cgccgcagca accggaatca ccggcgcccc acgtaccctc gcacgggcca 540
catcaacccc ggcgcaccgc accagcaccg ccctgggcaa agatgccaat cggcgaaccc 600
ccgcccgctc cgtccagacc gtctgcgtcc ccggccgaac caccgacccg gcctgccccc 660
caacactccc gacgtgcgcg ccggggtcac cgctatcgca cagacaccga acgaaacgtc 720
gggaaggtag caactggtcc atccatccag gcgcggctgc gggcagagga agcatccggc 780
gcgcagctcg cccccggaac ggagccctcg ccagcgccgt tgggccaacc gagatcgtat 840
ctggctccgc ccacccgccc cgcgccgaca gaacctcccc ccagcccctc gccgcagcgc 900
aactccggtc ggcgtgccga gcgacgcgtc caccccgatt tagccgccca acatgccgcg 960
gcgcaacctg attcaattac ggccgcaacc actggcggtc gtcgccgcaa gcgtgcagcg 1020
ccggatctcg acgcgacaca gaaatcctta aggccggcgg ccaaggggcc gaaggtgaag 1080
aaggtgaagc cccagaaacc gaaggccacg aagccgccca aagtggtgtc gcagcgcggc 1140
tggcgacatt gggtgcatgc gttgacgcga atcaacctgg gcctgtcacc cgacgagaag 1200
tacgagctgg acctgcacgc tcgagtccgc cgcaatcccc gcgggtcgta tcagatcgcc 1260
gtcgtcggtc tcaaaggtgg ggctggcaaa accacgctga cagcagcgtt ggggtcgacg 1320
ttggctcagg tgcgggccga ccggatcctg gctctagacg cggatccagg cgccggaaac 1380
ctcgccgatc gggtagggcg acaatcgggc gcgaccatcg ctgatgtgct tgcagaaaaa 1440
gagctgtcgc actacaacga catccgcgca cacactagcg tcaatgcggt caatctggaa 1500
gtgctgccgg caccggaata cagctcggcg cagcgcgcgc tcagcgacgc cgactggcat 1560
ttcatcgccg atcctgcgtc gaggttttac aacctcgtct tggctgattg tggggccggc 1620
ttcttcgacc cgctgacccg cggcgtgctg tccacggtgt ccggtgtcgt ggtcgtggca 1680
agtgtctcaa tcgacggcgc acaacaggcg tcggtcgcgt tggactggtt gcgcaacaac 1740
ggttaccaag atttggcgag ccgcgcatgc gtggtcatca atcacatcat gccgggagaa 1800
cccaatgtcg cagttaaaga cctggtgcgg catttcgaac agcaagttca acccggccgg 1860
gtcgtggtca tgccgtggga caggcacatt gcggccggaa ccgagatttc actcgacttg 1920
ctcgacccta tctacaagcg caaggtcctc gaattggccg cagcgctatc cgacgatttc 1980
gagagggctg gacgtcgttg a 2001

<210> SEQ ID NO 150
<211> LENGTH: 1950
<212> TYPE: DNA
<213> ORGANISM: Mycobacterium canettii

<400> SEQUENCE: 150
atggcggccg actacgacaa gctcttccgg ccgcacgaag gtatggaagc tccggacgat 60
acggcagcgc agccgttctt cgaccccagt gcttcgtttc cgccggcgcc cgcatcggca 120
aacctaccga agcccaacgg ccagactccg cccccgacgt ccgacggcct gtcggagcgg 180
ttcgtgtcgg ccccgccgcc accaccccca cccccacctc cgcctccgcc aactccgatg 240
ccgatcgccg caggagagcc gccctcgccg gaaccggccg catctaaacc acccacaccc 300
cccatgccca tcgccggacc cgaaccggcc ccacccaaac cacccgcacc tccgatgccc 360
atcgccggac ctgcacccac cccaaccgaa tcccagttgg cgccccccag accaccgaca 420
ccacaaacgc caaccggagc gccgcagcaa ccggaatcac cggcgcccca cgtaccctcg 480

-continued

```
cacgggccac aacaaccccg gcgcaccgca cccgcaccgc cctgggcaaa gatgcctatc    540

ggcgaacccc cgcccgctcc gtccagaccg tttgcgtccc cggccgaacc accgacccgg    600

cctgcccccc aacactcccg acgtgcgcgc cggggtcacc gctatcgcac agacaccgaa    660

cgaaacgtcg ggaaggtagc aactggtcca tccatccaag cgcggctgcg ggcagaggaa    720

gcatccggcg cgcagctcgc ccccggaacg gagccctcgc cggcgccgtt gggccaaccg    780

agatcgtatc tggctccgcc cacccgtccc gcctcgacag aacctccccc cagccccgcg    840

ccgcagcgcg actccggtcg gcgtgccgag cgacgcgtcc accccgactt agccgctcaa    900

catgctgcgg ctcaacctga ttcgattacg gccgcaacca ctggcggtcg tcgccgcaag    960

cgcgcagcgc ccgatctcga cgcgacacag aaatccttaa ggccggcggc caaggggccg   1020

aaggttaaga aggtgaagcc ccagaaaccg aaggccacga agccgcccaa agtggtgtcg   1080

cagcgcggct ggcgacattg ggtgcatgcg ttgacgcgaa tcaacctggg cctgtcaccc   1140

gacgagaagt acgagctgga cctgcacgct cgagtccgcc gcaatccccg cgggtcgtat   1200

cagatcgccg tcgtcggtct caaaggtggg gctggcaaaa ccacgctgac agcagcgttg   1260

gggtcgacgt tggctcaggt gcgggccgac cggatcctgg ctctagacgc ggatccaggc   1320

gccggaaacc tcgccgatcg ggtagggcga caatcgggcg cgaccatcgc tgatgtgctt   1380

gcagaaaaag agctgtcgca ctacaacgac atccgcgcac acaccagtgt caatgcggtc   1440

aatctggaag tgctgccggc accggaatac agctcggcgc agcgcgcgct cagcgacgcc   1500

gactggcatt tcatcgccga tccggcgtcg aggttttaca acctcgtctt ggctgattgt   1560

ggggccggct tcttcgaccc gctgacccgc ggcgtgctgt ccacggtgtc cggtgtcgtg   1620

gtcgtggcaa gtgtctcaat cgacggcgca cagcaagcct cggtcgcgtt ggactggttg   1680

cgcaacaacg gttaccaaga tttggcgagc cgcgcatgcg tggtcatcaa tcacatcatg   1740

ccgggagaac ccaatgtcgc agttaaagac ctggtgcggc atttcgaaca gcaagttcaa   1800

cccggccggg tcgtggtcat gccgtgggac aggcacattg cggccggaac cgagatttca   1860

ctcgacttgc tcgaccctat ctacaagcgc aaggtcctcg aattggccgc agcgctatcc   1920

gacgatttcg agagggctgg acgtcgttga                                    1950
```

```
<210> SEQ ID NO 151
<211> LENGTH: 98
<212> TYPE: DNA
<213> ORGANISM: Artificial Sequence
<220> FEATURE:
<223> OTHER INFORMATION: Mycobacterium africanum DNA fragment

<400> SEQUENCE: 151

agaaaaagag ctgtcgcact acaacgacat ccgcgcacac actagcgtca atgcggtcaa     60

tctggaagtg ctgccggcac cggaatacag ctcggcgc                             98


<210> SEQ ID NO 152
<211> LENGTH: 98
<212> TYPE: DNA
<213> ORGANISM: Artificial Sequence
<220> FEATURE:
<223> OTHER INFORMATION: Mycobacterium caprae DNA fragment

<400> SEQUENCE: 152

agaaaaagag ctgtcgcact acaacgacat ccgcgcacac actagcgtca atgcggtcaa     60

tctggaagtg ctgccggcac cggaatacag ctcggcgc                             98
```

<210> SEQ ID NO 153
<211> LENGTH: 98
<212> TYPE: DNA
<213> ORGANISM: Artificial Sequence
<220> FEATURE:
<223> OTHER INFORMATION: Mycobacterium canettii DNA fragment

<400> SEQUENCE: 153
agaaaaagag ctgtcgcact acaacgacat ccgcgcacac actagcgtca atgcggtcaa 60
tctggaagtg ctgccggcac cggaatacag ctcggcgc 98

<210> SEQ ID NO 154
<211> LENGTH: 98
<212> TYPE: DNA
<213> ORGANISM: Artificial Sequence
<220> FEATURE:
<223> OTHER INFORMATION: Mycobacterium pinnipedii DNA fragment

<400> SEQUENCE: 154
agaaaaagag ctgtcgcact acaacgacat ccgcgcacac actagcgtca atgcggtcaa 60
tctggaagtg ctgccggcac cggaatacag ctcggcgc 98

<210> SEQ ID NO 155
<211> LENGTH: 17
<212> TYPE: DNA
<213> ORGANISM: Artificial Sequence
<220> FEATURE:
<223> OTHER INFORMATION: Primer

<400> SEQUENCE: 155
tcaccgacca tgtccag 17

<210> SEQ ID NO 156
<211> LENGTH: 18
<212> TYPE: DNA
<213> ORGANISM: Artificial Sequence
<220> FEATURE:
<223> OTHER INFORMATION: Primer

<400> SEQUENCE: 156
cgttgcccaa tccgtatg 18

<210> SEQ ID NO 157
<211> LENGTH: 20
<212> TYPE: DNA
<213> ORGANISM: Artificial Sequence
<220> FEATURE:
<223> OTHER INFORMATION: Probe

<400> SEQUENCE: 157
cagcagtacc atcgccatcg 20

<210> SEQ ID NO 158
<211> LENGTH: 18
<212> TYPE: DNA
<213> ORGANISM: Artificial Sequence
<220> FEATURE:
<223> OTHER INFORMATION: Primer

<400> SEQUENCE: 158
acgaatccgg cgatgatc 18

<210> SEQ ID NO 159
<211> LENGTH: 17
<212> TYPE: DNA

<213> ORGANISM: Artificial Sequence
<220> FEATURE:
<223> OTHER INFORMATION: Primer

<400> SEQUENCE: 159
cgactgcaca cctggaa 17

<210> SEQ ID NO 160
<211> LENGTH: 16
<212> TYPE: DNA
<213> ORGANISM: Artificial Sequence
<220> FEATURE:
<223> OTHER INFORMATION: Probe

<400> SEQUENCE: 160
ttggccggcg ccggtt 16

<210> SEQ ID NO 161
<211> LENGTH: 18
<212> TYPE: DNA
<213> ORGANISM: Artificial Sequence
<220> FEATURE:
<223> OTHER INFORMATION: Primer

<400> SEQUENCE: 161
catcgctgat gtgcttgc 18

<210> SEQ ID NO 162
<211> LENGTH: 17
<212> TYPE: DNA
<213> ORGANISM: Artificial Sequence
<220> FEATURE:
<223> OTHER INFORMATION: Primer

<400> SEQUENCE: 162
tgcgccgagc tgtattc 17

<210> SEQ ID NO 163
<211> LENGTH: 21
<212> TYPE: DNA
<213> ORGANISM: Artificial Sequence
<220> FEATURE:
<223> OTHER INFORMATION: Probe

<400> SEQUENCE: 163
acactagcgt caatgcggtc a 21

<210> SEQ ID NO 164
<211> LENGTH: 17
<212> TYPE: DNA
<213> ORGANISM: Artificial Sequence
<220> FEATURE:
<223> OTHER INFORMATION: Primer

<400> SEQUENCE: 164
agaccgtgcg gatcttg 17

<210> SEQ ID NO 165
<211> LENGTH: 18
<212> TYPE: DNA
<213> ORGANISM: Artificial Sequence
<220> FEATURE:
<223> OTHER INFORMATION: Primer

<400> SEQUENCE: 165
catggagatc acccgtga 18

<210> SEQ ID NO 166
<211> LENGTH: 20
<212> TYPE: DNA
<213> ORGANISM: Artificial Sequence
<220> FEATURE:
<223> OTHER INFORMATION: Probe

<400> SEQUENCE: 166
tatcgggtac acaaagacga 20

<210> SEQ ID NO 167
<211> LENGTH: 17
<212> TYPE: DNA
<213> ORGANISM: Artificial Sequence
<220> FEATURE:
<223> OTHER INFORMATION: Primer

<400> SEQUENCE: 167
acggaacggt caagaac 17

<210> SEQ ID NO 168
<211> LENGTH: 18
<212> TYPE: DNA
<213> ORGANISM: Artificial Sequence
<220> FEATURE:
<223> OTHER INFORMATION: Primer

<400> SEQUENCE: 168
gctcaagaat cgtcgcta 18

<210> SEQ ID NO 169
<211> LENGTH: 19
<212> TYPE: DNA
<213> ORGANISM: Artificial Sequence
<220> FEATURE:
<223> OTHER INFORMATION: Probe

<400> SEQUENCE: 169
acgtccttgt gaccgcgac 19

<210> SEQ ID NO 170
<211> LENGTH: 17
<212> TYPE: DNA
<213> ORGANISM: Artificial Sequence
<220> FEATURE:
<223> OTHER INFORMATION: Primer

<400> SEQUENCE: 170
aacgggtcgg attctcc 17

<210> SEQ ID NO 171
<211> LENGTH: 18
<212> TYPE: DNA
<213> ORGANISM: Artificial Sequence
<220> FEATURE:
<223> OTHER INFORMATION: Primer

<400> SEQUENCE: 171
ccgaaaccct cgttgatc 18

<210> SEQ ID NO 172
<211> LENGTH: 17
<212> TYPE: DNA
<213> ORGANISM: Artificial Sequence
<220> FEATURE:

-continued

```
<223> OTHER INFORMATION: Probe

<400> SEQUENCE: 172

tcagccgccg gccaacc                                                17


<210> SEQ ID NO 173
<211> LENGTH: 21
<212> TYPE: DNA
<213> ORGANISM: Artificial Sequence
<220> FEATURE:
<223> OTHER INFORMATION: Probe

<400> SEQUENCE: 173

attggtcacc cggatttcgg t                                           21
```